US010633664B2

(12) United States Patent
Jessen et al.

(10) Patent No.: US 10,633,664 B2
(45) Date of Patent: *Apr. 28, 2020

(54) COMPOSITIONS AND METHODS FOR 3-HYDROXYPROPIONIC ACID PRODUCTION

(71) Applicant: CARGILL, INCORPORATED, Wayzata, MN (US)

(72) Inventors: Holly Jessen, Chanhassen, MN (US); Brian Rush, Minneapolis, MN (US); Jeanette Huryta, Excelsior, MN (US); Beth Mastel, Excelsior, MN (US); Alan Berry, Granite Bay, CA (US); Debbie Yaver, Davis, CA (US); Michael Catlett, West Sacramento, CA (US); Michelle Barnhart, Sacramento, CA (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/384,150

(22) Filed: Apr. 15, 2019

(65) Prior Publication Data

US 2019/0249181 A1 Aug. 15, 2019

Related U.S. Application Data

(63) Continuation of application No. 15/688,436, filed on Aug. 28, 2017, now Pat. No. 10,260,072, which is a continuation of application No. 15/060,036, filed on Mar. 3, 2016, now Pat. No. 9,777,280, which is a continuation of application No. 14/073,441, filed on Nov. 6, 2013, now abandoned, which is a continuation of application No. 13/301,556, filed on Nov. 21, 2011, now Pat. No. 9,090,918.

(60) Provisional application No. 61/535,181, filed on Sep. 15, 2011, provisional application No. 61/416,199, filed on Nov. 22, 2010.

(51) Int. Cl.
| | | |
|---|---|---|
| *C12N 1/20* | (2006.01) | |
| *C12N 15/52* | (2006.01) | |
| *C12N 1/18* | (2006.01) | |
| *C12N 9/04* | (2006.01) | |
| *C12N 9/10* | (2006.01) | |
| *C12N 9/88* | (2006.01) | |
| *C12N 9/00* | (2006.01) | |
| *C12P 7/42* | (2006.01) | |
| *C12N 15/81* | (2006.01) | |

(52) U.S. Cl.
CPC ............. *C12N 15/52* (2013.01); *C12N 1/18* (2013.01); *C12N 9/0006* (2013.01); *C12N 9/1096* (2013.01); *C12N 9/88* (2013.01); *C12N 9/93* (2013.01); *C12N 15/81* (2013.01); *C12N 15/815* (2013.01); *C12P 7/42* (2013.01); *C12Y 101/01059* (2013.01); *C12Y 206/01001* (2013.01); *C12Y 206/01018* (2013.01); *C12Y 206/01019* (2013.01); *C12Y 401/01031* (2013.01)

(58) Field of Classification Search
CPC . C12N 1/18; C12N 15/81; C12N 9/93; C12N 9/88
USPC .................................................. 435/254.21
See application file for complete search history.

(56) References Cited

U.S. PATENT DOCUMENTS

| | | | |
|---|---|---|---|
| 4,275,234 A | 6/1981 | Baniel et al. | |
| 4,771,001 A | 9/1988 | Bailey et al. | |
| 5,132,456 A | 7/1992 | King et al. | |
| 5,420,304 A | 5/1995 | Hillman et al. | |
| 5,510,526 A | 4/1996 | Baniel et al. | |
| 5,641,406 A | 6/1997 | Sarhaddar et al. | |
| 5,831,122 A | 11/1998 | Eyal et al. | |
| 6,329,183 B1 | 12/2001 | Skraly et al. | |
| 6,455,284 B1 | 9/2002 | Gokarn et al. | |
| 6,852,517 B1 | 2/2005 | Suthers et al. | |
| 7,326,557 B2 | 2/2008 | San et al. | |
| 7,846,688 B2 | 12/2010 | Gill et al. | |
| 7,987,056 B2 | 7/2011 | Gill et al. | |
| 8,030,045 B2 | 10/2011 | Jessen et al. | |
| 8,048,624 B1 | 11/2011 | Lynch et al. | |
| 8,809,027 B1 | 8/2014 | Mercogliano et al. | |
| 9,777,280 B2 * | 10/2017 | Jessen ...................... | C12N 1/18 |
| 10,260,072 B2 * | 4/2019 | Jessen ...................... | C12N 1/18 |
| 2001/0021978 A1 | 9/2001 | Asakai et al. | |
| 2005/0221466 A1 | 10/2005 | Liao et al. | |
| 2007/0037265 A1 | 2/2007 | Zhou et al. | |
| 2007/0107080 A1 | 5/2007 | Liao et al. | |
| 2009/0325248 A1 | 12/2009 | Marx et al. | |
| 2010/0021978 A1 | 1/2010 | Burk et al. | |
| 2011/0144377 A1 | 6/2011 | Eliot et al. | |
| 2014/0121118 A1 | 5/2014 | Warner | |

FOREIGN PATENT DOCUMENTS

| | | | |
|---|---|---|---|
| DE | 102005048818 A1 | 4/2007 | |
| EP | 1073722 B1 | 2/2010 | |
| EP | 2194122 A1 | 6/2010 | |

(Continued)

OTHER PUBLICATIONS

"GenBank Accession No. WP_011010232.1; Apr. 27, 2015. 1 Page."

(Continued)

*Primary Examiner* — Tekchand Saidha

(57) ABSTRACT

The present application discloses genetically modified yeast cells comprising an active 3-HP fermentation pathway, and the use of these cells to produce 3-HP.

5 Claims, 32 Drawing Sheets

Specification includes a Sequence Listing.

(56) References Cited

FOREIGN PATENT DOCUMENTS

| | | | |
|---|---|---|---|
| WO | 9300440 | A1 | 1/1993 |
| WO | 9914335 | A1 | 3/1999 |
| WO | 0071738 | A1 | 11/2000 |
| WO | 0116346 | A1 | 3/2001 |
| WO | 0242418 | A2 | 5/2002 |
| WO | 0242471 | A2 | 5/2002 |
| WO | 03049525 | A2 | 6/2003 |
| WO | 03062173 | A2 | 7/2003 |
| WO | 03082795 | A2 | 10/2003 |
| WO | 03102152 | A2 | 12/2003 |
| WO | 03102200 | A2 | 12/2003 |
| WO | 03102201 | A2 | 12/2003 |
| WO | 2004041421 | A2 | 5/2004 |
| WO | 2004076398 | A1 | 9/2004 |
| WO | 2005003074 | A1 | 1/2005 |
| WO | 2005118719 | A2 | 12/2005 |
| WO | 2006022664 | A2 | 3/2006 |
| WO | 2006047589 | A2 | 5/2006 |
| WO | 2007106524 | A2 | 9/2007 |
| WO | 2007130745 | A2 | 11/2007 |
| WO | 2008021765 | A2 | 2/2008 |
| WO | 2008027742 | A1 | 3/2008 |
| WO | 2008089102 | A2 | 7/2008 |
| WO | 2008091627 | A2 | 7/2008 |
| WO | 2009085935 | A2 | 7/2009 |
| WO | 2009089457 | A1 | 7/2009 |
| WO | 2010006076 | A2 | 1/2010 |
| WO | 2010011874 | A2 | 1/2010 |
| WO | 2010017230 | A2 | 2/2010 |
| WO | 2010031083 | A2 | 3/2010 |
| WO | 2010059424 | A2 | 5/2010 |
| WO | 2011038364 | A1 | 3/2011 |
| WO | 2011050037 | A1 | 4/2011 |
| WO | 2011059740 | A1 | 5/2011 |
| WO | 2011063363 | A2 | 5/2011 |
| WO | 2011094457 | A1 | 8/2011 |
| WO | 2011123505 | A1 | 10/2011 |
| WO | 2012021399 | A1 | 2/2012 |
| WO | 2012074818 | A2 | 6/2012 |
| WO | 2013192450 | A1 | 12/2013 |
| WO | 2013192451 | A1 | 12/2013 |
| WO | 2013192453 | A1 | 12/2013 |
| WO | 2014144367 | A1 | 9/2014 |
| WO | 2014144400 | A1 | 9/2014 |
| WO | 2014145096 | A1 | 9/2014 |
| WO | 2014145297 | A1 | 9/2014 |
| WO | 2014145332 | A1 | 9/2014 |

OTHER PUBLICATIONS

"Sequence alignment between Applicants' SEQ ID No. 139 & Accession No. AUR72538 (2008)".

Alber, et al., "Malonyl-coenzyme A reductase in the modified 3-hydroxypropionate cycle for autotrophic carbon fixation in archaeal *Metallosphaera* and *Sulfolobus* spp.", spp. J Bacteriol. Dec. 2006;188(24):8551-9.

Henry, "Discovery and analysis of novel metabolic pathways for the biosynthesis of industrial chemicals: 3-hydroxypropanoate", 2010, Biotechnol Bioeng 106 (3), 462-473.

Khoury, et al., "Computational design of Candida boidinii xylose reductase for altered cofactor specificity", vol. 18, Issue10, Oct. 2009, 2125-2138.

Myers, et al., "Activation of yeast pyruvate carboxylase: interactions between acyl coenzyme A compounds, aspartate, and substrates of the reaction", Biochemistry. Oct. 25, 1983;22(22):5090-6.

Richter, et al., "A single-point mutation enables lactate dehydrogenase from Bacillus subtilis to utilize NAD+ and NADP+ as cofactor", 2011, Eng. Life Sci. 11(1), 26-36.

Sauer, "2005, FEMS Micro. Rev. 29, 765-794".

Smith, et al., "2007—Uniport Access No. 027026".

Straathoff, et al., "Feasibility of acrylic acid production by fermentation", Appl Microbiol Biotechnol.67(6), Jun. 2005, 727-34.

Van Maris, et al., "Directed Evolution of Pyruvate Decarboxylase-Negative *Saccharomyces cerevisiae*, Yielding a C2-Independent, Glucose-Tolerant, and Pyruvate-Hyperproducing Yeast", Appl. and Envir. Micro. 70(1), 159-166, 2004.

Yamazawa, et al., "Crystal structure of serine dehydrogenase from *Escherichia coli*: important role of the C-terminal region for closed-complex formation", The Journal of Biochemistry, vol. 149, Issue 6, Jun. 1, 2011, pp. 701-712, https://doi.org/10.1093/jb/mvr024.

* cited by examiner

SEQUENCE LISTING

<160> NUMBER OF SEQ ID NOS: 351

<210> SEQ ID NO 1
<211> LENGTH: 3543
<212> TYPE: DNA
<213> ORGANISM: Issatchenkia orientalis

<400> SEQUENCE: 1

```
atgtcaactg tggaagatca ctcctcccta cataaattga gaaaggaatc tgagattctt      60
tccaatgcaa acaaaatctt agtggctaat agaggtgaaa ttccaattag aattttcagg     120
tcagcccatg aattgtcaat gcatactgtg gcgatctatt cccatgaaga tcggttgtcc     180
```

```
atgcataggt tgaaggccga cgaggcttat gcaatcggta agactggtca atattcgcca    240
gttcaagctt atctacaaat tgacgaaatt atcaaaatag caaaggaaca tgatgtttcc    300
atgatccatc caggttatgg tttcttatct gaaaactccg aattcgcaaa gaaggttgaa    360
gaatccggta tgatttgggt tgggcctcct gctgaagtta ttgattctgt tggtgacaag    420
gtttctgcaa gaaatttggc aattaaatgt gacgttcctg ttgttcctgg taccgatggt    480
ccaattgaag acattgaaca ggctaaacag tttgtggaac aatatggtta tcctgtcatt    540
ataaaggctg catttggtgg tggtggtaga ggtatgagag ttgttagaga aggtgatgat    600
atagttgatg ctttccaaag agcgtcatct gaagcaaagt ctgcctttgg taatggtact    660
tgttttattg aaagattttt ggataagcca aaacatattg aggttcaatt attggctgat    720
aattatggta acacaatcca tctctttgaa agagattgtt ctgttcaaag aagacatcaa    780
aaggttgttg aaattgcacc tgccaaaact ttacctgttg aagttagaaa tgctatatta    840
aaggatgctg taacgttagc taaaaccgct aactatagaa atgctggtac tgcagaattt    900
ttagttgatt cccaaaacag acattatttt attgaaatta atccaagaat tcaagttgaa    960
catacaatta ctgaagaaat cacgggtgtt gatattgttg ccgctcaaat tcaaattgct   1020
gcaggtgcat cattggaaca attgggtcta ttacaaaaca aaattacaac tagaggtttt   1080
gcaattcaat gtagaattac aaccgaggat cctgctaaga attttgcccc agatacaggt   1140
aaaattgagg tttatagatc tgcaggtggt aacggtgtca gattagatgg tggtaatggg   1200
tttgccggtg ctgttatatc tcctcattat gactcgatgt tggttaaatg ttcaacatct   1260
ggttctaact atgaaattgc cagaagaaag atgattagag ctttagttga atttagaatc   1320
agaggtgtca agaccaatat tccttttctta ttggcattgc taactcatcc agttttcatt   1380
tcgggtgatt gttggacaac ttttattgat gatacccctt cgttattcga atggtttct   1440
tcaaagaata gagcccaaaa attattggca tatattggtg acttgtgtgt caatggttct   1500
tcaattaaag gtcaaattgg tttccctaaa ttgaacaagg aagcagaaat cccagatttg   1560
ttggatccaa atgatgaggt tattgatgtt tctaaacctt ctaccaatgg tctaagaccg   1620
tatctattaa agtatggacc agatgcgttt tccaaaaaag ttcgtgaatt cgatggttgt   1680
atgattatgg ataccacctg gagagatgca catcaatcat tattggctac aagagttaga   1740
actattgatt tactgagaat tgctccaacg actagtcatg ccttacaaaa tgcatttgca   1800
ttagaatgtt ggggtggcgc aacatttgat gttgcgatga ggttcctcta tgaagatcct   1860
tgggagagat taagcaaact tagaaaggca gttccaaata ttcctttcca atgttattg   1920
agaggtgcta atggtgttgc ttattcgtca ttacctgata atgcaattga tcattttgtt   1980
aagcaagcaa aggataatgg tgttgatatt ttcagagtct ttgatgcttt gaacgatttg   2040
gaacaattga aggttggtgt tgatgctgtc aagaaagccg gaggtgttgt tgaagctaca   2100
gtttgttact caggtgatat gttaattcca ggtaaaaagt ataacttgga ttattattta   2160
gagactgttg gaaagattgt ggaaatgggt acccatattt taggtattaa ggatatggct   2220
ggcacgttaa agccaaaggc tgctaagttg ttgattggct cgatcagatc aaaatacccct   2280
gacttggtta tccatgtcca tacccatgac tctgctggta ccggtatttc aacttatgtt   2340
gcatgcgcat tggcaggtgc cgacattgtc gattgtgcaa tcaattcgat gtctggttta   2400
acctctcaac cttcaatgag tgcttttatt gctgctttag atggtgatat cgaaactggt   2460
gttccagaac atttttgcaag acaattagat gcatactggg cagaaatgag attgttatac   2520
tcatgtttcg aagccgactt gaagggacca gacccagaag tttataaaca tgaaattcca   2580
```

-continued

```
ggtggacagt tgactaacct aatcttccaa gcccaacaag ttggtttggg tgaacaatgg     2640
gaagaaacta agaagaagta tgaagatgct aacatgttgt tgggtgatat tgtcaaggtt     2700
accccaacct ccaaggttgt tggtgattta gcccaattta tggtttctaa taaattagaa     2760
aaagaagatg ttgaaaaact tgctaatgaa ttagatttcc cagattcagt tcttgatttc     2820
tttgaaggat taatgggtac accatatggt ggattcccag agcctttgag aacaaatgtc     2880
atttccggca agagaagaaa attaaaggg agaccaggtt tagaattaga acctttcaac      2940
ctcgaggaaa tcagagaaaa tttggtttcc agatttggtc caggtattac tgaatgtgat     3000
gttgcatctt ataacatgta tccaaaggtt tacgagcaat atcgtaaggt ggttgaaaaa     3060
tatggtgatt tatctgtttt accaacaaaa gcattttgg ctcctccaac tattggtgaa      3120
gaagttcatg tggaaattga gcaaggtaag actttgatta ttaagttatt agccattct      3180 gacttgtcta aatctcatgg tacaagagaa gtatactttg aattgaatgg tgaaatgaga     3240
aaggttacaa ttgaagataa aacagctgca attgagactg ttacaagagc aaaggctgac     3300
ggacacaatc caaatgaagt tggtgcgcca atggctggtg tcgttgttga agttagagtg     3360
aagcatggaa cagaagttaa gaagggtgat ccattagccg tttgagtgc aatgaaaatg      3420 gaaatggtta tttctgctcc tgttagtggt agggtcggtg aagttttgt caacgaaggc      3480 gattccgttg atatgggtga tttgcttgtg aaaattgcca agatgaagc gccagcagct     3540 taa                                                                  3543
```

<210> SEQ ID NO 2
<211> LENGTH: 1180
<212> TYPE: PRT
<213> ORGANISM: Issatchenkia orientalis

<400> SEQUENCE: 2

```
Met Ser Thr Val Glu Asp His Ser Ser Leu His Lys Leu Arg Lys Glu
1               5                   10                  15

Ser Glu Ile Leu Ser Asn Ala Asn Lys Ile Leu Val Ala Asn Arg Gly
            20                  25                  30

Glu Ile Pro Ile Arg Ile Phe Arg Ser Ala His Glu Leu Ser Met His
        35                  40                  45

Thr Val Ala Ile Tyr Ser His Glu Asp Arg Leu Ser Met His Arg Leu
    50                  55                  60

Lys Ala Asp Glu Ala Tyr Ala Ile Gly Lys Thr Gly Gln Tyr Ser Pro
65                  70                  75                  80

Val Gln Ala Tyr Leu Gln Ile Asp Glu Ile Lys Ile Ala Lys Glu
                85                  90                  95

His Asp Val Ser Met Ile His Pro Gly Tyr Gly Phe Leu Ser Glu Asn
            100                 105                 110

Ser Glu Phe Ala Lys Lys Val Glu Glu Ser Gly Met Ile Trp Val Gly
        115                 120                 125

Pro Pro Ala Glu Val Ile Asp Ser Val Gly Asp Lys Val Ser Ala Arg
    130                 135                 140

Asn Leu Ala Ile Lys Cys Asp Val Pro Val Pro Gly Thr Asp Gly
145                 150                 155                 160

Pro Ile Glu Asp Ile Glu Gln Ala Lys Gln Phe Val Glu Gln Tyr Gly
                165                 170                 175

Tyr Pro Val Ile Ile Lys Ala Ala Phe Gly Gly Gly Arg Gly Met
            180                 185                 190
```

-continued

Arg Val Val Arg Glu Gly Asp Asp Ile Val Asp Ala Phe Gln Arg Ala
        195                 200                 205
Ser Ser Glu Ala Lys Ser Ala Phe Gly Asn Gly Thr Cys Phe Ile Glu
    210                 215                 220
Arg Phe Leu Asp Lys Pro Lys His Ile Glu Val Gln Leu Leu Ala Asp
225                 230                 235                 240
Asn Tyr Gly Asn Thr Ile His Leu Phe Glu Arg Asp Cys Ser Val Gln
                245                 250                 255
Arg Arg His Gln Lys Val Val Glu Ile Ala Pro Ala Lys Thr Leu Pro
            260                 265                 270
Val Glu Val Arg Asn Ala Ile Leu Lys Asp Ala Val Thr Leu Ala Lys
        275                 280                 285
Thr Ala Asn Tyr Arg Asn Ala Gly Thr Ala Glu Phe Leu Val Asp Ser
    290                 295                 300
Gln Asn Arg His Tyr Phe Ile Glu Ile Asn Pro Arg Ile Gln Val Glu
305                 310                 315                 320
His Thr Ile Thr Glu Glu Ile Thr Gly Val Asp Ile Val Ala Ala Gln
                325                 330                 335
Ile Gln Ile Ala Ala Gly Ala Ser Leu Glu Gln Leu Gly Leu Leu Gln
            340                 345                 350
Asn Lys Ile Thr Thr Arg Gly Phe Ala Ile Gln Cys Arg Ile Thr Thr
        355                 360                 365
Glu Asp Pro Ala Lys Asn Phe Ala Pro Asp Thr Gly Lys Ile Glu Val
    370                 375                 380
Tyr Arg Ser Ala Gly Gly Asn Gly Val Arg Leu Asp Gly Gly Asn Gly
385                 390                 395                 400
Phe Ala Gly Ala Val Ile Ser Pro His Tyr Asp Ser Met Leu Val Lys
                405                 410                 415
Cys Ser Thr Ser Gly Ser Asn Tyr Glu Ile Ala Arg Arg Lys Met Ile
            420                 425                 430
Arg Ala Leu Val Glu Phe Arg Ile Arg Gly Val Lys Thr Asn Ile Pro
        435                 440                 445
Phe Leu Leu Ala Leu Leu Thr His Pro Val Phe Ile Ser Gly Asp Cys
    450                 455                 460
Trp Thr Thr Phe Ile Asp Asp Thr Pro Ser Leu Phe Glu Met Val Ser
465                 470                 475                 480
Ser Lys Asn Arg Ala Gln Lys Leu Leu Ala Tyr Ile Gly Asp Leu Cys
                485                 490                 495
Val Asn Gly Ser Ser Ile Lys Gly Gln Ile Gly Phe Pro Lys Leu Asn
            500                 505                 510
Lys Glu Ala Glu Ile Pro Asp Leu Leu Asp Pro Asn Asp Glu Val Ile
        515                 520                 525
Asp Val Ser Lys Pro Ser Thr Asn Gly Leu Arg Pro Tyr Leu Leu Lys
    530                 535                 540
Tyr Gly Pro Asp Ala Phe Ser Lys Lys Val Arg Glu Phe Asp Gly Cys
545                 550                 555                 560
Met Ile Met Asp Thr Thr Trp Arg Asp Ala His Gln Ser Leu Leu Ala
                565                 570                 575
Thr Arg Val Arg Thr Ile Asp Leu Leu Arg Ile Ala Pro Thr Thr Ser
            580                 585                 590
His Ala Leu Gln Asn Ala Phe Ala Leu Glu Cys Trp Gly Gly Ala Thr
        595                 600                 605
Phe Asp Val Ala Met Arg Phe Leu Tyr Glu Asp Pro Trp Glu Arg Leu

```
                610             615             620
Arg Gln Leu Arg Lys Ala Val Pro Asn Ile Pro Phe Gln Met Leu Leu
625             630             635             640

Arg Gly Ala Asn Gly Val Ala Tyr Ser Ser Leu Pro Asp Asn Ala Ile
                645             650             655

Asp His Phe Val Lys Gln Ala Lys Asp Asn Gly Val Asp Ile Phe Arg
            660             665             670

Val Phe Asp Ala Leu Asn Asp Leu Glu Gln Leu Lys Val Gly Val Asp
            675             680             685

Ala Val Lys Lys Ala Gly Gly Val Val Glu Ala Thr Val Cys Tyr Ser
690             695             700

Gly Asp Met Leu Ile Pro Gly Lys Lys Tyr Asn Leu Asp Tyr Tyr Leu
705             710             715             720

Glu Thr Val Gly Lys Ile Val Glu Met Gly Thr His Ile Leu Gly Ile
            725             730             735

Lys Asp Met Ala Gly Thr Leu Lys Pro Lys Ala Ala Lys Leu Leu Ile
            740             745             750

Gly Ser Ile Arg Ser Lys Tyr Pro Asp Leu Val Ile His Val His Thr
        755             760             765

His Asp Ser Ala Gly Thr Gly Ile Ser Thr Tyr Val Ala Cys Ala Leu
        770             775             780

Ala Gly Ala Asp Ile Val Asp Cys Ala Ile Asn Ser Met Ser Gly Leu
785             790             795             800

Thr Ser Gln Pro Ser Met Ser Ala Phe Ile Ala Ala Leu Asp Gly Asp
            805             810             815

Ile Glu Thr Gly Val Pro Glu His Phe Ala Arg Gln Leu Asp Ala Tyr
            820             825             830

Trp Ala Glu Met Arg Leu Leu Tyr Ser Cys Phe Glu Ala Asp Leu Lys
            835             840             845

Gly Pro Asp Pro Glu Val Tyr Lys His Glu Ile Pro Gly Gly Gln Leu
        850             855             860

Thr Asn Leu Ile Phe Gln Ala Gln Val Gly Leu Gly Glu Gln Trp
865             870             875             880

Glu Glu Thr Lys Lys Lys Tyr Glu Asp Ala Asn Met Leu Leu Gly Asp
                885             890             895

Ile Val Lys Val Thr Pro Thr Ser Lys Val Val Gly Asp Leu Ala Gln
            900             905             910

Phe Met Val Ser Asn Lys Leu Glu Lys Glu Asp Val Glu Lys Leu Ala
            915             920             925

Asn Glu Leu Asp Phe Pro Asp Ser Val Leu Asp Phe Phe Glu Gly Leu
        930             935             940

Met Gly Thr Pro Tyr Gly Gly Phe Pro Glu Pro Leu Arg Thr Asn Val
945             950             955             960

Ile Ser Gly Lys Arg Arg Lys Leu Lys Gly Arg Pro Gly Leu Glu Leu
            965             970             975

Glu Pro Phe Asn Leu Glu Glu Ile Arg Glu Asn Leu Val Ser Arg Phe
            980             985             990

Gly Pro Gly Ile Thr Glu Cys Asp Val Ala Ser Tyr Asn Met Tyr Pro
        995             1000            1005

Lys Val Tyr Glu Gln Tyr Arg Lys Val Val Glu Lys Tyr Gly Asp
        1010            1015            1020

Leu Ser Val Leu Pro Thr Lys Ala Phe Leu Ala Pro Pro Thr Ile
        1025            1030            1035
```

Gly Glu Glu Val His Val Glu Ile Glu Gln Gly Lys Thr Leu Ile
    1040                1045                1050

Ile Lys Leu Leu Ala Ile Ser Asp Leu Ser Lys Ser His Gly Thr
    1055                1060                1065

Arg Glu Val Tyr Phe Glu Leu Asn Gly Glu Met Arg Lys Val Thr
    1070                1075                1080

Ile Glu Asp Lys Thr Ala Ala Ile Glu Thr Val Thr Arg Ala Lys
    1085                1090                1095

Ala Asp Gly His Asn Pro Asn Glu Val Gly Ala Pro Met Ala Gly
    1100                1105                1110

Val Val Val Glu Val Arg Val Lys His Gly Thr Glu Val Lys Lys
    1115                1120                1125

Gly Asp Pro Leu Ala Val Leu Ser Ala Met Lys Met Glu Met Val
    1130                1135                1140

Ile Ser Ala Pro Val Ser Gly Arg Val Gly Glu Val Phe Val Asn
    1145                1150                1155

Glu Gly Asp Ser Val Asp Met Gly Asp Leu Leu Val Lys Ile Ala
    1160                1165                1170

Lys Asp Glu Ala Pro Ala Ala
    1175                1180

<210> SEQ ID NO 3
<211> LENGTH: 1154
<212> TYPE: PRT
<213> ORGANISM: Rhodobacter sphaeroides

<400> SEQUENCE: 3

Met Ala Glu Phe Arg Lys Ile Leu Ile Ala Asn Arg Gly Glu Ile Ala
1               5                   10                  15

Ile Arg Val Met Arg Ala Ala Asn Glu Met Gly Lys Lys Thr Val Ala
                20                  25                  30

Val Tyr Ala Glu Glu Asp Lys Leu Ser Leu His Arg Phe Lys Ala Asp
            35                  40                  45

Glu Ala Tyr Arg Ile Gly Glu Gly Leu Ser Pro Val Gly Ala Tyr Leu
        50                  55                  60

Ser Ile Pro Glu Ile Ile Arg Val Ala Gln Met Ser Gly Ala Asp Ala
65                  70                  75                  80

Ile His Pro Gly Tyr Gly Leu Leu Ser Glu Asn Pro Asp Phe Val Glu
                85                  90                  95

Ala Cys Asp Ala Ala Gly Ile Ala Phe Ile Gly Pro Lys Ala Glu Thr
            100                 105                 110

Met Arg Ala Leu Gly Asp Lys Ala Ser Ala Arg Arg Val Ala Met Ala
        115                 120                 125

Ala Gly Val Pro Val Ile Pro Ala Thr Glu Val Leu Gly Asp Asp Met
    130                 135                 140

Glu Glu Ile Lys Arg Gln Ala Ala Glu Ile Gly Tyr Pro Leu Met Leu
145                 150                 155                 160

Lys Ala Ser Trp Gly Gly Gly Gly Arg Gly Met Arg Pro Ile Thr Ser
                165                 170                 175

Glu Ala Glu Leu Ala Asp Lys Val Arg Glu Gly Arg Glu Ala Glu
            180                 185                 190

Ala Ala Phe Gly Asn Gly Glu Gly Tyr Leu Glu Lys Met Ile Gln Arg
        195                 200                 205

Ala Arg His Val Glu Val Gln Ile Leu Gly Asp Lys Tyr Gly Ala Ile

-continued

```
            210                 215                 220
Tyr His Leu Tyr Glu Arg Asp Cys Thr Val Gln Arg Arg Asn Gln Lys
225                 230                 235                 240

Val Val Glu Arg Ala Pro Ala Pro Tyr Leu Thr Glu Glu Gln Arg Thr
                245                 250                 255

Glu Ile Cys Glu Leu Gly Arg Arg Ile Cys Ala His Val Asn Tyr Glu
            260                 265                 270

Cys Ala Gly Thr Val Glu Phe Leu Met Asp Met Asp Ser Glu Lys Phe
            275                 280                 285

Tyr Phe Ile Glu Val Asn Pro Arg Val Gln Val Glu His Thr Val Thr
290                 295                 300

Glu Glu Val Thr Gly Ile Asp Ile Val Gln Ser Gln Ile Arg Ile Ala
305                 310                 315                 320

Glu Gly Ala Thr Leu Ala Glu Ala Thr Gly Cys Pro Ser Gln Asp Asp
                325                 330                 335

Ile Lys Leu Ser Gly His Ala Leu Gln Cys Arg Val Thr Thr Glu Asp
            340                 345                 350

Pro Gln Asn Asn Phe Ile Pro Asp Tyr Gly Arg Leu Thr Ala Tyr Arg
            355                 360                 365

Ser Ala Thr Gly Met Gly Ile Arg Leu Asp Gly Gly Thr Ala Tyr Ala
            370                 375                 380

Gly Gly Val Ile Thr Arg Tyr Tyr Asp Ser Leu Leu Val Lys Val Thr
385                 390                 395                 400

Ala Trp Ala Pro Thr Pro Glu Lys Ala Ile Ala Arg Met Asp Arg Ala
                405                 410                 415

Leu Arg Glu Phe Arg Ile Arg Gly Val Ala Thr Asn Ile Ala Phe Val
                420                 425                 430

Glu Asn Leu Leu Lys His Pro Ser Phe Leu Asp Tyr Ser Tyr Thr Thr
            435                 440                 445

Lys Phe Ile Asp Thr Thr Pro Asp Leu Phe Asn Phe Lys Pro Arg Arg
450                 455                 460

Asp Arg Ala Thr Lys Ile Leu Thr Tyr Ile Ala Asp Ile Thr Val Asn
465                 470                 475                 480

Gly His Pro Glu Thr Ala Gly Arg Val Arg Pro Ser Ala Glu Leu Lys
                485                 490                 495

Asp Pro Lys Ala Pro Glu Pro Lys Gly Ala Pro Gln Pro Gly Thr Arg
            500                 505                 510

Thr Leu Leu Glu Glu Lys Gly Pro Gln Ala Val Ala Asp Trp Met Ala
            515                 520                 525

Ala Gln Thr Arg Val Leu Met Thr Asp Thr Thr Met Arg Asp Gly His
            530                 535                 540

Gln Ser Leu Leu Ala Thr Arg Met Arg Ser Ile Asp Met Ile Lys Val
545                 550                 555                 560

Thr Pro Ala Tyr Ala Ala Asn Leu Gly Gly Leu Phe Ser Val Glu Cys
                565                 570                 575

Trp Gly Gly Ala Thr Phe Asp Val Ala Tyr Arg Phe Leu Gln Glu Cys
                580                 585                 590

Pro Trp Gln Arg Leu Arg Asp Ile Arg Ala Arg Leu Pro Asn Val Met
            595                 600                 605

Thr Gln Met Leu Leu Arg Ala Ser Asn Gly Val Gly Tyr Thr Asn Tyr
            610                 615                 620

Pro Asp Asn Val Val Gln Glu Phe Val Arg Gln Ala Ala Glu Thr Gly
625                 630                 635                 640
```

```
Val Asp Val Phe Arg Val Phe Asp Ser Leu Asn Trp Val Glu Asn Met
            645                 650                 655

Arg Val Ala Met Asp Ala Val Ile Glu Ala Asn Lys Val Cys Glu Gly
            660                 665                 670

Thr Ile Cys Tyr Thr Gly Asp Leu Leu Asp Pro Asp Arg Ser Lys Tyr
        675                 680                 685

Asp Leu Asn Tyr Tyr Val Gly Met Gly Arg Ala Leu Arg Asp Ala Gly
        690                 695                 700

Ala His Val Leu Gly Leu Lys Asp Met Ala Gly Leu Leu Lys Pro Ala
705                 710                 715                 720

Ala Ala Arg Val Leu Val Lys Ala Leu Lys Glu Glu Val Gly Leu Pro
                725                 730                 735

Ile His Phe His Thr His Asp Thr Ser Gly Ile Ala Gly Ala Thr Val
            740                 745                 750

Leu Ala Ala Cys Asp Ala Gly Val Asp Ala Val Asp Ala Ala Met Asp
            755                 760                 765

Ala Phe Ser Gly Gly Thr Ser Gln Pro Cys Leu Gly Ser Ile Val Glu
770                 775                 780

Ala Leu Lys His Thr Asp Arg Asp Thr Gly Leu Asp Ile Ala Ala Ile
785                 790                 795                 800

Arg Glu Ile Ser Asp Tyr Trp Gly His Val Arg Gln Gln Tyr Ser Ala
                805                 810                 815

Phe Glu Ser Gly Leu Pro Ser Pro Ala Ser Glu Val Tyr Leu His Glu
            820                 825                 830

Met Pro Gly Gly Gln Phe Thr Asn Leu Lys Ala Gln Ala Arg Ser Met
            835                 840                 845

Gly Leu Glu Glu Arg Trp Ser Glu Val Ala Gln Ala Tyr Ala Asp Ala
850                 855                 860

Asn Arg Met Phe Gly Asp Ile Val Lys Val Thr Pro Ser Ser Lys Val
865                 870                 875                 880

Val Gly Asp Met Ala Leu Met Met Val Ala Gln Gly Leu Thr Arg Glu
                885                 890                 895

Glu Val Glu Asp Pro Glu Val Glu Val Ser Phe Pro Asp Ser Val Val
            900                 905                 910

Asp Met Leu Lys Gly Asn Leu Gly Gln Pro His Gly Gly Trp Pro Glu
            915                 920                 925

Pro Ile Leu Lys Lys Val Leu Lys Gly Glu Ala Pro Ser Thr Glu Arg
930                 935                 940

Pro Gly Ala His Leu Pro Val Asp Ile Ala Ala Arg Glu Lys
945                 950                 955                 960

Leu Leu Ser Glu Ile Lys Gln Gly Asp Asp Pro Leu Asp Thr Ala
                965                 970                 975

Val Asp Ala Glu Asp Leu Asn Gly Tyr Leu Met Tyr Pro Lys Val Phe
            980                 985                 990

Thr Asp Tyr Arg Ala Arg His Arg Ile Tyr Gly Pro Val Arg Thr Leu
            995                 1000                1005

Pro Thr Arg Thr Phe Phe Tyr Gly Met Glu Pro Gly Glu Glu Ile
    1010                1015                1020

Ser Ala Glu Ile Asp Pro Gly Lys Thr Leu Glu Ile Arg Leu Ser
    1025                1030                1035

Ala Val Gly Glu Thr Ser Asp Asp Gly Asp Ala Lys Val Phe Phe
    1040                1045                1050
```

```
Glu Leu Asn Gly Gln Pro Arg Val Ile Arg Val Ala Asn Arg Ala
    1055                1060                1065

Val Lys Ala Lys Thr Ala Thr Arg Pro Lys Ala Gln Asp Gly Asn
    1070                1075                1080

Pro Ala His Val Gly Ala Pro Met Pro Gly Ser Val Ala Ser Val
    1085                1090                1095

Ala Val Ser Ala Gly Gln Lys Val Lys Pro Gly Asp Leu Leu Val
    1100                1105                1110

Thr Ile Glu Ala Met Lys Met Glu Thr Gly Leu His Ala Asp Arg
    1115                1120                1125

Ala Ala Thr Val Lys Ala Val His Val Gly Pro Gly Ala Gln Ile
    1130                1135                1140

Glu Ala Lys Asp Leu Leu Val Glu Leu Glu Asp
    1145                1150

<210> SEQ ID NO 4
<211> LENGTH: 1154
<212> TYPE: PRT
<213> ORGANISM: Rhizobium etli

<400> SEQUENCE: 4

Met Pro Ile Ser Lys Ile Leu Val Ala Asn Arg Ser Glu Ile Ala Ile
1               5                   10                  15

Arg Val Phe Arg Ala Ala Asn Glu Leu Gly Ile Lys Thr Val Ala Ile
                20                  25                  30

Trp Ala Glu Glu Asp Lys Leu Ala Leu His Arg Phe Lys Ala Asp Glu
            35                  40                  45

Ser Tyr Gln Val Gly Arg Gly Pro His Leu Ala Arg Asp Leu Gly Pro
        50                  55                  60

Ile Glu Ser Tyr Leu Ser Ile Asp Glu Val Ile Arg Val Ala Lys Leu
65                  70                  75                  80

Ser Gly Ala Asp Ala Ile His Pro Gly Tyr Gly Leu Leu Ser Glu Ser
                85                  90                  95

Pro Glu Phe Val Asp Ala Cys Asn Lys Ala Gly Ile Ile Phe Ile Gly
            100                 105                 110

Pro Lys Ala Asp Thr Met Arg Gln Leu Gly Asn Lys Val Ala Ala Arg
        115                 120                 125

Asn Leu Ala Ile Ser Val Gly Val Pro Val Val Pro Ala Thr Glu Pro
    130                 135                 140

Leu Pro Asp Asp Met Ala Glu Val Ala Lys Met Ala Ala Ala Ile Gly
145                 150                 155                 160

Tyr Pro Val Met Leu Lys Ala Ser Trp Gly Gly Gly Gly Arg Gly Met
                165                 170                 175

Arg Val Ile Arg Ser Glu Ala Asp Leu Ala Lys Glu Val Thr Glu Ala
            180                 185                 190

Lys Arg Glu Ala Met Ala Ala Phe Gly Lys Asp Glu Val Tyr Leu Glu
        195                 200                 205

Lys Leu Val Glu Arg Ala Arg His Val Glu Ser Gln Ile Leu Gly Asp
    210                 215                 220

Thr His Gly Asn Val Val His Leu Phe Glu Arg Asp Cys Ser Val Gln
225                 230                 235                 240

Arg Arg Asn Gln Lys Val Val Glu Arg Ala Pro Ala Pro Tyr Leu Ser
                245                 250                 255

Glu Ala Gln Arg Gln Glu Leu Ala Ala Tyr Ser Leu Lys Ile Ala Gly
            260                 265                 270
```

```
Ala Thr Asn Tyr Ile Gly Ala Gly Thr Val Glu Tyr Leu Met Asp Ala
            275                 280                 285

Asp Thr Gly Lys Phe Tyr Phe Ile Glu Val Asn Pro Arg Ile Gln Val
    290                 295                 300

Glu His Thr Val Thr Glu Val Val Thr Gly Ile Asp Ile Val Lys Ala
305                 310                 315                 320

Gln Ile His Ile Leu Asp Gly Ala Ala Ile Gly Thr Pro Gln Ser Gly
                325                 330                 335

Val Pro Asn Gln Glu Asp Ile Arg Leu Asn Gly His Ala Leu Gln Cys
            340                 345                 350

Arg Val Thr Thr Glu Asp Pro Glu His Asn Phe Ile Pro Asp Tyr Gly
            355                 360                 365

Arg Ile Thr Ala Tyr Arg Ser Ala Ser Gly Phe Gly Ile Arg Leu Asp
            370                 375                 380

Gly Gly Thr Ser Tyr Ser Gly Ala Ile Ile Thr Arg Tyr Tyr Asp Pro
385                 390                 395                 400

Leu Leu Val Lys Val Thr Ala Trp Ala Pro Asn Pro Leu Glu Ala Ile
                405                 410                 415

Ser Arg Met Asp Arg Ala Leu Arg Glu Phe Arg Ile Arg Gly Val Ala
            420                 425                 430

Thr Asn Leu Thr Phe Leu Glu Ala Ile Ile Gly His Pro Lys Phe Arg
            435                 440                 445

Asp Asn Ser Tyr Thr Thr Arg Phe Ile Asp Thr Thr Pro Glu Leu Phe
            450                 455                 460

Gln Gln Val Lys Arg Gln Asp Arg Ala Thr Lys Leu Leu Thr Tyr Leu
465                 470                 475                 480

Ala Asp Val Thr Val Asn Gly His Pro Glu Ala Lys Asp Arg Pro Lys
                485                 490                 495

Pro Leu Glu Asn Ala Ala Arg Pro Val Val Pro Tyr Ala Asn Gly Asn
            500                 505                 510

Gly Val Lys Asp Gly Thr Lys Gln Leu Leu Asp Thr Leu Gly Pro Lys
            515                 520                 525

Lys Phe Gly Glu Trp Met Arg Asn Glu Lys Arg Val Leu Leu Thr Asp
            530                 535                 540

Thr Thr Met Arg Asp Gly His Gln Ser Leu Leu Ala Thr Arg Met Arg
545                 550                 555                 560

Thr Tyr Asp Ile Ala Arg Ile Ala Gly Thr Tyr Ser His Ala Leu Pro
                565                 570                 575

Asn Leu Leu Ser Leu Glu Cys Trp Gly Gly Ala Thr Phe Asp Val Ser
            580                 585                 590

Met Arg Phe Leu Thr Glu Asp Pro Trp Glu Arg Leu Ala Leu Ile Arg
            595                 600                 605

Glu Gly Ala Pro Asn Leu Leu Leu Gln Met Leu Leu Arg Gly Ala Asn
            610                 615                 620

Gly Val Gly Tyr Thr Asn Tyr Pro Asp Asn Val Val Lys Tyr Phe Val
625                 630                 635                 640

Arg Gln Ala Ala Lys Gly Gly Ile Asp Leu Phe Arg Val Phe Asp Cys
                645                 650                 655

Leu Asn Trp Val Glu Asn Met Arg Val Ser Met Asp Ala Ile Ala Glu
            660                 665                 670

Glu Asn Lys Leu Cys Glu Ala Ala Ile Cys Tyr Thr Gly Asp Ile Leu
            675                 680                 685
```

```
Asn Ser Ala Arg Pro Lys Tyr Asp Leu Lys Tyr Tyr Thr Asn Leu Ala
    690             695                 700

Val Glu Leu Glu Lys Ala Gly His Ile Ile Ala Val Lys Asp Met
705             710                 715                 720

Ala Gly Leu Leu Lys Pro Ala Ala Lys Val Leu Phe Lys Ala Leu
                725             730                 735

Arg Glu Ala Thr Gly Leu Pro Ile His Phe His Thr His Asp Thr Ser
            740             745                 750

Gly Ile Ala Ala Ala Thr Val Leu Ala Ala Val Glu Ala Gly Val Asp
                755                 760             765

Ala Val Asp Ala Ala Met Asp Ala Leu Ser Gly Asn Thr Ser Gln Pro
770             775                 780

Cys Leu Gly Ser Ile Val Glu Ala Leu Ser Gly Ser Glu Arg Asp Pro
785             790                 795                 800

Gly Leu Asp Pro Ala Trp Ile Arg Arg Ile Ser Phe Tyr Trp Glu Ala
                805                 810                 815

Val Arg Asn Gln Tyr Ala Ala Phe Glu Ser Asp Leu Lys Gly Pro Ala
                820              825                830

Ser Glu Val Tyr Leu His Glu Met Pro Gly Gly Gln Phe Thr Asn Leu
            835                 840                 845

Lys Glu Gln Ala Arg Ser Leu Gly Leu Glu Thr Arg Trp His Gln Val
850                 855                 860

Ala Gln Ala Tyr Ala Asp Ala Asn Gln Met Phe Gly Asp Ile Val Lys
865                 870                 875                 880

Val Thr Pro Ser Ser Lys Val Val Gly Asp Met Ala Leu Met Met Val
                885                 890                 895

Ser Gln Asp Leu Thr Val Ala Asp Val Val Ser Pro Asp Arg Glu Val
            900                 905                 910

Ser Phe Pro Glu Ser Val Val Ser Met Leu Lys Gly Asp Leu Gly Gln
            915                 920                 925

Pro Pro Ser Gly Trp Pro Glu Ala Leu Gln Lys Ala Leu Lys Gly
            930                 935                 940

Glu Lys Pro Tyr Thr Val Arg Pro Gly Ser Leu Leu Lys Glu Ala Asp
945                 950                 955                 960

Leu Asp Ala Glu Arg Lys Val Ile Glu Lys Lys Leu Glu Arg Glu Val
                965                 970                 975

Ser Asp Phe Glu Phe Ala Ser Tyr Leu Met Tyr Pro Lys Val Phe Thr
            980                 985                 990

Asp Phe Ala Leu Ala Ser Asp Thr Tyr Gly Pro Val Ser Val Leu Pro
            995                 1000                1005

Thr Pro Ala Tyr Phe Tyr Gly Leu Ala Asp Gly Glu Glu Leu Phe
    1010                1015                1020

Ala Asp Ile Glu Lys Gly Lys Thr Leu Val Ile Val Asn Gln Ala
    1025                1030                1035

Val Ser Ala Thr Asp Ser Gln Gly Met Val Thr Val Phe Phe Glu
    1040                1045                1050

Leu Asn Gly Gln Pro Arg Ile Lys Val Pro Asp Arg Ala His
    1055                1060                1065

Gly Ala Thr Gly Ala Ala Val Arg Arg Lys Ala Glu Pro Gly Asn
    1070                1075                1080

Ala Ala His Val Gly Ala Pro Met Pro Gly Val Ile Ser Arg Val
    1085                1090                1095

Phe Val Ser Ser Gly Gln Ala Val Asn Ala Gly Asp Val Leu Val
```

```
                    1100                1105                1110
Ser Ile Glu Ala Met Lys Met Glu Thr Ala Ile His Ala Glu Lys
        1115                1120                1125

Asp Gly Thr Ile Ala Glu Val Leu Val Lys Ala Gly Asp Gln Ile
        1130                1135                1140

Asp Ala Lys Asp Leu Leu Ala Val Tyr Gly Gly
        1145                1150

<210> SEQ ID NO 5
<211> LENGTH: 602
<212> TYPE: PRT
<213> ORGANISM: Pseudomonas fluorescens

<400> SEQUENCE: 5

Met Thr Lys Lys Ile Phe Val Thr Asp Thr Ile Leu Arg Asp Ala His
1               5                   10                  15

Gln Ser Leu Leu Ala Thr Arg Met Arg Thr Glu Asp Met Leu Pro Ile
            20                  25                  30

Cys Asp Lys Leu Asp Lys Val Gly Tyr Trp Ser Leu Glu Cys Trp Gly
        35                  40                  45

Gly Ala Thr Phe Asp Ala Cys Val Arg Phe Leu Lys Glu Asp Pro Trp
    50                  55                  60

Glu Arg Leu Arg Gln Leu Arg Ala Ala Leu Pro Asn Thr Arg Leu Gln
65                  70                  75                  80

Met Leu Leu Arg Gly Gln Asn Leu Leu Gly Tyr Arg His Tyr Ser Asp
                85                  90                  95

Asp Val Val Lys Ala Phe Val Ala Lys Ala Val Asn Gly Ile Asp
                100                 105                 110

Val Phe Arg Ile Phe Asp Ala Met Asn Asp Val Arg Asn Leu Arg Val
            115                 120                 125

Ala Ile Glu Ala Val Lys Ala Ala Gly Lys His Ala Gln Gly Thr Ile
        130                 135                 140

Ala Tyr Thr Thr Ser Pro Val His Thr Ile Asp Ala Phe Val Ala Gln
145                 150                 155                 160

Ala Lys Gln Met Glu Ala Met Gly Cys Asp Ser Val Ala Ile Lys Asp
                165                 170                 175

Met Ala Gly Leu Leu Thr Pro Tyr Ala Thr Gly Glu Leu Val Arg Ala
            180                 185                 190

Leu Lys Ala Glu Gln Ser Leu Pro Val Phe Ile His Ser His Asp Thr
        195                 200                 205

Ala Gly Leu Ala Ala Met Cys Gln Leu Lys Ala Ile Glu Asn Gly Ala
    210                 215                 220

Asp His Ile Asp Thr Ala Ile Ser Ser Phe Ala Ser Gly Thr Ser His
225                 230                 235                 240

Pro Gly Thr Glu Ser Met Val Ala Ala Leu Lys Gly Thr Glu Phe Asp
                245                 250                 255

Thr Gly Leu Asn Leu Glu Leu Leu Gln Glu Ile Gly Leu Tyr Phe Tyr
            260                 265                 270

Ala Val Arg Lys Lys Tyr His Gln Phe Glu Ser Glu Phe Thr Ala Val
        275                 280                 285

Asp Thr Arg Val Gln Val Asn Gln Val Pro Gly Gly Met Ile Ser Asn
    290                 295                 300

Leu Ala Asn Gln Leu Lys Glu Gln Gly Ala Leu Asn Arg Met Gly Glu
305                 310                 315                 320
```

```
Val Leu Ala Glu Ile Pro Arg Val Arg Glu Asp Leu Gly Phe Pro Pro
                325                 330                 335

Leu Val Thr Pro Thr Ser Gln Ile Val Gly Thr Gln Ala Phe Phe Asn
            340                 345                 350

Val Leu Ala Gly Glu Arg Tyr Lys Thr Ile Thr Asn Glu Val Lys Leu
        355                 360                 365

Tyr Leu Gln Gly Gly Tyr Gly Lys Ala Pro Gly Thr Val Asn Glu Lys
    370                 375                 380

Leu Arg Arg Gln Ala Ile Gly Ser Glu Glu Val Ile Asp Val Arg Pro
385                 390                 395                 400

Ala Asp Leu Leu Lys Pro Glu Met Thr Lys Leu Arg Ala Asp Ile Gly
                405                 410                 415

Ala Leu Ala Lys Ser Glu Glu Asp Val Leu Thr Phe Ala Met Phe Pro
            420                 425                 430

Asp Ile Gly Arg Lys Phe Leu Glu Glu Arg Ala Ala Gly Thr Leu Thr
        435                 440                 445

Pro Glu Val Leu Leu Pro Ile Pro Glu Ala Gly Lys Val Ala Ser Ala
    450                 455                 460

Gly Gly Glu Gly Val Pro Thr Glu Phe Val Ile Asp Val His Gly Glu
465                 470                 475                 480

Thr Tyr Arg Val Asp Ile Thr Gly Val Gly Val Lys Ala Glu Gly Lys
                485                 490                 495

Arg His Phe Tyr Leu Ser Ile Asp Gly Met Pro Glu Val Val Phe
            500                 505                 510

Glu Pro Leu Asn Glu Phe Val Gly Gly Ser Ser Lys Arg Lys Gln
        515                 520                 525

Ala Ser Ala Pro Gly His Val Ser Thr Thr Met Pro Gly Asn Ile Val
    530                 535                 540

Asp Val Leu Val Lys Glu Gly Asp Thr Val Lys Ala Gly Gln Ala Val
545                 550                 555                 560

Leu Ile Thr Glu Ala Met Lys Met Glu Thr Glu Val Gln Ala Ala Ile
                565                 570                 575

Ala Gly Lys Val Thr Ala Ile His Val Ala Lys Gly Asp Arg Val Asn
            580                 585                 590

Pro Gly Glu Ile Leu Ile Glu Ile Glu Gly
        595                 600

<210> SEQ ID NO 6
<211> LENGTH: 481
<212> TYPE: PRT
<213> ORGANISM: Pseudomonas fluorescens

<400> SEQUENCE: 6

Met Val Pro Pro Ala Gln Gly Asn Leu Gln Val Ile Thr Lys Ile Leu
1               5                   10                  15

Ile Ala Asn Arg Gly Glu Ile Ala Val Arg Ile Val Arg Ala Cys Ala
            20                  25                  30

Glu Met Gly Ile Arg Ser Val Ala Ile Tyr Ser Asp Ala Asp Arg His
        35                  40                  45

Ala Leu His Val Lys Arg Ala Asp Glu Ala His Ser Ile Gly Ala Glu
    50                  55                  60

Pro Leu Ala Gly Tyr Leu Asn Pro Arg Lys Leu Val Asn Leu Ala Val
65                  70                  75                  80

Glu Thr Gly Cys Asp Ala Leu His Pro Gly Tyr Gly Phe Leu Ser Glu
                85                  90                  95
```

```
Asn Ala Glu Leu Ala Asp Ile Cys Ala Glu Arg Gly Ile Lys Phe Ile
            100                 105                 110

Gly Pro Ser Ala Glu Val Ile Arg Arg Met Gly Asp Lys Thr Glu Ala
        115                 120                 125

Arg Arg Ser Met Ile Lys Ala Gly Val Pro Val Thr Pro Gly Thr Glu
130                 135                 140

Gly Asn Val Ser Gly Ile Glu Glu Ala Leu Ser Glu Gly Asp Arg Ile
145                 150                 155                 160

Gly Tyr Pro Val Met Leu Lys Ala Thr Ser Gly Gly Gly Arg Gly
                165                 170                 175

Ile Arg Arg Cys Asn Ser Arg Glu Glu Leu Glu Gln Asn Phe Pro Arg
            180                 185                 190

Val Ile Ser Glu Ala Thr Lys Ala Phe Gly Ser Ala Glu Val Phe Leu
        195                 200                 205

Glu Lys Cys Ile Val Asn Pro Lys His Ile Glu Ala Gln Ile Leu Gly
    210                 215                 220

Asp Ser Phe Gly Asn Val Val His Leu Phe Glu Arg Asp Cys Ser Ile
225                 230                 235                 240

Gln Arg Arg Asn Gln Lys Leu Ile Glu Ile Ala Pro Ser Pro Gln Leu
                245                 250                 255

Thr Pro Glu Gln Arg Ala Tyr Ile Gly Asp Leu Ser Val Arg Ala Ala
            260                 265                 270

Lys Ala Val Gly Tyr Glu Asn Ala Gly Thr Val Glu Phe Leu Leu Ala
        275                 280                 285

Glu Gly Glu Val Tyr Phe Met Glu Met Asn Thr Arg Val Gln Val Glu
290                 295                 300

His Thr Ile Thr Glu Glu Ile Thr Gly Ile Asp Ile Val Arg Glu Gln
305                 310                 315                 320

Ile Arg Ile Ala Ser Gly Leu Pro Leu Ser Val Lys Gln Glu Asp Ile
                325                 330                 335

Gln His Arg Gly Phe Ala Leu Gln Phe Arg Ile Asn Ala Glu Asp Pro
            340                 345                 350

Lys Asn Asn Phe Leu Pro Ser Phe Gly Lys Ile Thr Arg Tyr Tyr Ala
        355                 360                 365

Pro Gly Gly Pro Gly Val Arg Thr Asp Thr Ala Ile Tyr Thr Gly Tyr
370                 375                 380

Thr Ile Pro Pro Phe Tyr Asp Ser Met Cys Leu Lys Leu Val Val Trp
385                 390                 395                 400

Ala Leu Thr Trp Glu Glu Ala Met Asp Arg Gly Leu Arg Ala Leu Asp
                405                 410                 415

Asp Met Arg Leu Gln Gly Val Lys Thr Thr Ala Ala Tyr Tyr Gln Glu
            420                 425                 430

Ile Leu Arg Asn Pro Glu Phe Arg Ser Gly Gln Phe Asn Thr Ser Phe
        435                 440                 445

Val Glu Ser His Pro Glu Leu Thr Asn Tyr Ser Ile Lys Arg Lys Pro
    450                 455                 460

Glu Glu Leu Ala Leu Ala Ile Ala Ala Ile Ala Ala His Ala Gly
465                 470                 475                 480

Leu

<210> SEQ ID NO 7
<211> LENGTH: 1140
<212> TYPE: PRT
```

<213> ORGANISM: Corynebacterium glutamicum

<400> SEQUENCE: 7

| | | | | | | | | | | | | | | |
|---|---|---|---|---|---|---|---|---|---|---|---|---|---|---|
|Met|Ser|Thr|His|Thr|Ser|Ser|Thr|Leu|Pro|Ala|Phe|Lys|Lys|Ile|Leu|
|1| | | |5| | | | |10| | | | |15| |

Val Ala Asn Arg Gly Glu Ile Ala Val Arg Ala Phe Arg Ala Ala Leu
                20                  25                  30

Glu Thr Gly Ala Ala Thr Val Ala Ile Tyr Pro Arg Glu Asp Arg Gly
            35                  40                  45

Ser Phe His Arg Ser Phe Ala Ser Glu Ala Val Arg Ile Gly Thr Glu
        50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
370                 375                 380

Ala Gln Leu Gly Gly Glu Ile Thr Ala His Phe Asp Ser Met Leu Val
385                 390                 395                 400

-continued

Lys Met Thr Cys Arg Gly Ser Asp Phe Glu Thr Ala Val Ala Arg Ala
                405                 410                 415
Gln Arg Ala Leu Ala Glu Phe Thr Val Ser Gly Val Ala Thr Asn Ile
            420                 425                 430
Gly Phe Leu Arg Ala Leu Leu Arg Glu Glu Asp Phe Thr Ser Lys Arg
        435                 440                 445
Ile Ala Thr Gly Phe Ile Ala Asp His Pro His Leu Leu Gln Ala Pro
450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
            500                 505                 510
Arg Asp Arg Leu Lys Gln Leu Gly Pro Ala Ala Phe Ala Arg Asp Leu
        515                 520                 525
Arg Glu Gln Asp Ala Leu Ala Val Thr Asp Thr Thr Phe Arg Asp Ala
    530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
            580                 585                 590
Asp Pro Trp Asp Arg Leu Asp Glu Leu Arg Glu Ala Met Pro Asn Val
        595                 600                 605
Asn Ile Gln Met Leu Leu Arg Gly Arg Asn Thr Val Gly Tyr Thr Pro
    610                 615                 620
Tyr Pro Asp Ser Val Cys Arg Ala Phe Val Lys Glu Ala Ala Ser Ser
625                 630                 635                 640
Gly Val Asp Ile Phe Arg Ile Phe Asp Ala Leu Asn Asp Val Ser Gln
                645                 650                 655
Met Arg Pro Ala Ile Asp Ala Val Leu Glu Thr Asn Thr Ala Val Ala
            660                 665                 670
Glu Val Ala Met Ala Tyr Ser Gly Asp Leu Ser Asp Pro Asn Glu Lys
        675                 680                 685
Leu Tyr Thr Leu Asp Tyr Tyr Leu Lys Met Ala Glu Glu Ile Val Lys
    690                 695                 700
Ser Gly Ala His Ile Leu Ala Ile Lys Asp Met Ala Gly Leu Leu Arg
705                 710                 715                 720
Pro Ala Ala Val Thr Lys Leu Val Thr Ala Leu Arg Arg Glu Phe Asp
                725                 730                 735
Leu Pro Val His Val His Thr His Asp Thr Ala Gly Gly Gln Leu Ala
            740                 745                 750
Thr Tyr Phe Ala Ala Ala Gln Ala Gly Ala Asp Ala Val Asp Gly Ala
        755                 760                 765
Ser Ala Pro Leu Ser Gly Thr Thr Ser Gln Pro Ser Leu Ser Ala Ile
    770                 775                 780
Val Ala Ala Phe Ala His Thr Arg Arg Asp Thr Gly Leu Ser Leu Glu
785                 790                 795                 800
Ala Val Ser Asp Leu Glu Pro Tyr Trp Glu Ala Val Arg Gly Leu Tyr
                805                 810                 815
Leu Pro Phe Glu Ser Gly Thr Pro Gly Pro Thr Gly Arg Val Tyr Arg

```
            820                 825                 830
His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
            930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
                995                 1000                1005

Glu Thr Leu Ile Arg Leu Pro Asp Val Arg Thr Pro Leu Leu Val
        1010                1015                1020

Arg Leu Asp Ala Ile Ser Glu Pro Asp Lys Gly Met Arg Asn
        1025                1030                1035

Val Val Ala Asn Val Asn Gly Gln Ile Arg Pro Met Arg Val Arg
        1040                1045                1050

Asp Arg Ser Val Glu Ser Val Thr Ala Thr Ala Glu Lys Ala Asp
        1055                1060                1065

Ser Ser Asn Lys Gly His Val Ala Ala Pro Phe Ala Gly Val Val
        1070                1075                1080

Thr Val Thr Val Ala Glu Gly Asp Glu Val Lys Ala Gly Asp Ala
        1085                1090                1095

Val Ala Ile Ile Glu Ala Met Lys Met Glu Ala Thr Ile Thr Ala
        1100                1105                1110

Ser Val Asp Gly Lys Ile Asp Arg Val Val Val Pro Ala Ala Thr
        1115                1120                1125

Lys Val Glu Gly Gly Asp Leu Ile Val Val Val Ser
        1130                1135                1140
```

<210> SEQ ID NO 8
<211> LENGTH: 1152
<212> TYPE: PRT
<213> ORGANISM: Sinorhizobium meliloti

<400> SEQUENCE: 8

```
Met Ser Ile Ser Lys Ile Leu Val Ala Asn Arg Ser Glu Ile Ala Ile
1               5                   10                  15

Arg Val Phe Arg Ala Ala Asn Glu Leu Gly Leu Lys Thr Val Ala Ile
            20                  25                  30

Trp Ala Glu Glu Asp Lys Leu Ala Leu His Arg Phe Lys Ala Asp Glu
        35                  40                  45
```

Ser Tyr Gln Val Gly Arg Gly Pro His Leu Pro Arg Asp Leu Gly Pro
 50                  55                  60

Ile Met Ser Tyr Leu Ser Ile Asp Glu Val Ile Arg Val Ala Lys Leu
65                  70                  75                  80

Ser Gly Ala Asp Ala Ile His Pro Gly Tyr Gly Leu Leu Ser Glu Ser
                85                  90                  95

Pro Glu Phe Ala Glu Ala Cys Ala Ala Asn Gly Ile Thr Phe Ile Gly
            100                 105                 110

Pro Lys Pro Glu Thr Met Arg Gln Leu Gly Asn Lys Val Ala Ala Arg
            115                 120                 125

Asn Leu Ala Ile Ser Ile Gly Val Pro Val Val Pro Ala Thr Glu Pro
130                 135                 140

Leu Pro Asp Asp Pro Glu Glu Ile Lys Arg Leu Ala Glu Glu Ile Gly
145                 150                 155                 160

Tyr Pro Val Met Leu Lys Ala Ser Trp Gly Gly Gly Arg Gly Met
                165                 170                 175

Arg Ala Ile Arg Asp Pro Lys Asp Leu Ile Arg Glu Val Thr Glu Ala
            180                 185                 190

Lys Arg Glu Ala Lys Ala Ala Phe Gly Lys Asp Glu Val Tyr Leu Glu
            195                 200                 205

Lys Leu Val Glu Arg Ala Arg His Val Glu Ser Gln Ile Leu Gly Asp
210                 215                 220

Thr His Gly Asn Val Val His Leu Phe Glu Arg Asp Cys Ser Ile Gln
225                 230                 235                 240

Arg Arg Asn Gln Lys Val Val Glu Arg Ala Pro Ala Pro Tyr Leu Asn
            245                 250                 255

Asp Ala Gln Arg Gln Glu Leu Ala Asp Tyr Ser Leu Lys Ile Ala Arg
            260                 265                 270

Ala Thr Asn Tyr Ile Gly Ala Gly Thr Val Glu Tyr Leu Met Asp Ser
            275                 280                 285

Asp Thr Gly Lys Phe Tyr Phe Ile Glu Val Asn Pro Arg Ile Gln Val
            290                 295                 300

Glu His Thr Val Thr Glu Val Val Thr Gly Ile Asp Ile Val Lys Ala
305                 310                 315                 320

Gln Ile His Ile Leu Asp Gly Phe Ala Ile Gly Ala Pro Glu Ser Gly
            325                 330                 335

Val Pro Arg Gln Glu Asp Ile Arg Leu Asn Gly His Ala Leu Gln Cys
            340                 345                 350

Arg Ile Thr Thr Glu Asp Pro Glu Gln Asn Phe Ile Pro Asp Tyr Gly
            355                 360                 365

Arg Ile Thr Ala Tyr Arg Gly Ala Thr Gly Phe Gly Ile Arg Leu Asp
            370                 375                 380

Gly Gly Thr Ala Tyr Ser Gly Ala Val Ile Thr Arg Tyr Tyr Asp Pro
385                 390                 395                 400

Leu Leu Glu Lys Val Thr Ala Trp Ala Pro Asn Pro Gly Glu Ala Ile
                405                 410                 415

Gln Arg Met Ile Arg Ala Leu Arg Glu Phe Arg Ile Arg Gly Val Ala
            420                 425                 430

Thr Asn Leu Thr Phe Leu Glu Ala Ile Ile Ser His Pro Lys Phe His
            435                 440                 445

Asp Asn Ser Tyr Thr Thr Arg Phe Ile Asp Thr Thr Pro Glu Leu Phe
450                 455                 460

Gln Gln Val Lys Arg Gln Asp Arg Ala Thr Lys Leu Leu Thr Tyr Leu

```
            465                 470                 475                 480
        Ala Asp Val Thr Val Asn Gly His Pro Glu Val Lys Gly Arg Pro Lys
                        485                 490                 495

Pro Ser Asp Asp Ile Ala Ala Pro Val Val Pro Phe Thr Gly Gly Asp
                        500                 505                 510

Val Lys Pro Gly Thr Lys Gln Arg Leu Asp Gln Leu Gly Pro Lys Lys
                        515                 520                 525

Phe Ala Glu Trp Val Lys Ala Gln Pro Glu Val Leu Ile Thr Asp Thr
                        530                 535                 540

Thr Met Arg Asp Gly His Gln Ser Leu Leu Ala Thr Arg Met Arg Thr
        545                 550                 555                 560

Tyr Asp Ile Ala Arg Ile Ala Gly Thr Tyr Ala Arg Ala Leu Pro Asn
                        565                 570                 575

Leu Phe Ser Leu Glu Cys Trp Gly Gly Ala Thr Phe Asp Val Ser Met
                        580                 585                 590

Arg Phe Leu Thr Glu Asp Pro Trp Glu Arg Leu Ala Met Val Arg Glu
                        595                 600                 605

Gly Ala Pro Asn Leu Leu Leu Gln Met Leu Leu Arg Gly Ala Asn Gly
                        610                 615                 620

Val Gly Tyr Lys Asn Tyr Pro Asp Asn Val Val Lys Tyr Phe Val Arg
        625                 630                 635                 640

Gln Ala Ala Lys Gly Gly Ile Asp Val Phe Arg Val Phe Asp Cys Leu
                        645                 650                 655

Asn Trp Val Glu Asn Met Arg Val Ala Met Asp Ala Val Ala Glu Glu
                        660                 665                 670

Asp Arg Ile Cys Glu Ala Ala Ile Cys Tyr Thr Gly Asp Ile Leu Asn
                        675                 680                 685

Ser Ala Arg Pro Lys Tyr Asp Leu Lys Tyr Tyr Thr Ala Leu Ala Ala
                        690                 695                 700

Glu Leu Glu Lys Ala Gly Ala His Met Ile Ala Val Lys Asp Met Ala
        705                 710                 715                 720

Gly Leu Leu Lys Pro Ala Ala Arg Val Leu Phe Lys Ala Leu Lys
                        725                 730                 735

Glu Ala Thr Gly Leu Pro Ile His Phe His Thr His Asp Thr Ser Gly
                        740                 745                 750

Ile Ala Ala Ala Thr Val Leu Ala Ala Val Glu Ser Gly Val Asp Val
                        755                 760                 765

Val Asp Ala Ala Met Asp Ala Leu Ser Gly Asn Thr Ser Gln Pro Cys
        770                 775                 780

Leu Gly Ser Ile Val Glu Ala Leu Ser Gly Ser Glu Arg Asp Pro Gly
        785                 790                 795                 800

Leu Asp Pro Glu Trp Ile Arg Arg Ile Ser Phe Tyr Trp Glu Ala Val
                        805                 810                 815

Arg His Gln Tyr Ala Ala Phe Glu Ser Asp Leu Lys Gly Pro Ala Ser
                        820                 825                 830

Glu Val Tyr Leu His Glu Met Pro Gly Gly Gln Phe Thr Asn Leu Lys
                        835                 840                 845

Glu Gln Ala Arg Ser Leu Gly Leu Glu Thr Arg Trp His Glu Val Ala
                        850                 855                 860

Gln Ala Tyr Ala Asp Ala Asn Arg Met Phe Gly Asp Ile Val Lys Val
        865                 870                 875                 880

Thr Pro Ser Ser Lys Val Val Gly Asp Met Ala Leu Met Met Val Ser
                        885                 890                 895
```

-continued

```
Gln Asp Leu Thr Val Ala Asp Val Glu Asn Pro Gly Lys Asp Ile Ala
            900                 905                 910
Phe Pro Glu Ser Val Val Ser Met Leu Lys Gly Asp Leu Gly Gln Pro
            915                 920                 925
Pro Gly Gly Trp Pro Glu Ala Leu Gln Lys Lys Ala Leu Lys Gly Glu
    930                 935                 940
Glu Pro Tyr Asp Ala Arg Pro Gly Ser Leu Leu Glu Asp Ala Asp Leu
945                 950                 955                 960
Asp Ala Glu Arg Lys Gly Ile Glu Glu Lys Leu Gly Arg Glu Val Thr
                965                 970                 975
Asp Phe Glu Phe Ala Ser Tyr Leu Met Tyr Pro Lys Val Phe Thr Asp
            980                 985                 990
Tyr Ala Val Ala Cys Glu Thr Tyr  Gly Pro Val Ser Val  Leu Pro Thr
            995                1000                1005
Pro Ala  Tyr Phe Tyr Gly Met  Ala Pro Gly Glu Glu  Leu Phe Ala
    1010                1015                1020
Asp Ile Glu Lys Gly Lys Thr  Leu Val Ile Leu Asn  Gln Ala Gln
    1025                1030                1035
Gly Glu  Ile Asp Glu Lys Gly  Met Val Lys Met Phe  Phe Glu Met
    1040                1045                1050
Asn Gly Gln Pro Arg Ser Ile  Lys Val Pro Asp Arg  Asn Arg Gly
    1055                1060                1065
Ala Ser Ala Ala Val Arg Arg  Lys Ala Glu Ala Gly  Asn Ala Ala
    1070                1075                1080
His Leu Gly Ala Pro Met Pro  Gly Val Ile Ser Thr  Val Ala Val
    1085                1090                1095
Ala Ser  Gly Gln Ser Val Lys  Ala Gly Asp Val Leu  Leu Ser Ile
    1100                1105                1110
Glu Ala  Met Lys Met Glu Thr  Ala Leu His Ala Glu  Lys Asp Gly
    1115                1120                1125
Val Ile  Ser Glu Val Leu Val  Arg Ala Gly Asp Gln  Ile Asp Ala
    1130                1135                1140
Lys Asp  Leu Leu Val Val Phe  Gly Gly
    1145                1150
```

<210> SEQ ID NO 9
<211> LENGTH: 2652
<212> TYPE: DNA
<213> ORGANISM: Escherichia coli

<400> SEQUENCE: 9

```
atgaacgaac aatattccgc attgcgtagt aatgtcagta tgctcggcaa agtgctggga      60
gaaaccatca aggatgcgtt gggagaacac attcttgaac gcgtagaaac tatccgtaag     120
ttgtcgaaat cttcacgcgc tggcaatgat gctaaccgcc aggagttgct caccaccta      180
caaaatttgt cgaacgacga gctgctgccc gttgcgcgtg cgtttagtca gttcctgaac     240
ctggccaaca ccgccgagca ataccacagc atttcgccga aggcgaagc tgccagcaac      300
ccggaagtga tcgcccgcac cctgcgtaaa ctgaaaaacc agccggaact gagcgaagac     360
accatcaaaa aagcagtgga atcgctgtcg ctggaactgg tcctcacggc tcacccaacc     420
gaaattaccc gtcgtacact gatccacaaa atggtggaag tgaacgcctg tttaaaacag     480
ctcgataaca aagatatcgc tgactacgaa cacaaccagc tgatgcgtcg cctgcgccag     540
ttgatcgccc agtcatggca taccgatgaa atccgtaagc tgcgtccaag cccggtagat    600
```

```
gaagccaaat ggggctttgc cgtagtggaa aacagcctgt ggcaaggcgt accaaattac    660
ctgcgcgaac tgaacgaaca actggaagag aacctcggct acaaactgcc cgtcgaattt    720
gttccggtcc gttttacttc gtggatgggc ggcgaccgcg acggcaaccc gaacgtcact    780
gccgatatca cccgccacgt cctgctactc agccgctgga agccaccga tttgttcctg    840 aaagatattc aggtgctggt ttctgaactg tcgatggttg aagcgacccc tgaactgctg    900
gcgctggttg cgaagaagg tgccgcagaa ccgtatcgct atctgatgaa aaacctgcgt    960
tctcgcctga tggcgacaca ggcatggctg gaagcgcgcc tgaaaggcga agaactgcca   1020
aaaccagaag gcctgctgac acaaaacgaa gaactgtggg aaccgctcta cgcttgctac   1080
cagtcacttc aggcgtgtgg catgggtatt atcgccaacg gcgatctgct cgacaccctg   1140
cgccgcgtga atgtttcgg cgtaccgctg gtccgtattg atatccgtca ggagagcacg   1200
cgtcataccg aagcgctggg cgagctgacc cgctacctcg gtatcggcga ctacgaaagc   1260
tggtcagagg ccgacaaaca ggcgttcctg atccgcgaac tgaactccaa acgtccgctt   1320
ctgccgcgca actggcaacc aagcgccgaa acgcgcgaag tgctcgatac ctgccaggtg   1380
attgccgaag caccgcaagg ctccattgcc gcctacgtga tctcgatggc gaaaacgccg   1440
tccgacgtac tggctgtcca cctgctgctg aaagaagcgg gtatcgggtt tgcgatgccg   1500
gttgctccgc tgtttgaaac cctcgatgat ctgaacaacg ccaacgatgt catgacccag   1560
ctgctcaata ttgactggta tcgtggcctg attcagggca acagatggt gatgattggc   1620 tattccgact cagcaaaaga tgcgggagtg atggcagctt cctgggcgca atatcaggca   1680
caggatgcat taatcaaaac ctgcgaaaaa gcgggtattg agctgacgtt gttccacggt   1740
cgcggcggtt ccattggtcg cggcggcgca cctgctcatg cggcgctgct gtcacaaccg   1800
ccaggaagcc tgaaaggcgg cctgcgcgta accgaacagg gcgagatgat ccgctttaaa   1860
tatggtctgc agaaatcac cgtcagcagc ctgtcgcttt ataccggggc gattctggaa   1920
gccaacctgc tgccaccgcc ggagccgaaa gagagctggc gtcgcattat ggatgaactg   1980
tcagtcatct cctgcgatgt ctaccgcggc tacgtacgtg aaaacaaaga ttttgtgcct   2040
tacttccgct ccgctacgcc ggaacaagaa ctgggcaaac tgccgttggg ttcacgtccg   2100
gcgaaacgtc gcccaaccgg cggcgtcgag tcactacgcg ccattccgtg gatcttcgcc   2160
tggacgcaaa accgtctgat gctccccgcc tggctgggtg caggtacggc gctgcaaaaa   2220
gtggtcgaag acggcaaaca gagcgagctg gaggctatgt gccgcgattg gccattcttc   2280
tcgacgcgtc tcggcatgct ggagatggtc ttcgccaaag cagacctgtg gctggcggaa   2340
tactatgacc aacgcctggt agacaaagca ctgtggccgt taggtaaaga gttacgcaac   2400
ctgcaagaag aagacatcaa agtggtgctg gcgattgcca acgattccca tctgatggcc   2460
gatctgccgt ggattgcaga gtctattcag ctacggaata tttacaccga cccgctgaac   2520
gtattgcagg ccgagttgct gcaccgctcc cgccaggcag aaaagaagg ccaggaaccg   2580 gatcctcgcg tcgaacaagc gttaatggtc actattgccg ggattgcggc aggtatgcgt   2640
aataccggct aa                                                       2652
```

<210> SEQ ID NO 10
<211> LENGTH: 883
<212> TYPE: PRT
<213> ORGANISM: Escherichia coli

<400> SEQUENCE: 10

```
Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
            35                  40                  45

Asn Asp Ala Asn Arg Gln Glu Leu Leu Thr Thr Leu Gln Asn Leu Ser
50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
                100                 105                 110

Asn Gln Pro Glu Leu Ser Glu Asp Thr Ile Lys Lys Ala Val Glu Ser
            115                 120                 125

Leu Ser Leu Glu Leu Val Leu Thr Ala His Pro Thr Glu Ile Thr Arg
        130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
                260                 265                 270

Trp Lys Ala Thr Asp Leu Phe Leu Lys Asp Ile Gln Val Leu Val Ser
            275                 280                 285

Glu Leu Ser Met Val Glu Ala Thr Pro Glu Leu Leu Ala Leu Val Gly
        290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
    370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
```

```
                420             425             430
Glu Leu Asn Ser Lys Arg Pro Leu Leu Pro Arg Asn Trp Gln Pro Ser
            435             440             445

Ala Glu Thr Arg Glu Val Leu Asp Thr Cys Gln Val Ile Ala Glu Ala
        450             455             460

Pro Gln Gly Ser Ile Ala Ala Tyr Val Ile Ser Met Ala Lys Thr Pro
465             470             475             480

Ser Asp Val Leu Ala Val His Leu Leu Leu Lys Glu Ala Gly Ile Gly
            485             490             495

Phe Ala Met Pro Val Ala Pro Leu Phe Glu Thr Leu Asp Asp Leu Asn
        500             505             510

Asn Ala Asn Asp Val Met Thr Gln Leu Leu Asn Ile Asp Trp Tyr Arg
    515             520             525

Gly Leu Ile Gln Gly Lys Gln Met Val Met Ile Gly Tyr Ser Asp Ser
    530             535             540

Ala Lys Asp Ala Gly Val Met Ala Ala Ser Trp Ala Gln Tyr Gln Ala
545             550             555             560

Gln Asp Ala Leu Ile Lys Thr Cys Glu Lys Ala Gly Ile Glu Leu Thr
            565             570             575

Leu Phe His Gly Arg Gly Gly Ser Ile Gly Arg Gly Gly Ala Pro Ala
        580             585             590

His Ala Ala Leu Leu Ser Gln Pro Pro Gly Ser Leu Lys Gly Gly Leu
    595             600             605

Arg Val Thr Glu Gln Gly Glu Met Ile Arg Phe Lys Tyr Gly Leu Pro
    610             615             620

Glu Ile Thr Val Ser Ser Leu Ser Leu Tyr Thr Gly Ala Ile Leu Glu
625             630             635             640

Ala Asn Leu Leu Pro Pro Glu Pro Lys Ser Trp Arg Arg Ile
            645             650             655

Met Asp Glu Leu Ser Val Ile Ser Cys Asp Val Tyr Arg Gly Tyr Val
        660             665             670

Arg Glu Asn Lys Asp Phe Val Pro Tyr Phe Arg Ser Ala Thr Pro Glu
    675             680             685

Gln Glu Leu Gly Lys Leu Pro Leu Gly Ser Arg Pro Ala Lys Arg Arg
    690             695             700

Pro Thr Gly Gly Val Glu Ser Leu Arg Ala Ile Pro Trp Ile Phe Ala
705             710             715             720

Trp Thr Gln Asn Arg Leu Met Leu Pro Ala Trp Leu Gly Ala Gly Thr
            725             730             735

Ala Leu Gln Lys Val Val Glu Asp Gly Lys Gln Ser Glu Leu Glu Ala
        740             745             750

Met Cys Arg Asp Trp Pro Phe Phe Ser Thr Arg Leu Gly Met Leu Glu
    755             760             765

Met Val Phe Ala Lys Ala Asp Leu Trp Leu Ala Glu Tyr Tyr Asp Gln
    770             775             780

Arg Leu Val Asp Lys Ala Leu Trp Pro Leu Gly Lys Glu Leu Arg Asn
785             790             795             800

Leu Gln Glu Glu Asp Ile Lys Val Val Leu Ala Ile Ala Asn Asp Ser
            805             810             815

His Leu Met Ala Asp Leu Pro Trp Ile Ala Glu Ser Ile Gln Leu Arg
        820             825             830

Asn Ile Tyr Thr Asp Pro Leu Asn Val Leu Gln Ala Glu Leu Leu His
    835             840             845
```

-continued

```
Arg Ser Arg Gln Ala Glu Lys Glu Gly Gln Glu Pro Asp Pro Arg Val
850                 855                 860

Glu Gln Ala Leu Met Val Thr Ile Ala Gly Ile Ala Ala Gly Met Arg
865                 870                 875                 880

Asn Thr Gly

<210> SEQ ID NO 11
<211> LENGTH: 483
<212> TYPE: PRT
<213> ORGANISM: Methanobacterium thermoautotrophicum

<400> SEQUENCE: 11

Met Lys Val Pro Arg Cys Met Ser Thr Gln His Pro Asp Asn Val Asn
1               5                   10                  15

Pro Pro Phe Phe Ala Glu Glu Pro Glu Leu Gly Gly Glu Asp Glu Ile
                20                  25                  30

Arg Glu Ala Tyr Tyr Val Phe Ser His Leu Gly Cys Asp Glu Gln Met
            35                  40                  45

Trp Asp Cys Glu Gly Lys Glu Val Asp Asn Tyr Val Val Lys Lys Leu
        50                  55                  60

Leu Thr Lys Tyr Gln Ala Phe Phe Arg Asp His Val Leu Gly Glu Asp
65                  70                  75                  80

Leu Arg Leu Thr Leu Arg Val Pro Asn Pro Thr Val Glu Arg Ala Glu
                85                  90                  95

Ala Lys Ile Leu Leu Glu Thr Leu Glu Ser Ile Pro Arg Ser Tyr Asp
            100                 105                 110

Thr Ala Ser Leu Phe Tyr Gly Met Asp Ala Ala Pro Val Phe Glu Val
        115                 120                 125

Ile Leu Pro Met Thr Ser Ser Ser Cys Leu Asn Arg Ile His Ser
130                 135                 140

Tyr Tyr Leu Asp Phe Val Lys Gly Lys Glu Arg Leu Gln Leu Ala Asp
145                 150                 155                 160

Gly Val Thr Val Lys Glu Trp Ile Gly Glu Phe Arg Pro Asp Glu Ile
                165                 170                 175

Asn Val Ile Pro Leu Phe Glu Asp His Glu Gly Met Leu Asn Ala Ala
            180                 185                 190

Lys Ile Thr Gly Glu Tyr Leu Asp Gly Lys Asp Ile Gln Glu Gln Arg
        195                 200                 205

Val Phe Leu Ala Arg Ser Asp Pro Ala Met Asn Tyr Gly Met Ile Ser
    210                 215                 220

Ala Thr Leu Leu Asn Arg Ile Ala Leu Ser Asp Phe Arg Asp Leu Glu
225                 230                 235                 240

Glu Glu Ser Gly Val Lys Leu Tyr Pro Ile Ile Gly Met Gly Ser Ala
                245                 250                 255

Pro Phe Arg Gly Asn Leu Arg Pro Asp Asn Val Glu Asp Val Thr Trp
            260                 265                 270

Glu Tyr Arg Gly Ala Tyr Thr Phe Thr Val Gln Ser Ser Phe Lys Tyr
        275                 280                 285

Asp His Glu Pro Ser Asp Val Ile Arg Gly Ile Lys Lys Leu Arg Ser
    290                 295                 300

Val Lys Pro Gly Arg Ala Ala Glu Ile Glu Arg Glu Ser Val Leu Glu
305                 310                 315                 320

Ile Ile Ser Ala Tyr Cys Arg Glu Tyr Arg Arg Gln Val Met Asp Leu
                325                 330                 335
```

```
Val Asp Ile Ile Asn Arg Val Ala Arg Tyr Val Pro Gly Arg Arg Lys
            340                 345                 350

Arg Lys Leu His Ile Gly Leu Phe Gly Tyr Ser Arg Ser Met Gly Asn
        355                 360                 365

Val Ser Leu Pro Arg Ala Ile Thr Phe Thr Ala Ala Leu Tyr Ser Leu
    370                 375                 380

Gly Val Pro Pro Glu Leu Leu Gly Phe Asn Ala Leu Ser Ser Gly Asp
385                 390                 395                 400

Leu Glu Phe Ile Glu Glu Val Tyr Pro Gly Leu Gly Arg Asp Leu His
            405                 410                 415

Asp Ala Ala Arg Tyr Ala Asn Pro Glu Ser Pro Phe Leu Ser Pro Glu
        420                 425                 430

Val Lys Ser Ser Phe Glu Glu Tyr Leu Glu Pro Glu Tyr Asp Glu Gly
    435                 440                 445

His Met Lys Thr Thr Glu Glu Ile Ile Arg Ala Leu Arg Ile Asn Arg
450                 455                 460

Thr Ala Asn Leu Gln Glu Leu Ile Leu Glu Ala Ala Ser Gln Arg Lys
465                 470                 475                 480

Phe Leu Gly

<210> SEQ ID NO 12
<211> LENGTH: 537
<212> TYPE: PRT
<213> ORGANISM: Clostridium perfringens

<400> SEQUENCE: 12

Met Lys Ile Pro Cys Ser Met Met Thr Gln His Pro Asp Asn Val Glu
1               5                   10                  15

Thr Tyr Ile Ser Ile Gln Gln Glu Pro Ala Glu Ala Ile Lys Gly Leu
            20                  25                  30

Thr Pro Gln Asp Lys Gly Gly Leu Gly Ile Glu Glu Val Met Ile Asp
        35                  40                  45

Phe Glu Gly Lys Leu Thr Pro Tyr His Gln Thr Ser Gln Ile Ala Leu
    50                  55                  60

Gly Leu Ile Ser Asn Gly Ile Ile Pro Gly Lys Asp Val Arg Val Thr
65                  70                  75                  80

Pro Arg Ile Pro Asn Ala Asn Lys Glu Ser Val Phe Arg Gln Leu Met
                85                  90                  95

Ser Ile Met Ser Ile Ile Glu Thr Asn Val Gln Ser Lys Glu Leu Thr
            100                 105                 110

Gly Thr Pro Ala Ile Ser Glu Val Val Pro Met Ile Glu Thr Gly
        115                 120                 125

Lys Glu Ile Ser Glu Phe Gln Asp Arg Val Asn Ser Val Val Asp Met
130                 135                 140

Gly Asn Lys Asn Tyr Lys Thr Lys Leu Asp Leu Asn Ser Val Arg Ile
145                 150                 155                 160

Ile Pro Leu Val Glu Asp Val Pro Ala Leu Ala Asn Ile Asp Arg Ile
                165                 170                 175

Leu Asp Glu His Tyr Glu Ile Glu Lys Ser Lys Gly His Ile Leu Lys
            180                 185                 190

Asp Leu Arg Ile Met Ile Ala Arg Ser Asp Thr Ala Met Ser Tyr Gly
        195                 200                 205

Leu Ile Ser Gly Val Leu Ser Val Leu Met Ala Val Asp Gly Ala Tyr
    210                 215                 220
```

Lys Trp Gly Glu Lys His Gly Val Thr Ile Ser Pro Ile Leu Gly Cys
225                 230                 235                 240

Gly Ser Leu Pro Phe Arg Gly His Phe Ser Glu Glu Asn Ile Asp Glu
            245                 250                 255

Ile Leu Ala Thr Tyr Ser Gly Ile Lys Thr Phe Thr Phe Gln Ser Ala
            260                 265                 270

Leu Arg Tyr Asp His Gly Glu Glu Ala Thr Lys His Ala Val Arg Glu
        275                 280                 285

Leu Lys Glu Lys Ile Ala Gln Ser Lys Pro Arg Asn Phe Ser Glu Glu
        290                 295                 300

Asp Lys Asp Leu Met Lys Glu Phe Ile Gly Ile Cys Ser Lys His Tyr
305                 310                 315                 320

Leu Gln Thr Phe Leu Lys Val Ile Asp Thr Val Ser Phe Val Ser Asp
            325                 330                 335

Phe Ile Pro Lys Asn Arg Asp Arg Leu Thr Lys Ala Lys Thr Gly Leu
            340                 345                 350

Glu Tyr Asn Arg Glu Val Ala Asn Leu Asp Asn Val Ala Asp Leu Val
        355                 360                 365

Lys Asp Glu Val Leu Lys Gln Glu Ile Leu Ser Ile Asp Asn Ser Lys
370                 375                 380

Glu Tyr Ala Val Pro Arg Ala Ile Ser Phe Thr Gly Ala Met Tyr Thr
385                 390                 395                 400

Leu Gly Met Pro Pro Glu Leu Met Gly Met Gly Arg Ala Leu Asn Glu
            405                 410                 415

Ile Lys Thr Lys Tyr Gly Gln Glu Gly Ile Asp Lys Leu Leu Glu Ile
            420                 425                 430

Tyr Pro Ile Leu Arg Lys Asp Leu Ala Phe Ala Arg Phe Ala Asn
        435                 440                 445

Gly Gly Val Ser Lys Lys Ile Ile Asp Glu Glu Ala Arg Gln Glu Tyr
450                 455                 460

Lys Glu Asp Met Lys Tyr Val Asn Glu Ile Leu Asn Leu Gly Leu Asp
465                 470                 475                 480

Tyr Asp Phe Leu Asn Glu Asn Glu Phe Tyr His Thr Leu Leu Lys Thr
            485                 490                 495

Thr Lys Pro Ile Ile Met His Leu Met Gly Leu Glu Glu Asn Val Met
            500                 505                 510

Arg Asn Ser Thr Glu Glu Leu Lys Ile Leu Asn Glu Trp Ile Val Arg
        515                 520                 525

Met Gly Lys Val Arg Gly Ser Ile Gly
530                 535

<210> SEQ ID NO 13
<211> LENGTH: 1260
<212> TYPE: DNA
<213> ORGANISM: Issatchenkia orientalis

<400> SEQUENCE: 13
atgtccagag gcttctttac tgagaacatt acgcaattgc caccagaccc tttgtttggt      60
cttaaggcca ggttcagcaa tgactcacgt gaaaacaagg tcgatttagg tattgggca     120 tatagggacg acaacggtaa gccatggatc ttaccatctg tcaggttggc cgaaaacttg    180
attcagaact cccagactac aaccatgag tacctaccaa tcggtggact tgctgatttc     240
acttctgctg cggcaagagt tgtatttgga ggcgattcta aagccatttc gcaaaaccgt    300

```
cttgtctcca tccagagttt gtcaggtaca ggtgccttac atgttgctgg tctatttatc    360
aagcgccaat acaagtctct tgatggcact tccgaagacc ctctaatata tctatcggaa    420
cctacatggg ccaaccacgt tcaaatcttt gaagttattg gtctcaagcc tgtattctat    480
ccatattggc atgccgcaag caagaccttg gatctgaagg ctacttaaa ggcaataaac     540
gatgctccag aagggtcggt ttttgtattg catgcaacgg ctcataaccc tactggtttg    600
gatccaacac aagaacaatg gatggagatt ttggccgcta taagtgccaa aaagcatctg    660
ccattatttg attgtgcata tcagggtttc acctccgggt ctctagatag agatgcttgg    720
gctgttcgag aagctgtcaa caatgacaag tacgaattcc cgggaattat tgtctgtcaa    780
tcgtttgcga aaatgttgg catgtatggt gaacggattg gtgcagttca tattgttcta    840
cctgaatcag acgcttccct aaacagcgcc atcttctccc aattgcaaaa gacaatcaga    900
tcggagattt ccaatccacc aggatacggt gcaaagattg tgtctaaagt tttgaacact    960
ccggaacttt acaaacagtg ggagcaagat ttgatcacca tgtcttcgag aatcactgca   1020
atgagaaagg agctagtaaa tgagctcgag cgtcttggaa cccctggcac ttggagacac   1080
atcaccgagc aacagggtat gttttccttt actggtttga acccggagca ggttgccaag   1140
ctagagaagg agcatggtgt ttatcttgtt cgtagtggac gtgcaagtat tgcaggcctc   1200
aacatgggaa acgtcaagta tgttgccaag gccattgact ctgtcgtgag agacctttag   1260
```

<210> SEQ ID NO 14
<211> LENGTH: 419
<212> TYPE: PRT
<213> ORGANISM: Issatchenkia orientalis

<400> SEQUENCE: 14

Met Ser Arg Gly Phe Phe Thr Glu Asn Ile Thr Gln Leu Pro Pro Asp
1               5                   10                  15

Pro Leu Phe Gly Leu Lys Ala Arg Phe Ser Asn Asp Ser Arg Glu Asn
            20                  25                  30

Lys Val Asp Leu Gly Ile Gly Ala Tyr Arg Asp Asp Asn Gly Lys Pro
        35                  40                  45

Trp Ile Leu Pro Ser Val Arg Leu Ala Glu Asn Leu Ile Gln Asn Ser
    50                  55                  60

Pro Asp Tyr Asn His Glu Tyr Leu Pro Ile Gly Gly Leu Ala Asp Phe
65                  70                  75                  80

Thr Ser Ala Ala Ala Arg Val Val Phe Gly Gly Asp Ser Lys Ala Ile
                85                  90                  95

Ser Gln Asn Arg Leu Val Ser Ile Gln Ser Leu Ser Gly Thr Gly Ala
            100                 105                 110

Leu His Val Ala Gly Leu Phe Ile Lys Arg Gln Tyr Lys Ser Leu Asp
        115                 120                 125

Gly Thr Ser Glu Asp Pro Leu Ile Tyr Leu Ser Glu Pro Thr Trp Ala
    130                 135                 140

Asn His Val Gln Ile Phe Glu Val Ile Gly Leu Lys Pro Val Phe Tyr
145                 150                 155                 160

Pro Tyr Trp His Ala Ala Ser Lys Thr Leu Asp Leu Lys Gly Tyr Leu
                165                 170                 175

Lys Ala Ile Asn Asp Ala Pro Glu Gly Ser Val Phe Val Leu His Ala
            180                 185                 190

Thr Ala His Asn Pro Thr Gly Leu Asp Pro Thr Gln Glu Gln Trp Met
        195                 200                 205

Glu Ile Leu Ala Ala Ile Ser Ala Lys Lys His Leu Pro Leu Phe Asp
    210                 215                 220

Cys Ala Tyr Gln Gly Phe Thr Ser Gly Ser Leu Asp Arg Asp Ala Trp
225                 230                 235                 240

Ala Val Arg Glu Ala Val Asn Asn Asp Lys Tyr Glu Phe Pro Gly Ile
            245                 250                 255

Ile Val Cys Gln Ser Phe Ala Lys Asn Val Gly Met Tyr Gly Glu Arg
        260                 265                 270

Ile Gly Ala Val His Ile Val Leu Pro Glu Ser Asp Ala Ser Leu Asn
            275                 280                 285

Ser Ala Ile Phe Ser Gln Leu Gln Lys Thr Ile Arg Ser Glu Ile Ser
    290                 295                 300

Asn Pro Pro Gly Tyr Gly Ala Lys Ile Val Ser Lys Val Leu Asn Thr
305                 310                 315                 320

Pro Glu Leu Tyr Lys Gln Trp Glu Gln Asp Leu Ile Thr Met Ser Ser
            325                 330                 335

Arg Ile Thr Ala Met Arg Lys Glu Leu Val Asn Glu Leu Glu Arg Leu
        340                 345                 350

Gly Thr Pro Gly Thr Trp Arg His Ile Thr Glu Gln Gln Gly Met Phe
    355                 360                 365

Ser Phe Thr Gly Leu Asn Pro Glu Gln Val Ala Lys Leu Glu Lys Glu
370                 375                 380

His Gly Val Tyr Leu Val Arg Ser Gly Arg Ala Ser Ile Ala Gly Leu
            385                 390                 395                 400

Asn Met Gly Asn Val Lys Tyr Val Ala Lys Ala Ile Asp Ser Val Val
        405                 410                 415

Arg Asp Leu

<210> SEQ ID NO 15
<211> LENGTH: 418
<212> TYPE: PRT
<213> ORGANISM: Saccharomyces cerevisiae

<400> SEQUENCE: 15

Met Ser Ala Thr Leu Phe Asn Asn Ile Glu Leu Leu Pro Pro Asp Ala
1               5                   10                  15

Leu Phe Gly Ile Lys Gln Arg Tyr Gly Gln Asp Gln Arg Ala Thr Lys
            20                  25                  30

Val Asp Leu Gly Ile Gly Ala Tyr Arg Asp Asp Asn Gly Lys Pro Trp
        35                  40                  45

Val Leu Pro Ser Val Lys Ala Ala Glu Lys Leu Ile His Asn Asp Ser
    50                  55                  60

Ser Tyr Asn His Glu Tyr Leu Gly Ile Thr Gly Leu Pro Ser Leu Thr
65                  70                  75                  80

Ser Asn Ala Ala Lys Ile Ile Phe Gly Thr Gln Ser Asp Ala Phe Gln
            85                  90                  95

Glu Asp Arg Val Ile Ser Val Gln Ser Leu Ser Gly Thr Gly Ala Leu
        100                 105                 110

His Ile Ser Ala Lys Phe Phe Ser Lys Phe Phe Pro Asp Lys Leu Val
    115                 120                 125

Tyr Leu Ser Lys Pro Thr Trp Ala Asn His Met Ala Ile Phe Glu Asn
130                 135                 140

Gln Gly Leu Lys Thr Ala Thr Tyr Pro Tyr Trp Ala Asn Glu Thr Lys
145                 150                 155                 160

```
Ser Leu Asp Leu Asn Gly Phe Leu Asn Ala Ile Gln Lys Ala Pro Glu
            165                 170                 175

Gly Ser Ile Phe Val Leu His Ser Cys Ala His Asn Pro Thr Gly Leu
        180                 185                 190

Asp Pro Thr Ser Glu Gln Trp Val Gln Ile Val Asp Ala Ile Ala Ser
        195                 200                 205

Lys Asn His Ile Ala Leu Phe Asp Thr Ala Tyr Gln Gly Phe Ala Thr
        210                 215                 220

Gly Asp Leu Asp Lys Asp Ala Tyr Ala Val Arg Leu Gly Val Glu Lys
225                 230                 235                 240

Leu Ser Thr Val Ser Pro Val Phe Val Cys Gln Ser Phe Ala Lys Asn
                245                 250                 255

Ala Gly Met Tyr Gly Glu Arg Val Gly Cys Phe His Leu Ala Leu Thr
            260                 265                 270

Lys Gln Ala Gln Asn Lys Thr Ile Lys Pro Ala Val Thr Ser Gln Leu
        275                 280                 285

Ala Lys Ile Ile Arg Ser Glu Val Ser Asn Pro Ala Tyr Gly Ala
        290                 295                 300

Lys Ile Val Ala Lys Leu Leu Glu Thr Pro Glu Leu Thr Glu Gln Trp
305                 310                 315                 320

His Lys Asp Met Val Thr Met Ser Ser Arg Ile Thr Lys Met Arg His
                325                 330                 335

Ala Leu Arg Asp His Leu Val Lys Leu Gly Thr Pro Gly Asn Trp Asp
            340                 345                 350

His Ile Val Asn Gln Cys Gly Met Phe Ser Phe Thr Gly Leu Thr Pro
        355                 360                 365

Gln Met Val Lys Arg Leu Glu Glu Thr His Ala Val Tyr Leu Val Ala
370                 375                 380

Ser Gly Arg Ala Ser Ile Ala Gly Leu Asn Gln Gly Asn Val Glu Tyr
385                 390                 395                 400

Val Ala Lys Ala Ile Asp Glu Val Val Arg Phe Tyr Thr Ile Glu Ala
                405                 410                 415

Lys Leu

<210> SEQ ID NO 16
<211> LENGTH: 396
<212> TYPE: PRT
<213> ORGANISM: Escherichia coli

<400> SEQUENCE: 16

Met Phe Glu Asn Ile Thr Ala Ala Pro Ala Asp Pro Ile Leu Gly Leu
1               5                   10                  15

Ala Asp Leu Phe Arg Ala Asp Glu Arg Pro Gly Lys Ile Asn Leu Gly
            20                  25                  30

Ile Gly Val Tyr Lys Asp Glu Thr Gly Lys Thr Pro Val Leu Thr Ser
        35                  40                  45

Val Lys Lys Ala Glu Gln Tyr Leu Leu Glu Asn Glu Thr Thr Lys Asn
    50                  55                  60

Tyr Leu Gly Ile Asp Gly Ile Pro Glu Phe Gly Arg Cys Thr Gln Glu
65                  70                  75                  80

Leu Leu Phe Gly Lys Gly Ser Ala Leu Ile Asn Asp Lys Arg Ala Arg
                85                  90                  95

Thr Ala Gln Thr Pro Gly Gly Thr Gly Ala Leu Arg Val Ala Ala Asp
            100                 105                 110
```

```
Phe Leu Ala Lys Asn Thr Ser Val Lys Arg Val Trp Val Ser Asn Pro
            115                 120                 125

Ser Trp Pro Asn His Lys Ser Val Phe Asn Ser Ala Gly Leu Glu Val
        130                 135                 140

Arg Glu Tyr Ala Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
            180                 185                 190

Gln Trp Gln Thr Leu Ala Gln Leu Ser Val Glu Lys Gly Trp Leu Pro
        195                 200                 205

Leu Phe Asp Phe Ala Tyr Gln Gly Phe Ala Arg Gly Leu Glu Glu Asp
210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
            260                 265                 270

Ser Gln Met Lys Ala Ala Ile Arg Ala Asn Tyr Ser Asn Pro Pro Ala
        275                 280                 285

His Gly Ala Ser Val Val Ala Thr Ile Leu Ser Asn Asp Ala Leu Arg
            290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Glu Lys Gly Ala Asn Arg
                325                 330                 335

Asp Phe Ser Phe Ile Ile Lys Gln Asn Gly Met Phe Ser Phe Ser Gly
            340                 345                 350

Leu Thr Lys Glu Gln Val Leu Arg Leu Arg Glu Glu Phe Gly Val Tyr
        355                 360                 365

Ala Val Ala Ser Gly Arg Val Asn Val Ala Gly Met Thr Pro Asp Asn
370                 375                 380

Met Ala Pro Leu Cys Glu Ala Ile Val Ala Val Leu
385                 390                 395

<210> SEQ ID NO 17
<211> LENGTH: 139
<212> TYPE: PRT
<213> ORGANISM: Streptomyces avermitilis

<400> SEQUENCE: 17

Met Leu Arg Thr Met Phe Lys Ser Lys Ile His Arg Ala Thr Val Thr
1               5                   10                  15

Gln Ala Asp Leu His Tyr Val Gly Ser Val Thr Ile Asp Ala Asp Leu
            20                  25                  30

Leu Asp Ala Ala Asp Leu Leu Pro Gly Glu Leu Val His Ile Val Asp
        35                  40                  45

Ile Thr Asn Gly Ala Arg Leu Glu Thr Tyr Val Ile Glu Gly Glu Arg
50                  55                  60

Gly Ser Gly Val Val Gly Ile Asn Gly Ala Ala His Leu Val His
65                  70                  75                  80

Pro Gly Asp Leu Val Ile Ile Ser Tyr Ala Gln Val Ser Asp Ala
                85                  90                  95
```

Glu Ala Arg Ala Leu Arg Pro Arg Val Val His Val Asp Arg Asp Asn
            100                 105                 110

Arg Val Val Ala Leu Gly Ala Asp Pro Ala Glu Pro Val Pro Gly Ser
        115                 120                 125

Asp Gln Ala Arg Ser Pro Gln Ala Val Thr Ala
        130                 135

<210> SEQ ID NO 18
<211> LENGTH: 127
<212> TYPE: PRT
<213> ORGANISM: Clostridium acetobutylicum

<400> SEQUENCE: 18

Met His Leu Asn Met Leu Lys Ser Lys Ile His Arg Ala Thr Val Val
1               5                   10                  15

Gln Ala Asp Leu Asn Tyr Val Gly Ser Ile Thr Ile Asp Arg Asn Leu
            20                  25                  30

Met Asp Lys Ala Asn Ile Leu Glu Tyr Glu Lys Val Glu Ile Ala Asn
        35                  40                  45

Ile Asn Asn Gly Ala Arg Phe Glu Thr Tyr Val Ile Ala Gly Glu Ala
    50                  55                  60

Gly Ser Gly Ile Ile Cys Leu Asn Gly Ala Ala Arg Cys Ala Gln
65                  70                  75                  80

Ala Gly Asp Lys Val Ile Ile Met Cys Tyr Cys Ser Leu Thr Pro Glu
                85                  90                  95

Glu Ala Ser Glu His Arg Pro Lys Val Val Phe Val Asn Asp Asp Asn
            100                 105                 110

Ser Ile Ser Asn Val Thr Glu Tyr Glu Lys His Gly Thr Ile Gly
        115                 120                 125

<210> SEQ ID NO 19
<211> LENGTH: 1404
<212> TYPE: DNA
<213> ORGANISM: Issatchenkia orientalis

<400> SEQUENCE: 19
atgtctatta gtgaaaaata ttttcctcaa gaacctcaat ctcctgaatt gaaaactgca      60
attccaggtc tcaatcaaa ggcaaagctc gaggaattat ctgctgtcta tgatacaaag     120
gctgcatatt ttgttaccga ctactacaaa tctcttggta actatattgt ggatgcagat    180
ggcaacaagc tactagattc ttattgccaa atctcttcta tcgcattggg ttacaataat    240
ccagcattat taaaagtagc acattctgat gaaatgacag ttgctttatg taacagacct    300
gctttggcat gttttccatc cactgattac tatgaaatac taagaaaggg attgttgtcc    360
gttgctccaa agggattaga taaggtttgt actgcacaca cgggatctga tgccaatgaa    420
atggcattta aggctgcatt tttgtttcaa gcaagtaaga agagaggtga caaaccattt    480
accagcgaag agctggaatc tgtcatggag aacaagttgc aggcacctc tgacatggtt    540 atcctgtcat ttgaaaaagg gttccatggt agattgtttg gatctttatc taccactaga    600
tctaaagcta ttcacaaact ggatattcct gcgtttgaat ggccaaaggc tccattccct    660
cagttaaagt atcctctgga tcaattccaa gctgaaaaca aagcagaaga gaaagatgt    720 ttgaaggctt tagaggaaat tattgtcaac tctcctgcca aaattgcagc tgcaatcatt    780
gaaccggtcc aatctgaagg tggtgataat catgcttcac cagaattctt ccaaggtatt    840 agaaaatca ccaaaaagca cggtgtcatt cttattgttg atgaagttca aacaggaggt    900

```
ggtgcttctg gtaagatgtg gttacatgaa cactatggca ttgtcccaga catcatgact    960
ttttctaaaa aaatgcaaaa tgcaggtttc ttttcagtg aagcaggtct tgctggggac    1020
caaccattca gacaattcaa tacctggtgc ggtgatccat caaaagctct aattgcaaga    1080
accataattg aagaaattaa agataagaac ctattgacta gtgttaccga acaggtgac    1140 tacctatatt caaagctcga agcaatttca gcaaagtatg acaaaatgat caacttgaga    1200
ggtaagggaa gaggtttctt tattgcattt gatgccccaa caccggagtt aagaaacaaa    1260
tttattgctg aatgtaagaa attaggttta acattggtg gatgcggtga acaaggtgtt    1320
agattgagac ctgcattagt ttttgaaaag aagcatgctg atatcttagc ctccattatt    1380
gatcaagctt tttccaaaat ttaa                                           1404

<210> SEQ ID NO 20
<211> LENGTH: 467
<212> TYPE: PRT
<213> ORGANISM: Issatchenkia orientalis

<400> SEQUENCE: 20

Met Ser Ile Ser Glu Lys Tyr Phe Pro Gln Glu Pro Gln Ser Pro Glu
1               5                   10                  15

Leu Lys Thr Ala Ile Pro Gly Pro Gln Ser Lys Ala Lys Leu Glu Glu
            20                  25                  30

Leu Ser Ala Val Tyr Asp Thr Lys Ala Ala Tyr Phe Val Thr Asp Tyr
        35                  40                  45

Tyr Lys Ser Leu Gly Asn Tyr Ile Val Asp Ala Asp Gly Asn Lys Leu
    50                  55                  60

Leu Asp Ser Tyr Cys Gln Ile Ser Ser Ile Ala Leu Gly Tyr Asn Asn
65                  70                  75                  80

Pro Ala Leu Leu Lys Val Ala His Ser Asp Glu Met Thr Val Ala Leu
                85                  90                  95

Cys Asn Arg Pro Ala Leu Ala Cys Phe Pro Ser Thr Asp Tyr Tyr Glu
            100                 105                 110

Ile Leu Lys Lys Gly Leu Leu Ser Val Ala Pro Lys Gly Leu Asp Lys
        115                 120                 125

Val Cys Thr Ala His Thr Gly Ser Asp Ala Asn Glu Met Ala Phe Lys
    130                 135                 140

Ala Ala Phe Leu Phe Gln Ala Ser Lys Lys Arg Gly Asp Lys Pro Phe
145                 150                 155                 160

Thr Ser Glu Glu Leu Glu Ser Val Met Glu Asn Lys Leu Pro Gly Thr
                165                 170                 175

Ser Asp Met Val Ile Leu Ser Phe Glu Lys Gly Phe His Gly Arg Leu
            180                 185                 190

Phe Gly Ser Leu Ser Thr Thr Arg Ser Lys Ala Ile His Lys Leu Asp
        195                 200                 205

Ile Pro Ala Phe Glu Trp Pro Lys Ala Pro Phe Pro Gln Leu Lys Tyr
    210                 215                 220

Pro Leu Asp Gln Phe Gln Ala Glu Asn Lys Ala Glu Glu Arg Cys
225                 230                 235                 240

Leu Lys Ala Leu Glu Glu Ile Val Asn Ser Pro Ala Lys Ile Ala
                245                 250                 255

Ala Ala Ile Ile Glu Pro Val Gln Ser Glu Gly Gly Asp Asn His Ala
            260                 265                 270

Ser Pro Glu Phe Phe Gln Gly Ile Arg Glu Ile Thr Lys Lys His Gly
```

```
                275                 280                 285
Val Ile Leu Ile Val Asp Glu Val Gln Thr Gly Gly Gly Ala Ser Gly
    290                 295                 300

Lys Met Trp Leu His Glu His Tyr Gly Ile Val Pro Asp Ile Met Thr
305                 310                 315                 320

Phe Ser Lys Lys Met Gln Asn Ala Gly Phe Phe Ser Glu Ala Gly
            325                 330                 335

Leu Ala Gly Asp Gln Pro Phe Arg Gln Phe Asn Thr Trp Cys Gly Asp
            340                 345                 350

Pro Ser Lys Ala Leu Ile Ala Arg Thr Ile Ile Glu Glu Ile Lys Asp
            355                 360                 365

Lys Asn Leu Leu Thr Ser Val Thr Glu Thr Gly Asp Tyr Leu Tyr Ser
    370                 375                 380

Lys Leu Glu Ala Ile Ser Ala Lys Tyr Asp Lys Met Ile Asn Leu Arg
385                 390                 395                 400

Gly Lys Gly Arg Gly Phe Phe Ile Ala Phe Asp Ala Pro Thr Pro Glu
                405                 410                 415

Leu Arg Asn Lys Phe Ile Ala Glu Cys Lys Lys Leu Gly Leu Asn Ile
            420                 425                 430

Gly Gly Cys Gly Glu Gln Gly Val Arg Leu Arg Pro Ala Leu Val Phe
        435                 440                 445

Glu Lys Lys His Ala Asp Ile Leu Ala Ser Ile Asp Gln Ala Phe
450                 455                 460

Ser Lys Ile
465

<210> SEQ ID NO 21
<211> LENGTH: 475
<212> TYPE: PRT
<213> ORGANISM: Saccharomyces kluyveri

<400> SEQUENCE: 21

Met Pro Ser Tyr Ser Val Ala Glu Leu Tyr Tyr Pro Asp Glu Pro Thr
1               5                   10                  15

Glu Pro Lys Ile Ser Thr Ser Ser Tyr Pro Gly Pro Lys Ala Lys Gln
            20                  25                  30

Glu Leu Glu Lys Leu Ser Asn Val Phe Asp Thr Arg Ala Ala Tyr Leu
        35                  40                  45

Leu Ala Asp Tyr Tyr Lys Ser Arg Gly Asn Tyr Ile Val Asp Gln Asp
    50                  55                  60

Gly Asn Val Leu Leu Asp Val Tyr Ala Gln Ile Ser Ser Ile Ala Leu
65                  70                  75                  80

Gly Tyr Asn Asn Pro Glu Ile Leu Lys Val Ala Lys Ser Asp Ala Met
                85                  90                  95

Ser Val Ala Leu Ala Asn Arg Pro Ala Leu Ala Cys Phe Pro Ser Asn
            100                 105                 110

Asp Tyr Gly Gln Leu Leu Glu Asp Gly Leu Leu Lys Ala Ala Pro Gln
        115                 120                 125

Gly Gln Asp Lys Ile Trp Thr Ala Leu Ser Gly Ser Asp Ala Asn Glu
    130                 135                 140

Thr Ala Phe Lys Ala Cys Phe Met Tyr Gln Ala Ala Lys Lys Arg Asn
145                 150                 155                 160

Gly Arg Ser Phe Ser Thr Glu Glu Leu Glu Ser Val Met Asp Asn Gln
                165                 170                 175
```

```
Leu Pro Gly Thr Ser Glu Met Val Ile Cys Ser Phe Glu Lys Gly Phe
                180                 185                 190

His Gly Arg Leu Phe Gly Ser Leu Ser Thr Thr Arg Ser Lys Pro Ile
            195                 200                 205

His Lys Leu Asp Ile Pro Ala Phe Asn Trp Pro Lys Ala Pro Phe Pro
        210                 215                 220

Asp Leu Lys Tyr Pro Leu Glu Glu Asn Lys Glu Ala Asn Lys Ala Glu
225                 230                 235                 240

Glu Ser Ser Cys Ile Glu Lys Phe Ser Gln Ile Val Gln Glu Trp Gln
                245                 250                 255

Gly Lys Ile Ala Ala Val Ile Ile Glu Pro Ile Gln Ser Glu Gly Gly
            260                 265                 270

Asp Asn His Ala Ser Ser Asp Phe Phe Gln Lys Leu Arg Glu Ile Thr
        275                 280                 285

Ile Glu Asn Gly Ile Leu Met Ile Val Asp Glu Val Gln Thr Gly Val
    290                 295                 300

Gly Ala Thr Gly Lys Met Trp Ala His Glu His Trp Asn Leu Ser Asn
305                 310                 315                 320

Pro Pro Asp Leu Val Thr Phe Ser Lys Lys Phe Gln Ala Ala Gly Phe
                325                 330                 335

Tyr Tyr His Asp Pro Lys Leu Gln Pro Asp Gln Pro Phe Arg Gln Phe
            340                 345                 350

Asn Thr Trp Cys Gly Asp Pro Ser Lys Ala Leu Ile Ala Lys Val Ile
        355                 360                 365

Tyr Glu Glu Ile Val Lys His Asp Leu Val Thr Arg Thr Ala Glu Val
    370                 375                 380

Gly Asn Tyr Leu Phe Asn Arg Leu Glu Lys Leu Phe Glu Gly Lys Asn
385                 390                 395                 400

Tyr Ile Gln Asn Leu Arg Gly Lys Gly Gln Gly Thr Tyr Ile Ala Phe
                405                 410                 415

Asp Phe Gly Thr Ser Ser Glu Arg Asp Ser Phe Leu Ser Arg Leu Arg
            420                 425                 430

Cys Asn Gly Ala Asn Val Ala Gly Cys Gly Asp Ser Ala Val Arg Leu
        435                 440                 445

Arg Pro Ser Leu Thr Phe Glu Glu Lys His Ala Asp Val Leu Val Ser
450                 455                 460

Ile Phe Asp Lys Thr Leu Arg Gln Leu Tyr Gly
465                 470                 475

<210> SEQ ID NO 22
<211> LENGTH: 451
<212> TYPE: PRT
<213> ORGANISM: Streptomyces avermitilis

<400> SEQUENCE: 22

Met Thr Pro Gln Pro Asn Pro Gln Val Gly Ala Ala Val Lys Ala Ala
1               5                   10                  15

Asp Arg Ala His Val Phe His Ser Trp Ser Ala Gln Glu Leu Ile Asp
                20                  25                  30

Pro Leu Ala Val Ala Gly Ala Glu Gly Ser Tyr Phe Trp Asp Tyr Asp
            35                  40                  45

Gly Arg Arg Tyr Leu Asp Phe Thr Ser Gly Leu Val Phe Thr Asn Ile
        50                  55                  60

Gly Tyr Gln His Pro Lys Val Val Ala Ala Ile Gln Glu Gln Ala Ala
65                  70                  75                  80
```

Ser Leu Thr Thr Phe Ala Pro Ala Phe Ala Val Glu Ala Arg Ser Glu
            85                  90                  95

Ala Ala Arg Leu Ile Ala Glu Arg Thr Pro Gly Asp Leu Asp Lys Ile
        100                 105                 110

Phe Phe Thr Asn Gly Gly Ala Asp Ala Ile Glu His Ala Val Arg Met
    115                 120                 125

Ala Arg Ile His Thr Gly Arg Pro Lys Val Leu Ser Ala Tyr Arg Ser
130                 135                 140

Tyr His Gly Gly Thr Gln Gln Ala Val Asn Ile Thr Gly Asp Pro Arg
145                 150                 155                 160

Arg Trp Ala Ser Asp Ser Ala Ser Ala Gly Val Val His Phe Trp Ala
                165                 170                 175

Pro Tyr Leu Tyr Arg Ser Arg Phe Tyr Ala Glu Thr Glu Gln Gln Glu
            180                 185                 190

Cys Glu Arg Ala Leu Glu His Leu Glu Thr Thr Ile Ala Phe Glu Gly
        195                 200                 205

Pro Gly Thr Ile Ala Ala Ile Val Leu Glu Thr Val Pro Gly Thr Ala
    210                 215                 220

Gly Ile Met Val Pro Pro Gly Tyr Leu Ala Gly Val Arg Glu Leu
225                 230                 235                 240

Cys Asp Lys Tyr Gly Ile Val Phe Val Leu Asp Glu Val Met Ala Gly
                245                 250                 255

Phe Gly Arg Thr Gly Glu Trp Phe Ala Ala Asp Leu Phe Asp Val Thr
            260                 265                 270

Pro Asp Leu Met Thr Phe Ala Lys Gly Val Asn Ser Gly Tyr Val Pro
        275                 280                 285

Leu Gly Gly Val Ala Ile Ser Gly Lys Ile Ala Glu Thr Phe Gly Lys
    290                 295                 300

Arg Ala Tyr Pro Gly Gly Leu Thr Tyr Ser Gly His Pro Leu Ala Cys
305                 310                 315                 320

Ala Ala Ala Val Ala Thr Ile Asn Val Met Ala Glu Gly Val Val
                325                 330                 335

Glu Asn Ala Ala Asn Leu Gly Ala Arg Val Ile Glu Pro Gly Leu Arg
            340                 345                 350

Glu Leu Ala Glu Arg His Pro Ser Val Gly Glu Val Arg Gly Val Gly
        355                 360                 365

Met Phe Trp Ala Leu Glu Leu Val Lys Asp Arg Glu Thr Arg Glu Pro
    370                 375                 380

Leu Val Pro Tyr Asn Ala Ala Gly Glu Ala Asn Ala Pro Met Ala Ala
385                 390                 395                 400

Phe Gly Ala Ala Ala Lys Ala Asn Gly Leu Trp Pro Phe Ile Asn Met
                405                 410                 415

Asn Arg Thr His Val Val Pro Pro Cys Asn Val Thr Glu Ala Glu Ala
            420                 425                 430

Lys Glu Gly Leu Ala Ala Leu Asp Ala Ala Leu Ser Val Ala Asp Glu
        435                 440                 445

Tyr Thr Val
    450

<210> SEQ ID NO 23
<211> LENGTH: 419
<212> TYPE: PRT
<213> ORGANISM: Streptomyces avermitilis

<400> SEQUENCE: 23

```
Met Ser Ala Leu Ser Pro His Leu Arg Gln Ala Thr Pro Val Val Ala
1               5                   10                  15

Val Arg Gly Glu Gly Val His Leu Tyr Gly Glu Asp Gly Arg Arg Tyr
            20                  25                  30

Leu Asp Phe Thr Ala Gly Ile Gly Val Thr Ser Thr Gly His Cys His
        35                  40                  45

Pro Arg Val Val Ala Ala Gln Glu Gln Ala Gly Thr Leu Val His
50                  55                  60

Gly Gln Tyr Thr Thr Val Leu His Pro Pro Leu Arg Arg Leu Val Asp
65                  70                  75                  80

Arg Leu Gly Glu Val Leu Pro Ala Gly Leu Asp Ser Leu Phe Phe Thr
                85                  90                  95

Asn Ser Gly Ser Glu Ala Val Glu Ala Ala Leu Arg Leu Ala Arg Gln
            100                 105                 110

Ala Thr Gly Arg Pro Asn Val Leu Val Cys His Gly Gly Phe His Gly
        115                 120                 125

Arg Thr Val Ala Ala Ala Met Thr Thr Ser Gly Thr Arg Phe Arg
130                 135                 140

Ser Gly Phe Ser Pro Leu Met Ser Gly Val Val Thr Pro Phe Pro
145                 150                 155                 160

Thr Ala Phe Arg Tyr Gly Trp Asp Glu Thr Ala Thr Arg Phe Ala
                165                 170                 175

Leu Gln Glu Leu Asp Tyr Thr Leu Arg Thr Ile Ser Ser Pro Asp Asp
            180                 185                 190

Thr Ala Ala Ile Ile Val Glu Pro Val Leu Gly Glu Gly Gly Tyr Val
        195                 200                 205

Pro Ala Thr Arg Ala Phe Leu Glu Gly Leu Arg Glu Arg Ala Asp Arg
210                 215                 220

His Gly Phe Val Leu Ile Leu Asp Glu Val Gln Thr Gly Val Gly Arg
225                 230                 235                 240

Thr Gly Arg Phe Trp Gly His Asp His Phe Gly Val Thr Pro Asp Ile
                245                 250                 255

Leu Ile Thr Ala Lys Gly Leu Ala Ser Gly Phe Pro Leu Ser Gly Ile
            260                 265                 270

Ala Ala Ser Ala Glu Leu Met Gly Lys Ala Trp Pro Gly Ser Gln Gly
        275                 280                 285

Gly Thr Tyr Gly Ala Asn Ala Val Ala Cys Ala Ala Cys Ala Thr
290                 295                 300

Leu Asp Val Val Arg Asp Glu Lys Leu Val Asp Asn Ala Glu Ala Met
305                 310                 315                 320

Gly Ala Arg Leu Arg Ala Gly Leu Ala Ala Val Ala Ala Thr Thr Pro
                325                 330                 335

Ala Ile Gly Asp Val Arg Gly Leu Gly Leu Met Leu Ala Ser Glu Phe
            340                 345                 350

Val Thr Glu Asp Gly Gly Pro Asp Pro Glu Thr Ala Ala Arg Val Gln
        355                 360                 365

Arg Ala Ala Val Asp Glu Gly Leu Leu Leu Leu Cys Gly Ala Trp
370                 375                 380

Asn Gln Val Val Arg Met Ile Pro Ala Leu Val Ile Asp Glu Ala Glu
385                 390                 395                 400

Val Asp Glu Gly Leu Arg Ala Trp Ser Ala Ala Val Glu Val Gly Val
                405                 410                 415
```

Pro Ala Arg

<210> SEQ ID NO 24
<211> LENGTH: 471
<212> TYPE: PRT
<213> ORGANISM: Saccharomyces cerevisiae

<400> SEQUENCE: 24

```
Met Ser Ile Cys Glu Gln Tyr Tyr Pro Glu Pro Thr Lys Pro Thr
1               5                   10                  15

Val Lys Thr Glu Ser Ile Pro Gly Pro Glu Ser Gln Lys Gln Leu Lys
                20                  25                  30

Glu Leu Gly Glu Val Phe Asp Thr Arg Pro Ala Tyr Phe Leu Ala Asp
            35                  40                  45

Tyr Glu Lys Ser Leu Gly Asn Tyr Ile Thr Asp Val Asp Gly Asn Thr
    50                  55                  60

Tyr Leu Asp Leu Tyr Ala Gln Ile Ser Ser Ile Ala Leu Gly Tyr Asn
65                  70                  75                  80

Asn Pro Ala Leu Ile Lys Ala Ala Gln Ser Pro Glu Met Ile Arg Ala
                85                  90                  95

Leu Val Asp Arg Pro Ala Leu Gly Asn Phe Pro Ser Lys Asp Leu Asp
            100                 105                 110

Lys Ile Leu Lys Gln Ile Leu Lys Ser Ala Pro Lys Gly Gln Asp His
        115                 120                 125

Val Trp Ser Gly Leu Ser Gly Ala Asp Ala Asn Glu Leu Ala Phe Lys
    130                 135                 140

Ala Ala Phe Ile Tyr Tyr Arg Ala Lys Gln Arg Gly Tyr Asp Ala Asp
145                 150                 155                 160

Phe Ser Glu Lys Glu Asn Leu Ser Val Met Asp Asn Asp Ala Pro Gly
                165                 170                 175

Ala Pro His Leu Ala Val Leu Ser Phe Lys Arg Ala Phe His Gly Arg
            180                 185                 190

Leu Phe Ala Ser Gly Ser Thr Thr Cys Ser Lys Pro Ile His Lys Leu
        195                 200                 205

Asp Phe Pro Ala Phe His Trp Pro His Ala Glu Tyr Pro Ser Tyr Gln
    210                 215                 220

Tyr Pro Leu Asp Glu Asn Ser Asp Ala Asn Arg Lys Glu Asp His
225                 230                 235                 240

Cys Leu Ala Ile Val Glu Glu Leu Ile Lys Thr Trp Ser Ile Pro Val
                245                 250                 255

Ala Ala Leu Ile Ile Glu Pro Ile Gln Ser Glu Gly Gly Asp Asn His
            260                 265                 270

Ala Ser Lys Tyr Phe Leu Gln Lys Leu Arg Asp Ile Thr Leu Lys Tyr
        275                 280                 285

Asn Val Val Tyr Ile Ile Asp Glu Val Gln Thr Gly Val Gly Ala Thr
    290                 295                 300

Gly Lys Leu Trp Cys His Glu Tyr Ala Asp Ile Gln Pro Pro Val Asp
305                 310                 315                 320

Leu Val Thr Phe Ser Lys Lys Phe Gln Ser Ala Gly Tyr Phe Phe His
                325                 330                 335

Asp Pro Lys Phe Ile Pro Asn Lys Pro Tyr Arg Gln Phe Asn Thr Trp
            340                 345                 350

Cys Gly Glu Pro Ala Arg Met Ile Ile Ala Gly Ala Ile Gly Gln Glu
        355                 360                 365
```

```
Ile Ser Asp Lys Lys Leu Thr Glu Gln Cys Ser Arg Val Gly Asp Tyr
    370                 375                 380

Leu Phe Lys Lys Leu Glu Gly Leu Gln Lys Lys Tyr Pro Glu Asn Phe
385                 390                 395                 400

Gln Asn Leu Arg Gly Lys Gly Arg Gly Thr Phe Ile Ala Trp Asp Leu
            405                 410                 415

Pro Thr Gly Glu Lys Arg Asp Leu Leu Leu Lys Lys Leu Lys Leu Asn
        420                 425                 430

Gly Cys Asn Val Gly Gly Cys Ala Val His Ala Val Arg Leu Arg Pro
        435                 440                 445

Ser Leu Thr Phe Glu Glu Lys His Ala Asp Ile Phe Ile Glu Ala Leu
    450                 455                 460

Ala Lys Ser Val Asn Glu Leu
465                 470

<210> SEQ ID NO 25
<211> LENGTH: 813
<212> TYPE: DNA
<213> ORGANISM: Issatchenkia orientalis

<400> SEQUENCE: 25
atgtttggta atatttccca aagacttgca ggcaagaaca tcctaattac aggtgcgtcc      60
actggtatcg gataccatac agcaaagtat tttgcagaag ctgcaaatgg agacttgaag     120
ttggttttgg ctgcaagaag aaaggagaag ctggaggcac taaaggcaga cttgcttgcc     180
aagtatccat ccatcaaagt ccatattgag agtttggatg tctccaaaac ggaaaccatt     240
gcacctttct taaaaggttt acctgaggaa ttttcaattg tcgacgtgtt ggtcaacaat     300
gcaggtaagg cgcttggttt ggatccaatt ggctctgtcg atccaaagga cgtggatgaa     360
atgttccaga ccaatgtttt gggtatgatt caattgaccc agttggttgt acagcaaatg     420
aaggagagaa actccgggga cattgtccaa ctaggttcag tggctggtag aaacccatac     480
ccaggtggtg gtatctactg tgcctccaag gccgcattga gatcttttac acatgtattg     540
agagaggaat tgattaatac caagattaga gtgattgaaa tcgagcctgg aaatgttgca     600
actgaggaat tttctttgac cagattcaaa ggtgataagt ccaaggccga aaaggtctat     660
gagggaaccg agccattgta tggtaccgat attgcagaat tgattctatt tgcagtttct     720
agacctcaaa acactgttat tgcagaaaca cttgttttg ctagtaacca agcttctgct     780
taccatattt tcagaggatc attagataaa tag                                  813

<210> SEQ ID NO 26
<211> LENGTH: 270
<212> TYPE: PRT
<213> ORGANISM: Issatchenkia orientalis

<400> SEQUENCE: 26

Met Phe Gly Asn Ile Ser Gln Arg Leu Ala Gly Lys Asn Ile Leu Ile
1               5                   10                  15

Thr Gly Ala Ser Thr Gly Ile Gly Tyr His Thr Ala Lys Tyr Phe Ala
            20                  25                  30

Glu Ala Ala Asn Gly Asp Leu Lys Leu Val Leu Ala Ala Arg Arg Lys
        35                  40                  45

Glu Lys Leu Glu Ala Leu Lys Ala Asp Leu Leu Ala Lys Tyr Pro Ser
    50                  55                  60

Ile Lys Val His Ile Glu Ser Leu Asp Val Ser Lys Thr Glu Thr Ile
```

```
              65                  70                  75                  80
Ala Pro Phe Leu Lys Gly Leu Pro Glu Glu Phe Ser Ile Val Asp Val
                    85                  90                  95

Leu Val Asn Asn Ala Gly Lys Ala Leu Gly Leu Asp Pro Ile Gly Ser
                    100                 105                 110

Val Asp Pro Lys Asp Val Asp Glu Met Phe Gln Thr Asn Val Leu Gly
                    115                 120                 125

Met Ile Gln Leu Thr Gln Leu Val Val Gln Gln Met Lys Glu Arg Asn
                    130                 135                 140

Ser Gly Asp Ile Val Gln Leu Gly Ser Val Ala Gly Arg Asn Pro Tyr
145                 150                 155                 160

Pro Gly Gly Gly Ile Tyr Cys Ala Ser Lys Ala Ala Leu Arg Ser Phe
                    165                 170                 175

Thr His Val Leu Arg Glu Glu Leu Ile Asn Thr Lys Ile Arg Val Ile
                    180                 185                 190

Glu Ile Glu Pro Gly Asn Val Ala Thr Glu Glu Phe Ser Leu Thr Arg
                    195                 200                 205

Phe Lys Gly Asp Lys Ser Lys Ala Glu Lys Val Tyr Glu Gly Thr Glu
                    210                 215                 220

Pro Leu Tyr Gly Thr Asp Ile Ala Glu Leu Ile Leu Phe Ala Val Ser
225                 230                 235                 240

Arg Pro Gln Asn Thr Val Ile Ala Glu Thr Leu Val Phe Ala Ser Asn
                    245                 250                 255

Gln Ala Ser Ala Tyr His Ile Phe Arg Gly Ser Leu Asp Lys
                    260                 265                 270

<210> SEQ ID NO 27
<211> LENGTH: 248
<212> TYPE: PRT
<213> ORGANISM: Escherichia coli

<400> SEQUENCE: 27

Met Ile Val Leu Val Thr Gly Ala Thr Ala Gly Phe Gly Glu Cys Ile
1               5                   10                  15

Thr Arg Arg Phe Ile Gln Gln Gly His Lys Val Ile Ala Thr Gly Arg
                    20                  25                  30

Arg Gln Glu Arg Leu Gln Glu Leu Lys Asp Glu Leu Gly Asp Asn Leu
                    35                  40                  45

Tyr Ile Ala Gln Leu Asp Val Arg Asn Arg Ala Ala Ile Glu Glu Met
                    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                    85                  90                  95

Glu Asp Trp Glu Thr Met Ile Asp Thr Asn Asn Lys Gly Leu Val Tyr
                    100                 105                 110

Met Thr Arg Ala Val Leu Pro Gly Met Val Glu Arg Asn His Gly His
                    115                 120                 125

Ile Ile Asn Ile Gly Ser Thr Ala Gly Ser Trp Pro Tyr Ala Gly Gly
                    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                    165                 170                 175
```

```
Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 28
<211> LENGTH: 298
<212> TYPE: PRT
<213> ORGANISM: Alcaligenes faecalis

<400> SEQUENCE: 28

Met Ser Asn Thr Ile Ala Phe Ile Gly Leu Gly His Met Gly Lys Pro
1               5                   10                  15

Met Ala Leu Asn Leu Leu Lys Ala Gly His Ser Leu Asn Val Phe Asp
            20                  25                  30

Leu Asn Ala Gln Ala Met Gln Glu Leu Gln Ala Ala Gly Ala Gln Val
        35                  40                  45

Gly Glu Ser Ala Val Gln Ile Ala Gln Asp Ala Gln Met Val Phe Thr
    50                  55                  60

Met Leu Pro Ala Gly Arg His Val Arg Gln Val Tyr Glu Gly Glu Asn
65                  70                  75                  80

Gly Leu Leu Gln Thr Val Ala Pro Gly Thr Val Leu Val Asp Cys Ser
                85                  90                  95

Thr Ile Asp Ala Gln Thr Ser Gln Asp Leu Ala Ala Lys Ala Ser Lys
            100                 105                 110

Leu Gly Leu Phe Met Leu Asp Ala Pro Val Ser Gly Gly Thr Gly Gly
        115                 120                 125

Ala Ile Ala Gly Thr Leu Thr Phe Met Val Gly Gly Glu Asp Gln Ala
    130                 135                 140

Leu Glu Lys Ala Arg Pro Tyr Leu Asp Ala Met Gly Lys Asn Ile Phe
145                 150                 155                 160

His Ala Gly Lys Ala Gly Ala Gly Gln Val Ala Lys Ile Cys Asn Asn
                165                 170                 175

Met Leu Leu Gly Ile Leu Met Ala Gly Thr Ala Glu Ala Leu Ala Leu
            180                 185                 190

Gly Val Ala His Gly Leu Asp Pro Ala Val Leu Ser Thr Ile Met Ala
        195                 200                 205

Arg Ser Ser Gly Arg Asn Trp Ala Thr Glu Leu Tyr Asn Pro Trp Pro
    210                 215                 220

Gly Val Met Pro Asp Val Pro Ala Ser Arg Asp Tyr Gln Gly Gly Phe
225                 230                 235                 240

Ala Thr Gly Leu Met Leu Lys Asp Leu Gly Leu Ala Ala Asp Ala Ala
                245                 250                 255

Val Ser Gln Asn Ser Ala Thr Pro Leu Gly Glu Leu Ala Arg Asn Leu
            260                 265                 270

Phe Ala Leu His Ala Ala Gln Gly Gln Asn Ala Gly Leu Asp Phe Ser
        275                 280                 285

Ser Ile Leu Asn Leu Tyr Arg Gln Lys His
    290                 295
```

<210> SEQ ID NO 29
<211> LENGTH: 314
<212> TYPE: PRT
<213> ORGANISM: Metallosphaera sedula

<400> SEQUENCE: 29

Met Thr Glu Lys Val Ser Val Gly Ala Gly Val Ile Gly Val Gly
1               5                   10                  15

Trp Ala Thr Leu Phe Ala Ser Lys Gly Tyr Ser Val Ser Leu Tyr Thr
                20                  25                  30

Glu Lys Lys Glu Thr Leu Asp Lys Gly Ile Glu Lys Leu Arg Asn Tyr
            35                  40                  45

Val Gln Val Met Lys Asn Asn Ser Gln Ile Thr Glu Asp Val Asn Thr
50                  55                  60

Val Ile Ser Arg Val Ser Pro Thr Thr Asn Leu Asp Glu Ala Val Arg
65                  70                  75                  80

Gly Ala Asn Phe Val Ile Glu Ala Val Ile Glu Asp Tyr Asp Ala Lys
                85                  90                  95

Lys Lys Ile Phe Gly Tyr Leu Asp Ser Val Leu Asp Lys Glu Val Ile
            100                 105                 110

Leu Ala Ser Ser Thr Ser Gly Leu Leu Ile Thr Glu Val Gln Lys Ala
            115                 120                 125

Met Ser Lys His Pro Glu Arg Ala Val Ile Ala His Pro Trp Asn Pro
130                 135                 140

Pro His Leu Leu Pro Leu Val Glu Ile Val Pro Gly Glu Lys Thr Ser
145                 150                 155                 160

Met Glu Val Val Glu Arg Thr Lys Ser Leu Met Glu Lys Leu Asp Arg
                165                 170                 175

Ile Val Val Leu Lys Lys Glu Ile Pro Gly Phe Ile Gly Asn Arg
            180                 185                 190

Leu Ala Phe Ala Leu Phe Arg Glu Ala Val Tyr Leu Val Asp Glu Gly
            195                 200                 205

Val Ala Thr Val Glu Asp Ile Asp Lys Val Met Thr Ala Ala Ile Gly
210                 215                 220

Leu Arg Trp Ala Phe Met Gly Pro Phe Leu Thr Tyr His Leu Gly Gly
225                 230                 235                 240

Gly Glu Gly Gly Leu Glu Tyr Phe Phe Asn Arg Gly Phe Gly Tyr Gly
                245                 250                 255

Ala Asn Glu Trp Met His Thr Leu Ala Lys Tyr Asp Lys Phe Pro Tyr
            260                 265                 270

Thr Gly Val Thr Lys Ala Ile Gln Gln Met Lys Glu Tyr Ser Phe Ile
            275                 280                 285

Lys Gly Lys Thr Phe Gln Glu Ile Ser Lys Trp Arg Asp Glu Lys Leu
290                 295                 300

Leu Lys Val Tyr Lys Leu Val Trp Glu Lys
305                 310

<210> SEQ ID NO 30
<211> LENGTH: 295
<212> TYPE: PRT
<213> ORGANISM: Pseudomonas putida

<400> SEQUENCE: 30

Met Arg Ile Ala Phe Ile Gly Leu Gly Asn Met Gly Ala Pro Met Ala
1               5                   10                  15

-continued

Arg Asn Leu Ile Lys Ala Gly His Gln Leu Asn Leu Phe Asp Leu Asn
            20                  25                  30

Lys Ala Val Leu Ala Glu Leu Ala Glu Leu Gly Gly Gln Ile Ser Pro
        35                  40                  45

Ser Pro Lys Asp Ala Ala Asn Ser Glu Leu Val Ile Thr Met Leu
    50                  55                  60

Pro Ala Ala Ala His Val Arg Ser Val Tyr Leu Asn Glu Asp Gly Val
65                  70                  75                  80

Leu Ala Gly Ile Arg Pro Gly Thr Pro Thr Val Asp Cys Ser Thr Ile
                85                  90                  95

Asp Pro Gln Thr Ala Arg Asp Val Ser Lys Ala Ala Ala Lys Gly
                100                 105                 110

Val Asp Met Gly Asp Ala Pro Val Ser Gly Gly Thr Gly Ala Ala
            115                 120                 125

Ala Gly Thr Leu Thr Phe Met Val Gly Ala Ser Thr Glu Leu Phe Ala
    130                 135                 140

Ser Leu Lys Pro Val Leu Glu Gln Met Gly Arg Asn Ile Val His Cys
145                 150                 155                 160

Gly Glu Val Gly Thr Gly Gln Ile Ala Lys Ile Cys Asn Asn Leu Leu
                165                 170                 175

Leu Gly Ile Ser Met Ile Gly Val Ser Glu Ala Met Ala Leu Gly Asn
            180                 185                 190

Ala Leu Gly Ile Asp Thr Lys Val Leu Ala Gly Ile Ile Asn Ser Ser
        195                 200                 205

Thr Gly Arg Cys Trp Ser Ser Asp Thr Tyr Asn Pro Trp Pro Gly Ile
210                 215                 220

Ile Glu Thr Ala Pro Ala Ser Arg Gly Tyr Thr Gly Gly Phe Gly Ala
225                 230                 235                 240

Glu Leu Met Leu Lys Asp Leu Gly Leu Ala Thr Glu Ala Ala Arg Gln
                245                 250                 255

Ala His Gln Pro Val Ile Leu Gly Ala Val Ala Gln Gln Leu Tyr Gln
            260                 265                 270

Ala Met Ser Leu Arg Gly Glu Gly Gly Lys Asp Phe Ser Ala Ile Val
        275                 280                 285

Glu Gly Tyr Arg Lys Lys Asp
    290                 295

<210> SEQ ID NO 31
<211> LENGTH: 295
<212> TYPE: PRT
<213> ORGANISM: Pseudomonas putida

<400> SEQUENCE: 31

Met Arg Ile Ala Phe Ile Gly Leu Gly Asn Met Gly Ala Pro Met Ala
1               5                   10                  15

Arg Asn Leu Ile Lys Ala Gly His Gln Leu Asn Leu Phe Asp Leu Asn
            20                  25                  30

Lys Thr Val Leu Ala Glu Leu Ala Glu Leu Gly Gly Gln Ile Ser Pro
        35                  40                  45

Ser Pro Lys Asp Ala Ala Ser Ser Glu Leu Val Ile Thr Met Leu
    50                  55                  60

Pro Ala Ala Ala His Val Arg Ser Val Tyr Leu Asn Asp Asp Gly Val
65                  70                  75                  80

Leu Ala Gly Ile Arg Pro Gly Thr Pro Thr Val Asp Cys Ser Thr Ile

```
            85                  90                  95
Asp Pro Gln Thr Ala Arg Asp Val Ser Lys Ala Ala Ala Lys Gly
            100                 105                 110

Val Asp Met Gly Asp Ala Pro Val Ser Gly Gly Thr Gly Ala Ala
            115                 120                 125

Ala Gly Thr Leu Thr Phe Met Val Gly Ala Ser Ala Glu Leu Phe Ala
    130                 135                 140

Ser Leu Lys Pro Val Leu Glu Gln Met Gly Arg Asn Ile Val His Cys
145                 150                 155                 160

Gly Glu Val Gly Thr Gly Gln Ile Ala Lys Ile Cys Asn Asn Leu Leu
                165                 170                 175

Leu Gly Ile Ser Met Ile Gly Val Ser Glu Ala Met Ala Leu Gly Asn
                180                 185                 190

Ala Leu Gly Ile Asp Thr Lys Val Leu Ala Gly Ile Ile Asn Ser Ser
            195                 200                 205

Thr Gly Arg Cys Trp Ser Ser Asp Thr Tyr Asn Pro Trp Pro Gly Ile
        210                 215                 220

Ile Glu Thr Ala Pro Ala Ser Arg Gly Tyr Thr Gly Phe Gly Ala
225                 230                 235                 240

Glu Leu Met Leu Lys Asp Leu Gly Leu Ala Thr Glu Ala Ala Arg Gln
                245                 250                 255

Ala His Gln Pro Val Ile Leu Gly Ala Val Ala Gln Leu Tyr Gln
            260                 265                 270

Ala Met Ser Leu Arg Gly Glu Gly Gly Lys Asp Phe Ser Ala Ile Val
        275                 280                 285

Glu Gly Tyr Arg Lys Lys Asp
        290                 295

<210> SEQ ID NO 32
<211> LENGTH: 298
<212> TYPE: PRT
<213> ORGANISM: Pseudomonas aeruginosa

<400> SEQUENCE: 32

Met Thr Asp Ile Ala Phe Leu Gly Leu Gly Asn Met Gly Gly Pro Met
1               5                   10                  15

Ala Ala Asn Leu Leu Lys Ala Gly His Arg Val Asn Val Phe Asp Leu
            20                  25                  30

Gln Pro Lys Ala Val Leu Gly Leu Val Glu Gln Gly Ala Gln Gly Ala
        35                  40                  45

Asp Ser Ala Leu Gln Cys Cys Glu Gly Ala Glu Val Val Ile Ser Met
    50                  55                  60

Leu Pro Ala Gly Gln His Val Glu Ser Leu Tyr Leu Gly Asp Asp Gly
65                  70                  75                  80

Leu Leu Ala Arg Val Ala Gly Lys Pro Leu Leu Ile Asp Cys Ser Thr
                85                  90                  95

Ile Ala Pro Glu Thr Ala Arg Lys Val Ala Glu Ala Ala Ala Ala Lys
            100                 105                 110

Gly Leu Thr Leu Leu Asp Ala Pro Val Ser Gly Gly Val Gly Ala
        115                 120                 125

Arg Ala Gly Thr Leu Ser Phe Ile Val Gly Gly Pro Ala Glu Gly Phe
    130                 135                 140

Ala Arg Ala Arg Pro Val Leu Glu Asn Met Gly Arg Asn Ile Phe His
145                 150                 155                 160
```

Ala Gly Asp His Gly Ala Gly Gln Val Ala Lys Ile Cys Asn Asn Met
            165                 170                 175

Leu Leu Gly Ile Leu Met Ala Gly Thr Ala Glu Ala Leu Ala Leu Gly
        180                 185                 190

Val Lys Asn Gly Leu Asp Pro Ala Val Leu Ser Glu Val Met Lys Gln
        195                 200                 205

Ser Ser Gly Gly Asn Trp Ala Leu Asn Leu Tyr Asn Pro Trp Pro Gly
    210                 215                 220

Val Met Pro Gln Ala Pro Ala Ser Asn Gly Tyr Ala Gly Gly Phe Gln
225                 230                 235                 240

Val Arg Leu Met Asn Lys Asp Leu Gly Leu Ala Leu Ala Asn Ala Gln
            245                 250                 255

Ala Val Gln Ala Ser Thr Pro Leu Gly Ala Leu Ala Arg Asn Leu Phe
            260                 265                 270

Ser Leu His Ala Gln Ala Asp Ala Glu His Glu Gly Leu Asp Phe Ser
        275                 280                 285

Ser Ile Gln Lys Leu Tyr Arg Gly Lys Asp
        290                 295

<210> SEQ ID NO 33
<211> LENGTH: 382
<212> TYPE: PRT
<213> ORGANISM: Ralstonia eutropha

<400> SEQUENCE: 33

Met Ala Phe Ile Tyr Tyr Leu Thr His Ile His Leu Asp Phe Gly Ala
1               5                   10                  15

Val Ser Leu Leu Lys Ser Glu Cys Glu Arg Ile Gly Ile Arg Arg Pro
            20                  25                  30

Leu Leu Val Thr Asp Lys Gly Val Val Ala Ala Gly Val Ala Gln Arg
        35                  40                  45

Ala Ile Asp Ala Met Gln Gly Leu Gln Val Ala Val Phe Asp Glu Thr
    50                  55                  60

Pro Ser Asn Pro Thr Glu Ala Met Val Arg Lys Ala Ala Ala Gln Tyr
65                  70                  75                  80

Arg Glu Ala Gly Cys Asp Gly Leu Val Ala Val Gly Gly Gly Ser Ser
            85                  90                  95

Ile Asp Leu Ala Lys Gly Ile Ala Ile Leu Ala Thr His Glu Gly Glu
        100                 105                 110

Leu Thr Thr Tyr Ala Thr Ile Glu Gly Gly Ser Ala Arg Ile Thr Asp
        115                 120                 125

Lys Ala Ala Pro Leu Ile Ala Val Pro Thr Thr Ser Gly Thr Gly Ser
    130                 135                 140

Glu Val Ala Arg Gly Ala Ile Ile Ile Leu Asp Asp Gly Arg Lys Leu
145                 150                 155                 160

Gly Phe His Ser Trp His Leu Leu Pro Lys Ser Ala Val Cys Asp Pro
            165                 170                 175

Glu Leu Thr Leu Gly Leu Pro Ala Gly Leu Thr Ala Ala Thr Gly Met
        180                 185                 190

Asp Ala Ile Ala His Cys Ile Glu Thr Phe Leu Ala Pro Ala Phe Asn
        195                 200                 205

Pro Pro Ala Asp Gly Ile Ala Leu Asp Gly Leu Glu Arg Gly Trp Gly
    210                 215                 220

His Ile Glu Arg Ala Thr Arg Asp Gly Gln Asp Arg Asp Ala Arg Leu
225                 230                 235                 240

Asn Met Met Ser Ala Ser Met Gln Gly Ala Met Ala Phe Gln Lys Gly
              245                 250                 255

Leu Gly Cys Val His Ser Leu Ser His Pro Leu Gly Gly Leu Lys Ile
            260                 265                 270

Asp Gly Arg Thr Gly Leu His His Gly Thr Leu Asn Ala Val Val Met
            275                 280                 285

Pro Ala Val Leu Arg Phe Asn Ala Asp Ala Pro Thr Val Val Arg Asp
290                 295                 300

Asp Arg Tyr Ala Arg Leu Arg Arg Ala Met His Leu Pro Asp Gly Ala
305                 310                 315                 320

Asp Ile Ala Gln Ala Val His Asp Met Thr Val Arg Leu Gly Leu Pro
                325                 330                 335

Thr Gly Leu Arg Gln Met Gly Val Thr Glu Asp Met Phe Asp Lys Val
            340                 345                 350

Ile Ala Gly Ala Leu Val Asp His Cys His Lys Thr Asn Pro Lys Glu
            355                 360                 365

Ala Ser Ala Ala Asp Tyr Arg Arg Met Leu Glu Gln Ser Met
370                 375                 380

<210> SEQ ID NO 34
<211> LENGTH: 371
<212> TYPE: PRT
<213> ORGANISM: Clostridium kluyveri

<400> SEQUENCE: 34

Met Lys Leu Leu Lys Leu Ala Pro Asp Val Tyr Lys Phe Asp Thr Ala
1               5                   10                  15

Glu Glu Phe Met Lys Tyr Phe Lys Val Gly Lys Gly Asp Phe Ile Leu
                20                  25                  30

Thr Asn Glu Phe Leu Tyr Lys Pro Phe Leu Glu Lys Phe Asn Asp Gly
            35                  40                  45

Ala Asp Ala Val Phe Gln Glu Lys Tyr Gly Leu Gly Glu Pro Ser Asp
        50                  55                  60

Glu Met Ile Asn Asn Ile Ile Lys Asp Ile Gly Asp Lys Gln Tyr Asn
65                  70                  75                  80

Arg Ile Ile Ala Val Gly Gly Gly Ser Val Ile Asp Ile Ala Lys Ile
                85                  90                  95

Leu Ser Leu Lys Tyr Thr Asp Asp Ser Leu Asp Leu Phe Glu Gly Lys
                100                 105                 110

Val Pro Leu Val Lys Asn Lys Glu Leu Ile Ile Val Pro Thr Thr Cys
            115                 120                 125

Gly Thr Gly Ser Glu Val Thr Asn Val Ser Val Ala Glu Leu Lys Arg
130                 135                 140

Arg His Thr Lys Lys Gly Ile Ala Ser Asp Glu Leu Tyr Ala Thr Tyr
145                 150                 155                 160

Ala Val Leu Val Pro Glu Phe Ile Lys Gly Leu Pro Tyr Lys Phe Phe
                165                 170                 175

Val Thr Ser Ser Val Asp Ala Leu Ile His Ala Thr Glu Ala Tyr Val
            180                 185                 190

Ser Pro Asn Ala Asn Pro Tyr Thr Asp Met Phe Ser Val Lys Ala Met
            195                 200                 205

Glu Leu Ile Leu Asn Gly Tyr Met Gln Met Val Glu Lys Gly Asn Asp
210                 215                 220

Tyr Arg Val Glu Ile Ile Glu Asp Phe Val Ile Gly Ser Asn Tyr Ala

```
                    225                 230                 235                 240
Gly Ile Ala Phe Gly Asn Ala Gly Val Gly Val His Ala Leu Ser
                245                 250                 255
Tyr Pro Ile Gly Gly Asn Tyr His Val Pro His Gly Glu Ala Asn Tyr
                260                 265                 270
Leu Phe Phe Thr Glu Ile Phe Lys Thr Tyr Tyr Glu Lys Asn Pro Asn
                275                 280                 285
Gly Lys Ile Lys Asp Val Asn Lys Leu Leu Ala Gly Ile Leu Lys Cys
                290                 295                 300
Asp Glu Ser Glu Ala Tyr Asp Ser Leu Ser Gln Leu Leu Asp Lys Leu
305                 310                 315                 320
Leu Ser Arg Lys Pro Leu Arg Glu Tyr Gly Met Lys Glu Glu Ile
                325                 330                 335
Glu Thr Phe Ala Asp Ser Val Ile Glu Gly Gln Gln Arg Leu Leu Val
                340                 345                 350
Asn Asn Tyr Glu Pro Phe Ser Arg Glu Asp Ile Val Asn Thr Tyr Lys
                355                 360                 365
Lys Leu Tyr
370

<210> SEQ ID NO 35
<211> LENGTH: 538
<212> TYPE: PRT
<213> ORGANISM: Mannheimia succiniciproducens

<400> SEQUENCE: 35

Met Thr Asp Leu Asn Gln Leu Thr Gln Glu Leu Gly Ala Leu Gly Ile
1               5                   10                  15
His Asp Val Gln Glu Val Val Tyr Asn Pro Ser Tyr Glu Leu Leu Phe
                20                  25                  30
Ala Glu Glu Thr Lys Pro Gly Leu Glu Gly Tyr Glu Lys Gly Thr Val
                35                  40                  45
Thr Asn Gln Gly Ala Val Ala Val Asn Thr Gly Ile Phe Thr Gly Arg
            50                  55                  60
Ser Pro Lys Asp Lys Tyr Ile Val Leu Asp Asp Lys Thr Lys Asp Thr
65              70                  75                  80
Val Trp Trp Thr Ser Glu Lys Val Lys Asn Asp Asn Lys Pro Met Ser
                85                  90                  95
Gln Asp Thr Trp Asn Ser Leu Lys Gly Leu Val Ala Asp Gln Leu Ser
                100                 105                 110
Gly Lys Arg Leu Phe Val Val Asp Ala Phe Cys Gly Ala Asn Lys Asp
                115                 120                 125
Thr Arg Leu Ala Val Arg Val Val Thr Glu Val Ala Trp Gln Ala His
            130                 135                 140
Phe Val Thr Asn Met Phe Ile Arg Pro Ser Ala Glu Glu Leu Lys Gly
145                 150                 155                 160
Phe Lys Pro Asp Phe Val Val Met Asn Gly Ala Lys Cys Thr Asn Pro
                165                 170                 175
Asn Trp Lys Glu Gln Gly Leu Asn Ser Glu Asn Phe Val Ala Phe Asn
                180                 185                 190
Ile Thr Glu Gly Val Gln Leu Ile Gly Gly Thr Trp Tyr Gly Gly Glu
                195                 200                 205
Met Lys Lys Gly Met Phe Ser Met Met Asn Tyr Phe Leu Pro Leu Arg
            210                 215                 220
```

```
Gly Ile Ala Ser Met His Cys Ser Ala Asn Val Gly Lys Asp Gly Asp
225                 230                 235                 240

Thr Ala Ile Phe Phe Gly Leu Ser Gly Thr Gly Lys Thr Thr Leu Ser
            245                 250                 255

Thr Asp Pro Lys Arg Gln Leu Ile Gly Asp Asp Glu His Gly Trp Asp
        260                 265                 270

Asp Glu Gly Val Phe Asn Phe Glu Gly Gly Cys Tyr Ala Lys Thr Ile
    275                 280                 285

Asn Leu Ser Ala Glu Asn Glu Pro Asp Ile Tyr Gly Ala Ile Lys Arg
290                 295                 300

Asp Ala Leu Glu Asn Val Val Leu Asp Asn Gly Asp Val Asp
305                 310                 315                 320

Tyr Ala Asp Gly Ser Lys Thr Glu Asn Thr Arg Val Ser Tyr Pro Ile
                325                 330                 335

Tyr His Ile Gln Asn Ile Val Lys Pro Val Ser Lys Ala Gly Pro Ala
            340                 345                 350

Thr Lys Val Ile Phe Leu Ser Ala Asp Ala Phe Gly Val Leu Pro Pro
        355                 360                 365

Val Ser Lys Leu Thr Pro Glu Gln Thr Lys Tyr Tyr Phe Leu Ser Gly
    370                 375                 380

Phe Thr Ala Lys Leu Ala Gly Thr Glu Arg Gly Ile Thr Glu Pro Thr
385                 390                 395                 400

Pro Thr Phe Ser Ala Cys Phe Gly Ala Ala Phe Leu Ser Leu His Pro
                405                 410                 415

Thr Gln Tyr Ala Glu Val Leu Val Lys Arg Met Gln Glu Ser Gly Ala
            420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
    450                 455                 460

Ile Asp Lys Ala Glu Met Gly Ser Leu Pro Ile Phe Asp Phe Ser Ile
465                 470                 475                 480

Pro Lys Ala Leu Pro Gly Val Asn Pro Ala Ile Leu Asp Pro Arg Asp
                485                 490                 495

Thr Tyr Ala Asp Lys Ala Gln Trp Glu Glu Lys Ala Gln Asp Leu Ala
            500                 505                 510

Gly Arg Phe Val Lys Asn Phe Glu Lys Tyr Thr Gly Thr Ala Glu Gly
        515                 520                 525

Gln Ala Leu Val Ala Ala Gly Pro Lys Ala
    530                 535

<210> SEQ ID NO 36
<211> LENGTH: 532
<212> TYPE: PRT
<213> ORGANISM: Anaerobiospirillum succiniciproducens

<400> SEQUENCE: 36

Met Ser Leu Ser Glu Ser Leu Ala Lys Tyr Gly Ile Thr Gly Ala Thr
1               5                   10                  15

Asn Ile Val His Asn Pro Ser His Glu Glu Leu Phe Ala Ala Glu Thr
                20                  25                  30

Gln Ala Ser Leu Glu Gly Phe Glu Lys Gly Thr Val Thr Glu Met Gly
            35                  40                  45

Ala Val Asn Val Met Thr Gly Val Tyr Thr Gly Arg Ser Pro Lys Asp
        50                  55                  60
```

```
Lys Phe Ile Val Lys Asn Glu Ala Ser Lys Glu Ile Trp Trp Thr Ser
 65                  70                  75                  80

Asp Glu Phe Lys Asn Asp Asn Lys Pro Val Thr Glu Glu Ala Trp Ala
                 85                  90                  95

Gln Leu Lys Ala Leu Ala Gly Lys Glu Leu Ser Asn Lys Pro Leu Tyr
            100                 105                 110

Val Val Asp Leu Phe Cys Gly Ala Asn Glu Asn Thr Arg Leu Lys Ile
        115                 120                 125

Arg Phe Val Met Glu Val Ala Trp Gln Ala His Phe Val Thr Asn Met
    130                 135                 140

Phe Ile Arg Pro Thr Glu Glu Leu Lys Gly Phe Glu Pro Asp Phe
145                 150                 155                 160

Val Val Leu Asn Ala Ser Lys Ala Lys Val Glu Asn Phe Lys Glu Leu
                165                 170                 175

Gly Leu Asn Ser Glu Thr Ala Val Val Phe Asn Leu Ala Glu Lys Met
            180                 185                 190

Gln Ile Ile Leu Asn Thr Trp Tyr Gly Gly Glu Met Lys Lys Gly Met
        195                 200                 205

Phe Ser Met Met Asn Phe Tyr Leu Pro Leu Gln Gly Ile Ala Ala Met
210                 215                 220

His Cys Ser Ala Asn Thr Asp Leu Glu Gly Lys Asn Thr Ala Ile Phe
225                 230                 235                 240

Phe Gly Leu Ser Gly Thr Gly Lys Thr Thr Leu Ser Thr Asp Pro Lys
                245                 250                 255

Arg Leu Leu Ile Gly Asp Asp Glu His Gly Trp Asp Asp Asp Gly Val
            260                 265                 270

Phe Asn Phe Glu Gly Gly Cys Tyr Ala Lys Val Ile Asn Leu Ser Lys
        275                 280                 285

Glu Asn Glu Pro Asp Ile Trp Gly Ala Ile Lys Arg Asn Ala Leu Leu
    290                 295                 300

Glu Asn Val Thr Val Asp Ala Asn Gly Lys Val Asp Phe Ala Asp Lys
305                 310                 315                 320

Ser Val Thr Glu Asn Thr Arg Val Ser Tyr Pro Ile Phe His Ile Lys
                325                 330                 335

Asn Ile Val Lys Pro Val Ser Lys Ala Pro Ala Ala Lys Arg Val Ile
            340                 345                 350

Phe Leu Ser Ala Asp Ala Phe Gly Val Leu Pro Pro Val Ser Ile Leu
        355                 360                 365

Ser Lys Glu Gln Thr Lys Tyr Tyr Phe Leu Ser Gly Phe Thr Ala Lys
    370                 375                 380

Leu Ala Gly Thr Glu Arg Gly Ile Thr Glu Pro Thr Pro Thr Phe Ser
385                 390                 395                 400

Ser Cys Phe Gly Ala Ala Phe Leu Thr Leu Pro Pro Thr Lys Tyr Ala
                405                 410                 415

Glu Val Leu Val Lys Arg Met Glu Ala Ser Gly Ala Lys Ala Tyr Leu
            420                 425                 430

Val Asn Thr Gly Trp Asn Gly Thr Gly Lys Arg Ile Ser Ile Lys Asp
        435                 440                 445

Thr Arg Gly Ile Ile Asp Ala Ile Leu Asp Gly Ser Ile Asp Thr Ala
    450                 455                 460

Asn Thr Ala Thr Ile Pro Tyr Phe Asn Phe Thr Val Pro Thr Glu Leu
465                 470                 475                 480
```

```
Lys Gly Val Asp Thr Lys Ile Leu Asp Pro Arg Asn Thr Tyr Ala Asp
                485                 490                 495

Ala Ser Glu Trp Glu Val Lys Ala Lys Asp Leu Ala Gly Arg Phe Gln
            500                 505                 510

Lys Asn Phe Lys Lys Phe Glu Ser Leu Gly Gly Asp Leu Val Lys Ala
            515                 520                 525

Gly Pro Gln Leu
        530

<210> SEQ ID NO 37
<211> LENGTH: 538
<212> TYPE: PRT
<213> ORGANISM: Actinobacillus succinogenes

<400> SEQUENCE: 37

Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
            35                  40                  45

Thr Thr Leu Gly Ala Val Ala Val Asp Thr Gly Ile Phe Thr Gly Arg
    50                  55                  60

Ser Pro Lys Asp Lys Tyr Ile Val Cys Asp Glu Thr Thr Lys Asp Thr
65              70                  75                  80

Val Trp Trp Asn Ser Glu Ala Ala Lys Asn Asp Asn Lys Pro Met Thr
                85                  90                  95

Gln Glu Thr Trp Lys Ser Leu Arg Glu Leu Val Ala Lys Gln Leu Ser
            100                 105                 110

Gly Lys Arg Leu Phe Val Val Glu Gly Tyr Cys Gly Ala Ser Glu Lys
            115                 120                 125

His Arg Ile Gly Val Arg Met Val Thr Glu Val Ala Trp Gln Ala His
        130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Ile Gln Leu Ile Gly Gly Thr Trp Tyr Gly Gly Glu
            195                 200                 205

Met Lys Lys Gly Met Phe Ser Met Met Asn Tyr Phe Leu Pro Leu Lys
        210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Glu Ser Gly Val Phe Asn Phe Glu Gly Gly Cys Tyr Ala Lys Thr Ile
            275                 280                 285

Asn Leu Ser Gln Glu Asn Glu Pro Asp Ile Tyr Gly Ala Ile Arg Arg
        290                 295                 300

Asp Ala Leu Leu Glu Asn Val Val Val Arg Ala Asp Gly Ser Val Asp
305                 310                 315                 320
```

```
Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
            340                 345                 350

Thr Lys Val Ile Phe Leu Thr Ala Asp Ala Phe Gly Val Leu Pro Pro
        355                 360                 365

Val Ser Lys Leu Thr Pro Glu Gln Thr Glu Tyr Tyr Phe Leu Ser Gly
    370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
            420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
    450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                485                 490                 495

Thr Tyr Ala Asp Lys Ala Gln Trp Gln Val Lys Ala Glu Asp Leu Ala
            500                 505                 510

Asn Arg Phe Val Lys Asn Phe Val Lys Tyr Thr Ala Asn Pro Glu Ala
        515                 520                 525

Ala Lys Leu Val Gly Ala Gly Pro Lys Ala
    530                 535

<210> SEQ ID NO 38
<211> LENGTH: 618
<212> TYPE: PRT
<213> ORGANISM: Ralstonia eutropha

<400> SEQUENCE: 38

Met Asn His Pro Ser Met Gln Gly Thr Thr Ala Leu Asn Val Pro Ala
1               5                   10                  15

Trp Val Arg Asn Gln Lys Leu Val Ala Trp Val Ala Glu Ile Ala Ala
                20                  25                  30

Leu Thr Lys Pro Glu Arg Ile His Trp Cys Asp Gly Ser Gln Glu Glu
            35                  40                  45

Tyr Asp Arg Leu Cys Glu Gln Met Val Ala Ala Gly Thr Leu Lys Arg
        50                  55                  60

Leu Asn Pro Ala Lys Arg Lys Asn Ser Tyr Leu Ala Leu Ser Asp Pro
65                  70                  75                  80

Ser Asp Val Ala Arg Val Glu Arg Thr Phe Ile Cys Ser Gln Lys
                85                  90                  95

Lys Glu Asp Ala Gly Pro Thr Asn Asn Trp Val Ala Pro Ala Glu Met
            100                 105                 110

Arg Thr Thr Leu Asn Gly Leu Phe Asp Gly Cys Met Arg Gly Arg Thr
        115                 120                 125

Leu Tyr Val Val Pro Phe Ser Met Gly Pro Leu Gly Ser Pro Ile Ala
    130                 135                 140

His Ile Gly Val Glu Leu Ser Asp Ser Pro Tyr Val Ala Val Asn Met
```

```
                145                 150                 155                 160
        Arg Ile Met Thr Arg Met Gly Lys Ala Val Tyr Asp Val Leu Gly Thr
                        165                 170                 175
        Asp Gly Asp Phe Val Pro Cys Val His Thr Val Gly Lys Pro Leu Ala
                        180                 185                 190
        Ala Gly Glu Lys Asp Val Pro Trp Pro Cys Asn Pro Thr Lys Tyr Ile
                        195                 200                 205
        Val His Phe Pro Glu Ser Arg Glu Ile Trp Ser Phe Gly Ser Gly Tyr
                210                 215                 220
        Gly Gly Asn Ala Leu Leu Gly Lys Lys Cys Phe Ala Leu Arg Ile Ala
        225                 230                 235                 240
        Ser Thr Met Gly Arg Asp Glu Gly Trp Leu Ala Glu His Met Leu Ile
                        245                 250                 255
        Leu Gly Val Thr Ser Pro Glu Gly Lys Lys Phe His Val Ala Ala Ala
                        260                 265                 270
        Phe Pro Ser Ala Cys Gly Lys Thr Asn Phe Ala Met Leu Ile Pro Pro
                        275                 280                 285
        Lys Gly Phe Glu Gly Trp Lys Val Thr Thr Ile Gly Asp Asp Ile Ala
                290                 295                 300
        Trp Ile Lys Pro Gly Lys Asp Gly Arg Leu Tyr Ala Ile Asn Pro Glu
        305                 310                 315                 320
        Ala Gly Tyr Phe Gly Val Ala Pro Gly Thr Ser Glu Lys Thr Asn Phe
                        325                 330                 335
        Asn Ala Met Ala Thr Leu Lys Glu Asn Val Ile Phe Thr Asn Val Ala
                        340                 345                 350
        Leu Thr Asp Asp Gly Asp Val Trp Trp Glu Gly Met Thr Lys Glu Ala
                        355                 360                 365
        Pro Ala His Leu Thr Asp Trp Gln Gly Lys Asp Trp Thr Pro Glu Ile
                        370                 375                 380
        Ala Lys Ala Thr Gly Ala Lys Ala Ala His Pro Asn Ala Arg Phe Thr
        385                 390                 395                 400
        Ala Pro Ala Ser Gln Cys Pro Ser Ile Asp Glu Asn Trp Asp Asn Pro
                        405                 410                 415
        Ala Gly Val Pro Ile Asp Ala Phe Ile Phe Gly Gly Arg Arg Ser Thr
                        420                 425                 430
        Thr Val Pro Leu Val Thr Glu Ala Arg Asn Trp Thr Glu Gly Val Tyr
                        435                 440                 445
        Met Ala Ala Thr Met Gly Ser Glu Thr Thr Ala Ala Ala Ala Gly Gln
                450                 455                 460
        Gln Gly Val Val Arg Arg Asp Pro Phe Ala Met Leu Pro Phe Cys Gly
        465                 470                 475                 480
        Tyr Asn Met Ser Asp Tyr Phe Gly His Trp Leu Ala Leu Gly Gln Lys
                        485                 490                 495
        Leu Glu Ala Ala Gly Ala Lys Leu Pro Lys Ile Tyr Cys Val Asn Trp
                        500                 505                 510
        Phe Arg Lys Asp Ala Asp Gly Asn Phe Val Trp Pro Gly Phe Gly Glu
                        515                 520                 525
        Asn Met Arg Val Leu Ser Trp Met Ile Asp Arg Val Glu Gly Lys Gly
                        530                 535                 540
        Glu Gly Ala Glu His Val Phe Gly Thr Ser Pro Arg Tyr Glu Asp Leu
        545                 550                 555                 560
        Asn Trp Ser Gly Val Glu Phe Ser Val Ala Gln Phe Thr Gln Val Thr
                        565                 570                 575
```

Ser Ile Asp Ala Asp Ala Trp Lys Gln Glu Leu Ala Leu His Asp Glu
            580                 585                 590

Leu Phe Thr Gln Leu Lys His Asn Leu Pro Gln Ala Leu Ala Glu Ala
            595                 600                 605

Arg Ala Ala Leu Gly Lys Arg Leu Glu Gly
            610                 615

<210> SEQ ID NO 39
<211> LENGTH: 540
<212> TYPE: PRT
<213> ORGANISM: Escherichia coli

<400> SEQUENCE: 39

Met Arg Val Asn Asn Gly Leu Thr Pro Gln Glu Leu Glu Ala Tyr Gly
1               5                   10                  15

Ile Ser Asp Val His Asp Ile Val Tyr Asn Pro Ser Tyr Asp Leu Leu
                20                  25                  30

Tyr Gln Glu Glu Leu Asp Pro Ser Leu Thr Gly Tyr Glu Arg Gly Val
            35                  40                  45

Leu Thr Asn Leu Gly Ala Val Ala Val Asp Thr Gly Ile Phe Thr Gly
        50                  55                  60

Arg Ser Pro Lys Asp Lys Tyr Ile Val Arg Asp Asp Thr Thr Arg Asp
65                  70                  75                  80

Thr Phe Trp Trp Ala Asp Lys Gly Lys Gly Lys Asn Asp Asn Lys Pro
                85                  90                  95

Leu Ser Pro Glu Thr Trp Gln His Leu Lys Gly Leu Val Thr Arg Gln
            100                 105                 110

Leu Ser Gly Lys Arg Leu Phe Val Val Asp Ala Phe Cys Gly Ala Asn
        115                 120                 125

Pro Asp Thr Arg Leu Ser Val Arg Phe Ile Thr Glu Val Ala Trp Gln
130                 135                 140

Ala His Phe Val Lys Asn Met Phe Ile Arg Pro Ser Asp Glu Glu Leu
145                 150                 155                 160

Ala Gly Phe Lys Pro Asp Phe Ile Val Met Asn Gly Ala Lys Cys Thr
                165                 170                 175

Asn Pro Gln Trp Lys Glu Gln Gly Leu Asn Ser Glu Asn Phe Val Ala
            180                 185                 190

Phe Asn Leu Thr Glu Arg Met Gln Leu Ile Gly Gly Thr Trp Tyr Gly
        195                 200                 205

Gly Glu Met Lys Lys Gly Met Phe Ser Met Met Asn Tyr Leu Leu Pro
    210                 215                 220

Leu Lys Gly Ile Ala Ser Met His Cys Ser Ala Asn Val Gly Glu Lys
225                 230                 235                 240

Gly Asp Val Ala Val Phe Phe Gly Leu Ser Gly Thr Gly Lys Thr Thr
                245                 250                 255

Leu Ser Thr Asp Pro Lys Arg Arg Leu Ile Gly Asp Asp Glu His Gly
            260                 265                 270

Trp Asp Asp Asp Gly Val Phe Asn Phe Glu Gly Gly Cys Tyr Ala Lys
        275                 280                 285

Thr Ile Lys Leu Ser Lys Glu Ala Glu Pro Glu Ile Tyr Asn Ala Ile
    290                 295                 300

Arg Arg Asp Ala Leu Leu Glu Asn Val Thr Val Arg Glu Asp Gly Thr
305                 310                 315                 320

Ile Asp Phe Asp Asp Gly Ser Lys Thr Glu Asn Thr Arg Val Ser Tyr

```
                      325                 330                 335
Pro Ile Tyr His Ile Asp Asn Ile Val Lys Pro Val Ser Lys Ala Gly
                340                 345                 350
His Ala Thr Lys Val Ile Phe Leu Thr Ala Asp Ala Phe Gly Val Leu
            355                 360                 365
Pro Pro Val Ser Arg Leu Thr Ala Asp Gln Thr Gln Tyr His Phe Leu
370                 375                 380
Ser Gly Phe Thr Ala Lys Leu Ala Gly Thr Glu Arg Gly Ile Thr Glu
385                 390                 395                 400
Pro Thr Pro Thr Phe Ser Ala Cys Phe Gly Ala Ala Phe Leu Ser Leu
                405                 410                 415
His Pro Thr Gln Tyr Ala Glu Val Leu Val Lys Arg Met Gln Ala Ala
                420                 425                 430
Gly Ala Gln Ala Tyr Leu Val Asn Thr Gly Trp Asn Gly Thr Gly Lys
                435                 440                 445
Arg Ile Ser Ile Lys Asp Thr Arg Ala Ile Ile Asp Ala Ile Leu Asn
            450                 455                 460
Gly Ser Leu Asp Asn Ala Glu Thr Phe Thr Leu Pro Met Phe Asn Leu
465                 470                 475                 480
Ala Ile Pro Thr Glu Leu Pro Gly Val Asp Thr Lys Ile Leu Asp Pro
                485                 490                 495
Arg Asn Thr Tyr Ala Ser Pro Glu Gln Trp Gln Glu Lys Ala Glu Thr
                500                 505                 510
Leu Ala Lys Leu Phe Ile Asp Asn Phe Asp Lys Tyr Thr Asp Thr Pro
            515                 520                 525
Ala Gly Ala Ala Leu Val Ala Ala Gly Pro Lys Leu
530                 535                 540

<210> SEQ ID NO 40
<211> LENGTH: 236
<212> TYPE: PRT
<213> ORGANISM: Lactococcus lactis

<400> SEQUENCE: 40

Met Ser Glu Ile Thr Gln Leu Phe Gln Tyr Asn Thr Leu Gly Ala Leu
1               5                   10                  15
Met Ala Gly Leu Tyr Glu Gly Thr Met Thr Ile Gly Glu Leu Leu Lys
                20                  25                  30
His Gly Asp Leu Gly Ile Gly Thr Leu Asp Ser Ile Asp Gly Glu Leu
            35                  40                  45
Ile Val Leu Asp Gly Lys Ala Tyr Gln Ala Lys Gly Asp Lys Thr Ile
        50                  55                  60
Val Glu Leu Thr Asp Asp Ile Lys Val Pro Tyr Ala Ala Val Val Pro
65                  70                  75                  80
His Gln Ala Glu Val Val Phe Lys Gln Lys Phe Thr Val Ser Asp Lys
                85                  90                  95
Glu Leu Glu Asp Arg Ile Glu Ser Tyr Phe Asp Gly Gln Asn Leu Phe
            100                 105                 110
Arg Ser Ile Lys Ile Thr Gly Lys Phe Pro Lys Met His Val Arg Met
        115                 120                 125
Ile Pro Arg Ala Lys Ser Gly Thr Lys Phe Val Glu Val Ser Gln Asn
    130                 135                 140
Gln Pro Glu Tyr Thr Glu Glu Asn Ile Lys Gly Thr Ile Val Gly Ile
145                 150                 155                 160
```

Trp Thr Pro Glu Met Phe His Gly Val Ser Val Ala Gly Tyr His Leu
                165                 170                 175

His Phe Ile Ser Glu Asp Phe Thr Phe Gly Gly His Val Leu Asp Phe
            180                 185                 190

Ile Ile Asp Asn Gly Thr Val Glu Ile Gly Ala Ile Asp Gln Leu Asn
        195                 200                 205

Gln Ser Phe Pro Val Gln Asp Arg Lys Phe Leu Phe Ala Asp Leu Asp
    210                 215                 220

Ile Glu Ala Leu Lys Lys Asp Ile Asp Val Ala Glu
225                 230                 235

<210> SEQ ID NO 41
<211> LENGTH: 239
<212> TYPE: PRT
<213> ORGANISM: Streptococcus thermophilus

<400> SEQUENCE: 41

Met Ser Glu Ala Ile Lys Leu Phe Gln Tyr Asn Thr Leu Gly Ala Leu
1               5                   10                  15

Met Ala Gly Leu Tyr Gly Gly Thr Leu Thr Val Gly Glu Leu Leu Glu
            20                  25                  30

His Gly Asp Leu Gly Leu Gly Thr Leu Asp Ser Ile Asp Gly Glu Leu
        35                  40                  45

Ile Val Leu Asp Gly Lys Ala Tyr Gln Ala Lys Gly Ser Glu Gly Lys
    50                  55                  60

Val Glu Val Val Glu Val Ser Pro Asp Glu Lys Val Pro Tyr Ala Ala
65                  70                  75                  80

Val Val Pro His Gln Ala Glu Val Ile Phe Arg Gln Arg Tyr Glu Met
                85                  90                  95

Thr Asp Lys Glu Leu Glu Asp Arg Ile Glu Ser Tyr Tyr Asp Gly Val
            100                 105                 110

Asn Leu Phe Arg Ser Ile Lys Ile Lys Gly His Phe Lys His Met His
        115                 120                 125

Val Arg Met Ile Pro Lys Ser Asn Ala Asp Ile Lys Phe Ala Asp Val
    130                 135                 140

Ala Thr Arg Gln Pro Glu Tyr Glu Val Asp Asp Ile Ser Gly Thr Ile
145                 150                 155                 160

Val Gly Ile Trp Thr Pro Glu Met Phe His Gly Val Ser Val Ala Gly
                165                 170                 175

Tyr His Leu His Phe Ile Ser Asp Asp Leu Thr Phe Gly Gly His Val
            180                 185                 190

Met Asp Phe Val Ile Glu Asn Gly Ile Ile Glu Val Gly Pro Val Asp
        195                 200                 205

Gln Leu Asp Gln Arg Phe Pro Val Gln Asp Arg Gln Tyr Leu Phe Ala
    210                 215                 220

Lys Phe Asn Val Asp Glu Met Arg Lys Asp Ile Thr Lys Ala Glu
225                 230                 235

<210> SEQ ID NO 42
<211> LENGTH: 285
<212> TYPE: PRT
<213> ORGANISM: Brevibacillus brevis

<400> SEQUENCE: 42

Met Lys Lys Asn Ile Ile Thr Ser Ile Thr Ser Leu Ala Leu Val Ala
1               5                   10                  15

Gly Leu Ser Leu Thr Ala Phe Ala Ala Thr Thr Ala Thr Val Pro Ala
            20                  25                  30

Pro Pro Ala Lys Gln Glu Ser Lys Pro Ala Val Ala Ala Asn Pro Ala
        35                  40                  45

Pro Lys Asn Val Leu Phe Gln Tyr Ser Thr Ile Asn Ala Leu Met Leu
    50                  55                  60

Gly Gln Phe Glu Gly Asp Leu Thr Leu Lys Asp Leu Lys Leu Arg Gly
65                  70                  75                  80

Asp Met Gly Leu Gly Thr Ile Asn Asp Leu Asp Gly Glu Met Ile Gln
                85                  90                  95

Met Gly Thr Lys Phe Tyr Gln Ile Asp Ser Thr Gly Lys Leu Ser Glu
            100                 105                 110

Leu Pro Glu Ser Val Lys Thr Pro Phe Ala Val Thr Thr His Phe Glu
        115                 120                 125

Pro Lys Glu Lys Thr Thr Leu Thr Asn Val Gln Asp Tyr Asn Gln Leu
    130                 135                 140

Thr Lys Met Leu Glu Glu Lys Phe Glu Asn Lys Asn Val Phe Tyr Ala
145                 150                 155                 160

Val Lys Leu Thr Gly Thr Phe Lys Met Val Lys Ala Arg Thr Val Pro
                165                 170                 175

Lys Gln Thr Arg Pro Tyr Pro Gln Leu Thr Glu Val Thr Lys Lys Gln
            180                 185                 190

Ser Glu Phe Glu Phe Lys Asn Val Lys Gly Thr Leu Ile Gly Phe Tyr
        195                 200                 205

Thr Pro Asn Tyr Ala Ala Ala Leu Asn Val Pro Gly Phe His Leu His
    210                 215                 220

Phe Ile Thr Glu Asp Lys Thr Ser Gly Gly His Val Leu Asn Leu Gln
225                 230                 235                 240

Phe Asp Asn Ala Asn Leu Glu Ile Ser Pro Ile His Glu Phe Asp Val
                245                 250                 255

Gln Leu Pro His Thr Asp Asp Phe Ala His Ser Asp Leu Thr Gln Val
            260                 265                 270

Thr Thr Ser Gln Val His Gln Ala Glu Ser Glu Arg Lys
        275                 280                 285

<210> SEQ ID NO 43
<211> LENGTH: 259
<212> TYPE: PRT
<213> ORGANISM: Enterobacter aerogenes

<400> SEQUENCE: 43

Met Met Met His Ser Ser Ala Cys Asp Cys Glu Ala Ser Leu Cys Glu
1               5                   10                  15

Thr Leu Arg Gly Phe Ser Ala Gln His Pro Asp Ser Val Ile Tyr Gln
            20                  25                  30

Thr Ser Leu Met Ser Ala Leu Leu Ser Gly Val Tyr Val Gly Glu Thr
        35                  40                  45

Thr Ile Ala Asp Leu Leu Ala His Gly Asp Phe Gly Leu Gly Thr Phe
    50                  55                  60

Asn Glu Leu Asp Gly Glu Met Ile Ala Phe Ser Gln Val Tyr Gln
65                  70                  75                  80

Leu Arg Ala Asp Gly Ser Ala Arg Ala Ala Lys Pro Glu Gln Lys Thr
                85                  90                  95

Pro Phe Ala Val Met Thr Trp Phe Gln Pro Gln Tyr Arg Lys Thr Phe
            100                 105                 110

```
Asn Gly Pro Val Ser Arg Gln Gln Ile His Asp Val Ile Asp Gln Gln
            115                 120                 125

Ile Pro Ser Asp Asn Leu Phe Cys Val Arg Ile Asp Gly Asn Phe Arg
            130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
            165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Gln Gly
            195                 200                 205

Gly Gly His Leu Leu Asp Tyr Gln Leu Glu Ser Gly Val Leu Thr Phe
            210                 215                 220

Gly Glu Ile His Lys Leu Met Ile Asp Leu Pro Ala Asp Ser Ala Phe
225                 230                 235                 240

Leu Gln Ala Asn Leu His Pro Ser Asn Leu Asp Ala Ala Ile Arg Ala
            245                 250                 255

Val Glu Asn

<210> SEQ ID NO 44
<211> LENGTH: 1231
<212> TYPE: PRT
<213> ORGANISM: Mycobacterium tuberculosis

<400> SEQUENCE: 44

Met Ala Asn Ile Ser Ser Pro Phe Gly Gln Asn Glu Trp Leu Val Glu
1               5                   10                  15

Glu Met Tyr Arg Lys Phe Arg Asp Asp Pro Ser Ser Val Asp Pro Ser
            20                  25                  30

Trp His Glu Phe Leu Val Asp Tyr Ser Pro Glu Pro Thr Ser Gln Pro
            35                  40                  45

Ala Ala Glu Pro Thr Arg Val Thr Ser Pro Leu Val Ala Glu Arg Ala
            50                  55                  60

Ala Ala Ala Ala Pro Gln Ala Pro Pro Lys Pro Ala Asp Thr Ala Ala
65                  70                  75                  80

Ala Gly Asn Gly Val Val Ala Ala Leu Ala Ala Lys Thr Ala Val Pro
            85                  90                  95

Pro Pro Ala Glu Gly Asp Glu Val Ala Val Leu Arg Gly Ala Ala Ala
            100                 105                 110

Ala Val Val Lys Asn Met Ser Ala Ser Leu Glu Val Pro Thr Ala Thr
            115                 120                 125

Ser Val Arg Ala Val Pro Ala Lys Leu Leu Ile Asp Asn Arg Ile Val
            130                 135                 140

Ile Asn Asn Gln Leu Lys Arg Thr Arg Gly Gly Lys Ile Ser Phe Thr
145                 150                 155                 160

His Leu Leu Gly Tyr Ala Leu Val Gln Ala Val Lys Lys Phe Pro Asn
            165                 170                 175

Met Asn Arg His Tyr Thr Glu Val Asp Gly Lys Pro Thr Ala Val Thr
            180                 185                 190

Pro Ala His Thr Asn Leu Gly Leu Ala Ile Asp Leu Gln Gly Lys Asp
            195                 200                 205

Gly Lys Arg Ser Leu Val Val Ala Gly Ile Lys Arg Cys Glu Thr Met
            210                 215                 220
```

```
Arg Phe Ala Gln Phe Val Thr Ala Tyr Glu Asp Ile Val Arg Arg Ala
225                 230                 235                 240

Arg Asp Gly Lys Leu Thr Thr Glu Asp Phe Ala Gly Val Thr Ile Ser
            245                 250                 255

Leu Thr Asn Pro Gly Thr Ile Gly Thr Val His Ser Val Pro Arg Leu
            260                 265                 270

Met Pro Gly Gln Gly Ala Ile Ile Gly Val Gly Ala Met Glu Tyr Pro
            275                 280                 285

Ala Glu Phe Gln Gly Ala Ser Glu Glu Arg Ile Ala Glu Leu Gly Ile
            290                 295                 300

Gly Lys Leu Ile Thr Leu Thr Ser Thr Tyr Asp His Arg Ile Ile Gln
305                 310                 315                 320

Gly Ala Glu Ser Gly Asp Phe Leu Arg Thr Ile His Glu Leu Leu Leu
                325                 330                 335

Ser Asp Gly Phe Trp Asp Glu Val Phe Arg Glu Leu Ser Ile Pro Tyr
                340                 345                 350

Leu Pro Val Arg Trp Ser Thr Asp Asn Pro Asp Ser Ile Val Asp Lys
                355                 360                 365

Asn Ala Arg Val Met Asn Leu Ile Ala Ala Tyr Arg Asn Arg Gly His
370                 375                 380

Leu Met Ala Asp Thr Asp Pro Leu Arg Leu Asp Lys Ala Arg Phe Arg
385                 390                 395                 400

Ser His Pro Asp Leu Glu Val Leu Thr His Gly Leu Thr Leu Trp Asp
                405                 410                 415

Leu Asp Arg Val Phe Lys Val Asp Gly Phe Ala Gly Ala Gln Tyr Lys
                420                 425                 430

Lys Leu Arg Asp Val Leu Gly Leu Leu Arg Asp Ala Tyr Cys Arg His
                435                 440                 445

Ile Gly Val Glu Tyr Ala His Ile Leu Asp Pro Glu Gln Lys Glu Trp
                450                 455                 460

Leu Glu Gln Arg Val Glu Thr Lys His Val Lys Pro Thr Val Ala Gln
465                 470                 475                 480

Gln Lys Tyr Ile Leu Ser Lys Leu Asn Ala Ala Glu Ala Phe Glu Thr
                485                 490                 495

Phe Leu Gln Thr Lys Tyr Val Gly Gln Lys Arg Phe Ser Leu Glu Gly
                500                 505                 510

Ala Glu Ser Val Ile Pro Met Met Asp Ala Ala Ile Asp Gln Cys Ala
                515                 520                 525

Glu His Gly Leu Asp Glu Val Val Ile Gly Met Pro His Arg Gly Arg
                530                 535                 540

Leu Asn Val Leu Ala Asn Ile Val Gly Lys Pro Tyr Ser Gln Ile Phe
545                 550                 555                 560

Thr Glu Phe Glu Gly Asn Leu Asn Pro Ser Gln Ala His Gly Ser Gly
                565                 570                 575

Asp Val Lys Tyr His Leu Gly Ala Thr Gly Leu Tyr Leu Gln Met Phe
                580                 585                 590

Gly Asp Asn Asp Ile Gln Val Ser Leu Thr Ala Asn Pro Ser His Leu
                595                 600                 605

Glu Ala Val Asp Pro Val Leu Glu Gly Leu Val Arg Ala Lys Gln Asp
                610                 615                 620

Leu Leu Asp His Gly Ser Ile Asp Ser Asp Gly Gln Arg Ala Phe Ser
625                 630                 635                 640
```

```
Val Val Pro Leu Met Leu His Gly Asp Ala Ala Phe Ala Gly Gln Gly
                645                 650                 655

Val Val Ala Glu Thr Leu Asn Leu Ala Asn Leu Pro Gly Tyr Arg Val
            660                 665                 670

Gly Gly Thr Ile His Ile Ile Val Asn Asn Gln Ile Gly Phe Thr Thr
        675                 680                 685

Ala Pro Glu Tyr Ser Arg Ser Ser Glu Tyr Cys Thr Asp Val Ala Lys
690                 695                 700

Met Ile Gly Ala Pro Ile Phe His Val Asn Gly Asp Pro Glu Ala
705                 710                 715                 720

Cys Val Trp Val Ala Arg Leu Ala Val Asp Phe Arg Gln Arg Phe Lys
                725                 730                 735

Lys Asp Val Val Ile Asp Met Leu Cys Tyr Arg Arg Arg Gly His Asn
            740                 745                 750

Glu Gly Asp Asp Pro Ser Met Thr Asn Pro Tyr Val Tyr Asp Val Val
        755                 760                 765

Asp Thr Lys Arg Gly Ala Arg Lys Ser Tyr Thr Glu Ala Leu Ile Gly
770                 775                 780

Arg Gly Asp Ile Ser Met Lys Glu Ala Glu Asp Ala Leu Arg Asp Tyr
785                 790                 795                 800

Gln Gly Gln Leu Glu Arg Val Phe Asn Glu Val Arg Glu Leu Glu Lys
                805                 810                 815

His Gly Val Gln Pro Ser Glu Ser Val Glu Ser Asp Gln Met Ile Pro
            820                 825                 830

Ala Gly Leu Ala Thr Ala Val Asp Lys Ser Leu Leu Ala Arg Ile Gly
        835                 840                 845

Asp Ala Phe Leu Ala Leu Pro Asn Gly Phe Thr Ala His Pro Arg Val
850                 855                 860

Gln Pro Val Leu Glu Lys Arg Arg Glu Met Ala Tyr Glu Gly Lys Ile
865                 870                 875                 880

Asp Trp Ala Phe Gly Glu Leu Leu Ala Leu Gly Ser Leu Val Ala Glu
                885                 890                 895

Gly Lys Leu Val Arg Leu Ser Gly Gln Asp Ser Arg Arg Gly Thr Phe
            900                 905                 910

Ser Gln Arg His Ser Val Leu Ile Asp Arg His Thr Gly Glu Glu Phe
        915                 920                 925

Thr Pro Leu Gln Leu Leu Ala Thr Asn Ser Asp Gly Ser Pro Thr Gly
930                 935                 940

Gly Lys Phe Leu Val Tyr Asp Ser Pro Leu Ser Glu Tyr Ala Ala Val
945                 950                 955                 960

Gly Phe Glu Tyr Gly Tyr Thr Val Gly Asn Pro Asp Ala Val Val Leu
                965                 970                 975

Trp Glu Ala Gln Phe Gly Asp Phe Val Asn Gly Ala Gln Ser Ile Ile
            980                 985                 990

Asp Glu Phe Ile Ser Ser Gly Glu Ala Lys Trp Gly Gln Leu Ser Asn
        995                 1000                1005

Val Val Leu Leu Leu Pro His Gly His Glu Gly Gln Gly Pro Asp
    1010                1015                1020

His Thr Ser Ala Arg Ile Glu Arg Phe Leu Gln Leu Trp Ala Glu
    1025                1030                1035

Gly Ser Met Thr Ile Ala Met Pro Ser Thr Pro Ser Asn Tyr Phe
    1040                1045                1050

His Leu Leu Arg Arg His Ala Leu Asp Gly Ile Gln Arg Pro Leu
```

```
                    1055                1060                1065
Ile Val Phe Thr Pro Lys Ser Met Leu Arg His Lys Ala Ala Val
        1070                1075                1080

Ser Glu Ile Lys Asp Phe Thr Glu Ile Lys Phe Arg Ser Val Leu
        1085                1090                1095

Glu Glu Pro Thr Tyr Glu Asp Gly Ile Gly Asp Arg Asn Lys Val
        1100                1105                1110

Ser Arg Ile Leu Leu Thr Ser Gly Lys Leu Tyr Tyr Glu Leu Ala
        1115                1120                1125

Ala Arg Lys Ala Lys Asp Asn Arg Asn Asp Leu Ala Ile Val Arg
        1130                1135                1140

Leu Glu Gln Leu Ala Pro Leu Pro Arg Arg Arg Leu Arg Glu Thr
        1145                1150                1155

Leu Asp Arg Tyr Glu Asn Val Lys Glu Phe Phe Trp Val Gln Glu
        1160                1165                1170

Glu Pro Ala Asn Gln Gly Ala Trp Pro Arg Phe Gly Leu Glu Leu
        1175                1180                1185

Pro Glu Leu Leu Pro Asp Lys Leu Ala Gly Ile Lys Arg Ile Ser
        1190                1195                1200

Arg Arg Ala Met Ser Ala Pro Ser Ser Gly Ser Ser Lys Val His
        1205                1210                1215

Ala Val Glu Gln Gln Glu Ile Leu Asp Glu Ala Phe Gly
        1220                1225                1230

<210> SEQ ID NO 45
<211> LENGTH: 985
<212> TYPE: PRT
<213> ORGANISM: Bradyrhizobium japonicum

<400> SEQUENCE: 45

Met Ser Arg Gln Asp Ala Asn Ala Ala Phe Ala Leu Ser Ser Phe Leu
1               5                   10                  15

Gln Gly Thr Asn Ala Thr Tyr Ile Asp Glu Ile Tyr Ala Arg Tyr Glu
            20                  25                  30

Lys Asp Pro Ser Ser Val Asp Ala Glu Trp Gln Glu Phe Phe Lys Ser
        35                  40                  45

Leu Lys Asp Gln Pro Asp Asp Val Arg Arg Asn Ala Glu Gly Pro Ser
    50                  55                  60

Trp Glu Arg Ala Asn Trp Pro Leu Thr Pro Gln Asp Asp Leu Thr Ser
65                  70                  75                  80

Ala Leu Asp Gly Asn Trp Ala Glu Val Glu Lys Ala Val Gly Gly Lys
                85                  90                  95

Ile Ala Ala Lys Ala Gln Ala Lys Gly Ala Asp Ile Ser Ser Ala Asp
            100                 105                 110

Leu Leu Gln Ala Thr Arg Asp Ser Val Arg Ala Leu Met Leu Ile Arg
        115                 120                 125

Ser Tyr Arg Met Arg Gly His Phe His Ala Lys Leu Asp Pro Leu Gly
    130                 135                 140

Ile Glu Ala Pro Arg Asn Arg Glu Glu Leu Asp Pro Arg Thr Tyr Gly
145                 150                 155                 160

Phe Ser Glu Ala Asp Phe Asp Arg Lys Ile Phe Leu Asp His Val Leu
                165                 170                 175

Gly Leu Glu Tyr Gly Thr Leu Arg Glu Ile Thr Ala Ile Cys Glu Arg
            180                 185                 190
```

-continued

Thr Tyr Cys Gln Thr Leu Gly Val Glu Phe Met His Ile Ser Asn Ala
            195                 200                 205

Ala Gln Lys Ala Trp Ile Gln Glu Arg Ile Glu Gly Pro Asp Lys Glu
    210                 215                 220

Ile Ser Phe Thr Arg Glu Gly Arg Ala Ile Leu Thr Lys Leu Val
225                 230                 235                 240

Glu Ala Glu Gly Phe Glu Lys Phe Cys Asp Thr Lys Phe Thr Gly Thr
                245                 250                 255

Lys Arg Phe Gly Leu Asp Gly Ala Glu Ser Leu Ile Pro Ala Leu Glu
            260                 265                 270

Gln Ile Ile Lys Arg Gly Gly Asn Leu Gly Val Lys Glu Ile Val Leu
        275                 280                 285

Gly Met Pro His Arg Gly Arg Leu Asn Val Leu Thr Gln Val Met Gly
    290                 295                 300

Lys Ala His Arg Ala Leu Phe His Glu Phe Lys Gly Gly Ser Ala Asn
305                 310                 315                 320

Pro Asp Ala Val Glu Gly Ser Gly Asp Val Lys Tyr His Leu Gly Ala
                325                 330                 335

Ser Ser Asp Arg Glu Phe Asp Gly Asn Arg Ile His Leu Ser Leu Thr
            340                 345                 350

Ala Asn Pro Ser His Leu Glu Ile Val Asp Pro Val Val Leu Gly Lys
        355                 360                 365

Val Arg Ala Lys Gln Asp Gln His Gly Asp Pro Pro Asp Met Arg Ile
    370                 375                 380

Ser Val Met Pro Leu Leu Met His Gly Asp Ala Ala Phe Ala Gly Gln
385                 390                 395                 400

Gly Val Val Ala Glu Cys Phe Gly Leu Ser Asp Leu Lys Gly Tyr Arg
                405                 410                 415

Thr Gly Gly Ser Val His Phe Ile Val Asn Asn Gln Ile Gly Phe Thr
            420                 425                 430

Thr Tyr Pro Arg Tyr Ser Arg Ser Ser Pro Tyr Pro Ser Asp Val Ala
        435                 440                 445

Lys Met Ile Asp Ala Pro Ile Phe His Val Asn Gly Asp Asp Pro Glu
    450                 455                 460

Ala Val Val Phe Ala Ala Lys Val Ala Thr Glu Phe Arg Gln Lys Phe
465                 470                 475                 480

His Lys Pro Val Val Ile Asp Met Phe Cys Tyr Arg Arg His Gly His
                485                 490                 495

Asn Glu Gly Asp Glu Pro Ala Phe Thr Gln Pro Val Met Tyr Lys Lys
            500                 505                 510

Ile Ala Ala His Pro Ser Thr Leu Glu Leu Tyr Ala Arg Arg Leu Ile
        515                 520                 525

Ser Glu Gly Val Met Thr Glu Gly Glu Val Asp Lys Ala Lys Ala Asp
    530                 535                 540

Trp Arg Ala Arg Leu Asp Ala Glu Phe Glu Ala Gly Thr Ser Tyr Lys
545                 550                 555                 560

Pro Asn Lys Ala Asp Trp Leu Asp Gly Lys Trp Ala Gly Phe Lys Ile
                565                 570                 575

Ala Asp Gln Glu Glu Asp Ala Arg Arg Gly Val Thr Gly Val Asp Ile
            580                 585                 590

Thr Ala Leu Lys Asp Ile Gly Arg Lys Ile Thr Lys Val Pro Asp Gly
        595                 600                 605

Phe Arg Val His Arg Thr Ile Gln Arg Phe Leu Glu Asn Arg Ser Lys

```
                610             615             620
Ala Ile Asp Ser Gly Ala Gly Ile Asp Trp Ala Thr Gly Glu Ala Leu
625                 630                 635                 640

Ala Phe Cys Ser Leu Leu Asn Glu Asn His His Val Arg Leu Ser Gly
                645                 650                 655

Gln Asp Ser Glu Arg Gly Thr Phe Ser Gln Arg His Ser Val Leu Ile
            660                 665                 670

Asp Gln Glu Asp Glu Ser Arg Tyr Thr Pro Phe Asn His Leu Gly His
            675                 680                 685

Glu Gln Gly His Tyr Glu Val Ile Asn Ser Leu Leu Ser Glu Ala
        690                 695                 700

Val Leu Gly Phe Glu Tyr Gly Tyr Ser Leu Ala Glu Pro Asn Thr Leu
705                 710                 715                 720

Thr Leu Trp Glu Ala Gln Phe Gly Asp Phe Ala Asn Gly Ala Gln Val
                725                 730                 735

Val Phe Asp Gln Phe Ile Ser Ser Gly Glu Arg Lys Trp Leu Arg Met
            740                 745                 750

Ser Gly Leu Val Cys Leu Leu Pro His Gly Tyr Glu Gly Gln Gly Pro
        755                 760                 765

Glu His Ser Ser Ala Arg Leu Glu Arg Tyr Leu Gln Met Cys Ala Glu
    770                 775                 780

Asp Asn Met Gln Val Val Tyr Pro Thr Thr Pro Ala Asn Tyr Phe His
785                 790                 795                 800

Val Leu Arg Arg Gln Leu His Arg Glu Ile Arg Lys Pro Leu Ile Leu
                805                 810                 815

Met Thr Pro Lys Ser Leu Leu Arg His Lys Arg Ala Val Ser Arg Leu
            820                 825                 830

Glu Glu Leu Ala Lys Gly Thr Thr Phe His Arg Ile Leu Tyr Asp Asp
        835                 840                 845

Ala Gln Met Leu Pro Thr Asp Ala Ile Lys Leu Val Pro Asp Glu Lys
    850                 855                 860

Ile Arg Arg Ile Val Leu Cys Ser Gly Lys Val Tyr Tyr Asp Leu Tyr
865                 870                 875                 880

Glu Glu Arg Glu Lys Arg Gly Ile Asp Asp Ile Tyr Leu Met Arg Val
                885                 890                 895

Glu Gln Leu Tyr Pro Val Pro Leu Lys Ala Leu Val Ala Glu Leu Ser
            900                 905                 910

Arg Phe Lys Lys Ala Glu Val Val Trp Cys Gln Glu Glu Pro Arg Asn
        915                 920                 925

Met Gly Ala Trp His Phe Ile Glu Pro Tyr Leu Glu Trp Val Leu Asn
    930                 935                 940

Gln Val Asn Gly Val Ser Arg Arg Pro Arg Tyr Val Gly Arg Ala Ala
945                 950                 955                 960

Ser Ala Ala Thr Ala Thr Gly Leu Met Ser Lys His Gln Ala Gln Leu
                965                 970                 975

Lys Ala Phe Leu Asp Glu Ala Leu Ser
            980                 985

<210> SEQ ID NO 46
<211> LENGTH: 995
<212> TYPE: PRT
<213> ORGANISM: Rhizobium loti

<400> SEQUENCE: 46
```

```
Met Ala Arg Gln Asp Gln Thr Asn Asp Gln Phe Ser Leu Thr Ser Phe
1               5                   10                  15

Leu Tyr Gly Gly Asn Ala Asp Tyr Ile Asp Ala Leu Tyr Ala Ala Tyr
            20                  25                  30

Glu Asp Asp Pro Ala Ser Val Asn Pro Glu Trp Gln Glu Phe Phe Ala
            35                  40                  45

Gly Leu Lys Asp Asp Ala Gly Asp Val Arg Arg Asn Ala Lys Gly Ala
50                  55                  60

Ser Trp Ala Lys Pro Ser Trp Pro Leu Gln Ala Asn Gly Glu Leu Val
65                  70                  75                  80

Ser Ala Leu Asp Gly Asn Trp Gly Ile Val Glu Lys His Leu Glu Lys
                85                  90                  95

Lys Val Lys Asp Lys Ala Val Thr Asn Gly Val Val Leu Ser Asp Ala
                100                 105                 110

Asp Val His Gln Ala Thr Arg Asp Ser Val Arg Ala Ile Met Met Ile
            115                 120                 125

Arg Ala Tyr Arg Met Arg Gly His Leu His Ala Asn Leu Asp Pro Leu
        130                 135                 140

Gly Ile Ala Lys Pro Leu Glu Asp Tyr Asn Glu Leu Ser Pro Glu Asn
145                 150                 155                 160

Tyr Gly Phe Thr Ala Ala Asp Tyr Asp Arg Pro Ile Phe Leu Asp Asn
            165                 170                 175

Val Leu Gly Leu Glu Phe Gly Thr Ile Arg Gln Met Leu Glu Ile Leu
            180                 185                 190

Thr Arg Thr Tyr Cys Ser Thr Leu Gly Val Glu Phe Met His Ile Ser
        195                 200                 205

Asp Pro Glu Glu Lys Ala Trp Ile Gln Ala Arg Ile Glu Gly Ala Asp
    210                 215                 220

Lys Glu Ile Ser Phe Thr Asn Thr Gly Lys Lys Ala Ile Leu Gln Lys
225                 230                 235                 240

Leu Val Glu Ala Glu Gly Phe Glu Gln Phe Ile Asp Val Lys Tyr Lys
                245                 250                 255

Gly Thr Lys Arg Phe Gly Leu Asp Gly Gly Glu Ala Leu Ile Pro Ala
            260                 265                 270

Leu Glu Gln Ile Val Lys Arg Gly Gln Leu Gly Met Lys Glu Ile
            275                 280                 285

Val Leu Gly Met Ala His Arg Gly Arg Leu Asn Val Leu Ser Gln Val
        290                 295                 300

Met Ala Lys Pro His Arg Ala Ile Phe His Glu Phe Lys Gly Gly Ser
305                 310                 315                 320

Ala Ala Pro Asp Glu Val Glu Gly Ser Gly Asp Val Lys Tyr His Leu
                325                 330                 335

Gly Ala Ser Ser Asp Arg Glu Phe Asp Gly Asn Lys Val His Leu Ser
            340                 345                 350

Leu Thr Ala Asn Pro Ser His Leu Glu Ile Val Asp Pro Val Val Met
        355                 360                 365

Gly Lys Ala Arg Ala Lys Gln Asp Tyr Leu Phe Gly Arg Gly Arg Glu
370                 375                 380

Glu Ile Val Pro Leu Glu Arg Ala Lys Val Leu Pro Leu Leu Leu
385                 390                 395                 400

His Gly Asp Ala Ala Phe Ala Gly Gln Gly Val Ile Ala Glu Ile Leu
                405                 410                 415

Gly Leu Ser Gly Leu Arg Gly His Arg Val Ala Gly Thr Leu His Phe
```

```
            420                 425                 430
Ile Ile Asn Asn Gln Ile Gly Phe Thr Thr Asn Pro Arg Phe Ser Arg
            435                 440                 445
Ser Ser Pro Tyr Pro Ser Asp Val Ala Lys Met Ile Glu Ala Pro Ile
    450                 455                 460
Phe His Val Asn Gly Asp Pro Glu Ala Val Val His Ala Thr Lys
465                 470                 475                 480
Val Ala Ile Glu Phe Arg Met Lys Phe His Lys Pro Val Val Asp
                485                 490                 495
Met Phe Cys Tyr Arg Arg Phe Gly His Asn Glu Gly Asp Glu Pro Ala
            500                 505                 510
Phe Thr Gln Pro Ile Met Tyr Arg Asn Ile Arg Thr His Lys Thr Thr
            515                 520                 525
Val Gln Ile Tyr Ala Asp Arg Leu Ile Ala Glu Gly His Ile Thr Gln
            530                 535                 540
Ala Glu Leu Asp Gln Met Lys Ala Asp Trp Arg Ala His Leu Glu Ser
545                 550                 555                 560
Glu Trp Glu Val Gly Gln His Tyr Lys Pro Asn Lys Ala Asp Trp Leu
                565                 570                 575
Asp Gly Ala Trp Ser Gly Leu Arg Thr Ala Asp Asn Gln Asp Glu Gln
                580                 585                 590
Arg Arg Gly Lys Thr Ala Val Pro Val Lys Thr Leu Lys Glu Ile Gly
            595                 600                 605
Lys Lys Leu Thr Glu Val Pro Lys Gly Phe Glu Ala His Lys Thr Ile
            610                 615                 620
Ile Arg Phe Leu Glu Asn Arg Arg Glu Ala Ile Glu Ser Gly Glu Gly
625                 630                 635                 640
Ile Asp Trp Ser Thr Ala Glu Ala Leu Ala Phe Gly Ala Ile Leu Leu
                645                 650                 655
Asp Gly Asn Pro Ile Arg Leu Ser Gly Gln Asp Ser Glu Arg Gly Thr
                660                 665                 670
Phe Ser Gln Arg His Ser Val Leu Tyr Asp Gln Arg Asp Glu Thr Arg
            675                 680                 685
Tyr Ile Pro Leu Asn Asn Leu Ser Ala Ala Gln Ala Gly Tyr Glu Val
            690                 695                 700
Ile Asn Ser Met Leu Ser Glu Glu Ala Val Leu Gly Phe Glu Tyr Gly
705                 710                 715                 720
Tyr Ser Leu Ala Glu Pro Lys Ala Leu Thr Leu Trp Glu Ala Gln Phe
                725                 730                 735
Gly Asp Phe Ala Asn Gly Ala Gln Val Val Phe Asp Gln Phe Ile Ser
            740                 745                 750
Ser Gly Glu Arg Lys Trp Leu Arg Met Ser Gly Leu Val Cys Leu Leu
            755                 760                 765
Pro His Gly Tyr Glu Gly Gln Gly Pro Glu His Ser Ser Ala Arg Leu
            770                 775                 780
Glu Arg Phe Leu Gln Leu Cys Ala Glu Asp Asn Met Gln Val Ala Asn
785                 790                 795                 800
Cys Thr Thr Pro Ala Asn Tyr Phe His Ile Leu Arg Arg Gln Leu Lys
                805                 810                 815
Arg Asp Phe Arg Lys Pro Leu Ile Leu Met Thr Pro Lys Ser Leu Leu
            820                 825                 830
Arg His Lys Arg Ala Val Ser Thr Leu Pro Glu Ile Ser Gly Glu Ser
            835                 840                 845
```

```
Ser Phe His Arg Leu Leu Trp Asp Asp Ala Gln Leu Leu Pro Asn Gln
        850                 855                 860

Pro Ile Lys Leu Thr Lys Asp Ser Lys Ile Arg Arg Val Val Leu Cys
865                 870                 875                 880

Ser Gly Lys Val Tyr Tyr Asp Leu Tyr Glu Glu Arg Glu Lys Arg Gly
                885                 890                 895

Ile Asn Asp Ile Tyr Leu Leu Arg Val Glu Gln Leu Tyr Pro Phe Pro
                900                 905                 910

Ala Lys Ala Leu Ile Thr Glu Leu Ser Arg Phe Arg Asn Ala Glu Met
                915                 920                 925

Val Trp Cys Gln Glu Pro Lys Asn Met Gly Ala Trp Ser Phe Ile
        930                 935                 940

Asp Pro Tyr Leu Glu Trp Val Leu Ala His Ile Asp Ala Lys His Gln
945                 950                 955                 960

Arg Val Arg Tyr Thr Gly Arg Pro Ala Ala Ala Ser Pro Ala Thr Gly
                965                 970                 975

Leu Met Ser Lys His Leu Ala Gln Leu Ala Ala Leu Leu Glu Asp Ala
                980                 985                 990

Leu Gly Glu
        995

<210> SEQ ID NO 47
<211> LENGTH: 547
<212> TYPE: PRT
<213> ORGANISM: Lactococcus lactis

<400> SEQUENCE: 47

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
                20                  25                  30

Asp Gln Ile Ile Ser Arg Glu Asp Met Lys Trp Ile Gly Asn Ala Asn
            35                  40                  45

Glu Leu Asn Ala Ser Tyr Met Ala Asp Gly Tyr Ala Arg Thr Lys Lys
50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
                100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Tyr
130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
                180                 185                 190

Val Ile Leu Ser Lys Ile Glu Glu Ser Leu Lys Asn Ala Gln Lys Pro
            195                 200                 205

Val Val Ile Ala Gly His Glu Val Ile Ser Phe Gly Leu Glu Lys Thr
```

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
            245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
        290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
            340                 345                 350

Pro Leu Ser Gln Asp Arg Leu Trp Gln Ala Val Glu Ser Leu Thr Gln
        355                 360                 365

Ser Asn Glu Thr Ile Val Ala Glu Gln Gly Thr Ser Phe Phe Gly Ala
370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
        450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Val Asn Arg Met Tyr Trp Ile Glu Leu Val Leu Glu Lys
        515                 520                 525

Glu Asp Ala Pro Lys Leu Leu Lys Lys Met Gly Lys Leu Phe Ala Glu
530                 535                 540

Gln Asn Lys
545

<210> SEQ ID NO 48
<211> LENGTH: 1728
<212> TYPE: DNA
<213> ORGANISM: Issatchenkia orientalis

<400> SEQUENCE: 48
atgactgaca aaatctccct aggtacttat ctgtttgaaa agttaaagga agcaggctct      60
tattccatct ttggtgttcc tggtgatttc aatttggcat tgttggacca cgtcaaggaa     120
gttgaaggca ttagatgggt cggtaacgct aacgagttga atgccggcta cgaagctgat     180

```
ggttatgcaa gaatcaatgg atttgcatcc ctaatcacca cctttggtgt cggtgaattg     240
tctgccgtca atgccattgc aggttcttat gctgaacacg tcccattgat ccatattgtt     300
ggtatgcctt ccttgtctgc tatgaagaac aacttgttgt tacaccatac cttgggtgac     360
acaagattcg acaacttcac cgaaatgtca agaaaatca gtgcaaaggt tgaaattgtt      420
tacgatttgg aatcagctcc aaaattaatt aataacttga ttgaaaccgc ttatcacaca     480
aagagaccag tctacttggg acttccttcc aactttgctg atgaattggt tccagcggca     540
ttagttaagg aaaacaagtt acatttagaa gaacctctaa caacccccgt tgctgaagaa     600
gaattcattc ataacgttgt tgaaatggtc aagaaggcag aaaaaccaat cattctcgtt     660
gacgcttgtg ctgcaagaca taacatttct aaggaagtga gagagttggc taaaattgact    720 aaattccctg tcttcaccac cccaatgggt aaatctactg ttgatgaaga tgatgaagaa     780
ttctttggct tatacttggg ttctctatct gctccagatg ttaaggacat tgttggccca     840
accgattgta tcttatcctt aggtggttta ccttctgatt tcaacaccgg ttccttctca     900
tatggttaca ccactaagaa tgtcgttgaa ttccattcca actactgtaa attcaaatct     960
gcaacttatg aaaacttgat gatgaagggc gcagtccaaa gattgatcag cgaattgaag    1020
aatattaagt attccaatgt ctcaacttta tctccaccaa aatctaaatt tgcttacgaa    1080
tctgcaaagg ttgctccaga aggtatcatc actcaagatt acctgtggaa gagattatct    1140
tacttcttaa agccaagaga tatcattgtc actgaaactg gtacttcctc ctttggtgtc    1200
ttggctaccc acttaccaag agattcaaag tctatctccc aagtcttatg gggttccatt    1260
ggtttctcct taccagctgc agttggtgct gcatttgctg ctgaagatgc acacaaacaa    1320
actggcgaac aagaaagaag aactgttttg tttattggtg atggttcttt acaattgact    1380
gtccaatcaa tctcagatgc tgcaagatgg aacatcaagc catacatctt catcttaaac    1440
aacagaggtt acactatcga aaagttgatc cacggtcgtc atgaggacta caaccaaatt    1500
caaccatggg atcaccaatt gttattgaag ctctttgctg acaagaccca atatgaaaac    1560
catgttgtta atccgctaa ggacttggac gctttgatga aggatgaagc attcaacaag    1620
gaagataaga ttagagtcat tgaattattc ttggatgaat tcgatgctcc agaaatcttg    1680
gttgctcaag ctaaattatc tgatgaaatc aactctaaag ccgcttaa                 1728
```

<210> SEQ ID NO 49
<211> LENGTH: 575
<212> TYPE: PRT
<213> ORGANISM: Issatchenkia orientalis

<400> SEQUENCE: 49

Met Thr Asp Lys Ile Ser Leu Gly Thr Tyr Leu Phe Glu Lys Leu Lys
1               5                   10                  15

Glu Ala Gly Ser Tyr Ser Ile Phe Gly Val Pro Gly Asp Phe Asn Leu
            20                  25                  30

Ala Leu Leu Asp His Val Lys Glu Val Glu Gly Ile Arg Trp Val Gly
        35                  40                  45

Asn Ala Asn Glu Leu Asn Ala Gly Tyr Glu Ala Asp Gly Tyr Ala Arg
    50                  55                  60

Ile Asn Gly Phe Ala Ser Leu Ile Thr Thr Phe Gly Val Gly Glu Leu
65                  70                  75                  80

Ser Ala Val Asn Ala Ile Ala Gly Ser Tyr Ala Glu His Val Pro Leu
                85                  90                  95

Ile His Ile Val Gly Met Pro Ser Leu Ser Ala Met Lys Asn Asn Leu

```
            100                 105                 110
Leu Leu His His Thr Leu Gly Asp Thr Arg Phe Asp Asn Phe Thr Glu
            115                 120                 125
Met Ser Lys Lys Ile Ser Ala Lys Val Glu Ile Val Tyr Asp Leu Glu
            130                 135                 140
Ser Ala Pro Lys Leu Ile Asn Asn Leu Ile Glu Thr Ala Tyr His Thr
145                 150                 155                 160
Lys Arg Pro Val Tyr Leu Gly Leu Pro Ser Asn Phe Ala Asp Glu Leu
                    165                 170                 175
Val Pro Ala Ala Leu Val Lys Glu Asn Lys Leu His Leu Glu Glu Pro
                    180                 185                 190
Leu Asn Asn Pro Val Ala Glu Glu Phe Ile His Asn Val Val Glu
            195                 200                 205
Met Val Lys Lys Ala Glu Lys Pro Ile Ile Leu Val Asp Ala Cys Ala
            210                 215                 220
Ala Arg His Asn Ile Ser Lys Glu Val Arg Glu Leu Ala Lys Leu Thr
225                 230                 235                 240
Lys Phe Pro Val Phe Thr Thr Pro Met Gly Lys Ser Thr Val Asp Glu
                    245                 250                 255
Asp Asp Glu Glu Phe Phe Gly Leu Tyr Leu Gly Ser Leu Ser Ala Pro
            260                 265                 270
Asp Val Lys Asp Ile Val Gly Pro Thr Asp Cys Ile Leu Ser Leu Gly
            275                 280                 285
Gly Leu Pro Ser Asp Phe Asn Thr Gly Ser Phe Ser Tyr Gly Tyr Thr
            290                 295                 300
Thr Lys Asn Val Val Glu Phe His Ser Asn Tyr Cys Lys Phe Lys Ser
305                 310                 315                 320
Ala Thr Tyr Glu Asn Leu Met Met Lys Gly Ala Val Gln Arg Leu Ile
                    325                 330                 335
Ser Glu Leu Lys Asn Ile Lys Tyr Ser Asn Val Ser Thr Leu Ser Pro
            340                 345                 350
Pro Lys Ser Lys Phe Ala Tyr Glu Ser Ala Lys Val Ala Pro Glu Gly
            355                 360                 365
Ile Ile Thr Gln Asp Tyr Leu Trp Lys Arg Leu Ser Tyr Phe Leu Lys
            370                 375                 380
Pro Arg Asp Ile Ile Val Thr Glu Thr Gly Thr Ser Ser Phe Gly Val
385                 390                 395                 400
Leu Ala Thr His Leu Pro Arg Asp Ser Lys Ser Ile Ser Gln Val Leu
                    405                 410                 415
Trp Gly Ser Ile Gly Phe Ser Leu Pro Ala Ala Val Gly Ala Ala Phe
            420                 425                 430
Ala Ala Glu Asp Ala His Lys Gln Thr Gly Glu Gln Glu Arg Arg Thr
            435                 440                 445
Val Leu Phe Ile Gly Asp Gly Ser Leu Gln Leu Thr Val Gln Ser Ile
            450                 455                 460
Ser Asp Ala Ala Arg Trp Asn Ile Lys Pro Tyr Ile Phe Ile Leu Asn
465                 470                 475                 480
Asn Arg Gly Tyr Thr Ile Glu Lys Leu Ile His Gly Arg His Glu Asp
                    485                 490                 495
Tyr Asn Gln Ile Gln Pro Trp Asp His Gln Leu Leu Leu Lys Leu Phe
            500                 505                 510
Ala Asp Lys Thr Gln Tyr Glu Asn His Val Val Lys Ser Ala Lys Asp
            515                 520                 525
```

-continued

Leu Asp Ala Leu Met Lys Asp Glu Ala Phe Asn Lys Glu Asp Lys Ile
          530                 535                 540

Arg Val Ile Glu Leu Phe Leu Asp Glu Phe Asp Ala Pro Glu Ile Leu
545                 550                 555                 560

Val Ala Gln Ala Lys Leu Ser Asp Glu Ile Asn Ser Lys Ala Ala
                565                 570                 575

<210> SEQ ID NO 50
<211> LENGTH: 563
<212> TYPE: PRT
<213> ORGANISM: Saccharomyces cerevisiae

<400> SEQUENCE: 50

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
                20                  25                  30

Leu Leu Asp Lys Ile Tyr Glu Val Glu Gly Met Arg Trp Ala Gly Asn
            35                  40                  45

Ala Asn Glu Leu Asn Ala Ala Tyr Ala Ala Asp Gly Tyr Ala Arg Ile
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr 325                 330                 335
Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
        370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
            450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
            515                 520                 525

Asp Asn Ser Lys Ile Arg Met Ile Glu Ile Met Leu Pro Val Phe Asp
        530                 535                 540

Ala Pro Gln Asn Leu Val Glu Gln Ala Lys Leu Thr Ala Ala Thr Asn
545                 550                 555                 560

Ala Lys Gln

<210> SEQ ID NO 51
<211> LENGTH: 563
<212> TYPE: PRT
<213> ORGANISM: Kluyveromyces lactis

<400> SEQUENCE: 51

Met Ser Glu Ile Thr Leu Gly Arg Tyr Leu Phe Glu Arg Leu Lys Gln
1               5                   10                  15

Val Glu Val Gln Thr Ile Phe Gly Leu Pro Gly Asp Phe Asn Leu Ser
            20                  25                  30

Leu Leu Asp Asn Ile Tyr Glu Val Pro Gly Met Arg Trp Ala Gly Asn
        35                  40                  45

Ala Asn Glu Leu Asn Ala Ala Tyr Ala Ala Asp Gly Tyr Ala Arg Leu
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Val Ser Ser Gln Ala Lys Gln Leu Leu
            100                 105                 110

Leu His His Thr Leu Gly Asn Gly Asp Phe Thr Val Phe His Arg Met
        115                 120                 125

Ser Ser Asn Ile Ser Glu Thr Thr Ala Met Ile Thr Asp Ile Asn Thr

```
            130                 135                 140
Ala Pro Ala Glu Ile Asp Arg Cys Ile Arg Thr Thr Tyr Val Ser Gln
145                 150                 155                 160

Arg Pro Val Tyr Leu Gly Leu Pro Ala Asn Leu Val Asp Leu Thr Val
                165                 170                 175

Pro Ala Ser Leu Leu Asp Thr Pro Ile Asp Leu Ser Leu Lys Pro Asn
            180                 185                 190

Asp Pro Glu Ala Glu Glu Val Ile Glu Asn Val Leu Gln Leu Ile
                195                 200                 205

Lys Glu Ala Lys Asn Pro Val Ile Leu Ala Asp Ala Cys Cys Ser Arg
210                 215                 220

His Asp Ala Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Lys His
                245                 250                 255

Pro Arg Phe Gly Gly Val Tyr Val Gly Thr Leu Ser Ser Pro Ala Val
                260                 265                 270

Lys Glu Ala Val Glu Ser Ala Asp Leu Val Leu Ser Val Gly Ala Leu
            275                 280                 285

Leu Ser Asp Phe Asn Thr Gly Ser Phe Ser Tyr Ser Tyr Lys Thr Lys
            290                 295                 300

Asn Ile Val Glu Phe His Ser Asp Tyr Thr Lys Ile Arg Ser Ala Thr
305                 310                 315                 320

Phe Pro Gly Val Gln Met Lys Phe Ala Leu Gln Lys Leu Leu Thr Lys
                325                 330                 335

Val Ala Asp Ala Ala Lys Gly Tyr Lys Pro Val Pro Val Pro Ser Glu
            340                 345                 350

Pro Glu His Asn Glu Ala Val Ala Asp Ser Thr Pro Leu Lys Gln Glu
            355                 360                 365

Trp Val Trp Thr Gln Val Gly Glu Phe Leu Arg Glu Gly Asp Val Val
            370                 375                 380

Ile Thr Glu Thr Gly Thr Ser Ala Phe Gly Ile Asn Gln Thr His Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Arg Leu Ile
465                 470                 475                 480

His Gly Glu Thr Ala Gln Tyr Asn Cys Ile Gln Asn Trp Gln His Leu
                485                 490                 495

Glu Leu Leu Pro Thr Phe Gly Ala Lys Asp Tyr Glu Ala Val Arg Val
            500                 505                 510

Ser Thr Thr Gly Glu Trp Asn Lys Leu Thr Thr Asp Glu Lys Phe Gln
            515                 520                 525

Asp Asn Thr Arg Ile Arg Leu Ile Glu Val Met Leu Pro Thr Met Asp
530                 535                 540

Ala Pro Ser Asn Leu Val Lys Gln Ala Gln Leu Thr Ala Ala Thr Asn
545                 550                 555                 560
```

Ala Lys Asn

<210> SEQ ID NO 52
<211> LENGTH: 568
<212> TYPE: PRT
<213> ORGANISM: Zymomonas mobilis

<400> SEQUENCE: 52

```
Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205

Arg Asp Lys Val Ala Val Leu Val Gly Ser Lys Leu Arg Ala Ala Gly
    210                 215                 220

Ala Glu Glu Ala Ala Val Lys Phe Ala Asp Ala Leu Gly Gly Ala Val
225                 230                 235                 240

Ala Thr Met Ala Ala Lys Ser Phe Phe Pro Glu Glu Asn Pro His Tyr
                245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
    290                 295                 300

Val Leu Ala Glu Pro Arg Ser Val Val Asn Gly Ile Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
        355                 360                 365
```

Glu Ile Ala Arg Gln Val Glu Ala Leu Leu Thr Pro Asn Thr Thr Val
    370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
                420                 425                 430

Arg Asn Ile Leu Met Val Gly Asp Gly Ser Phe Gln Leu Thr Ala Gln
                435                 440                 445

Glu Val Ala Gln Met Val Arg Leu Lys Leu Pro Val Ile Ile Phe Leu
    450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
                500                 505                 510

Lys Thr Gly Gly Glu Leu Ala Glu Ala Ile Lys Val Ala Leu Ala Asn
    515                 520                 525

Thr Asp Gly Pro Thr Leu Ile Glu Cys Phe Ile Gly Arg Glu Asp Cys
530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
                565

<210> SEQ ID NO 53
<211> LENGTH: 557
<212> TYPE: PRT
<213> ORGANISM: Acetobacter pasteurianus

<400> SEQUENCE: 53

Met Thr Tyr Thr Val Gly Met Tyr Leu Ala Glu Arg Leu Val Gln Ile
1               5                   10                  15

Gly Leu Lys His His Phe Ala Val Gly Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
                100                 105                 110

His His Thr Ile Gly Lys Thr Asp Tyr Ser Tyr Gln Leu Glu Met Ala
            115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val 165                 170                 175
Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Lys Asn
            195                 200                 205

Arg Pro Ala Pro Val Met Leu Leu Gly Ser Lys Leu Arg Ala Ala Asn
            210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
                260                 265                 270

Leu Val Glu Thr Ser Asp Ala Leu Leu Cys Ile Ala Pro Val Phe Asn
            275                 280                 285

Asp Tyr Ser Thr Val Gly Trp Ser Gly Met Pro Lys Gly Pro Asn Val
            290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
            370                 375                 380

Gly Asp Ser Trp Phe Asn Ala Met Arg Met Thr Leu Ala Gly Ala Arg
385                 390                 395                 400

Val Glu Leu Glu Met Gln Trp Gly His Ile Gly Trp Ser Val Pro Ser
                405                 410                 415

Ala Phe Gly Asn Ala Met Gly Ser Gln Asp Arg Gln His Val Val Met
            420                 425                 430

Val Gly Asp Gly Ser Phe Gln Leu Thr Ala Gln Glu Val Ala Gln Met
            435                 440                 445

Val Arg Tyr Glu Leu Pro Val Ile Ile Phe Leu Ile Asn Asn Arg Gly
            450                 455                 460

Tyr Val Ile Glu Ile Ala Ile His Asp Gly Pro Tyr Asn Tyr Ile Lys
465                 470                 475                 480

Asn Trp Asp Tyr Ala Gly Leu Met Glu Val Phe Asn Ala Gly Glu Gly
                485                 490                 495

His Gly Leu Gly Leu Lys Ala Thr Thr Pro Lys Glu Leu Thr Glu Ala
            500                 505                 510

Ile Ala Arg Ala Lys Ala Asn Thr Arg Gly Pro Thr Leu Ile Glu Cys
            515                 520                 525

Gln Ile Asp Arg Thr Asp Cys Thr Asp Met Leu Val Gln Trp Gly Arg
            530                 535                 540

Lys Val Ala Ser Thr Asn Ala Arg Lys Thr Thr Leu Ala
545                 550                 555

<210> SEQ ID NO 54
<211> LENGTH: 528
<212> TYPE: PRT
<213> ORGANISM: Pseudomonas putida

<400> SEQUENCE: 54

```
Met Ala Ser Val His Gly Thr Thr Tyr Glu Leu Leu Arg Arg Gln Gly
1               5                   10                  15

Ile Asp Thr Val Phe Gly Asn Pro Gly Ser Asn Glu Leu Pro Phe Leu
            20                  25                  30

Lys Asp Phe Pro Glu Asp Phe Arg Tyr Ile Leu Ala Leu Gln Glu Ala
        35                  40                  45

Cys Val Val Gly Ile Ala Asp Gly Tyr Ala Gln Ala Ser Arg Lys Pro
50                  55                  60

Ala Phe Ile Asn Leu His Ser Ala Ala Gly Thr Gly Asn Ala Met Gly
65                  70                  75                  80

Ala Leu Ser Asn Ala Trp Asn Ser His Ser Pro Leu Ile Val Thr Ala
                85                  90                  95

Gly Gln Gln Thr Arg Ala Met Ile Gly Val Glu Ala Leu Leu Thr Asn
            100                 105                 110

Val Asp Ala Ala Asn Leu Pro Arg Pro Leu Val Lys Trp Ser Tyr Glu
        115                 120                 125

Pro Ala Ser Ala Ala Glu Val Pro His Ala Met Ser Arg Ala Ile His
    130                 135                 140

Met Ala Ser Met Ala Pro Gln Gly Pro Val Tyr Leu Ser Val Pro Tyr
145                 150                 155                 160

Asp Asp Trp Asp Lys Asp Ala Asp Pro Gln Ser His His Leu Phe Asp
                165                 170                 175

Arg His Val Ser Ser Ser Val Arg Leu Asn Asp Gln Asp Leu Asp Ile
            180                 185                 190

Leu Val Lys Ala Leu Asn Ser Ala Ser Asn Pro Ala Ile Val Leu Gly
        195                 200                 205

Pro Asp Val Asp Ala Ala Asn Ala Asn Ala Asp Cys Val Met Leu Ala
    210                 215                 220

Glu Arg Leu Lys Ala Pro Val Trp Val Ala Pro Ser Ala Pro Arg Cys
225                 230                 235                 240

Pro Phe Pro Thr Arg His Pro Cys Phe Arg Gly Leu Met Pro Ala Gly
                245                 250                 255

Ile Ala Ala Ile Ser Gln Leu Leu Glu Gly His Asp Val Val Leu Val
            260                 265                 270

Ile Gly Ala Pro Val Phe Arg Tyr His Gln Tyr Asp Pro Gly Gln Tyr
        275                 280                 285

Leu Lys Pro Gly Thr Arg Leu Ile Ser Val Thr Cys Asp Pro Leu Glu
    290                 295                 300

Ala Ala Arg Ala Pro Met Gly Asp Ala Ile Val Ala Asp Ile Gly Ala
305                 310                 315                 320

Met Ala Ser Ala Leu Ala Asn Leu Val Glu Glu Ser Ser Arg Gln Leu
                325                 330                 335

Pro Thr Ala Ala Pro Glu Pro Ala Lys Val Asp Gln Asp Ala Gly Arg
            340                 345                 350

Leu His Pro Glu Thr Val Phe Asp Thr Leu Asn Asp Met Ala Pro Glu
        355                 360                 365

Asn Ala Ile Tyr Leu Asn Glu Ser Thr Ser Thr Thr Ala Gln Met Trp
    370                 375                 380

Gln Arg Leu Asn Met Arg Asn Pro Gly Ser Tyr Tyr Phe Cys Ala Ala
385                 390                 395                 400

Gly Gly Leu Gly Phe Ala Leu Pro Ala Ala Ile Gly Val Gln Leu Ala
```

```
                   405                 410                 415
Glu Pro Glu Arg Gln Val Ile Ala Val Ile Gly Asp Gly Ser Ala Asn
            420                 425                 430

Tyr Ser Ile Ser Ala Leu Trp Thr Ala Ala Gln Tyr Asn Ile Pro Thr
            435                 440                 445

Ile Phe Val Ile Met Asn Asn Gly Thr Tyr Gly Ala Leu Arg Trp Phe
            450                 455                 460

Ala Gly Val Leu Glu Ala Glu Asn Val Pro Gly Leu Asp Val Pro Gly
465                 470                 475                 480

Ile Asp Phe Arg Ala Leu Ala Lys Gly Tyr Gly Val Gln Ala Leu Lys
            485                 490                 495

Ala Asp Asn Leu Glu Gln Leu Lys Gly Ser Leu Gln Glu Ala Leu Ser
            500                 505                 510

Ala Lys Gly Pro Val Leu Ile Glu Val Ser Thr Val Ser Pro Val Lys
            515                 520                 525

<210> SEQ ID NO 55
<211> LENGTH: 528
<212> TYPE: PRT
<213> ORGANISM: Pseudomonas aeruginosa

<400> SEQUENCE: 55

Met Lys Thr Val His Ser Ala Ser Tyr Glu Ile Leu Arg Arg His Gly
1               5                   10                  15

Leu Thr Thr Val Phe Gly Asn Pro Gly Ser Asn Glu Leu Pro Phe Leu
            20                  25                  30

Lys Asp Phe Pro Glu Asp Phe Arg Tyr Ile Leu Gly Leu His Glu Gly
            35                  40                  45

Ala Val Val Gly Met Ala Asp Gly Phe Ala Leu Ala Ser Gly Arg Pro
        50                  55                  60

Ala Phe Val Asn Leu His Ala Ala Gly Thr Gly Asn Gly Met Gly
65                  70                  75                  80

Ala Leu Thr Asn Ala Trp Tyr Ser His Ser Pro Leu Val Ile Thr Ala
            85                  90                  95

Gly Gln Gln Val Arg Ser Met Ile Gly Val Glu Ala Met Leu Ala Asn
            100                 105                 110

Val Asp Ala Gly Gln Leu Pro Lys Pro Leu Val Lys Trp Ser His Glu
        115                 120                 125

Pro Ala Cys Ala Gln Asp Val Pro Arg Ala Leu Ser Gln Ala Ile Gln
130                 135                 140

Thr Ala Ser Leu Pro Pro Arg Ala Pro Val Tyr Leu Ser Ile Pro Tyr
145                 150                 155                 160

Asp Asp Trp Ala Gln Pro Ala Pro Ala Gly Val Glu His Leu Ala Ala
            165                 170                 175

Arg Gln Val Ser Gly Ala Ala Leu Pro Ala Pro Ala Leu Leu Ala Glu
            180                 185                 190

Leu Gly Glu Arg Leu Ser Arg Ser Arg Asn Pro Val Leu Val Leu Gly
            195                 200                 205

Pro Asp Val Asp Gly Ala Asn Ala Asn Gly Leu Ala Val Glu Leu Ala
        210                 215                 220

Glu Lys Leu Arg Met Pro Ala Trp Val Ala Pro Ser Ala Ser Arg Cys
225                 230                 235                 240

Pro Phe Pro Thr Arg His Ala Cys Phe Arg Gly Val Leu Pro Ala Ala
            245                 250                 255
```

```
Ile Ala Gly Ile Ser Arg Leu Leu Asp Gly His Asp Leu Ile Leu Val
            260                 265                 270

Val Gly Ala Pro Val Phe Arg Tyr His Gln Phe Ala Pro Gly Asp Tyr
            275                 280                 285

Leu Pro Ala Gly Ala Glu Leu Val Gln Val Thr Cys Asp Pro Gly Glu
            290                 295                 300

Ala Ala Arg Ala Pro Met Gly Asp Ala Leu Val Gly Asp Ile Ala Leu
305                 310                 315                 320

Thr Leu Glu Ala Leu Leu Glu Gln Val Arg Pro Ser Ala Arg Pro Leu
                    325                 330                 335

Pro Glu Ala Leu Pro Arg Pro Ala Leu Ala Glu Glu Gly Gly Pro
            340                 345                 350

Leu Arg Pro Glu Thr Val Phe Asp Val Ile Asp Ala Leu Ala Pro Arg
            355                 360                 365

Asp Ala Ile Phe Val Lys Glu Ser Thr Ser Thr Val Thr Ala Phe Trp
            370                 375                 380

Gln Arg Val Glu Met Arg Glu Pro Gly Ser Tyr Phe Pro Ala Ala
385                 390                 395                 400

Gly Gly Leu Gly Phe Gly Leu Pro Ala Ala Val Gly Ala Gln Leu Ala
                    405                 410                 415

Gln Pro Arg Arg Gln Val Ile Gly Ile Gly Asp Gly Ser Ala Asn
            420                 425                 430

Tyr Gly Ile Thr Ala Leu Trp Ser Ala Ala Gln Tyr Arg Val Pro Ala
                    435                 440                 445

Val Phe Ile Ile Leu Lys Asn Gly Thr Tyr Gly Ala Leu Arg Trp Phe
450                 455                 460

Ala Gly Val Leu Glu Val Pro Asp Ala Pro Gly Leu Asp Val Pro Gly
465                 470                 475                 480

Leu Asp Phe Cys Ala Ile Ala Arg Gly Tyr Gly Val Glu Ala Leu His
            485                 490                 495

Ala Ala Thr Arg Glu Glu Leu Glu Gly Ala Leu Lys His Ala Leu Ala
            500                 505                 510

Ala Asp Arg Pro Val Leu Ile Glu Val Pro Thr Gln Thr Ile Glu Pro
            515                 520                 525

<210> SEQ ID NO 56
<211> LENGTH: 526
<212> TYPE: PRT
<213> ORGANISM: Pseudomonas stutzeri

<400> SEQUENCE: 56

Met Ala Ser Val His Ser Ile Thr Tyr Glu Leu Leu Arg Arg Gln Gly
1               5                   10                  15

Ile Asp Thr Val Phe Gly Asn Pro Gly Ser Asn Glu Leu Pro Phe Leu
            20                  25                  30

Lys Asp Phe Pro Glu Asp Phe Arg Tyr Ile Leu Ala Leu Gln Glu Ala
            35                  40                  45

Cys Val Val Gly Ile Ala Asp Gly Tyr Ala Gln Ala Ser Arg Lys Pro
        50                  55                  60

Ala Phe Ile Asn Leu His Ser Ala Ala Gly Thr Gly Asn Ala Met Gly
65                  70                  75                  80

Ala Met Ser Asn Ala Trp Asn Cys His Ser Pro Leu Ile Val Thr Ala
                85                  90                  95

Gly Gln Gln Asn Arg Ala Met Ile Gly Val Glu Ala Leu Leu Thr Asn
            100                 105                 110
```

```
Val Asp Ala Ala Ser Leu Pro Arg Pro Leu Val Lys Trp Ser Tyr Glu
        115                 120                 125

Pro Ala Ser Ala Ala Glu Val Pro His Ala Met Ser Arg Ala Ile His
130                 135                 140

Met Ala Ser Met Ala Pro Arg Gly Pro Val Tyr Leu Ser Val Pro Tyr
145                 150                 155                 160

Asp Asp Trp Asp Lys Glu Ala Asp Pro Gln Ser His His Leu Tyr Asp
                165                 170                 175

Arg Ser Val Asn Ser Ala Val Arg Leu Asn Asp Gln Asp Leu Glu Val
                180                 185                 190

Leu Val Glu Ala Leu Asn Ser Ser Asn Pro Ala Ile Val Leu Gly
        195                 200                 205

Pro Asp Val Asp Ser Ala Asn Ala Asn Ala Asp Cys Val Thr Leu Ala
        210                 215                 220

Glu Arg Leu Lys Ala Pro Val Trp Val Ala Pro Ser Ala Pro Arg Cys
225                 230                 235                 240

Pro Phe Pro Thr Arg His Pro Cys Phe Arg Gly Leu Met Pro Ala Gly
                245                 250                 255

Ile Ala Ala Ile Ser Gln Leu Leu Glu Gly His Asp Val Leu Val
        260                 265                 270

Ile Gly Ala Pro Val Phe Arg Tyr His Gln Tyr Asp Pro Gly Gln Tyr
        275                 280                 285

Leu Lys Pro Gly Thr Arg Leu Ile Ser Ile Thr Cys Asp Pro Leu Glu
        290                 295                 300

Ala Ala Arg Ala Pro Met Gly Asp Ala Ile Val Ala Asp Ile Gly Thr
305                 310                 315                 320

Met Thr Ala Ala Leu Ala Ser Arg Ile Gly Glu Ser Glu Arg Gln Leu
                325                 330                 335

Pro Ala Val Leu Pro Ser Pro Glu Arg Val Asn Gln Asp Ala Gly Arg
                340                 345                 350

Leu Arg Pro Glu Thr Val Phe Asp Thr Leu Asn Glu Met Ala Pro Glu
            355                 360                 365

Asp Ala Ile Tyr Leu Asn Glu Ser Thr Ser Thr Thr Ala Gln Met Trp
            370                 375                 380

Gln Arg Leu Asn Met Arg Asn Pro Gly Ser Tyr Tyr Phe Cys Ala Ala
385                 390                 395                 400

Gly Gly Leu Gly Phe Ala Leu Pro Ala Ala Ile Gly Val Gln Leu Ala
                405                 410                 415

Glu Pro Asp Arg Gln Val Ile Ala Val Ile Gly Asp Gly Ser Ala Asn
            420                 425                 430

Tyr Ser Ile Ser Ala Leu Trp Thr Ala Ala His Tyr Asn Ile Pro Ala
            435                 440                 445

Ile Phe Leu Ile Met Asn Asn Gly Thr Tyr Gly Ala Leu Arg Trp Phe
450                 455                 460

Ala Gly Val Leu Glu Ala Glu Asn Val Pro Gly Leu Asp Val Pro Gly
465                 470                 475                 480

Ile Asp Phe Cys Ala Ile Ala Lys Gly Tyr Gly Ile Pro Ala Leu Lys
                485                 490                 495

Ala Asp Asn Leu Glu Gln Leu Lys Gly Ser Ile His Glu Ala Leu Ser
            500                 505                 510

Ala Lys Gly Pro Val Leu Ile Glu Val Ser Thr Val Ser Leu
            515                 520                 525
```

```
<210> SEQ ID NO 57
<211> LENGTH: 528
<212> TYPE: PRT
<213> ORGANISM: Pseudomonas fluorescens

<400> SEQUENCE: 57

Met Lys Thr Val His Ser Ala Ser Tyr Asp Ile Leu Arg Gln Gln Gly
1               5                   10                  15

Leu Thr Thr Val Phe Gly Asn Pro Gly Ser Asn Glu Leu Pro Phe Leu
            20                  25                  30

Lys Gly Phe Pro Glu Asp Phe Arg Tyr Ile Leu Gly Leu His Glu Gly
        35                  40                  45

Ala Val Val Gly Met Ala Asp Gly Phe Ala Leu Ala Ser Gly Gln Pro
    50                  55                  60

Ala Phe Val Asn Leu His Ala Ala Gly Thr Gly Asn Gly Met Gly
65                  70                  75                  80

Ala Leu Thr Asn Ala Trp Tyr Ser His Ser Pro Leu Val Ile Thr Ala
                85                  90                  95

Gly Gln Gln Val Arg Ser Met Ile Gly Val Glu Ala Met Leu Ala Asn
            100                 105                 110

Val Asp Ala Pro Gln Leu Pro Lys Pro Leu Val Lys Trp Ser Ala Glu
        115                 120                 125

Pro Ala Cys Ala Glu Asp Val Pro Arg Ala Leu Ser Gln Ala Ile His
    130                 135                 140

Met Ala Asn Gln Ala Pro Lys Gly Pro Val Tyr Leu Ser Ile Pro Tyr
145                 150                 155                 160

Asp Asp Trp Ala Arg Pro Ala Pro Ala Gly Val Glu His Leu Ala Arg
                165                 170                 175

Arg Gln Val Ala Thr Ala Gly Leu Pro Ser Ala Ala Gln Leu Arg Ser
            180                 185                 190

Leu Val Gln Arg Leu Ala Ala Ala Arg Asn Pro Val Leu Val Leu Gly
        195                 200                 205

Pro Asp Val Asp Gly Ser Arg Ser Asn His Leu Ala Val Gln Leu Ala
    210                 215                 220

Glu Lys Leu Arg Met Pro Ala Trp Val Ala Pro Ser Ala Ser Arg Cys
225                 230                 235                 240

Pro Phe Pro Thr Arg His Pro Ser Phe Arg Gly Val Leu Pro Ala Ala
                245                 250                 255

Ile Ala Gly Ile Ser Arg Cys Leu Ala Asp His Asp Leu Ile Leu Val
            260                 265                 270

Val Gly Ala Pro Val Phe Arg Tyr His Gln Phe Ala Pro Gly Asp Tyr
        275                 280                 285

Leu Pro Ala Gly Thr Glu Leu His Ile Thr Cys Asp Pro Gly Glu
    290                 295                 300

Ala Ala Arg Ala Pro Met Gly Asp Ala Leu Val Gly Asp Ile Val Glu
305                 310                 315                 320

Thr Leu Gln Ala Leu Val Trp Ala Leu Pro Asp Cys Asp Arg Pro Gln
                325                 330                 335

Pro Gln Ala Leu Pro Pro Ala Ala Pro Val Glu Glu Leu Gly Gly Leu
            340                 345                 350

Leu Arg Pro Glu Thr Val Phe Asp Val Ile Asp Glu Leu Ala Pro Lys
        355                 360                 365

Asp Ala Ile Tyr Val Lys Glu Ser Thr Ser Thr Val Gly Ala Phe Trp
    370                 375                 380
```

-continued

Gln Arg Val Glu Met Arg Glu Pro Gly Ser Tyr Tyr Phe Pro Ala Ala
385                 390                 395                 400

Gly Gly Leu Gly Phe Gly Leu Pro Ala Ala Val Gly Val Gln Leu Ala
            405                 410                 415

Arg Pro Glu Arg Arg Val Ile Gly Val Ile Gly Asp Gly Ser Ala Asn
        420                 425                 430

Tyr Gly Ile Thr Ala Leu Trp Thr Ala Ala Gln Tyr Gln Ile Pro Val
    435                 440                 445

Val Phe Ile Ile Leu Lys Asn Gly Thr Tyr Gly Ala Leu Arg Trp Phe
450                 455                 460

Ala Gly Val Leu Gln Val Ser Asp Ala Pro Gly Leu Asp Val Pro Gly
465                 470                 475                 480

Leu Asp Phe Cys Ala Ile Gly Arg Gly Tyr Gly Val His Ser Val Gln
                485                 490                 495

Ala Asn Thr Arg Glu Ala Phe Ala Gln Ala Leu Ser Glu Ala Leu Ala
            500                 505                 510

Gly Asp Arg Pro Val Leu Ile Glu Val Pro Thr Leu Thr Ile Glu Pro
        515                 520                 525

<210> SEQ ID NO 58
<211> LENGTH: 1220
<212> TYPE: PRT
<213> ORGANISM: Chloroflexus aurantiacus

<400> SEQUENCE: 58

Met Ala Thr Gly Glu Ser Met Ser Gly Thr Gly Arg Leu Ala Gly Lys
1               5                   10                  15

Ile Ala Leu Ile Thr Gly Gly Ala Gly Asn Ile Gly Ser Glu Leu Thr
            20                  25                  30

Arg Arg Phe Leu Ala Glu Gly Ala Thr Val Ile Ile Ser Gly Arg Asn
        35                  40                  45

Arg Ala Lys Leu Thr Ala Leu Ala Glu Met Gln Ala Glu Ala Gly Val
    50                  55                  60

Pro Ala Lys Arg Ile Asp Leu Glu Val Met Asp Gly Ser Asp Pro Val
65                  70                  75                  80

Ala Val Arg Ala Gly Ile Glu Ala Ile Val Ala Arg His Gly Gln Ile
                85                  90                  95

Asp Ile Leu Val Asn Asn Ala Gly Ser Ala Gly Ala Gln Arg Arg Leu
            100                 105                 110

Ala Glu Ile Pro Leu Thr Glu Ala Glu Leu Gly Pro Gly Ala Glu Glu
        115                 120                 125

Thr Leu His Ala Ser Ile Ala Asn Leu Leu Gly Met Gly Trp His Leu
    130                 135                 140

Met Arg Ile Ala Ala Pro His Met Pro Val Gly Ser Ala Val Ile Asn
145                 150                 155                 160

Val Ser Thr Ile Phe Ser Arg Ala Glu Tyr Tyr Gly Arg Ile Pro Tyr
                165                 170                 175

Val Thr Pro Lys Ala Ala Leu Asn Ala Leu Ser Gln Leu Ala Ala Arg
            180                 185                 190

Glu Leu Gly Ala Arg Gly Ile Arg Val Asn Thr Ile Phe Pro Gly Pro
        195                 200                 205

Ile Glu Ser Asp Arg Ile Arg Thr Val Phe Gln Arg Met Asp Gln Leu
    210                 215                 220

Lys Gly Arg Pro Glu Gly Asp Thr Ala His His Phe Leu Asn Thr Met

```
            225                 230                 235                 240
Arg Leu Cys Arg Ala Asn Asp Gln Gly Ala Leu Glu Arg Arg Phe Pro
                245                 250                 255

Ser Val Gly Asp Val Ala Asp Ala Ala Val Phe Leu Ala Ser Ala Glu
                260                 265                 270

Ser Ala Ala Leu Ser Gly Glu Thr Ile Glu Val Thr His Gly Met Glu
                275                 280                 285

Leu Pro Ala Cys Ser Glu Thr Ser Leu Leu Ala Arg Thr Asp Leu Arg
                290                 295                 300

Thr Ile Asp Ala Ser Gly Arg Thr Thr Leu Ile Cys Ala Gly Asp Gln
305                 310                 315                 320

Ile Glu Glu Val Met Ala Leu Thr Gly Met Leu Arg Thr Cys Gly Ser
                325                 330                 335

Glu Val Ile Ile Gly Phe Arg Ser Ala Ala Leu Ala Gln Phe Glu
                340                 345                 350

Gln Ala Val Asn Glu Ser Arg Arg Leu Ala Gly Ala Asp Phe Thr Pro
                355                 360                 365

Pro Ile Ala Leu Pro Leu Asp Pro Arg Asp Pro Ala Thr Ile Asp Ala
370                 375                 380

Val Phe Asp Trp Ala Gly Glu Asn Thr Gly Gly Ile His Trp Ile Leu
385                 390                 395                 400

Pro Ala Thr Ser His Glu Pro Ala Pro Cys Val Ile Glu Val Asp Asp
                405                 410                 415

Glu Arg Val Leu Asn Phe Leu Ala Asp Glu Ile Thr Gly Thr Ile Val
                420                 425                 430

Ile Ala Ser Arg Leu Ala Arg Tyr Trp Gln Ser Gln Arg Leu Thr Pro
                435                 440                 445

Gly Ala Arg Ala Arg Gly Pro Arg Val Ile Phe Leu Ser Asn Gly Ala
                450                 455                 460

Asp Gln Asn Gly Asn Val Tyr Gly Arg Ile Gln Ser Ala Ala Ile Gly
465                 470                 475                 480

Gln Leu Ile Arg Val Trp Arg His Glu Ala Glu Leu Asp Tyr Gln Arg
                485                 490                 495

Ala Ser Ala Ala Gly Asp His Val Leu Pro Pro Val Trp Ala Asn Gln
                500                 505                 510

Ile Val Arg Phe Ala Asn Arg Ser Leu Glu Gly Leu Glu Phe Ala Cys
                515                 520                 525

Ala Trp Thr Ala Gln Leu Leu His Ser Gln Arg His Ile Asn Glu Ile
                530                 535                 540

Thr Leu Asn Ile Pro Ala Asn Ile Ser Ala Thr Thr Gly Ala Arg Ser
545                 550                 555                 560

Ala Ser Val Gly Trp Ala Glu Ser Leu Ile Gly Leu His Leu Gly Lys
                565                 570                 575

Val Ala Leu Ile Thr Gly Gly Ser Ala Gly Ile Gly Gly Gln Ile Gly
                580                 585                 590

Arg Leu Leu Ala Leu Ser Gly Ala Arg Val Met Leu Ala Ala Arg Asp
                595                 600                 605

Arg His Lys Leu Glu Gln Met Gln Ala Met Ile Gln Ser Glu Leu Ala
                610                 615                 620

Glu Val Gly Tyr Thr Asp Val Glu Asp Arg Val His Ile Ala Pro Gly
625                 630                 635                 640

Cys Asp Val Ser Ser Glu Ala Gln Leu Ala Asp Leu Val Glu Arg Thr
                645                 650                 655
```

```
Leu Ser Ala Phe Gly Thr Val Asp Tyr Leu Ile Asn Ala Gly Ile
            660                 665                 670

Ala Gly Val Glu Glu Met Val Ile Asp Met Pro Val Glu Gly Trp Arg
            675                 680                 685

His Thr Leu Phe Ala Asn Leu Ile Ser Asn Tyr Ser Leu Met Arg Lys
    690                 695                 700

Leu Ala Pro Leu Met Lys Lys Gln Gly Ser Gly Tyr Ile Leu Asn Val
705                 710                 715                 720

Ser Ser Tyr Phe Gly Glu Lys Asp Ala Ala Ile Pro Tyr Pro Asn
                725                 730                 735

Arg Ala Asp Tyr Ala Val Ser Lys Ala Gly Gln Arg Ala Met Ala Glu
            740                 745                 750

Val Phe Ala Arg Phe Leu Gly Pro Glu Ile Gln Ile Asn Ala Ile Ala
            755                 760                 765

Pro Gly Pro Val Glu Gly Asp Arg Leu Arg Gly Thr Gly Glu Arg Pro
            770                 775                 780

Gly Leu Phe Ala Arg Arg Ala Arg Leu Ile Leu Glu Asn Lys Arg Leu
785                 790                 795                 800

Asn Glu Leu His Ala Ala Leu Ile Ala Ala Ala Arg Thr Asp Glu Arg
            805                 810                 815

Ser Met His Glu Leu Val Glu Leu Leu Leu Pro Asn Asp Val Ala Ala
            820                 825                 830

Leu Glu Gln Asn Pro Ala Ala Pro Thr Ala Leu Arg Glu Leu Ala Arg
            835                 840                 845

Arg Phe Arg Ser Glu Gly Asp Pro Ala Ala Ser Ser Ser Ser Ala Leu
            850                 855                 860

Leu Asn Arg Ser Ile Ala Ala Lys Leu Leu Ala Arg Leu His Asn Gly
865                 870                 875                 880

Gly Tyr Val Leu Pro Ala Asp Ile Phe Ala Asn Leu Pro Asn Pro Pro
                885                 890                 895

Asp Pro Phe Phe Thr Arg Ala Gln Ile Asp Arg Glu Ala Arg Lys Val
            900                 905                 910

Arg Asp Gly Ile Met Gly Met Leu Tyr Leu Gln Arg Met Pro Thr Glu
            915                 920                 925

Phe Asp Val Ala Met Ala Thr Val Tyr Leu Ala Asp Arg Asn Val
            930                 935                 940

Ser Gly Glu Thr Phe His Pro Ser Gly Gly Leu Arg Tyr Glu Arg Thr
945                 950                 955                 960

Pro Thr Gly Gly Glu Leu Phe Gly Leu Pro Ser Glu Arg Leu Ala
            965                 970                 975

Glu Leu Val Gly Ser Thr Val Tyr Leu Ile Gly Glu His Leu Thr Glu
            980                 985                 990

His Leu Asn Leu Leu Ala Met Tyr  Leu Glu Arg Tyr Gly  Ala Arg Gln
            995                 1000                1005

Val Trp  Ile Val Glu Thr  Thr Gly Ala Glu Thr  Met Arg Arg
        1010                1015                1020

Leu Leu  His Asp His Val Glu  Ala Gly Arg Leu Met  Thr Ile Val
        1025                1030                1035

Ala Gly  Asp Gln Ile Glu Ala  Ala Ile Asp Gln Ala  Ile Thr Arg
        1040                1045                1050

Tyr Gly  Arg Pro Gly Pro Val  Val Cys Thr Pro Phe  Arg Pro Leu
        1055                1060                1065
```

```
Pro Thr Val Pro Leu Val Gly Arg Lys Asp Ser Asp Trp Ser Thr
    1070            1075                1080
Val Leu Ser Glu Ala Glu Phe Ala Glu Leu Cys Glu His Gln Leu
    1085            1090                1095
Thr His His Phe Arg Val Ala Arg Lys Ile Ala Leu Ser Asp Gly
    1100            1105                1110
Ala Ser Leu Ala Leu Val Thr Pro Glu Thr Thr Ala Thr Ser Thr
    1115            1120                1125
Thr Glu Gln Phe Ala Leu Ala Asn Phe Ile Lys Thr Thr Leu His
    1130            1135                1140
Ala Phe Thr Ala Thr Ile Gly Val Glu Ser Glu Arg Thr Ala Gln
    1145            1150                1155
Arg Ile Leu Ile Asn Gln Val Asp Leu Thr Arg Arg Ala Arg Ala
    1160            1165                1170
Glu Glu Pro Arg Asp Pro His Glu Arg Gln Gln Glu Leu Glu Arg
    1175            1180                1185
Phe Ile Glu Ala Val Leu Leu Val Thr Ala Pro Leu Pro Pro Glu
    1190            1195                1200
Ala Asp Thr Arg Tyr Ala Gly Arg Ile His Arg Gly Arg Ala Ile
    1205            1210                1215
Thr Val
    1220

<210> SEQ ID NO 59
<211> LENGTH: 1229
<212> TYPE: PRT
<213> ORGANISM: Roseiflexus castenholzii

<400> SEQUENCE: 59

Met Ser Thr Val Arg Arg Leu Glu Gly Lys Val Ala Leu Ile Thr Gly
1               5                   10                  15
Gly Ala Gly Asn Ile Gly Glu Val Ile Thr Arg Arg Phe Leu Ala Glu
            20                  25                  30
Gly Ala Thr Val Val Ile Thr Gly Arg Asn Ala Glu Lys Leu Ala Val
        35                  40                  45
Tyr Arg Arg Arg Leu Ile Asp Glu Arg Val Ala Pro Glu Arg Val
    50                  55                  60
Val Ala Leu Arg Met Asp Gly Ser Asp Ile Ala Gln Val Arg Ala Gly
65                  70                  75                  80
Val Ala Gln Ile Val His Gly Gly Thr Asp Val Pro Ile Pro Leu His
                85                  90                  95
Arg Ile Asp Ile Leu Val Asn Asn Ala Gly Ser Ala Gly Pro Arg Arg
            100                 105                 110
Arg Leu Val Asp Ile Pro Leu Glu Pro Ser Glu Val Gln Pro Pro Asp
        115                 120                 125
Ser Glu Thr Leu Ala Gln Ala Val Gly Asn Leu Val Gly Ile Thr Trp
    130                 135                 140
Asn Leu Thr Arg Ala Ala Ala Pro His Met Pro Ser Gly Ser Ser Val
145                 150                 155                 160
Ile Asn Ile Ser Thr Ile Phe Ser Arg Thr Asp Tyr Tyr Gly Arg Ile
                165                 170                 175
Ala Tyr Val Ala Pro Lys Ala Ala Leu Asn Ala Leu Ser Asp Gly Leu
            180                 185                 190
Ala Arg Glu Leu Gly Val Arg Gly Ile Arg Val Asn Thr Ile Tyr Pro
        195                 200                 205
```

Gly Pro Ile Glu Ser Glu Arg Ile Tyr Thr Met Phe Gln Ala Met Asp
          210                 215                 220

Ala Leu Lys Gly Gln Pro Glu Gly Asp Thr Ala Ser Gly Phe Leu Arg
225                 230                 235                 240

Met Met Arg Leu Ser Arg Ile Asp Gln Asn Gly Glu Val Val Lys Arg
                245                 250                 255

Phe Pro Ser Pro Val Asp Val Ala Asn Thr Ala Val Phe Leu Ala Ser
            260                 265                 270

Asp Glu Ser Ala Ala Phe Thr Gly His Ala Phe Glu Val Thr His Gly
        275                 280                 285

Met Glu Val Pro Thr Glu Ser Arg Thr Thr Phe Val Ser Arg Pro Gly
    290                 295                 300

Leu Arg Ser Val Asp Ala Thr Gly Lys Val Ile Leu Ile Cys Ala Gly
305                 310                 315                 320

Asp Gln Val Asp Asp Ala Val Ala Leu Ala Asp Thr Leu Arg Ser Cys
                325                 330                 335

Arg Ala Thr Val Val Ile Gly Phe Arg Asp Pro Arg Ala Leu Glu Lys
            340                 345                 350

Ala Ser Val Leu Leu Arg Glu Pro Arg His Ala Leu Ala Ala Asp Met
        355                 360                 365

Tyr Gly Arg Pro Thr Met Thr Ala Glu Ala Arg Leu Val Arg Leu Asp
    370                 375                 380

Pro Leu Asp Pro Arg Ala Ala Ala Gln Thr Leu Glu Gln Ile His Ala
385                 390                 395                 400

Glu Leu Gly Ala Ile His His Ala Val Val Leu Pro Gly Gln Ser Arg
                405                 410                 415

His Ala Pro Ser Ala Ser Leu Ile Glu Val Asp Asp Gln Val Val Glu
            420                 425                 430

Arg Phe Leu His Gln Glu Leu Val Gly Thr Ile Ala Leu Ala Arg Glu
        435                 440                 445

Leu Ala Arg Phe Trp Glu Glu Tyr Pro Ser Gly Ser Ser Met His Arg
    450                 455                 460

Val Leu Phe Val Ser Asn Pro Asp Asp Gln Gln Gly Asn Gln Tyr Ser
465                 470                 475                 480

His Ile Leu Arg Ala Ala Val Glu Gln Leu Val Arg Val Trp Arg His
                485                 490                 495

Glu Ser Glu Tyr Asp Ser Val Asn Pro Ala His Gln Glu Gly Gln
            500                 505                 510

Ser Ser Ala Ala Val Trp Ala Asn Gln Leu Ile Arg Tyr Val Asn Asn
        515                 520                 525

Glu Met Ala Asn Leu Asp Phe Thr Cys Ala Trp Val Ala Lys Leu Leu
    530                 535                 540

Gly Ser Asp Arg Arg Ile Ala Glu Ile Asn Leu Tyr Leu Pro Glu Glu
545                 550                 555                 560

Ile Val Gly Thr Ile Gly Val His Asn Pro Gly Phe Gly Trp Ala Glu
                565                 570                 575

Ser Leu Phe Gly Leu His Met Gly Lys Val Ala Leu Ile Thr Gly Gly
            580                 585                 590

Ser Ala Gly Ile Gly Gly Gln Ile Gly Arg Leu Leu Ala Leu Ser Gly
        595                 600                 605

Ala His Val Met Leu Ala Ala Arg Asn Ala Asp Gln Leu Glu Gln Met
    610                 615                 620

Arg Ala Ser Ile Val Arg Glu Val Arg Asp Ala Ser Tyr Pro Asp Ala
625                 630                 635                 640

Glu Ser Arg Val Ala Ile Phe Pro Gly Ser Asp Val Ser Asp Ile Asp
            645                 650                 655

Gly Leu Glu Arg Leu Val Asn His Thr Val Arg Val Phe Gly Lys Val
        660                 665                 670

Asp Tyr Leu Ile Asn Asn Ala Gly Ile Ala Gly Ala Glu Glu Met Val
    675                 680                 685

Ile Asp Met Pro Val Asp Ala Trp Arg His Thr Leu Arg Ala Asn Leu
690                 695                 700

Ile Ser Asn Tyr Ala Leu Leu Arg Arg Leu Ala Pro Gln Met Lys Ala
705                 710                 715                 720

Ala Gly Gly Ala Tyr Val Leu Asn Val Ser Ser Tyr Phe Gly Gly Glu
                725                 730                 735

Lys Tyr Val Ala Ile Pro Tyr Pro Asn Arg Ser Asp Tyr Ala Val Ser
            740                 745                 750

Lys Ala Gly Gln Arg Ala Met Val Glu Ser Leu Ala Arg Phe Leu Gly
        755                 760                 765

Pro Glu Ile Gln Ile Asn Ala Ile Ala Pro Gly Pro Val Glu Gly Glu
    770                 775                 780

Arg Leu Lys Gly Ala Gly Ser Arg Pro Gly Leu Phe Met Arg Arg Ala
785                 790                 795                 800

Arg Leu Ile Leu Glu Asn Lys Arg Leu Asn Glu Val Phe Ala Ala Leu
                805                 810                 815

Leu Ala Ala Arg His Glu Gly Ala Thr Ile Ala Asp Leu Leu Pro Asp
            820                 825                 830

Leu Phe Ala Asn Asp Ile Gln Ser Ile Ala Asn Ser Ala Ala Met Pro
        835                 840                 845

Ala Pro Leu Arg Arg Leu Ala Thr Met Leu Arg Glu Thr Ser Asp Ala
    850                 855                 860

Gly Gly Ser Ala Gln Ser Tyr Leu Met Asn Ala Thr Ile Ala Arg Lys
865                 870                 875                 880

Leu Leu Asn Arg Leu Glu Asn Gly Gly Tyr Ile Thr Leu His Asp Arg
                885                 890                 895

Arg Ala Leu Thr Val Glu Pro Pro Glu Pro Phe Phe Thr Glu Ala Gln
            900                 905                 910

Ile Glu Arg Glu Ala Ile Lys Val Arg Asp Gly Ile Leu Gly Met Leu
        915                 920                 925

His Leu Gln Arg Met Pro Thr Glu Phe Asp Val Ala Leu Ala Thr Val
    930                 935                 940

Phe Tyr Leu Ala Asp Arg Asn Val Thr Gly Glu Thr Phe His Pro Ser
945                 950                 955                 960

Gly Gly Leu Arg Phe Glu Arg Thr Val Thr Glu Gly Glu Leu Phe Gly
                965                 970                 975

Lys Pro Gly Gln Gln Arg Leu Glu Arg Leu Lys Gly Ser Val Val Tyr
            980                 985                 990

Leu Ile Gly Glu His Leu Arg Gln His Leu Val Leu Leu Ala Arg Thr
        995                 1000                1005

Phe Leu Asp Glu Ile His Val Ala Arg Val Val Leu Leu Thr Glu
        1010                1015                1020

Thr Thr Gln Ala Ala Thr Asp Leu Ala Ala Glu Leu Ser Asp Tyr
        1025                1030                1035

Glu Ala Ala Gly Arg Phe Val Val Ile Pro Thr Cys Gly Asp Ile

```
            1040                1045                1050
Glu Gly Gly Ile Asp Arg Ala Met Ala Glu Tyr Gly Arg Pro Gly
        1055                1060                1065

Pro Val Ile Ser Thr Pro Phe Arg Pro Leu Pro Asp Arg Ala Leu
        1070                1075                1080

Ser Ala Arg Asn Gly Asp Trp Ser Ser Val Leu Thr Thr Ala Glu
        1085                1090                1095

Phe Glu Glu Leu Val Glu Gln Gln Ile Thr His His Phe Arg Val
        1100                1105                1110

Ala Arg Lys Ala Gly Leu Ile Glu Gly Ala Asn Val Thr Leu Val
        1115                1120                1125

Thr Pro Pro Thr Ser Ala Arg Ser Thr Ser Glu Glu Phe Ala Leu
        1130                1135                1140

Ala Asn Phe Val Lys Thr Thr Leu His Ala Leu Thr Ala Thr Ala
        1145                1150                1155

Gly Ala Glu Ser Glu Arg Thr Val Pro His Val Pro Val Asn Gln
        1160                1165                1170

Val Asp Leu Thr Arg Arg Ala Arg Ser Glu Glu Pro Arg Thr Pro
        1175                1180                1185

Ser Glu Glu Glu Glu Leu Gln Arg Phe Val Asn Ala Val Leu
        1190                1195                1200

Leu Thr Ser Ala Pro Leu Pro Thr Pro Leu Glu Ser Arg Tyr Arg
        1205                1210                1215

Ala Arg Ile Tyr Arg Gly Asn Ala Ile Thr Val
        1220                1225

<210> SEQ ID NO 60
<211> LENGTH: 1217
<212> TYPE: PRT
<213> ORGANISM: Erythrobacter sp.

<400> SEQUENCE: 60

Met Ser Lys Glu Gly Asn Ala Ala Lys Gly Arg Leu Glu Gly Lys Val
1               5                   10                  15

Ala Leu Ile Thr Gly Ala Ala Gly Asn Leu Gly Asn Glu Ile Ser Arg
            20                  25                  30

Ala Phe Ala Arg Glu Gly Ala Phe Val Val Met Thr Gly Arg Thr Glu
        35                  40                  45

Glu Arg Ile Ser Ala Ala Arg Glu Gln Leu Ile Ala Asp Thr Gly Val
    50                  55                  60

Ala Pro Glu Arg Ile Asp Thr Ala Val Leu Asp Gly Gly Asn Pro Asp
65                  70                  75                  80

Ser Ile Arg Ala Ala Met Ala Lys Leu Arg Lys Glu Tyr Gly Arg Ile
                85                  90                  95

Asp Ile Leu Ile Asn Asn Ala Gly Ser Ala Gly Pro Lys Gln Pro Leu
            100                 105                 110

His Asn Val Pro Leu Ser Pro Gln Glu Met Glu Ala Cys Gly Asp Thr
        115                 120                 125

Glu Thr Val Arg Asp Ala Met Leu Asn Ile Leu Gly Val Thr Trp Asn
    130                 135                 140

Met Ala Arg Ile Val Ala Pro Met Met Pro Val Gly Gly Ala Met Val
145                 150                 155                 160

Asn Ile Ser Thr Ile Phe Ser His Thr Arg Tyr Tyr Gly Arg Thr Ala
                165                 170                 175
```

```
Tyr Val Val Pro Lys Ala Ala Leu Asn Ala Leu Ser Asn Gln Leu Ala
                180                 185                 190

Ser Glu Leu Gly Pro Arg Gly Ile Arg Val Asn Thr Val Phe Pro Gly
            195                 200                 205

Pro Ile Glu Ser Asp Arg Ile Arg Thr Val Phe Ala Ala Met Asp Glu
        210                 215                 220

Val Gln Ser Gln Pro Lys Asp Thr Thr Ala Asn Tyr Phe Thr Gly Arg
225                 230                 235                 240

Met Ala Leu Thr Arg Ser Val Asn Gly Lys Val Asp Gly Lys Pro Leu
                245                 250                 255

Pro Asn Pro Lys Asp Ile Ala Gly Thr Cys Leu Phe Leu Ala Ser Glu
            260                 265                 270

Glu Ala Ala Gly Ile Ala Gly Glu Val Asp Val Thr His Gly Leu
        275                 280                 285

Ser Ala Asn Arg Thr Ser Ala Ser Thr Tyr Met Thr Arg Pro Ser Met
        290                 295                 300

Arg Ser Leu Asp Gly Ala Gly Leu Asn Ile Phe Ile Val Ser Gly Glu
305                 310                 315                 320

Asn Trp Asp Asp Ala Leu Val Ala Ala His Thr Leu Ile Gly Ser Gly
                325                 330                 335

Ala Lys Val Arg Leu Gly Leu Ala Arg Asn Ala Asp Val Ala Gln Ala
            340                 345                 350

Asn Ala Arg Leu Lys Ala Gln Gly Ile Gly Glu Leu Thr Val Thr
        355                 360                 365

Arg Phe Asn Arg Ala Glu Pro Asp Ala Met Glu Asp Ala Leu Ala Ala
370                 375                 380

Phe Ser Gly Asp Val Asp Gly Ala Ile Thr Gly Ala Ile Ile Leu Pro
385                 390                 395                 400

Val Lys Pro Ser Gly His Phe Thr Gly Ser Leu Leu Ala Ala Asp Asp
            405                 410                 415

Asp Thr Val Thr Lys Phe Met Asp Thr Glu Leu Val Gly Ala Ile Ala
                420                 425                 430

Val Ser Arg Ser Leu Ala Arg Tyr Trp His Gly Arg Glu Asp Leu Gln
            435                 440                 445

Ser Pro Pro Arg Cys Val Phe Met Thr Asn Pro Gly Asp Pro Leu Gly
        450                 455                 460

Asn Ser Phe Ala Ser Val Leu Ser Ala Gly Ile Thr Gln Leu Ile Arg
465                 470                 475                 480

Ile Trp Arg Asp Glu Glu Arg Val Gln Ala Gly Asn Gly Ser Thr Glu
                485                 490                 495

His Ala Val Trp Ser Asn Gln Ile Val Arg His Thr Asn Thr Glu Asp
            500                 505                 510

Glu Asn Thr Arg Phe Ala Ser Gly His Ala Thr Arg Val Leu Phe Arg
        515                 520                 525

Glu Gln His Ile Ala Glu Ile Asp Leu Lys Leu Pro Ala Asn Ile Ser
        530                 535                 540

Glu Glu Thr Gly Ser Arg Lys Ala Met Val Gly Phe Ala Glu Asn Ile
545                 550                 555                 560

Thr Gly Leu His Leu Gly Lys Val Ala Phe Ile Thr Gly Gly Ser Ala
                565                 570                 575

Gly Ile Gly Gly Gln Val Ala Arg Leu Leu Ala Leu Ala Gly Ala Lys
            580                 585                 590

Val Met Met Val Ala Arg Arg Glu Ser Glu Leu Val Ala Ala Arg Asp
```

-continued

```
            595                 600                 605
Arg Ile Val Gly Glu Leu Gln Asp Ile Gly Phe Ala Gly Val Glu Arg
    610                 615                 620

Arg Val Lys Tyr Met Ala Asp Ile Asp Val Ser Asp Phe Ala Ser Leu
625                 630                 635                 640

Asp Lys Ala Val Asp Ala Thr Leu Glu Glu Phe Gly Arg Ile Asp Tyr
                645                 650                 655

Leu Ile Asn Asn Ala Gly Val Ala Gly Ala Glu Asp Met Val Ile Asp
                660                 665                 670

Met Glu Pro Glu Ala Trp Arg Phe Thr Leu Asp Ala Asn Leu Ile Ser
            675                 680                 685

Asn Tyr His Leu Met Gln Arg Val Pro Leu Met Lys Glu Gln Gly
            690                 695                 700

Ser Gly Tyr Val Leu Asn Val Ser Ser Tyr Phe Gly Gly Glu Lys Phe
705                 710                 715                 720

Leu Ala Val Ala Tyr Pro Asn Arg Ala Asp Tyr Gly Leu Ser Lys Ala
                725                 730                 735

Gly Gln Arg Ala Met Val Glu Ala Phe Ser Pro Phe Leu Gly Pro Glu
            740                 745                 750

Val Gln Cys Asn Ala Ile Ala Pro Gly Pro Val Asp Gly Asp Arg Leu
            755                 760                 765

Ser Gly Thr Gly Lys Pro Gly Leu Phe Gln Arg Arg Ala Lys Leu
770                 775                 780

Ile Leu Glu Asn Lys Arg Leu Asn Ala Val Tyr Ser Ala Val Ile His
785                 790                 795                 800

Ala Ile Arg Glu Gly Gly Asp Ala Ala Lys Ile Leu Thr Arg Leu Ser
                805                 810                 815

Arg Asn Ser Thr Ser Thr Leu Ser His Asp Ala Glu Ala Pro Glu Glu
                820                 825                 830

Leu Arg Lys Leu Ala Leu Asp Phe Ala Ser Gln Gly Asp Gly Leu Cys
            835                 840                 845

Thr Trp Asp Gln Tyr Leu Leu Thr Asp Ala Met Ala Gln Arg Leu Leu
            850                 855                 860

Val Arg Leu Gln Leu Gly Gly Phe Leu Leu Gly Ser Asn Glu Trp Ala
865                 870                 875                 880

Ser Leu Ser Ser Ser Glu Gln Thr Trp Leu Lys Leu Ser Pro Pro Asp
                885                 890                 895

Asp Lys Pro Phe Leu Pro Ala Ala Gln Val Asp Lys Val Ala Asn Gly
            900                 905                 910

Val Gly Lys Gly Val Ile Ser Gln Leu His Leu Gly Ala Met Pro Thr
            915                 920                 925

Glu Ala Glu Val Ala Gln Ala Thr Val Phe Phe Leu Ala Asp Arg Ala
            930                 935                 940

Val Ser Gly Glu Thr Phe Met Pro Ser Gly Gly Leu Arg Val Glu Arg
945                 950                 955                 960

Ser Asn Thr Glu Arg Glu Met Phe Gly Ser Pro Lys Gln Glu Arg Ile
                965                 970                 975

Asp Lys Met Lys Gly Lys Thr Val Trp Ile Ile Gly Glu His Leu Ser
            980                 985                 990

Asp Tyr Val Ala Ala Thr Ile Glu Glu Leu Val Ser Gly Cys Gly Val
            995                 1000                1005

Ala Lys Val Val Leu Ile Ala Lys Asp Lys Ser Gly Glu Lys Ala
    1010                1015                1020
```

-continued

Val Arg Asp Gln Leu Pro Asn Asp Leu Ser Lys Asp Ala Leu Glu
    1025            1030            1035

Val Leu Ile Ala Gly Asp Gly Leu Glu Glu Ala Met Asp Glu Ala
    1040            1045            1050

Leu Gly His Trp Gly Lys Pro Thr Thr Val Leu Ser Met Pro Gly
    1055            1060            1065

Glu Pro Leu Pro Asp His Leu Phe Glu Gly Gly Asn Pro Leu Ser
    1070            1075            1080

Thr Lys Asp Phe Ala His Met Val Glu Ala Asn Ile Thr Arg His
    1085            1090            1095

Tyr Arg Val Thr Arg Lys Ala Ser Leu Tyr Asp Gly Cys Gln Val
    1100            1105            1110

Val Leu Val Ser Pro Asp Val Pro Tyr Gly Ser Asp Gly Pro Gly
    1115            1120            1125

Val Ala Leu Ala Asn Phe Val Lys Thr Ser Leu His Ala Phe Thr
    1130            1135            1140

Ala Thr Val Ala Val Glu Asn Glu Arg Leu Val His Asp Val Pro
    1145            1150            1155

Val Asn Gln Ile Asn Leu Thr Arg Arg Val Ser Ser Glu Glu Pro
    1160            1165            1170

Arg Asp Ala Asp Glu His Ala Glu Glu Leu Arg Arg Phe Thr Arg
    1175            1180            1185

Ala Val Leu Leu Val Gly Ala Pro Leu Pro Asp Ala Gln Asp Ser
    1190            1195            1200

Arg Tyr Arg Ser Lys Ile Tyr Arg Gly Thr Ser Met Thr Val
    1205            1210            1215

<210> SEQ ID NO 61
<211> LENGTH: 357
<212> TYPE: PRT
<213> ORGANISM: Metallosphaera sedula

<400> SEQUENCE: 61

Met Arg Arg Thr Leu Lys Ala Ala Ile Leu Gly Ala Thr Gly Leu Val
1               5                   10                  15

Gly Ile Glu Tyr Val Arg Met Leu Ala Asp His Pro Tyr Ile Lys Pro
                20                  25                  30

Thr Tyr Leu Ala Gly Lys Gly Ser Val Gly Lys Pro Tyr Gly Glu Ile
            35                  40                  45

Val Arg Trp Gln Thr Val Gly Asn Val Pro Lys Glu Val Ala Asn Gln
        50                  55                  60

Glu Val Lys Pro Thr Asp Pro Lys Leu Met Asp Asp Val Asp Ile Ile
65                  70                  75                  80

Phe Ser Pro Leu Pro Gln Gly Ala Ala Gly Pro Val Glu Glu Gln Phe
                85                  90                  95

Ala Lys Leu Gly Phe Asn Val Ile Ser Asn Ser Pro Asp His Arg Phe
            100                 105                 110

Asp Met Asp Val Pro Met Ile Ile Pro Glu Val Asn Pro His Thr Val
        115                 120                 125

Thr Leu Ile Asp Glu Gln Arg Lys Arg Arg Asp Trp Lys Gly Phe Ile
    130                 135                 140

Val Thr Thr Pro Leu Cys Thr Ala Gln Gly Ala Ala Ile Pro Leu Thr
145                 150                 155                 160

Pro Ile Tyr Gln Asn Phe Lys Met Ser Gly Val Met Ile Thr Thr Met

-continued

```
                165                 170                 175
    Gln Ser Leu Ser Gly Ala Gly Tyr Pro Gly Ile Ala Ser Leu Asp Ile
                180                 185                 190

Val Asp Asn Ala Leu Pro Leu Gly Asp Gly Tyr Asp Ala Lys Thr Val
                195                 200                 205

Lys Glu Ile Thr Arg Ile Leu Ser Glu Val Lys Arg Asn Val Gln Glu
                210                 215                 220

Pro Gly Val Asn Glu Ile Thr Leu Asp Ala Thr Thr His Arg Ile Ala
    225                 230                 235                 240

Thr Ile His Gly His Tyr Glu Val Ala Tyr Val Thr Phe Lys Glu Asp
                    245                 250                 255

Thr Asp Val Arg Lys Val Met Glu Ser Met Glu Ser Phe Lys Gly Glu
                260                 265                 270

Pro Gln Asp Leu Lys Leu Pro Thr Ala Pro Glu Lys Pro Ile Ile Val
                275                 280                 285

Thr Thr Gln Asp Ala Arg Pro Gln Val Phe Phe Asp Arg Trp Ala Gly
                290                 295                 300

Asn Pro Pro Gly Met Ser Val Val Gly Arg Leu Lys Gln Val Asn
    305                 310                 315                 320

Pro Arg Thr Ile Arg Phe Val Ser Leu Ile His Asn Thr Val Arg Gly
                    325                 330                 335

Ala Ala Gly Gly Gly Val Leu Thr Ala Glu Leu Leu Val Glu Lys Gly
                340                 345                 350

Tyr Ile Asp Lys Arg
            355

<210> SEQ ID NO 62
<211> LENGTH: 356
<212> TYPE: PRT
<213> ORGANISM: Sulfolobus tokodaii

<400> SEQUENCE: 62

Met Arg Arg Thr Leu Lys Ala Ala Ile Leu Gly Ala Thr Gly Leu Val
    1               5                   10                  15

Gly Ile Glu Tyr Val Arg Met Leu Ser Asn His Pro Tyr Ile Lys Pro
                20                  25                  30

Ala Tyr Leu Ala Gly Lys Gly Ser Val Gly Lys Pro Tyr Gly Glu Val
                35                  40                  45

Val Arg Trp Gln Thr Val Gly Gln Val Pro Lys Glu Ile Ala Asp Met
        50                  55                  60

Glu Ile Lys Pro Thr Asp Pro Lys Leu Met Asp Asp Val Asp Ile Ile
    65                  70                  75                  80

Phe Ser Pro Leu Pro Gln Gly Ala Ala Gly Pro Val Glu Glu Gln Phe
                    85                  90                  95

Ala Lys Glu Gly Phe Pro Val Ile Ser Asn Ser Pro Asp His Arg Phe
                100                 105                 110

Asp Pro Asp Val Pro Leu Leu Val Pro Glu Leu Asn Pro His Thr Ile
                115                 120                 125

Ser Leu Ile Asp Glu Gln Arg Lys Arg Glu Trp Lys Gly Phe Ile
                130                 135                 140

Val Thr Thr Pro Leu Cys Thr Ala Gln Gly Ala Ala Ile Pro Leu Gly
    145                 150                 155                 160

Ala Ile Phe Lys Asp Tyr Lys Met Asp Gly Ala Phe Ile Thr Thr Ile
                    165                 170                 175
```

-continued

Gln Ser Leu Ser Gly Ala Gly Tyr Pro Gly Ile Pro Ser Leu Asp Val
                180                 185                 190

Val Asp Asn Ile Leu Pro Leu Gly Asp Gly Tyr Asp Ala Lys Thr Ile
            195                 200                 205

Lys Glu Ile Phe Arg Ile Leu Ser Glu Val Lys Arg Asn Val Asp Glu
        210                 215                 220

Pro Lys Leu Glu Asp Val Ser Leu Ala Ala Thr Thr His Arg Ile Ala
225                 230                 235                 240

Thr Ile His Gly His Tyr Glu Val Leu Tyr Val Ser Phe Lys Glu Glu
                245                 250                 255

Thr Ala Ala Glu Lys Val Lys Glu Thr Leu Glu Asn Phe Arg Gly Glu
            260                 265                 270

Pro Gln Asp Leu Lys Leu Pro Thr Ala Pro Ser Lys Pro Ile Ile Val
        275                 280                 285

Met Asn Glu Asp Thr Arg Pro Gln Val Tyr Phe Asp Arg Trp Ala Gly
290                 295                 300

Asp Ile Pro Gly Met Ser Val Val Val Gly Arg Leu Lys Gln Val Asn
305                 310                 315                 320

Lys Arg Met Ile Arg Leu Val Ser Leu Ile His Asn Thr Val Arg Gly
                325                 330                 335

Ala Ala Gly Gly Gly Ile Leu Ala Ala Glu Leu Leu Val Glu Lys Gly
            340                 345                 350

Tyr Ile Glu Lys
        355

<210> SEQ ID NO 63
<211> LENGTH: 482
<212> TYPE: PRT
<213> ORGANISM: Saccharomyces cerevisiae

<400> SEQUENCE: 63

Met Ser Ala Phe Val Arg Val Val Pro Arg Ile Ser Arg Ser Ser Val
1               5                   10                  15

Leu Thr Arg Ser Leu Arg Leu Gln Leu Arg Cys Tyr Ala Ser Tyr Pro
            20                  25                  30

Glu His Thr Ile Ile Gly Met Pro Ala Leu Ser Pro Thr Met Thr Gln
        35                  40                  45

Gly Asn Leu Ala Ala Trp Thr Lys Lys Glu Gly Asp Gln Leu Ser Pro
    50                  55                  60

Gly Glu Val Ile Ala Glu Ile Glu Thr Asp Lys Ala Gln Met Asp Phe
65                  70                  75                  80

Glu Phe Gln Glu Asp Gly Tyr Leu Ala Lys Ile Leu Val Pro Glu Gly
                85                  90                  95

Thr Lys Asp Ile Pro Val Asn Lys Pro Ile Ala Val Tyr Val Glu Asp
            100                 105                 110

Lys Ala Asp Val Pro Ala Phe Lys Asp Phe Lys Leu Glu Asp Ser Gly
        115                 120                 125

Ser Asp Ser Lys Thr Ser Thr Lys Ala Gln Pro Ala Glu Pro Gln Ala
    130                 135                 140

Glu Lys Lys Gln Glu Ala Pro Ala Glu Glu Thr Lys Thr Ser Ala Pro
145                 150                 155                 160

Glu Ala Lys Lys Ser Asp Val Ala Ala Pro Gln Gly Arg Ile Phe Ala
                165                 170                 175

Ser Pro Leu Ala Lys Thr Ile Ala Leu Glu Lys Gly Ile Ser Leu Lys
            180                 185                 190

Asp Val His Gly Thr Gly Pro Arg Gly Arg Ile Thr Lys Ala Asp Ile
            195                 200                 205

Glu Ser Tyr Leu Glu Lys Ser Ser Lys Gln Ser Ser Gln Thr Ser Gly
210                 215                 220

Ala Ala Ala Ala Thr Pro Ala Ala Thr Ser Ser Thr Thr Ala Gly
225                 230                 235                 240

Ser Ala Pro Ser Pro Ser Ser Thr Ala Ser Tyr Glu Asp Val Pro Ile
            245                 250                 255

Ser Thr Met Arg Ser Ile Ile Gly Glu Arg Leu Leu Gln Ser Thr Gln
            260                 265                 270

Gly Ile Pro Ser Tyr Ile Val Ser Ser Lys Ile Ser Ile Ser Lys Leu
            275                 280                 285

Leu Lys Leu Arg Gln Ser Leu Asn Ala Thr Ala Asn Asp Lys Tyr Lys
            290                 295                 300

Leu Ser Ile Asn Asp Leu Leu Val Lys Ala Ile Thr Val Ala Ala Lys
305                 310                 315                 320

Arg Val Pro Asp Ala Asn Ala Tyr Trp Leu Pro Asn Glu Asn Val Ile
            325                 330                 335

Arg Lys Phe Lys Asn Val Asp Val Ser Val Ala Val Ala Thr Pro Thr
            340                 345                 350

Gly Leu Leu Thr Pro Ile Val Lys Asn Cys Glu Ala Lys Gly Leu Ser
            355                 360                 365

Gln Ile Ser Asn Glu Ile Lys Glu Leu Val Lys Arg Ala Arg Ile Asn
            370                 375                 380

Lys Leu Ala Pro Glu Glu Phe Gln Gly Gly Thr Ile Cys Ile Ser Asn
385                 390                 395                 400

Met Gly Met Asn Asn Ala Val Asn Met Phe Thr Ser Ile Ile Asn Pro
            405                 410                 415

Pro Gln Ser Thr Ile Leu Ala Ile Ala Thr Val Glu Arg Val Ala Val
            420                 425                 430

Glu Asp Ala Ala Ala Glu Asn Gly Phe Ser Phe Asp Asn Gln Val Thr
            435                 440                 445

Ile Thr Gly Thr Phe Asp His Arg Thr Ile Asp Gly Ala Lys Gly Ala
            450                 455                 460

Glu Phe Met Lys Glu Leu Lys Thr Val Ile Glu Asn Pro Leu Glu Met
465                 470                 475                 480

Leu Leu

<210> SEQ ID NO 64
<211> LENGTH: 420
<212> TYPE: PRT
<213> ORGANISM: Saccharomyces cerevisiae

<400> SEQUENCE: 64

Met Leu Ala Ala Ser Phe Lys Arg Gln Pro Ser Gln Leu Val Arg Gly
1               5                   10                  15

Leu Gly Ala Val Leu Arg Thr Pro Thr Arg Ile Gly His Val Arg Thr
            20                  25                  30

Met Ala Thr Leu Lys Thr Thr Asp Lys Lys Ala Pro Glu Asp Ile Glu
            35                  40                  45

Gly Ser Asp Thr Val Gln Ile Glu Leu Pro Glu Ser Ser Phe Glu Ser
            50                  55                  60

Tyr Met Leu Glu Pro Pro Asp Leu Ser Tyr Glu Thr Ser Lys Ala Thr
65                  70                  75                  80

Leu Leu Gln Met Tyr Lys Asp Met Val Ile Ile Arg Arg Met Glu Met
                85                  90                  95

Ala Cys Asp Ala Leu Tyr Lys Ala Lys Lys Ile Arg Gly Phe Cys His
            100                 105                 110

Leu Ser Val Gly Gln Glu Ala Ile Ala Val Gly Ile Glu Asn Ala Ile
        115                 120                 125

Thr Lys Leu Asp Ser Ile Ile Thr Ser Tyr Arg Cys His Gly Phe Thr
    130                 135                 140

Phe Met Arg Gly Ala Ser Val Lys Ala Val Leu Ala Glu Leu Met Gly
145                 150                 155                 160

Arg Arg Ala Gly Val Ser Tyr Gly Lys Gly Gly Ser Met His Leu Tyr
                165                 170                 175

Ala Pro Gly Phe Tyr Gly Gly Asn Gly Ile Val Gly Ala Gln Val Pro
            180                 185                 190

Leu Gly Ala Gly Leu Ala Phe Ala His Gln Tyr Lys Asn Glu Asp Ala
        195                 200                 205

Cys Ser Phe Thr Leu Tyr Gly Asp Gly Ala Ser Asn Gln Gly Gln Val
    210                 215                 220

Phe Glu Ser Phe Asn Met Ala Lys Leu Trp Asn Leu Pro Val Val Phe
225                 230                 235                 240

Cys Cys Glu Asn Asn Lys Tyr Gly Met Gly Thr Ala Ala Ser Arg Ser
                245                 250                 255

Ser Ala Met Thr Glu Tyr Phe Lys Arg Gly Gln Tyr Ile Pro Gly Leu
            260                 265                 270

Lys Val Asn Gly Met Asp Ile Leu Ala Val Tyr Gln Ala Ser Lys Phe
        275                 280                 285

Ala Lys Asp Trp Cys Leu Ser Gly Lys Gly Pro Leu Val Leu Glu Tyr
    290                 295                 300

Glu Thr Tyr Arg Tyr Gly Gly His Ser Met Ser Asp Pro Gly Thr Thr
305                 310                 315                 320

Tyr Arg Thr Arg Asp Glu Ile Gln His Met Arg Ser Lys Asn Asp Pro
                325                 330                 335

Ile Ala Gly Leu Lys Met His Leu Ile Asp Leu Gly Ile Ala Thr Glu
            340                 345                 350

Ala Glu Val Lys Ala Tyr Asp Lys Ser Ala Arg Lys Tyr Val Asp Glu
        355                 360                 365

Gln Val Glu Leu Ala Asp Ala Ala Pro Pro Glu Ala Lys Leu Ser
    370                 375                 380

Ile Leu Phe Glu Asp Val Tyr Val Lys Gly Thr Glu Thr Pro Thr Leu
385                 390                 395                 400

Arg Gly Arg Ile Pro Glu Asp Thr Trp Asp Phe Lys Lys Gln Gly Phe
                405                 410                 415

Ala Ser Arg Asp
            420

<210> SEQ ID NO 65
<211> LENGTH: 366
<212> TYPE: PRT
<213> ORGANISM: Saccharomyces cerevisiae

<400> SEQUENCE: 65

Met Phe Ser Arg Leu Pro Thr Ser Leu Ala Arg Asn Val Ala Arg Arg
1               5                   10                  15

Ala Pro Thr Ser Phe Val Arg Pro Ser Ala Ala Ala Ala Ala Leu Arg

```
            20                  25                  30
Phe Ser Ser Thr Lys Thr Met Thr Val Arg Glu Ala Leu Asn Ser Ala
        35                  40                  45

Met Ala Glu Glu Leu Asp Arg Asp Asp Val Phe Leu Ile Gly Glu
 50                  55                  60

Glu Val Ala Gln Tyr Asn Gly Ala Tyr Lys Val Ser Lys Gly Leu Leu
 65                  70                  75                  80

Asp Arg Phe Gly Glu Arg Arg Val Val Asp Thr Pro Ile Thr Glu Tyr
                85                  90                  95

Gly Phe Thr Gly Leu Ala Val Gly Ala Ala Leu Lys Gly Leu Lys Pro
            100                 105                 110

Ile Val Glu Phe Met Ser Phe Asn Phe Ser Met Gln Ala Ile Asp His
            115                 120                 125

Val Val Asn Ser Ala Ala Lys Thr His Tyr Met Ser Gly Gly Thr Gln
        130                 135                 140

Lys Cys Gln Met Val Phe Arg Gly Pro Asn Gly Ala Ala Val Gly Val
145                 150                 155                 160

Gly Ala Gln His Ser Gln Asp Phe Ser Pro Trp Tyr Gly Ser Ile Pro
                165                 170                 175

Gly Leu Lys Val Leu Val Pro Tyr Ser Ala Glu Asp Ala Arg Gly Leu
            180                 185                 190

Leu Lys Ala Ala Ile Arg Asp Pro Asn Pro Val Val Phe Leu Glu Asn
        195                 200                 205

Glu Leu Leu Tyr Gly Glu Ser Phe Glu Ile Ser Glu Glu Ala Leu Ser
    210                 215                 220

Pro Glu Phe Thr Leu Pro Tyr Lys Ala Lys Ile Glu Arg Glu Gly Thr
225                 230                 235                 240

Asp Ile Ser Ile Val Thr Tyr Thr Arg Asn Val Gln Phe Ser Leu Glu
                245                 250                 255

Ala Ala Glu Ile Leu Gln Lys Lys Tyr Gly Val Ser Ala Glu Val Ile
            260                 265                 270

Asn Leu Arg Ser Ile Arg Pro Leu Asp Thr Glu Ala Ile Ile Lys Thr
        275                 280                 285

Val Lys Lys Thr Asn His Leu Ile Thr Val Glu Ser Thr Phe Pro Ser
    290                 295                 300

Phe Gly Val Gly Ala Glu Ile Val Ala Gln Val Met Glu Ser Glu Ala
305                 310                 315                 320

Phe Asp Tyr Leu Asp Ala Pro Ile Gln Arg Val Thr Gly Ala Asp Val
                325                 330                 335

Pro Thr Pro Tyr Ala Lys Glu Leu Glu Asp Phe Ala Phe Pro Asp Thr
            340                 345                 350

Pro Thr Ile Val Lys Ala Val Lys Glu Val Leu Ser Ile Glu
        355                 360                 365

<210> SEQ ID NO 66
<211> LENGTH: 499
<212> TYPE: PRT
<213> ORGANISM: Saccharomyces cerevisiae

<400> SEQUENCE: 66

Met Leu Arg Ile Arg Ser Leu Leu Asn Asn Lys Arg Ala Phe Ser Ser
1               5                   10                  15

Thr Val Arg Thr Leu Thr Ile Asn Lys Ser His Asp Val Ile Ile
            20                  25                  30
```

-continued

```
Gly Gly Gly Pro Ala Gly Tyr Val Ala Ile Lys Ala Ala Gln Leu
         35                  40                  45
Gly Phe Asn Thr Ala Cys Val Glu Lys Arg Gly Lys Leu Gly Gly Thr
 50                  55                  60
Cys Leu Asn Val Gly Cys Ile Pro Ser Lys Ala Leu Leu Asn Asn Ser
 65                  70                  75                  80
His Leu Phe His Gln Met His Thr Glu Ala Gln Lys Arg Gly Ile Asp
                 85                  90                  95
Val Asn Gly Asp Ile Lys Ile Asn Val Ala Asn Phe Gln Lys Ala Lys
                100                 105                 110
Asp Asp Ala Val Lys Gln Leu Thr Gly Gly Ile Glu Leu Leu Phe Lys
                115                 120                 125
Lys Asn Lys Val Thr Tyr Tyr Lys Gly Asn Gly Ser Phe Glu Asp Glu
                130                 135                 140
Thr Lys Ile Arg Val Thr Pro Val Asp Gly Leu Glu Gly Thr Val Lys
145                 150                 155                 160
Glu Asp His Ile Leu Asp Val Lys Asn Ile Ile Val Ala Thr Gly Ser
                165                 170                 175
Glu Val Thr Pro Phe Pro Gly Ile Glu Ile Asp Glu Glu Lys Ile Val
                180                 185                 190
Ser Ser Thr Gly Ala Leu Ser Leu Lys Glu Ile Pro Lys Arg Leu Thr
        195                 200                 205
Ile Ile Gly Gly Gly Ile Ile Gly Leu Glu Met Gly Ser Val Tyr Ser
        210                 215                 220
Arg Leu Gly Ser Lys Val Thr Val Val Glu Phe Gln Pro Gln Ile Gly
225                 230                 235                 240
Ala Ser Met Asp Gly Glu Val Ala Lys Ala Thr Gln Lys Phe Leu Lys
                245                 250                 255
Lys Gln Gly Leu Asp Phe Lys Leu Ser Thr Lys Val Ile Ser Ala Lys
                260                 265                 270
Arg Asn Asp Asp Lys Asn Val Val Glu Ile Val Val Glu Asp Thr Lys
                275                 280                 285
Thr Asn Lys Gln Glu Asn Leu Glu Ala Glu Val Leu Leu Val Ala Val
        290                 295                 300
Gly Arg Arg Pro Tyr Ile Ala Gly Leu Gly Ala Glu Lys Ile Gly Leu
305                 310                 315                 320
Glu Val Asp Lys Arg Gly Arg Leu Val Ile Asp Asp Gln Phe Asn Ser
                325                 330                 335
Lys Phe Pro His Ile Lys Val Val Gly Asp Val Thr Phe Gly Pro Met
                340                 345                 350
Leu Ala His Lys Ala Glu Glu Gly Ile Ala Ala Val Glu Met Leu
        355                 360                 365
Lys Thr Gly His Gly His Val Asn Tyr Asn Asn Ile Pro Ser Val Met
        370                 375                 380
Tyr Ser His Pro Glu Val Ala Trp Val Gly Lys Thr Glu Glu Gln Leu
385                 390                 395                 400
Lys Glu Ala Gly Ile Asp Tyr Lys Ile Gly Lys Phe Pro Phe Ala Ala
                405                 410                 415
Asn Ser Arg Ala Lys Thr Asn Gln Asp Thr Glu Gly Phe Val Lys Ile
                420                 425                 430
Leu Ile Asp Ser Lys Thr Glu Arg Ile Leu Gly Ala His Ile Ile Gly
        435                 440                 445
Pro Asn Ala Gly Glu Met Ile Ala Glu Ala Gly Leu Ala Leu Glu Tyr
```

```
            450                 455                 460
Gly Ala Ser Ala Glu Asp Val Ala Arg Val Cys His Ala His Pro Thr
465                 470                 475                 480

Leu Ser Glu Ala Phe Lys Glu Ala Asn Met Ala Ala Tyr Asp Lys Ala
                485                 490                 495

Ile His Cys

<210> SEQ ID NO 67
<211> LENGTH: 887
<212> TYPE: PRT
<213> ORGANISM: Escherichia coli

<400> SEQUENCE: 67

Met Ser Glu Arg Phe Pro Asn Asp Val Asp Pro Ile Glu Thr Arg Asp
1               5                   10                  15

Trp Leu Gln Ala Ile Glu Ser Val Ile Arg Glu Gly Val Glu Arg
            20                  25                  30

Ala Gln Tyr Leu Ile Asp Gln Leu Leu Ala Glu Ala Arg Lys Gly Gly
        35                  40                  45

Val Asn Val Ala Ala Gly Thr Gly Ile Ser Asn Tyr Ile Asn Thr Ile
50                  55                  60

Pro Val Glu Glu Gln Pro Glu Tyr Pro Gly Asn Leu Glu Leu Glu Arg
65                  70                  75                  80

Arg Ile Arg Ser Ala Ile Arg Trp Asn Ala Ile Met Thr Val Leu Arg
                85                  90                  95

Ala Ser Lys Lys Asp Leu Glu Leu Gly Gly His Met Ala Ser Phe Gln
            100                 105                 110

Ser Ser Ala Thr Ile Tyr Asp Val Cys Phe Asn His Phe Arg Ala
        115                 120                 125

Arg Asn Glu Gln Asp Gly Gly Asp Leu Val Tyr Phe Gln Gly His Ile
130                 135                 140

Ser Pro Gly Val Tyr Ala Arg Ala Phe Leu Glu Gly Arg Leu Thr Gln
145                 150                 155                 160

Glu Gln Leu Asp Asn Phe Arg Gln Glu Val His Gly Asn Gly Leu Ser
                165                 170                 175

Ser Tyr Pro His Pro Lys Leu Met Pro Glu Phe Trp Gln Phe Pro Thr
            180                 185                 190

Val Ser Met Gly Leu Gly Pro Ile Gly Ala Ile Tyr Gln Ala Lys Phe
        195                 200                 205

Leu Lys Tyr Leu Glu His Arg Gly Leu Lys Asp Thr Ser Lys Gln Thr
210                 215                 220

Val Tyr Ala Phe Leu Gly Asp Gly Glu Met Asp Glu Pro Glu Ser Lys
225                 230                 235                 240

Gly Ala Ile Thr Ile Ala Thr Arg Glu Lys Leu Asp Asn Leu Val Phe
                245                 250                 255

Val Ile Asn Cys Asn Leu Gln Arg Leu Asp Gly Pro Val Thr Gly Asn
            260                 265                 270

Gly Lys Ile Ile Asn Glu Leu Glu Gly Ile Phe Glu Gly Ala Gly Trp
        275                 280                 285

Asn Val Ile Lys Val Met Trp Gly Ser Arg Trp Asp Glu Leu Leu Arg
290                 295                 300

Lys Asp Thr Ser Gly Lys Leu Ile Gln Leu Met Asn Glu Thr Val Asp
305                 310                 315                 320

Gly Asp Tyr Gln Thr Phe Lys Ser Lys Asp Gly Ala Tyr Val Arg Glu
```

-continued

```
              325                 330                 335
His Phe Phe Gly Lys Tyr Pro Glu Thr Ala Ala Leu Val Ala Asp Trp
            340                 345                 350

Thr Asp Glu Gln Ile Trp Ala Leu Asn Arg Gly Gly His Asp Pro Lys
            355                 360                 365

Lys Ile Tyr Ala Ala Phe Lys Ala Gln Glu Thr Lys Gly Lys Ala
            370                 375             380

Thr Val Ile Leu Ala His Thr Ile Lys Gly Tyr Gly Met Gly Asp Ala
385                 390                 395                 400

Ala Glu Gly Lys Asn Ile Ala His Gln Val Lys Lys Met Asn Met Asp
                405                 410                 415

Gly Val Arg His Ile Arg Asp Arg Phe Asn Val Pro Val Ser Asp Ala
                420                 425                 430

Asp Ile Glu Lys Leu Pro Tyr Ile Thr Phe Pro Glu Gly Ser Glu Glu
                435                 440                 445

His Thr Tyr Leu His Ala Gln Arg Gln Lys Leu His Gly Tyr Leu Pro
            450                 455                 460

Ser Arg Gln Pro Asn Phe Thr Glu Lys Leu Glu Leu Pro Ser Leu Gln
465                 470                 475                 480

Asp Phe Gly Ala Leu Leu Glu Glu Gln Ser Lys Glu Ile Ser Thr Thr
                485                 490                 495

Ile Ala Phe Val Arg Ala Leu Asn Val Met Leu Lys Asn Lys Ser Ile
            500                 505                 510

Lys Asp Arg Leu Val Pro Ile Ile Ala Asp Glu Ala Arg Thr Phe Gly
            515                 520                 525

Met Glu Gly Leu Phe Arg Gln Ile Gly Ile Tyr Ser Pro Asn Gly Gln
            530                 535                 540

Gln Tyr Thr Pro Gln Asp Arg Glu Gln Val Ala Tyr Tyr Lys Glu Asp
545                 550                 555                 560

Glu Lys Gly Gln Ile Leu Gln Glu Gly Ile Asn Glu Leu Gly Ala Gly
                565                 570                 575

Cys Ser Trp Leu Ala Ala Ala Thr Ser Tyr Ser Thr Asn Asn Leu Pro
            580                 585                 590

Met Ile Pro Phe Tyr Ile Tyr Tyr Ser Met Phe Gly Phe Gln Arg Ile
            595                 600                 605

Gly Asp Leu Cys Trp Ala Ala Gly Asp Gln Gln Ala Arg Gly Phe Leu
            610                 615                 620

Ile Gly Gly Thr Ser Gly Arg Thr Thr Leu Asn Gly Glu Gly Leu Gln
625                 630                 635                 640

His Glu Asp Gly His Ser His Ile Gln Ser Leu Thr Ile Pro Asn Cys
                645                 650                 655

Ile Ser Tyr Asp Pro Ala Tyr Ala Tyr Glu Val Ala Val Ile Met His
            660                 665                 670

Asp Gly Leu Glu Arg Met Tyr Gly Glu Lys Gln Glu Asn Val Tyr Tyr
            675                 680                 685

Tyr Ile Thr Thr Leu Asn Glu Asn Tyr His Met Pro Ala Met Pro Glu
            690                 695                 700

Gly Ala Glu Glu Gly Ile Arg Lys Gly Ile Tyr Lys Leu Glu Thr Ile
705                 710                 715                 720

Glu Gly Ser Lys Gly Lys Val Gln Leu Leu Gly Ser Gly Ser Ile Leu
                725                 730                 735

Arg His Val Arg Glu Ala Ala Glu Ile Leu Ala Lys Asp Tyr Gly Val
            740                 745                 750
```

-continued

```
Gly Ser Asp Val Tyr Ser Val Thr Ser Phe Thr Glu Leu Ala Arg Asp
            755                 760                 765

Gly Gln Asp Cys Glu Arg Trp Asn Met Leu His Pro Leu Glu Thr Pro
    770                 775                 780

Arg Val Pro Tyr Ile Ala Gln Val Met Asn Asp Ala Pro Ala Val Ala
785                 790                 795                 800

Ser Thr Asp Tyr Met Lys Leu Phe Ala Glu Gln Val Arg Thr Tyr Val
                805                 810                 815

Pro Ala Asp Asp Tyr Arg Val Leu Gly Thr Asp Gly Phe Gly Arg Ser
            820                 825                 830

Asp Ser Arg Glu Asn Leu Arg His His Phe Glu Val Asp Ala Ser Tyr
        835                 840                 845

Val Val Val Ala Ala Leu Gly Glu Leu Ala Lys Arg Gly Glu Ile Asp
    850                 855                 860

Lys Lys Val Val Ala Asp Ala Ile Ala Lys Phe Asn Ile Asp Ala Asp
865                 870                 875                 880

Lys Val Asn Pro Arg Leu Ala
                885

<210> SEQ ID NO 68
<211> LENGTH: 630
<212> TYPE: PRT
<213> ORGANISM: Escherichia coli

<400> SEQUENCE: 68

Met Ala Ile Glu Ile Lys Val Pro Asp Ile Gly Ala Asp Glu Val Glu
1               5                   10                  15

Ile Thr Glu Ile Leu Val Lys Val Gly Asp Lys Val Glu Ala Glu Gln
            20                  25                  30

Ser Leu Ile Thr Val Glu Gly Asp Lys Ala Ser Met Glu Val Pro Ser
        35                  40                  45

Pro Gln Ala Gly Ile Val Lys Glu Ile Lys Val Ser Val Gly Asp Lys
    50                  55                  60

Thr Gln Thr Gly Ala Leu Ile Met Ile Phe Asp Ser Ala Asp Gly Ala
65                  70                  75                  80

Ala Asp Ala Ala Pro Ala Gln Ala Glu Glu Lys Lys Glu Ala Ala Pro
                85                  90                  95

Ala Ala Ala Pro Ala Ala Ala Ala Lys Asp Val Asn Val Pro Asp
            100                 105                 110

Ile Gly Ser Asp Glu Val Glu Val Thr Glu Ile Leu Val Lys Val Gly
        115                 120                 125

Asp Lys Val Glu Ala Glu Gln Ser Leu Ile Thr Val Glu Gly Asp Lys
    130                 135                 140

Ala Ser Met Glu Val Pro Ala Pro Phe Ala Gly Thr Val Lys Glu Ile
145                 150                 155                 160

Lys Val Asn Val Gly Asp Lys Val Ser Thr Gly Ser Leu Ile Met Val
                165                 170                 175

Phe Glu Val Ala Gly Glu Ala Gly Ala Ala Pro Ala Ala Lys Gln
            180                 185                 190

Glu Ala Ala Pro Ala Ala Ala Pro Ala Pro Ala Ala Gly Val Lys Glu
        195                 200                 205

Val Asn Val Pro Asp Ile Gly Gly Asp Glu Val Glu Val Thr Glu Val
    210                 215                 220

Met Val Lys Val Gly Asp Lys Val Ala Ala Glu Gln Ser Leu Ile Thr
```

```
             225                 230                 235                 240
    Val Glu Gly Asp Lys Ala Ser Met Glu Val Pro Ala Pro Phe Ala Gly
                    245                 250                 255

Val Val Lys Glu Leu Lys Val Asn Val Gly Asp Lys Val Lys Thr Gly
                    260                 265                 270

Ser Leu Ile Met Ile Phe Glu Val Gly Ala Ala Pro Ala Ala Ala
                    275                 280                 285

Pro Ala Lys Gln Glu Ala Ala Pro Ala Pro Ala Ala Lys Ala Glu
    290                 295                 300

Ala Pro Ala Ala Ala Pro Ala Ala Lys Ala Glu Gly Lys Ser Glu Phe
    305                 310                 315                 320

Ala Glu Asn Asp Ala Tyr Val His Ala Thr Pro Leu Ile Arg Arg Leu
                    325                 330                 335

Ala Arg Glu Phe Gly Val Asn Leu Ala Lys Val Lys Gly Thr Gly Arg
                    340                 345                 350

Lys Gly Arg Ile Leu Arg Glu Asp Val Gln Ala Tyr Val Lys Glu Ala
                    355                 360                 365

Ile Lys Arg Ala Glu Ala Ala Pro Ala Ala Thr Gly Gly Gly Ile Pro
                    370                 375                 380

Gly Met Leu Pro Trp Pro Lys Val Asp Phe Ser Lys Phe Gly Glu Ile
    385                 390                 395                 400

Glu Glu Val Glu Leu Gly Arg Ile Gln Lys Ile Ser Gly Ala Asn Leu
                    405                 410                 415

Ser Arg Asn Trp Val Met Ile Pro His Val Thr His Phe Asp Lys Thr
                    420                 425                 430

Asp Ile Thr Glu Leu Glu Ala Phe Arg Lys Gln Gln Asn Glu Glu Ala
                    435                 440                 445

Ala Lys Arg Lys Leu Asp Val Lys Ile Thr Pro Val Val Phe Ile Met
                    450                 455                 460

Lys Ala Val Ala Ala Ala Leu Glu Gln Met Pro Arg Phe Asn Ser Ser
    465                 470                 475                 480

Leu Ser Glu Asp Gly Gln Arg Leu Thr Leu Lys Lys Tyr Ile Asn Ile
                    485                 490                 495

Gly Val Ala Val Asp Thr Pro Asn Gly Leu Val Val Pro Val Phe Lys
                    500                 505                 510

Asp Val Asn Lys Lys Gly Ile Ile Glu Leu Ser Arg Glu Leu Met Thr
                    515                 520                 525

Ile Ser Lys Lys Ala Arg Asp Gly Lys Leu Thr Ala Gly Glu Met Gln
                    530                 535                 540

Gly Gly Cys Phe Thr Ile Ser Ser Ile Gly Gly Leu Gly Thr Thr His
    545                 550                 555                 560

Phe Ala Pro Ile Val Asn Ala Pro Glu Val Ala Ile Leu Gly Val Ser
                    565                 570                 575

Lys Ser Ala Met Glu Pro Val Trp Asn Gly Lys Glu Phe Val Pro Arg
                    580                 585                 590

Leu Met Leu Pro Ile Ser Leu Ser Phe Asp His Arg Val Ile Asp Gly
                    595                 600                 605

Ala Asp Gly Ala Arg Phe Ile Thr Ile Ile Asn Asn Thr Leu Ser Asp
                    610                 615                 620

Ile Arg Arg Leu Val Met
    625                 630

<210> SEQ ID NO 69
```

```
<211> LENGTH: 474
<212> TYPE: PRT
<213> ORGANISM: Escherichia coli

<400> SEQUENCE: 69

Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
```

```
                385                 390                 395                 400
Phe Asp Lys Glu Ser His Arg Val Ile Gly Gly Ala Ile Val Gly Thr
                    405                 410                 415

Asn Gly Gly Glu Leu Gly Glu Ile Gly Leu Ala Ile Glu Met Gly
                420                 425                 430

Cys Asp Ala Glu Asp Ile Ala Leu Thr Ile His Ala His Pro Thr Leu
                435                 440                 445

His Glu Ser Val Gly Leu Ala Ala Glu Val Phe Glu Gly Ser Ile Thr
                450                 455                 460

Asp Leu Pro Asn Pro Lys Ala Lys Lys Lys
465                 470

<210> SEQ ID NO 70
<211> LENGTH: 371
<212> TYPE: PRT
<213> ORGANISM: Bacillus subtilis

<400> SEQUENCE: 70

Met Ala Ala Lys Thr Lys Lys Ala Ile Val Asp Ser Lys Lys Gln Phe
1               5                   10                  15

Asp Ala Ile Lys Lys Gln Phe Glu Thr Phe Gln Ile Leu Asn Glu Lys
                20                  25                  30

Gly Glu Val Val Asn Glu Ala Ala Met Pro Asp Leu Thr Asp Asp Gln
            35                  40                  45

Leu Lys Glu Leu Met Arg Arg Met Val Phe Thr Arg Val Leu Asp Gln
50                  55                  60

Arg Ser Ile Ser Leu Asn Arg Gln Gly Arg Leu Gly Phe Tyr Ala Pro
65                  70                  75                  80

Thr Ala Gly Gln Glu Ala Ser Gln Ile Ala Thr His Phe Ala Leu Glu
                85                  90                  95

Lys Glu Asp Phe Val Leu Pro Gly Tyr Arg Asp Val Pro Gln Leu Ile
                100                 105                 110

Trp His Gly Leu Pro Leu Tyr Gln Ala Phe Leu Phe Ser Arg Gly His
            115                 120                 125

Phe Arg Gly Asn Gln Met Pro Asp Asp Val Asn Ala Leu Ser Pro Gln
130                 135                 140

Ile Ile Ile Gly Ala Gln Tyr Ile Gln Thr Ala Gly Val Ala Leu Gly
145                 150                 155                 160

Leu Lys Lys Arg Gly Lys Lys Ala Val Ala Ile Thr Tyr Thr Gly Asp
                165                 170                 175

Gly Gly Ala Ser Gln Gly Asp Phe Tyr Glu Gly Ile Asn Phe Ala Gly
            180                 185                 190

Ala Tyr Lys Ala Pro Ala Ile Phe Val Val Gln Asn Asn Arg Tyr Ala
        195                 200                 205

Ile Ser Thr Pro Val Glu Lys Gln Ser Ala Ala Glu Thr Ile Ala Gln
210                 215                 220

Lys Ala Val Ala Ala Gly Ile Val Gly Val Gln Val Asp Gly Met Asp
225                 230                 235                 240

Pro Leu Ala Val Tyr Ala Ala Thr Ala Glu Ala Arg Glu Arg Ala Ile
                245                 250                 255

Asn Gly Glu Gly Pro Thr Leu Ile Glu Thr Leu Thr Phe Arg Tyr Gly
            260                 265                 270

Pro His Thr Met Ala Gly Asp Asp Pro Thr Lys Tyr Arg Thr Lys Glu
        275                 280                 285
```

Ile Glu Asn Glu Trp Glu Gln Lys Asp Pro Leu Val Arg Phe Arg Ala
    290                 295                 300

Phe Leu Glu Asn Lys Gly Leu Trp Ser Glu Glu Glu Ala Lys Val
305                 310                 315                 320

Ile Glu Asp Ala Lys Glu Ile Lys Gln Ala Ile Lys Lys Ala Asp
                325                 330                 335

Ala Glu Pro Lys Gln Lys Val Thr Asp Leu Met Lys Ile Met Tyr Glu
        340                 345                 350

Lys Met Pro His Asn Leu Glu Gln Phe Glu Ile Tyr Thr Gln Lys
            355                 360                 365

Glu Ser Lys
    370

<210> SEQ ID NO 71
<211> LENGTH: 325
<212> TYPE: PRT
<213> ORGANISM: Bacillus subtilis

<400> SEQUENCE: 71

Met Ala Gln Met Thr Met Ile Gln Ala Ile Thr Asp Ala Leu Arg Thr
1               5                   10                  15

Glu Leu Lys Asn Asp Glu Asn Val Leu Val Phe Gly Glu Asp Val Gly
            20                  25                  30

Val Asn Gly Gly Val Phe Arg Ala Thr Glu Gly Leu Gln Lys Glu Phe
        35                  40                  45

Gly Glu Asp Arg Val Phe Asp Thr Pro Leu Ala Glu Ser Gly Ile Gly
    50                  55                  60

Gly Leu Ala Leu Gly Leu Gly Leu Asn Gly Phe Arg Pro Val Met Glu
65                  70                  75                  80

Ile Gln Phe Phe Gly Phe Val Tyr Glu Val Met Asp Ser Val Ser Gly
                85                  90                  95

Gln Met Ala Arg Met Arg Tyr Arg Ser Gly Gly Arg Trp Thr Ser Pro
            100                 105                 110

Val Thr Ile Arg Ser Pro Phe Gly Gly Gly Val His Thr Pro Glu Leu
        115                 120                 125

His Ala Asp Ser Leu Glu Gly Leu Val Ala Gln Gln Pro Gly Ile Lys
130                 135                 140

Val Val Ile Pro Ser Thr Pro Tyr Asp Ala Lys Gly Leu Leu Ile Ser
145                 150                 155                 160

Ala Ile Arg Asp Asn Asp Pro Val Val Phe Leu Glu His Met Lys Leu
                165                 170                 175

Tyr Arg Ser Phe Arg Gln Glu Val Pro Glu Glu Tyr Thr Ile Glu
            180                 185                 190

Leu Gly Lys Ala Asp Val Lys Arg Glu Gly Thr Asp Leu Ser Ile Ile
        195                 200                 205

Thr Tyr Gly Ala Met Val His Glu Ser Leu Lys Ala Ala Asp Glu Leu
    210                 215                 220

Glu Lys Asp Gly Ile Ser Ala Glu Val Val Asp Leu Arg Thr Val Ser
225                 230                 235                 240

Pro Leu Asp Ile Asp Thr Ile Ile Ala Ser Val Glu Lys Thr Gly Arg
                245                 250                 255

Ala Ile Val Val Gln Glu Ala Gln Lys Gln Ala Gly Ile Ala Ala Asn
            260                 265                 270

Val Val Ala Glu Ile Asn Asp Arg Ala Ile Leu Ser Leu Glu Ala Pro
        275                 280                 285

```
Val Leu Arg Val Ala Ala Pro Asp Thr Val Phe Pro Phe Ser Gln Ala
    290                 295                 300

Glu Ser Val Trp Leu Pro Asn His Lys Asp Val Leu Glu Thr Ala Arg
305                 310                 315                 320

Lys Val Leu Glu Phe
                325

<210> SEQ ID NO 72
<211> LENGTH: 442
<212> TYPE: PRT
<213> ORGANISM: Bacillus subtilis

<400> SEQUENCE: 72

Met Ala Phe Glu Phe Lys Leu Pro Asp Ile Gly Glu Gly Ile His Glu
1               5                   10                  15

Gly Glu Ile Val Lys Trp Phe Val Lys Pro Asn Asp Glu Val Asp Glu
                20                  25                  30

Asp Asp Val Leu Ala Glu Val Gln Asn Asp Lys Ala Val Val Glu Ile
            35                  40                  45

Pro Ser Pro Val Lys Gly Lys Val Leu Glu Leu Lys Val Glu Glu Gly
        50                  55                  60

Thr Val Ala Thr Val Gly Gln Thr Ile Ile Thr Phe Asp Ala Pro Gly
65                  70                  75                  80

Tyr Glu Asp Leu Gln Phe Lys Gly Ser Asp Glu Ser Asp Ala Lys
                85                  90                  95

Thr Glu Ala Gln Val Gln Ser Thr Ala Glu Ala Gly Gln Asp Val Ala
            100                 105                 110

Lys Glu Glu Gln Ala Gln Glu Pro Ala Lys Ala Thr Gly Ala Gly Gln
        115                 120                 125

Gln Asp Gln Ala Glu Val Asp Pro Asn Lys Arg Val Ile Ala Met Pro
    130                 135                 140

Ser Val Arg Lys Tyr Ala Arg Glu Lys Gly Val Asp Ile Arg Lys Val
145                 150                 155                 160

Thr Gly Ser Gly Asn Asn Gly Arg Val Val Lys Glu Asp Ile Asp Ser
                165                 170                 175

Phe Val Asn Gly Gly Ala Gln Glu Ala Ala Pro Gln Glu Thr Ala Ala
            180                 185                 190

Pro Gln Glu Thr Ala Ala Lys Pro Ala Ala Pro Ala Pro Glu Gly
        195                 200                 205

Glu Phe Pro Glu Thr Arg Glu Lys Met Ser Gly Ile Arg Lys Ala Ile
    210                 215                 220

Ala Lys Ala Met Val Asn Ser Lys His Thr Ala Pro His Val Thr Leu
225                 230                 235                 240

Met Asp Glu Val Asp Val Thr Asn Leu Val Ala His Arg Lys Gln Phe
                245                 250                 255

Lys Gln Val Ala Ala Asp Gln Gly Ile Lys Leu Thr Tyr Leu Pro Tyr
            260                 265                 270

Val Val Lys Ala Leu Thr Ser Ala Leu Lys Lys Phe Pro Val Leu Asn
        275                 280                 285

Thr Ser Ile Asp Asp Lys Thr Asp Glu Val Ile Gln Lys His Tyr Phe
    290                 295                 300

Asn Ile Gly Ile Ala Ala Asp Thr Glu Lys Gly Leu Leu Val Pro Val
305                 310                 315                 320

Val Lys Asn Ala Asp Arg Lys Ser Val Phe Glu Ile Ser Asp Glu Ile
```

```
                    325                 330                 335
Asn Gly Leu Ala Thr Lys Ala Arg Glu Gly Lys Leu Ala Pro Ala Glu
                340                 345                 350
Met Lys Gly Ala Ser Cys Thr Ile Thr Asn Ile Gly Ser Ala Gly Gly
                355                 360                 365
Gln Trp Phe Thr Pro Val Ile Asn His Pro Glu Val Ala Ile Leu Gly
            370                 375                 380
Ile Gly Arg Ile Ala Glu Lys Ala Ile Val Arg Asp Gly Glu Ile Val
385                 390                 395                 400
Ala Ala Pro Val Leu Ala Leu Ser Leu Ser Phe Asp His Arg Met Ile
                405                 410                 415
Asp Gly Ala Thr Ala Gln Asn Ala Leu Asn His Ile Lys Arg Leu Leu
                420                 425                 430
Asn Asp Pro Gln Leu Ile Leu Met Glu Ala
                435                 440

<210> SEQ ID NO 73
<211> LENGTH: 470
<212> TYPE: PRT
<213> ORGANISM: Bacillus subtilis

<400> SEQUENCE: 73

Met Val Val Gly Asp Phe Pro Ile Glu Thr Asp Thr Leu Val Ile Gly
1               5                   10                  15
Ala Gly Pro Gly Gly Tyr Val Ala Ala Ile Arg Ala Ala Gln Leu Gly
                20                  25                  30
Gln Lys Val Thr Val Val Glu Lys Ala Thr Leu Gly Gly Val Cys Leu
            35                  40                  45
Asn Val Gly Cys Ile Pro Ser Lys Ala Leu Ile Asn Ala Gly His Arg
    50                  55                  60
Tyr Glu Asn Ala Lys His Ser Asp Asp Met Gly Ile Thr Ala Glu Asn
65                  70                  75                  80
Val Thr Val Asp Phe Thr Lys Val Gln Glu Trp Lys Ala Ser Val Val
                85                  90                  95
Asn Lys Leu Thr Gly Gly Val Ala Gly Leu Leu Lys Gly Asn Lys Val
                100                 105                 110
Asp Val Val Lys Gly Glu Ala Tyr Phe Val Asp Ser Asn Ser Val Arg
            115                 120                 125
Val Met Asp Glu Asn Ser Ala Gln Thr Tyr Thr Phe Lys Asn Ala Ile
    130                 135                 140
Ile Ala Thr Gly Ser Arg Pro Ile Glu Leu Pro Asn Phe Lys Tyr Ser
145                 150                 155                 160
Glu Arg Val Leu Asn Ser Thr Gly Ala Leu Ala Leu Lys Glu Ile Pro
                165                 170                 175
Lys Lys Leu Val Val Ile Gly Gly Tyr Ile Gly Thr Glu Leu Gly
                180                 185                 190
Thr Ala Tyr Ala Asn Phe Gly Thr Glu Leu Val Ile Leu Glu Gly Gly
            195                 200                 205
Asp Glu Ile Leu Pro Gly Phe Glu Lys Gln Met Ser Ser Leu Val Thr
    210                 215                 220
Arg Arg Leu Lys Lys Lys Gly Asn Val Glu Ile His Thr Asn Ala Met
225                 230                 235                 240
Ala Lys Gly Val Glu Glu Arg Pro Asp Gly Val Thr Val Thr Phe Glu
                245                 250                 255
```

Val Lys Gly Glu Glu Lys Thr Val Asp Ala Asp Tyr Val Leu Ile Thr
            260                 265                 270

Val Gly Arg Arg Pro Asn Thr Asp Glu Leu Gly Leu Glu Gln Val Gly
            275                 280                 285

Ile Glu Met Thr Asp Arg Gly Ile Val Lys Thr Asp Lys Gln Cys Arg
            290                 295                 300

Thr Asn Val Pro Asn Ile Tyr Ala Ile Gly Asp Ile Ile Glu Gly Pro
305                 310                 315                 320

Pro Leu Ala His Lys Ala Ser Tyr Glu Gly Lys Ile Ala Ala Glu Ala
            325                 330                 335

Ile Ala Gly Glu Pro Ala Glu Ile Asp Tyr Leu Gly Ile Pro Ala Val
            340                 345                 350

Val Phe Ser Glu Pro Glu Leu Ala Ser Val Gly Tyr Thr Glu Ala Gln
            355                 360                 365

Ala Lys Glu Glu Gly Leu Asp Ile Val Ala Ala Lys Phe Pro Phe Ala
            370                 375                 380

Ala Asn Gly Arg Ala Leu Ser Leu Asn Glu Thr Asp Gly Phe Met Lys
385                 390                 395                 400

Leu Ile Thr Arg Lys Glu Asp Gly Leu Val Ile Gly Ala Gln Ile Ala
            405                 410                 415

Gly Ala Ser Ala Ser Asp Met Ile Ser Glu Leu Ser Leu Ala Ile Glu
            420                 425                 430

Gly Gly Met Thr Ala Glu Asp Ile Ala Met Thr Ile His Ala His Pro
            435                 440                 445

Thr Leu Gly Glu Ile Thr Met Glu Ala Ala Glu Val Ala Ile Gly Ser
            450                 455                 460

Pro Ile His Ile Val Lys
465                 470

<210> SEQ ID NO 74
<211> LENGTH: 2123
<212> TYPE: PRT
<213> ORGANISM: Saccharomyces cerevisiae

<400> SEQUENCE: 74

Met Arg Ser Ile Arg Lys Trp Ala Tyr Glu Thr Phe Asn Asp Glu Lys
1               5                   10                  15

Ile Ile Gln Phe Val Val Met Ala Thr Pro Asp Asp Leu His Ala Asn
            20                  25                  30

Ser Glu Tyr Ile Arg Met Ala Asp Gln Tyr Val Gln Val Pro Gly Gly
            35                  40                  45

Thr Asn Asn Asn Asn Tyr Ala Asn Ile Asp Leu Ile Leu Asp Val Ala
50                  55                  60

Glu Gln Thr Asp Val Asp Ala Val Trp Ala Trp Gly His Ala Ser
65                  70                  75                  80

Glu Asn Pro Cys Leu Pro Glu Leu Leu Ala Ser Ser Gln Arg Lys Ile
            85                  90                  95

Leu Phe Ile Gly Pro Pro Gly Arg Ala Met Arg Ser Leu Gly Asp Lys
            100                 105                 110

Ile Ser Thr Ile Val Ala Gln Ser Ala Lys Ile Pro Cys Ile Pro
            115                 120                 125

Trp Ser Gly Ser His Ile Asp Thr Ile His Ile Asp Asn Lys Thr Asn
            130                 135                 140

Phe Val Ser Val Pro Asp Asp Val Tyr Val Arg Gly Cys Cys Ser Ser
145                 150                 155                 160

```
Pro Glu Asp Ala Leu Glu Lys Ala Lys Leu Ile Gly Phe Pro Val Met
            165                 170                 175

Ile Lys Ala Ser Glu Gly Gly Gly Lys Gly Ile Arg Arg Val Asp
        180                 185                 190

Asn Glu Asp Asp Phe Ile Ala Leu Tyr Arg Gln Ala Val Asn Glu Thr
            195                 200                 205

Pro Gly Ser Pro Met Phe Val Met Lys Val Val Thr Asp Ala Arg His
        210                 215                 220

Leu Glu Val Gln Leu Leu Ala Asp Gln Tyr Gly Thr Asn Ile Thr Leu
225                 230                 235                 240

Phe Gly Arg Asp Cys Ser Ile Gln Arg His Gln Lys Ile Ile Glu
            245                 250                 255

Glu Ala Pro Val Thr Ile Thr Lys Pro Glu Thr Phe Gln Arg Met Glu
            260                 265                 270

Arg Ala Ala Ile Arg Leu Gly Glu Leu Val Gly Tyr Val Ser Ala Gly
        275                 280                 285

Thr Val Glu Tyr Leu Tyr Ser Pro Lys Asp Asp Lys Phe Tyr Phe Leu
        290                 295                 300

Glu Leu Asn Pro Arg Leu Gln Val Glu His Pro Thr Thr Glu Met Ile
305                 310                 315                 320

Ser Gly Val Asn Leu Pro Ala Thr Gln Leu Gln Ile Ala Met Gly Ile
            325                 330                 335

Pro Met His Met Ile Ser Asp Ile Arg Lys Leu Tyr Gly Leu Asp Pro
            340                 345                 350

Thr Gly Thr Ser Tyr Ile Asp Phe Lys Asn Leu Lys Arg Pro Ser Pro
        355                 360                 365

Lys Gly His Cys Ile Ser Cys Arg Ile Thr Ser Glu Asp Pro Asn Glu
        370                 375                 380

Gly Phe Lys Pro Ser Thr Gly Lys Ile His Glu Leu Asn Phe Arg Ser
385                 390                 395                 400

Ser Ser Asn Val Trp Gly Tyr Phe Ser Val Gly Asn Asn Gly Ala Ile
            405                 410                 415

His Ser Phe Ser Asp Ser Gln Phe Gly His Ile Phe Ala Val Gly Asn
            420                 425                 430

Asp Arg Gln Asp Ala Lys Gln Asn Met Val Leu Ala Leu Lys Asp Phe
        435                 440                 445

Ser Ile Arg Gly Glu Phe Lys Thr Pro Ile Glu Tyr Leu Ile Glu Leu
        450                 455                 460

Leu Glu Thr Arg Asp Phe Glu Ser Asn Asn Ile Ser Thr Gly Trp Leu
465                 470                 475                 480

Asp Asp Leu Ile Leu Lys Asn Leu Ser Ser Asp Ser Lys Leu Asp Pro
            485                 490                 495

Thr Leu Ala Ile Ile Cys Gly Ala Ala Met Lys Ala Tyr Val Phe Thr
            500                 505                 510

Glu Lys Val Arg Asn Lys Tyr Leu Glu Leu Leu Arg Arg Gly Gln Val
        515                 520                 525

Pro Pro Lys Asp Phe Leu Lys Thr Lys Phe Pro Val Asp Phe Ile Phe
        530                 535                 540

Asp Asn Asn Arg Tyr Leu Phe Asn Val Ala Gln Ser Ser Glu Glu Gln
545                 550                 555                 560

Phe Ile Leu Ser Ile Asn Lys Ser Gln Cys Glu Val Asn Val Gln Lys
            565                 570                 575
```

```
Leu Ser Ser Asp Cys Leu Leu Ile Ser Val Asp Gly Lys Cys His Thr
                580                 585                 590

Val Tyr Trp Lys Asp Asp Ile Arg Gly Thr Arg Leu Ser Ile Asp Ser
            595                 600                 605

Asn Thr Ile Phe Leu Glu Ala Glu Leu Asn Pro Thr Gln Val Ile Ser
        610                 615                 620

Pro Thr Pro Gly Lys Leu Val Lys Tyr Leu Val Arg Ser Gly Asp His
625                 630                 635                 640

Val Phe Ala Gly Gln Gln Tyr Ala Glu Ile Glu Met Lys Met Gln
                645                 650                 655

Met Pro Leu Val Ala Lys Ser Asp Gly Val Ile Glu Leu Leu Arg Gln
                660                 665                 670

Pro Gly Ser Ile Ile Glu Ala Gly Asp Val Ile Ala Lys Leu Thr Leu
                675                 680                 685

Asp Ser Pro Ser Lys Ala Asn Glu Ser Ser Leu Tyr Arg Gly Glu Leu
        690                 695                 700

Pro Val Leu Gly Pro Pro Leu Ile Glu Gly Ser Arg Pro Asn His Lys
705                 710                 715                 720

Leu Arg Val Leu Ile Asn Arg Leu Glu Asn Ile Leu Asn Gly Tyr His
                725                 730                 735

Glu Asn Ser Gly Ile Glu Thr Thr Leu Lys Glu Leu Ile Lys Ile Leu
                740                 745                 750

Arg Asp Gly Arg Leu Pro Tyr Ser Glu Trp Asp Ser Gln Ile Ser Thr
                755                 760                 765

Val Arg Asn Arg Leu Pro Arg Gln Leu Asn Glu Gly Leu Gly Asn Leu
                770                 775                 780

Val Lys Lys Ser Val Ser Phe Pro Ala Lys Glu Leu His Lys Leu Met
785                 790                 795                 800

Lys Arg Tyr Leu Glu Glu Asn Thr Asn Asp His Val Val Tyr Val Ala
            805                 810                 815

Leu Gln Pro Leu Leu Lys Ile Ser Glu Arg Tyr Ser Glu Gly Leu Ala
            820                 825                 830

Asn His Glu Cys Glu Ile Phe Leu Lys Leu Ile Lys Lys Tyr Tyr Ala
            835                 840                 845

Val Glu Lys Ile Phe Glu Asn His Asp Ile His Glu Glu Arg Asn Leu
850                 855                 860

Leu Asn Leu Arg Arg Lys Asp Leu Thr Asn Leu Lys Lys Ile Leu Cys
865                 870                 875                 880

Ile Ser Leu Ser His Ala Asn Val Val Ala Lys Asn Lys Leu Val Thr
                885                 890                 895

Ala Ile Leu His Glu Tyr Glu Pro Leu Cys Gln Asp Ser Ser Lys Met
                900                 905                 910

Ser Leu Lys Phe Arg Ala Val Ile His Asp Leu Ala Ser Leu Glu Ser
            915                 920                 925

Lys Trp Ala Lys Glu Val Ala Lys Ala Arg Ser Val Leu Leu Arg
930                 935                 940

Gly Ile Phe Pro Pro Ile Lys Lys Arg Lys Glu His Ile Lys Thr Leu
945                 950                 955                 960

Leu Gln Leu His Ile Lys Asp Thr Gly Ala Glu Asn Ile His Ser Arg
                965                 970                 975

Asn Ile Tyr Ser Cys Met Arg Asp Phe Gly Asn Leu Ile His Ser Asn
            980                 985                 990

Leu Ile Gln Leu Gln Asp Leu Phe  Phe Phe Phe Gly His  Gln Asp Thr
```

```
              995                1000              1005
Ala  Leu  Ser  Ser  Ile  Ala  Ser  Glu  Ile  Tyr  Ala  Arg  Tyr  Ala  Tyr
          1010               1015               1020

Gly  Asn  Tyr  Gln  Leu  Lys  Ser  Ile  Lys  Ile  His  Lys  Gly  Ala  Pro
          1025               1030               1035

Asp  Leu  Leu  Met  Ser  Trp  Gln  Phe  Ser  Ser  Leu  Arg  Asn  Tyr  Leu
          1040               1045               1050

Val  Asn  Ser  Asp  Gly  Glu  Ser  Asp  Glu  Phe  Thr  Lys  Leu  Ser  Lys
          1055               1060               1065

Pro  Pro  Ser  Thr  Ser  Gly  Lys  Ser  Ser  Ala  Asn  Ser  Phe  Gly  Leu
          1070               1075               1080

Leu  Val  Asn  Met  Arg  Ala  Leu  Glu  Ser  Leu  Glu  Lys  Thr  Leu  Asp
          1085               1090               1095

Glu  Val  Tyr  Glu  Gln  Ile  His  Ile  Pro  Glu  Glu  Arg  Leu  Ser  Ser
          1100               1105               1110

Gly  Glu  Asn  Ser  Leu  Ile  Val  Asn  Ile  Leu  Ser  Pro  Ile  Arg  Tyr
          1115               1120               1125

Arg  Ser  Glu  Asn  Asp  Leu  Ile  Lys  Thr  Leu  Lys  Ile  Lys  Leu  His
          1130               1135               1140

Glu  Asn  Glu  Arg  Gly  Leu  Ser  Lys  Leu  Lys  Val  Asn  Arg  Ile  Thr
          1145               1150               1155

Phe  Ala  Phe  Ile  Ala  Ala  Asn  Ala  Pro  Ala  Val  Lys  Phe  Tyr  Ser
          1160               1165               1170

Phe  Asp  Gly  Thr  Thr  Tyr  Asp  Glu  Ile  Ser  Gln  Ile  Arg  Asn  Met
          1175               1180               1185

Asp  Pro  Ser  Tyr  Glu  Ala  Pro  Leu  Glu  Leu  Gly  Lys  Met  Ser  Asn
          1190               1195               1200

Tyr  Lys  Ile  Arg  Ser  Leu  Pro  Thr  Tyr  Asp  Ser  Ser  Ile  Arg  Ile
          1205               1210               1215

Phe  Glu  Gly  Ile  Ser  Lys  Phe  Thr  Pro  Leu  Asp  Lys  Arg  Phe  Phe
          1220               1225               1230

Val  Arg  Lys  Ile  Ile  Asn  Ser  Phe  Met  Tyr  Asn  Asp  Gln  Lys  Thr
          1235               1240               1245

Thr  Glu  Glu  Asn  Leu  Lys  Ala  Glu  Ile  Asn  Ala  Gln  Val  Val  Tyr
          1250               1255               1260

Met  Leu  Glu  His  Leu  Gly  Ala  Val  Asp  Ile  Ser  Asn  Ser  Asp  Leu
          1265               1270               1275

Asn  His  Ile  Phe  Leu  Ser  Phe  Asn  Thr  Val  Leu  Asn  Ile  Pro  Val
          1280               1285               1290

His  Arg  Leu  Glu  Glu  Ile  Val  Ser  Thr  Ile  Leu  Lys  Thr  His  Glu
          1295               1300               1305

Thr  Arg  Leu  Phe  Gln  Glu  Arg  Ile  Thr  Asp  Val  Glu  Ile  Cys  Ile
          1310               1315               1320

Ser  Val  Glu  Cys  Leu  Glu  Thr  Lys  Lys  Pro  Ala  Pro  Leu  Arg  Leu
          1325               1330               1335

Leu  Ile  Ser  Asn  Lys  Ser  Gly  Tyr  Val  Val  Lys  Ile  Glu  Thr  Tyr
          1340               1345               1350

Tyr  Glu  Lys  Ile  Gly  Lys  Asn  Gly  Asn  Leu  Ile  Leu  Glu  Pro  Cys
          1355               1360               1365

Ser  Glu  Gln  Ser  His  Tyr  Ser  Gln  Lys  Ser  Leu  Ser  Leu  Pro  Tyr
          1370               1375               1380

Ser  Val  Lys  Asp  Trp  Leu  Gln  Pro  Lys  Arg  Tyr  Lys  Ala  Gln  Phe
          1385               1390               1395
```

```
Met Gly Thr Thr Tyr Val Tyr Asp Phe Pro Gly Leu Phe His Gln
    1400            1405            1410

Ala Ala Ile Gln Gln Trp Lys Arg Tyr Phe Pro Lys His Lys Leu
    1415            1420            1425

Asn Asp Ser Phe Phe Ser Trp Val Glu Leu Ile Glu Gln Asn Gly
    1430            1435            1440

Asn Leu Ile Lys Val Asn Arg Glu Pro Gly Leu Asn Asn Ile Gly
    1445            1450            1455

Met Val Ala Phe Glu Ile Met Val Gln Thr Pro Glu Tyr Pro Glu
    1460            1465            1470

Gly Arg Asn Met Ile Val Ile Ser Asn Asp Ile Thr Tyr Asn Ile
    1475            1480            1485

Gly Ser Phe Gly Pro Arg Glu Asp Leu Phe Phe Asp Arg Val Thr
    1490            1495            1500

Asn Tyr Ala Arg Glu Arg Gly Ile Pro Arg Ile Tyr Leu Ala Ala
    1505            1510            1515

Asn Ser Gly Ala Lys Leu Gly Ile Ala Glu Glu Leu Ile Pro Leu
    1520            1525            1530

Phe Arg Val Ala Trp Asn Asp Pro Ser Asp Pro Thr Lys Gly Phe
    1535            1540            1545

Gln Tyr Leu Tyr Leu Ala Pro Lys Asp Met Gln Leu Leu Lys Asp
    1550            1555            1560

Ser Gly Lys Gly Asn Ser Val Val Val Glu His Lys Met Val Tyr
    1565            1570            1575

Gly Glu Glu Arg Tyr Ile Ile Lys Ala Ile Val Gly Phe Glu Glu
    1580            1585            1590

Gly Leu Gly Val Glu Cys Leu Gln Gly Ser Gly Leu Ile Ala Gly
    1595            1600            1605

Ala Thr Ser Lys Ala Tyr Arg Asp Ile Phe Thr Ile Thr Ala Val
    1610            1615            1620

Thr Cys Arg Ser Val Gly Ile Gly Ser Tyr Leu Val Arg Leu Gly
    1625            1630            1635

Gln Arg Thr Ile Gln Val Glu Asp Lys Pro Ile Ile Leu Thr Gly
    1640            1645            1650

Ala Ser Ala Ile Asn Lys Val Leu Gly Thr Asp Ile Tyr Thr Ser
    1655            1660            1665

Asn Leu Gln Ile Gly Gly Thr Gln Ile Met Tyr Lys Asn Gly Ile
    1670            1675            1680

Ala His Leu Thr Ala Ser Asn Asp Met Lys Ala Ile Glu Lys Ile
    1685            1690            1695

Met Thr Trp Leu Ser Tyr Val Pro Ala Lys Arg Asp Met Ser Pro
    1700            1705            1710

Pro Leu Leu Glu Thr Met Asp Arg Trp Asp Arg Asp Val Asp Phe
    1715            1720            1725

Lys Pro Ala Lys Gln Val Pro Tyr Glu Ala Arg Trp Leu Ile Glu
    1730            1735            1740

Gly Lys Trp Asp Ser Asn Asn Asn Phe Gln Ser Gly Leu Phe Asp
    1745            1750            1755

Lys Asp Ser Phe Phe Glu Thr Leu Ser Gly Trp Ala Lys Gly Val
    1760            1765            1770

Ile Val Gly Arg Ala Arg Leu Gly Gly Ile Pro Val Gly Val Ile
    1775            1780            1785
```

Ala Val Glu Thr Lys Thr Ile Glu Glu Ile Ile Pro Ala Asp Pro
1790            1795                1800

Ala Asn Leu Asp Ser Ser Glu Phe Ser Val Lys Glu Ala Gly Gln
1805            1810                1815

Val Trp Tyr Pro Asn Ser Ala Phe Lys Thr Ala Gln Thr Ile Asn
1820            1825                1830

Asp Phe Asn Tyr Gly Glu Gln Leu Pro Leu Ile Ile Leu Ala Asn
1835            1840                1845

Trp Arg Gly Phe Ser Gly Gly Gln Arg Asp Met Tyr Asn Glu Val
1850            1855                1860

Leu Lys Tyr Gly Ser Phe Ile Val Asp Ala Leu Val Asp Tyr Lys
1865            1870                1875

Gln Pro Ile Leu Ile Tyr Ile Pro Pro Phe Gly Glu Leu Arg Gly
1880            1885                1890

Gly Ser Trp Val Val Ile Asp Pro Thr Ile Asn Pro Glu Gln Met
1895            1900                1905

Glu Met Tyr Ala Asp Val Glu Ser Arg Gly Gly Val Leu Glu Pro
1910            1915                1920

Asp Gly Val Val Ser Ile Lys Tyr Arg Lys Glu Lys Met Ile Glu
1925            1930                1935

Thr Met Ile Arg Leu Asp Ser Thr Tyr Gly His Leu Arg Arg Thr
1940            1945                1950

Leu Thr Glu Lys Lys Leu Ser Leu Glu Lys Gln Asn Asp Leu Thr
1955            1960                1965

Lys Arg Leu Lys Ile Arg Glu Arg Gln Leu Ile Pro Ile Tyr Asn
1970            1975                1980

Gln Ile Ser Ile Gln Phe Ala Asp Leu His Asp Arg Ser Thr Arg
1985            1990                1995

Met Leu Val Lys Gly Val Ile Arg Asn Glu Leu Glu Trp Lys Lys
2000            2005                2010

Ser Arg Arg Phe Leu Tyr Trp Arg Leu Arg Arg Leu Asn Glu
2015            2020                2025

Gly Gln Val Ile Lys Arg Leu Gln Lys Lys Thr Cys Asp Asn Lys
2030            2035                2040

Thr Lys Met Lys Tyr Asp Asp Leu Leu Lys Ile Val Gln Ser Trp
2045            2050                2055

Tyr Asn Asp Leu Asp Val Asn Asp Asp Arg Ala Val Val Glu Phe
2060            2065                2070

Ile Glu Arg Asn Ser Lys Lys Ile Asp Leu Asn Ile Glu Glu Phe
2075            2080                2085

Glu Ile Ser Leu Leu Ile Asp Glu Leu Lys Lys Lys Phe Glu Asp
2090            2095                2100

Arg Arg Gly Asn Ile Val Leu Glu Glu Leu Thr Arg Leu Val Asp
2105            2110                2115

Ser Lys Arg Lys Arg
2120

<210> SEQ ID NO 75
<211> LENGTH: 319
<212> TYPE: PRT
<213> ORGANISM: Escherichia coli

<400> SEQUENCE: 75

Met Ser Leu Asn Phe Leu Asp Phe Glu Gln Pro Ile Ala Glu Leu Glu
1               5                   10                  15

Ala Lys Ile Asp Ser Leu Thr Ala Val Ser Arg Gln Asp Glu Lys Leu
           20                  25                  30

Asp Ile Asn Ile Asp Glu Glu Val His Arg Leu Arg Glu Lys Ser Val
       35                  40                  45

Glu Leu Thr Arg Lys Ile Phe Ala Asp Leu Gly Ala Trp Gln Ile Ala
 50                  55                  60

Gln Leu Ala Arg His Pro Gln Arg Pro Tyr Thr Leu Asp Tyr Val Arg
65                  70                  75                  80

Leu Ala Phe Asp Glu Phe Asp Glu Leu Ala Gly Asp Arg Ala Tyr Ala
                85                  90                  95

Asp Asp Lys Ala Ile Val Gly Gly Ile Ala Arg Leu Asp Gly Arg Pro
            100                 105                 110

Val Met Ile Ile Gly His Gln Lys Gly Arg Glu Thr Lys Glu Lys Ile
            115                 120                 125

Arg Arg Asn Phe Gly Met Pro Ala Pro Glu Gly Tyr Arg Lys Ala Leu
130                 135                 140

Arg Leu Met Gln Met Ala Glu Arg Phe Lys Met Pro Ile Ile Thr Phe
145                 150                 155                 160

Ile Asp Thr Pro Gly Ala Tyr Pro Gly Val Gly Ala Glu Glu Arg Gly
                165                 170                 175

Gln Ser Glu Ala Ile Ala Arg Asn Leu Arg Glu Met Ser Arg Leu Gly
            180                 185                 190

Val Pro Val Val Cys Thr Val Ile Gly Glu Gly Gly Ser Gly Gly Ala
            195                 200                 205

Leu Ala Ile Gly Val Gly Asp Lys Val Asn Met Leu Gln Tyr Ser Thr
            210                 215                 220

Tyr Ser Val Ile Ser Pro Glu Gly Cys Ala Ser Ile Leu Trp Lys Ser
225                 230                 235                 240

Ala Asp Lys Ala Pro Leu Ala Ala Glu Ala Met Gly Ile Ile Ala Pro
                245                 250                 255

Arg Leu Lys Glu Leu Lys Leu Ile Asp Ser Ile Ile Pro Glu Pro Leu
            260                 265                 270

Gly Gly Ala His Arg Asn Pro Glu Ala Met Ala Ala Ser Leu Lys Ala
            275                 280                 285

Gln Leu Leu Ala Asp Leu Ala Asp Leu Asp Val Leu Ser Thr Glu Asp
            290                 295                 300

Leu Lys Asn Arg Arg Tyr Gln Arg Leu Met Ser Tyr Gly Tyr Ala
305                 310                 315

<210> SEQ ID NO 76
<211> LENGTH: 156
<212> TYPE: PRT
<213> ORGANISM: Escherichia coli

<400> SEQUENCE: 76

Met Asp Ile Arg Lys Ile Lys Lys Leu Ile Glu Leu Val Glu Glu Ser
1               5                   10                  15

Gly Ile Ser Glu Leu Glu Ile Ser Glu Gly Glu Glu Ser Val Arg Ile
            20                  25                  30

Ser Arg Ala Ala Pro Ala Ala Ser Phe Pro Val Met Gln Gln Ala Tyr
        35                  40                  45

Ala Ala Pro Met Met Gln Gln Pro Ala Gln Ser Asn Ala Ala Ala Pro
 50                  55                  60

Ala Thr Val Pro Ser Met Glu Ala Pro Ala Ala Ala Glu Ile Ser Gly

```
                65                  70                  75                  80
His Ile Val Arg Ser Pro Met Val Gly Thr Phe Tyr Arg Thr Pro Ser
                    85                  90                  95

Pro Asp Ala Lys Ala Phe Ile Glu Val Gly Gln Lys Val Asn Val Gly
                100                 105                 110

Asp Thr Leu Cys Ile Val Glu Ala Met Lys Met Met Asn Gln Ile Glu
                115                 120                 125

Ala Asp Lys Ser Gly Thr Val Lys Ala Ile Leu Val Glu Ser Gly Gln
130                 135                 140

Pro Val Glu Phe Asp Glu Pro Leu Val Val Ile Glu
145                 150                 155

<210> SEQ ID NO 77
<211> LENGTH: 449
<212> TYPE: PRT
<213> ORGANISM: Escherichia coli

<400> SEQUENCE: 77

Met Leu Asp Lys Ile Val Ile Ala Asn Arg Gly Glu Ile Ala Leu Arg
1               5                   10                  15

Ile Leu Arg Ala Cys Lys Glu Leu Gly Ile Lys Thr Val Ala Val His
                20                  25                  30

Ser Ser Ala Asp Arg Asp Leu Lys His Val Leu Leu Ala Asp Glu Thr
            35                  40                  45

Val Cys Ile Gly Pro Ala Pro Ser Val Lys Ser Tyr Leu Asn Ile Pro
        50                  55                  60

Ala Ile Ile Ser Ala Ala Glu Ile Thr Gly Ala Val Ala Ile His Pro
65                  70                  75                  80

Gly Tyr Gly Phe Leu Ser Glu Asn Ala Asn Phe Ala Glu Gln Val Glu
                85                  90                  95

Arg Ser Gly Phe Ile Phe Ile Gly Pro Lys Ala Glu Thr Ile Arg Leu
                100                 105                 110

Met Gly Asp Lys Val Ser Ala Ile Ala Ala Met Lys Lys Ala Gly Val
            115                 120                 125

Pro Cys Val Pro Gly Ser Asp Gly Pro Leu Gly Asp Asp Met Asp Lys
        130                 135                 140

Asn Arg Ala Ile Ala Lys Arg Ile Gly Tyr Pro Val Ile Ile Lys Ala
145                 150                 155                 160

Ser Gly Gly Gly Gly Arg Gly Met Arg Val Val Arg Gly Asp Ala
                165                 170                 175

Glu Leu Ala Gln Ser Ile Ser Met Thr Arg Ala Glu Ala Lys Ala Ala
                180                 185                 190

Phe Ser Asn Asp Met Val Tyr Met Glu Lys Tyr Leu Glu Asn Pro Arg
                195                 200                 205

His Val Glu Ile Gln Val Leu Ala Asp Gly Gln Gly Asn Ala Ile Tyr
            210                 215                 220

Leu Ala Glu Arg Asp Cys Ser Met Gln Arg Arg His Gln Lys Val Val
225                 230                 235                 240

Glu Glu Ala Pro Ala Pro Gly Ile Thr Pro Glu Leu Arg Arg Tyr Ile
                245                 250                 255

Gly Glu Arg Cys Ala Lys Ala Cys Val Asp Ile Gly Tyr Arg Gly Ala
                260                 265                 270

Gly Thr Phe Glu Phe Leu Phe Glu Asn Gly Glu Phe Tyr Phe Ile Glu
            275                 280                 285
```

```
Met Asn Thr Arg Ile Gln Val Glu His Pro Val Thr Glu Met Ile Thr
    290                 295                 300

Gly Val Asp Leu Ile Lys Glu Gln Leu Arg Ile Ala Ala Gly Gln Pro
305                 310                 315                 320

Leu Ser Ile Lys Gln Glu Val His Val Arg Gly His Ala Val Glu
                325                 330                 335

Cys Arg Ile Asn Ala Glu Asp Pro Asn Thr Phe Leu Pro Ser Pro Gly
                340                 345                 350

Lys Ile Thr Arg Phe His Ala Pro Gly Gly Phe Gly Val Arg Trp Glu
                355                 360                 365

Ser His Ile Tyr Ala Gly Tyr Thr Val Pro Pro Tyr Tyr Asp Ser Met
    370                 375                 380

Ile Gly Lys Leu Ile Cys Tyr Gly Glu Asn Arg Asp Val Ala Ile Ala
385                 390                 395                 400

Arg Met Lys Asn Ala Leu Gln Glu Leu Ile Ile Asp Gly Ile Lys Thr
                405                 410                 415

Asn Val Asp Leu Gln Ile Arg Ile Met Asn Asp Glu Asn Phe Gln His
                420                 425                 430

Gly Gly Thr Asn Ile His Tyr Leu Glu Lys Lys Leu Gly Leu Gln Glu
                435                 440                 445

Lys
```

<210> SEQ ID NO 78
<211> LENGTH: 304
<212> TYPE: PRT
<213> ORGANISM: Escherichia coli

<400> SEQUENCE: 78

```
Met Ser Trp Ile Glu Arg Ile Lys Ser Asn Ile Thr Pro Thr Arg Lys
1               5                   10                  15

Ala Ser Ile Pro Glu Gly Val Trp Thr Lys Cys Asp Ser Cys Gly Gln
                20                  25                  30

Val Leu Tyr Arg Ala Glu Leu Glu Arg Asn Leu Glu Val Cys Pro Lys
            35                  40                  45

Cys Asp His His Met Arg Met Thr Ala Arg Asn Arg Leu His Ser Leu
50                  55                  60

Leu Asp Glu Gly Ser Leu Val Glu Leu Gly Ser Glu Leu Glu Pro Lys
65                  70                  75                  80

Asp Val Leu Lys Phe Arg Asp Ser Lys Lys Tyr Lys Asp Arg Leu Ala
                85                  90                  95

Ser Ala Gln Lys Glu Thr Gly Glu Lys Asp Ala Leu Val Val Met Lys
                100                 105                 110

Gly Thr Leu Tyr Gly Met Pro Val Val Ala Ala Phe Glu Phe Ala
            115                 120                 125

Phe Met Gly Gly Ser Met Gly Ser Val Val Gly Ala Arg Phe Val Arg
130                 135                 140

Ala Val Glu Gln Ala Leu Glu Asp Asn Cys Pro Leu Ile Cys Phe Ser
145                 150                 155                 160

Ala Ser Gly Gly Ala Arg Met Gln Glu Ala Leu Met Ser Leu Met Gln
                165                 170                 175

Met Ala Lys Thr Ser Ala Ala Leu Ala Lys Met Gln Glu Arg Gly Leu
                180                 185                 190

Pro Tyr Ile Ser Val Leu Thr Asp Pro Thr Met Gly Gly Val Ser Ala
                195                 200                 205
```

```
Ser Phe Ala Met Leu Gly Asp Leu Asn Ile Ala Glu Pro Lys Ala Leu
    210                 215                 220

Ile Gly Phe Ala Gly Pro Arg Val Ile Glu Gln Thr Val Arg Glu Lys
225                 230                 235                 240

Leu Pro Pro Gly Phe Gln Arg Ser Glu Phe Leu Ile Glu Lys Gly Ala
                245                 250                 255

Ile Asp Met Ile Val Arg Arg Pro Glu Met Arg Leu Lys Leu Ala Ser
                260                 265                 270

Ile Leu Ala Lys Leu Met Asn Leu Pro Ala Pro Asn Pro Glu Ala Pro
            275                 280                 285

Arg Glu Gly Val Val Pro Pro Val Pro Asp Gln Glu Pro Glu Ala
    290                 295                 300
```

<210> SEQ ID NO 79
<211> LENGTH: 282
<212> TYPE: PRT
<213> ORGANISM: Chloroflexus aurantiacus

<400> SEQUENCE: 79

```
Met Glu Glu Thr Ala Ile Pro Gln Ser Leu Thr Pro Trp Asp Arg Val
1               5                   10                  15

Gln Leu Ala Arg His Pro Gln Arg Pro His Thr Leu Asp Tyr Ile Ala
            20                  25                  30

Ala Leu Cys Glu Asp Phe Val Glu Leu His Gly Asp Arg Arg Phe Gly
        35                  40                  45

Asp Asp Pro Ala Met Val Gly Gly Met Ala Thr Phe Ala Gly Gln Thr
    50                  55                  60

Val Met Val Ile Gly His Gln Lys Gly Asn Asp Thr Arg Glu Asn Met
65                  70                  75                  80

Arg Arg Asn Phe Gly Met Pro His Pro Glu Gly Tyr Arg Lys Ala Gln
                85                  90                  95

Arg Leu Met Arg His Ala Glu Lys Phe Gly Leu Pro Val Ile Cys Phe
            100                 105                 110

Val Asp Thr Pro Ala Ala Asp Pro Thr Lys Ser Ser Glu Glu Arg Gly
        115                 120                 125

Gln Ala Asn Ala Ile Ala Glu Ser Ile Met Leu Met Thr Thr Leu Arg
    130                 135                 140

Val Pro Ser Ile Ala Val Val Ile Gly Glu Gly Gly Ser Gly Gly Ala
145                 150                 155                 160

Leu Ala Ile Ser Val Ala Asp Arg Ile Leu Met Gln Glu Asn Ala Ile
                165                 170                 175

Tyr Ser Val Ala Pro Pro Glu Ala Ala Ala Ser Ile Leu Trp Arg Asp
            180                 185                 190

Ala Ala Lys Ala Pro Glu Ala Ala Arg Ala Leu Lys Leu Thr Ala Ala
        195                 200                 205

Asp Leu Tyr Asp Leu Arg Ile Ile Asp Glu Val Ile Pro Glu Pro Pro
    210                 215                 220

Gly Gly Ala His Ala Asp Arg Leu Thr Ala Ile Thr Thr Val Gly Glu
225                 230                 235                 240

Arg Leu Arg Val His Leu Ala Asp Leu Gln Gln Arg Asp Ile Asp Thr
                245                 250                 255

Leu Leu Arg Glu Arg Tyr Arg Lys Tyr Arg Ser Met Gly Gln Tyr Gln
            260                 265                 270

Glu Gln Gln Met Asp Phe Phe Gly Arg Met
        275                 280
```

<210> SEQ ID NO 80
<211> LENGTH: 180
<212> TYPE: PRT
<213> ORGANISM: Chloroflexus aurantiacus

<400> SEQUENCE: 80

```
Met Met Leu Trp Gly Ala Met Lys Asp Glu Thr Thr Glu Leu Pro Ala
1               5                   10                  15

Asp Gln Pro Asp Pro Phe Gly Leu Ala Val Arg Val Leu Leu Gln
            20                  25                  30

Met Leu Glu Gln Ser Asp Val Tyr Glu Ile Thr Ile Glu Asn Gly Asn
        35                  40                  45

Ala Lys Leu His Val Lys Arg Gly Gln Pro Gly Gly Val Ile Tyr Ser
    50                  55                  60

Ala Pro Leu Pro Thr Ala Pro Val Pro Ser Pro Ser Leu Pro Ala Thr
65                  70                  75                  80

Pro Val Thr Pro Phe Val Gln Pro Pro Ala Pro Glu Gly Pro Pro
                85                  90                  95

Val Glu Met Pro Ala Gly His Thr Ile Thr Ala Pro Met Val Gly Thr
            100                 105                 110

Phe Tyr Ala Ala Pro Ser Pro Arg Asp Arg Pro Phe Val Gln Glu Gly
        115                 120                 125

Asp Glu Val Arg Val Gly Asp Thr Val Gly Ile Val Glu Ala Met Lys
    130                 135                 140

Met Met Asn Glu Ile Glu Ser Asp Val Ala Gly Arg Val Ala Arg Ile
145                 150                 155                 160

Leu Val Lys Asn Gly Gln Pro Val Glu Tyr Gly Gln Pro Leu Met Val
                165                 170                 175

Ile Glu Pro Leu
            180
```

<210> SEQ ID NO 81
<211> LENGTH: 455
<212> TYPE: PRT
<213> ORGANISM: Chloroflexus aurantiacus

<400> SEQUENCE: 81

```
Met Ile Arg Lys Val Leu Val Ala Asn Arg Gly Glu Ile Ala Val Arg
1               5                   10                  15

Ile Ile Arg Ala Cys Gln Glu Leu Gly Ile Arg Thr Val Val Ala Tyr
            20                  25                  30

Ser Thr Ala Asp Arg Asp Ser Leu Ala Val Arg Leu Ala Asp Glu Ala
        35                  40                  45

Val Cys Ile Gly Pro Pro Ala Ala Lys Ser Tyr Leu Asn Ala Pro
    50                  55                  60

Ala Leu Ile Ser Ala Ala Leu Val Ser Gly Cys Asp Ala Ile His Pro
65                  70                  75                  80

Gly Tyr Gly Phe Leu Ser Glu Asn Pro Tyr Phe Ala Glu Met Cys Ala
                85                  90                  95

Asp Cys Lys Leu Thr Phe Ile Gly Pro Pro Glu Pro Ile Arg Leu
            100                 105                 110

Met Gly Asp Lys Ala Ile Gly Arg Glu Thr Met Arg Lys Ala Gly Val
        115                 120                 125

Pro Thr Val Pro Gly Ser Asp Gly Glu Val Arg Ser Leu Glu Glu Ala
    130                 135                 140
```

Ile Asp Val Ala Arg Gln Ile Gly Tyr Pro Val Leu Leu Lys Pro Ser
145                 150                 155                 160

Gly Gly Gly Gly Arg Gly Met Arg Val Ala Tyr Asp Glu Ala Asp
                165                 170                 175

Leu Gln Arg Ala Phe Pro Thr Ala Arg Ala Glu Ala Glu Ala Phe
            180                 185                 190

Gly Asn Gly Ala Leu Leu Glu Lys Tyr Leu Thr Arg Val Arg His
            195                 200                 205

Val Glu Ile Gln Val Leu Ala Asp Gln Tyr Gly His Ala Ile His Leu
210                 215                 220

Gly Glu Arg Asp Cys Ser Ala Gln Arg His Gln Lys Ile Val Glu
225                 230                 235                 240

Glu Ala Pro Ser Pro Ala Val Thr Pro Glu Leu Arg Glu Arg Met Gly
                245                 250                 255

Ala Asp Ala Val Arg Gly Ile Lys Ser Ile Gly Tyr Val Asn Ala Gly
            260                 265                 270

Thr Leu Glu Phe Leu Leu Asp Gln Asp Gly Asn Tyr Tyr Phe Ile Glu
            275                 280                 285

Met Asn Thr Arg Ile Gln Val Glu His Pro Val Thr Glu Gln Val Thr
290                 295                 300

Gly Ile Asp Leu Val Arg Trp Gln Leu Leu Ile Ala Ser Gly Glu Arg
305                 310                 315                 320

Leu Thr Leu Arg Gln Glu Asp Ile Lys Ile Thr Arg His Ala Ile Glu
                325                 330                 335

Cys Arg Ile Asn Ala Glu Asp Pro Glu Arg Asp Phe Leu Pro Ala Ser
            340                 345                 350

Gly Glu Val Glu Phe Tyr Leu Pro Pro Gly Gly Pro Gly Val Arg Val
            355                 360                 365

Asp Ser His Leu Tyr Ser Gly Tyr Thr Pro Pro Gly Thr Tyr Asp Ser
370                 375                 380

Leu Leu Ala Lys Ile Ile Thr Phe Gly Asp Thr Arg Asp Glu Ala Leu
385                 390                 395                 400

Asn Arg Met Arg Arg Ala Leu Asn Glu Cys Val Ile Thr Gly Ile Lys
                405                 410                 415

Thr Thr Ile Pro Phe Gln Leu Ala Leu Ile Asp Asp Pro Glu Phe Arg
            420                 425                 430

Ala Gly Arg Ile His Thr Gly Tyr Val Ala Glu Leu Leu Arg Gln Trp
            435                 440                 445

Lys Glu Thr Leu Asn Pro Val
450                 455

<210> SEQ ID NO 82
<211> LENGTH: 305
<212> TYPE: PRT
<213> ORGANISM: Chloroflexus aurantiacus

<400> SEQUENCE: 82

Met Lys Glu Phe Phe Arg Leu Ser Arg Lys Gly Phe Thr Gly Arg Glu
1               5                   10                  15

Asp Gln Asp Ser Ala Gln Ile Pro Asp Asp Leu Trp Val Lys Cys Ser
            20                  25                  30

Ser Cys Arg Glu Leu Ile Tyr Lys Lys Gln Leu Asn Asp Asn Leu Lys
            35                  40                  45

Val Cys Pro Lys Cys Gly His His Met Arg Leu Ser Ala His Glu Trp

```
                    50                  55                  60

Leu Gly Leu Leu Asp Val Gly Ser Phe Arg Glu Met Asp Ala Asn Leu
 65                  70                  75                  80

Leu Pro Thr Asp Pro Leu Gly Phe Val Thr Asp Glu Ser Tyr Ala
                 85                  90                  95

Ala Lys Leu Ala Lys Thr Gln Gln Arg Thr Gly Met Ala Asp Ala Val
                100                 105                 110

Ile Ala Gly Ile Gly Ala Ile Ser Asn Met Gln Ile Cys Val Ala Val
                115                 120                 125

Ala Asp Phe Ser Phe Met Gly Ala Ser Met Gly Ser Val Tyr Gly Glu
        130                 135                 140

Lys Met Ala Arg Ser Ala Glu Arg Ala Ala Glu Leu Gly Val Pro Leu
145                 150                 155                 160

Leu Thr Ile Asn Thr Ser Gly Gly Ala Arg Gln Gln Glu Gly Val Ile
                165                 170                 175

Gly Leu Met Gln Met Ala Lys Val Thr Met Ala Leu Thr Arg Leu Ala
                180                 185                 190

Asp Ala Gly Gln Pro His Ile Ala Leu Leu Val Asp Pro Cys Tyr Gly
        195                 200                 205

Gly Val Thr Ala Ser Tyr Pro Ser Val Ala Asp Ile Ile Ala Glu
        210                 215                 220

Pro Gly Ala Asn Ile Gly Phe Ala Gly Lys Arg Leu Ile Glu Gln Ile
225                 230                 235                 240

Met Arg Gln Lys Leu Pro Ala Gly Phe Gln Thr Ala Glu Phe Met Leu
                245                 250                 255

Glu His Gly Met Ile Asp Met Val Val Pro Arg Ser Glu Met Arg Asp
                260                 265                 270

Thr Leu Ala Arg Ile Leu Arg Leu Tyr Arg Gln Arg Ser Thr Ser Pro
        275                 280                 285

Ala Lys Ala Glu Leu Ala Gly Arg Arg Ala Thr Leu Pro Gln Pro Ile
        290                 295                 300

Met
305

<210> SEQ ID NO 83
<211> LENGTH: 378
<212> TYPE: PRT
<213> ORGANISM: Bacillus subtilis

<400> SEQUENCE: 83

Met Ile Ile Gly Val Pro Lys Glu Ile Lys Asn Asn Glu Asn Arg Val
 1               5                  10                  15

Ala Leu Thr Pro Gly Gly Val Ser Gln Leu Ile Ser Asn Gly His Arg
                 20                  25                  30

Val Leu Val Glu Thr Gly Ala Gly Leu Gly Ser Gly Phe Glu Asn Glu
         35                  40                  45

Ala Tyr Glu Ser Ala Gly Ala Glu Ile Ile Ala Asp Pro Lys Gln Val
        50                  55                  60

Trp Asp Ala Glu Met Val Met Lys Val Lys Glu Pro Leu Pro Glu Glu
 65                  70                  75                  80

Tyr Val Tyr Phe Arg Lys Gly Leu Val Leu Phe Thr Tyr Leu His Leu
                 85                  90                  95

Ala Ala Glu Pro Glu Leu Ala Gln Ala Leu Lys Asp Lys Gly Val Thr
                100                 105                 110
```

```
Ala Ile Ala Tyr Glu Thr Val Ser Glu Gly Arg Thr Leu Pro Leu Leu
            115                 120                 125

Thr Pro Met Ser Glu Val Ala Gly Arg Met Ala Ala Gln Ile Gly Ala
130                 135                 140

Gln Phe Leu Glu Lys Pro Lys Gly Gly Lys Gly Ile Leu Leu Ala Gly
145                 150                 155                 160

Val Pro Gly Val Ser Arg Gly Lys Val Thr Ile Ile Gly Gly Gly Val
                165                 170                 175

Val Gly Thr Asn Ala Ala Lys Met Ala Val Gly Leu Gly Ala Asp Val
            180                 185                 190

Thr Ile Ile Asp Leu Asn Ala Asp Arg Leu Arg Gln Leu Asp Asp Ile
            195                 200                 205

Phe Gly His Gln Ile Lys Thr Leu Ile Ser Asn Pro Val Asn Ile Ala
            210                 215                 220

Asp Ala Val Ala Glu Ala Asp Leu Leu Ile Cys Ala Val Leu Ile Pro
225                 230                 235                 240

Gly Ala Lys Ala Pro Thr Leu Val Thr Glu Glu Met Val Lys Gln Met
                245                 250                 255

Lys Pro Gly Ser Val Ile Val Asp Val Ala Ile Asp Gln Gly Gly Ile
            260                 265                 270

Val Glu Thr Val Asp His Ile Thr Thr His Asp Gln Pro Thr Tyr Glu
            275                 280                 285

Lys His Gly Val Val His Tyr Ala Val Ala Asn Met Pro Gly Ala Val
            290                 295                 300

Pro Arg Thr Ser Thr Ile Ala Leu Thr Asn Val Thr Val Pro Tyr Ala
305                 310                 315                 320

Leu Gln Ile Ala Asn Lys Gly Ala Val Lys Ala Leu Ala Asp Asn Thr
                325                 330                 335

Ala Leu Arg Ala Gly Leu Asn Thr Ala Asn Gly His Val Thr Tyr Glu
            340                 345                 350

Ala Val Ala Arg Asp Leu Gly Tyr Glu Tyr Val Pro Ala Glu Lys Ala
            355                 360                 365

Leu Gln Asp Glu Ser Ser Val Ala Gly Ala
370                 375

<210> SEQ ID NO 84
<211> LENGTH: 505
<212> TYPE: PRT
<213> ORGANISM: Schizosaccharomyces pombe

<400> SEQUENCE: 84

Met Phe Thr Asp Tyr Pro Asn Asp Ile Asn Cys Glu Ser Pro Arg Met
1               5                   10                  15

Ser Asp Leu Asp Gly Phe Cys Gln Asn Ala Phe Ser Asp Leu Asn Ser
                20                  25                  30

Leu Asn Gln Gln Val Phe Lys Ala Asn Tyr Ala Val Arg Gly Ala Leu
            35                  40                  45

Ala Ile Leu Ala Asp Glu Ile Gln Asp Leu Leu Glu Asn Pro Ser
50                  55                  60

Ser Tyr Pro Phe Ser Glu Ile Val Tyr Ala Asn Ile Gly Asn Pro Gln
65                  70                  75                  80

Gln Met Gly Gln Ser Pro Ile Thr Phe Val Arg Gln Val Leu Ser Leu
                85                  90                  95

Cys Gln Tyr Pro Thr Leu Leu Asp His Ala Glu Glu Lys Trp Phe Gln
                100                 105                 110
```

```
Asn Leu Phe Pro Thr Asp Val Val Gln Arg Ser Lys Met Leu Leu Lys
            115                 120                 125

Glu Ser Gly Ser Leu Gly Ala Tyr Ser Ala Ser Gln Gly Ile Pro Leu
            130                 135                 140

Val Arg Arg His Val Ala Asp Phe Ile Arg Ala Arg Asp Gly Phe Asp
145                 150                 155                 160

Cys Glu Pro Ser Asp Ile Tyr Leu Thr Ser Gly Ala Ser His Ala Ala
                165                 170                 175

Arg Leu Ile Met Thr Leu Ile Ile Ala Arg Pro Thr Asp Gly Val Met
                180                 185                 190

Val Pro Ala Pro Gln Tyr Pro Leu Tyr Gly Ala Gln Ile Asp Leu Met
                195                 200                 205

Ser Gly Ser Met Val Ser Tyr Ser Leu Ser Glu Glu Asn Asn Trp Asp
                210                 215                 220

Ile Asp Phe Asp Gln Phe Lys Lys Ser Phe Asp Glu Ala Ser Lys Lys
225                 230                 235                 240

Gly Ile Asn Val Arg Leu Cys Val Val Ile Asn Pro Gly Asn Pro Thr
                245                 250                 255

Gly Ala Cys Ile Ser Glu Asn Ser Met Glu Lys Val Leu Arg Phe Ala
                260                 265                 270

Lys Ala Lys Gly Ile Val Leu Leu Ala Asp Glu Val Tyr Gln Asn Asn
                275                 280                 285

Ile Tyr Gln Asn Lys Phe His Ser Phe Arg Arg Lys Leu Gly Glu Leu
                290                 295                 300

Arg Glu Lys Glu Pro Asp Asn His Trp Asp Gln Val Ser Leu Ile Ser
305                 310                 315                 320

Val Asn Ser Val Ser Lys Gly Gln Phe Gly Glu Cys Gly Gln Arg Gly
                325                 330                 335

Gly Tyr Leu Asp Val Val Asn Ile Pro Glu Pro Ala Lys Asp Gln Ile
                340                 345                 350

Leu Lys Leu Ala Thr Ile Asp Ile Cys Pro Pro Val Ala Gly Gln Leu
                355                 360                 365

Leu Val Asp Met Leu Val Asn Pro Pro Lys Pro Gly Asp Pro Ser Tyr
                370                 375                 380

Asp Leu Phe Ile Lys Glu Val Asp Glu Ile His Glu Ala Leu Arg Leu
385                 390                 395                 400

Gln Cys Arg Gln Leu Tyr Glu Gly Thr Lys Arg Met Lys Arg Val Ser
                405                 410                 415

Cys Leu Glu Pro His Gly Ala Met Tyr Leu His Pro Ser Val Ser Leu
                420                 425                 430

Pro Glu Lys Leu Ile Thr Thr Ala Lys Ala Gln Lys Ile Gln Pro Asp
                435                 440                 445

Glu Phe Tyr Ala Ile Glu Leu Leu Lys Arg Ser Gly Ile Cys Val Val
                450                 455                 460

Pro Gly Ser Gly Phe Gly Gln Pro Glu Gly Asp Tyr His Ile Arg Ile
465                 470                 475                 480

Thr Phe Leu Ala Lys Gly Thr Glu Tyr Ile Glu Arg Phe Val Lys Ala
                485                 490                 495

His Asn Glu Ile Met Asp Leu Tyr Glu
                500                 505

<210> SEQ ID NO 85
<211> LENGTH: 507
```

<212> TYPE: PRT
<213> ORGANISM: Saccharomyces cerevisiae

<400> SEQUENCE: 85

```
Met Thr Met Thr His Gln Gln Asp Leu Lys Gly Val Phe Thr Ala Lys
1               5                   10                  15

Asp Leu Asp Phe Lys Pro Ala Gly Lys Ile Thr Lys Lys Asp Leu Asn
            20                  25                  30

Thr Gly Val Thr Lys Ala Glu Tyr Ala Val Arg Gly Ala Ile Pro Thr
        35                  40                  45

Arg Ala Asp Glu Leu Lys Glu Leu Lys Lys Asn Pro Glu Val Leu
    50                  55                  60

Pro Phe Asp Asp Ile Ile Asn Ala Asn Ile Gly Asn Pro Gln Gln Leu
65                  70                  75                  80

Asp Gln Lys Pro Leu Thr Phe Thr Arg Gln Val Leu Ala Ile Leu Glu
                85                  90                  95

Tyr Pro Glu Ile Leu Arg Val Gly His Asn Glu Leu Ala Ser Leu Asn
            100                 105                 110

Leu Phe Ser Arg Asp Ala Leu Glu Arg Ala Glu Arg Leu Leu Asn Asp
        115                 120                 125

Ile Gly Gly Ser Ile Gly Ala Tyr Ser His Ser Gln Gly Val Pro Gly
130                 135                 140

Ile Arg Gln Thr Val Ala Asp Phe Ile Thr Arg Arg Asp Gly Gly Glu
145                 150                 155                 160

Pro Ala Thr Pro Glu Asp Ile Tyr Leu Thr Thr Gly Ala Ser Ser Ala
                165                 170                 175

Ala Thr Ser Leu Leu Ser Leu Leu Cys Lys Asp Ser Gln Thr Gly Leu
            180                 185                 190

Leu Ile Pro Ile Pro Gln Tyr Pro Leu Tyr Thr Ala Ser Ala Ser Leu
        195                 200                 205

Phe Asn Ala Gln Val Leu Pro Tyr Tyr Leu Asp Glu Glu Ser Asn Trp
210                 215                 220

Ser Thr Asn Ser Asp Glu Ile Glu Lys Val Val Gln Asp Ala Leu Lys
225                 230                 235                 240

Lys Gln Ile Arg Pro Ser Val Leu Ile Val Ile Asn Pro Gly Asn Pro
                245                 250                 255

Thr Gly Ala Val Leu Ser Glu Gly Thr Ile Ala Arg Ile Cys Leu Ile
            260                 265                 270

Ala Ala Lys Tyr Gly Ile Thr Ile Ile Ser Asp Glu Val Tyr Gln Glu
        275                 280                 285

Asn Ile Phe Asn Asp Val Lys Phe His Ser Met Lys Lys Val Leu Arg
290                 295                 300

Lys Leu Gln His Leu Tyr Pro Gly Lys Phe Asp Asn Val Gln Leu Ala
305                 310                 315                 320

Ser Leu His Ser Ile Ser Lys Gly Phe Met Asp Glu Cys Gly Gln Arg
                325                 330                 335

Gly Gly Tyr Met Glu Ile Ile Gly Phe Ser Gln Glu Ile Arg Asp Ala
            340                 345                 350

Leu Phe Lys Leu Met Ser Ile Ser Ile Cys Ser Val Val Thr Gly Gln
        355                 360                 365

Ala Val Val Asp Leu Met Val Lys Pro Pro Gln Pro Gly Asp Glu Ser
370                 375                 380

Tyr Glu Gln Asp His Asp Glu Arg Leu Lys Ile Phe His Glu Met Arg
385                 390                 395                 400
```

-continued

```
Thr Arg Ala Asn Leu Leu Tyr Glu Thr Phe Lys Glu Leu Glu Gly Ile
                405                 410                 415
Glu Cys Gln Lys Pro Gln Gly Ala Met Tyr Leu Phe Pro Arg Leu Val
            420                 425                 430
Leu Pro Lys Lys Ala Leu Cys Glu Ser Glu Arg Leu Gly Ile Glu Pro
        435                 440                 445
Asp Glu Phe Tyr Cys Thr Ser Leu Leu Glu Ser Thr Gly Ile Cys Thr
450                 455                 460
Val Pro Gly Ser Gly Phe Gly Gln Arg Pro Gly Thr Tyr His Val Arg
465                 470                 475                 480
Thr Thr Phe Leu Ala Pro Gly Thr Lys Trp Ile Gln Asp Trp Lys Glu
                485                 490                 495
Phe His Gln Asp Phe Phe Ser Lys Tyr Arg Asn
            500                 505

<210> SEQ ID NO 86
<211> LENGTH: 471
<212> TYPE: PRT
<213> ORGANISM: Bacillus subtilis

<400> SEQUENCE: 86

Met Lys Asn Lys Trp Tyr Lys Pro Lys Arg His Trp Lys Glu Ile Glu
1               5                   10                  15
Leu Trp Lys Asp Val Pro Glu Glu Lys Trp Asn Asp Trp Leu Trp Gln
            20                  25                  30
Leu Thr His Thr Val Arg Thr Leu Asp Asp Leu Lys Lys Val Ile Asn
        35                  40                  45
Leu Thr Glu Asp Glu Glu Glu Gly Val Arg Ile Ser Thr Lys Thr Ile
    50                  55                  60
Pro Leu Asn Ile Thr Pro Tyr Tyr Ala Ser Leu Met Asp Pro Asp Asn
65                  70                  75                  80
Pro Arg Cys Pro Val Arg Met Gln Ser Val Pro Leu Ser Glu Glu Met
                85                  90                  95
His Lys Thr Lys Tyr Asp Leu Glu Asp Pro Leu His Glu Asp Glu Asp
            100                 105                 110
Ser Pro Val Pro Gly Leu Thr His Arg Tyr Pro Asp Arg Val Leu Phe
        115                 120                 125
Leu Val Thr Asn Gln Cys Ser Met Tyr Cys Arg Tyr Cys Thr Arg Arg
    130                 135                 140
Arg Phe Ser Gly Gln Ile Gly Met Gly Val Pro Lys Lys Gln Leu Asp
145                 150                 155                 160
Ala Ala Ile Ala Tyr Ile Arg Glu Thr Pro Glu Ile Arg Asp Cys Leu
                165                 170                 175
Ile Ser Gly Gly Asp Gly Leu Leu Ile Asn Asp Gln Ile Leu Glu Tyr
            180                 185                 190
Ile Leu Lys Glu Leu Arg Ser Ile Pro His Leu Glu Val Ile Arg Ile
        195                 200                 205
Gly Thr Arg Ala Pro Val Val Phe Pro Gln Arg Ile Thr Asp His Leu
    210                 215                 220
Cys Glu Ile Leu Lys Lys Tyr His Pro Val Trp Leu Asn Thr His Phe
225                 230                 235                 240
Asn Thr Ser Ile Glu Met Thr Glu Glu Ser Val Glu Ala Cys Glu Lys
                245                 250                 255
Leu Val Asn Ala Gly Val Pro Val Gly Asn Gln Ala Val Val Leu Ala
```

-continued

```
                260                 265                 270
Gly Ile Asn Asp Ser Val Pro Ile Met Lys Lys Leu Met His Asp Leu
            275                 280                 285

Val Lys Ile Arg Val Arg Pro Tyr Tyr Ile Tyr Gln Cys Asp Leu Ser
        290                 295                 300

Glu Gly Ile Gly His Phe Arg Ala Pro Val Ser Lys Gly Leu Glu Ile
305                 310                 315                 320

Ile Glu Gly Leu Arg Gly His Thr Ser Gly Tyr Ala Val Pro Thr Phe
                325                 330                 335

Val Val Asp Ala Pro Gly Gly Gly Lys Ile Ala Leu Gln Pro Asn
            340                 345                 350

Tyr Val Leu Ser Gln Ser Pro Asp Lys Val Ile Leu Arg Asn Phe Glu
        355                 360                 365

Gly Val Ile Thr Ser Tyr Pro Glu Pro Glu Asn Tyr Ile Pro Asn Gln
            370                 375                 380

Ala Asp Ala Tyr Phe Glu Ser Val Phe Pro Glu Thr Ala Asp Lys Lys
385                 390                 395                 400

Glu Pro Ile Gly Leu Ser Ala Ile Phe Ala Asp Lys Glu Val Ser Phe
                405                 410                 415

Thr Pro Glu Asn Val Asp Arg Ile Lys Arg Arg Glu Ala Tyr Ile Ala
            420                 425                 430

Asn Pro Glu His Glu Thr Leu Lys Asp Arg Arg Glu Lys Arg Asp Gln
        435                 440                 445

Leu Lys Glu Lys Lys Phe Leu Ala Gln Gln Lys Lys Gln Lys Glu Thr
    450                 455                 460

Glu Cys Gly Gly Asp Ser Ser
465                 470

<210> SEQ ID NO 87
<211> LENGTH: 416
<212> TYPE: PRT
<213> ORGANISM: Porphyromonas gingivalis

<400> SEQUENCE: 87

Met Ala Glu Ser Arg Arg Lys Tyr Tyr Phe Pro Asp Val Thr Asp Glu
1               5                   10                  15

Gln Trp Asn Asp Trp His Trp Gln Val Leu Asn Arg Ile Glu Thr Leu
            20                  25                  30

Asp Gln Leu Lys Lys Tyr Val Thr Leu Thr Ala Glu Glu Glu Gly
        35                  40                  45

Val Lys Glu Ser Leu Lys Val Leu Arg Met Ala Ile Thr Pro Tyr Tyr
    50                  55                  60

Leu Ser Leu Ile Asp Pro Glu Asn Pro Asn Cys Pro Ile Arg Lys Gln
65                  70                  75                  80

Ala Ile Pro Thr His Gln Glu Leu Val Arg Ala Pro Glu Asp Gln Val
                85                  90                  95

Asp Pro Leu Ser Glu Asp Glu Asp Ser Pro Val Pro Gly Leu Thr His
            100                 105                 110

Arg Tyr Pro Asp Arg Val Leu Phe Leu Ile Thr Asp Lys Cys Ser Met
        115                 120                 125

Tyr Cys Arg His Cys Thr Arg Arg Arg Phe Ala Gly Gln Lys Asp Ala
    130                 135                 140

Ser Ser Pro Ser Glu Arg Ile Asp Arg Cys Ile Asp Tyr Ile Ala Asn
145                 150                 155                 160
```

Thr Pro Thr Val Arg Asp Val Leu Leu Ser Gly Gly Asp Ala Leu Leu
                165                 170                 175

Val Ser Asp Glu Arg Leu Glu Tyr Ile Leu Lys Arg Leu Arg Glu Ile
            180                 185                 190

Pro His Val Glu Ile Val Arg Ile Gly Ser Arg Thr Pro Val Val Leu
        195                 200                 205

Pro Gln Arg Ile Thr Pro Gln Leu Val Asp Met Leu Lys Lys Tyr His
    210                 215                 220

Pro Val Trp Leu Asn Thr His Phe Asn His Pro Asn Glu Val Thr Glu
225                 230                 235                 240

Glu Ala Val Glu Ala Cys Glu Arg Met Ala Asn Ala Gly Ile Pro Leu
                245                 250                 255

Gly Asn Gln Thr Val Leu Leu Arg Gly Ile Asn Asp Cys Thr His Val
            260                 265                 270

Met Lys Arg Leu Val His Leu Leu Val Lys Met Arg Val Arg Pro Tyr
        275                 280                 285

Tyr Ile Tyr Val Cys Asp Leu Ser Leu Gly Ile Gly His Phe Arg Thr
    290                 295                 300

Pro Val Ser Lys Gly Ile Glu Ile Ile Glu Asn Leu Arg Gly His Thr
305                 310                 315                 320

Ser Gly Tyr Ala Val Pro Thr Phe Val Asp Ala Pro Gly Gly Gly
                325                 330                 335

Gly Lys Ile Pro Val Met Pro Asn Tyr Val Val Ser Gln Ser Pro Arg
            340                 345                 350

His Val Val Leu Arg Asn Tyr Glu Gly Val Ile Thr Thr Tyr Thr Glu
        355                 360                 365

Pro Glu Asn Tyr His Glu Glu Cys Asp Cys Glu Asp Cys Arg Ala Gly
    370                 375                 380

Lys His Lys Glu Gly Val Ala Ala Leu Ser Gly Gly Gln Gln Leu Ala
385                 390                 395                 400

Ile Glu Pro Ser Asp Leu Ala Arg Lys Lys Arg Lys Phe Asp Lys Asn
                405                 410                 415

<210> SEQ ID NO 88
<211> LENGTH: 425
<212> TYPE: PRT
<213> ORGANISM: Fusobacterium nucleatum

<400> SEQUENCE: 88

Met Asn Thr Val Asn Thr Arg Lys Lys Phe Phe Pro Asn Val Thr Asp
1               5                   10                  15

Glu Glu Trp Asn Asp Trp Thr Trp Gln Val Lys Asn Arg Ile Glu Lys
            20                  25                  30

Ile Asp Asp Leu Lys Lys Tyr Val Glu Leu Ser Ala Glu Glu Glu Glu
        35                  40                  45

Gly Val Val Arg Thr Leu Glu Thr Leu Arg Met Ala Ile Thr Pro Tyr
    50                  55                  60

Tyr Phe Ser Leu Ile Asp Met Asn Ser Asp Arg Cys Pro Ile Arg Lys
65                  70                  75                  80

Gln Ala Ile Pro Thr Ile Gln Glu Ile His Gln Ser Asp Ala Asp Leu
                85                  90                  95

Leu Asp Pro Leu His Glu Asp Glu Asp Ser Pro Val Pro Gly Leu Thr
            100                 105                 110

His Arg Tyr Pro Asp Arg Val Leu Leu Leu Ile Thr Asp Met Cys Ser
        115                 120                 125

```
Met Tyr Cys Arg His Cys Thr Arg Arg Arg Phe Ala Gly Ser Ser Asp
            130                 135                 140

Asp Ala Met Pro Met Asp Arg Ile Asp Lys Ala Ile Glu Tyr Ile Ala
145                 150                 155                 160

Lys Thr Pro Gln Val Arg Asp Val Leu Ser Gly Gly Asp Ala Leu
                165                 170                 175

Leu Val Ser Asp Lys Lys Leu Glu Ser Ile Ile Gln Lys Leu Arg Ala
            180                 185                 190

Ile Pro His Val Glu Ile Ile Arg Ile Gly Ser Arg Thr Pro Val Val
                195                 200                 205

Leu Pro Gln Arg Ile Thr Pro Glu Leu Cys Asn Met Leu Lys Lys Tyr
            210                 215                 220

His Pro Ile Trp Leu Asn Thr His Phe Asn His Pro Gln Glu Val Thr
225                 230                 235                 240

Pro Glu Ala Lys Lys Ala Cys Glu Met Leu Ala Asp Ala Gly Val Pro
                245                 250                 255

Leu Gly Asn Gln Thr Val Leu Leu Arg Gly Ile Asn Asp Ser Val Pro
            260                 265                 270

Val Met Lys Arg Leu Val His Asp Leu Val Met Met Arg Val Arg Pro
            275                 280                 285

Tyr Tyr Ile Tyr Gln Cys Asp Leu Ser Met Gly Leu Glu His Phe Arg
            290                 295                 300

Thr Pro Val Ser Lys Gly Ile Glu Ile Ile Glu Gly Leu Arg Gly His
305                 310                 315                 320

Thr Ser Gly Tyr Ala Val Pro Thr Phe Val Val Asp Ala Pro Gly Gly
                325                 330                 335

Gly Gly Lys Thr Pro Val Met Pro Gln Tyr Val Ile Ser Gln Ser Pro
            340                 345                 350

His Arg Val Val Leu Arg Asn Phe Glu Gly Val Ile Thr Thr Tyr Thr
                355                 360                 365

Glu Pro Glu Asn Tyr Thr His Glu Pro Cys Tyr Asp Glu Glu Lys Phe
370                 375                 380

Glu Lys Met Tyr Glu Ile Ser Gly Val Tyr Met Leu Asp Glu Gly Leu
385                 390                 395                 400

Lys Met Ser Leu Glu Pro Ser His Leu Ala Arg His Glu Arg Asn Lys
                405                 410                 415

Lys Arg Ala Glu Ala Glu Gly Lys Lys
            420                 425

<210> SEQ ID NO 89
<211> LENGTH: 517
<212> TYPE: PRT
<213> ORGANISM: Megasphaera elsdenii

<400> SEQUENCE: 89

Met Arg Lys Val Glu Ile Ile Thr Ala Glu Gln Ala Ala Gln Leu Val
1               5                   10                  15

Lys Asp Asn Asp Thr Ile Thr Ser Ile Gly Phe Val Ser Ser Ala His
                20                  25                  30

Pro Glu Ala Leu Thr Lys Ala Leu Glu Lys Arg Phe Leu Asp Thr Asn
            35                  40                  45

Thr Pro Gln Asn Leu Thr Tyr Ile Tyr Ala Gly Ser Gln Gly Lys Arg
        50                  55                  60

Asp Gly Arg Ala Ala Glu His Leu Ala His Thr Gly Leu Leu Lys Arg
```

```
            65                  70                  75                  80
Ala Ile Ile Gly His Trp Gln Thr Val Pro Ala Ile Gly Lys Leu Ala
                    85                  90                  95

Val Glu Asn Lys Ile Glu Ala Tyr Asn Phe Ser Gln Gly Thr Leu Val
                100                 105                 110

His Trp Phe Arg Ala Leu Ala Gly His Lys Leu Gly Val Phe Thr Asp
                115                 120                 125

Ile Gly Leu Glu Thr Phe Leu Asp Pro Arg Gln Leu Gly Gly Lys Leu
130                 135                 140

Asn Asp Val Thr Lys Glu Asp Leu Val Lys Leu Ile Glu Val Asp Gly
145                 150                 155                 160

His Glu Gln Leu Phe Tyr Pro Thr Phe Pro Val Asn Val Ala Phe Leu
                165                 170                 175

Arg Gly Thr Tyr Ala Asp Glu Ser Gly Asn Ile Thr Met Asp Glu Glu
                180                 185                 190

Ile Gly Pro Phe Glu Ser Thr Ser Val Ala Gln Ala Val His Asn Cys
                195                 200                 205

Gly Gly Lys Val Val Gln Val Lys Asp Val Val Ala His Gly Ser
                210                 215                 220

Leu Asp Pro Arg Met Val Lys Ile Pro Gly Ile Tyr Val Asp Tyr Val
225                 230                 235                 240

Val Val Ala Ala Pro Glu Asp His Gln Gln Thr Tyr Asp Cys Glu Tyr
                245                 250                 255

Asp Pro Ser Leu Ser Gly Glu His Arg Ala Pro Glu Gly Ala Thr Asp
                260                 265                 270

Ala Ala Leu Pro Met Ser Ala Lys Lys Ile Ile Gly Arg Arg Gly Ala
                275                 280                 285

Leu Glu Leu Thr Glu Asn Ala Val Val Asn Leu Gly Val Gly Ala Pro
                290                 295                 300

Glu Tyr Val Ala Ser Val Ala Gly Glu Glu Gly Ile Ala Asp Thr Ile
305                 310                 315                 320

Thr Leu Thr Val Glu Gly Gly Ala Ile Gly Gly Val Pro Gln Gly Gly
                325                 330                 335

Ala Arg Phe Gly Ser Ser Arg Asn Ala Asp Ala Ile Ile Asp His Thr
                340                 345                 350

Tyr Gln Phe Asp Phe Tyr Asp Gly Gly Leu Asp Ile Ala Tyr Leu
                355                 360                 365

Gly Leu Ala Gln Cys Asp Gly Ser Gly Asn Ile Asn Val Ser Lys Phe
                370                 375                 380

Gly Thr Asn Val Ala Gly Cys Gly Gly Phe Pro Asn Ile Ser Gln Gln
385                 390                 395                 400

Thr Pro Asn Val Tyr Phe Cys Gly Thr Phe Thr Ala Gly Gly Leu Lys
                405                 410                 415

Ile Ala Val Glu Asp Gly Lys Val Lys Ile Leu Gln Glu Gly Lys Ala
                420                 425                 430

Lys Lys Phe Ile Lys Ala Val Asp Gln Ile Thr Phe Asn Gly Ser Tyr
                435                 440                 445

Ala Ala Arg Asn Gly Lys His Val Leu Tyr Ile Thr Glu Arg Cys Val
                450                 455                 460

Phe Glu Leu Thr Lys Glu Gly Leu Lys Leu Ile Glu Val Ala Pro Gly
465                 470                 475                 480

Ile Asp Ile Glu Lys Asp Ile Leu Ala His Met Asp Phe Lys Pro Ile
                485                 490                 495
```

Ile Asp Asn Pro Lys Leu Met Asp Ala Arg Leu Phe Gln Asp Gly Pro
500 505 510

Met Gly Leu Lys Lys
515

<210> SEQ ID NO 90
<211> LENGTH: 145
<212> TYPE: PRT
<213> ORGANISM: Clostridium propionicum

<400> SEQUENCE: 90

Met Val Gly Lys Lys Val Val His His Leu Met Met Ser Ala Lys Asp
1 5 10 15

Ala His Tyr Thr Gly Asn Leu Val Asn Gly Ala Arg Ile Val Asn Gln
20 25 30

Trp Gly Asp Val Gly Thr Glu Leu Met Val Tyr Val Asp Gly Asp Ile
35 40 45

Ser Leu Phe Leu Gly Tyr Lys Asp Ile Glu Phe Thr Ala Pro Val Tyr
50 55 60

Val Gly Asp Phe Met Glu Tyr His Gly Trp Ile Glu Lys Val Gly Asn
65 70 75 80

Gln Ser Tyr Thr Cys Lys Phe Glu Ala Trp Lys Val Ala Thr Met Val
85 90 95

Asp Ile Thr Asn Pro Gln Asp Thr Arg Ala Thr Ala Cys Glu Pro Pro
100 105 110

Val Leu Cys Gly Arg Ala Thr Gly Ser Leu Phe Ile Ala Lys Lys Asp
115 120 125

Gln Arg Gly Pro Gln Glu Ser Ser Phe Lys Glu Arg Lys His Pro Gly
130 135 140

Glu
145

<210> SEQ ID NO 91
<211> LENGTH: 260
<212> TYPE: PRT
<213> ORGANISM: Phytophthora sojae

<400> SEQUENCE: 91

Met Ala Ala Glu Tyr Glu Ser Ile Leu Thr Glu Val Arg Gly Lys Val
1 5 10 15

Ala Ile Ile Thr Leu Asn Arg Pro Lys Ala Leu Asn Ala Leu Cys Ser
20 25 30

Pro Leu Ile Glu Glu Leu Asn Gly Ala Ala His Ala Phe Asp Ala Asp
35 40 45

Pro Ser Ile Gly Ala Ile Val Ile Thr Gly Ser Gly Ser Lys Ala Phe
50 55 60

Ala Ala Gly Ala Asp Ile Lys Glu Met Ala Thr Lys Thr Phe Val Asp
65 70 75 80

Ala Tyr Lys Ser Asn Met Phe Ala Asn Trp Gly Asp Ile Thr Lys Val
85 90 95

Ser Lys Pro Val Ile Ala Ala Val Asn Gly Tyr Ala Leu Gly Gly Gly
100 105 110

Cys Glu Leu Ala Met Leu Cys Asp Leu Ile Ile Ala Gly Asp Ser Ala
115 120 125

Lys Phe Gly Gln Pro Glu Ile Thr Leu Gly Thr Ile Pro Gly Cys Gly
130 135 140

```
Gly Thr Gln Arg Leu Ile Arg Ala Val Gly Lys Ser Lys Ala Met Glu
145                 150                 155                 160

Met Ile Leu Thr Gly Asn Met Ile Asp Ala Gln Gln Ala Glu Arg Asp
                165                 170                 175

Gly Leu Val Ala Arg Val Val Pro Ala Asp Gln Leu Leu Asp Glu Ala
            180                 185                 190

Leu Lys Thr Ala Asn Lys Ile Ala Ser Phe Ser Gln Pro Val Val Lys
        195                 200                 205

Met Ala Lys Glu Ala Val Asn Ala Ala Tyr Glu Gln Ser Leu Gln Glu
    210                 215                 220

Gly Leu Lys Tyr Glu Ser Arg Leu Phe Trp Ser Ser Phe Ala Thr Lys
225                 230                 235                 240

Asp Gln Lys Glu Gly Met Ala Ala Phe Val Glu Lys Arg Lys Ala Asp
                245                 250                 255

Phe Lys Asp Glu
            260

<210> SEQ ID NO 92
<211> LENGTH: 258
<212> TYPE: PRT
<213> ORGANISM: Chloroflexus aurantiacus

<400> SEQUENCE: 92

Met Ser Glu Glu Ser Leu Val Leu Ser Thr Ile Glu Gly Pro Ile Ala
1               5                   10                  15

Ile Leu Thr Leu Asn Arg Pro Gln Ala Leu Asn Ala Leu Ser Pro Ala
            20                  25                  30

Leu Ile Asp Asp Leu Ile Arg His Leu Glu Ala Cys Asp Ala Asp Asp
        35                  40                  45

Thr Ile Arg Val Ile Ile Ile Thr Gly Ala Gly Arg Ala Phe Ala Ala
    50                  55                  60

Gly Ala Asp Ile Lys Ala Met Ala Asn Ala Thr Pro Ile Asp Met Leu
65                  70                  75                  80

Thr Ser Gly Met Ile Ala Arg Trp Ala Arg Ile Ala Ala Val Arg Lys
                85                  90                  95

Pro Val Ile Ala Ala Val Asn Gly Tyr Ala Leu Gly Gly Gly Cys Glu
            100                 105                 110

Leu Ala Met Met Cys Asp Ile Ile Ile Ala Ser Glu Asn Ala Gln Phe
        115                 120                 125

Gly Gln Pro Glu Ile Asn Leu Gly Ile Ile Pro Gly Ala Gly Gly Thr
    130                 135                 140

Gln Arg Leu Thr Arg Ala Leu Gly Pro Tyr Arg Ala Met Glu Leu Ile
145                 150                 155                 160

Leu Thr Gly Ala Thr Ile Ser Ala Gln Glu Ala Leu Ala His Gly Leu
                165                 170                 175

Val Cys Arg Val Cys Pro Pro Gly Ser Leu Leu Asp Glu Ala Arg Arg
            180                 185                 190

Ile Ala Gln Thr Ile Ala Thr Lys Ser Pro Leu Ala Val Gln Leu Ala
        195                 200                 205

Lys Glu Ala Val Arg Met Ala Ala Glu Thr Thr Val Arg Glu Gly Leu
    210                 215                 220

Ala Ile Glu Leu Arg Asn Phe Tyr Leu Leu Phe Ala Ser Ala Asp Gln
225                 230                 235                 240

Lys Glu Gly Met Gln Ala Phe Ile Glu Lys Arg Ala Pro Asn Phe Ser
```

245                 250                 255

Gly Arg

<210> SEQ ID NO 93
<211> LENGTH: 288
<212> TYPE: PRT
<213> ORGANISM: Rhodospirillum rubrum

<400> SEQUENCE: 93

Met Ala Ala Pro Gly Pro Ala Ala Arg Pro Arg Ala Ala Arg
1               5                   10                  15

Gln Ser Arg Met Ile Leu Pro Pro Leu Arg Glu Gln Ala Gln Met Ala
            20                  25                  30

Tyr Glu Asn Ile Leu Val Glu Thr Asn Gly Lys Val Gly Ile Val Thr
        35                  40                  45

Leu Asn Arg Pro Lys Ala Leu Asn Ala Leu Ser Ala Gly Leu Val Arg
    50                  55                  60

Asp Leu Gly Ala Ala Leu Asp Ala Phe Glu Ala Asp Val Asn Val His
65                  70                  75                  80

Val Ile Val Leu Thr Gly Ser Asp Lys Ala Phe Ala Ala Gly Ala Asp
                85                  90                  95

Ile Lys Glu Met Ala Glu Lys Ser Tyr Met Asp Ala Tyr Leu Glu Asp
            100                 105                 110

Phe Ile Thr Lys Gly Trp Glu Arg Val Thr Thr Cys Arg Lys Pro Ile
        115                 120                 125

Ile Ala Ala Val Ala Gly Phe Ala Leu Gly Gly Gly Cys Glu Met Ala
    130                 135                 140

Met Met Cys Asp Phe Ile Ile Ala Ala Gln Asn Ala Lys Phe Gly Gln
145                 150                 155                 160

Pro Glu Ile Asn Leu Gly Thr Leu Pro Gly Ala Gly Thr Gln Arg
                165                 170                 175

Leu Thr Arg Phe Val Gly Lys Ser Lys Ala Met Asp Met Cys Leu Thr
            180                 185                 190

Gly Arg Met Met Asp Ala Asp Glu Ala Trp Lys Cys Gly Leu Val Ser
        195                 200                 205

Arg Ile Val Pro Val Asp Asp Leu Lys Asp Glu Val Leu Lys Ile Ala
    210                 215                 220

Glu Ala Ile Ala Asp Lys Ser Leu Pro Ile Thr Met Met Val Lys Glu
225                 230                 235                 240

Ala Val Asn Ala Ala Tyr Glu Thr Thr Leu Ala Gln Gly Val Arg Phe
                245                 250                 255

Glu Arg Arg Leu Phe Gln Ala Ser Phe Ala Thr Asp Asp Gln Lys Glu
            260                 265                 270

Gly Met Asn Ala Phe Ile Glu Lys Arg Gln Pro Ser Phe Thr Asp Arg
        275                 280                 285

<210> SEQ ID NO 94
<211> LENGTH: 258
<212> TYPE: PRT
<213> ORGANISM: Rhodobacter capsulatus

<400> SEQUENCE: 94

Met Ser Tyr Gln Thr Leu Ile Val Glu Ile Ala Asp Gly Val Ala Leu
1               5                   10                  15

Ile Arg Leu Asn Arg Pro Glu Ala Leu Asn Ala Leu Asn Ser Gln Leu
            20                  25                  30

```
Leu Gly Glu Leu Ala Ala Ala Leu Ser Thr Leu Asp Ala Asp Pro Ala
            35                  40                  45

Val Arg Cys Phe Val Leu Thr Gly Ser Asp Lys Ala Phe Ala Ala Gly
    50                  55                  60

Ala Asp Ile Lys Glu Met Ala Asp Lys Ser Phe Val Asp Met Leu Lys
65                  70                  75                  80

Leu Asp Phe Phe Gly Thr Glu Gly Asp Ala Ile Leu Arg Thr Arg Lys
                85                  90                  95

Pro Val Ile Ala Ala Val Ala Gly Tyr Ala Leu Gly Gly Gly Cys Glu
                100                 105                 110

Leu Ala Met Met Cys Asp Phe Ile Leu Cys Ala Glu Asn Ala Lys Phe
                115                 120                 125

Gly Gln Pro Glu Ile Asn Leu Gly Val Val Ala Gly Ile Gly Gly Thr
                130                 135                 140

Gln Arg Leu Thr Arg Phe Val Gly Lys Ser Lys Ser Met Glu Met His
145                 150                 155                 160

Leu Thr Gly Arg Phe Met Asp Ala Ala Glu Ala Glu Arg Ser Gly Leu
                165                 170                 175

Val Ser Arg Val Leu Pro Leu Ala Asp Leu Leu Pro Glu Ala Leu Ala
                180                 185                 190

Thr Ala Arg Lys Ile Ala Glu Lys Ser Ala Ile Ala Thr Met Val Ala
                195                 200                 205

Lys Asp Cys Val Asn Arg Ala Tyr Glu Thr Thr Leu Arg Glu Gly Val
210                 215                 220

Leu Tyr Glu Arg Arg Val Phe His Ala Leu Phe Ala Thr Glu Asp Gln
225                 230                 235                 240

Lys Glu Gly Met Ala Ala Phe Ala Glu Lys Arg Pro Ala Lys Phe Ala
                245                 250                 255

Asp Lys

<210> SEQ ID NO 95
<211> LENGTH: 290
<212> TYPE: PRT
<213> ORGANISM: Homo sapiens

<400> SEQUENCE: 95

Met Ala Ala Leu Arg Val Leu Leu Ser Cys Ala Arg Gly Pro Leu Arg
1               5                   10                  15

Pro Pro Val Arg Cys Pro Ala Trp Arg Pro Phe Ala Ser Gly Ala Asn
                20                  25                  30

Phe Glu Tyr Ile Ile Ala Glu Lys Arg Gly Lys Asn Asn Thr Val Gly
            35                  40                  45

Leu Ile Gln Leu Asn Arg Pro Lys Ala Leu Asn Ala Leu Cys Asp Gly
            50                  55                  60

Leu Ile Asp Glu Leu Asn Gln Ala Leu Lys Ile Phe Glu Glu Asp Pro
65                  70                  75                  80

Ala Val Gly Ala Ile Val Leu Thr Gly Gly Asp Lys Ala Phe Ala Ala
                85                  90                  95

Gly Ala Asp Ile Lys Glu Met Gln Asn Leu Ser Phe Gln Asp Cys Tyr
                100                 105                 110

Ser Ser Lys Phe Leu Lys His Trp Asp His Leu Thr Gln Val Lys Lys
            115                 120                 125

Pro Val Ile Ala Ala Val Asn Gly Tyr Ala Phe Gly Gly Gly Cys Glu
            130                 135                 140
```

```
Leu Ala Met Met Cys Asp Ile Ile Tyr Ala Gly Glu Lys Ala Gln Phe
145                 150                 155                 160

Ala Gln Pro Glu Ile Leu Ile Gly Thr Ile Pro Gly Ala Gly Gly Thr
            165                 170                 175

Gln Arg Leu Thr Arg Ala Val Gly Lys Ser Leu Ala Met Glu Met Val
        180                 185                 190

Leu Thr Gly Asp Arg Ile Ser Ala Gln Asp Ala Lys Gln Ala Gly Leu
    195                 200                 205

Val Ser Lys Ile Cys Pro Val Glu Thr Leu Val Glu Glu Ala Ile Gln
210                 215                 220

Cys Ala Glu Lys Ile Ala Ser Asn Ser Lys Ile Val Ala Met Ala
225                 230                 235                 240

Lys Glu Ser Val Asn Ala Ala Phe Glu Met Thr Leu Thr Glu Gly Ser
                245                 250                 255

Lys Leu Glu Lys Lys Leu Phe Tyr Ser Thr Phe Ala Thr Asp Asp Arg
            260                 265                 270

Lys Glu Gly Met Thr Ala Phe Val Glu Lys Arg Lys Ala Asn Phe Lys
        275                 280                 285

Asp Gln
    290

<210> SEQ ID NO 96
<211> LENGTH: 399
<212> TYPE: PRT
<213> ORGANISM: Pseudomonas fluorescens

<400> SEQUENCE: 96

Met Arg Val Val Leu Cys Lys Phe Ala Leu Leu Arg Ser His Asp Gly
1               5                   10                  15

Ser Ser Ala Asn Ile Leu Ile Lys Asn Asn Lys Ser Arg Glu Leu Ser
            20                  25                  30

Met Thr Ala Gln Val Ser Thr Glu Ala Ser His Ala Ala Ile Leu Gln
        35                  40                  45

Asp Glu Val Leu Ala Glu Val Arg Asn His Ile Gly His Leu Thr Leu
    50                  55                  60

Asn Arg Pro Ala Gly Leu Asn Ala Leu Thr Leu Gln Met Val Arg Ser
65                  70                  75                  80

Leu Thr Ser Gln Leu Gln Ala Trp Ser Asp Asp Pro Gln Val Tyr Ala
                85                  90                  95

Val Val Leu Arg Gly Ala Gly Glu Lys Ala Phe Cys Ala Gly Gly Asp
            100                 105                 110

Ile Arg Ser Leu Tyr Asp Ser Phe Lys Asn Gly Asp Thr Leu His Gln
        115                 120                 125

Asp Phe Phe Val Glu Glu Tyr Ala Leu Asp Leu Ala Ile His His Tyr
    130                 135                 140

Arg Lys Pro Val Leu Ala Leu Met Asp Gly Phe Val Leu Gly Gly Gly
145                 150                 155                 160

Met Gly Leu Val Gln Gly Ala Asp Leu Arg Val Val Thr Glu Arg Ser
                165                 170                 175

Arg Leu Ala Met Pro Glu Val Ala Ile Gly Tyr Phe Pro Asp Val Gly
            180                 185                 190

Gly Ser Tyr Phe Leu Pro Arg Ile Pro Gly Glu Leu Gly Ile Tyr Leu
        195                 200                 205

Gly Val Thr Gly Val Gln Ile Arg Ala Ala Asp Ala Leu Tyr Cys Gly
```

```
    210                 215                 220

Leu Ala Asp Trp Tyr Leu Asp Ser His Lys Leu Ala Asp Leu Asp Gln
225                 230                 235                 240

Lys Leu Asp Asn Leu Arg Trp His Asp Ser Pro Leu Lys Asp Leu Gln
                245                 250                 255

Gly Ala Leu Ala Arg Leu Ala Val Gln Gln Leu Pro Asp Ala Pro Leu
            260                 265                 270

Ala Ala Leu Arg Pro Ala Ile Asp His Phe Phe Ala Leu Pro Asp Val
        275                 280                 285

Pro Ser Ile Val Glu Gln Leu Gln Gln Val Thr Val Ala Asp Ser His
    290                 295                 300

Glu Trp Ala Leu Asn Thr Val Ser Leu Met Gln Thr Arg Ser Pro Leu
305                 310                 315                 320

Ala Met Ala Val Thr Leu Glu Met Leu Arg Arg Gly Arg Arg Leu Ser
                325                 330                 335

Leu Glu Gln Cys Phe Ala Leu Glu Leu His Leu Asp Arg Gln Trp Phe
            340                 345                 350

Glu Arg Gly Asp Leu Ile Glu Gly Val Arg Ala Leu Ile Ile Asp Lys
        355                 360                 365

Asp Lys Ser Pro Arg Trp Asn Pro Pro Thr Leu His Gly Leu Ala Leu
    370                 375                 380

Asn His Val Glu Ser Phe Phe His His Phe Glu Lys Val Val Lys
385                 390                 395

<210> SEQ ID NO 97
<211> LENGTH: 351
<212> TYPE: PRT
<213> ORGANISM: Bacillus cereus

<400> SEQUENCE: 97

Met Thr Glu Gln Val Leu Phe Ser Val Ser Glu Asn Gly Val Ala Thr
1               5                   10                  15

Ile Thr Leu Asn Arg Pro Lys Ala Leu Asn Ser Leu Ser Tyr Asp Met
            20                  25                  30

Leu Gln Pro Ile Gly Gln Lys Leu Lys Glu Trp Glu His Asp Glu Arg
        35                  40                  45

Ile Ala Leu Ile Val Leu Lys Gly Ala Gly Thr Lys Gly Phe Cys Ala
    50                  55                  60

Gly Gly Asp Ile Lys Thr Leu Tyr Glu Ala Arg Ser Asn Glu Val Ala
65                  70                  75                  80

Leu Gln His Ala Glu Arg Phe Phe Glu Glu Glu Tyr Glu Ile Asp Thr
                85                  90                  95

Tyr Ile Tyr Gln Tyr Thr Lys Pro Ile Ile Ala Cys Leu Asp Gly Ile
            100                 105                 110

Val Met Gly Gly Gly Val Gly Leu Thr Asn Gly Ala Lys Tyr Arg Ile
        115                 120                 125

Val Thr Glu Arg Thr Lys Trp Ala Met Pro Glu Met Asn Ile Gly Phe
    130                 135                 140

Phe Pro Asp Val Gly Ala Ala Tyr Phe Leu Asn Lys Ala Pro Gly Tyr
145                 150                 155                 160

Thr Gly Arg Phe Val Ala Leu Thr Ala Ser Ile Leu Lys Ala Ser Asp
                165                 170                 175

Val Leu Phe Ile Asn Ala Ala Asp Tyr Phe Met Thr Ser Asp Ser Leu
            180                 185                 190
```

```
Pro Glu Phe Leu Thr Glu Leu Glu Ser Val Asn Trp His Lys Glu Asp
            195                 200                 205

Asp Val His Thr Asn Leu Lys Glu Val Ile Arg Thr Phe Ala Thr Ala
210                 215                 220

Pro Asn Leu Glu Ser Glu Leu Ala Pro Ser Leu Glu Val Ile Asn Ser
225                 230                 235                 240

His Phe Ala Phe Asp Thr Ile Glu Glu Ile His Ser Leu Glu Lys
            245                 250                 255

Asp Glu Ser Ser Phe Ala Leu Lys Lys Glu Ile Leu Leu Ser Lys
            260                 265                 270

Ser Pro Ile Ser Leu Lys Val Thr Leu Lys Gln Phe Ile Asp Gly Gln
            275                 280                 285

Asp Lys Ser Val Glu Glu Cys Phe Ala Thr Asp Leu Ile Leu Ala Lys
290                 295                 300

Asn Phe Met Arg His Glu Asp Phe Glu Gly Val Arg Ser Val Val
305                 310                 315                 320

Val Asp Lys Asp Gln Asn Pro Asn Tyr Lys Tyr Lys Gln Leu Ser Asp
                        325                 330                 335

Val Ser Glu Glu Asp Val Asn Arg Phe Phe Asn Leu Leu Asn Ala
                340                 345                 350

<210> SEQ ID NO 98
<211> LENGTH: 381
<212> TYPE: PRT
<213> ORGANISM: Homo sapiens

<400> SEQUENCE: 98

Met Trp Arg Leu Met Ser Arg Phe Asn Ala Phe Lys Arg Thr Asn Thr
1               5                   10                  15

Ile Leu His His Leu Arg Met Ser Lys His Thr Asp Ala Ala Glu Glu
                20                  25                  30

Val Leu Leu Glu Lys Lys Gly Cys Ala Gly Val Ile Thr Leu Asn Arg
            35                  40                  45

Pro Lys Phe Leu Asn Ala Leu Thr Leu Asn Met Ile Arg Gln Ile Tyr
        50                  55                  60

Pro Gln Leu Lys Lys Trp Glu Gln Asp Pro Glu Thr Phe Val Ile Ile
65                  70                  75                  80

Ile Lys Gly Ala Gly Gly Lys Ala Phe Cys Ala Gly Gly Asp Ile Arg
                85                  90                  95

Val Ile Ser Glu Ala Glu Lys Ala Lys Gln Lys Ile Ala Pro Val Phe
            100                 105                 110

Phe Arg Glu Glu Tyr Met Leu Asn Asn Ala Val Gly Ser Cys Gln Lys
        115                 120                 125

Pro Tyr Val Ala Leu Ile His Gly Ile Thr Met Gly Gly Gly Val Gly
    130                 135                 140

Leu Ser Val His Gly Gln Phe Arg Val Ala Thr Glu Lys Cys Leu Phe
145                 150                 155                 160

Ala Met Pro Glu Thr Ala Ile Gly Leu Phe Pro Asp Val Gly Gly Gly
                165                 170                 175

Tyr Phe Phe Ala Thr Thr Pro Arg Lys Thr Trp Leu Pro Cys Ile
            180                 185                 190

Asn Gly Phe Arg Leu Lys Gly Arg Asp Val Tyr Arg Ala Gly Ile Ala
        195                 200                 205

Thr His Phe Val Asp Ser Glu Lys Leu Ala Met Leu Glu Glu Asp Leu
    210                 215                 220
```

```
Leu Ala Leu Lys Ser Pro Ser Lys Glu Asn Ile Ala Ser Val Leu Glu
225                 230                 235                 240

Asn Tyr His Thr Glu Ser Lys Ile Asp Arg Asp Lys Ser Phe Ile Leu
            245                 250                 255

Glu Glu His Met Asp Lys Ile Asn Ser Cys Phe Ser Ala Asn Thr Val
            260                 265                 270

Glu Glu Ile Ile Glu Asn Leu Gln Gln Asp Gly Ser Ser Phe Ala Leu
            275                 280                 285

Glu Gln Leu Lys Val Ile Asn Lys Met Ser Pro Thr Ser Leu Lys Ile
            290                 295                 300

Thr Leu Arg Gln Leu Met Glu Gly Ser Ser Lys Thr Leu Gln Glu Val
305                 310                 315                 320

Leu Thr Met Glu Tyr Arg Leu Ser Gln Ala Cys Met Arg Gly His Asp
                325                 330                 335

Phe His Glu Gly Val Arg Ala Val Leu Ile Asp Lys Asp Gln Ser Pro
                340                 345                 350

Lys Trp Lys Pro Ala Asp Leu Lys Glu Val Thr Glu Asp Leu Asn
                355                 360                 365

Asn His Phe Lys Ser Leu Gly Ser Ser Asp Leu Lys Phe
            370                 375                 380

<210> SEQ ID NO 99
<211> LENGTH: 261
<212> TYPE: PRT
<213> ORGANISM: Megasphaera elsdenii

<400> SEQUENCE: 99

Val Lys Thr Val Tyr Thr Leu Gly Ile Asp Val Gly Ser Ser Ser Ser
1               5                   10                  15

Lys Ala Val Ile Leu Glu Asp Gly Lys Lys Ile Val Ala His Ala Val
            20                  25                  30

Val Glu Ile Gly Thr Gly Ser Thr Gly Pro Glu Arg Val Leu Asp Glu
            35                  40                  45

Val Phe Lys Asp Thr Asn Leu Lys Ile Glu Asp Met Ala Asn Ile Ile
50                  55                  60

Ala Thr Gly Tyr Gly Arg Phe Asn Val Asp Cys Ala Lys Gly Glu Val
65                  70                  75                  80

Ser Glu Ile Thr Cys His Ala Lys Gly Ala Leu Phe Glu Cys Pro Gly
                85                  90                  95

Thr Thr Thr Ile Leu Asp Ile Gly Gly Gln Asp Val Lys Ser Ile Lys
            100                 105                 110

Leu Asn Gly Gln Gly Leu Val Met Gln Phe Ala Met Asn Asp Lys Cys
            115                 120                 125

Ala Ala Gly Thr Gly Arg Phe Leu Asp Val Met Ser Lys Val Leu Glu
            130                 135                 140

Ile Pro Met Ser Glu Met Gly Asp Trp Tyr Phe Lys Ser Lys His Pro
145                 150                 155                 160

Ala Ala Val Ser Ser Thr Cys Thr Val Phe Ala Glu Ser Glu Val Ile
                165                 170                 175

Ser Leu Leu Ser Lys Asn Val Pro Lys Glu Asp Ile Val Ala Gly Val
            180                 185                 190

His Gln Ser Ile Ala Ala Lys Ala Cys Ala Leu Val Arg Arg Val Gly
            195                 200                 205

Val Gly Glu Asp Leu Thr Met Thr Gly Gly Gly Ser Arg Asp Pro Gly
```

```
            210                 215                 220
Val Val Asp Ala Val Ser Lys Glu Leu Gly Ile Pro Val Arg Val Ala
225                 230                 235                 240

Leu His Pro Gln Ala Val Gly Ala Leu Gly Ala Ala Leu Ile Ala Tyr
                245                 250                 255

Asp Lys Ile Lys Lys
            260

<210> SEQ ID NO 100
<211> LENGTH: 428
<212> TYPE: PRT
<213> ORGANISM: Megasphaera elsdenii

<400> SEQUENCE: 100

Met Ser Glu Glu Lys Thr Val Asp Ile Glu Ser Met Ser Lys Glu
1               5                   10                  15

Ala Leu Gly Tyr Phe Leu Pro Lys Val Asp Glu Asp Ala Arg Lys Ala
                20                  25                  30

Lys Lys Glu Gly Arg Leu Val Cys Trp Ser Ala Ser Val Ala Pro Pro
            35                  40                  45

Glu Phe Cys Thr Ala Met Asp Ile Ala Ile Val Tyr Pro Glu Thr His
50                  55                  60

Ala Ala Gly Ile Gly Ala Arg His Gly Ala Pro Ala Met Leu Glu Val
65                  70                  75                  80

Ala Glu Asn Lys Gly Tyr Asn Gln Asp Ile Cys Ser Tyr Cys Arg Val
                85                  90                  95

Asn Met Gly Tyr Met Glu Leu Leu Lys Gln Gln Ala Leu Thr Gly Glu
                100                 105                 110

Thr Pro Glu Val Leu Lys Asn Ser Pro Ala Ser Pro Ile Pro Leu Pro
            115                 120                 125

Asp Val Val Leu Thr Cys Asn Asn Ile Cys Asn Thr Leu Leu Lys Trp
130                 135                 140

Tyr Glu Asn Leu Ala Lys Glu Leu Asn Val Pro Leu Ile Asn Ile Asp
145                 150                 155                 160

Val Pro Phe Asn His Glu Phe Pro Val Thr Lys His Ala Lys Gln Tyr
                165                 170                 175

Ile Val Gly Glu Phe Lys His Ala Ile Lys Gln Leu Glu Asp Leu Cys
            180                 185                 190

Gly Arg Pro Phe Asp Tyr Asp Lys Phe Phe Glu Val Gln Lys Gln Thr
        195                 200                 205

Gln Arg Ser Ile Ala Ala Trp Asn Lys Ile Ala Thr Tyr Phe Gln Tyr
    210                 215                 220

Lys Pro Ser Pro Leu Asn Gly Phe Asp Leu Phe Asn Tyr Met Gly Leu
225                 230                 235                 240

Ala Val Ala Ala Arg Ser Leu Asn Tyr Ser Glu Ile Thr Phe Asn Lys
                245                 250                 255

Phe Leu Lys Glu Leu Asp Glu Lys Val Ala Asn Lys Lys Trp Ala Phe
            260                 265                 270

Gly Glu Asn Glu Lys Ser Arg Val Thr Trp Glu Gly Ile Ala Val Trp
        275                 280                 285

Ile Ala Leu Gly His Thr Phe Lys Glu Leu Lys Gly Gln Gly Ala Leu
        290                 295                 300

Met Thr Gly Ser Ala Tyr Pro Gly Met Trp Asp Val Ser Tyr Glu Pro
305                 310                 315                 320
```

```
Gly Asp Leu Glu Ser Met Ala Glu Ala Tyr Ser Arg Thr Tyr Ile Asn
                325                 330                 335

Cys Cys Leu Glu Gln Arg Gly Ala Val Leu Glu Lys Val Val Arg Asp
            340                 345                 350

Gly Lys Cys Asp Gly Leu Ile Met His Gln Asn Arg Ser Cys Lys Asn
        355                 360                 365

Met Ser Leu Leu Asn Asn Glu Gly Gly Gln Arg Ile Gln Lys Asn Leu
370                 375                 380

Gly Val Pro Tyr Val Ile Phe Asp Gly Asp Gln Thr Asp Ala Arg Asn
385                 390                 395                 400

Phe Ser Glu Ala Gln Phe Asp Thr Arg Val Glu Ala Leu Ala Glu Met
                405                 410                 415

Met Ala Asp Lys Lys Ala Asn Glu Gly Gly Asn His
                420                 425

<210> SEQ ID NO 101
<211> LENGTH: 372
<212> TYPE: PRT
<213> ORGANISM: Megasphaera elsdenii

<400> SEQUENCE: 101

Met Ser Gln Ile Asp Glu Leu Ile Ser Lys Leu Gln Glu Val Ser Asn
1               5                   10                  15

His Pro Gln Lys Thr Val Leu Asn Tyr Lys Lys Gln Gly Lys Gly Leu
                20                  25                  30

Val Gly Met Met Pro Tyr Tyr Ala Pro Glu Glu Ile Val Tyr Ala Ala
            35                  40                  45

Gly Tyr Leu Pro Val Gly Met Phe Gly Ser Gln Asn Pro Gln Ile Ser
        50                  55                  60

Ala Ala Arg Thr Tyr Leu Pro Pro Phe Ala Cys Ser Leu Met Gln Ala
65                  70                  75                  80

Asp Met Glu Leu Gln Leu Asn Gly Thr Tyr Asp Cys Leu Asp Ala Val
                85                  90                  95

Ile Phe Ser Val Pro Cys Asp Thr Leu Arg Cys Met Ser Gln Lys Trp
                100                 105                 110

His Gly Lys Ala Pro Val Ile Val Phe Thr Gln Pro Gln Asn Arg Lys
            115                 120                 125

Ile Arg Pro Ala Val Asp Phe Leu Lys Ala Glu Tyr Glu His Val Arg
        130                 135                 140

Thr Glu Leu Gly Arg Ile Leu Asn Val Lys Ile Ser Asp Leu Ala Ile
145                 150                 155                 160

Gln Glu Ala Ile Lys Val Tyr Asn Glu Asn Arg Gln Val Met Arg Glu
                165                 170                 175

Phe Cys Asp Val Ala Ala Gln Tyr Pro Gln Ile Phe Thr Pro Ile Lys
                180                 185                 190

Arg His Asp Val Ile Lys Ala Arg Trp Phe Met Asp Lys Ala Glu His
            195                 200                 205

Thr Ala Leu Val Arg Glu Leu Ile Asp Ala Val Lys Lys Glu Pro Val
        210                 215                 220

Gln Pro Trp Asn Gly Lys Lys Val Ile Leu Ser Gly Ile Met Ala Glu
225                 230                 235                 240

Pro Asp Glu Phe Leu Asp Ile Phe Ser Glu Phe Asn Ile Ala Val Val
                245                 250                 255

Ala Asp Asp Leu Ala Gln Glu Ser Arg Gln Phe Arg Thr Asp Val Pro
                260                 265                 270
```

```
Ser Gly Ile Asp Pro Leu Glu Gln Leu Ala Gln Gln Trp Gln Asp Phe
        275                 280                 285

Asp Gly Cys Pro Leu Ala Leu Asn Glu Asp Lys Pro Arg Gly Gln Met
290                 295                 300

Leu Ile Asp Met Thr Lys Lys Tyr Asn Ala Asp Ala Val Val Ile Cys
305                 310                 315                 320

Met Met Arg Phe Cys Asp Pro Glu Glu Phe Asp Tyr Pro Ile Tyr Lys
                325                 330                 335

Pro Glu Phe Glu Ala Ala Gly Val Arg Tyr Thr Val Leu Asp Leu Asp
                340                 345                 350

Ile Glu Ser Pro Ser Leu Glu Gln Leu Arg Thr Arg Ile Gln Ala Phe
        355                 360                 365

Ser Glu Ile Leu
        370

<210> SEQ ID NO 102
<211> LENGTH: 519
<212> TYPE: PRT
<213> ORGANISM: Saccharomyces cerevisiae

<400> SEQUENCE: 102

Met Phe Ser Arg Ser Thr Leu Cys Leu Lys Thr Ser Ala Ser Ser Ile
1               5                   10                  15

Gly Arg Leu Gln Leu Arg Tyr Phe Ser His Leu Pro Met Thr Val Pro
            20                  25                  30

Ile Lys Leu Pro Asn Gly Leu Glu Tyr Glu Gln Pro Thr Gly Leu Phe
        35                  40                  45

Ile Asn Asn Lys Phe Val Pro Ser Lys Gln Asn Lys Thr Phe Glu Val
    50                  55                  60

Ile Asn Pro Ser Thr Glu Glu Ile Cys His Ile Tyr Glu Gly Arg
65                  70                  75                  80

Glu Asp Asp Val Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
            100                 105                 110

Tyr Arg Leu Ala Glu Leu Ile Glu Gln Asp Lys Asp Val Ile Ala Ser
        115                 120                 125

Ile Glu Thr Leu Asp Asn Gly Lys Ala Ile Ser Ser Ser Arg Gly Asp
    130                 135                 140

Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
                165                 170                 175

Thr Lys Arg Gln Pro Leu Gly Val Cys Gly Gln Ile Ile Pro Trp Asn
            180                 185                 190

Phe Pro Leu Leu Met Trp Ala Trp Lys Ile Ala Pro Ala Leu Val Thr
        195                 200                 205

Gly Asn Thr Val Val Leu Lys Thr Ala Glu Ser Thr Pro Leu Ser Ala
    210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
                245                 250                 255

Asn His Pro Lys Ile Lys Lys Val Ala Phe Thr Gly Ser Thr Ala Thr
```

260                 265                 270
Gly Arg His Ile Tyr Gln Ser Ala Ala Gly Leu Lys Lys Val Thr
            275                 280                 285
Leu Glu Leu Gly Gly Lys Ser Pro Asn Ile Val Phe Ala Asp Ala Glu
        290                 295                 300
Leu Lys Lys Ala Val Gln Asn Ile Ile Leu Gly Ile Tyr Tyr Asn Ser
305                 310                 315                 320
Gly Glu Val Cys Cys Ala Gly Ser Arg Val Tyr Val Glu Ser Ile
                325                 330                 335
Tyr Asp Lys Phe Ile Glu Glu Phe Lys Ala Ala Ser Glu Ser Ile Lys
            340                 345                 350
Val Gly Asp Pro Phe Asp Glu Ser Thr Phe Gln Gly Ala Gln Thr Ser
        355                 360                 365
Gln Met Gln Leu Asn Lys Ile Leu Lys Tyr Val Asp Ile Gly Lys Asn
    370                 375                 380
Glu Gly Ala Thr Leu Ile Thr Gly Gly Glu Arg Leu Gly Ser Lys Gly
385                 390                 395                 400
Tyr Phe Ile Lys Pro Thr Val Phe Gly Asp Val Lys Glu Asp Met Arg
                405                 410                 415
Ile Val Lys Glu Glu Ile Phe Gly Pro Val Val Thr Val Thr Lys Phe
            420                 425                 430
Lys Ser Ala Asp Glu Val Ile Asn Met Ala Asn Asp Ser Glu Tyr Gly
        435                 440                 445
Leu Ala Ala Gly Ile His Thr Ser Asn Ile Thr Ala Leu Lys Val
    450                 455                 460
Ala Asp Arg Val Asn Ala Gly Thr Val Trp Ile Asn Thr Tyr Asn Asp
465                 470                 475                 480
Phe His His Ala Val Pro Phe Gly Gly Phe Asn Ala Ser Gly Leu Gly
                485                 490                 495
Arg Glu Met Ser Val Asp Ala Leu Gln Asn Tyr Leu Gln Val Lys Ala
            500                 505                 510
Val Arg Ala Lys Leu Asp Glu
        515

<210> SEQ ID NO 103
<211> LENGTH: 495
<212> TYPE: PRT
<213> ORGANISM: Escherichia coli

<400> SEQUENCE: 103

Met Asn Phe His His Leu Ala Tyr Trp Gln Asp Lys Ala Leu Ser Leu
1               5                   10                  15
Ala Ile Glu Asn Arg Leu Phe Ile Asn Gly Glu Tyr Thr Ala Ala Ala
            20                  25                  30
Glu Asn Glu Thr Phe Glu Thr Val Asp Pro Val Thr Gln Ala Pro Leu
        35                  40                  45
Ala Lys Ile Ala Arg Gly Lys Ser Val Asp Ile Asp Arg Ala Met Ser
    50                  55                  60
Ala Ala Arg Gly Val Phe Glu Arg Gly Asp Trp Ser Leu Ser Ser Pro
65                  70                  75                  80
Ala Lys Arg Lys Ala Val Leu Asn Lys Leu Ala Asp Leu Met Glu Ala
            85                  90                  95
His Ala Glu Glu Leu Ala Leu Leu Glu Thr Leu Asp Thr Gly Lys Pro
        100                 105                 110

```
Ile Arg His Ser Leu Arg Asp Asp Ile Pro Gly Ala Ala Arg Ala Ile
            115                 120                 125

Arg Trp Tyr Ala Glu Ala Ile Asp Lys Val Tyr Gly Glu Val Ala Thr
130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Thr Cys Trp
                165                 170                 175

Lys Leu Gly Pro Ala Leu Ala Ala Gly Asn Ser Val Ile Leu Lys Pro
                180                 185                 190

Ser Glu Lys Ser Pro Leu Ser Ala Ile Arg Leu Ala Gly Leu Ala Lys
            195                 200                 205

Glu Ala Gly Leu Pro Asp Gly Val Leu Asn Val Val Thr Gly Phe Gly
            210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Lys Ser
                260                 265                 270

Ala Asn Ile Val Phe Ala Asp Cys Pro Asp Leu Gln Gln Ala Ala Ser
            275                 280                 285

Ala Thr Ala Ala Gly Ile Phe Tyr Asn Gln Gly Gln Val Cys Ile Ala
            290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
                325                 330                 335

Pro Ala Thr Thr Met Gly Thr Leu Ile Asp Cys Ala His Ala Asp Ser
                340                 345                 350

Val His Ser Phe Ile Arg Glu Gly Glu Ser Lys Gly Gln Leu Leu Leu
            355                 360                 365

Asp Gly Arg Asn Ala Gly Leu Ala Ala Ala Ile Gly Pro Thr Ile Phe
370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
                405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
            435                 440                 445

Val Phe Val Asn Asn Tyr Asn Asp Gly Asp Met Thr Val Pro Phe Gly
450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
                485                 490                 495

<210> SEQ ID NO 104
<211> LENGTH: 495
<212> TYPE: PRT
<213> ORGANISM: Klebsiella pneumoniae

<400> SEQUENCE: 104
```

```
Met Asn Phe Gln His Leu Ala Tyr Trp Gln Glu Lys Ala Lys Asn Leu
1               5                   10                  15

Ala Ile Glu Thr Arg Leu Phe Ile Asn Gly Glu Tyr Cys Ala Ala Ala
                20                  25                  30

Asp Asn Thr Thr Phe Glu Thr Ile Asp Pro Ala Ala Gln Gln Thr Leu
            35                  40                  45

Ala Gln Val Ala Arg Gly Lys Lys Ala Asp Val Glu Arg Ala Val Lys
        50                  55                  60

Ala Ala Arg Gln Ala Phe Asp Asn Gly Asp Trp Ser Gln Ala Ser Pro
65                  70                  75                  80

Ala Gln Arg Lys Ala Ile Leu Thr Arg Phe Ala Asp Leu Met Glu Ala
                85                  90                  95

His Arg Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
        115                 120                 125

Arg Trp Tyr Ala Glu Ala Leu Asp Lys Val Tyr Gly Glu Val Ala Pro
130                 135                 140

Thr Gly Ser Asn Glu Leu Ala Met Ile Val Arg Glu Pro Ile Gly Val
145                 150                 155                 160

Ile Ala Ala Val Val Pro Trp Asn Phe Pro Leu Leu Leu Ala Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Thr Ala Leu Arg Leu Ala Gly Leu Ala Lys
        195                 200                 205

Glu Ala Gly Leu Pro Asp Gly Val Leu Asn Val Val Ser Gly Phe Gly
210                 215                 220

His Glu Ala Gly Gln Ala Leu Ala Leu His Pro Asp Val Glu Val Ile
225                 230                 235                 240

Thr Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Gly Lys Ser
            260                 265                 270

Ala Asn Ile Val Phe Ala Asp Cys Pro Asp Leu Gln Gln Ala Val Arg
        275                 280                 285

Ala Thr Ala Gly Gly Ile Phe Tyr Asn Gln Gly Gln Val Cys Ile Ala
290                 295                 300

Gly Thr Arg Leu Leu Leu Glu Glu Ser Ile Ala Asp Glu Phe Leu Ala
305                 310                 315                 320

Arg Leu Lys Ala Glu Ala Gln His Trp Gln Pro Gly Asn Pro Leu Asp
                325                 330                 335

Pro Asp Thr Thr Met Gly Met Leu Ile Asp Asn Thr His Ala Asp Asn
            340                 345                 350

Val His Ser Phe Ile Arg Gly Gly Glu Ser Gln Ser Thr Leu Phe Leu
        355                 360                 365

Asp Gly Arg Lys Asn Pro Trp Pro Ala Ala Val Gly Pro Thr Ile Phe
370                 375                 380

Val Asp Val Asp Pro Ala Ser Thr Leu Ser Arg Glu Glu Ile Phe Gly
385                 390                 395                 400

Pro Val Leu Val Val Thr Arg Phe Lys Ser Glu Glu Glu Ala Leu Lys
                405                 410                 415
```

Leu Ala Asn Asp Ser Asp Tyr Gly Leu Gly Ala Ala Val Trp Thr Arg
            420                 425                 430

Asp Leu Ser Arg Ala His Arg Met Ser Arg Arg Leu Lys Ala Gly Ser
        435                 440                 445

Val Phe Val Asn Asn Tyr Asn Asp Gly Asp Met Thr Val Pro Phe Gly
    450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ala Leu Glu Ser
                485                 490                 495

<210> SEQ ID NO 105
<211> LENGTH: 1053
<212> TYPE: DNA
<213> ORGANISM: Issatchenkia orientalis

<400> SEQUENCE: 105
atgtcttacg aaatcccaca acacaaaag gcctgtgtct tttacgaaaa cggcggccca       60
atcacataca aggacattcc agttccaaag ccaaaaccta ctgagatttt agtcaaggtt      120
ctgtactctg gtgtctgcca caccgacttg cacgcatgga agggtgactg gcctctagct      180
accaagttgc cattggttgg tggtcacgaa ggtgccggtg ttgttgttgc caagggtgaa      240
aacgtcacct cttttgagat tggtgattac gcaggtatca agtggttgaa tggttcatgt      300
atgggttgtg aattctgtga acaaggtgct gaaccaaaact gtcctaaggc cgacttgagt     360
ggttacaccc cgacggttc cttccaacag tatgctactg ctgacgctat tcaagctgca      420
cacatctcca aggaaaccga cttggctggt gttgctccaa tcttgtgtgc aggtgtcact     480
gtctacaagg ctttaaagac tgcagacctt agagcaggtg aatgggtttg tatttccggt    540
gcagctggtg gtttaggttc tcttgctatt caatatgcaa aggctatggg tctgagagtt    600
gttggtattg acggtggtga cgaaaagaag gaattgtgta atcccttgg tgctgaagca      660 tttattgatt tcacaaagac caaggatatc gtcaaggctg tccaagaggc aaccaatggt    720
ggtccacatg tgtcatcaa tgtctctgtc tctgaagctg caatttctca atcttgtgaa     780
tacgttagac ctctaggtaa ggttgttctt gttggtttac cagcaggcgc acaagtcaaa    840
actggtgtct ttgaagccgt tgtcaagtct attgaaatta agggttctta tgtcggtaac    900
agaaaggata ccgccgaagc acttgacttc tacactagag gcttggtcaa gtctccattc    960
aagattgtcg tttatccga attgccaaaa gtctttgaac tcatggaaca gggtaagatt    1020
ttaggtagaa tggtcttaga cacctccaaa taa                                  1053

<210> SEQ ID NO 106
<211> LENGTH: 350
<212> TYPE: PRT
<213> ORGANISM: Issatchenkia orientalis

<400> SEQUENCE: 106

Met Ser Tyr Glu Ile Pro Gln Thr Gln Lys Ala Cys Val Phe Tyr Glu
1               5                   10                  15

Asn Gly Gly Pro Ile Thr Tyr Lys Asp Ile Pro Val Pro Lys Pro Lys
            20                  25                  30

Pro Thr Glu Ile Leu Val Lys Val Leu Tyr Ser Gly Val Cys His Thr
        35                  40                  45

Asp Leu His Ala Trp Lys Gly Asp Trp Pro Leu Ala Thr Lys Leu Pro
    50                  55                  60

```
Leu Val Gly Gly His Glu Gly Ala Gly Val Val Ala Lys Gly Glu
 65                  70                  75                  80

Asn Val Thr Ser Phe Glu Ile Gly Asp Tyr Ala Gly Ile Lys Trp Leu
                 85                  90                  95

Asn Gly Ser Cys Met Gly Cys Glu Phe Cys Glu Gln Gly Ala Glu Pro
            100                 105                 110

Asn Cys Pro Lys Ala Asp Leu Ser Gly Tyr Thr His Asp Gly Ser Phe
        115                 120                 125

Gln Gln Tyr Ala Thr Ala Asp Ala Ile Gln Ala His Ile Ser Lys
130                 135                 140

Glu Thr Asp Leu Ala Gly Val Ala Pro Ile Leu Cys Ala Gly Val Thr
145                 150                 155                 160

Val Tyr Lys Ala Leu Lys Thr Ala Asp Leu Arg Ala Gly Glu Trp Val
                165                 170                 175

Cys Ile Ser Gly Ala Ala Gly Gly Leu Gly Ser Leu Ala Ile Gln Tyr
            180                 185                 190

Ala Lys Ala Met Gly Leu Arg Val Val Gly Ile Asp Gly Gly Asp Glu
        195                 200                 205

Lys Lys Glu Leu Cys Lys Ser Leu Gly Ala Glu Ala Phe Ile Asp Phe
210                 215                 220

Thr Lys Thr Lys Asp Ile Val Lys Ala Val Gln Glu Ala Thr Asn Gly
225                 230                 235                 240

Gly Pro His Gly Val Ile Asn Val Ser Val Ser Glu Ala Ala Ile Ser
                245                 250                 255

Gln Ser Cys Glu Tyr Val Arg Pro Leu Gly Lys Val Val Leu Val Gly
            260                 265                 270

Leu Pro Ala Gly Ala Gln Val Lys Thr Gly Val Phe Glu Ala Val Val
        275                 280                 285

Lys Ser Ile Glu Ile Lys Gly Ser Tyr Val Gly Asn Arg Lys Asp Thr
290                 295                 300

Ala Glu Ala Leu Asp Phe Tyr Thr Arg Gly Leu Val Lys Ser Pro Phe
305                 310                 315                 320

Lys Ile Val Gly Leu Ser Glu Leu Pro Lys Val Phe Glu Leu Met Glu
                325                 330                 335

Gln Gly Lys Ile Leu Gly Arg Met Val Leu Asp Thr Ser Lys
            340                 345                 350

<210> SEQ ID NO 107
<211> LENGTH: 1131
<212> TYPE: DNA
<213> ORGANISM: Issatchenkia orientalis

<400> SEQUENCE: 107
atgtttgcat caaccttcag aagtcaagct gtaagagctg caagatttac tagattccaa      60
tccacttttg ccattcctga gaagcaaatg ggtgttatct ttgaaactca tggtggtcct     120
ttacaataca aggaaattcc agttccaaaa ccaaaaccaa ctgaaatttt aatcaatgtt     180
aaatactctg gtgtctgcca taccgattta cacgcatgga aggtgactg gccattacca     240 gcaaagttac ccctagttgg tgtcacgaa ggtgcgggca tgttgttgc gaaaggttct      300 gcagttacca actttgagat ggcgattat gctggtatta gtggttaaa cggttcatgt       360 atgtcatgtg aattctgtga acaaggtgat gaatctaact gtgaacatgc cgatttgagt     420
ggttatactc atgatggttc tttccaacaa tatgccactg ctgacgctat tcaagctgca    480
aagatcccaa agggtaccga cttatctgaa gttgcgccaa ttttatgtgc tggtgttact     540
```

```
gtctataaag ctttgaaaac tgctgattta agagcaggtc aatgggttgc gatttctggt    600
gccgctggtg gtctaggttc tcttgctgtc aatatgcaa aggcaatggg tctaagagtt     660
ttaggtatcg atggtggtga aggtaaaaag gaacttttg aacaatgtgg tggtgatgtg     720
tttatcgatt tcaccagata cccaagagat gcacctgaaa agatggttgc tgatattaag    780
gctgcaacta acggtttggg tccacacggt gttatcaatg tctctgtctc cccagctgct    840
atctctcaat catgtgacta tgttagagca actggtaagg ttgtccttgt cggtatgcca    900
tctggtgctg tctgtaagtc tgatgtcttc actcatgttg ttaaatcctt acaaattaaa    960
ggttcttatg ttggtaacag agcagatacc agagaagctt tggaattctt taatgaaggt   1020
aaggtcagat ctccaatcaa ggttgtccca ttatctactt tacctgaaat ttacgaattg   1080
atggagcaag gtaagatttt aggtagatac gttgttgata cttctaaata a            1131
```

<210> SEQ ID NO 108
<211> LENGTH: 376
<212> TYPE: PRT
<213> ORGANISM: Issatchenkia orientalis

<400> SEQUENCE: 108

```
Met Phe Ala Ser Thr Phe Arg Ser Gln Ala Val Arg Ala Ala Arg Phe
1               5                   10                  15

Thr Arg Phe Gln Ser Thr Phe Ala Ile Pro Glu Lys Gln Met Gly Val
            20                  25                  30

Ile Phe Glu Thr His Gly Gly Pro Leu Gln Tyr Lys Glu Ile Pro Val
        35                  40                  45

Pro Lys Pro Lys Pro Thr Glu Ile Leu Ile Asn Val Lys Tyr Ser Gly
    50                  55                  60

Val Cys His Thr Asp Leu His Ala Trp Lys Gly Asp Trp Pro Leu Pro
65                  70                  75                  80

Ala Lys Leu Pro Leu Val Gly Gly His Glu Gly Ala Gly Ile Val Val
                85                  90                  95

Ala Lys Gly Ser Ala Val Thr Asn Phe Glu Ile Gly Asp Tyr Ala Gly
            100                 105                 110

Ile Lys Trp Leu Asn Gly Ser Cys Met Ser Cys Glu Phe Cys Glu Gln
        115                 120                 125

Gly Asp Glu Ser Asn Cys Glu His Ala Asp Leu Ser Gly Tyr Thr His
    130                 135                 140

Asp Gly Ser Phe Gln Gln Tyr Ala Thr Ala Asp Ala Ile Gln Ala Ala
145                 150                 155                 160

Lys Ile Pro Lys Gly Thr Asp Leu Ser Glu Val Ala Pro Ile Leu Cys
                165                 170                 175

Ala Gly Val Thr Val Tyr Lys Ala Leu Lys Thr Ala Asp Leu Arg Ala
            180                 185                 190

Gly Gln Trp Val Ala Ile Ser Gly Ala Ala Gly Gly Leu Gly Ser Leu
        195                 200                 205

Ala Val Gln Tyr Ala Lys Ala Met Gly Leu Arg Val Leu Gly Ile Asp
    210                 215                 220

Gly Gly Glu Gly Lys Lys Glu Leu Phe Glu Gln Cys Gly Gly Asp Val
225                 230                 235                 240

Phe Ile Asp Phe Thr Arg Tyr Pro Arg Asp Ala Pro Glu Lys Met Val
                245                 250                 255

Ala Asp Ile Lys Ala Ala Thr Asn Gly Leu Gly Pro His Gly Val Ile
            260                 265                 270
```

Asn Val Ser Val Ser Pro Ala Ala Ile Ser Gln Ser Cys Asp Tyr Val
        275                 280                 285

Arg Ala Thr Gly Lys Val Val Leu Val Gly Met Pro Ser Gly Ala Val
        290                 295                 300

Cys Lys Ser Asp Val Phe Thr His Val Val Lys Ser Leu Gln Ile Lys
305                 310                 315                 320

Gly Ser Tyr Val Gly Asn Arg Ala Asp Thr Arg Glu Ala Leu Glu Phe
                325                 330                 335

Phe Asn Glu Gly Lys Val Arg Ser Pro Ile Lys Val Pro Leu Ser
                340                 345                 350

Thr Leu Pro Glu Ile Tyr Glu Leu Met Glu Gln Gly Lys Ile Leu Gly
        355                 360                 365

Arg Tyr Val Val Asp Thr Ser Lys
        370                 375

<210> SEQ ID NO 109
<211> LENGTH: 1134
<212> TYPE: DNA
<213> ORGANISM: Issatchenkia orientalis

<400> SEQUENCE: 109
atgttatcca agaccatcac tgctgcattg aggggcaata caactcgtac tgcattcaga      60
atcaatgcca ttagaagttt agcgatccca gctattccag agacacaaaa gggtgttatc    120
ttttatgaga acggaggtga actattttac aaggacattc agttccaaa gccaaagcca     180
aatgagattt tggtgaatgt caagtattct ggtgtttgtc ataccgattt acacgcatgg    240
aaaggtgact ggcctttggc gaccaagttg ccattggttg gtggacatga aggtgccgga    300
gttgttgttg ctaaggggga caatgtcacc aactttgaaa ttgcgattga tgccggtatc    360
aagtggttga atggttcatg tatggggtgt gaattttgcc aacaaggtgc agagccaaac    420
tgtccacagg ccgacttgag tggttacacc catgacgggt cctttcaaca atatgccact    480
gccgatgctg ttcaggcagc aagattcct cagggcactg atttggctca gttgcgcca     540
attttatgtg caggtattac tgtctataag gcttttaaaga ctgcagaatt aagaccaggt    600
caatgggttg ccatttctgg tgctgctgga ggtttaggtt ctcttgctgt tcaatatgcc    660
aaggccatgg gtttgagagt tttgggtatt gatggtggtg aggagaaggg caagtttgca    720
aagtctcttg gagctgaagt tttcattgat ttcaccaaat ccaaggacat tgtcaaggat    780
atccaagagg ccaccaatgg tggtccacat ggtgtcatta atgtttctgt ttctccagct    840
gctatttctc aaagtaccca gtatgtcaga accttgggta aggttgtcct tgttggatta    900
ccagcgcatg ctgtatgcga gtcttcggtt ttcgaccatg ttgtcaagtc gattcaaatt    960
agaggctctt atgttggtaa cagggaagat actagtgagg ctattgattt tttcaccagg   1020
ggtttagtga agtcaccaat taagattgtt ggtttgagtg agttgccaaa gatctatgaa   1080
ttgatggagc aaggtaagat tttaggcaga tatgttgttg acacttcgaa atga         1134

<210> SEQ ID NO 110
<211> LENGTH: 377
<212> TYPE: PRT
<213> ORGANISM: Issatchenkia orientalis

<400> SEQUENCE: 110

Met Leu Ser Lys Thr Ile Thr Ala Ala Leu Arg Gly Asn Thr Thr Arg
1               5                   10                  15

Thr Ala Phe Arg Ile Asn Ala Ile Arg Ser Leu Ala Ile Pro Ala Ile
                20                  25                  30

Pro Glu Thr Gln Lys Gly Val Ile Phe Tyr Glu Asn Gly Gly Glu Leu
            35                  40                  45

Phe Tyr Lys Asp Ile Pro Val Pro Lys Pro Lys Pro Asn Glu Ile Leu
        50                  55                  60

Val Asn Val Lys Tyr Ser Gly Val Cys His Thr Asp Leu His Ala Trp
65                  70                  75                  80

Lys Gly Asp Trp Pro Leu Ala Thr Lys Leu Pro Leu Val Gly Gly His
                85                  90                  95

Glu Gly Ala Gly Val Val Ala Lys Gly Asp Asn Val Thr Asn Phe
            100                 105                 110

Glu Ile Gly Asp Tyr Ala Gly Ile Lys Trp Leu Asn Gly Ser Cys Met
        115                 120                 125

Gly Cys Glu Phe Cys Gln Gln Gly Ala Glu Pro Asn Cys Pro Gln Ala
130                 135                 140

Asp Leu Ser Gly Tyr Thr His Asp Gly Ser Phe Gln Gln Tyr Ala Thr
145                 150                 155                 160

Ala Asp Ala Val Gln Ala Ala Lys Ile Pro Gln Gly Thr Asp Leu Ala
                165                 170                 175

Gln Val Ala Pro Ile Leu Cys Ala Gly Ile Thr Val Tyr Lys Ala Leu
            180                 185                 190

Lys Thr Ala Glu Leu Arg Pro Gly Gln Trp Val Ala Ile Ser Gly Ala
        195                 200                 205

Ala Gly Gly Leu Gly Ser Leu Ala Val Gln Tyr Ala Lys Ala Met Gly
210                 215                 220

Leu Arg Val Leu Gly Ile Asp Gly Gly Glu Glu Lys Gly Lys Phe Ala
225                 230                 235                 240

Lys Ser Leu Gly Ala Glu Val Phe Ile Asp Phe Thr Lys Ser Lys Asp
                245                 250                 255

Ile Val Lys Asp Ile Gln Glu Ala Thr Asn Gly Gly Pro His Gly Val
            260                 265                 270

Ile Asn Val Ser Val Ser Pro Ala Ala Ile Ser Gln Ser Thr Gln Tyr
        275                 280                 285

Val Arg Thr Leu Gly Lys Val Val Leu Val Gly Leu Pro Ala His Ala
290                 295                 300

Val Cys Glu Ser Ser Val Phe Asp His Val Val Lys Ser Ile Gln Ile
305                 310                 315                 320

Arg Gly Ser Tyr Val Gly Asn Arg Glu Asp Thr Ser Glu Ala Ile Asp
                325                 330                 335

Phe Phe Thr Arg Gly Leu Val Lys Ser Pro Ile Lys Ile Val Gly Leu
            340                 345                 350

Ser Glu Leu Pro Lys Ile Tyr Glu Leu Met Glu Gln Gly Lys Ile Leu
        355                 360                 365

Gly Arg Tyr Val Val Asp Thr Ser Lys
370                 375

<210> SEQ ID NO 111
<211> LENGTH: 1347
<212> TYPE: DNA
<213> ORGANISM: Issatchenkia orientalis

<400> SEQUENCE: 111
atgtctcctt cacaaattaa cgttgacaac ttatctaatt ggactgaaga attcaaatct    60

```
gacgccaaga ctcaaatcgg gggttctgta ttgcaacatt ccaacattga tgaggtcttg    120
attaacagag atgcagaaat cgccaacaag catatcttca accacaagat tgaaattgaa    180
ggtctacctg tcatggatca gaaggcttct ggtagatgtt ggttgtttgc atcgactaac    240
ttgatgcgtg ttactgcaat gaagaaatac aatttgaagg aaatcaagct ttccccatcg    300
tatttgtttt tctatgacaa attggaaaga gcaaactatt tccttgaaca aatcatcgac    360
actcataagg aaccaatcga ttcaagattg gttcaatatt tcctgaccaa tccagttgaa    420
gatggtggtc aattcaccat gatggcacaa attgctacca aatacggtgt tgttcctgat    480
caagtctacc cagattcttt caacacaacc acttcgagga ttatgaacag attagtcaac    540
cacagattac gttcttatgc aatgacttta cgtaacgctc tagatgaagg taaagatgta    600
atgtccttga agaatgagat gcaaaaagaa atttatcgtt tgctaacaat gttccttggt    660
aacccaccaa agccaaacga gagtttgtc tgggaattca ccgataaaga tggtaaatat    720
gaatctatta aaactacacc attaaaatat gcaactgaag ttttggattt ccatgctcca    780
gaatatgttt ccttgttaaa tgacccaaga ataagtata caagatggt tcaagttgaa    840
agattaggta atgttgctgg tggcgaacca gttgcatact taaacttaga aattgaaaag    900
ttatctcaag ctgttgttaa cagaatcaaa aataacaaac cagttttctt tggtaccgat    960
acacctaaat ttatggataa aagtagaggt attatggata tcaatttatg ggactatgag   1020
ttattaggtt atgatgtccg taccatgtca agaaggaaa gagttgtttt tggtgattct   1080
ttaatgaccc acgctatgtt gattactgca gtgcacgttg atgaaaatgg caaacctgtc   1140
agatacagag tcgaaaacag ttggggtacc aagagtggtc aagaaggtta ttacacaatg   1200
acccaagaat attttgaaga gtacgtttat caagtagtca ttgaaaagag tgaatttgct   1260
gccctaaacc tcgatgtttc cattctggag gataaagaac cagtcgtctt gccaccttat   1320
gaccctatgg gtgcacttgc tttataa                                      1347
```

```
<210> SEQ ID NO 112
<211> LENGTH: 448
<212> TYPE: PRT
<213> ORGANISM: Issatchenkia orientalis

<400> SEQUENCE: 112

Met Ser Pro Ser Gln Ile Asn Val Asp Asn Leu Ser Asn Trp Thr Glu
1               5                   10                  15

Glu Phe Lys Ser Asp Ala Lys Thr Gln Ile Gly Gly Ser Val Leu Gln
            20                  25                  30

His Ser Asn Ile Asp Glu Val Leu Ile Asn Arg Asp Ala Glu Ile Ala
        35                  40                  45

Asn Lys His Ile Phe Asn His Lys Ile Glu Ile Glu Gly Leu Pro Val
    50                  55                  60

Met Asp Gln Lys Ala Ser Gly Arg Cys Trp Leu Phe Ala Ser Thr Asn
65                  70                  75                  80

Leu Met Arg Val Thr Ala Met Lys Lys Tyr Asn Leu Lys Glu Ile Lys
                85                  90                  95

Leu Ser Pro Ser Tyr Leu Phe Phe Tyr Asp Lys Leu Glu Arg Ala Asn
            100                 105                 110

Tyr Phe Leu Glu Gln Ile Ile Asp Thr His Lys Glu Pro Ile Asp Ser
        115                 120                 125

Arg Leu Val Gln Tyr Phe Leu Thr Asn Pro Val Glu Asp Gly Gly Gln
    130                 135                 140
```

```
Phe Thr Met Met Ala Gln Ile Ala Thr Lys Tyr Gly Val Val Pro Asp
145                 150                 155                 160

Gln Val Tyr Pro Asp Ser Phe Asn Thr Thr Ser Arg Ile Met Asn
                165                 170                 175

Arg Leu Val Asn His Arg Leu Arg Ser Tyr Ala Met Thr Leu Arg Asn
                180                 185                 190

Ala Leu Asp Glu Gly Lys Asp Val Met Ser Leu Lys Asn Glu Met Gln
            195                 200                 205

Lys Glu Ile Tyr Arg Leu Leu Thr Met Phe Leu Gly Asn Pro Pro Lys
        210                 215                 220

Pro Asn Glu Glu Phe Val Trp Glu Phe Thr Asp Lys Asp Gly Lys Tyr
225                 230                 235                 240

Glu Ser Ile Lys Thr Thr Pro Leu Lys Tyr Ala Thr Glu Val Leu Asp
                245                 250                 255

Phe His Ala Pro Glu Tyr Val Ser Leu Leu Asn Asp Pro Arg Asn Lys
                260                 265                 270

Tyr Asn Lys Met Val Gln Val Glu Arg Leu Gly Asn Val Ala Gly Gly
            275                 280                 285

Glu Pro Val Ala Tyr Leu Asn Leu Glu Ile Glu Lys Leu Ser Gln Ala
        290                 295                 300

Val Val Asn Arg Ile Lys Asn Asn Lys Pro Val Phe Phe Gly Thr Asp
305                 310                 315                 320

Thr Pro Lys Phe Met Asp Lys Ser Arg Gly Ile Met Asp Ile Asn Leu
                325                 330                 335

Trp Asp Tyr Glu Leu Leu Gly Tyr Asp Val Arg Thr Met Ser Lys Lys
                340                 345                 350

Glu Arg Val Val Phe Gly Asp Ser Leu Met Thr His Ala Met Leu Ile
            355                 360                 365

Thr Ala Val His Val Asp Glu Asn Gly Lys Pro Val Arg Tyr Arg Val
        370                 375                 380

Glu Asn Ser Trp Gly Thr Lys Ser Gly Gln Glu Gly Tyr Tyr Thr Met
385                 390                 395                 400

Thr Gln Glu Tyr Phe Glu Glu Tyr Val Tyr Gln Val Val Ile Glu Lys
                405                 410                 415

Ser Glu Phe Ala Ala Leu Asn Leu Asp Val Ser Ile Leu Glu Asp Lys
                420                 425                 430

Glu Pro Val Val Leu Pro Pro Tyr Asp Pro Met Gly Ala Leu Ala Leu
            435                 440                 445

<210> SEQ ID NO 113
<211> LENGTH: 1737
<212> TYPE: DNA
<213> ORGANISM: Issatchenkia orientalis

<400> SEQUENCE: 113
atgttactca gatcactaaa ctcttctgct cgttgtgtca acaaacaac cagaacaaag      60 gttaggtatc tcagccacgt cagtggtgca agcatggcga aacctacatt gaagaacaac     120
tcgagagaat ccaacaaatc cagaaactat ctaattgctg ctgtgacagc attggctgta     180
tcaacctcaa ttggagttgc cgtacatgtg aaggacccct tgtataacga tgctaccggc     240
agtgattctc cgagaagtat atctgttgac gagtttgtca agcataattc acaaaacgac     300
tgttggattg caatcaatgg caaggtttat gatttcactg atttattcc aaaccatcca     360 ggtggggtac ctccattagt taatcatgct ggttatgatg gtactaaact ttatgagaaa     420
```

```
ttgcatccaa aaggtacaat tgagaaattc ttgccaaagg ataagtttct gggtgtgtta    480
gatggtgaag cgccaaaatt ggaagcagac tatttggtgg acgatgatga acaagagaga    540
ctggattatt tgaacaactt acctcctttg tcatctattc agaatgttta tgatttcgaa    600
tacttggcca agaagatttt acctaaagat gcctgggcat attattcttg tggtgccgat    660
gatgaaatca caatgagaga aaccattat gcttatcaaa gagtttattt cagaccaaga     720
atttgtgttg atgtcaagga agttgatact tcttatgaaa tgttaggcac taaaacctct    780
gttccttttt atgtatctgc caccgctttg gctaaattag gccatcctga tggtgaatgc    840
tcaattgcta gaggcgctgg taaggaaggt gtcgttcaaa tgatttcgac cctttcctca    900
atgtcattag atgaaattgc cgctgctaga attccaggtg caacccaatg gttccaatta    960
tacattaatg aggatagaaa tgtcgctaaa ggtctggtca acatgcaga agacttgggt    1020 atgaaggcta tctttataac tgttgatgct ccttctctag gtaacagaga aaaggataaa    1080
agattaaagt ttgttaatga caccgatgtc gatttgggtg attccgcaga tcgaaacagt    1140
ggtgcttcaa aggcactatc ttcgttcatt gatgcttctg tctcttggaa tgacgtcaaa    1200
gcggtcaagt cgtggactaa attgcctgtc ttagttaaag gtgttcaaac agttgaagac    1260
gttattgaag cttacgatgc tggttgtcaa ggtgttgttt tgtcaaacca cggtggtagg    1320
caactagata ctgctcctcc tccaatcgaa ttattagctg aaactgttcc aactttgaag    1380
agattgggta aattaagacc agattttgaa attttaattg acggtggtgt caaaagaggt    1440
accgatattt tgaaagcagt cgcaatcggt ggccaagatg tcagagtttc agttggtatg    1500
ggtagacctt tctatatgc caactcttgc tatggtgaag caggtgttag aaaattaatt     1560
caaaatctaa aggatgaatt agaaatggat atgagattgt tgggtgtcac taaaatggac    1620
cagctatctt cgaaacatgt cgatactaaa cgtttgattg gtagagatgc gatcaactat    1680
ttgtatgata atgtatacag cccaatcgaa accgttaaat tcaacaatga agattga       1737
```

<210> SEQ ID NO 114
<211> LENGTH: 578
<212> TYPE: PRT
<213> ORGANISM: Issatchenkia orientalis

<400> SEQUENCE: 114

```
Met Leu Leu Arg Ser Leu Asn Ser Ser Ala Arg Cys Val Lys Gln Thr
1               5                   10                  15

Thr Arg Thr Lys Val Arg Tyr Leu Ser His Val Ser Gly Ala Ser Met
            20                  25                  30

Ala Lys Pro Thr Leu Lys Asn Asn Ser Arg Glu Ser Asn Lys Ser Arg
        35                  40                  45

Asn Tyr Leu Ile Ala Ala Val Thr Ala Leu Ala Val Ser Thr Ser Ile
    50                  55                  60

Gly Val Ala Val His Val Lys Asp Pro Leu Tyr Asn Asp Ala Thr Gly
65                  70                  75                  80

Ser Asp Ser Pro Arg Ser Ile Ser Val Asp Glu Phe Val Lys His Asn
                85                  90                  95

Ser Gln Asn Asp Cys Trp Ile Ala Ile Asn Gly Lys Val Tyr Asp Phe
            100                 105                 110

Thr Asp Phe Ile Pro Asn His Pro Gly Gly Val Pro Pro Leu Val Asn
        115                 120                 125

His Ala Gly Tyr Asp Gly Thr Lys Leu Tyr Glu Lys Leu His Pro Lys
    130                 135                 140
```

```
Gly Thr Ile Glu Lys Phe Leu Pro Lys Asp Lys Phe Leu Gly Val Leu
145                 150                 155                 160

Asp Gly Glu Ala Pro Lys Leu Glu Ala Asp Tyr Leu Val Asp Asp Asp
            165                 170                 175

Glu Gln Glu Arg Leu Asp Tyr Leu Asn Asn Leu Pro Pro Leu Ser Ser
        180                 185                 190

Ile Gln Asn Val Tyr Asp Phe Glu Tyr Leu Ala Lys Lys Ile Leu Pro
    195                 200                 205

Lys Asp Ala Trp Ala Tyr Tyr Ser Cys Gly Ala Asp Asp Glu Ile Thr
210                 215                 220

Met Arg Glu Asn His Tyr Ala Tyr Gln Arg Val Tyr Phe Arg Pro Arg
225                 230                 235                 240

Ile Cys Val Asp Val Lys Glu Val Asp Thr Ser Tyr Glu Met Leu Gly
            245                 250                 255

Thr Lys Thr Ser Val Pro Phe Tyr Val Ser Ala Thr Ala Leu Ala Lys
            260                 265                 270

Leu Gly His Pro Asp Gly Glu Cys Ser Ile Ala Arg Gly Ala Gly Lys
        275                 280                 285

Glu Gly Val Val Gln Met Ile Ser Thr Leu Ser Ser Met Ser Leu Asp
290                 295                 300

Glu Ile Ala Ala Ala Arg Ile Pro Gly Ala Thr Gln Trp Phe Gln Leu
305                 310                 315                 320

Tyr Ile Asn Glu Asp Arg Asn Val Ala Lys Gly Leu Val Lys His Ala
            325                 330                 335

Glu Asp Leu Gly Met Lys Ala Ile Phe Ile Thr Val Asp Ala Pro Ser
        340                 345                 350

Leu Gly Asn Arg Glu Lys Asp Lys Arg Leu Lys Phe Val Asn Asp Thr
        355                 360                 365

Asp Val Asp Leu Gly Asp Ser Ala Asp Arg Asn Ser Gly Ala Ser Lys
        370                 375                 380

Ala Leu Ser Ser Phe Ile Asp Ala Ser Val Ser Trp Asn Asp Val Lys
385                 390                 395                 400

Ala Val Lys Ser Trp Thr Lys Leu Pro Val Leu Val Lys Gly Val Gln
            405                 410                 415

Thr Val Glu Asp Val Ile Glu Ala Tyr Asp Ala Gly Cys Gln Gly Val
            420                 425                 430

Val Leu Ser Asn His Gly Gly Arg Gln Leu Asp Thr Ala Pro Pro
            435                 440                 445

Ile Glu Leu Leu Ala Glu Thr Val Pro Thr Leu Lys Arg Leu Gly Lys
450                 455                 460

Leu Arg Pro Asp Phe Glu Ile Leu Ile Asp Gly Gly Val Lys Arg Gly
465                 470                 475                 480

Thr Asp Ile Leu Lys Ala Val Ala Ile Gly Gly Gln Asp Val Arg Val
            485                 490                 495

Ser Val Gly Met Gly Arg Pro Phe Leu Tyr Ala Asn Ser Cys Tyr Gly
        500                 505                 510

Glu Ala Gly Val Arg Lys Leu Ile Gln Asn Leu Lys Asp Glu Leu Glu
        515                 520                 525

Met Asp Met Arg Leu Leu Gly Val Thr Lys Met Asp Gln Leu Ser Ser
        530                 535                 540

Lys His Val Asp Thr Lys Arg Leu Ile Gly Arg Asp Ala Ile Asn Tyr
545                 550                 555                 560

Leu Tyr Asp Asn Val Tyr Ser Pro Ile Glu Thr Val Lys Phe Asn Asn
```

Glu Asp

<210> SEQ ID NO 115
<211> LENGTH: 1698
<212> TYPE: DNA
<213> ORGANISM: Issatchenkia orientalis
<220> FEATURE:
<221> NAME/KEY: misc_feature
<222> LOCATION: (941)..(941)
<223> OTHER INFORMATION: N= A, C, T, or G
<220> FEATURE:
<221> NAME/KEY: misc_feature
<222> LOCATION: (943)..(943)
<223> OTHER INFORMATION: N= A, C, T, or G

<400> SEQUENCE: 115

```
atgttaagat cccagttcaa aaacattttg aaaaatgtta acaagaacca ttctctaagg      60
agaactttta cttccagcac ctcaaaggct ggaaaaaatg cttcatacaa tgccaagatt     120
atatctgcaa ccgtggcctc gattgttgca gcagctggct cttatatgtt ggtccagcct     180
tcactagcta atgatgaggc acagtctgct aatccaacta ggaagatctc tgttgacgaa     240
tttgttaaac acaaccatgc cgatgattgt tggatcactg ttaacggtaa cgtctatgac     300
ttgactgatt tcatttcaat gcatccaggt ggtactaccc cattgattca aaatgcaggt     360
cacgacgcaa ctgaaattta caacaagatt catccaaagg gtacaatcga gaacttctta     420
ccaaaggaaa agcaattggg tgttttggat ggtgaagctc ctaaaatcga gttgtgctt      480
gacgaaaagg agaaacacag attggagttg ttgaatcatc tccctgctct ttccagaatt     540
caaaacattt atgatttcga acatattgct tctagagttt gagcgaccaa gcatggaac      600
tactattcat gtggtgccga agatgaaatc accttgaggg aaaatcatta tgcttaccaa     660
agaatctact ttaagccaaa atgttgtgtc aatgttgcag aagttgatac ctctcatgaa     720
attttaggta caaaagcttc tgttcctttc tacgtttccg cagccgcttc tgcaaagttg     780
gggcacgagg atggtgaatg ttccattgct agaggtgcag gtaaggaagg cgttattcaa     840
atgatttctt ccttctcttc caactctttg gaggaaattg cagaatccag aattcctggt     900
gcaacacaat ggtttcaatt atacgttaat gaagacaagg ntnttgtgaa gaagacttta     960
aaaagggccg aaaacttggg tatgaaggcc atctttgtca ctgtggacgc tgctagtaga    1020
ggtaatagag aaaaagacat tacaatgaga attaccgaag atacagatga gttaatagac    1080
gattcttctg ttagagctgg ttctaccctct ggtgcattgc cagctttcat tgacaagagg    1140
ctgacttggg atgaagttaa ggatatcatt tcatggacca agttaccagt tttgctgaag    1200
ggtgttcaaa gaactgatga tattgagaag gcaattgata ttggttgtaa gggtgttgtc    1260
ttgtccaatc atggtggtag acaattagat acttctcctc ctccaataga agttatggct    1320
gaatctgttc caatcctaaa gcaaaagggt aaactggatc caaatttcag tattttcgtt    1380
gatggtggtg ttagaagagg tacagatatt ttgaaagctt tggctattgg tggcagagac    1440
tgtaaagttg ctgttggtct gggtagacct ttcctttatg caaatactgg ttatggtgaa    1500
aagggtgtca gaaaggccgt gcaaattcta agagaagaat taaaggctga catgagaatg    1560
ttgggcgtta cctctttgaa cgagctagac gactcttaca ttgacaccag aagattacta    1620
ggtagagatg ctgttaacca catatacaac aacaactact acccaatgtc taagattcaa    1680
ttcaaaaacg aaaaataa                                                  1698
```

```
<210> SEQ ID NO 116
<211> LENGTH: 565
<212> TYPE: PRT
<213> ORGANISM: Issatchenkia orientalis
<220> FEATURE:
<221> NAME/KEY: MISC_FEATURE
<222> LOCATION: (314)..(314)
<223> OTHER INFORMATION: Xaa = Asp, Gly, Ala, or Val
<220> FEATURE:
<221> NAME/KEY: MISC_FEATURE
<222> LOCATION: (315)..(315)
<223> OTHER INFORMATION: Xaa = Ile, Val, Leu, or Phe

<400> SEQUENCE: 116
```

Met Leu Arg Ser Gln Phe Lys Asn Ile Leu Lys Asn Val Asn Lys Asn
1               5                   10                  15

His Ser Leu Arg Arg Thr Phe Thr Ser Ser Thr Ser Lys Ala Gly Lys
            20                  25                  30

Asn Ala Ser Tyr Asn Ala Lys Ile Ile Ser Ala Thr Val Ala Ser Ile
        35                  40                  45

Val Ala Ala Ala Gly Ser Tyr Met Leu Val Gln Pro Ser Leu Ala Asn
    50                  55                  60

Asp Glu Ala Gln Ser Ala Asn Pro Thr Arg Lys Ile Ser Val Asp Glu
65                  70                  75                  80

Phe Val Lys His Asn His Ala Asp Asp Cys Trp Ile Thr Val Asn Gly
                85                  90                  95

Asn Val Tyr Asp Leu Thr Asp Phe Ile Ser Met His Pro Gly Gly Thr
            100                 105                 110

Thr Pro Leu Ile Gln Asn Ala Gly His Asp Ala Thr Glu Ile Tyr Asn
        115                 120                 125

Lys Ile His Pro Lys Gly Thr Ile Glu Asn Phe Leu Pro Lys Glu Lys
    130                 135                 140

Gln Leu Gly Val Leu Asp Gly Glu Ala Pro Lys Ile Glu Val Val Leu
145                 150                 155                 160

Asp Glu Lys Glu Lys His Arg Leu Glu Leu Asn His Leu Pro Ala
                165                 170                 175

Leu Ser Arg Ile Gln Asn Ile Tyr Asp Phe Glu His Ile Ala Ser Arg
            180                 185                 190

Val Leu Ser Asp Gln Ala Trp Asn Tyr Tyr Ser Cys Gly Ala Glu Asp
        195                 200                 205

Glu Ile Thr Leu Arg Glu Asn His Tyr Ala Tyr Gln Arg Ile Tyr Phe
    210                 215                 220

Lys Pro Lys Cys Cys Val Asn Val Ala Glu Val Asp Thr Ser His Glu
225                 230                 235                 240

Ile Leu Gly Thr Lys Ala Ser Val Pro Phe Tyr Val Ser Ala Ala Ala
                245                 250                 255

Ser Ala Lys Leu Gly His Glu Asp Gly Glu Cys Ser Ile Ala Arg Gly
            260                 265                 270

Ala Gly Lys Glu Gly Val Ile Gln Met Ile Ser Ser Phe Ser Ser Asn
        275                 280                 285

Ser Leu Glu Glu Ile Ala Glu Ser Arg Ile Pro Gly Ala Thr Gln Trp
    290                 295                 300

Phe Gln Leu Tyr Val Asn Glu Asp Lys Xaa Xaa Val Lys Lys Thr Leu
305                 310                 315                 320

Lys Arg Ala Glu Asn Leu Gly Met Lys Ala Ile Phe Val Thr Val Asp
                325                 330                 335

Ala Ala Ser Arg Gly Asn Arg Glu Lys Asp Ile Thr Met Arg Ile Thr

```
              340              345              350
Glu Asp Thr Asp Glu Leu Ile Asp Asp Ser Ser Val Arg Ala Gly Ser
        355                  360                  365
Thr Ser Gly Ala Leu Pro Ala Phe Ile Asp Lys Arg Leu Thr Trp Asp
        370                  375                  380
Glu Val Lys Asp Ile Ile Ser Trp Thr Lys Leu Pro Val Leu Leu Lys
385                  390                  395                  400
Gly Val Gln Arg Thr Asp Asp Ile Glu Lys Ala Ile Asp Ile Gly Cys
                405                  410                  415
Lys Gly Val Val Leu Ser Asn His Gly Gly Arg Gln Leu Asp Thr Ser
                420                  425                  430
Pro Pro Pro Ile Glu Val Met Ala Glu Ser Val Pro Ile Leu Lys Gln
                435                  440                  445
Lys Gly Lys Leu Asp Pro Asn Phe Ser Ile Phe Val Asp Gly Gly Val
        450                  455                  460
Arg Arg Gly Thr Asp Ile Leu Lys Ala Leu Ala Ile Gly Gly Arg Asp
465                  470                  475                  480
Cys Lys Val Ala Val Gly Leu Gly Arg Pro Phe Leu Tyr Ala Asn Thr
                485                  490                  495
Gly Tyr Gly Glu Lys Gly Val Arg Lys Ala Val Gln Ile Leu Arg Glu
                500                  505                  510
Glu Leu Lys Ala Asp Met Arg Met Leu Gly Val Thr Ser Leu Asn Glu
                515                  520                  525
Leu Asp Asp Ser Tyr Ile Asp Thr Arg Arg Leu Leu Gly Arg Asp Ala
        530                  535                  540
Val Asn His Ile Tyr Asn Asn Tyr Tyr Pro Met Ser Lys Ile Gln
545                  550                  555                  560
Phe Lys Asn Glu Lys
                565

<210> SEQ ID NO 117
<211> LENGTH: 1167
<212> TYPE: DNA
<213> ORGANISM: Issatchenkia orientalis

<400> SEQUENCE: 117
atggtgtccc ctgctgaaag attatctact attgcgtcca caatcaagcc aaacagaaaa     60
gattctacat cattacaacc agaagactat ccggaacatc cgttcaaggt gacggttgtt    120
ggttccggta actgggggtg tacaattgcc aaggttatag cggaaaacac cgttgagaga    180
cctcgtcaat ttcaaagaga tgttaatatg tgggtctatg aagaattgat tgaaggcgaa    240
aagttgactg aaatcataaa taccaaacac gaaaacgtca agtacttgcc aggtatcaag    300
ttgccagtta acgttgttgc agttccagac attgttgagg cttgtgcagg ctcagacttg    360
attgtcttta atattcctca ccaattttta ccaagaattt tatcccaatt aaagggtaag    420
gtgaatccaa aggctagagc aatttcttgt ttgaaaggtt tggatgtcaa tcctaatgga    480
tgtaagttgc tctccactgt tattactgaa gagttgggta tttattgtgg tgccttatca    540
ggtgctaatt tagctcctga agttgcacaa tgtaaatggt cggaaacaac tgttgcatat    600
acaattccgg acgatttcag aggtaaaggc aaggatattg accatcaaat tctaaagagt    660
ttgttccata gaccttattt ccatgttcgt gttattagtg atgttgcagg tatttccatt    720
gccggtgcac tcaagaatgt cgttgctatg gctgctggat tgtcgaaggc tttaggttgg    780
ggtgataatg caaaggctgc agtcatgaga ataggtttgg tggaaaccat tcaatttgcc    840
```

```
aagactttt tcgatggctg tcatgctgca acctttactc atgaatctgc aggtgttgcc      900
gacctaatca ctacctgtgc cggcggccgt aacgttagag ttggtagata tatggcacaa      960
cattctgtct ctgcaacgga ggctgaagaa aagttgttga atggccaatc ctgtcaaggt     1020
atccacacaa ctagggaagt ttacgagttc ctctccaaca tgggcaggac agatgagttc     1080
ccactattta ccaccaccta ccgtatcatc tacgaaaact tcccaattga agctgcca      1140 gaatgccttg aacctgtgga agattaa                                          1167
```

<210> SEQ ID NO 118
<211> LENGTH: 388
<212> TYPE: PRT
<213> ORGANISM: Issatchenkia orientalis

<400> SEQUENCE: 118

```
Met Val Ser Pro Ala Glu Arg Leu Ser Thr Ile Ala Ser Thr Ile Lys
1               5                   10                  15

Pro Asn Arg Lys Asp Ser Thr Ser Leu Gln Pro Glu Asp Tyr Pro Glu
            20                  25                  30

His Pro Phe Lys Val Thr Val Val Gly Ser Gly Asn Trp Gly Cys Thr
        35                  40                  45

Ile Ala Lys Val Ile Ala Glu Asn Thr Val Glu Arg Pro Arg Gln Phe
    50                  55                  60

Gln Arg Asp Val Asn Met Trp Val Tyr Glu Glu Leu Ile Glu Gly Glu
65                  70                  75                  80

Lys Leu Thr Glu Ile Ile Asn Thr Lys His Glu Asn Val Lys Tyr Leu
                85                  90                  95

Pro Gly Ile Lys Leu Pro Val Asn Val Val Ala Val Pro Asp Ile Val
            100                 105                 110

Glu Ala Cys Ala Gly Ser Asp Leu Ile Val Phe Asn Ile Pro His Gln
        115                 120                 125

Phe Leu Pro Arg Ile Leu Ser Gln Leu Lys Gly Lys Val Asn Pro Lys
    130                 135                 140

Ala Arg Ala Ile Ser Cys Leu Lys Gly Leu Asp Val Asn Pro Asn Gly
145                 150                 155                 160

Cys Lys Leu Leu Ser Thr Val Ile Thr Glu Glu Leu Gly Ile Tyr Cys
                165                 170                 175

Gly Ala Leu Ser Gly Ala Asn Leu Ala Pro Glu Val Ala Gln Cys Lys
            180                 185                 190

Trp Ser Glu Thr Thr Val Ala Tyr Thr Ile Pro Asp Asp Phe Arg Gly
        195                 200                 205

Lys Gly Lys Asp Ile Asp His Gln Ile Leu Lys Ser Leu Phe His Arg
    210                 215                 220

Pro Tyr Phe His Val Arg Val Ile Ser Asp Val Ala Gly Ile Ser Ile
225                 230                 235                 240

Ala Gly Ala Leu Lys Asn Val Val Ala Met Ala Gly Phe Val Glu
                245                 250                 255

Gly Leu Gly Trp Gly Asp Asn Ala Lys Ala Ala Val Met Arg Ile Gly
            260                 265                 270

Leu Val Glu Thr Ile Gln Phe Ala Lys Thr Phe Phe Asp Gly Cys His
        275                 280                 285

Ala Ala Thr Phe Thr His Glu Ser Ala Gly Val Ala Asp Leu Ile Thr
    290                 295                 300

Thr Cys Ala Gly Gly Arg Asn Val Arg Val Gly Arg Tyr Met Ala Gln
```

```
                305                 310                 315                 320
His Ser Val Ser Ala Thr Glu Ala Glu Lys Leu Leu Asn Gly Gln
                    325                 330                 335

Ser Cys Gln Gly Ile His Thr Thr Arg Glu Val Tyr Glu Phe Leu Ser
                    340                 345                 350

Asn Met Gly Arg Thr Asp Glu Phe Pro Leu Phe Thr Thr Thr Tyr Arg
                    355                 360                 365

Ile Ile Tyr Glu Asn Phe Pro Ile Glu Lys Leu Pro Glu Cys Leu Glu
                    370                 375                 380

Pro Val Glu Asp
385

<210> SEQ ID NO 119
<211> LENGTH: 1566
<212> TYPE: DNA
<213> ORGANISM: Issatchenkia orientalis

<400> SEQUENCE: 119
atgttgtccc tctctaaaca gtcaagaaac tttttcaaat tgaactattt ttcagtcacc      60
caaatagcaa aaatgtctgc aacttccgtc actttcccaa ttatcaacga aacttaccaa     120
cagccaaccg ggcttttcat caacaatgaa tttgttagtg caaagtcagg taagactttt     180
gatgttaaca ccccaattga tgagtctctc atttgtaaag tccaacaggc cgatgctgaa     240
gatgttgaaa ttgccgttca agcagcatct aaagcttaca gacttggag atttacaccg      300 ccaaatgaaa gaggcagata cttgaacaaa ttggccgatt tgatggacga aagagagac      360 ttacttgcca aaattgaatc ccttgataat ggtaaggcct acattgtgc aaaattcgat      420 gtcaatcttg tcattgaata tttcagatac tgtgcaggtt actgtgataa aatcgatggt     480
agaacaatta caaccgatgt agaacatttt acctacacta gaaaggaacc tttaggtgtc     540
tgtggtgcaa ttacaccttg gaacttccca ttgctgatgt ttgcttggaa aatcggcccg     600
gctttagcaa ccggtaatac cattatcttg aagcctgcca gtgcaacacc tctatcaaac     660
ctctttactt gtaccttgat caaggaggcg ggcattccag ccggtgttgt taatgttgtt     720
ccaggttccg gtagaggctg tggtaactcc attttacaac atcctaaaat taagaaggtt     780
gcgtttaccg gatctacaga agttggtaaa actgttatga ggaatgtgc taattccatc      840 aaaaaggtta ctctcgaatt gggtggtaag tctccaaaca ttgttttcaa agactgtaac     900
gttgaacaaa ccattcaaaa tttgattact ggtatttttct tcaatggtgg tgaagtctgt    960
tgtgctggtt ctagaattta cattgaagca accgatgaga aatggtatac tgaattcttg    1020
accaaattca aggagactgt tgaaaaatta aagattggta acccatttga gagggtgtt    1080 ttccaaggtg cacaaaccac tccagatcaa ttccaaactg tcttggacta catcaccgct    1140
gctaacgaat ccagcttgaa actattaact ggtggtaaaa gaattggcaa taagggatac    1200
tttgttgagc caactatctt ctacgatgtt cctcaaaatt ccaagttaac tcaagaagaa    1260
atctttggtc cagttgctgt tgttttacct ttcaagtcca ctgaagaatt gattgaaaag    1320
gcaaatgatt ccgattttgg cttaggttcc ggtattcaca ctgaagattt caacaaggca    1380
atttgggttt ccgaaaggct tgaagcaggt tctgtttgga tcaacactta caatgatttc    1440
cacccagctg ctccattcgg tggttacaag gaatccggta ttggcagaga aatgggtatt    1500
gaagctttcg acaactatac tcaaaccaag ttagttagag ctagagttaa caagccagct    1560
ttttag                                                               1566
```

-continued

```
<210> SEQ ID NO 120
<211> LENGTH: 521
<212> TYPE: PRT
<213> ORGANISM: Issatchenkia orientalis

<400> SEQUENCE: 120

Met Leu Ser Leu Ser Lys Gln Ser Arg Asn Phe Phe Lys Leu Asn Tyr
1               5                   10                  15

Phe Ser Val Thr Gln Ile Ala Lys Met Ser Ala Thr Ser Val Thr Phe
            20                  25                  30

Pro Ile Ile Asn Glu Thr Tyr Gln Gln Pro Thr Gly Leu Phe Ile Asn
        35                  40                  45

Asn Glu Phe Val Ser Ala Lys Ser Gly Lys Thr Phe Asp Val Asn Thr
    50                  55                  60

Pro Ile Asp Glu Ser Leu Ile Cys Lys Val Gln Ala Asp Ala Glu
65                  70                  75                  80

Asp Val Glu Ile Ala Val Gln Ala Ala Ser Lys Ala Tyr Lys Thr Trp
                85                  90                  95

Arg Phe Thr Pro Pro Asn Glu Arg Gly Arg Tyr Leu Asn Lys Leu Ala
            100                 105                 110

Asp Leu Met Asp Glu Lys Arg Asp Leu Leu Ala Lys Ile Glu Ser Leu
        115                 120                 125

Asp Asn Gly Lys Ala Leu His Cys Ala Lys Phe Asp Val Asn Leu Val
    130                 135                 140

Ile Glu Tyr Phe Arg Tyr Cys Ala Gly Tyr Cys Asp Lys Ile Asp Gly
145                 150                 155                 160

Arg Thr Ile Thr Thr Asp Val Glu His Phe Thr Tyr Thr Arg Lys Glu
                165                 170                 175

Pro Leu Gly Val Cys Gly Ala Ile Thr Pro Trp Asn Phe Pro Leu Leu
            180                 185                 190

Met Phe Ala Trp Lys Ile Gly Pro Ala Leu Ala Thr Gly Asn Thr Ile
        195                 200                 205

Ile Leu Lys Pro Ala Ser Ala Thr Pro Leu Ser Asn Leu Phe Thr Cys
    210                 215                 220

Thr Leu Ile Lys Glu Ala Gly Ile Pro Ala Gly Val Val Asn Val Val
225                 230                 235                 240

Pro Gly Ser Gly Arg Gly Cys Gly Asn Ser Ile Leu Gln His Pro Lys
                245                 250                 255

Ile Lys Lys Val Ala Phe Thr Gly Ser Thr Glu Val Gly Lys Thr Val
            260                 265                 270

Met Lys Glu Cys Ala Asn Ser Ile Lys Lys Val Thr Leu Glu Leu Gly
        275                 280                 285

Gly Lys Ser Pro Asn Ile Val Phe Lys Asp Cys Asn Val Glu Gln Thr
    290                 295                 300

Ile Gln Asn Leu Ile Thr Gly Ile Phe Phe Asn Gly Gly Glu Val Cys
305                 310                 315                 320

Cys Ala Gly Ser Arg Ile Tyr Ile Glu Ala Thr Asp Glu Lys Trp Tyr
                325                 330                 335

Thr Glu Phe Leu Thr Lys Phe Glu Thr Val Glu Lys Leu Lys Ile
            340                 345                 350

Gly Asn Pro Phe Glu Glu Gly Val Phe Gln Gly Ala Gln Thr Thr Pro
        355                 360                 365

Asp Gln Phe Gln Thr Val Leu Asp Tyr Ile Thr Ala Ala Asn Glu Ser
    370                 375                 380
```

Ser Leu Lys Leu Leu Thr Gly Gly Lys Arg Ile Gly Asn Lys Gly Tyr
385                 390                 395                 400

Phe Val Glu Pro Thr Ile Phe Tyr Asp Val Pro Gln Asn Ser Lys Leu
            405                 410                 415

Thr Gln Glu Glu Ile Phe Gly Pro Val Ala Val Leu Pro Phe Lys
        420                 425                 430

Ser Thr Glu Glu Leu Ile Glu Lys Ala Asn Asp Ser Asp Phe Gly Leu
        435                 440                 445

Gly Ser Gly Ile His Thr Glu Asp Phe Asn Lys Ala Ile Trp Val Ser
        450                 455                 460

Glu Arg Leu Glu Ala Gly Ser Val Trp Ile Asn Thr Tyr Asn Asp Phe
465                 470                 475                 480

His Pro Ala Ala Pro Phe Gly Gly Tyr Lys Glu Ser Gly Ile Gly Arg
                485                 490                 495

Glu Met Gly Ile Glu Ala Phe Asp Asn Tyr Thr Gln Thr Lys Leu Val
            500                 505                 510

Arg Ala Arg Val Asn Lys Pro Ala Phe
            515                 520

<210> SEQ ID NO 121
<211> LENGTH: 1506
<212> TYPE: DNA
<213> ORGANISM: Issatchenkia orientalis

<400> SEQUENCE: 121

```
atgtcagcac tgttcagaac cattgagact ccaaacggta aaaccctgga acaaccactg      60
ggtctcttca tcgacaatga gtgggtgaaa acaaaccgta cttttgagac cattaatccg     120
tccacaggtg aggcgatctg tcatgtttac cgtgctgggg tccaggaggt gaacgacgct     180
gtcgaagctg caaatagagc atttagaaac gaatcttggt caggtctaac tggttctcaa     240
cgtggcgatt tactgtatcg catgtaccaa gttatcaaaa gagacgccga gagcattgca     300
tcgattgagt ccatggataa tggtaaaccg tatgctgcag aatgcctaga tggagattta     360
ggtgaagctg ctgacgtttt caaatattat gccggttggg ccgacaagat caccggtgaa     420
ctcattggct cgagtgtatt gggtaagaat aagatgtgtt atgtcgagcc tacaccactg     480
ggtgccgttg gcggtatagt cccttggaat ttcccgttta ccatgatggc atggaaaatt     540
gccccggcac tggcgacggg ttgtacagtg ttatgaagt caagtgaagt cacaccgttg     600
acggcattat ggtatggcaa gattgcactt gaagtgggtc tacctaaagg tgtacttaac     660
atcctctccg gttttggatc ggatgttgga tcggccatgg cttcacatcc aaagttggct     720
aagatagcgt tcactggctc aactgcaact ggtaaaaaaa tcatggaagc agcaggtggt     780
tccaacttga aaaaggttac actagagtgt ggtggtaaat ctccttacat tgtttttgat     840
gatgctgact agaattggc agtagaatgg gcatattggg gtatttggta taacaaaggt     900
gaggtttgta cttcaacttc gagatttttg attcaggaag acatttacga taagtttgtt     960
gagagttttg ttgagttgac caagacgaga gcaatcactg ctgatccgtt tgatgataga    1020
tgcactatcg ggcctttggt ttctagctca cagtacgaaa aagtcaaaaa gtacgttgaa    1080
ataggtaaaa atgaaggagc aaagctacta actggcaaat tcatcgacgg gccaggctat    1140
ttctgtgagc catttatctt cagtgaatgc actgacgata tgacaatcat gaaagaggaa    1200
atctttggcc ctgttgtggg gattactaaa ttctcaacgg ttaaagaggc gatcgagaga    1260
gccaatgcta cgacttacgg tttaggagct gcgttgtttt cctctaacat aacaaaggca    1320
```

```
cattctgtgg ctgccaagtt ggaggctgga atggtgtgga tcaattctaa tggtgattct    1380
gatatccaca ttccatttgg tggttccaaa atgagtggta taggtaggga gttggggcca    1440
tacgcactag acttgtttac tgagaaaaag gcagttcatg tcaacttatc gcttccggtc    1500
aagtga                                                               1506
```

<210> SEQ ID NO 122
<211> LENGTH: 501
<212> TYPE: PRT
<213> ORGANISM: Issatchenkia orientalis

<400> SEQUENCE: 122

```
Met Ser Ala Leu Phe Arg Thr Ile Glu Thr Pro Asn Gly Lys Thr Leu
1               5                   10                  15

Glu Gln Pro Leu Gly Leu Phe Ile Asp Asn Gly Trp Val Lys Thr Asn
            20                  25                  30

Arg Thr Phe Glu Thr Ile Asn Pro Ser Thr Gly Glu Ala Ile Cys His
        35                  40                  45

Val Tyr Arg Ala Gly Val Gln Glu Val Asn Asp Ala Val Glu Ala Ala
    50                  55                  60

Asn Arg Ala Phe Arg Asn Glu Ser Trp Ser Gly Leu Thr Gly Ser Gln
65                  70                  75                  80

Arg Gly Asp Leu Leu Tyr Arg Met Tyr Gln Val Ile Lys Arg Asp Ala
                85                  90                  95

Glu Ser Ile Ala Ser Ile Glu Ser Met Asp Asn Gly Lys Pro Tyr Ala
            100                 105                 110

Ala Glu Cys Leu Asp Gly Asp Leu Gly Glu Ala Ala Asp Val Phe Lys
        115                 120                 125

Tyr Tyr Ala Gly Trp Ala Asp Lys Ile Thr Gly Glu Leu Ile Gly Ser
    130                 135                 140

Ser Val Leu Gly Lys Asn Lys Met Cys Tyr Val Glu Pro Thr Pro Leu
145                 150                 155                 160

Gly Ala Val Gly Gly Ile Val Pro Trp Asn Phe Pro Phe Thr Met Met
                165                 170                 175

Ala Trp Lys Ile Ala Pro Ala Leu Ala Thr Gly Cys Thr Val Val Met
            180                 185                 190

Lys Ser Ser Glu Val Thr Pro Leu Thr Ala Leu Trp Tyr Gly Lys Ile
        195                 200                 205

Ala Leu Glu Val Gly Leu Pro Lys Gly Val Leu Asn Ile Leu Ser Gly
    210                 215                 220

Phe Gly Ser Asp Val Gly Ser Ala Met Ala Ser His Pro Lys Leu Ala
225                 230                 235                 240

Lys Ile Ala Phe Thr Gly Ser Thr Ala Thr Gly Lys Lys Ile Met Glu
                245                 250                 255

Ala Ala Gly Gly Ser Asn Leu Lys Lys Val Thr Leu Glu Cys Gly Gly
            260                 265                 270

Lys Ser Pro Tyr Ile Val Phe Asp Asp Ala Asp Leu Glu Leu Ala Val
        275                 280                 285

Glu Trp Ala Tyr Trp Gly Ile Trp Tyr Asn Lys Gly Glu Val Cys Thr
    290                 295                 300

Ser Thr Ser Arg Phe Leu Ile Gln Glu Asp Ile Tyr Asp Lys Phe Val
305                 310                 315                 320

Glu Ser Phe Val Glu Leu Thr Lys Thr Arg Ala Ile Thr Ala Asp Pro
                325                 330                 335
```

```
Phe Asp Asp Arg Cys Thr Ile Gly Pro Leu Val Ser Ser Gln Tyr
            340                 345                 350
Glu Lys Val Lys Lys Tyr Val Glu Ile Gly Lys Asn Glu Gly Ala Lys
            355                 360                 365
Leu Leu Thr Gly Lys Phe Ile Asp Gly Pro Gly Tyr Phe Cys Glu Pro
        370                 375                 380
Phe Ile Phe Ser Glu Cys Thr Asp Asp Met Thr Ile Met Lys Glu Glu
385                 390                 395                 400
Ile Phe Gly Pro Val Val Gly Ile Thr Lys Phe Ser Thr Val Lys Glu
                405                 410                 415
Ala Ile Glu Arg Ala Asn Ala Thr Thr Tyr Gly Leu Gly Ala Ala Leu
            420                 425                 430
Phe Ser Ser Asn Ile Thr Lys Ala His Ser Val Ala Ala Lys Leu Glu
        435                 440                 445
Ala Gly Met Val Trp Ile Asn Ser Asn Gly Asp Ser Asp Ile His Ile
    450                 455                 460
Pro Phe Gly Gly Ser Lys Met Ser Gly Ile Gly Arg Glu Leu Gly Pro
465                 470                 475                 480
Tyr Ala Leu Asp Leu Phe Thr Glu Lys Lys Ala Val His Val Asn Leu
                485                 490                 495
Ser Leu Pro Val Lys
            500

<210> SEQ ID NO 123
<211> LENGTH: 1506
<212> TYPE: DNA
<213> ORGANISM: Issatchenkia orientalis

<400> SEQUENCE: 123
atggctcttc cacttgcaac tacaatctcc ttatcaagcg gcaaaacatt agaacagcca      60
attggtttat ttattgataa tgaatttgtc aatccaattt ctgtttctaa tgcaagaaca     120
ctaacaacct tcaacccaag cacaggtgag ccaataaccg atgttcattg tgcctcagct     180
gcagatgttg atgttgcggt aaatgctgca acaaggcaa tggaaacatg gaaagacatt      240
gatcctactg ttcgtgtcga actttactac aaattggcca gcttagttga cgagcattcc     300
caagcaattg ctgaaattga agcactagac tcgggtaaac cattgtactc gaatgcactg     360
gcggatgttc aatcggttgc tgagtactta aggtactgtg ccggttgggc ggataaatta     420
cacggtacgc aaattccaat aaactctaag gtaatggcta ttacaaaacg tgtacccta     480
gttgtcggct gcatcattcc atggaactac ccaatttcaa tggcctcctg gaagttctgt     540
ccagcattgg ctgccggatg tactattgta atgaagtcaa gtgagataac cccgttatcg     600
ttactttatt ttgcgaattt ggtcaaatta gcaggtttcc ctaagggtgt ttttaatgtc     660
gtctctggat tggtgatga tgttggctca gcgctttcaa atcacccaaa gttgggtaag     720
attgcattta caggctcgac cttgaccggg caaaaggtga tggcggatgc tgccagatca     780
aatttgaaaa gcgtatcttt ggaatgtggt ggtaaatctc cacttattgt cttcgaagat     840
gcagaattgg atgaatgcgt taatgggca agttttggtg tcatgtataa caccggacaa     900
aattgtactg ccaattctcg tattattgtg catgataagg tttatgatca atttatcgaa     960
aagttcctgt ctcaactcaa ggaagattgg aaaatgggag atgtcatgaa tgaaaagact    1020
acattgggac cacttgtcag ccaacaacaa tatgagcgtg ttcagtcgta tattgatata    1080
ggtgtcaaag aagggctac actgattcaa ccgcttaagg agagcactcc atcaaatgga    1140
```

```
ttctacatct ctcctactgt ttttactaac gttaaggaag atatgagaat tgttaaggag    1200
gaaatatttg gtcctgtcgt aactatctcc aaattctcaa ctgaggaaga ggcaatttca    1260
aaggcgaatg atacaattta tggcttagct gcaatgttat ttactactaa ttttgaacgt    1320
gccaacagag ttgctgataa gctggaagct ggcagtgtgt acattaatag ctctaacaac    1380
gagagtacca agttccatt tggaggaatg aagatgagtg gtattggaag agagttgggg     1440
caagaagcat ttaatttgta cactgttaca aagagtattt attatagtta tggtgctaag    1500
ctttaa                                                                1506
```

<210> SEQ ID NO 124
<211> LENGTH: 501
<212> TYPE: PRT
<213> ORGANISM: Issatchenkia orientalis

<400> SEQUENCE: 124

```
Met Ala Leu Pro Leu Ala Thr Thr Ile Ser Leu Ser Ser Gly Lys Thr
1               5                   10                  15

Leu Glu Gln Pro Ile Gly Leu Phe Ile Asp Asn Glu Phe Val Asn Pro
            20                  25                  30

Ile Ser Val Ser Asn Ala Arg Thr Leu Thr Thr Phe Asn Pro Ser Thr
        35                  40                  45

Gly Glu Pro Ile Thr Asp Val His Cys Ala Ser Ala Ala Asp Val Asp
    50                  55                  60

Val Ala Val Asn Ala Ala Asn Lys Ala Met Glu Thr Trp Lys Asp Ile
65                  70                  75                  80

Asp Pro Thr Val Arg Val Glu Leu Leu Leu Lys Leu Ala Ser Leu Val
                85                  90                  95

Asp Glu His Ser Gln Ala Ile Ala Glu Ile Ala Leu Asp Ser Gly
            100                 105                 110

Lys Pro Leu Tyr Ser Asn Ala Leu Ala Asp Val Gln Ser Val Ala Glu
        115                 120                 125

Tyr Leu Arg Tyr Cys Ala Gly Trp Ala Asp Lys Leu His Gly Thr Gln
    130                 135                 140

Ile Pro Ile Asn Ser Lys Val Met Ala Ile Thr Lys Arg Val Pro Leu
145                 150                 155                 160

Val Val Gly Cys Ile Ile Pro Trp Asn Tyr Pro Ile Ser Met Ala Ser
                165                 170                 175

Trp Lys Phe Cys Pro Ala Leu Ala Ala Gly Cys Thr Ile Val Met Lys
            180                 185                 190

Ser Ser Glu Ile Thr Pro Leu Ser Leu Leu Tyr Phe Ala Asn Leu Val
        195                 200                 205

Lys Leu Ala Gly Phe Pro Lys Gly Val Phe Asn Val Val Ser Gly Phe
    210                 215                 220

Gly Asp Asp Val Gly Ser Ala Leu Ser Asn His Pro Lys Leu Gly Lys
225                 230                 235                 240

Ile Ala Phe Thr Gly Ser Thr Leu Thr Gly Gln Lys Val Met Ala Asp
                245                 250                 255

Ala Ala Arg Ser Asn Leu Lys Ser Val Ser Leu Glu Cys Gly Gly Lys
            260                 265                 270

Ser Pro Leu Ile Val Phe Glu Asp Ala Glu Leu Asp Glu Cys Val Lys
        275                 280                 285

Trp Ala Ser Phe Gly Val Met Tyr Asn Thr Gly Gln Asn Cys Thr Ala
    290                 295                 300
```

```
Asn Ser Arg Ile Ile Val His Asp Lys Val Tyr Asp Gln Phe Ile Glu
305                 310                 315                 320

Lys Phe Leu Ser Gln Leu Lys Glu Asp Trp Lys Met Gly Asp Val Met
            325                 330                 335

Asn Glu Lys Thr Thr Leu Gly Pro Leu Val Ser Gln Gln Gln Tyr Glu
        340                 345                 350

Arg Val Gln Ser Tyr Ile Asp Ile Gly Val Lys Glu Gly Ala Thr Leu
    355                 360                 365

Ile Gln Pro Leu Lys Glu Ser Thr Pro Ser Asn Gly Phe Tyr Ile Ser
370                 375                 380

Pro Thr Val Phe Thr Asn Val Lys Glu Asp Met Arg Ile Val Lys Glu
385                 390                 395                 400

Glu Ile Phe Gly Pro Val Val Thr Ile Ser Lys Phe Ser Thr Glu Glu
                405                 410                 415

Glu Ala Ile Ser Lys Ala Asn Asp Thr Ile Tyr Gly Leu Ala Ala Met
            420                 425                 430

Leu Phe Thr Thr Asn Phe Glu Arg Ala Asn Arg Val Ala Asp Lys Leu
        435                 440                 445

Glu Ala Gly Ser Val Tyr Ile Asn Ser Ser Asn Asn Glu Ser Thr Lys
    450                 455                 460

Val Pro Phe Gly Gly Met Lys Met Ser Gly Ile Gly Arg Glu Leu Gly
465                 470                 475                 480

Gln Glu Ala Phe Asn Leu Tyr Thr Val Thr Lys Ser Ile Tyr Tyr Ser
                485                 490                 495

Tyr Gly Ala Lys Leu
            500

<210> SEQ ID NO 125
<211> LENGTH: 1544
<212> TYPE: DNA
<213> ORGANISM: Issatchenkia orientalis
<220> FEATURE:
<221> NAME/KEY: misc_feature
<222> LOCATION: (1319)..(1319)
<223> OTHER INFORMATION: N= A, C, G, OR T

<400> SEQUENCE: 125
atgatgggcg caactacagc aaaaattagt attccaaatg gtaacaaata cgagcaacct      60
acaggtttgt tcatcaatgg tgagtttgtt gcttcaagtg atggtaaaac tgcagaagtt     120
gagaatccag gcaatggaaa cattgtatgt tctgtccact tagcttctat tgaggatatt     180
aataccgccg tagaagctgc tgaagatgca tttttcaaaa ggtgggccac catcagtggt     240
aaagccaagg gagaatactt gagtaagatt gccgatctaa tcgttaaata ttctgatcaa     300
ttggcagatc tagaggctat tgaatcaggt aagccaaagg acaccaatgc aatctttgat     360
gttttacatt cggctgatgt tttcagatac tatgctggca aggctgtcac tgcacaaagc     420
ggcaagacta tcgagtccga actctccaaa tttacataca cagtttacga gcccatggt      480 gtttgtgccg ctatcatcgc atggaacttc ccaatgagca catttgcgtg gaaagttgcg     540
gcatgtttag ctgctggtaa tacaatggtt gtcaaaactt ccgagctgac tccgttatct     600
gcattgttca tgtgtaagat tttccaagaa gcagatctac ctgctggagt tataaacgtc     660
acatgtggtt taggttctgt tgcaggtgtt cgattgagtg aacatgaaaa ggttcagaaa     720
atttcgttta ctggctccac tggcgttggt aagttgatcc aagaatccgc agcaaagtct     780
aacttaaagt attgtacgct tgaatgtggt ggtaagtctc cgttagtgat ttacgaggat     840
```

-continued

```
gcagatcttg agcaagcagt gaagtgggct gcctttggta ttttttttcaa caaaggtgaa      900 atttgcacag cctcttccag aatatatgtt caagaatcag tctatgacaa atttttgact      960
atgtacaagg atcatgtgga agaagcctat gttcaaggag aacagtttgc cactggtgtt     1020
aacgttgggc ctactgtctg caaagcccaa caagagaaaa tactggccta cattgaaagt     1080
gccaagcaag aaggtggtag aattatcact ggtggtaaaa taccatctta cacgaacaaa     1140
aatggttact atctcgaacc aacaattatt gcagattgta accaggatat gaaggtagtc     1200
agggaagaga ttttcggacc agtcgttact gtatccaaat tcactagtga tgaagaagcc     1260
atcaaattaa gcaatgattc cgaatatggc ttggcagcat atttattcac tystsrasna     1320
ssrgttyrgy taaaatyrth thraaggacc tcgttagatc tcagaattat atcagaaaag     1380
tgcaaagcgg acaggtcttt gtcaacttca cctttgcggc tgatttcagg ttgccatttg     1440
gcggatataa gatgagtggt aacggaagag agcttggtga tgaaggactg agtgctttcc     1500
agcaagtcaa agcagtacac attaatctca ctgggaagtt gtaa                     1544
```

<210> SEQ ID NO 126
<211> LENGTH: 503
<212> TYPE: PRT
<213> ORGANISM: Issatchenkia orientalis

<400> SEQUENCE: 126

```
Met Met Gly Ala Thr Thr Ala Lys Ile Ser Ile Pro Asn Gly Asn Lys
1               5                   10                  15

Tyr Glu Gln Pro Thr Gly Leu Phe Ile Asn Gly Glu Phe Val Ala Ser
            20                  25                  30

Ser Asp Gly Lys Thr Ala Glu Val Glu Asn Pro Gly Asn Gly Asn Ile
        35                  40                  45

Val Cys Ser Val His Leu Ala Ser Ile Glu Asp Ile Asn Thr Ala Val
    50                  55                  60

Glu Ala Ala Glu Asp Ala Phe Phe Lys Arg Trp Ala Thr Ile Ser Gly
65                  70                  75                  80

Lys Ala Lys Gly Glu Tyr Leu Ser Lys Ile Ala Asp Leu Ile Val Lys
                85                  90                  95

Tyr Ser Asp Gln Leu Ala Asp Leu Glu Ala Ile Glu Ser Gly Lys Pro
            100                 105                 110

Lys Asp Thr Asn Ala Ile Phe Asp Val Leu His Ser Ala Asp Val Phe
        115                 120                 125

Arg Tyr Tyr Ala Gly Lys Ala Val Thr Ala Gln Ser Gly Lys Thr Ile
    130                 135                 140

Glu Ser Glu Leu Ser Lys Phe Thr Tyr Thr Val Tyr Glu Pro Tyr Gly
145                 150                 155                 160

Val Cys Ala Ala Ile Ile Ala Trp Asn Phe Pro Met Ser Thr Phe Ala
                165                 170                 175

Trp Lys Val Ala Ala Cys Leu Ala Ala Gly Asn Thr Met Val Val Lys
            180                 185                 190

Thr Ser Glu Leu Thr Pro Leu Ser Ala Leu Phe Met Cys Lys Ile Phe
        195                 200                 205

Gln Glu Ala Asp Leu Pro Ala Gly Val Ile Asn Val Thr Cys Gly Leu
    210                 215                 220

Gly Ser Val Ala Gly Val Arg Leu Ser Glu His Glu Lys Val Gln Lys
225                 230                 235                 240

Ile Ser Phe Thr Gly Ser Thr Gly Val Gly Lys Leu Ile Gln Glu Ser
```

```
                    245                 250                 255
Ala Ala Lys Ser Asn Leu Lys Tyr Cys Thr Leu Glu Cys Gly Gly Lys
            260                 265                 270

Ser Pro Leu Val Ile Tyr Glu Asp Ala Asp Leu Glu Gln Ala Val Lys
        275                 280                 285

Trp Ala Ala Phe Gly Ile Phe Phe Asn Lys Gly Glu Ile Cys Thr Ala
290                 295                 300

Ser Ser Arg Ile Tyr Val Gln Glu Ser Val Tyr Asp Lys Phe Leu Thr
305                 310                 315                 320

Met Tyr Lys Asp His Val Glu Glu Ala Tyr Val Gln Gly Gln Phe
                325                 330                 335

Ala Thr Gly Val Asn Val Gly Pro Thr Val Cys Lys Ala Gln Gln Glu
            340                 345                 350

Lys Ile Leu Ala Tyr Ile Glu Ser Ala Lys Gln Glu Gly Gly Arg Ile
        355                 360                 365

Ile Thr Gly Gly Lys Ile Pro Ser Tyr Thr Asn Lys Asn Gly Tyr Tyr
    370                 375                 380

Leu Glu Pro Thr Ile Ile Ala Asp Cys Asn Gln Asp Met Lys Val Val
385                 390                 395                 400

Arg Glu Glu Ile Phe Gly Pro Val Val Thr Val Ser Lys Phe Thr Ser
                405                 410                 415

Asp Glu Glu Ala Ile Lys Leu Ser Asn Asp Ser Glu Tyr Gly Leu Ala
            420                 425                 430

Ala Tyr Leu Phe Thr Lys Asp Leu Val Arg Ser Gln Asn Tyr Ile Arg
        435                 440                 445

Lys Val Gln Ser Gly Gln Val Phe Val Asn Phe Thr Phe Ala Ala Asp
    450                 455                 460

Phe Arg Leu Pro Phe Gly Gly Tyr Lys Met Ser Gly Asn Gly Arg Glu
465                 470                 475                 480

Leu Gly Asp Glu Gly Leu Ser Ala Phe Gln Gln Val Lys Ala Val His
                485                 490                 495

Ile Asn Leu Thr Gly Lys Leu
            500

<210> SEQ ID NO 127
<211> LENGTH: 1716
<212> TYPE: DNA
<213> ORGANISM: Issatchenkia orientalis
<220> FEATURE:
<221> NAME/KEY: misc_feature
<222> LOCATION: (655)..(655)
<223> OTHER INFORMATION: n is a, c, g, or t

<400> SEQUENCE: 127
atggctccaa ctgctgttga tatccataac gagtacaaac agaatgtttc caacgaacag      60
gaaattcctt tcaacaaaac tgaaagaaag tcatcgattg catctaaatt aggactgaat     120
ccagacgcta agattcacta caattctgct gttcctatat tatacgaaga tggtttaaag     180
gaaaaaggta caccatttc ctcttctggt gcattgattg cattctctgg ttccaaaaca      240
ggtagatctc caaggacaa agaattgtc gatgaagaga cttcaacaga caacatctgg      300
tggggtccag tcaataagaa ggttgatgaa aacacttgga atatctcgaa atctagagcg     360
attgattatt tgagaacaag agagaaggtt tacattatcg atgcttttgc tggttgggat     420
ccaagataca gaattaaggt tagaattgtc tgtgctagag cttaccatgc tttgttcatg     480
aagaatatgt taattagacc aacaacggaa gaattaaaga actttggtga gcctgatttc     540
```

```
accatttgga atgcaggtca attccctgct aatgtttaca ctaagggtat gacttcttca    600
acttctgttg aaataaattt caagtctthr ysgymtthrs rsrthrsrva gtasnhyssr    660
atggaaatgg ttatcctagg tactgaatac gcaggtgaaa tgaagaaagg tatctttacc    720
gttatgttct acttgatgcc aatcagacac aaggttttaa ctttacactc ttctgcaaat    780
caaggtaaaa aggatggtga tgtcacatta ttctttggtt tatctggtac aggtaaaaca    840
accttgtctg cagatcctca tagagaattg attggtgatg atgaacattg ctggtctgat    900
catggtgttt tcaacattga aggtggatgt tatgctaagt gtttggactt atctgctgaa    960
agagaacctg agattttcaa tgcaattagg tttggatctg tcttggagaa tgttgtctat   1020
gatccagttg atagaactgt tgactattcc gctgctaatg tcactgaaaa tactagatgt   1080
gcttatccta tcgactttat tccttctgct aagatcccat gtctggcaga ttctcatcca   1140
aagaatattg ttcttttaac ttgtgatgca agaggtgttt tgccacctgt ctccaagcta   1200
actaatgcac aagtcatgta tcactttatc tctggttaca cctccaagat ggcaggtacc   1260
gaagttggtg tcactgaacc agaagcaacc ttctctgcat gttttggtca accttttctta  1320
gttttacatc caatgaaata cgcacaacaa ctctctgata aaatggctga acattcttcc   1380
accgcttggt tattgaatac cggttggact ggtcaatctt atgttaaagg tggtaagaga   1440
tgtccattga gtatactag agcaatttta gatgctattc actctggtga gcttgcaaaa    1500
caggaattcg aaacataccc tactttcggt ttacaagttc caaaaacttg tccaggtgtc   1560
ccagaaagtg ttctgaaccc atctaaacac tgggctactg gtgaagctga tttcaaggct   1620
gaagtcacta acttggctaa attatttgct gagaactttg aaaagtattc tgcagaatgt   1680
actgcagaag ttgttgctgc tggtcctgct ttataa                             1716

<210> SEQ ID NO 128
<211> LENGTH: 560
<212> TYPE: PRT
<213> ORGANISM: Issatchenkia orientalis

<400> SEQUENCE: 128

Met Ala Pro Thr Ala Val Asp Ile His Asn Glu Tyr Lys Gln Asn Val
1               5                   10                  15

Ser Asn Glu Gln Glu Ile Pro Phe Asn Lys Thr Glu Arg Lys Ser Ser
            20                  25                  30

Ile Ala Ser Lys Leu Gly Leu Asn Pro Asp Ala Lys Ile His Tyr Asn
        35                  40                  45

Ser Ala Val Pro Ile Leu Tyr Glu Asp Gly Leu Lys Glu Lys Gly Thr
    50                  55                  60

Thr Ile Ser Ser Gly Ala Leu Ile Ala Phe Ser Gly Ser Lys Thr
65                  70                  75                  80

Gly Arg Ser Pro Lys Asp Lys Arg Ile Val Asp Glu Thr Ser Thr
                85                  90                  95

Asp Asn Ile Trp Trp Gly Pro Val Asn Lys Val Asp Glu Asn Thr
            100                 105                 110

Trp Asn Ile Ser Lys Ser Arg Ala Ile Asp Tyr Leu Arg Thr Arg Glu
        115                 120                 125

Lys Val Tyr Ile Ile Asp Ala Phe Ala Gly Trp Asp Pro Arg Tyr Arg
    130                 135                 140

Ile Lys Val Arg Ile Val Cys Ala Arg Ala Tyr His Ala Leu Phe Met
145                 150                 155                 160
```

```
Lys Asn Met Leu Ile Arg Pro Thr Thr Glu Glu Leu Lys Asn Phe Gly
            165                 170                 175

Glu Pro Asp Phe Thr Ile Trp Asn Ala Gly Gln Phe Pro Ala Asn Val
            180                 185                 190

Tyr Thr Lys Gly Met Thr Ser Ser Thr Ser Val Glu Ile Asn Phe Lys
            195                 200                 205

Ser Met Glu Met Val Ile Leu Gly Thr Glu Tyr Ala Gly Glu Met Lys
            210                 215                 220

Lys Gly Ile Phe Thr Val Met Phe Tyr Leu Met Pro Ile Arg His Lys
225                 230                 235                 240

Val Leu Thr Leu His Ser Ser Ala Asn Gln Gly Lys Lys Asp Gly Asp
            245                 250                 255

Val Thr Leu Phe Phe Gly Leu Ser Gly Thr Gly Lys Thr Thr Leu Ser
            260                 265                 270

Ala Asp Pro His Arg Glu Leu Ile Gly Asp Asp Glu His Cys Trp Ser
            275                 280                 285

Asp His Gly Val Phe Asn Ile Glu Gly Gly Cys Tyr Ala Lys Cys Leu
            290                 295                 300

Asp Leu Ser Ala Glu Arg Glu Pro Glu Ile Phe Asn Ala Ile Arg Phe
305                 310                 315                 320

Gly Ser Val Leu Glu Asn Val Val Tyr Asp Pro Val Asp Arg Thr Val
            325                 330                 335

Asp Tyr Ser Ala Ala Asn Val Thr Glu Asn Thr Arg Cys Ala Tyr Pro
            340                 345                 350

Ile Asp Phe Ile Pro Ser Ala Lys Ile Pro Cys Leu Ala Asp Ser His
            355                 360                 365

Pro Lys Asn Ile Val Leu Leu Thr Cys Asp Ala Arg Gly Val Leu Pro
            370                 375                 380

Pro Val Ser Lys Leu Thr Asn Ala Gln Val Met Tyr His Phe Ile Ser
385                 390                 395                 400

Gly Tyr Thr Ser Lys Met Ala Gly Thr Glu Val Gly Val Thr Glu Pro
            405                 410                 415

Glu Ala Thr Phe Ser Ala Cys Phe Gly Gln Pro Phe Leu Val Leu His
            420                 425                 430

Pro Met Lys Tyr Ala Gln Gln Leu Ser Asp Lys Met Ala Glu His Ser
            435                 440                 445

Ser Thr Ala Trp Leu Leu Asn Thr Gly Trp Thr Gly Gln Ser Tyr Val
            450                 455                 460

Lys Gly Gly Lys Arg Cys Pro Leu Lys Tyr Thr Arg Ala Ile Leu Asp
465                 470                 475                 480

Ala Ile His Ser Gly Glu Leu Ala Lys Gln Glu Phe Glu Thr Tyr Pro
            485                 490                 495

Thr Phe Gly Leu Gln Val Pro Lys Thr Cys Pro Gly Val Pro Glu Ser
            500                 505                 510

Val Leu Asn Pro Ser Lys His Trp Ala Thr Gly Glu Ala Asp Phe Lys
            515                 520                 525

Ala Glu Val Thr Asn Leu Ala Lys Leu Phe Ala Glu Asn Phe Glu Lys
            530                 535                 540

Tyr Ser Ala Glu Cys Thr Ala Glu Val Val Ala Ala Gly Pro Ala Leu
545                 550                 555                 560

<210> SEQ ID NO 129
<211> LENGTH: 267
<212> TYPE: PRT
```

<213> ORGANISM: Saccharomyces cerevisiae

<400> SEQUENCE: 129

```
Met Ser Gln Gly Arg Lys Ala Ala Glu Arg Leu Ala Lys Lys Thr Val
1               5                   10                  15
Leu Ile Thr Gly Ala Ser Ala Gly Ile Gly Lys Ala Thr Ala Leu Glu
            20                  25                  30
Tyr Leu Glu Ala Ser Asn Gly Asp Met Lys Leu Ile Leu Ala Ala Arg
        35                  40                  45
Arg Leu Glu Lys Leu Glu Glu Leu Lys Lys Thr Ile Asp Gln Glu Phe
    50                  55                  60
Pro Asn Ala Lys Val His Val Ala Gln Leu Asp Ile Thr Gln Ala Glu
65                  70                  75                  80
Lys Ile Lys Pro Phe Ile Glu Asn Leu Pro Gln Glu Phe Lys Asp Ile
                85                  90                  95
Asp Ile Leu Val Asn Asn Ala Gly Lys Ala Leu Gly Ser Asp Arg Val
            100                 105                 110
Gly Gln Ile Ala Thr Glu Asp Ile Gln Asp Val Phe Asp Thr Asn Val
        115                 120                 125
Thr Ala Leu Ile Asn Ile Thr Gln Ala Val Leu Pro Ile Phe Gln Ala
    130                 135                 140
Lys Asn Ser Gly Asp Ile Val Asn Leu Gly Ser Ile Ala Gly Arg Asp
145                 150                 155                 160
Ala Tyr Pro Thr Gly Ser Ile Tyr Cys Ala Ser Lys Phe Ala Val Gly
                165                 170                 175
Ala Phe Thr Asp Ser Leu Arg Lys Glu Leu Ile Asn Thr Lys Ile Arg
            180                 185                 190
Val Ile Leu Ile Ala Pro Gly Leu Val Glu Thr Glu Phe Ser Leu Val
        195                 200                 205
Arg Tyr Arg Gly Asn Glu Glu Gln Ala Lys Asn Val Tyr Lys Asp Thr
    210                 215                 220
Thr Pro Leu Met Ala Asp Asp Val Ala Asp Leu Ile Val Tyr Ala Thr
225                 230                 235                 240
Ser Arg Lys Gln Asn Thr Val Ile Ala Asp Thr Leu Ile Phe Pro Thr
                245                 250                 255
Asn Gln Ala Ser Pro His His Ile Phe Arg Gly
            260                 265
```

<210> SEQ ID NO 130
<211> LENGTH: 420
<212> TYPE: DNA
<213> ORGANISM: Streptomyces avermitilis

<400> SEQUENCE: 130

```
atgttaagaa ccatgttcaa atctaagatt cacagagcaa ctgttactca agcagatctc      60
cattatgttg gttccgttac tattgatgca gacttgttag acgcagcaga cttgttgcca     120
ggtgaattgg ttcacatcgt tgacattacg aacggtgcta gattggaaac ttacgtcatt     180
gaaggtgaac gtggttccgg tgttgttggt atcaatggtg ctgccgctca tttagttcat     240
cctggtgatc ttgttatcat tatctcctat gcacaagttt cagatgcaga agcacgtgca     300
ttgcgtccaa gagttgttca cgttgacaga gacaatagag ttgttgcgct tggtgcggat     360
ccagccgaac cagtcccagg ttccgaccaa gctagatccc cacaagctgt tactgcataa     420
```

<210> SEQ ID NO 131

<211> LENGTH: 384
<212> TYPE: DNA
<213> ORGANISM: Clostridium acetobutylicum

<400> SEQUENCE: 131

```
atgcacttga acatgttgaa gtccaagatc cacagagcta ccgtcgttca agcagacttg      60
aactacgtcg gttccatcac catcgacaga aacttgatgg acaaggcaaa catcttggaa     120
tacgaaaagg tcgagatcgc aaacatcaac aacggtgcaa gattcgaaac ctacgtcatc     180
gctggtgagg ctggttccgg tatcatctgt ttgaacggtg ctgctgcaag atgtgcacaa     240
gcgggtgaca aggttatcat catgtgttac tgttccttga ccccagaaga agcttccgag     300
cacagaccaa aggtcgtttt cgtcaacgac gacaactcca tctccaacgt caccgaatac     360
gagaagcacg gcaccatcgg ttaa                                             384
```

<210> SEQ ID NO 132
<211> LENGTH: 354
<212> TYPE: DNA
<213> ORGANISM: Helicobacter pylori

<400> SEQUENCE: 132

```
atgaccttcg agatgttgta ctccaagatc cacagagcaa ccatcaccga cgcaaacttg      60
aactacatcg gctccatcac catcgacgag gacttggcta agttggctaa gttgagagag     120
ggtatgaagg tcgaaatcgt cgacgtcaac aacggcgaga gattctccac ctacgtcatc     180
ttgggtaaga gagaggtga aatctgcgtc aacggtgcag cagccagaaa ggtcgctatc     240
ggtgacgtcg tcatcatctt ggcttacgca tccatgaacg aggacgagat caacgctcac     300
aagccatcca tcgtcttggt cgacgaaaag aacgaaatct ggaaaaggg ttaa            354
```

<210> SEQ ID NO 133
<211> LENGTH: 117
<212> TYPE: PRT
<213> ORGANISM: Helicobacter pylori

<400> SEQUENCE: 133

```
Met Thr Phe Glu Met Leu Tyr Ser Lys Ile His Arg Ala Thr Ile Thr
 1                5                  10                  15

Asp Ala Asn Leu Asn Tyr Ile Gly Ser Ile Thr Ile Asp Glu Asp Leu
             20                  25                  30

Ala Lys Leu Ala Lys Leu Arg Glu Gly Met Lys Val Glu Ile Val Asp
         35                  40                  45

Val Asn Asn Gly Glu Arg Phe Ser Thr Tyr Val Ile Leu Gly Lys Lys
     50                  55                  60

Arg Gly Glu Ile Cys Val Asn Gly Ala Ala Ala Arg Lys Val Ala Ile
 65                  70                  75                  80

Gly Asp Val Val Ile Ile Leu Ala Tyr Ala Ser Met Asn Glu Asp Glu
                 85                  90                  95

Ile Asn Ala His Lys Pro Ser Ile Val Leu Val Asp Glu Lys Asn Glu
            100                 105                 110

Ile Leu Glu Lys Gly
        115
```

<210> SEQ ID NO 134
<211> LENGTH: 387
<212> TYPE: DNA
<213> ORGANISM: Bacillus sp. TS25

<400> SEQUENCE: 134

```
atgtacagaa ccatgatgaa gtccaagttg cacagagcga ccgtcaccga agcaaacttg    60
aactacgtcg gttccatcac catcgaccaa gacttgatgg aagctgcaga catcttggaa   120
aacgagaagg tccaaatcgt caacaacaac aacggtgcta gattcgaaac ctacgtcatc   180
gctggtccaa gaggctccgg caccatctgt ttgaacggtg cagcagcaag attggtccaa   240
ccaggtgaca ccgttatcat catctcctac gcaatgttgg aagaagccga ggctagaaag   300
caccaacctg tcgtcgtttt gttgaaccca gacaacacca tccaagaatt gatcagagaa   360
acccacggtg ctaccgctac cgtctaa                                       387
```

```
<210> SEQ ID NO 135
<211> LENGTH: 128
<212> TYPE: PRT
<213> ORGANISM: Bacillus sp. TS25

<400> SEQUENCE: 135
```

Met Tyr Arg Thr Met Met Lys Ser Lys Leu His Arg Ala Thr Val Thr
1               5                   10                  15

Glu Ala Asn Leu Asn Tyr Val Gly Ser Ile Thr Ile Asp Gln Asp Leu
            20                  25                  30

Met Glu Ala Ala Asp Ile Leu Glu Asn Glu Lys Val Gln Ile Val Asn
        35                  40                  45

Asn Asn Asn Gly Ala Arg Phe Glu Thr Tyr Val Ile Ala Gly Pro Arg
    50                  55                  60

Gly Ser Gly Thr Ile Cys Leu Asn Gly Ala Ala Ala Arg Leu Val Gln
65                  70                  75                  80

Pro Gly Asp Thr Val Ile Ile Ile Ser Tyr Ala Met Leu Glu Glu Ala
                85                  90                  95

Glu Ala Arg Lys His Gln Pro Val Val Val Leu Leu Asn Pro Asp Asn
            100                 105                 110

Thr Ile Gln Glu Leu Ile Arg Glu Thr His Gly Ala Thr Ala Thr Val
        115                 120                 125

```
<210> SEQ ID NO 136
<211> LENGTH: 411
<212> TYPE: DNA
<213> ORGANISM: Corynebacterium glutamicum

<400> SEQUENCE: 136
atgttgagaa ccatcttggg ttccaaaatc cacagagcta ccgttaccca agcagacttg    60
gactacgttg gttcagtcac catcgatgca gacttggttc atgccgcagg tttgatcgaa   120
ggtgaaaagg ttgccatcgt cgacatcacc aatggcgcta gattggaaac ctacgttatc   180
gttggtgatg ctggcaccgg taacatctgt atcaacggtg cagcagcaca cttgatcaac   240
ccaggtgatt tggttatcat catgtcctac ttgcaagcta ccgatgcaga ggccaaggct   300
tacgaaccaa agatcgttca cgtcgacgca gacaacagaa tcgttgcttt gggtaacgac   360
ttggcagaag ctttgcctgg ttccggtttg ttgacctcaa gatctatcta a            411
```

```
<210> SEQ ID NO 137
<211> LENGTH: 136
<212> TYPE: PRT
<213> ORGANISM: Corynebacterium glutamicum

<400> SEQUENCE: 137
```

Met Leu Arg Thr Ile Leu Gly Ser Lys Ile His Arg Ala Thr Val Thr
1               5                   10                  15

```
Gln Ala Asp Leu Asp Tyr Val Gly Ser Val Thr Ile Asp Ala Asp Leu
            20                  25                  30

Val His Ala Ala Gly Leu Ile Glu Gly Glu Lys Val Ala Ile Val Asp
        35                  40                  45

Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala His Leu Ile Asn
65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Ala Asp Asn
            100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
    130                 135
```

<210> SEQ ID NO 138
<211> LENGTH: 384
<212> TYPE: DNA
<213> ORGANISM: Bacillus licheniformis

<400> SEQUENCE: 138

```
atgtacagaa ccttgatgtc cgctaagttg cacagagcta gagtcaccga agcaaacttg      60
aactacgttg gttccgtcac catcgacgag gacttgttgg acgcagtcgg tatgatggca     120
aacgaaaagg tccaaatcgt caacaacaac aacggtgcta gattggaaac ctacatcatc     180
cctggtgaga gaggttccgg tgtcgtctgt ttgaacggtg ctgcagctag attggtccaa     240
gttggtgacg tcgttatcat cgtttcctac gccatgatgt ccgaagaaga agcaaagacc     300
cacaagccaa aggtcgctgt tttgaacgaa agaaacgaaa tcgaagagat gttgggtcaa     360
gaaccagcta gaaccatctt gtaa                                            384
```

<210> SEQ ID NO 139
<211> LENGTH: 127
<212> TYPE: PRT
<213> ORGANISM: Bacillus licheniformis

<400> SEQUENCE: 139

```
Met Tyr Arg Thr Leu Met Ser Ala Lys Leu His Arg Ala Arg Val Thr
1               5                   10                  15

Glu Ala Asn Leu Asn Tyr Val Gly Ser Val Thr Ile Asp Glu Asp Leu
            20                  25                  30

Leu Asp Ala Val Gly Met Met Ala Asn Glu Lys Val Gln Ile Val Asn
        35                  40                  45

Asn Asn Asn Gly Ala Arg Leu Glu Thr Tyr Ile Ile Pro Gly Glu Arg
    50                  55                  60

Gly Ser Gly Val Val Cys Leu Asn Gly Ala Ala Ala Arg Leu Val Gln
65                  70                  75                  80

Val Gly Asp Val Val Ile Ile Val Ser Tyr Ala Met Met Ser Glu Glu
                85                  90                  95

Glu Ala Lys Thr His Lys Pro Lys Val Ala Val Leu Asn Glu Arg Asn
            100                 105                 110

Glu Ile Glu Glu Met Leu Gly Gln Glu Pro Ala Arg Thr Ile Leu
            115                 120                 125
```

<210> SEQ ID NO 140
<211> LENGTH: 1356
<212> TYPE: DNA
<213> ORGANISM: Streptomyces avermitilis

<400> SEQUENCE: 140

| | | | | | |
|---|---|---|---|---|---|
| atgacaccac | agccaaaccc | acaagtcggt | gcagcagtca | agctgcaga | tagagcacac | 60 |
| gtcttccact | cttggtctgc | acaagaattg | atcgatccat | ggctgttgc | tggtgcagag | 120 |
| ggttcctact | tctgggatta | cgatggtaga | cgttaccttg | acttcacctc | cggcttagtc | 180 |
| ttcaccaaca | tcggttacca | acacccaaag | gttgtcgcag | ctatccaaga | acaagccgca | 240 |
| tctttgacta | catttgcccc | agctttcgca | gttgaagcaa | gatccgaagc | tgcaagattg | 300 |
| atcgctgagc | gtactccagg | tgatttagac | aaaatcttct | tcaccaacgg | tggcgcagat | 360 |
| gctatcgagc | acgctgttcg | tatggcaaga | atccacgctg | gtagaccaaa | ggtcttatcc | 420 |
| gcatacagat | cataccacgg | tggtacacaa | caggcagtca | acatcactgg | tgatccaagg | 480 |
| agatgggcat | ccgattccgc | ttctgctggc | gttgtccact | tctgggctcc | atacttatac | 540 |
| agatccagat | tctacgccga | aactgagcaa | caagaatgtg | agcgtgctct | tgagcacttg | 600 |
| gaaactacta | tcgccttcga | aggtccaggt | actattgccg | ctatcgtttt | ggaaactgtc | 660 |
| ccaggtactg | ctggtatcat | ggttcctcca | ccaggttact | tagcaggtgt | tagagaattg | 720 |
| tgtgacaaat | acggtatcgt | cttcgtcttg | atgaagtca | tggctggttt | cggcagaact | 780 |
| ggcgaatggt | tcgctgcaga | cttattcgat | gttaccccag | acttgatgac | cttcgctaag | 840 |
| ggtgtcaact | caggttacgt | tccattgggt | ggtgttgcta | tctccggcaa | aatcgcagag | 900 |
| actttcggta | agagagctta | cccaggtggt | ttgacgtact | ccggtcaccc | tcttgcttgc | 960 |
| gcagccgctg | ttgctactat | caacgttatg | gcagaagaag | gtgtcgttga | aaacgctgca | 1020 |
| aacttgggtg | ctagagttat | cgaaccaggt | ttgagagaac | ttgcagagag | acacccatca | 1080 |
| gttggtgaag | ttagaggtgt | tggtatgttc | tgggctttgg | aattggttaa | ggatagagaa | 1140 |
| accagagaac | ctttggtccc | atacaatgcc | gctggtgaag | cgaacgcacc | aatggctgct | 1200 |
| ttcggtgcag | ctgcaaaggc | aaacggtttg | tggccattca | tcaacatgaa | cagaacccac | 1260 |
| gttgttcctc | cttgtaacgt | taccgaagcc | gaagctaaag | aaggcttggc | agcattggat | 1320 |
| gcagctttat | ctgttgcaga | tgagtacact | gtctaa | | | 1356 |

<210> SEQ ID NO 141
<211> LENGTH: 1416
<212> TYPE: DNA
<213> ORGANISM: Saccharomyces cerevisiae

<400> SEQUENCE: 141

| | | | | | |
|---|---|---|---|---|---|
| atgtccatct | gtgagcaata | ctacccagaa | gaaccaacca | agccaaccgt | caagaccgaa | 60 |
| tccatccctg | gtccagaatc | ccaaaagcaa | ttgaaggaat | tgggtgaagt | tttcgacacc | 120 |
| agaccagctt | acttcttggc | agactacgaa | aagtccttgg | gtaactacat | caccgacgtc | 180 |
| gacggtaaca | cctacttgga | cttgtacgct | caaatctcct | ccatcgcctt | gggttacaac | 240 |
| aacccagcat | tgatcaaagc | cgctcaatcc | cagaaatga | tcagagcatt | ggttgacaga | 300 |
| ccagccttgg | gtaacttccc | ttccaaggac | ttggacaaga | tcttgaagca | aatcttgaag | 360 |
| tccgctccaa | agggtcagga | ccacgtctgg | tccggtttgt | ccggtgcaga | cgcaaacgaa | 420 |
| ttggctttca | aggctgcatt | catctactac | agagctaagc | aaagaggtta | cgacgcagac | 480 |
| ttctccgaaa | aggaaaactt | gtccgttatg | gacaacgacg | caccaggtgc | tccacacttg | 540 |

```
gcagttttgt ccttcaagag agctttccac ggtagattgt tcgcatccgg ttccactacc      600
tgttccaagc caatccacaa gttggacttc cctgctttcc actggccaca cgccgaatac      660
ccatcctacc agtacccttt ggacgaaaac tccgacgcaa acagaaagga ggacgaccac      720
tgcttggcaa tcgttgaaga attgatcaag acctggtcca tccctgttgc tgcgttgatc      780
atcgaaccaa tccaatccga gggtggtgac aaccacgcct ccaagtactt cttgcaaaag      840
ttgagagaca tcaccttgaa gtacaacgtc gtctacatca tcgacgaagt ccaaactggc      900
gttggcgcaa ccggtaagtt gtggtgtcac gaatacgcag acatccagcc tccagtcgac      960
ttggtcacct tctccaagaa gttccaatcc gctggctact tcttccacga ccctaagttc     1020
atcccaaaca agccatacag acaattcaac acctggtgtg gtgaaccagc aagaatgatc     1080
atcgcaggtg caatcggtca agagatctcc gacaagaagt tgaccgaaca atgctccaga     1140
gtcggtgact acttgttcaa gaagttggaa ggtttgcaaa agaagtaccc agagaacttc     1200
caaaacttga gaggtaaggg tagaggcacc ttcatcgctt gggacttgcc aactggcgag     1260
aagagagact tgttgttgaa gaagttgaag ttgaacggct gtaacgttgg tggctgtgct     1320
gttcacgcag tcagattgag accttccttg accttcgaag agaagcacgc agacatcttc     1380
atcgaagctt tggctaagtc cgtcaacgaa ttgtaa                              1416

<210> SEQ ID NO 142
<211> LENGTH: 1428
<212> TYPE: DNA
<213> ORGANISM: Saccharomyces kluyveri

<400> SEQUENCE: 142
atgccatcct actccgttgc agaattgtac tacccagacg aacctaccga acctaagatc       60
tccacctcct cctacccagg tccaaaggca aagcaagaat tggaaaagtt gtccaacgtc      120
ttcgacacca gagcagctta cttgttggca gactactaca agtcccgtgg taactacatc      180
gttgaccagg acggtaacgt cttgttggac gtttacgctc aaatctcctc catcgccttg      240
ggttacaaca acccagaaat cttgaaggtt gcaaagtccg acgcaatgtc cgttgcattg      300
gccaaccgtc cagcattggc ttgtttccca tccaacgact acggtcaatt gttggaagac      360
ggtttgttga aggcagcacc acaaggtcaa gacaagatct ggaccgcttt gtccggttcc      420
gacgcaaacg aaaccgcctt caaagcctgc ttcatgtacc aagctgcgaa gaagagaaac      480
ggtagatcct tctccaccga agaattggaa tccgttatgg acaaccaatt gccaggcacc      540
tccgaaatgg ttatctgttc cttcgaaaag ggtttccacg tcgtttgtt cggttccttg      600 tccactacca gatccaagcc tatccacaag ttggacatcc cagctttcaa ctggcctaaa      660
gccccattcc cagacttgaa gtaccattg gaagaaaaca aggaagccaa caaggctgaa      720
gaatcctcct gtatcgaaaa gttctcccaa atcgttcaag agtggcaagg taagatcgct      780
gcagttatca tcgaaccaat ccagtccgag ggtggcgaca ccacgcttc ctccgacttc      840 ttccaaaagt tgagagaaat caccatcgaa aacggtatct tgatgatcgt cgacgaagtt      900
caaaccggtg tcggtgctac cggcaagatg tgggcacacg aacactggaa cttgtccaac      960
cctccagact tggttacctt ctccaagaag ttccaagcag caggttctac taccacgac     1020 ccaaagttgc aaccagacca gccattcaga cagttcaaca cctggtgtgg tgacccatcc     1080
aaggctttga tcgccaaggt tatctacgaa gaaatcgtta agcacgactt ggtcaccaga     1140
actgccgaag tcggtaacta cttgttcaac agattggaaa agttgttcga aggtaagaac     1200
```

```
tacatccaga acttgagagg taagggtcaa ggcacctaca tcgctttcga cttcggcacc   1260
tcctccgaga gagactcctt cttgtccaga ttgagatgta acggtgcaaa cgtcgctggt   1320
tgcggtgact ccgctgtcag attgagacca tccttgacct tcgaagagaa gcacgcagac   1380
gtcttggttt ccatcttcga caagaccttg agacaattgt acggctaa               1428
```

<210> SEQ ID NO 143
<211> LENGTH: 747
<212> TYPE: DNA
<213> ORGANISM: Escherichia coli

<400> SEQUENCE: 143

```
atgatcgttt tggtcaccgg tgcaaccgca ggtttcggcg aatgtatcac cagaagattc    60
atccagcagg gtcacaaggt tatcgctacc ggtagaagac aagagagatt gcaagaattg   120
aaggacgagt tgggtgacaa cttgtacatc gctcaattgg acgttagaaa cagagcagct   180
atcgaagaaa tgttggcatc cttgccagct gaatggtgca acatcgacat cttggtcaac   240
aacgctggtt tggcattggg tatggaacca gctcacaagg ctagtgttga ggactgggag   300
accatgatcg acaccaacaa caagggtttg gtctacatga ccagagcagt tttgcctggt   360
atggttgaaa gaaaccacgg tcacatcatc aacatcggtt ccaccgctgg ttcctggcca   420
tacgctggcg gtaacgtcta cggtgctacc aaggctttcg ttagacagtt ctccttgaac   480
ttgagaaccg acttgcacgg caccgctgtt agagttaccg catcgaacc aggtttggtt   540 ggtggcaccg aattctccaa cgtcagattc aagggcgacg acggtaaggc tgaaaagacc   600
taccaaaaca ccgtcgcttt gaccccagaa gacgtttcag aggctgtttg gtgggtcagt   660
accttgccag cacacgtcaa catcaacacc ttggaaatga tgccagtcac ccaatcctac   720
gcaggtttga acgttcacag acaataa                                       747
```

<210> SEQ ID NO 144
<211> LENGTH: 804
<212> TYPE: DNA
<213> ORGANISM: Saccharomyces cerevisiae

<400> SEQUENCE: 144

```
atgtcccaag gtagaaaggc agcagaaaga ttggcaaaga gaccgtctt gatcaccggt    60 gcgtccgctg gtatcggtaa ggctaccgcg ttggagtact tggaagcatc caacggtgac   120
atgaagttga tcttggcagc aagaagattg gagaagttgg aagaattgaa gaagaccatc   180
gaccaagaat tcccaaacgc taaggtccac gttgcacaat tggacatcac ccaagcagag   240
aagatcaagc cattcatcga aaacttgcca caagaattca aggacatcga catcttggtc   300
aacaacgctg gtaaggcgtt gggttccgac agagttggtc aaatcgcaac cgaagacatc   360
caagacgtct tcgacaccaa cgtcaccgct ttgatcaaca tcacccaagc tgttttgcca   420
atcttccaag cgaagaactc cggtgacatc gtcaacttgg ttccatcgc tggtagagac   480 gcatacccaa ccggctccat ctactgcgcc tccaagttcg ctgtcggtgc tttcaccgac   540
tccttgagaa aggaattgat caacaccaag atcagagtca tcttgattgc ccctggtttg   600
gtcgaaaccg aattctcctt ggttagatac agaggtaacg aagaacaagc aaagaacgtt   660
tacaaggaca ctaccccatt gatggccgac gacgttgcag acttgatcgt ttacgctacc   720
tccagaaagc aaaacaccgt tatcgcagac accttgatct tcccaaccaa ccaagcatcc   780
ccacaccaca tcttcagagg ttaa                                          804
```

```
<210> SEQ ID NO 145
<211> LENGTH: 420
<212> TYPE: DNA
<213> ORGANISM: Streptomyces avermitilis

<400> SEQUENCE: 145
atgcttagaa ccatgttcaa atccaagatc cacagagcaa ccgtcactca agcagatttg      60
cattacgttg gttctgttac tattgacgca gacttacttg atgcagccga tttacttcct     120
ggtgagcttg ttcatattgt tgatatcacc aatggtgcgc gtcttgaaac ctatgtcatt     180
gagggtgaac gtggttccgg tgtcgtcggt atcaatggcg cagctgcaca cctcgtccat     240
ccaggtgacc tggtcatcat catttcttat gcacaggtct ccgatgctga gcccgtgcc      300 ttaagaccaa gagtcgttca cgtcgacaga gataacagag ttgtcgcttt aggtgcagac     360
ccagcagagc cagttccagg ttccgatcaa gctagatcac acaggctgt taccgcctaa     420

<210> SEQ ID NO 146
<211> LENGTH: 420
<212> TYPE: DNA
<213> ORGANISM: Streptomyces avermitilis

<400> SEQUENCE: 146
atgttaagaa ctatgtttaa gtccaagatt cacagagcta ccgtcaccca agcagatttg      60
cattacgtcg gttccgttac cattgatgca gatttactcg atgcggcaga cttgttacct     120
ggtgaactag ttcacattgt tgacattacc aatggtgcta gattggaaac ttacgtcatt     180
gaaggtgaaa gaggtagtgg tgtcgttggt atcaatggtg cagctgctca cttagttcac     240
ccaggtgact tagtcatcat catttcatat gcacaagttt ccgatgcgga agctagagca     300
ttaagaccaa gagttgttca tgttgataga gacaacagag tcgttgcact tggtgcagat     360
cctgctgaac cagttccagg ttcagatcaa gctaggtctc acaagcagt tactgcataa     420

<210> SEQ ID NO 147
<211> LENGTH: 420
<212> TYPE: DNA
<213> ORGANISM: Streptomyces avermitilis

<400> SEQUENCE: 147
atgttaagaa ctatgttcaa gagtaagatt catagggcta ccgttaccca ggcagatcta      60
cattatgttg gttctgttac cattgacgca gatttgttgg atgcagcaga cttgttacca     120
ggtgaactcg ttcacattgt cgatatcacc aacggtgcca gactggaaac ttatgtcatt     180
gaaggtgaga gaggcagtgg tgttgtcggc attaacggtg ccgcagcaca cttggttcat     240
ccaggtgact tggtcatcat catttcttac gcacaagtct ccgatgccga agctagagca     300
ttgagaccta gagtcgttca cgttgacaga gacaatagag ttgttgctct tggtgcagat     360
ccagctgagc cagttccagg ttccgatcaa gcgagatctc ctcaagctgt tactgcataa     420

<210> SEQ ID NO 148
<211> LENGTH: 384
<212> TYPE: DNA
<213> ORGANISM: Bacillus licheniformis

<400> SEQUENCE: 148
atgtatagaa ccttgatgag tgcaaagctt cacagagcaa gagtcactga agcaaacttg      60
aactacgttg gttctgttac tattgacgaa gacttacttg atgcagtcgg tatgatggca     120
aacgagaaag ttcaaattgt caacaataac aatggtgcgc gtcttgaaac ctatatcatt     180
```

```
cctggtgaac gtggttccgg tgtcgtctgc ttgaatggcg cagctgcaag gctcgtccaa    240
gttggtgacg tcgtcatcat tgtttcttat gcaatgatgt ccgaagaaga agccaaaaca    300
cataagccaa aggtcgctgt cctcaatgaa agaaacgaaa ttgaggaaat gttaggtcag    360
gaaccagcga gaaccatctt ataa                                           384

<210> SEQ ID NO 149
<211> LENGTH: 384
<212> TYPE: DNA
<213> ORGANISM: Bacillus licheniformis

<400> SEQUENCE: 149
atgtatagaa ccttgatgag tgcaaagctt cacagagcaa gagtcactga agcaaacttg     60
aactacgttg gttctgttac tattgacgaa gacttacttg atgcagtcgg tatgatggca    120
aacgagaaag ttcaaattgt caacaataac aatggtgcgc gtcttgaaac ctatatcatt    180
cctggtgaac gtggttccgg tgtcgtctgc ttgaatggcg cagctgcaag gctcgtccaa    240
gttggtgacg tcgtcatcat tgtttcttat gcaatgatgt ccgaagaaga agccaaaaca    300
cataagccaa aggtcgctgt cctcaatgaa agaaacgaaa ttgaggaaat gttaggtcag    360
gaaccagcga gaaccatctt ataa                                           384

<210> SEQ ID NO 150
<211> LENGTH: 384
<212> TYPE: DNA
<213> ORGANISM: Bacillus licheniformis

<400> SEQUENCE: 150
atgtacagaa cgttaatgtc tgccaagtta cacagagcga gagttactga agcaaatctc     60
aactatgttg gttcagttac cattgatgag gatctattgg atgctgttgg tatgatggca    120
aatgaaaagg ttcaaatcgt caataacaac aatggtgcta gattagaaac ttacatcatt    180
cctggtgaaa gaggttcagg tgttgtttgc ttaaacggtg ctgccgcaag attagttcaa    240
gtcggtgatg ttgttatcat cgtctcttat gctatgatga gtgaggaaga agctaagact    300
cataagccta aggttgccgt tctcaatgag aaaacgaaa tcgaagaaat gcttggccaa    360
gaacctgcca gaaccatcct gtaa                                           384

<210> SEQ ID NO 151
<211> LENGTH: 384
<212> TYPE: DNA
<213> ORGANISM: Bacillus licheniformis

<400> SEQUENCE: 151
atgtatagaa cattgatgtc tgcaaagttg catagggctc gtgttactga ggcaaatcta     60
aactacgtcg gttccgtcac aatcgatgaa gatctactcg atgccgttgg tatgatggcc    120
aatgaaaaag ttcaaattgt caacaacaac aacggtgcaa gattggagac ctatatcatt    180
cctggtgaaa gaggttcagg tgttgtttgt ctgaacggtg ctgctgcgag gttggtccaa    240
gtcggtgatg ttgtcattat cgtttcttat gcaatgatgt cagaagaaga agctaagacc    300
cataagccaa aggttgctgt tttgaacgaa agaaatgaga ttgaggaaat gttaggtcaa    360
gaaccagcaa gaacaatctt ataa                                           384

<210> SEQ ID NO 152
<211> LENGTH: 54
<212> TYPE: DNA
<213> ORGANISM: Issatchenkia orientalis
```

```
<400> SEQUENCE: 152
taaaacgacg gccagtgaat tccgcggcgg ccgcgagtcc atcggttcct gtca         54

<210> SEQ ID NO 153
<211> LENGTH: 59
<212> TYPE: DNA
<213> ORGANISM: Issatchenkia orientalis

<400> SEQUENCE: 153
cataagaaaa tcaaagacag aaggcgcgcc tttgctagca tttttgtgtt ttgctgtgt   59

<210> SEQ ID NO 154
<211> LENGTH: 59
<212> TYPE: DNA
<213> ORGANISM: Artificial Sequence
<220> FEATURE:
<223> OTHER INFORMATION: Artificial primer

<400> SEQUENCE: 154
acacagcaaa acacaaaaat gctagcaaag gcgcgccttc tgtctttgat tttcttatg   59

<210> SEQ ID NO 155
<211> LENGTH: 45
<212> TYPE: DNA
<213> ORGANISM: Artificial Sequence
<220> FEATURE:
<223> OTHER INFORMATION: ARTIFICIAL PRIMER

<400> SEQUENCE: 155
gggggaaaga actaccaata ggcctccttt aattcggaga aaatc                  45

<210> SEQ ID NO 156
<211> LENGTH: 45
<212> TYPE: DNA
<213> ORGANISM: Artificial Sequence
<220> FEATURE:
<223> OTHER INFORMATION: ARTIFICIAL PRIMER

<400> SEQUENCE: 156
gattttctcc gaattaaagg aggcctattg gtagttcttt ccccc                  45

<210> SEQ ID NO 157
<211> LENGTH: 51
<212> TYPE: DNA
<213> ORGANISM: Artificial Sequence
<220> FEATURE:
<223> OTHER INFORMATION: ARTIFICIAL PRIMER

<400> SEQUENCE: 157
aaaataaact agtaaaataa attaattaat tatctagaga gggggttata t           51

<210> SEQ ID NO 158
<211> LENGTH: 51
<212> TYPE: DNA
<213> ORGANISM: Artificial Sequence
<220> FEATURE:
<223> OTHER INFORMATION: ARTIFICIAL PRIMER

<400> SEQUENCE: 158
atataacccc ctctctagat aattaattaa tttatttttac tagtttattt t          51

<210> SEQ ID NO 159
<211> LENGTH: 53
<212> TYPE: DNA
```

```
<213> ORGANISM: Artificial Sequence
<220> FEATURE:
<223> OTHER INFORMATION: ARTIFICIAL PRIMER

<400> SEQUENCE: 159
gaccatgatt acgccaagct ccgcggcggc cgcccagtca aaaccttctt ctc        53

<210> SEQ ID NO 160
<211> LENGTH: 52
<212> TYPE: DNA
<213> ORGANISM: Artificial Sequence
<220> FEATURE:
<223> OTHER INFORMATION: ARTIFICIAL PRIMER

<400> SEQUENCE: 160
taaaacgacg gccagtgaat tccgcggcgg ccgcctttga aggagcttgc ca         52

<210> SEQ ID NO 161
<211> LENGTH: 49
<212> TYPE: DNA
<213> ORGANISM: Artificial Sequence
<220> FEATURE:
<223> OTHER INFORMATION: ARTIFICIAL PRIMER

<400> SEQUENCE: 161
ctattccttc tcaaattgc tgtttaaacg cgttgaagat ctattctcc              49

<210> SEQ ID NO 162
<211> LENGTH: 49
<212> TYPE: DNA
<213> ORGANISM: Artificial Sequence
<220> FEATURE:
<223> OTHER INFORMATION: ARTIFICIAL PRIMER

<400> SEQUENCE: 162
ggagaataga tcttcaacgc gtttaaacag caatttgagg aaggaatag             49

<210> SEQ ID NO 163
<211> LENGTH: 55
<212> TYPE: DNA
<213> ORGANISM: Artificial Sequence
<220> FEATURE:
<223> OTHER INFORMATION: ARTIFICIAL PRIMER

<400> SEQUENCE: 163
aatgttcatt ttacattcag atgttaatta aggtctagat gtgtttgttt gtgtg      55

<210> SEQ ID NO 164
<211> LENGTH: 55
<212> TYPE: DNA
<213> ORGANISM: Artificial Sequence
<220> FEATURE:
<223> OTHER INFORMATION: ARTIFICIAL PRIMER

<400> SEQUENCE: 164
cacacaaaca aacacatcta gaccttaatt aacatctgaa tgtaaaatga acatt      55

<210> SEQ ID NO 165
<211> LENGTH: 53
<212> TYPE: DNA
<213> ORGANISM: Artificial Sequence
<220> FEATURE:
<223> OTHER INFORMATION: ARTIFICIAL PRIMER

<400> SEQUENCE: 165
gaccatgatt acgccaagct ccgcggcggc cgcaatgcca agagttatgg ggc        53
```

<210> SEQ ID NO 166
<211> LENGTH: 23
<212> TYPE: DNA
<213> ORGANISM: Artificial Sequence
<220> FEATURE:
<223> OTHER INFORMATION: ARTIFICIAL PRIMER

<400> SEQUENCE: 166
ggctacccta tatatggtga gcg                                    23

<210> SEQ ID NO 167
<211> LENGTH: 21
<212> TYPE: DNA
<213> ORGANISM: Artificial Sequence
<220> FEATURE:
<223> OTHER INFORMATION: ARTIFICIAL PRIMER

<400> SEQUENCE: 167
gggtccaagt tatccaagca g                                      21

<210> SEQ ID NO 168
<211> LENGTH: 29
<212> TYPE: DNA
<213> ORGANISM: Artificial Sequence
<220> FEATURE:
<223> OTHER INFORMATION: ARTIFICIAL PRIMER

<400> SEQUENCE: 168
ccttaattaa ccgtaaagtt gtctcaatg                              29

<210> SEQ ID NO 169
<211> LENGTH: 55
<212> TYPE: DNA
<213> ORGANISM: Artificial Sequence
<220> FEATURE:
<223> OTHER INFORMATION: ARTIFICIAL PRIMER

<400> SEQUENCE: 169
cagcaaaaca caaaaattct agaaaattta attaacatct gaatgtaaaa tgaac    55

<210> SEQ ID NO 170
<211> LENGTH: 55
<212> TYPE: DNA
<213> ORGANISM: Artificial Sequence
<220> FEATURE:
<223> OTHER INFORMATION: ARTIFICIAL PRIMER

<400> SEQUENCE: 170
gttcatttta cattcagatg ttaattaaat tttctagaat ttttgtgttt tgctg    55

<210> SEQ ID NO 171
<211> LENGTH: 32
<212> TYPE: DNA
<213> ORGANISM: Artificial Sequence
<220> FEATURE:
<223> OTHER INFORMATION: ARTIFICIAL PRIMER

<400> SEQUENCE: 171
gctctagata aaatgccctc ttattctgtc gc                          32

<210> SEQ ID NO 172
<211> LENGTH: 20
<212> TYPE: DNA
<213> ORGANISM: Artificial Sequence
<220> FEATURE:

<223> OTHER INFORMATION: ARTIFICIAL PRIMER

<400> SEQUENCE: 172

```
gactggatca ttatgactcc                                                  20
```

<210> SEQ ID NO 173
<211> LENGTH: 44
<212> TYPE: DNA
<213> ORGANISM: Artificial Sequence
<220> FEATURE:
<223> OTHER INFORMATION: ARTIFICIAL PRIMER

<400> SEQUENCE: 173

```
acgccttgcc aaatgcggcc gcgagtccat cggttcctgt caga                       44
```

<210> SEQ ID NO 174
<211> LENGTH: 49
<212> TYPE: DNA
<213> ORGANISM: Artificial Sequence
<220> FEATURE:
<223> OTHER INFORMATION: ARTIFICIAL PRIMER

<400> SEQUENCE: 174

```
tcaaagacag aattaattaa gctctagaat ttttgtgttt tgctgtgtt                  49
```

<210> SEQ ID NO 175
<211> LENGTH: 49
<212> TYPE: DNA
<213> ORGANISM: Artificial Sequence
<220> FEATURE:
<223> OTHER INFORMATION: ARTIFICIAL PRIMER

<400> SEQUENCE: 175

```
aacacaaaaa ttctagagct taattaattc tgtctttgat tttcttatg                  49
```

<210> SEQ ID NO 176
<211> LENGTH: 32
<212> TYPE: DNA
<213> ORGANISM: Artificial Sequence
<220> FEATURE:
<223> OTHER INFORMATION: ARTIFICIAL PRIMER

<400> SEQUENCE: 176

```
gtttaaacct ttaattcgga gaaaatctga tc                                    32
```

<210> SEQ ID NO 177
<211> LENGTH: 30
<212> TYPE: DNA
<213> ORGANISM: Artificial Sequence
<220> FEATURE:
<223> OTHER INFORMATION: ARTIFICIAL PRIMER

<400> SEQUENCE: 177

```
gttaacggta ccgagctcta agtagtggtg                                       30
```

<210> SEQ ID NO 178
<211> LENGTH: 41
<212> TYPE: DNA
<213> ORGANISM: Artificial Sequence
<220> FEATURE:
<223> OTHER INFORMATION: ARTIFICIAL PRIMER

<400> SEQUENCE: 178

```
aaccgatgga ctcgcggccg catttggcaa ggcgtatcta t                          41
```

```
<210> SEQ ID NO 179
<211> LENGTH: 30
<212> TYPE: DNA
<213> ORGANISM: Artificial Sequence
<220> FEATURE:
<223> OTHER INFORMATION: ARTIFICIAL PRIMER

<400> SEQUENCE: 179
ggcgccagca atttgaggaa ggaataggag                                      30

<210> SEQ ID NO 180
<211> LENGTH: 52
<212> TYPE: DNA
<213> ORGANISM: Artificial Sequence
<220> FEATURE:
<223> OTHER INFORMATION: ARTIFICIAL PRIMER

<400> SEQUENCE: 180
aaactattag attaattaag ctcgcgatgt gtttgtttgt gtgttttgtg tg             52

<210> SEQ ID NO 181
<211> LENGTH: 52
<212> TYPE: DNA
<213> ORGANISM: Artificial Sequence
<220> FEATURE:
<223> OTHER INFORMATION: ARTIFICIAL PRIMER

<400> SEQUENCE: 181
caaacaaaca catcgcgagc ttaattaatc taatagttta atcacagctt at             52

<210> SEQ ID NO 182
<211> LENGTH: 42
<212> TYPE: DNA
<213> ORGANISM: Artificial Sequence
<220> FEATURE:
<223> OTHER INFORMATION: ARTIFICIAL PRIMER

<400> SEQUENCE: 182
tacattatgg tagcggccgc gtgtgacatt ttgatccact cg                        42

<210> SEQ ID NO 183
<211> LENGTH: 47
<212> TYPE: DNA
<213> ORGANISM: Artificial Sequence
<220> FEATURE:
<223> OTHER INFORMATION: ARTIFICIAL PRIMER

<400> SEQUENCE: 183
tggatcaaaa tgtcacacgc ggccgctacc ataatgtatg cgttgag                   47

<210> SEQ ID NO 184
<211> LENGTH: 27
<212> TYPE: DNA
<213> ORGANISM: Artificial Sequence
<220> FEATURE:
<223> OTHER INFORMATION: ARTIFICIAL PRIMER

<400> SEQUENCE: 184
gggccctaaa agtgttggtg tattaga                                         27

<210> SEQ ID NO 185
<211> LENGTH: 33
<212> TYPE: DNA
<213> ORGANISM: Artificial Sequence
<220> FEATURE:
<223> OTHER INFORMATION: ARTIFICIAL PRIMER
```

```
<400> SEQUENCE: 185
gctagctcaa caaactcttt atcagattta gca                                    33

<210> SEQ ID NO 186
<211> LENGTH: 30
<212> TYPE: DNA
<213> ORGANISM: Artificial Sequence
<220> FEATURE:
<223> OTHER INFORMATION: ARTIFICIAL PRIMER

<400> SEQUENCE: 186
gctagcgagg aaaagaagtc taacctttgt                                        30

<210> SEQ ID NO 187
<211> LENGTH: 35
<212> TYPE: DNA
<213> ORGANISM: Artificial Sequence
<220> FEATURE:
<223> OTHER INFORMATION: ARTIFICIAL PRIMER

<400> SEQUENCE: 187
tcgcgataaa atgtcaactg tggaagatca ctcct                                  35

<210> SEQ ID NO 188
<211> LENGTH: 27
<212> TYPE: DNA
<213> ORGANISM: Artificial Sequence
<220> FEATURE:
<223> OTHER INFORMATION: ARTIFICIAL PRIMER

<400> SEQUENCE: 188
ttaattaagc tgctggcgct tcatctt                                           27

<210> SEQ ID NO 189
<211> LENGTH: 32
<212> TYPE: DNA
<213> ORGANISM: Artificial Sequence
<220> FEATURE:
<223> OTHER INFORMATION: ARTIFICIAL PRIMER

<400> SEQUENCE: 189
tcgcgataaa atgtccagag gcttctttac tg                                     32

<210> SEQ ID NO 190
<211> LENGTH: 30
<212> TYPE: DNA
<213> ORGANISM: Artificial Sequence
<220> FEATURE:
<223> OTHER INFORMATION: ARTIFICIAL PRIMER

<400> SEQUENCE: 190
ttaattaact aaaggtctct cacgacagag                                        30

<210> SEQ ID NO 191
<211> LENGTH: 40
<212> TYPE: DNA
<213> ORGANISM: Artificial Sequence
<220> FEATURE:
<223> OTHER INFORMATION: ARTIFICIAL PRIMER

<400> SEQUENCE: 191
gttaacccgg tttaaacata gcctcatgaa atcagccatt                             40

<210> SEQ ID NO 192
<211> LENGTH: 44
```

```
<212> TYPE: DNA
<213> ORGANISM: Artificial Sequence
<220> FEATURE:
<223> OTHER INFORMATION: ARTIFICIAL PRIMER

<400> SEQUENCE: 192
gggcccatat ggcgcccggg gcgttgaaga tctattctcc agca            44

<210> SEQ ID NO 193
<211> LENGTH: 30
<212> TYPE: DNA
<213> ORGANISM: Artificial Sequence
<220> FEATURE:
<223> OTHER INFORMATION: ARTIFICIAL PRIMER

<400> SEQUENCE: 193
gtttaaacga ttggtagttc tttccccctc                            30

<210> SEQ ID NO 194
<211> LENGTH: 46
<212> TYPE: DNA
<213> ORGANISM: Artificial Sequence
<220> FEATURE:
<223> OTHER INFORMATION: ARTIFICIAL PRIMER

<400> SEQUENCE: 194
aataaattaa gggcccttta tcgcgagagg gggttatatg tgtaaa          46

<210> SEQ ID NO 195
<211> LENGTH: 50
<212> TYPE: DNA
<213> ORGANISM: Artificial Sequence
<220> FEATURE:
<223> OTHER INFORMATION: ARTIFICIAL PRIMER

<400> SEQUENCE: 195
tataaccccc tctcgcgata aagggcccctt aatttatttt actagtttat     50

<210> SEQ ID NO 196
<211> LENGTH: 27
<212> TYPE: DNA
<213> ORGANISM: Artificial Sequence
<220> FEATURE:
<223> OTHER INFORMATION: ARTIFICIAL PRIMER

<400> SEQUENCE: 196
gtttaaactt ttgtagcacc tcctggt                               27

<210> SEQ ID NO 197
<211> LENGTH: 48
<212> TYPE: DNA
<213> ORGANISM: Artificial Sequence
<220> FEATURE:
<223> OTHER INFORMATION: ARTIFICIAL PRIMER

<400> SEQUENCE: 197
cagcaaaaca caaaaagcta gctaaaatgt tacgtaccat gttcaaaa        48

<210> SEQ ID NO 198
<211> LENGTH: 46
<212> TYPE: DNA
<213> ORGANISM: Artificial Sequence
<220> FEATURE:
<223> OTHER INFORMATION: ARTIFICIAL PRIMER

<400> SEQUENCE: 198
```

-continued gaaaatcaaa gacagaaggc gcgccttatg ctgtaacagc ctgcgg        46

<210> SEQ ID NO 199
<211> LENGTH: 49
<212> TYPE: DNA
<213> ORGANISM: Artificial Sequence
<220> FEATURE:
<223> OTHER INFORMATION: ARTIFICIAL PRIMER

<400> SEQUENCE: 199
cagcaaaaca caaaaagcta gctaaaatgt taagaaccat gttcaaatc        49

<210> SEQ ID NO 200
<211> LENGTH: 47
<212> TYPE: DNA
<213> ORGANISM: Artificial Sequence
<220> FEATURE:
<223> OTHER INFORMATION: ARTIFICIAL PRIMER

<400> SEQUENCE: 200
gaaaatcaaa gacagaaggc gcgccttatg cagtaacagc ttgtggg        47

<210> SEQ ID NO 201
<211> LENGTH: 20
<212> TYPE: DNA
<213> ORGANISM: Artificial Sequence
<220> FEATURE:
<223> OTHER INFORMATION: ARTIFICIAL PRIMER

<400> SEQUENCE: 201
gcatggtggt gcaagcgacg        20

<210> SEQ ID NO 202
<211> LENGTH: 19
<212> TYPE: DNA
<213> ORGANISM: Artificial Sequence
<220> FEATURE:
<223> OTHER INFORMATION: ARTIFICIAL PRIMER

<400> SEQUENCE: 202
ggtgctgcat ttgctgctg        19

<210> SEQ ID NO 203
<211> LENGTH: 25
<212> TYPE: DNA
<213> ORGANISM: Artificial Sequence
<220> FEATURE:
<223> OTHER INFORMATION: ARTIFICIAL PRIMER

<400> SEQUENCE: 203
tgtatacagg atcgaagaat agaag        25

<210> SEQ ID NO 204
<211> LENGTH: 22
<212> TYPE: DNA
<213> ORGANISM: Artificial Sequence
<220> FEATURE:
<223> OTHER INFORMATION: ARTIFICIAL PRIMER

<400> SEQUENCE: 204
gaacgtctac aacgaggtga ac        22

<210> SEQ ID NO 205
<211> LENGTH: 21
<212> TYPE: DNA
<213> ORGANISM: Artificial Sequence

```
<220> FEATURE:
<223> OTHER INFORMATION: ARTIFICIAL PRIMER

<400> SEQUENCE: 205
ggcgcgcctc gcgataaaat g                                              21

<210> SEQ ID NO 206
<211> LENGTH: 32
<212> TYPE: DNA
<213> ORGANISM: Artificial Sequence
<220> FEATURE:
<223> OTHER INFORMATION: ARTIFICIAL PRIMER

<400> SEQUENCE: 206
agggccctta attaattatg cagtaacagc tt                                  32

<210> SEQ ID NO 207
<211> LENGTH: 20
<212> TYPE: DNA
<213> ORGANISM: Artificial Sequence
<220> FEATURE:
<223> OTHER INFORMATION: ARTIFICIAL PRIMER

<400> SEQUENCE: 207
cgctacgata cgctacgata                                                20

<210> SEQ ID NO 208
<211> LENGTH: 20
<212> TYPE: DNA
<213> ORGANISM: Artificial Sequence
<220> FEATURE:
<223> OTHER INFORMATION: ARTIFICIAL PRIMER

<400> SEQUENCE: 208
ctcccttccc tgatagaagg                                                20

<210> SEQ ID NO 209
<211> LENGTH: 21
<212> TYPE: DNA
<213> ORGANISM: Artificial Sequence
<220> FEATURE:
<223> OTHER INFORMATION: ARTIFICIAL PRIMER

<400> SEQUENCE: 209
ggggagcaat ttgccaccag g                                              21

<210> SEQ ID NO 210
<211> LENGTH: 25
<212> TYPE: DNA
<213> ORGANISM: Artificial Sequence
<220> FEATURE:
<223> OTHER INFORMATION: ARTIFICIAL PRIMER

<400> SEQUENCE: 210
ctccttcatt taactatacc agacg                                          25

<210> SEQ ID NO 211
<211> LENGTH: 26
<212> TYPE: DNA
<213> ORGANISM: Artificial Sequence
<220> FEATURE:
<223> OTHER INFORMATION: ARTIFICIAL PRIMER

<400> SEQUENCE: 211
gacagatgta aggaccaata gtgtcc                                         26
```

<210> SEQ ID NO 212
<211> LENGTH: 23
<212> TYPE: DNA
<213> ORGANISM: Artificial Sequence
<220> FEATURE:
<223> OTHER INFORMATION: ARTIFICIAL PRIMER

<400> SEQUENCE: 212
ccatatcgaa atctagcccg tcc                                    23

<210> SEQ ID NO 213
<211> LENGTH: 58
<212> TYPE: DNA
<213> ORGANISM: Artificial Sequence
<220> FEATURE:
<223> OTHER INFORMATION: ARTIFICIAL PRIMER

<400> SEQUENCE: 213
cataagaaaa tcaaagacag aaggcgcgcc tttgctagct ttttgtgttt tgctgtgt     58

<210> SEQ ID NO 214
<211> LENGTH: 19
<212> TYPE: DNA
<213> ORGANISM: Artificial Sequence
<220> FEATURE:
<223> OTHER INFORMATION: ARTIFICIAL PRIMER

<400> SEQUENCE: 214
attggacaca acattatat                                         19

<210> SEQ ID NO 215
<211> LENGTH: 46
<212> TYPE: DNA
<213> ORGANISM: Artificial Sequence
<220> FEATURE:
<223> OTHER INFORMATION: ARTIFICIAL PRIMER

<400> SEQUENCE: 215
gtaaaacgac ggccagtgaa ttgttaacat aggctccaac atctcg           46

<210> SEQ ID NO 216
<211> LENGTH: 38
<212> TYPE: DNA
<213> ORGANISM: Artificial Sequence
<220> FEATURE:
<223> OTHER INFORMATION: ARTIFICIAL PRIMER

<400> SEQUENCE: 216
ggaaccgatg gactcgcggc cgcgtgggat attggaag                    38

<210> SEQ ID NO 217
<211> LENGTH: 22
<212> TYPE: DNA
<213> ORGANISM: Artificial Sequence
<220> FEATURE:
<223> OTHER INFORMATION: ARTIFICIAL PRIMER

<400> SEQUENCE: 217
ggaggtgcta caaaaggaat tc                                     22

<210> SEQ ID NO 218
<211> LENGTH: 48
<212> TYPE: DNA
<213> ORGANISM: Artificial Sequence
<220> FEATURE:
<223> OTHER INFORMATION: ARTIFICIAL PRIMER

```
<400> SEQUENCE: 218
gaccatgatt acgccaagct ccgcggagtc aaaaccttct tctctacc                      48

<210> SEQ ID NO 219
<211> LENGTH: 46
<212> TYPE: DNA
<213> ORGANISM: Artificial Sequence
<220> FEATURE:
<223> OTHER INFORMATION: ARTIFICIAL PRIMER

<400> SEQUENCE: 219
gtaaaacgac ggccagtgaa ttctttgaag gagcttgcca agaaac                        46

<210> SEQ ID NO 220
<211> LENGTH: 23
<212> TYPE: DNA
<213> ORGANISM: Artificial Sequence
<220> FEATURE:
<223> OTHER INFORMATION: ARTIFICIAL PRIMER

<400> SEQUENCE: 220
cctattcctt cctcaaattg ctg                                                 23

<210> SEQ ID NO 221
<211> LENGTH: 38
<212> TYPE: DNA
<213> ORGANISM: Artificial Sequence
<220> FEATURE:
<223> OTHER INFORMATION: ARTIFICIAL PRIMER

<400> SEQUENCE: 221
ataactcttg gcattgcggc cgccaagtta gttagagc                                 38

<210> SEQ ID NO 222
<211> LENGTH: 51
<212> TYPE: DNA
<213> ORGANISM: Artificial Sequence
<220> FEATURE:
<223> OTHER INFORMATION: ARTIFICIAL PRIMER

<400> SEQUENCE: 222
atgaccatga ttacgccaag ctccgcggca aagacggtgt attagtgctt g                  51

<210> SEQ ID NO 223
<211> LENGTH: 64
<212> TYPE: DNA
<213> ORGANISM: Artificial Sequence
<220> FEATURE:
<223> OTHER INFORMATION: ARTIFICIAL PRIMER

<400> SEQUENCE: 223
cacaaaacac acaaacaaac acagctagca aggcgcgcc atctaatagt ttaatcacag          60
ctta                                                                     64

<210> SEQ ID NO 224
<211> LENGTH: 47
<212> TYPE: DNA
<213> ORGANISM: Artificial Sequence
<220> FEATURE:
<223> OTHER INFORMATION: ARTIFICIAL PRIMER

<400> SEQUENCE: 224
gccgttgcag caaatgtcga ggcctgtgtg acattttgat ccactcg                       47
```

<210> SEQ ID NO 225
<211> LENGTH: 47
<212> TYPE: DNA
<213> ORGANISM: Artificial Sequence
<220> FEATURE:
<223> OTHER INFORMATION: ARTIFICIAL PRIMER

<400> SEQUENCE: 225
cgagtggatc aaaatgtcac acaggcctcg acatttgctg caacggc     47

<210> SEQ ID NO 226
<211> LENGTH: 51
<212> TYPE: DNA
<213> ORGANISM: Artificial Sequence
<220> FEATURE:
<223> OTHER INFORMATION: ARTIFICIAL PRIMER

<400> SEQUENCE: 226
cattttacat tcagatgtta attaattatc tagatgttgt tgttgttgtc g     51

<210> SEQ ID NO 227
<211> LENGTH: 51
<212> TYPE: DNA
<213> ORGANISM: Artificial Sequence
<220> FEATURE:
<223> OTHER INFORMATION: ARTIFICIAL PRIMER

<400> SEQUENCE: 227
cgacaacaac aacaacatct agataattaa ttaacatctg aatgtaaaat g     51

<210> SEQ ID NO 228
<211> LENGTH: 51
<212> TYPE: DNA
<213> ORGANISM: Artificial Sequence
<220> FEATURE:
<223> OTHER INFORMATION: ARTIFICIAL PRIMER

<400> SEQUENCE: 228
gctctaacta acttggcggc cgcttttatt ataaaattat atattattct t     51

<210> SEQ ID NO 229
<211> LENGTH: 47
<212> TYPE: DNA
<213> ORGANISM: Artificial Sequence
<220> FEATURE:
<223> OTHER INFORMATION: ARTIFICIAL PRIMER

<400> SEQUENCE: 229
aacacacaaa caaacacagc tagctaaaat gttaagaact atgttta     47

<210> SEQ ID NO 230
<211> LENGTH: 46
<212> TYPE: DNA
<213> ORGANISM: Artificial Sequence
<220> FEATURE:
<223> OTHER INFORMATION: ARTIFICIAL PRIMER

<400> SEQUENCE: 230
gattaaacta ttagatggcg cgccttatgc agtaactgct tgtgga     46

<210> SEQ ID NO 231
<211> LENGTH: 42
<212> TYPE: DNA
<213> ORGANISM: Artificial Sequence
<220> FEATURE:
<223> OTHER INFORMATION: ARTIFICIAL PRIMER

<400> SEQUENCE: 231
cgacggccag tgaattcgtt aacccgtttc gatgggattc cc                    42

<210> SEQ ID NO 232
<211> LENGTH: 46
<212> TYPE: DNA
<213> ORGANISM: Artificial Sequence
<220> FEATURE:
<223> OTHER INFORMATION: ARTIFICIAL PRIMER

<400> SEQUENCE: 232
caggaaccga tggactcgcg gccgctccct tctctaaatg gactgc                46

<210> SEQ ID NO 233
<211> LENGTH: 48
<212> TYPE: DNA
<213> ORGANISM: Artificial Sequence
<220> FEATURE:
<223> OTHER INFORMATION: ARTIFICIAL PRIMER

<400> SEQUENCE: 233
tatataattt tataataaaa gcggccgcac cagggggttta gtgaagtc              48

<210> SEQ ID NO 234
<211> LENGTH: 47
<212> TYPE: DNA
<213> ORGANISM: Artificial Sequence
<220> FEATURE:
<223> OTHER INFORMATION: ARTIFICIAL PRIMER

<400> SEQUENCE: 234
catgattacg ccaagctccg cggccataac tgacatttat ggtaagg               47

<210> SEQ ID NO 235
<211> LENGTH: 21
<212> TYPE: DNA
<213> ORGANISM: Artificial Sequence
<220> FEATURE:
<223> OTHER INFORMATION: ARTIFICIAL PRIMER

<400> SEQUENCE: 235
ccaacaatct taattggtga c                                           21

<210> SEQ ID NO 236
<211> LENGTH: 20
<212> TYPE: DNA
<213> ORGANISM: Artificial Sequence
<220> FEATURE:
<223> OTHER INFORMATION: ARTIFICIAL PRIMER

<400> SEQUENCE: 236
ggctgttacc gcctaattaa                                             20

<210> SEQ ID NO 237
<211> LENGTH: 23
<212> TYPE: DNA
<213> ORGANISM: Artificial Sequence
<220> FEATURE:
<223> OTHER INFORMATION: ARTIFICIAL PRIMER

<400> SEQUENCE: 237
gttcttaaca ttttagctag ctg                                         23

<210> SEQ ID NO 238

```
<211> LENGTH: 30
<212> TYPE: DNA
<213> ORGANISM: Artificial Sequence
<220> FEATURE:
<223> OTHER INFORMATION: ARTIFICIAL PRIMER

<400> SEQUENCE: 238
acgcgtcgac tcgacatttg ctgcaacggc                                    30

<210> SEQ ID NO 239
<211> LENGTH: 29
<212> TYPE: DNA
<213> ORGANISM: Artificial Sequence
<220> FEATURE:
<223> OTHER INFORMATION: ARTIFICIAL PRIMER

<400> SEQUENCE: 239
ctagtctaga tgttgttgtt gttgtcgtt                                     29

<210> SEQ ID NO 240
<211> LENGTH: 49
<212> TYPE: DNA
<213> ORGANISM: Artificial Sequence
<220> FEATURE:
<223> OTHER INFORMATION: ARTIFICIAL PRIMER

<400> SEQUENCE: 240
caaaacacag caaaacacaa aaagctagca tgtatagaac cttgatgag               49

<210> SEQ ID NO 241
<211> LENGTH: 40
<212> TYPE: DNA
<213> ORGANISM: Artificial Sequence
<220> FEATURE:
<223> OTHER INFORMATION: ARTIFICIAL PRIMER

<400> SEQUENCE: 241
caaagacaga aggcgcgcct tataagatgg ttctcgctgg                         40

<210> SEQ ID NO 242
<211> LENGTH: 50
<212> TYPE: DNA
<213> ORGANISM: Artificial Sequence
<220> FEATURE:
<223> OTHER INFORMATION: ARTIFICIAL PRIMER

<400> SEQUENCE: 242
caaaacacac aaacaaacac agctagcatg tacagaacgt taatgtctgc              50

<210> SEQ ID NO 243
<211> LENGTH: 47
<212> TYPE: DNA
<213> ORGANISM: Artificial Sequence
<220> FEATURE:
<223> OTHER INFORMATION: ARTIFICIAL PRIMER

<400> SEQUENCE: 243
gtgattaaac tattagatgg cgcgccttac aggatggttc tggcagg                 47

<210> SEQ ID NO 244
<211> LENGTH: 703
<212> TYPE: DNA
<213> ORGANISM: Issatchenkia orientalis

<400> SEQUENCE: 244
gagtccatcg gttcctgtca gatgggatac tcttgacgtg gaaaattcaa acagaaaaaa   60
```

| aacccccaata atgaaaaata acactacgtt atatccgtgg tatcctctat cgtatcgtat | 120 |
| cgtagcgtat cgtagcgtac cgtatcacag tatagtctaa tattccgtat cttattgtat | 180 |
| cctatcctat tcgatcctat tgtatttcag tgcaccattt taatttctat tgctataatg | 240 |
| tccttattag ttgccactgt gaggtgacca atggacgagg cgagccgtt cagaagccgc | 300 |
| gaagggtgtt cttcccatga atttcttaag gagggcggct cagctccgag agtgaggcga | 360 |
| gacgtctcgg tcagcgtatc ccccttcctc ggcttttaca aatgatgcgc tcttaatagt | 420 |
| gtgtcgttat cctttttggca ttgacggggg agggaaattg attgagcgca tccatatttt | 480 |
| tgcggactgc tgaggacaat ggtggttttt ccgggtggcg tgggctacaa atgatacgat | 540 |
| ggttttttc ttttcggaga aggcgtataa aaggacacg gagaacccat ttattctaaa | 600 |
| aacagttgag cttctttaat tatttttga tataatattc tattattata tattttcttc | 660 |
| ccaataaaac aaaataaaac aaaacacagc aaaacacaaa aat | 703 |

<210> SEQ ID NO 245
<211> LENGTH: 961
<212> TYPE: DNA
<213> ORGANISM: Issatchenkia orientalis

<400> SEQUENCE: 245

| agcaatttga ggaaggaata ggagaaggag aagcaatttc taggaaagag caaggtgtgc | 60 |
| aacagcatgc tctgaatgat attttcagca atagttcagt tgaagaacct gttggcgtat | 120 |
| ctacatcact tcctacaaac aacaccacga attgcgtccg tggtgacgca actacgaatg | 180 |
| gcattgtcaa tgccaatgcc agtgcacata cacgtgcaag tcccaccggt tccctgcccg | 240 |
| gctatggtag agacaagaag gacgataccg catcgacat caacagtttc aacagcaatg | 300 |
| cgtttggcgt cgacgcgtcg atgggctgc cgtatttgga tttggacggg ctagatttcg | 360 |
| atatggatat ggatatggat atggatatgg agatgaattt gaatttagat ttgggtcttg | 420 |
| atttgggggtt ggaattaaaa ggggataaca atgagggttt tcctgttgat ttaaacaatg | 480 |
| gacgtgggag gtgattgatt taacctgatc caaaaggggt atgtctattt tttagagtgt | 540 |
| gtctttgtgt caaattatgg tagaatgtgt aaagtagtat aaactttcct ctcaaatgac | 600 |
| gaggtttaaa acaccccccg ggtgagccga gccgagaatg gggcaattgt tcaatgtgaa | 660 |
| atagaagtat cgagtgagaa acttgggtgt tggccagcca aggggggaagg aaaatggcgc | 720 |
| gaatgctcag gtgagattgt tttggaattg ggtgaagcga ggaaatgagc gacccggagg | 780 |
| ttgtgacttt agtggcggag gaggacggag gaaaagccaa gagggaagtg tatataaggg | 840 |
| gagcaatttg ccaccaggat agaattggat gagttataat tctactgtat ttattgtata | 900 |
| atttatttct ccttttatat caaacacatt acaaaacaca caaaacacac aaacaaacac | 960 |
| a | 961 |

<210> SEQ ID NO 246
<211> LENGTH: 992
<212> TYPE: DNA
<213> ORGANISM: Issatchenkia orientalis

<400> SEQUENCE: 246

| tattggtagt tctttccccc tctcaagctg gcgtgaaatg caaccttacg gcgtctacgt | 60 |
| tactacaagg tccagaaagt gtaggtattg ctactatttt tattttttat tggttctgga | 120 |
| gaaatgcaga cagtcaatga acacaactgt ctcaatatgc atctatgcac atgcacacac | 180 |

```
acacacatca caggtacccc tacaaagaga ggtctcttga taatgtttca ttaccacgtg    240 gcatccccc cccccccccc aataaacaag tggccgagtt ccctgttgc agaggaggac      300 aaaaaaccg ctggtgttgg taccattatg cagcaactag cacaacaaac aaccgaccca    360
gacatacaaa tcaacaacac ttcgccaaag cacccttc cagggaggat ccactcccaa     420
cgtctctcca taatgtctct gttggcccat gtctctgtcg ttgacaccgt aaccacacca   480
accaacccgt ccattgtact gggatggtcg tccatagaca cctctccaac ggggaacacc   540
tcattcgtaa accgccaagg ttaccgttcc tcctgactcg ccccgttgtt gatgctgcgc    600
acctgtggtt gcccaacatg gttgtatatc gtgtaaccac accaacacat gtgcagcaca    660
tgtgtttaaa agagtgtcat ggaggtggat catgatggaa gtggacttta ccacttggga    720
actgtctcca ctcccgggaa gaaaagaccc ggcgtatcac gcggttgcct caatggggca    780
atttggaagg agaaatatag ggaaaatcac gtcgctctcg gacggggaag agttccagac    840 tatgagggg ggggtggta tataaagaca ggagatgtcc accccagag agaggaagaa      900 gttggaactt tagaagagag agataacttt ccccagtgtc catcaataca aaccaaaca     960 caaactctat atttacacat ataacccccct ct                                992

<210> SEQ ID NO 247
<211> LENGTH: 613
<212> TYPE: DNA
<213> ORGANISM: Issatchenkia orientalis

<400> SEQUENCE: 247
ttgctgcaac ggcaacatca atgtccacgt ttacacacct acatttatat ctatatttat     60
atttatattt atttatttat gctacttagc ttctatagtt agttaatgca ctcacgatat    120
tcaaaattga caccctcaa ctactcccta ctattgtcta ctactgtcta ctactcctct     180
ttactatagc tgctcccaat aggctccacc aataggctct gtcaatacat tttgcgccgc    240
cacctttcag gttgtgtcac tcctgaagga ccatattggg taatcgtgca atttctggaa    300
gagagtccgc gagaagtgag gccccactg taaatcctcg aggggggcatg gagtatgggg    360 catggaggat ggaggatggg gggggggggg gggaaaatag gtagcgaaag gacccgctat    420
caccccaccc ggagaactcg ttgccgggaa gtcatatttc gacactccgg ggagtctata    480
aaaggcgggt tttgtcttt gccagttgat gttgctgaga ggacttgttt gccgtttctt    540
ccgatttaac agtatagaat caaccactgt taattataca cgttatacta acacaacaaa    600
aacaaaaaca acg                                                       613

<210> SEQ ID NO 248
<211> LENGTH: 399
<212> TYPE: DNA
<213> ORGANISM: Issatchenkia orientalis

<400> SEQUENCE: 248
tctgtctttg attttcttat gttattcaaa acatctgccc caaaatctaa cgattatata     60
tattcctacg tataactgta tagctaatta ttgatttatt tgtacataaa aaccacataa    120
atgtaaaagc aagaaaaaaa ataactaagg agaaggatca atatctcatt tataatgctc    180
gccaaagcag cgtacgtgaa ttttaatcaa gacatcaaca aatcttgcaa cttggttata    240
tcgcttcttc acccactcac ccgctttct acattgttga acacaaatat atacaggggt    300
atgtctcaag gtcaagtgca gtttcaacag agactacctc aaggtacctc ttcagaaatg    360
cagaacttca ctcttgatca gattttctcc gaattaaag                           399
```

<210> SEQ ID NO 249
<211> LENGTH: 422
<212> TYPE: DNA
<213> ORGANISM: Issatchenkia orientalis

<400> SEQUENCE: 249

```
atctaatagt ttaatcacag cttatagtct attatagttt tcttttttaa acattgttgt      60
attttgtccc ccccectcta attgatgatg attatcctat aagaatccaa taaaacgatg     120
gaaactaata ctttctcctt tgtcatgtgg tctttagtat ttcttgaaca ttggctctga     180
tttctcgact ttatagtcct attaaaatct ctgttagttc tcgatcgttg tatctcgttt     240
cttgtctctt tggtggatga ttttgcgtgc gaacatgttt ttttcccttt ctctcaccat     300
catcgtgtag ttcttgtcac catcccccca cccccttcctt ctctcattga ttctataaga    360
gcttatccac agaggtgcag taacgaggta gtttaacctt cgagtggatc aaaatgtcac     420
ac                                                                    422
```

<210> SEQ ID NO 250
<211> LENGTH: 421
<212> TYPE: DNA
<213> ORGANISM: Issatchenkia orientalis

<400> SEQUENCE: 250

```
tttatttttac tagtttatttt ttgctcctga aataggatt acaaacactt aaagtcttta     60
attacaacta tatataatat tctgttggtt ttcttgaatt ggttcgctgc gattcatgcc    120
tcccattcac caaaggtgga gtgggaaata acggttttac tgcggtaatt agcagaggca    180
agaacaggat acacttttttg atgataaatc tgtattatag tcgagcctat ttaggaaatc    240
aaattttctt gtgtttactt tcaaataaa taatgttcga aaattttttac tttactcctt     300
catttaacta taccagacgt tatatcatca acaccttctg accatataca gctcaagatg    360
tttaagagtc tgttaaattt tttcaatcca tttcatggag taccaggagg tgctacaaaa    420
g                                                                    421
```

<210> SEQ ID NO 251
<211> LENGTH: 281
<212> TYPE: DNA
<213> ORGANISM: Issatchenkia orientalis

<400> SEQUENCE: 251

```
catctgaatg taaaatgaac attaaaatga attactaaac tttacgtcta ctttacaatc      60
tataaacttt gtttaatcat ataacgaaat acactaatac acaatcctgt acgtatgtaa    120
tacttttatc catcaaggat tgagaaaaaa aagtaatgat tccctgggcc attaaaactt    180
agaccccaa gcttggatag gtcactctct attttcgttt ctcccttccc tgatagaagg     240
gtgatatgta attaagaata atatataatt ttataataaa a                        281
```

<210> SEQ ID NO 252
<211> LENGTH: 1394
<212> TYPE: DNA
<213> ORGANISM: Issatchenkia orientalis

<400> SEQUENCE: 252

```
catagcctca tgaaatcagc catttgcttt tgttcaacga tcttttgaaa ttgttgttgt      60
tcttggtagt taagttgatc catccttggct tatgttgtgt gtatgttgta gttattctta   120
```

```
gtatattcct gtcctgagtt tagtgaaaca taatatcgcc ttgaaatgaa aatgctgaaa      180
ttcgtcgaca tacaattttt caaactttt ttttttcttg gtgcacggac atgttttaa       240 aggaagtact ctataccagt tattcttcac aaatttaatt gctggagaat agatcttcaa     300
cgctttaata aagtagtttg tttgtcaagg atggcgtcat acaaagaaag atcagaatca    360
cacacttccc ctgttgctag gagactttc tccatcatgg aggaaaagaa gtctaacctt     420
tgtgcatcat tggatattac tgaaactgaa aagcttctct ctattttgga cactattggt    480
ccttacatct gtctagttaa aacacacatc gatattgttt ctgattttac gtatgaagga    540
actgtgttgc ctttgaagga gcttgccaag aaacataatt ttatgatttt tgaagataga   600
aaatttgctg atattggtaa cactgttaaa aatcaatata atctggtgt cttccgtatt    660 gccgaatggg ctgacatcac taatgcacat ggtgtaacgg gtgcaggtat tgtttctggc    720
ttgaaggagg cagcccaaga aacaaccagt gaacctagag gtttgctaat gcttgctgag    780
ttatcatcaa agggttcttt agcatatggt gaatatacag aaaaaacagt agaaattgct    840
aaatctgata aagagtttgt cattggtttt attgcgcaac acgatatggg cggtagagaa    900
gaaggttttg actggatcat tatgactcca ggggttggtt tagatgacaa aggtgatgca    960
cttggtcaac aatatagaac tgttgatgaa gttgtaaaga ctggaacgga tatcataatt   1020
gttggtagag gtttgtacgg tcaaggaaga gatcctatag agcaagctaa aagataccaa   1080
caagctggtt ggaatgctta tttaaacaga tttaaatgat tcttacacaa agatttgata   1140
catgtacact agtttaaata agcatgaaaa gaattacaca agcaaaaaaa aaaaaataaa   1200
tgaggtactt tacgttcacc tacaaccaaa aaaactagat agagtaaaat cttaagattt   1260
agaaaaagtt gtttaacaaa ggctttagta tgtgaatttt taatgtagca aagcgataac   1320
taataaacat aaacaaaagt atggttttct ttatcagtca aatcattatc gattgattgt   1380
tccgcgtatc tgca                                                      1394
```

<210> SEQ ID NO 253
<211> LENGTH: 523
<212> TYPE: DNA
<213> ORGANISM: Issatchenkia orientalis

<400> SEQUENCE: 253

```
gtataaactg tatgtcatta taaacaggga aggttgacat tgtctagcgg caatcattgt     60
ctcatttggt tcattaactt tggttctgtt cttggaaacg ggtaccaact ctctcagagt    120
gcttcaaaaa ttttcagca catttggtta gacatgaact ttctctgctg gttaaggatt    180
cagaggtgaa gtcttgaaca caatcgttga aacatctgtc cacaagagat gtgtatagcc    240
tcatgaaatc agccatttgc ttttgttcaa cgatctttg aaattgttgt tgttcttggt    300
agttaagttg atccatcttg gcttatgttg tgtgtatgtt gtagttattc ttagtatatt    360
cctgtcctga gttagtgaa acataatatc gccttgaaat gaaatgctg aaattcgtcg    420 acatacaatt tttcaaactt ttttttttc ttggtgcacg gacatgtttt taaggaagt    480 actctatacc agttattctt caccctgcag ggtacgtagc atg                     523
```

<210> SEQ ID NO 254
<211> LENGTH: 626
<212> TYPE: DNA
<213> ORGANISM: Issatchenkia orientalis
<220> FEATURE:
<221> NAME/KEY: misc_feature
<222> LOCATION: (28)..(28)
<223> OTHER INFORMATION: n is a, c, g, or t

<400> SEQUENCE: 254

```
gggcaacaaa gcctcccaga tttgatanat tttcaatttg tgctttgaat catgacttcc    60
acctgtttgg tccgcaagaa cacgtaaatg cgcaatttgt ttctcccttc tgcttaaaaa   120
ccatgcacct ttaatattat ctggaaagat aagaacaga attgttgcgt agaaacaagt    180
agcagagccg taaatgagaa aaatatactt ccaagctggt aatttcccct ttattagtcc   240
aatacagtgt ccgaagaccc caccaagaat accagcaagg gtgttgaaat ataatgtaga   300
tcttagtggt tgttctgatt tcttccacca cattccgcta ataatcataa aagacggtaa   360
tattccggct tcaaatacgc caagaaaaaa cctcacggta accaaccac caaagctatg    420
acatgcagcc atgcacataa gtaagccgcc ccaaatgaac aaacaaatag acacaaattt   480
gccaattcta actcgtggca acaaaaaaaa ggatatgaac tcacctaata aataaccgaa   540
ataaaaagta gaagcaactg tggaaaattg agaaccatgt aaatttgtgt cttctttcaa   600
tgtataaaca gccgcaatac ctaggg                                        626
```

<210> SEQ ID NO 255
<211> LENGTH: 1416
<212> TYPE: DNA
<213> ORGANISM: Saccharomyces cerevisiae

<400> SEQUENCE: 255

```
atgtttgctt tctactttct caccgcatgc accactttga agggtgtttt cggagtttct    60
ccgagttaca atggtcttgg tctcacccca cagatgggtt gggacagctg gaatacgttt   120
gcctgcgatg tcagtgaaca gctacttcta gacactgctg atagaatttc tgacttgggg   180
ctaaaggata tgggttacaa gtatgtcatc ctagatgact gttggtctag cggcagggat   240
tccgacggtt tcctcgttgc agacaagcac aaatttccca acggtatggg ccatgttgca   300
gaccacctgc ataataacag ctttcttttc ggtatgtatt cgtctgctgg tgagtacacc   360
tgtgctgggt accctgggtc tctggggcgt gaggaagaag atgctcaatt ctttgcaaat   420
aaccgcgttg actacttgaa gtatgataat tgttacaata aaggtcaatt tggtacacca   480
gacgtttctt accaccgtta caaggccatg tcagatgctt tgaataaaac tggtaggcct   540
atttcctatt ctctatgtaa ctggggtcag gatttgacat tttactgggg ctctggtatc   600
gccaattctt ggagaatgag cggagatatt actgctgagt tcaccctgtcc agatagcaga   660
tgtccctgtg acggtgacga atatgattgc aagtacgccg gtttccattg ttctattatg   720
aatattctta caaggcagc tccaatgggg caaaatgcag gtgttggtgg ttggaacgat   780
ctggacaatc tagaggtcgg agtcggtaat ttgactgacg atgaggaaaa ggcccatttc   840
tctatgtggg caatggtaaa gtccccactt atcattggtg ccgacgtgaa tcacttaaag   900
gcatcttcgt actcgatcta cagtcaagcc tctgtcatcg caattaatca agatccaaag   960
ggtattccag ccacaagagt ctggagatat tatgtttcag acaccgatga atatggacaa  1020
ggtgaaattc aaatgtggag tggtccgctt gacaatggtg accaagtggt tgctttattg  1080
aatggaggaa gcgtagcaag accaatgaac acgaccttgg aagagatttt ctttgacagc  1140
aatttgggtt caaggaact gacatcgact tgggatattt acgacttatg gccaacagaa  1200
gttgacaact ctacggcgtc tgctatcctt gaacagaata aggcagccac cggtattctc  1260
tacaatgcta cagagcagtc ttataaagac ggtttgtcta agaatgatac aagactgttt  1320
ggccagaaaa ttggtagtct ttctccaaat gctatactta acacaactgt tccagctcat  1380
```

```
ggtatcgcct tctataggtt gagaccctcg gcttaa                              1416
```

<210> SEQ ID NO 256
<211> LENGTH: 707
<212> TYPE: DNA
<213> ORGANISM: Kluyveromyces thermotolerans

<400> SEQUENCE: 256

```
cactcgcaag ctgtgccatc gcccaacggt taattataag aaatcaacat cagccaacaa     60
ctattttcgt cccctctttt tcagtggtaa cgagcaatta cattagtaag agactatttt    120
cttcagtgat ttgtaatttt ttttcagtga tttgtaattc tttctcgaaa tatgcgggct    180
taacttatcc ggacattcac tacatgcaag gaaaaacgag aaccgcggag atttcctcag    240
taagtaacaa tgatgatctt tttacgcttc atcatcactt tccaaagttc taagctataa    300
gttcaagcct agatacgctg aaaaactcct gaccaacaat gtaaagaaaa caattacaat    360
tgtaaggttg aaaacatcta aaatgaaat atttattgt acatgcacac cctgatagtc     420
attctcttac ttcatccctg aaagacgtgg ctgtacaaga gttggaatcg caaggtcatg    480
aggttaaagt tagtgatctt tatgctcaaa agtggaaggc ctcaatagac cgtgacgact    540
tcgagcagct tttcgcaaga agagaggtta aaaatacccc aagcttctta tgaagcgtat    600
gccagaggag cattaacaaa agacgtaaat caggaacagg aaaaacttat tgggcggac    660
tttgtcattt tgtcgtttcc tatatggtgg tcttctatgc cggctag                  707
```

<210> SEQ ID NO 257
<211> LENGTH: 655
<212> TYPE: DNA
<213> ORGANISM: Kluyveromyces thermotolerans

<400> SEQUENCE: 257

```
ggttaattat aagaaatcaa catcagccaa caactatttt cgtcccctc ttttcagtgg     60
taacgagcaa ttacattagt aagagactat tttcttcagt gatttgtaat ttttttcag    120
tgatttgtaa ttcttttctcg aaatatgcgg gcttaactta tccggacatt cactacatgc    180
aaggaaaaac gagaaccgcg gagatttcct cagtaagtaa caatgatgat cttttacgc    240
ttcatcatca ctttccaaag ttctaagcta aagttcaag cctagatacg ctgaaaaact    300
cctgaccaac aatgtaaaga aacaattac aattgtaagg ttgaaaacat ctaaaaatga    360
atatttttat tgtacatgca caccctgata gtcattctct tacttcatcc ctgaaagacg    420
tggctgtaca agagttggaa tcgcaaggtc atgaggttaa agttagtgat ctttatgctc    480
aaaagtggaa ggcctcaata gaccgtgacg acttcgagca gcttttcgca agaagagagg    540
ttaaaaatac cccaagcttc ttatgaagcg tatgccagag gagcattaac aaaagacgta    600
aatcaggaac aggaaaaact tatttgggcg gactttgtca ttttgtcgtt tccta         655
```

<210> SEQ ID NO 258
<211> LENGTH: 523
<212> TYPE: DNA
<213> ORGANISM: Issatchenkia orientalis

<400> SEQUENCE: 258

```
gtataaactg tatgtcatta taaacaggga aggttgacat tgtctagcgg caatcattgt     60
ctcatttggt tcattaactt tggttctgtt cttggaaacg ggtaccaact ctctcagagt    120
gcttcaaaaa ttttcagca catttggtta gacatgaact ttctctgctg ttaaggatt     180
cagaggtgaa gtcttgaaca caatcgttga acatctgtc cacaagagat gtgtatagcc    240
```

```
tcatgaaatc agccatttgc ttttgttcaa cgatcttttg aaattgttgt tgttcttggt        300
agttaagttg atccatcttg gcttatgttg tgtgtatgtt gtagttattc ttagtatatt        360
cctgtcctga gtttagtgaa acataatatc gccttgaaat gaaaatgctg aaattcgtcg        420
acatacaatt tttcaaactt ttttttttc ttggtgcacg gacatgtttt taaaggaagt         480
actctatacc agttattctt caccctgcag ggtacgtagc atg                         523
```

<210> SEQ ID NO 259
<211> LENGTH: 707
<212> TYPE: DNA
<213> ORGANISM: Issatchenkia orientalis

<400> SEQUENCE: 259

```
tgataacagc aatctgcatg tggattcata atattaggtg tttattgtgg gtattaacgt         60
gtctacctgc tttagctggg gctattatgg taaataagat tgatccacac gaaaatcgac        120
atgctgcatt agctggaatt tatttgatgg gattctacaa tgtgccatgg acattaatgt        180
tggcgttggt atcttcaaac acctcaggat ctaccaagaa gacgttcatg tatgtttctg        240
ttgcagtttg gtatgcagtt ggtaacatta tcggtccata tttttcaaa ggttctcaag         300 caccaaagta tccgatgggg atacatgcca tggaagcttc cttttcaatt atggcgttca        360
ccggtatcct ttactatctt atgctgagaa tacagaataa acaaaagcaa tcgttaacta       420
tgaatgatat aaaacactta gaatacgcgg aacaatcaat cgataatgat ttgactgata        480
aagaaaacca tacttttgtt tatgtttatt agttatcgct ttgctacatt aaaaattcac        540
atactaaagc ctttgttaaa caactttttc taaatcataa gatttactc tatctagttt         600 ttttggttgt aggtgaacgt aaagtacctc atttaatttt tttttgcttg tgtaattctt        660
ttcatgctta tttaaactag tgtacatgta tcaaatcttt gtgtaag                     707
```

<210> SEQ ID NO 260
<211> LENGTH: 22
<212> TYPE: DNA
<213> ORGANISM: Artificial Sequence
<220> FEATURE:
<223> OTHER INFORMATION: ARTIFICIAL PRIMER

<400> SEQUENCE: 260

```
gcaactgatg ttcacgaatg cg                                                 22
```

<210> SEQ ID NO 261
<211> LENGTH: 20
<212> TYPE: DNA
<213> ORGANISM: Artificial Sequence
<220> FEATURE:
<223> OTHER INFORMATION: ARTIFICIAL PRIMER

<400> SEQUENCE: 261

```
ttgccgttgc agcaaatctc                                                    20
```

<210> SEQ ID NO 262
<211> LENGTH: 20
<212> TYPE: DNA
<213> ORGANISM: Artificial Sequence
<220> FEATURE:
<223> OTHER INFORMATION: ARTIFICIAL PRIMER

<400> SEQUENCE: 262

```
aatgatccat ggtccgagag                                                    20
```

<210> SEQ ID NO 263
<211> LENGTH: 21
<212> TYPE: DNA
<213> ORGANISM: Artificial Sequence
<220> FEATURE:
<223> OTHER INFORMATION: ARTIFICIAL PRIMER

<400> SEQUENCE: 263
acggcagtat accctatcag g                                              21

<210> SEQ ID NO 264
<211> LENGTH: 28
<212> TYPE: DNA
<213> ORGANISM: Artificial Sequence
<220> FEATURE:
<223> OTHER INFORMATION: ARTIFICIAL PRIMER

<400> SEQUENCE: 264
gcaccaagag cagttttccc atctattg                                       28

<210> SEQ ID NO 265
<211> LENGTH: 36
<212> TYPE: DNA
<213> ORGANISM: Artificial Sequence
<220> FEATURE:
<223> OTHER INFORMATION: ARTIFICIAL PRIMER

<400> SEQUENCE: 265
ccatatagtt cttttctaac atcaacatca cacttc                              36

<210> SEQ ID NO 266
<211> LENGTH: 37
<212> TYPE: DNA
<213> ORGANISM: Artificial Sequence
<220> FEATURE:
<223> OTHER INFORMATION: ARTIFICIAL PRIMER

<400> SEQUENCE: 266
ggagaataga tcttcaacgc tttaataaag tagtttg                             37

<210> SEQ ID NO 267
<211> LENGTH: 25
<212> TYPE: DNA
<213> ORGANISM: Artificial Sequence
<220> FEATURE:
<223> OTHER INFORMATION: ARTIFICIAL PRIMER

<400> SEQUENCE: 267
cgtgttgcgc aataaaacca atgac                                          25

<210> SEQ ID NO 268
<211> LENGTH: 20
<212> TYPE: DNA
<213> ORGANISM: Artificial Sequence
<220> FEATURE:
<223> OTHER INFORMATION: ARTIFICIAL PRIMER

<400> SEQUENCE: 268
cctcgaagag cttgaatttg                                                20

<210> SEQ ID NO 269
<211> LENGTH: 20
<212> TYPE: DNA
<213> ORGANISM: Artificial Sequence
<220> FEATURE:
<223> OTHER INFORMATION: ARTIFICIAL PRIMER -continued

<400> SEQUENCE: 269
gtagtgaatg tccggataag                                               20

<210> SEQ ID NO 270
<211> LENGTH: 20
<212> TYPE: DNA
<213> ORGANISM: Artificial Sequence
<220> FEATURE:
<223> OTHER INFORMATION: ARTIFICIAL PRIMER

<400> SEQUENCE: 270
gcaaggtcat gaggttaaag                                               20

<210> SEQ ID NO 271
<211> LENGTH: 20
<212> TYPE: DNA
<213> ORGANISM: Artificial Sequence
<220> FEATURE:
<223> OTHER INFORMATION: ARTIFICIAL PRIMER

<400> SEQUENCE: 271
aacacttatg gcgtctcctc                                               20

<210> SEQ ID NO 272
<211> LENGTH: 23
<212> TYPE: DNA
<213> ORGANISM: Artificial Sequence
<220> FEATURE:
<223> OTHER INFORMATION: ARTIFICIAL DNA PRIMER

<400> SEQUENCE: 272
cgaaccaatt caagaaaacc aac                                           23

<210> SEQ ID NO 273
<211> LENGTH: 18
<212> TYPE: DNA
<213> ORGANISM: Artificial Sequence
<220> FEATURE:
<223> OTHER INFORMATION: ARTIFICIAL DNA PRIMER

<400> SEQUENCE: 273
tctgtccctt ggcgacgc                                                 18

<210> SEQ ID NO 274
<211> LENGTH: 21
<212> TYPE: DNA
<213> ORGANISM: Artificial Sequence
<220> FEATURE:
<223> OTHER INFORMATION: ARTIFICIAL DNA PRIMER

<400> SEQUENCE: 274
cttttcaaac agataagtac c                                             21

<210> SEQ ID NO 275
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 275
atgggctgac ctgaaaattc                                               20

<210> SEQ ID NO 276

```
<211> LENGTH: 23
<212> TYPE: DNA
<213> ORGANISM: Artificial Sequence
<220> FEATURE:
<223> OTHER INFORMATION: ARTIFICIAL DNA PRIMER

<400> SEQUENCE: 276
gctgaaaata tcattcagag cat                                          23

<210> SEQ ID NO 277
<211> LENGTH: 18
<212> TYPE: DNA
<213> ORGANISM: Artificial Sequence
<220> FEATURE:
<223> OTHER INFORMATION: ARTIFICIAL DNA PRIMER

<400> SEQUENCE: 277
actgttgatg tcgatgcc                                                18

<210> SEQ ID NO 278
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 278
tctgaatgca gtacgagttg                                              20

<210> SEQ ID NO 279
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 279 gaaggggtc caagttatcc                                               20

<210> SEQ ID NO 280
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 280
gatatgggcg gtagagaaga                                              20

<210> SEQ ID NO 281
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 281
gctccttcaa aggcaacaca                                              20

<210> SEQ ID NO 282
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 282
```

```
tgaactatca catgaacgta                                               20

<210> SEQ ID NO 283
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 283
tcaaggtagg gtcacttaac                                               20

<210> SEQ ID NO 284
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 284
tgattccttc aatcacaggt                                               20

<210> SEQ ID NO 285
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 285
aaccgaccta tcgaatgcct                                               20

<210> SEQ ID NO 286
<211> LENGTH: 51
<212> TYPE: DNA
<213> ORGANISM: Artificial Sequence
<220> FEATURE:
<223> OTHER INFORMATION: ARTIFICIAL DNA PRIMER

<400> SEQUENCE: 286
accatgatta cgccaagctt ggtaccttgg ggtttacgct tacagcgtac t            51

<210> SEQ ID NO 287
<211> LENGTH: 61
<212> TYPE: DNA
<213> ORGANISM: Artificial Sequence
<220> FEATURE:
<223> OTHER INFORMATION: ARTIFICIAL DNA PRIMER

<400> SEQUENCE: 287
tcaacgcccc gggggatctg gatccgcggc cgcaagaaat tcctttcttt tccccttat    60
a                                                                   61

<210> SEQ ID NO 288
<211> LENGTH: 58
<212> TYPE: DNA
<213> ORGANISM: Artificial Sequence
<220> FEATURE:
<223> OTHER INFORMATION: ARTIFICIAL DNA PRIMER

<400> SEQUENCE: 288
aaccgatgga ctcctcgagg gatccgcggc cgcgcataac aaaattgtgc ctaaccca     58

<210> SEQ ID NO 289
```

```
<211> LENGTH: 53
<212> TYPE: DNA
<213> ORGANISM: Artificial Sequence
<220> FEATURE:
<223> OTHER INFORMATION: ARTIFICIAL DNA PRIMER

<400> SEQUENCE: 289
acgactcact atagggcgaa ttgggccccg ggaaaaggag agagaaaagg aga         53

<210> SEQ ID NO 290
<211> LENGTH: 55
<212> TYPE: DNA
<213> ORGANISM: Artificial Sequence
<220> FEATURE:
<223> OTHER INFORMATION: ARTIFICIAL DNA PRIMER

<400> SEQUENCE: 290
tatgaccatg attacgccaa gcttggtacc tcctacagaa gtagcaccag cacca       55

<210> SEQ ID NO 291
<211> LENGTH: 60
<212> TYPE: DNA
<213> ORGANISM: Artificial Sequence
<220> FEATURE:
<223> OTHER INFORMATION: ARTIFICIAL DNA PRIMER

<400> SEQUENCE: 291
ggaaccgatg gactcctcga gggatccgcg gccgcagact accgtgtaaa taagagtacc  60

<210> SEQ ID NO 292
<211> LENGTH: 61
<212> TYPE: DNA
<213> ORGANISM: Artificial Sequence
<220> FEATURE:
<223> OTHER INFORMATION: ARTIFICIAL DNA PRIMER

<400> SEQUENCE: 292
tcttcaacgc cccgggggat ctggatccgc ggccgcattt gatataaacg cttctataat  60
a                                                                 61

<210> SEQ ID NO 293
<211> LENGTH: 58
<212> TYPE: DNA
<213> ORGANISM: Artificial Sequence
<220> FEATURE:
<223> OTHER INFORMATION: ARTIFICIAL DNA PRIMER

<400> SEQUENCE: 293
gtaatacgac tcactatagg gcgaattggg cccaacatct gctgctgtaa tatattca    58

<210> SEQ ID NO 294
<211> LENGTH: 25
<212> TYPE: DNA
<213> ORGANISM: Artificial Sequence
<220> FEATURE:
<223> OTHER INFORMATION: ARTIFICIAL DNA PRIMER

<400> SEQUENCE: 294
gcatgtctgt taactctcaa accat                                       25

<210> SEQ ID NO 295
<211> LENGTH: 23
<212> TYPE: DNA
<213> ORGANISM: Artificial Sequence
<220> FEATURE:
<223> OTHER INFORMATION: ARTIFICIAL DNA PRIMER
```

<400> SEQUENCE: 295
tccataatcc aatagatcat ccc                                                    23

<210> SEQ ID NO 296
<211> LENGTH: 22
<212> TYPE: DNA
<213> ORGANISM: Artificial Sequence
<220> FEATURE:
<223> OTHER INFORMATION: ARTIFICIAL DNA PRIMER

<400> SEQUENCE: 296
aacacaatgg aaccaaccta gt                                                     22

<210> SEQ ID NO 297
<211> LENGTH: 45
<212> TYPE: DNA
<213> ORGANISM: Artificial Sequence
<220> FEATURE:
<223> OTHER INFORMATION: ARTIFICIAL DNA PRIMER

<400> SEQUENCE: 297
atttacacgg tagtctgcgg ccgccatagc ctcatgaaat cagcc                            45

<210> SEQ ID NO 298
<211> LENGTH: 40
<212> TYPE: DNA
<213> ORGANISM: Artificial Sequence
<220> FEATURE:
<223> OTHER INFORMATION: ARTIFICIAL DNA PRIMER

<400> SEQUENCE: 298
ctctaggttc actggttgtt tcttgggctg cctccttcaa                                  40

<210> SEQ ID NO 299
<211> LENGTH: 40
<212> TYPE: DNA
<213> ORGANISM: Artificial Sequence
<220> FEATURE:
<223> OTHER INFORMATION: ARTIFICIAL DNA PRIMER

<400> SEQUENCE: 299
ttgaaggagg cagcccaaga acaaccagt gaacctagag                                   40

<210> SEQ ID NO 300
<211> LENGTH: 56
<212> TYPE: DNA
<213> ORGANISM: Artificial Sequence
<220> FEATURE:
<223> OTHER INFORMATION: ARTIFICIAL DNA PRIMER

<400> SEQUENCE: 300
tattatagaa gcgtttatat caaatgcggc cgcggatcca gatcccccgg ggcgtt                56

<210> SEQ ID NO 301
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 301
aatgatcaac ttgagaggta                                                        20

<210> SEQ ID NO 302

```
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 302
caggtctgtt acataaagca                                              20

<210> SEQ ID NO 303
<211> LENGTH: 21
<212> TYPE: DNA
<213> ORGANISM: Artificial Sequence
<220> FEATURE:
<223> OTHER INFORMATION: ARTIFICIAL DNA PRIMER

<400> SEQUENCE: 303
gtttacgctc aaatctcctc c                                            21

<210> SEQ ID NO 304
<211> LENGTH: 24
<212> TYPE: DNA
<213> ORGANISM: Artificial Sequence
<220> FEATURE:
<223> OTHER INFORMATION: ARTIFICIAL DNA PRIMER

<400> SEQUENCE: 304
ggtacatgaa gcaggctttg aagg                                         24

<210> SEQ ID NO 305
<211> LENGTH: 24
<212> TYPE: DNA
<213> ORGANISM: Artificial Sequence
<220> FEATURE:
<223> OTHER INFORMATION: ARTIFICIAL DNA PRIMER

<400> SEQUENCE: 305
gattgtgtcc gtcagccttt gctc                                         24

<210> SEQ ID NO 306
<211> LENGTH: 21
<212> TYPE: DNA
<213> ORGANISM: Artificial Sequence
<220> FEATURE:
<223> OTHER INFORMATION: ARTIFICIAL DNA PRIMER

<400> SEQUENCE: 306
taccatattt tcagaggatc a                                            21

<210> SEQ ID NO 307
<211> LENGTH: 21
<212> TYPE: DNA
<213> ORGANISM: Artificial Sequence
<220> FEATURE:
<223> OTHER INFORMATION: ARTIFICIAL DNA PRIMER

<400> SEQUENCE: 307
aggatgttct tgcctgcaag t                                            21

<210> SEQ ID NO 308
<211> LENGTH: 26
<212> TYPE: DNA
<213> ORGANISM: Artificial Sequence
<220> FEATURE:
<223> OTHER INFORMATION: ARTIFICIAL DNA PRIMER

<400> SEQUENCE: 308
```
gatgatatag ttgatgcttt ccaaag                                            26

<210> SEQ ID NO 309
<211> LENGTH: 33
<212> TYPE: DNA
<213> ORGANISM: Artificial Sequence
<220> FEATURE:
<223> OTHER INFORMATION: ARTIFICIAL DNA PRIMER

<400> SEQUENCE: 309
gggccccttc atttacgaaa taaagtgccg cgg                                    33

<210> SEQ ID NO 310
<211> LENGTH: 40
<212> TYPE: DNA
<213> ORGANISM: Artificial Sequence
<220> FEATURE:
<223> OTHER INFORMATION: ARTIFICIAL DNA PRIMER

<400> SEQUENCE: 310
gcggccgcaa ataaatttaa aataaacgat atcaaaattc                             40

<210> SEQ ID NO 311
<211> LENGTH: 30
<212> TYPE: DNA
<213> ORGANISM: Artificial Sequence
<220> FEATURE:
<223> OTHER INFORMATION: ARTIFICIAL DNA PRIMER

<400> SEQUENCE: 311
cgacgccaaa gaagggctca gccgaaaaag                                        30

<210> SEQ ID NO 312
<211> LENGTH: 32
<212> TYPE: DNA
<213> ORGANISM: Artificial Sequence
<220> FEATURE:
<223> OTHER INFORMATION: ARTIFICIAL DNA PRIMER

<400> SEQUENCE: 312
ccatttcttt ttcggctgag cccttctttg gc                                     32

<210> SEQ ID NO 313
<211> LENGTH: 32
<212> TYPE: DNA
<213> ORGANISM: Artificial Sequence
<220> FEATURE:
<223> OTHER INFORMATION: ARTIFICIAL DNA PRIMER

<400> SEQUENCE: 313
gcggccgcaa taacctcagg gagaactttg gc                                     32

<210> SEQ ID NO 314
<211> LENGTH: 30
<212> TYPE: DNA
<213> ORGANISM: Artificial Sequence
<220> FEATURE:
<223> OTHER INFORMATION: ARTIFICIAL DNA PRIMER

<400> SEQUENCE: 314
gagctcccaa acaaggtctc agtaggatcg                                        30

<210> SEQ ID NO 315
<211> LENGTH: 28
<212> TYPE: DNA

```
<213> ORGANISM: Artificial Sequence
<220> FEATURE:
<223> OTHER INFORMATION: ARTIFICIAL DNA PRIMER

<400> SEQUENCE: 315
cgccataagg agaggctgta gatttgtc                                        28

<210> SEQ ID NO 316
<211> LENGTH: 25
<212> TYPE: DNA
<213> ORGANISM: Artificial Sequence
<220> FEATURE:
<223> OTHER INFORMATION: ARTIFICIAL DNA PRIMER

<400> SEQUENCE: 316
ccaggacatc ttgcttgcaa tgtcg                                           25

<210> SEQ ID NO 317
<211> LENGTH: 34
<212> TYPE: DNA
<213> ORGANISM: Artificial Sequence
<220> FEATURE:
<223> OTHER INFORMATION: ARTIFICIAL DNA PRIMER

<400> SEQUENCE: 317
gttccatcgg gcccctaaag gtctctcacg acag                                 34

<210> SEQ ID NO 318
<211> LENGTH: 33
<212> TYPE: DNA
<213> ORGANISM: Artificial Sequence
<220> FEATURE:
<223> OTHER INFORMATION: ARTIFICIAL DNA PRIMER

<400> SEQUENCE: 318
caaacacatc gcgataaaat gtccagaggc ttc                                  33

<210> SEQ ID NO 319
<211> LENGTH: 22
<212> TYPE: DNA
<213> ORGANISM: Artificial Sequence
<220> FEATURE:
<223> OTHER INFORMATION: ARTIFICIAL DNA PRIMER

<400> SEQUENCE: 319
gcaagacctt ggatctgaag gg                                              22

<210> SEQ ID NO 320
<211> LENGTH: 25
<212> TYPE: DNA
<213> ORGANISM: Artificial Sequence
<220> FEATURE:
<223> OTHER INFORMATION: ARTIFICIAL DNA PRIMER

<400> SEQUENCE: 320
cgaaccaatt caagaaaacc aacag                                           25

<210> SEQ ID NO 321
<211> LENGTH: 28
<212> TYPE: DNA
<213> ORGANISM: Artificial Sequence
<220> FEATURE:
<223> OTHER INFORMATION: ARTIFICIAL DNA PRIMER

<400> SEQUENCE: 321
gggcccgtcc cttggcgacg ccctgatc                                        28
```

<210> SEQ ID NO 322
<211> LENGTH: 33
<212> TYPE: DNA
<213> ORGANISM: Artificial Sequence
<220> FEATURE:
<223> OTHER INFORMATION: ARTIFICIAL DNA PRIMER

<400> SEQUENCE: 322
gcggccgcta tttttgtgtt ttgctgtgtt ttg                         33

<210> SEQ ID NO 323
<211> LENGTH: 37
<212> TYPE: DNA
<213> ORGANISM: Artificial Sequence
<220> FEATURE:
<223> OTHER INFORMATION: ARTIFICIAL DNA PRIMER

<400> SEQUENCE: 323
gcggccgcca tctgaatgta aaatgaacat taaaatg                     37

<210> SEQ ID NO 324
<211> LENGTH: 29
<212> TYPE: DNA
<213> ORGANISM: Artificial Sequence
<220> FEATURE:
<223> OTHER INFORMATION: ARTIFICIAL DNA PRIMER

<400> SEQUENCE: 324
gagctccccc agttgttgtt gcaattaac                              29

<210> SEQ ID NO 325
<211> LENGTH: 22
<212> TYPE: DNA
<213> ORGANISM: Artificial Sequence
<220> FEATURE:
<223> OTHER INFORMATION: ARTIFICIAL DNA PRIMER

<400> SEQUENCE: 325
gaagagacgt acaagatccg cc                                     22

<210> SEQ ID NO 326
<211> LENGTH: 22
<212> TYPE: DNA
<213> ORGANISM: Artificial Sequence
<220> FEATURE:
<223> OTHER INFORMATION: ARTIFICIAL DNA PRIMER

<400> SEQUENCE: 326
taggaatggt gcatcatcca ac                                     22

<210> SEQ ID NO 327
<211> LENGTH: 40
<212> TYPE: DNA
<213> ORGANISM: Artificial Sequence
<220> FEATURE:
<223> OTHER INFORMATION: ARTIFICIAL DNA PRIMER

<400> SEQUENCE: 327
ttcttatctg aaaactccga gttcgcaaag aaggttgaag                  40

<210> SEQ ID NO 328
<211> LENGTH: 45
<212> TYPE: DNA
<213> ORGANISM: Artificial Sequence
<220> FEATURE:

<223> OTHER INFORMATION: ARTIFICIAL DNA PRIMER

<400> SEQUENCE: 328
ttattgaaat taatccaagg attcaagttg aacatacaat tactg         45

<210> SEQ ID NO 329
<211> LENGTH: 42
<212> TYPE: DNA
<213> ORGANISM: Artificial Sequence
<220> FEATURE:
<223> OTHER INFORMATION: ARTIFICIAL DNA PRIMER

<400> SEQUENCE: 329
tttccaaaaa agttcgtgag ttcgatggtt gtatgattat gg         42

<210> SEQ ID NO 330
<211> LENGTH: 22
<212> TYPE: DNA
<213> ORGANISM: Artificial Sequence
<220> FEATURE:
<223> OTHER INFORMATION: ARTIFICIAL DNA PRIMER

<400> SEQUENCE: 330
cctctaccac caccaccaaa tg         22

<210> SEQ ID NO 331
<211> LENGTH: 24
<212> TYPE: DNA
<213> ORGANISM: Artificial Sequence
<220> FEATURE:
<223> OTHER INFORMATION: ARTIFICIAL DNA PRIMER

<400> SEQUENCE: 331
gggaagaaac taagaagaag tatg         24

<210> SEQ ID NO 332
<211> LENGTH: 44
<212> TYPE: DNA
<213> ORGANISM: Artificial Sequence
<220> FEATURE:
<223> OTHER INFORMATION: ARTIFICIAL DNA PRIMER

<400> SEQUENCE: 332
caatccttct agagaggggg ttatatgtgt aaatatagag tttg         44

<210> SEQ ID NO 333
<211> LENGTH: 36
<212> TYPE: DNA
<213> ORGANISM: Artificial Sequence
<220> FEATURE:
<223> OTHER INFORMATION: ARTIFICIAL DNA PRIMER

<400> SEQUENCE: 333
ttctaccctc gagattggtt ctttccccct ctcaag         36

<210> SEQ ID NO 334
<211> LENGTH: 44
<212> TYPE: DNA
<213> ORGANISM: Artificial Sequence
<220> FEATURE:
<223> OTHER INFORMATION: ARTIFICIAL DNA PRIMER

<400> SEQUENCE: 334
gtggtcaatc tagaaaatat gactgacaaa atctccctag gtac         44

-continued

```
<210> SEQ ID NO 335
<211> LENGTH: 30
<212> TYPE: DNA
<213> ORGANISM: Artificial Sequence
<220> FEATURE:
<223> OTHER INFORMATION: ARTIFICIAL DNA PRIMER

<400> SEQUENCE: 335
caattttgga gctgattcca aatcgtaaac                                       30

<210> SEQ ID NO 336
<211> LENGTH: 31
<212> TYPE: DNA
<213> ORGANISM: Artificial Sequence
<220> FEATURE:
<223> OTHER INFORMATION: ARTIFICIAL DNA PRIMER

<400> SEQUENCE: 336
caagagtatc ccatctgaca ggaaccgatg g                                     31

<210> SEQ ID NO 337
<211> LENGTH: 27
<212> TYPE: DNA
<213> ORGANISM: Artificial Sequence
<220> FEATURE:
<223> OTHER INFORMATION: ARTIFICIAL DNA PRIMER

<400> SEQUENCE: 337
gctggagaat agatcttcaa cgccccg                                          27

<210> SEQ ID NO 338
<211> LENGTH: 29
<212> TYPE: DNA
<213> ORGANISM: Artificial Sequence
<220> FEATURE:
<223> OTHER INFORMATION: ARTIFICIAL DNA PRIMER

<400> SEQUENCE: 338
cggagaaggc gtataaaaag gacacggag                                        29

<210> SEQ ID NO 339
<211> LENGTH: 47
<212> TYPE: DNA
<213> ORGANISM: Artificial Sequence
<220> FEATURE:
<223> OTHER INFORMATION: ARTIFICIAL DNA PRIMER

<400> SEQUENCE: 339
ggataaaagt attacatacg tacaggattg tgtattagtg tatttcg                    47

<210> SEQ ID NO 340
<211> LENGTH: 40
<212> TYPE: DNA
<213> ORGANISM: Artificial Sequence
<220> FEATURE:
<223> OTHER INFORMATION: ARTIFICIAL DNA PRIMER

<400> SEQUENCE: 340
cctccagtgt ttttctctct gtctctttgt ttttttttc                             40

<210> SEQ ID NO 341
<211> LENGTH: 46
<212> TYPE: DNA
<213> ORGANISM: Artificial Sequence
<220> FEATURE:
<223> OTHER INFORMATION: ARTIFICIAL DNA PRIMER
```

<400> SEQUENCE: 341
ggttaattaa tttatttgta cataaaaacc acataaatgt aaaagc       46

<210> SEQ ID NO 342
<211> LENGTH: 35
<212> TYPE: DNA
<213> ORGANISM: Artificial Sequence
<220> FEATURE:
<223> OTHER INFORMATION: ARTIFICIAL DNA PRIMER

<400> SEQUENCE: 342
gaattccttt aattcggaga aaatctgatc aagag       35

<210> SEQ ID NO 343
<211> LENGTH: 945
<212> TYPE: DNA
<213> ORGANISM: Metallosphaera sedula

<400> SEQUENCE: 343
atgaccgaaa aggtctccgt cgtcggtgca ggcgtcatcg gtgtcggttg ggctaccttg       60
ttcgcttcca agggttactc cgtctccttg tacaccgaaa agaaggaaac cttggacaag      120
ggtatcgaaa agttgcgtaa ctacgtccaa gtcatgaaga caactccca aatcaccgaa       180
gacgtcaaca ccgtcatctc cagagttttcc cctactacca acttggacga agccgttaga      240
ggtgcaaact cgtcatcga ggctgtcatc gaagactacg acgctaagaa gagatcttc        300
ggttacttgg actccgtctt ggacaaggaa gttatcttgg catcctccac ctccggtttg      360
ttgatcaccg aagtccaaaa ggctatgtcc aagcacccag aaagagctgt catcgcccac      420
ccatggaacc caccacactt gttgcctttg gtcgaaatcg ttccaggtga agacctcc        480
atggaagtcg ttgagagaac caagtccttg atggaaaagt ggacagaat cgtcgtcgtt       540
ttgaagaagg aaatcccagg tttcatcggt aacagattgg cattcgcttt gttcagagaa      600
gctgtctact ggttgacga gggtgtcgca accgtcgagg acatcgacaa ggttatgact       660
gccgctatcg gcttgagatg ggccttcatg ggtccattct tgacctacca cttgggtggt      720
ggtgagggtg gtttggaata cttcttcaac agaggtttcg gttacggtgc caacgaatgg      780
atgcacacct ggctaagta cgacaagttc ccatacaccg tgtcaccaa ggccatccag        840
caaatgaagg aatactcctt catcaagggt aagaccttcc aagagatctc caagtggaga      900
gacgaaaagt tgttgaaggt ctacaagttg gtctgggaaa agtaa       945

<210> SEQ ID NO 344
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 344
agggtacctt agtacgaagg       20

<210> SEQ ID NO 345
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 345
ctattcttac gatgaaggcg       20

<210> SEQ ID NO 346
<211> LENGTH: 31
<212> TYPE: DNA
<213> ORGANISM: Artificial Sequence
<220> FEATURE:
<223> OTHER INFORMATION: ARTIFICIAL DNA PRIMER

<400> SEQUENCE: 346
ccttaattaa ttatccacgg aagatatgat g                              31

<210> SEQ ID NO 347
<211> LENGTH: 32
<212> TYPE: DNA
<213> ORGANISM: Artificial Sequence
<220> FEATURE:
<223> OTHER INFORMATION: ARTIFICIAL DNA PRIMER

<400> SEQUENCE: 347
gctctagata aaatgtccca aggtagaaaa gc                             32

<210> SEQ ID NO 348
<211> LENGTH: 30
<212> TYPE: DNA
<213> ORGANISM: Artificial Sequence
<220> FEATURE:
<223> OTHER INFORMATION: ARTIFICIAL DNA PRIMER

<400> SEQUENCE: 348
gctagctaaa atgtttggta atatttccca                                30

<210> SEQ ID NO 349
<211> LENGTH: 28
<212> TYPE: DNA
<213> ORGANISM: Artificial Sequence
<220> FEATURE:
<223> OTHER INFORMATION: ARTIFICIAL DNA PRIMER

<400> SEQUENCE: 349
ttaattaact atttatctaa tgatcctc                                  28

<210> SEQ ID NO 350
<211> LENGTH: 41
<212> TYPE: DNA
<213> ORGANISM: Artificial Sequence
<220> FEATURE:
<223> OTHER INFORMATION: ARTIFICIAL DNA PRIMER

<400> SEQUENCE: 350
tctagataaa atgtctatta gtgaaaaata ttttcctcaa g                   41

<210> SEQ ID NO 351
<211> LENGTH: 43
<212> TYPE: DNA
<213> ORGANISM: Artificial Sequence
<220> FEATURE:
<223> OTHER INFORMATION: ARTIFICIAL DNA PRIMER

<400> SEQUENCE: 351
ttaattaact tttaaatttt ggaaaaagct tgatcaataa tgg                 43

COMPOSITIONS AND METHODS FOR 3-HYDROXYPROPIONIC ACID PRODUCTION

CROSS-REFERENCE TO RELATED APPLICATIONS

This application is a Continuation of U.S. patent application Ser. No. 15/688,436, filed Aug. 28, 2017, which is a Continuation of U.S. patent application Ser. No. 15/060,036, filed Mar. 3, 2016, which is a Continuation of U.S. patent application Ser. No. 14/073,441, filed Nov. 6, 2013, which is a Continuation of U.S. patent application Ser. No. 13/301,556, filed Nov. 21, 2011, which claims the benefit of U.S. Provisional Application No. 61/535,181, filed Sep. 15, 2011 and U.S. Provisional Application No. 61/416,199, filed Nov. 22, 2010. The content of these applications is hereby incorporated by reference in its entirety.

REFERENCE TO SEQUENCE LISTING

This application contains a Sequence Listing in computer readable form, which is incorporated herein by reference.

BACKGROUND 3-hydroxypropionic acid (3-HP) is a three carbon carboxylic acid identified by the U.S. Department of Energy as one of the top 12 high-potential building block chemicals that can be made by fermentation. Alternative names for 3-HP, which is an isomer of lactic (2-hydroxypropionic) acid, include ethylene lactic acid and 3-hydroxypropionate. 3-HP is an attractive renewable platform chemical, with 100% theoretical yield from glucose, multiple functional groups that allow it to participate in a variety of chemical reactions, and low toxicity. 3-HP can be used as a substrate to form several commodity chemicals, such as 1,3-propanediol, malonic acid, acrylamide, and acrylic acid. Acrylic acid is a large-volume chemical (>7 billion lbs/year) used to make acrylate esters and superabsorbent polymers, and is currently derived from catalytic oxidation of propylene. Fermentative production of 3-HP would provide a sustainable alternative to petrochemicals as the feedstock for these commercially-significant chemicals, thus reducing energy consumption, US dependence on foreign oil, and the production of greenhouse gases.

Bacteria can be used to ferment sugars to organic acids. However, bacteria present certain drawbacks for large-scale organic acid production. As organic acids are produced, the fermentation medium becomes increasingly acidic. Lower pH conditions are actually preferable, because the resultant product is partially or wholly in the acid form. However, most bacteria that produce organic acids do not perform well in strongly acidic environments, and therefore either die or begin producing so slowly that they become economically unviable as the medium becomes more acidic. To prevent this, it becomes necessary to buffer the medium to maintain a higher pH. However, this makes recovery of the organic acid product more difficult and expensive.

There has been increasing interest in recent years around the use of yeast to ferment sugars to organic acids. Yeasts are used as biocatalysts in a number of industrial fermentations, and present several advantages over bacteria. While many bacteria are unable to synthesize certain amino acids or proteins that they need to grow and metabolize sugars efficiently, most yeast species can synthesize their necessary amino acids or proteins from inorganic nitrogen compounds. Yeasts are also not susceptible to bacteriophage infection, which can lead to loss of productivity or of whole fermentation runs in bacteria.

Although yeasts are attractive candidates for organic acid production, they present several difficulties. First, pathway engineering in yeast is typically more difficult than in bacteria. Enzymes in yeast are compartmentalized in the cytoplasm, mitochondria, or peroxisomes, whereas in bacteria they are pooled in the cytoplasm. This means that targeting signals may need to be removed to ensure that all the enzymes of the biosynthetic pathway co-exist in the same compartment within a single cell. Control of transport of pathway intermediates between the compartments may also be necessary to maximize carbon flow to the desired product. Second, not all yeast species meet the necessary criteria for economic fermentation on a large scale. In fact, only a small percentage of yeasts possess the combination of sufficiently high volumetric and specific sugar utilization with the ability to grow robustly under low pH conditions. The U.S. Department of Energy has estimated that production rates of approximately 2.5 g/L/hour are necessary for economic fermentations of several organic acids, including 3-HP (http://www1.eere.energy.gov/biomass/pdfs/35523.pdf).

Although many yeast species naturally ferment hexose sugars to ethanol, few if any naturally produce significant yields of organic acids. This has led to efforts to genetically modify various yeast species to produce organic acids. Genetically modified yeast strains that produce lactic acid have been previously developed by disrupting or deleting the native pyruvate decarboxylase (PDC) gene and inserting a lactate dehydrogenase (LDH) gene to eliminate ethanol production (see, e.g., WO99/14335, WO00/71738, WO02/42471, WO03/049525, WO03/102152 and WO03/102201). This alteration diverts sugar metabolism from ethanol production to lactic acid production. The fermentation products and pathways for yeast differ from those of bacteria, and thus different engineering approaches are necessary to maximize yield. Other native products that may require elimination or reduction in order to enhance organic acid product yield or purity are glycerol, acetate, and diols. The reduction of glycerol in genetically altered yeast strains is described in, for example, WO07/106524.

Unlike lactic acid, 3-HP is not a major end product of any pathway known in nature, being found in only trace amounts in some bacteria and fungi. Thus, a greater deal of genetic engineering is necessary to generate yeast that produce 3-HP. A *Saccharomyces cerevisiae* strain was previously engineered to produce 3-HP at very low levels through a lactate intermediate (see WO02/042418). However, the tolerance level of wild-type *S. cerevisiae* is insufficient to make it an optimal host for 3-HP production. Therefore, there is a need for improved yeast strains that generate 3-HP in a more cost-effective manner on an industrial scale.

SUMMARY

Provided herein in certain embodiments are genetically modified yeast cells comprising an active 3-HP fermentation pathway from PEP, pyruvate, and/or glycerol to 3-HP. In certain embodiments, the cells provided herein contain one or more 3-HP pathway genes encoding enzymes with PPC, PYC, AAT, ADC, BAAT, gabT, 3-HPDH, HIBADH, 4-hydroxybutyrate dehydrogenase, ACC, AAM, alanine dehydrogenase, aldehyde dehydrogenase, BCKA, KGD, 4-aminobutyrate aminotransferase, β-alanyl-CoA ammonia lyase, Co-A acylating malonate semialdehyde dehydrogenase, CoA synthetase, CoA transferase, glycerol dehydratase, IPDA, LDH, lactyl-CoA dehydratase, malate decarboxylase, malate dehydrogenase, malonyl-CoA reductase, OAA formatelyase, OAA dehydrogenase, pyruvate/alanine aminotransferase, PDH, 2-keto acid decarboxylase, 3-HP-CoA dehydratase, 3-HP-CoA hydrolase, or 3-hydroxyisobutyryl-CoA hydrolase activity.

Provided herein in certain embodiments are genetically modified yeast cells comprising an active 3-HP fermentation pathway from PEP or pyruvate to 3-HP, wherein the cells contain one or more genes encoding enzymes with PPC, PYC, AAT, ADC, BAAT, gabT, 3-HPDH, HIBADH, and 4-hydroxybutyrate dehydrogenase activity. In certain embodiments, one or more of the 3-HP pathway genes are exogenous, and in these embodiments the genes may be derived from a yeast, fungal, bacterial, plant, insect, or mammalian source. For example, the cells may contain a yeast PYC gene derived from *I. orientalis* or a bacterial PYC gene derived from *R. sphaeroides, R. etii, P. fluorescens, C. glutamicum*, or *S. meliloti*; a bacterial PPC gene derived from *E. coli, M. thermoautotrophicum*, or *C. perfringens*, a yeast AAT gene derived from *I. orientalis* or *S. cerevisiae* or a bacterial AAT gene derived from *E. coli*; a bacterial ADC gene derived from *S. avermitilis, C. acetobutylicum, H. pylori, B. licheniformis*, or *C. glutamicum*; a yeast BAAT gene derived from *I. orientalis* or *S. kluyvenri* or a bacterial BAAT gene derived from *S. avermitilis*; a yeast gabT gene derived from *S. cerevisiae* or a bacterial gabT gene derived from *S. avermitilis*; a yeast 3-HPDH gene derived from *I. orientalis* or *S. cerevisiae* or a bacterial 3-HPDH gene derived from *E. coli* or *M. sedula*; a bacterial HIBADH gene derived from *A. faecalis, P. putida*, or *P. aeruginosa*; and/or a yeast 4-hydroxybutyrate dehydrogenase gene derived from *C. kluyveri* or a bacterial 4-hydroxybutyrate dehydrogenase gene derived from *R. eutropha*.

Provided herein in certain embodiments are genetically modified yeast cells comprising an active 3-HP fermentation pathway from PEP or pyruvate to 3-HP, wherein the cells contain one or more genes encoding enzymes with PPC, malate dehydrogenase, and malate decarboxylase activity. In certain embodiments, one or more of the 3-HP pathway genes are exogenous, and in these embodiments the genes may be derived from a yeast, fungal, bacterial, plant, insect, or mammalian source.

Provided herein in certain embodiments are genetically modified yeast cells comprising an active 3-HP fermentation pathway from PEP or pyruvate to 3-HP, wherein the cells contain one or more genes encoding enzymes with PPC, 2-keto acid decarboxylase, KGD, BCKA, indolepyruvate decarboxylase, 3-HPDH, HIBADH, or 4-hydroxybutyrate dehydrogenase activity. In certain embodiments, one or more of the 3-HP pathway genes are exogenous, and in these embodiments the genes may be derived from a yeast, fungal, bacterial, plant, insect, or mammalian source.

Provided herein in certain embodiments are genetically modified yeast cells comprising an active 3-HP fermentation pathway from PEP or pyruvate to 3-HP, wherein the cells contain one or more genes encoding enzymes with PPC, OAA formatelyase, malonyl-CoA reductase, Co-A acylating malonate semialdehyde dehydrogenase, 3-HPDH, HIBADH, and 4-hydroxybutyrate dehydrogenase activity. In certain embodiments, one or more of the 3-HP pathway genes are exogenous, and in these embodiments the genes may be derived from a yeast, fungal, bacterial, plant, insect, or mammalian source.

Provided herein in certain embodiments are genetically modified yeast cells comprising an active 3-HP fermentation pathway from pyruvate to 3-HP, wherein the cells contain one or more genes encoding enzymes with PDH, acetyl-CoA carboxylase, malonyl-CoA reductase, CoA acylating malonate semialdehyde dehydrogenase, 3-HPDH, HIBADH, and 4-hydroxybutyrate dehydrogenase activity. In certain embodiments, one or more of the 3-HP pathway genes are exogenous, and in these embodiments the genes may be derived from a yeast, fungal, bacterial, plant, insect, or mammalian source.

Provided herein in certain embodiments are genetically modified yeast cells comprising an active 3-HP fermentation pathway from pyruvate to 3-HP, wherein the cells contain one or more genes encoding enzymes with alanine dehydrogenase, pyruvate/alanine aminotransferase, alanine 2,3 aminomutase, CoA transferase, CoA synthetase, β-alanyl-CoA ammonia lyase, 3-HP-CoA dehydratase, 3-HP-CoA hydrolase, 3-hydroxyisobutyryl-CoA hydrolase, BAAT, 3-HPDH, HIBADH, and 4-hydroxybutyrate dehydrogenase activity. In certain embodiments, one or more of the 3-HP pathway genes are exogenous, and in these embodiments the genes may be derived from a yeast, fungal, bacterial, plant, insect, or mammalian source.

Provided herein in certain embodiments are genetically modified yeast cells comprising an active 3-HP fermentation pathway from pyruvate to 3-HP, wherein the cells contain one or more genes encoding enzymes with LDH, CoA transferase, lactyl-CoA dehydratase, 3-HP-CoA dehydratase, 3-HP-CoA hydrolase, and 3-hydroxyisobutyryl-CoA hydrolase activity. In certain embodiments, one or more of the 3-HP pathway genes are exogenous, and in these embodiments the genes may be derived from a yeast, fungal, bacterial, plant, insect, or mammalian source.

Provided herein in certain embodiments are genetically modified yeast cells comprising an active 3-HP fermentation pathway from PEP or pyruvate to 3-HP, wherein the cells contain one or more genes encoding enzymes with glycerol dehydratase and aldehyde dehydrogenase activity. In certain embodiments, one or more of the 3-HP pathway genes are exogenous, and in these embodiments the genes may be derived from a yeast, fungal, bacterial, plant, insect, or mammalian source.

The genetically modified yeast cells provided herein may be any yeast species. In certain embodiments, the cells are Crabtree-negative, and in certain of these embodiments they belong to the genus *Issatchenkia, Candida, Kluyveromyces, Pichia, Schizosaccharomyces, Torulaspora, Zygosaccharomyces*, or *Saccharomyces*. In certain of these embodiments, the cells may belong to the *I. orientalis/P. fermentans* clade or the *Saccharomyces* clade, and in these embodiments they may be *I. orientalis, C. lambica*, or *S. bulderi*. In certain embodiments, the yeast cells may be 3-HP resistant yeast cells. 3-HP resistance may be a native trait of the cells or it result from the cells having undergone mutation and/or selection before, during, or after introduction of genetic modifications related to an active 3-HP fermentation pathway, or a combination thereof. In certain embodiments, the yeast cells may exhibit a degree of tolerance to organic acids other than 3-HP, other fermentation products or byproducts, and/or various media components that is greater than that exhibited by wild-type yeast cells of the same species. In certain embodiments, the yeast cells have undergone mutation and/or selection, such that the mutated and/or selected cells possess a higher degree of resistance to 3-HP than a wild-type cell of the same species. In some of these embodiments, the cell has undergone mutation and/or selection before being genetically modified with the one or more exogenous 3-HP pathway genes. In some embodiments, the cell has undergone selection in the presence of lactic acid or 3-HP. In some embodiments, the selection is chemostat selection.

In addition to modifications related to an active 3-HP fermentation pathway, the cells provided herein may contain deletions or disruptions of one or more native genes. For example, the cells may contain deletions or disruptions of one or more PDC, ADH, GAL6, CYB2A, CYB2B, GPD, GPP, ALD, or PCK genes. In certain embodiments, these deletions or disruptions may be coupled to the introduction of one or more genes related to an active 3-HP fermentation pathway.

Provided herein in certain embodiments are methods of producing 3-HP using the genetically modified yeast cells provided herein by culturing the cells in the presence of at least one carbon source and isolating 3-HP from the culture medium. In certain of these embodiments, the carbon source may be selected from one or more of glucose, xylose, arabinose, sucrose, fructose, cellulose, glucose oligomers, and glycerol.

DETAILED DESCRIPTION

Figure 1:
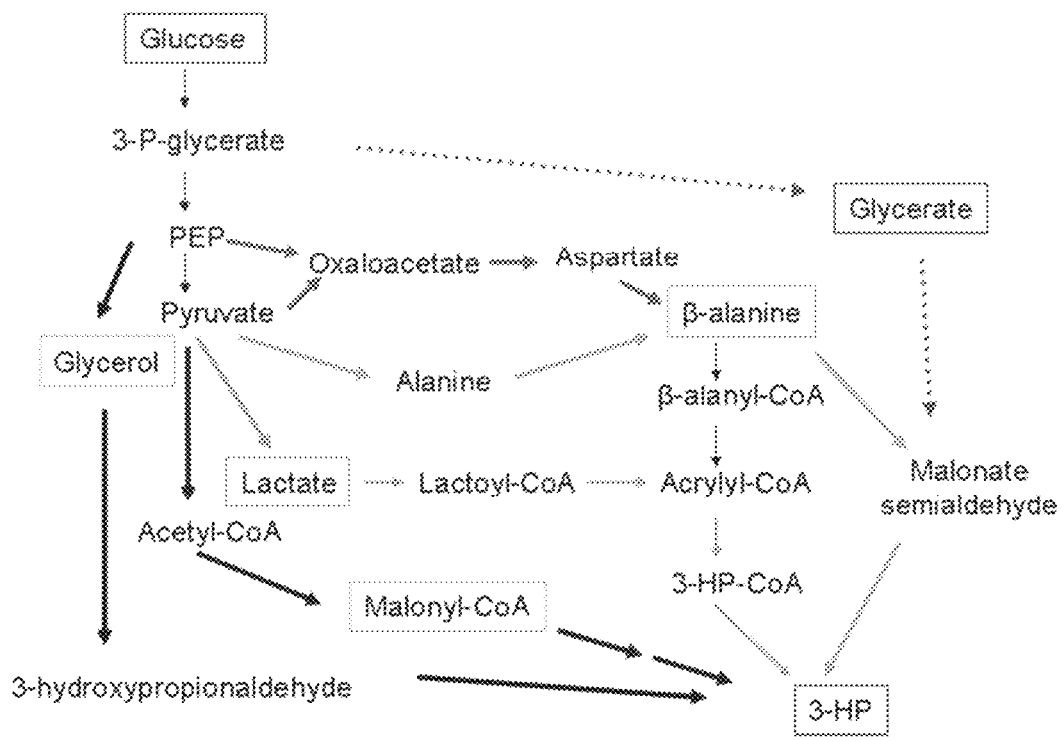
FIG. 1: Summary of select 3-HP fermentation pathways

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

All references cited herein are incorporated by reference in their entirety.

Abbreviations

3-HP, 3-hydroxypropionic acid; 3-HPA, 3-hydroxypropionaldehyde; 3-HPDH, 3-hydroxypropionic acid dehydrogenase; AAM, alanine 2,3 aminomutase; AAT, aspartate aminotransferase; ACC, acetyl-CoA carboxylase; ADC, aspartate 1-decarboxylase; AKG, alpha-ketoglutarate; ALD, aldehyde dehydrogenase; BAAT, β-alanine aminotransferase; BCKA, branched-chain alpha-keto acid decarboxylase; bp, base pairs; CYB2, L-(+)-lactate-cytochrome c oxidoreductase; CYC, iso-2-cytochrome c; EMS, ethane methyl sulfonase; ENO, enolase; gabT, 4-aminobutyrate aminotransferase; GAPDH, glyceraldehyde-3-phosphate dehydrogenase 3; GPD, glycerol 3-phosphate dehydrogenase; GPP, glycerol 3-phosphate phosphatase; HIBADH, 3-hydroxyisobutyrate dehydrogenase; IPDA, indolepyruvate decarboxylase; KGD, alpha-ketoglutarate decarboxylase; LDH, lactate dehydrogenase; MAE, malic enzyme; OAA, oxaloacetate; PCK, phosphoenolpyruvate carboxykinase; PDC, pyruvate decarboxylase; PDH, pyruvate dehydrogenase; PEP, phosphoenolpyruvate; PGK, phosphoglycerate kinase; PPC, phosphoenolpyruvate carboxylase; PYC, pyruvate carboxylase; RKI, ribose 5-phosphate ketolisomerase; TAL, transaldolase; TEF1, translation elongation factor-1; TEF2, translation elongation factor-2; TKL, transketolase; XDH, xylitol dehydrogenase; XR, xylose reductase; YP, yeast extract/peptone.

Description

Provided herein are genetically modified yeast cells for the production of 3-HP, methods of making these yeast cells, and methods of using these cells to produce 3-HP. "3-HP" as used herein includes salt and acid forms of 3-hydroxypropionic acid.

A number of 3-HP fermentation pathways are known in the art (see, e.g., U.S. Pat. Nos. 6,852,517; 7,309,597; US Pub. No. 2001/0021978; US Pub. No. 2008/0199926; WO02/42418; and WO10/031083, all incorporated by reference herein). 3-HP fermentation pathways operate via a series of intermediates that may include phosphoenolpyruvate (PEP), pyruvate, oxaloacetate (OAA), aspartate, β-alanine, malonate semialdehyde, malate, malonyl-CoA, acetyl-CoA, alanine, lactate, lactyl-CoA, acrylyl-CoA, glycerol, 3-hydroxypropionaldehyde (3-HPA), β-alanyl-CoA, 3-HP-CoA, and glycerate. An overview of several of the known 3-HP fermentation pathways is set forth in FIG. 1.

As disclosed herein, a set of yeast cells from various species were tested for 3-HP resistance. Cells exhibiting 3-HP resistance were further evaluated based on their growth rates and glucose consumption rates in media containing varying concentrations of 3-HP. Based on these experiments, a set of ideal host cells for 3-HP production were identified. These host cells were then genetically modified to contain an active 3-HP fermentation pathway, resulting in genetically modified yeast cells that produce 3-HP under low pH conditions.

Provided herein in certain embodiments are genetically modified yeast cells having at least one active 3-HP fermentation pathway from PEP, pyruvate, and/or glycerol to 3-HP. A yeast cell having an "active 3-HP fermentation pathway" as used herein produces active enzymes necessary to catalyze each reaction in a 3-HP fermentation pathway, and therefore is capable of producing 3-HP in measurable yields when cultured under fermentation conditions in the presence of at least one fermentable sugar. A yeast cell having an active 3-HP fermentation pathway comprises one or more 3-HP pathway genes. A "3-HP pathway gene" as used herein refers to the coding region of a nucleotide sequence that encodes an enzyme involved in a 3-HP fermentation pathway.

In certain embodiments, the yeast cells provided herein have an active 3-HP fermentation pathway that proceeds through PEP or pyruvate, OAA, aspartate, β-alanine, and malonate semialdehyde intermediates (see, e.g., US Pub. No. 2010/0021978, FIG. 1). In these embodiments, the yeast cells comprise a set of 3-HP fermentation pathway genes comprising one or more of pyruvate carboxylase (PYC), PEP carboxylase (PPC), aspartate aminotransferase (AAT), aspartate 1-decarboxylase (ADC), β-alanine aminotransferase (BAAT), aminobutyrate aminotransferase (gabT), 3-HP dehydrogenase (3-HPDH), 3-hydroxyisobutyrate dehydrogenase (HIBADH), and 4-hydroxybutyrate dehydrogenase genes. The 3-HP fermentation pathway genes may also include a PEP carboxykinase (PCK) gene that has been modified to produce a polypeptide that preferably catalyzes the conversion of PEP to OAA (native PCK genes generally produce a polypeptide that preferably catalyzes the reverse reaction of OAA to PEP).

In certain embodiments, the yeast cells provided herein have an active 3-HP fermentation pathway that proceeds through PEP or pyruvate, OAA, and malate intermediates (see, e.g., US Pub. No. 2010/0021978, FIG. 4). In these embodiments, the yeast cells comprise a set of 3-HP fermentation pathway genes comprising one or more of PPC, PYC, malate dehydrogenase, and malate decarboxylase genes. The 3-HP fermentation pathway genes may also include a PCK gene that has been modified to produce a polypeptide that preferably catalyzes the conversion of PEP to OAA.

In certain embodiments, the yeast cells provided herein have an active 3-HP fermentation pathway that proceeds through PEP or pyruvate, OAA, and malonate semialdehyde intermediates (see, e.g., US Pub. No. 2010/0021978, FIG. 1). In these embodiments, the yeast cells comprise a set of 3-HP fermentation pathway genes comprising one or more of PPC, PYC, 2-keto acid decarboxylase, alpha-ketoglutarate (AKG) decarboxylase (KGD), branched-chain alpha-keto acid decarboxylase (BCKA), indolepyruvate decarboxylase (IPDA), 3-HPDH, HIBADH, and 4-hydroxybutyrate dehydrogenase genes. The 3-HP fermentation pathway genes may also include a PCK gene that has been modified to produce a polypeptide that preferably catalyzes the conversion of PEP to OAA. Further, the 3-HP fermentation pathway genes may include a PDC gene and/or benzoylformate decarboxylase gene that has been modified to encode a polypeptide capable of catalyzing the conversion of OAA to malonate semialdehyde.

In certain embodiments, the yeast cells provided herein have an active 3-HP fermentation pathway that proceeds through PEP or pyruvate, OAA, malonyl-CoA, and malonate semialdehyde intermediates, wherein the malonate semialdehyde intermediate is optional (see, e.g., US Pub. No. 2010/0021978, FIG. 2). In these embodiments, the yeast cells comprise a set of 3-HP fermentation pathway genes comprising one or more of PPC, PYC, OAA formatelyase, malonyl-CoA reductase, CoA acylating malonate semialdehyde dehydrogenase, 3-HPDH, HIBADH, and 4-hydroxybutyrate dehydrogenase genes. The 3-HP fermentation pathway genes may also include a PCK gene that has been modified to produce a polypeptide that preferably catalyzes the conversion of PEP to OAA. Further, the 3-HP fermentation pathway genes may include an OAA dehydrogenase gene derived by modifying a 2-keto-acid dehydrogenase gene to produce a polypeptide that catalyzes the conversion of OAA to malonyl-CoA.

In certain embodiments, the yeast cells provided herein have an active 3-HP fermentation pathway that proceeds through pyruvate, acetyl-CoA, malonyl-CoA, and malonate semialdehyde intermediates, wherein the malonate semialdehyde intermediate is optional (see, e.g., WO02/042418, FIG. 44). In these embodiments, the yeast cells comprise a set of 3-HP fermentation pathway genes comprising one or more of pyruvate dehydrogenase (PDH), acetyl-CoA carboxylase (ACC), malonyl-CoA reductase, CoA acylating malonate semialdehyde dehydrogenase, 3-HPDH, HIBADH, and 4-hydroxybutyrate dehydrogenase genes.

In certain embodiments, the yeast cells provided herein have an active 3-HP fermentation pathway that proceeds through pyruvate, alanine, β-alanine, β-alanyl-CoA, acrylyl-CoA, 3-HP-CoA, and malonate semialdehyde intermediates, wherein the β-alanyl-CoA, acrylyl-CoA, 3-HP-CoA, and malonate semialdehyde intermediates are optional (β-alanine can be converted to 3-HP via a malonate semialdehyde intermediate or via β-alanyl-CoA, acrylyl-CoA, and 3-HP-CoA intermediates (see, e.g., U.S. Pat. No. 7,309,597, FIG. 1). In these embodiments, the yeast cells comprise a set of 3-HP fermentation pathway genes comprising one or more of alanine dehydrogenase, pyruvate/alanine aminotransferase, alanine 2,3 aminomutase, CoA transferase, CoA synthetase, β-alanyl-CoA ammonia lyase, 3-HP-CoA dehydratase, 3-HP-CoA hydrolase, 3-hydroxyisobutyryl-CoA hydrolase, BAAT, 3-HPDH, HIBADH, and 4-hydroxybutyrate dehydrogenase genes.

In certain embodiments, the yeast cells provided herein have an active 3-HP fermentation pathway that proceeds through pyruvate, lactate, lactyl-CoA, acrylyl-CoA, and 3-HP-CoA intermediates (see, e.g., WO02/042418, FIG. 1). In these embodiments, the yeast cells comprise a set of 3-HP fermentation pathway genes comprising one or more of LDH, CoA transferase, CoA synthetase, lactyl-CoA dehydratase, 3-HP-CoA dehydratase, 3-HP-CoA hydrolase, and 3-hydroxyisobutyryl-CoA hydrolase genes.

In certain embodiments, the yeast cells provided herein have an active 3-HP fermentation pathway that proceeds through glycerol and 3-HPA intermediates (see, e.g., U.S. Pat. No. 6,852,517). In these embodiments, the yeast cells comprise a set of 3-HP fermentation pathway genes comprising one or more of glycerol dehydratase and aldehyde dehydrogenase genes.

In certain embodiments, the yeast cells provided herein have an active 3-HP fermentation pathway that proceeds through PEP or pyruvate, OAA, aspartate, β-alanine, β-alanyl-CoA, acrylyl-CoA, 3-HP-CoA, and alanine intermediates, wherein the OAA, aspartate, and alanine intermediates are optional (PEP or pyruvate can be converted to 0-alanine via OAA and aspartate or via alanine) (see WO02/042418, FIG. 54; U.S. Pat. No. 7,309,597, FIG. 1). In these embodiments, the yeast cells comprise a set of 3-HP fermentation pathway genes comprising one or more of PPC, PYC, AAT, ADC, CoA transferase, CoA synthetase, β-alanyl-CoA ammonia lyase, 3-HP-CoA dehydratase, 3-HP-CoA hydrolase, 3-hydroxyisobutyrl-CoA hydrolase, alanine dehydrogenase, pyruvate/alanine aminotransferase, and AAM genes. The 3-HP fermentation pathway genes may also include a PCK gene that has been modified to produce a polypeptide that preferably catalyzes the conversion of PEP to OAA.

The 3-HP fermentation pathway genes in the yeast cells provided herein may be endogenous or exogenous. "Endogenous" as used herein with regard to genetic components such as genes, promoters, and terminator sequences means that the genetic component is present at a particular location in the genome of a native form of a particular yeast cell. "Exogenous" as used herein with regard to genetic components means that the genetic component is not present at a particular location in the genome of a native form of a particular yeast cell. "Native" as used herein with regard to a yeast cell refers to a wild-type yeast cell of a particular yeast species. "Native" as used herein with regard to a metabolic pathway refers to a metabolic pathway that exists and is active in a native yeast cell.

An exogenous genetic component may have either a native or non-native sequence. An exogenous genetic component with a native sequence comprises a sequence identical to (apart from individual-to-individual mutations which do not affect function) a genetic component that is present in the genome of a native cell (i.e., the exogenous genetic component is identical to an endogenous genetic component). However, the exogenous component is present at a different location in the host cell genome than the endogenous component. For example, an exogenous PYC gene that is identical to an endogenous PYC gene may be inserted into a yeast cell, resulting in a modified cell with a non-native (increased) number of PYC gene copies. An exogenous genetic component with a non-native sequence comprises a sequence that is not found in the genome of a native cell. For example, an exogenous PYC gene from a particular species may be inserted into a yeast cell of another species. An exogenous gene is preferably integrated into the host cell genome in a functional manner, meaning that it is capable of producing an active protein in the host cell. However, in certain embodiments the exogenous gene may be introduced into the cell as part of a vector that is stably maintained in the host cytoplasm.

In certain embodiments, the yeast cells provided herein comprise one or more exogenous 3-HP fermentation pathway genes. In certain embodiments, the genetically modified yeast cells disclosed herein comprise a single exogenous gene. In other embodiments, the yeast cells comprise multiple exogenous genes. In these embodiments, the yeast cells may comprise multiple copies of a single exogenous gene and/or copies of two or more different exogenous genes. Yeast cells comprising multiple exogenous genes may comprise any number of exogenous genes. For example, these yeast cells may comprise 1 to 20 exogenous genes, and in certain preferred embodiments they may comprise 1 to 7 exogenous genes. Multiple copies of an exogenous gene may be integrated at a single locus such that they are adjacent to one another. Alternatively, they may be integrated at several loci within the host cell's genome.

In certain embodiments, the yeast cells provided herein comprise one or more endogenous 3-HP fermentation pathway genes. In certain of these embodiments, the cells may be engineered to overexpress one or more of these endogenous genes, meaning that the modified cells express the endogenous gene at a higher level than a native cell under at least some conditions. In certain of these embodiments, the endogenous gene being overexpressed may be operatively linked to one or more exogenous regulatory elements. For example, one or more native or non-native exogenous strong promoters may be introduced into a cell such that they are operatively linked to one or more endogenous 3-HP pathway genes.

3-HP fermentation pathway genes in the modified yeast cells provided herein may be operatively linked to one or more regulatory elements such as a promoter or terminator. As used herein, the term "promoter" refers to an untranslated sequence located upstream (i.e., 5') to the translation start codon of a gene (generally within about 1 to 1000 base pairs (bp), preferably within about 1 to 500 bp) which controls the start of transcription of the gene. The term "terminator" as used herein refers to an untranslated sequence located downstream (i.e., 3') to the translation finish codon of a gene (generally within about 1 to 1000 bp, preferably within about 1 to 500 bp, and especially within about 1 to 100 bp) which controls the end of transcription of the gene. A promoter or terminator is "operatively linked" to a gene if its position in the genome relative to that of the gene is such that the promoter or terminator, as the case may be, performs its transcriptional control function. Suitable promoters and terminators are described, for example, in WO99/14335, WO00/71738, WO02/42471, WO03/102201, WO03/102152 and WO03/049525 (all incorporated by reference herein in their entirety).

Regulatory elements linked to 3-HP fermentation pathway genes in the cells provided herein may be endogenous or exogenous. For example, an exogenous 3-HP fermentation pathway gene may be inserted into a yeast cell such that it is under the transcriptional control of an endogenous promoter and/or terminator. Alternatively, the exogenous 3-HP fermentation pathway gene may be linked to one or more exogenous regulatory elements. For example, an exogenous gene may be introduced into the cell as part of a gene expression construct that comprises one or more exogenous regulatory elements. In certain embodiments, exogenous regulatory elements, or at least the functional portions of exogenous regulatory elements, may comprise native sequences. In other embodiments, exogenous regulatory elements may comprise non-native sequences. In these embodiments, the exogenous regulatory elements may comprise a sequence with a relatively high degree of sequence identity to a native regulatory element. For example, an exogenous gene may be linked to an exogenous promoter or terminator having at least 50%, at least 60%, at least 70%, at least 80%, or at least 90% sequence identity to a native promoter or terminator. Sequence identity percentages for nucleotide or amino acid sequences can be calculated by methods known in the art, such as for example using BLAST (National Center for Biological Information (NCBI) Basic Local Alignment Search Tool) version 2.2.1 software with default parameters. For example, a sequences having an identity score of at least 90%, using the BLAST version 2.2.1 algorithm with default parameters is considered to have at least 90% sequence identity. The BLAST software is available from the NCBI, Bethesda, Md.

In certain aspects, a regulatory element (e.g., a promoter) linked to a 3-HP fermentation pathway gene in the cells provided herein may be foreign to the pathway gene. A regulatory element that is foreign to a pathway gene is a regulatory element that is not liked to the gene in its natural form. The skilled artisan can appreciate that a regulatory element foreign to a pathway gene can be endogenous or exogenous, depending on the pathway gene and its relation to the yeast cell. In some instances, an endogenous 3-HP fermentation pathway gene is operatively linked to a regulatory element (e.g., a promoter) that is foreign to the pathway gene. In other instances, an exogenous 3-HP fermentation pathway gene is operatively linked to an exogenous regulatory element (e.g., a promoter) that is foreign to the pathway gene.

In those embodiments wherein multiple exogenous genes are inserted into a host cell, each exogenous gene may be under the control of a different regulatory element, or two or more exogenous genes may be under the control of the same regulatory elements. For example, where a first exogenous gene is linked to a first regulatory element, a second exogenous gene may also be linked to the first regulatory element, or it may be linked to a second regulatory element. The first and second regulatory elements may be identical or share a high degree of sequence identity, or they be wholly unrelated.

Examples of promoters that may be linked to one or more 3-HP fermentation pathway genes in the yeast cells provided herein include, but are not limited to, promoters for PDC1, phosphoglycerate kinase (PGK), xylose reductase (XR), xylitol dehydrogenase (XDH), L-(+)-lactate-cytochrome c oxidoreductase (CYB2), translation elongation factor-1 (TEF1), translation elongation factor-2 (TEF2), enolase (ENO1), glyceraldehyde-3-phosphate dehydrogenase (GAPDH), and orotidine 5'-phosphate decarboxylase (URA3) genes. In these examples, the 3-HP fermentation pathway genes may be linked to endogenous or exogenous promoters for PDC1, PGK, XR, XDH, CYB2, TEF1, TEF2, ENO1, GAPDH, or URA3 genes. Where the promoters are exogenous, they may be identical to or share a high degree of sequence identity (i.e., at least about 80%, at least about 85%, at least about 90%, at least about 95%, or at least about 99%) with native promoters for PDC1, PGK, XR, XDH, CYB2, TEF1, TEF2, ENO1, GAPDH, or URA3 genes.

Examples of terminators that may be linked to one or more 3-HP fermentation pathway genes in the yeast cells provided herein include, but are not limited to, terminators for PDC1, XR, XDH, transaldolase (TAL), transketolase (TKL), ribose 5-phosphate ketol-isomerase (RKI), CYB2, or iso-2-cytochrome c (CYC) genes or the galactose family of genes (especially the GAL10 terminator). In these examples, the 3-HP fermentation pathway genes may be linked to endogenous or exogenous terminators for PDC1, XR, XDH, TAL, TKL, RKI, CYB2, or CYC genes or galactose family genes. Where the terminators are exogenous, they may be identical to or share a high degree of sequence identity (i.e., at least about 80%, at least about 85%, at least about 90%, at least about 95%, or at least about 99%) with native terminators for PDC1, XR, XDH, TAL, TKL, RKI, CYB2, or CYC genes or galactose family genes. In certain embodiments, 3-HP fermentation pathway genes are linked to a terminator that comprises a functional portion of a native GAL10 gene native to the host cell or a sequence that shares at least 80%, at least 85%, at least 90%, or at least 95% sequence identity with a native GAL10 terminator.

Exogenous genes may be inserted into a yeast host cell via any method known in the art. In preferred embodiments, the genes are integrated into the host cell genome. Exogenous genes may be integrated into the genome in a targeted or a random manner. In those embodiments where the gene is integrated in a targeted manner, it may be integrated into the loci for a particular gene, such that integration of the exogenous gene is coupled to deletion or disruption of a native gene. For example, introduction of an exogenous 3-HP pathway gene may be coupled to deletion or disruption of one or more genes encoding enzymes involved in other fermentation product pathways. Alternatively, the exogenous gene may be integrated into a portion of the genome that does not correspond to a gene.

Targeted integration and/or deletion may utilize an integration construct. The term "construct" as used herein refers to a DNA sequence that is used to transform a host cell. The construct may be, for example, a circular plasmid or vector, a portion of a circular plasmid or vector (such as a restriction enzyme digestion product), a linearized plasmid or vector, or a PCR product prepared using a plasmid or genomic DNA as a template. Methods for transforming a yeast cell with an exogenous construct are described in, for example, WO99/14335, WO00/71738, WO02/42471, WO03/102201, WO03/102152, and WO03/049525. An integration construct can be assembled using two cloned target DNA sequences from an insertion site target. The two target DNA sequences may be contiguous or non-contiguous in the native host genome. In this context, "non-contiguous" means that the DNA sequences are not immediately adjacent to one another in the native genome, but are instead are separated by a region that is to be deleted. "Contiguous" sequences as used herein are directly adjacent to one another in the native genome. Where targeted integration is to be coupled to deletion or disruption of a target gene, the integration construct may also be referred to as a deletion construct. In a deletion construct, one of the target sequences may include a region 5' to the promoter of the target gene, all or a portion of the promoter region, all or a portion of the target gene coding sequence, or some combination thereof. The other target sequence may include a region 3' to the terminator of the target gene, all or a portion of the terminator region, and/or all or a portion of the target gene coding sequence. Where targeted integration is not to be coupled to deletion or disruption of a native gene, the target sequences are selected such that insertion of an intervening sequence will not disrupt native gene expression. An integration or deletion construct is prepared such that the two target sequences are oriented in the same direction in relation to one another as they natively appear in the genome of the host cell. Where an integration or deletion construct is used to introduce an exogenous gene into a host cell, a gene expression cassette is cloned into the construct between the two target gene sequences to allow for expression of the exogenous gene. The gene expression cassette contains the exogenous gene, and may further include one or more regulatory sequences such as promoters or terminators operatively linked to the exogenous gene. Deletion constructs can also be constructed that do not contain a gene expression cassette. Such constructs are designed to delete or disrupt a gene sequence without the insertion of an exogenous gene.

An integration or deletion construct may comprise one or more selection marker cassettes cloned into the construct between the two target gene sequences. The selection marker cassette contains at least one selection marker gene that allows for selection of transformants. A "selection marker gene" is a gene that encodes a protein needed for the survival and/or growth of the transformed cell in a selective culture medium, and therefore can be used to apply selection pressure to the cell. Successful transformants will contain the selection marker gene, which imparts to the successfully transformed cell at least one characteristic that provides a basis for selection. Typical selection marker genes encode proteins that (a) confer resistance to antibiotics or other toxins (e.g., resistance to bleomycin or zeomycin (e.g., *Streptoalloteichus hindustanus* ble gene), aminoglycosides such as G418 or kanamycin (e.g., kanamycin resistance gene from transposon Tn903), or hygromycin (e.g., aminoglycoside antibiotic resistance gene from *E. coli*)), (b) complement auxotrophic deficiencies of the cell (e.g., deficiencies in leucine (e.g., *K. marxianus* LEU2 gene), uracil (e.g., *K. marxianus*, *S. cerevisiae*, or *I. orientalis* URA3 gene), or tryptophan (e.g., *K. marxianus*, *S. cerevisiae*, or *I. orientalis* TRP gene)), (c) enable the cell to synthesize critical nutrients not available from simple media, or (d) confer the ability for the cell to grow on a particular carbon source (e.g., MEL5 gene from *S. cerevisiae*, which encodes the alpha-galactosidase (melibiase) enzyme and confers the ability to grow on melibiose as the sole carbon source). Preferred selection markers include the URA3 gene, zeocin resistance gene, G418 resistance gene, MEL5 gene, and hygromycin resistance gene. Another preferred selection marker is an L-lactate:ferricytochrome c oxidoreductase (CYB2) gene cassette, provided that the host cell either natively lacks such a gene or that its native CYB2 gene(s) are first deleted or disrupted. A selection marker gene is operatively linked to one or more promoter and/or terminator sequences that are operable in the host cell. In certain embodiments, these promoter and/or terminator sequences are exogenous promoter and/or terminator sequences that are included in the selection marker cassette. Suitable promoters and terminators are as described herein.

An integration or deletion construct is used to transform the host cell. Transformation may be accomplished using, for example, electroporation and/or chemical transformation (e.g., calcium chloride, lithium acetate-based, etc.) methods. Selection or screening based on the presence or absence of the selection marker may be performed to identify successful transformants. In successful transformants, homologous recombination events at the locus of the target site results in the disruption or the deletion of the target site sequence. Where the construct targets a native gene for deletion or disruption, all or a portion of the native target gene, its promoter, and/or its terminator may be deleted during this recombination event. The expression cassette, selection marker cassette, and any other genetic material between the target sequences in the integration construct is inserted into the host genome at the locus corresponding to the target sequences. Analysis by PCR or Southern analysis can be performed to confirm that the desired insertion/deletion has taken place.

In some embodiments, cell transformation may be performed using DNA from two or more constructs, PCR products, or a combination thereof, rather than a single construct or PCR product. In these embodiments, the 3' end of one integration fragment overlaps with the 5' end of another integration fragment. In one example, one construct will contain the first sequence from the locus of the target sequence and a non-functional part of the marker gene cassette, while the other will contain the second sequence from the locus of the target sequence and a second non-functional part of the marker gene cassette. The parts of the marker gene cassette are selected such that they can be combined to form a complete cassette. The cell is transformed with these pieces simultaneously, resulting in the formation of a complete, functional marker or structural gene cassette. Successful transformants can be selected for on the basis of the characteristic imparted by the selection marker. In another example, the selection marker resides on one fragment but the target sequences are on separate fragments, so that the integration fragments have a high probability of integrating at the site of interest. In other embodiments, transformation from three linear DNAs can be used to integrate exogenous genetic material. In these embodiments, one fragment overlaps on the 5' end with a second fragment and on the 3' end with a third fragment.

An integration or deletion construct may be designed such that the selection marker gene and some or all of its regulatory elements can become spontaneously deleted as a result of a subsequent homologous recombination event. A convenient way of accomplishing this is to design the construct such that the selection marker gene and/or regulatory elements are flanked by repeat sequences. Repeat sequences are identical DNA sequences, native or non-native to the host cell, and oriented on the construct in the same or opposite direction with respect to one another. The repeat sequences are advantageously about 50 to 1500 bp in length, and do not have to encode for anything. Inclusion of the repeat sequences permits a homologous recombination event to occur, which results in deletion of the selection marker gene and one of the repeat sequences. Since homologous recombination occurs with relatively low frequency, it may be necessary to grow transformants for several rounds on nonselective media to allow for the spontaneous homologous recombination to occur in some of the cells. Cells in which the selection marker gene has become spontaneously deleted can be selected or screened on the basis of their loss of the selection characteristic imparted by the selection marker gene. In certain cases, expression of a recombinase enzyme may enhance recombination between the repeated sites.

An exogenous 3-HP fermentation pathway gene in the modified yeast cells provided herein may be derived from a source gene from any suitable source. For example, an exogenous gene may be derived from a yeast, fungal, bacterial, plant, insect, or mammalian source. As used herein, an exogenous gene that is "derived from" a native source gene encodes a polypeptide that 1) is identical to a polypeptide encoded by the native gene, 2) shares at least 50%, at least 60%, at least 70%, at least 80%, at least 85%, at least 90%, at least 95%, at least 97%, or at least 99% sequence identity with a polypeptide encoded by the native gene, and/or 3) has the same function in a 3-HP fermentation pathway as the polypeptide encoded by the native gene. For example, a PYC gene that is derived from a *I. orientalis* PYC gene may encode a polypeptide comprising the amino acid sequence of SEQ ID NO: 2, a polypeptide with at least 50%, at least 60%, at least 70%, at least 80%, at least 85%, at least 90%, at least 95%, at least 97%, or at least 99% sequence identity to the amino acid sequence of SEQ ID NO: 2, and/or a polypeptide that has the ability to catalyze the conversion of pyruvate to OAA. A gene derived from a native gene may comprise a nucleotide sequence with at least 50%, at least 60%, at least 70%, at least 80%, at least 85%, at least 90%, at least 95%, at least 97%, or at least 99% sequence identity to the coding region of the native gene. In certain embodiments, a gene derived from a native gene may comprise a nucleotide sequence that is identical to the coding region of the source gene. For example, a PYC gene that is derived from a *I. orientalis* PYC gene may comprise the nucleotide sequence of SEQ ID NO: 1 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO: 1.

In certain embodiments of the modified yeast cells provided herein, the native source gene from which the exogenous 3-HP fermentation pathway gene is derived produces a polypeptide that is involved in a 3-HP fermentation pathway. In other embodiments, however, the native source gene may encode a polypeptide that is not involved in a 3-HP fermentation pathway or that catalyzes a reverse reaction in a 3-HP fermentation pathway. In these embodiments, the exogenous 3-HP pathway gene will have undergone one or more targeted or random mutations versus the native source gene that result in modified activity and/or substrate preference. For example, a native source gene may be mutated to generate a gene that encodes a polypeptide with increased activity in a desired reaction direction and/or decreased activity in a non-desired direction in a 3-HP fermentation pathway. For example, where the native source gene encodes a polypeptide capable of catalyzing both a forward and reverse reactions in a 3-HP fermentation pathway, the gene may be modified such that the resultant exogenous gene has increased activity in the forward direction and decreased activity in the reverse direction. Similarly, a native source gene may be mutated to produce a gene that encodes a polypeptide with different substrate preference than the native polypeptide. For example, a 3-HP pathway gene may be mutated to produce a polypeptide with the ability to act on a substrate that is either not preferred or not acted on at all by the native polypeptide. In these embodiments, the polypeptide encoded by the exogenous 3-HP pathway gene may catalyze a reaction that the polypeptide encoded by the native source gene is completely incapable of catalyzing. A native source gene may also be mutated such that the resultant 3-HP pathway gene exhibits decreased feedback inhibition at the DNA, RNA, or protein level in the presence of one or more downstream 3-HP pathway intermediates or side products.

In certain embodiments of the modified yeast cells provided herein, an exogenous 3-HP pathway gene may be derived from the host yeast species. For example, where the host cell is *I. orientalis*, an exogenous gene may be derived from an *I. orientalis* gene. In these embodiments, the exogenous gene may comprise a nucleotide sequence identical to the coding region of the native gene, such that incorporation of the exogenous gene into the host cell increases the copy number of a native gene sequence and/or changes the regulation or expression level of the gene if under the control of a promoter that is different from the promoter that drives expression of the gene in a wild-type cell. In other embodiments, the exogenous 3-HP pathway gene may comprise a nucleotide sequence that differs from the coding region of a native 3-HP pathway gene, but nonetheless encodes a polypeptide that is identical to the polypeptide encoded by the native 3-HP pathway gene. In still other embodiments, the exogenous 3-HP pathway gene may comprise a nucleotide sequence that encodes a polypeptide with at least 50%, at least 60%, at least 70%, at least 80%, at least 85%, at least 90%, at least 95%, at least 97%, or at least 99% sequence identity to a polypeptide encoded by one or more native 3-HP pathway genes. In certain of these embodiments, the exogenous gene comprises a nucleotide sequence with at least 50%, at least 60%, at least 70%, at least 80%, at least 85%, at least 90%, at least 95%, at least 97%, or at least 99% sequence identity to one or more native genes. In still other embodiments, the exogenous 3-HP gene may encode a polypeptide that has less than 50% sequence identity to a polypeptide encoded by a native 3-HP pathway gene but which nonetheless has the same function as the native polypeptide in a 3-HP fermentation pathway (i.e., the ability to catalyze the same reaction). A native source gene may be subjected to mutagenesis if necessary to provide a coding sequence starting with the usual eukaryotic starting codon (ATG), or for other purposes.

In other embodiments, the exogenous 3-HP pathway gene may be derived from a species that is different than that of the host yeast cell. In certain of these embodiments, the exogenous 3-HP pathway gene may be derived from a different yeast species than the host cell. For example, where the host cell is *I. orientalis*, the exogenous gene may be derived from *S. cerevisiae*. In other embodiments, the exogenous 3-HP pathway gene may be derived from a fungal, bacterial, plant, insect, or mammalian source. For example, where the host cell is *I. orientalis*, the exogenous gene may be derived from a bacterial source such as *E. coli*. In those embodiments where the exogenous 3-HP pathway gene is derived from a non-yeast source, the exogenous gene sequence may be codon-optimized for expression in a yeast host cell.

In those embodiments where the exogenous 3-HP pathway gene is derived from a species other than the host cell species, the exogenous gene may encode a polypeptide identical to a polypeptide encoded by a native 3-HP pathway gene from the source organism. In certain of these embodiments, the exogenous 3-HP pathway gene may be identical to a native 3-HP pathway gene from the source organism. In other embodiments, the exogenous gene may share at least 50%, at least 60%, at least 70%, at least 80%, at least 85%, at least 90%, at least 95%, at least 97%, or at least 99% sequence identity to a native 3-HP pathway gene from the source organism. In other embodiments, the exogenous 3-HP pathway gene may encode a polypeptide that shares at least 50%, at least 60%, at least 70%, at least 80%, at least 85%, at least 90%, at least 95%, at least 97%, or at least 99% sequence identity with a polypeptide encoded by a native 3-HP pathway gene from the source organism. In certain of these embodiments, the exogenous gene may comprise a nucleotide sequence with at least 50%, at least 60%, at least 70%, at least 80%, at least 85%, at least 90%, at least 95%, at least 97%, or at least 99% sequence identity to one or more native 3-HP pathway genes from the source organism. In still other embodiments, the exogenous 3-HP gene may encode a polypeptide that has less than 50% sequence identity to a polypeptide encoded by a native 3-HP pathway gene from the source organism, but which nonetheless has the same function as the native polypeptide from the source organism in a 3-HP fermentation pathway.

In certain embodiments, the yeast cells provided herein express one or more 3-HP pathway genes encoding enzymes selected from the group consisting of ACC (catalyzes the conversion of acetyl-CoA to malonyl-CoA), alanine 2,3 aminomutase (AAM, catalyzes the conversion of alanine to β-alanine), alanine dehydrogenase (catalyzes the conversion of pyruvate to alanine), aldehyde dehydrogenase (catalyzes the conversion of 3-HPA to 3-HP), KGD (catalyzes the conversion of OAA to malonate semialdehyde), AAT (catalyzes the conversion of OAA to aspartate), ADC (catalyzes the conversion of aspartate to β-alanine), BCKA (catalyzes the conversion of OAA to malonate semialdehyde), BAAT (catalyzes the conversion of β-alanine to malonate semialdehyde), 4-aminobutyrate aminotransferase (gabT, catalyzes the conversion of 1-alanine to malonate semialdehyde), β-alanyl-CoA ammonia lyase (catalyzes the conversion of β-alanyl-CoA to acrylyl-CoA), Co-A acylating malonate semialdehyde dehydrogenase (catalyzes the conversion of malonyl-CoA to malonate semialdehyde), CoA synthetase (catalyzes the conversion of β-alanine to β-alanyl-CoA or the conversion of lactate to lactyl-CoA), CoA transferase (catalyzes the conversion of 1-alanine to β-alanyl-CoA and/or the conversion of lactate to lactyl-CoA), glycerol dehydratase (catalyzes the conversion of glycerol to 3-HPA), IPDA (catalyzes the conversion of OAA to malonate semialdehyde), LDH (catalyzes the conversion of pyruvate to lactate), lactyl-CoA dehydratase (catalyzes the conversion of lactyl-CoA to acrylyl-CoA), malate decarboxylase (catalyzes the conversion of malate to 3-HP), malate dehydrogenase (catalyzes the conversion of OAA to malate), malonyl-CoA reductase (catalyzes the conversion of malonyl-CoA to malonate semialdehyde or 3-HP), OAA formatelyase (also known as pyruvate-formate lyase and ketoacid formate-lyase, catalyzes the conversion of OAA to malonyl-CoA), OAA dehydrogenase (catalyzes the conversion of OAA to malonyl CoA); PPC (catalyzes the conversion of PEP to OAA), pyruvate/alanine aminotransferase (catalyzes the conversion of pyruvate to alanine), PYC (catalyzes the conversion of pyruvate to OAA), PDH (catalyzes the conversion of pyruvate to acetyl-CoA), 2-keto acid decarboxylase (catalyzes the conversion of OAA to malonate semialdehyde), 3-HP-CoA dehydratase (also known as acrylyl-CoA hydratase, catalyzes the conversion of acrylyl-CoA to 3-HP-CoA), 3-HPDH (catalyzes the conversion of malonate semialdehyde to 3-HP), 3-HP-CoA hydrolase (catalyzes the conversion of 3-HP-CoA to 3-HP), HIBADH (catalyzes the conversion of malonate semialdehyde to 3-HP), 3-hydroxy-isobutyryl-CoA hydrolase (catalyzes the conversion of 3-HP-CoA to 3-HP), and 4-hydroxybutyrate dehydrogenase (catalyzes the conversion of malonate semialdehyde to 3-HP). For each of these enzyme activities, the reaction of interest in parentheses may be a result of native or non-native activity.

A "pyruvate carboxylase gene" or "PYC gene" as used herein refers to any gene that encodes a polypeptide with pyruvate carboxylase activity, meaning the ability to catalyze the conversion of pyruvate, $CO_2$, and ATP to OAA, ADP, and phosphate. In certain embodiments, a PYC gene may be derived from a yeast source. For example, the PYC gene may be derived from an *I. orientalis* PYC gene encoding the amino acid sequence set forth in SEQ ID NO: 2. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 2. In certain embodiments, an *I. orientalis*-derived PYC gene may comprise the nucleotide sequence set forth in SEQ ID NO: 1 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 1. In other embodiments, the PYC gene may be derived from a bacterial source. For example, the PYC gene may be derived from one of the few bacterial species that use only PYC and not PPC (see below) for anaplerosis, such as *R. sphaeroides*, or from a bacterial species that possesses both PYC and PPC, such as *R. etli*. The amino acid sequences encoded by the PYC genes of *R. sphaeroides* and *R. etli* are set forth in SEQ ID NOs: 3 and 4, respectively. A PYC gene may be derived from a gene encoding the amino acid sequence of SEQ ID NOs: 3 or 4, or from a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NOs: 3 or 4. Alternatively, the PYC gene may be derived from a PYC gene encoding an enzyme that does not have a dependence on acetyl-CoA for activation, such as a *P. fluorescens* PYC gene encoding the amino acid sequence set forth in SEQ ID NO: 5 (carboxytransferase subunit) or SEQ ID NO: 6 (biotin carboxylase subunit), a *C. glutamicum* PYC gene of encoding the amino acid sequence set forth in SEQ ID NO: 7, or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NOs: 5, 6, or 7. A PYC gene may also be derived from a PYC gene that encodes an enzyme that is not inhibited by aspartate, such as an *S. meliloti* PYC gene encoding the amino acid sequence set forth in SEQ ID NO: 8 (Sauer FEMS Microbiol Rev 29:765 (2005), or from a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NO: 8.

A "PEP carboxylase gene" or "PPC gene" as used herein refers to any gene that encodes a polypeptide with PEP carboxylase activity, meaning the ability to catalyze the conversion of PEP and $CO_2$ to OAA and phosphate. In certain embodiments, a PPC gene may be derived from a bacterial PPC gene. For example, the PPC gene may be derived from an *E. coli* PPC gene encoding the amino acid sequence set forth in SEQ ID NO: 10 or an amino acid sequence with at least 50%, at least 60%, at least 70%, at least 80%, at least 85%, at least 90%, at least 95%, at least 97%, or at least 99% sequence identity to the amino acid sequence of SEQ ID NO: 10. In certain embodiments, an *E. coli*-derived PPC gene may comprise the nucleotide sequence set forth in SEQ ID NO: 9 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 9. In other embodiments, a PPC gene may be derived from an "A" type PPC, found in many archea and a limited number of bacteria, that is not activated by acetyl CoA and is less inhibited by aspartate.

For example, a PPC gene may be derived from an *M. thermoautotrophicum* PPC A gene encoding the amino acid sequence set forth in SEQ ID NO: 11, a *C. perfringens* PPC A gene encoding the amino acid sequence set forth in SEQ ID NO: 12, or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NOs: 11 or 12. In certain of these embodiments, the gene may have undergone one or more mutations versus the native gene in order to generate an enzyme with improved characteristics. For example, the gene may have been mutated to encode a PPC polypeptide with increased resistance to aspartate feedback versus the native polypeptide. In other embodiments, the PPC gene may be derived from a plant source.

An "aspartate aminotransferase gene" or "AAT gene" as used herein refers to any gene that encodes a polypeptide with aspartate aminotransferase activity, meaning the ability to catalyze the conversion of OAA to aspartate. Enzymes having aspartate aminotransferase activity are classified as EC 2.6.1.1. In certain embodiments, an AAT gene may be derived from a yeast source such as *I. orientalis* or *S. cerevisiae*. For example, the AAT gene may be derived from an *I. orientalis* AAT gene encoding the amino acid sequence set forth in SEQ ID NO: 14 or an *S. cerevisiae* AAT2 gene encoding the amino acid sequence set forth in SEQ ID NO: 15. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs: 14 or 15. In certain embodiments, an *I. orientalis*-derived AAT gene may comprise the nucleotide sequence set forth in SEQ ID NO: 13 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 13. In other embodiments, the AAT gene may be derived from a bacterial source. For example, the AAT gene may be derived from an *E. coli* aspC gene encoding a polypeptide comprising the amino acid sequence set forth in SEQ ID NO: 16. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 16.

An "aspartate decarboxylase gene" or "ADC gene" as used herein refers to any gene that encodes a polypeptide with aspartate decarboxylase activity, meaning the ability to catalyze the conversion of aspartate to β-alanine. Enzymes having aspartate decarboxylase activity are classified as EC 4.1.1.11. In certain embodiments, an ADC gene may be derived from a bacterial source. Because an active aspartate decarboxylase may require proteolytic processing of an inactive proenzyme, in these embodiments the yeast host cell should be selected to support formation of an active enzyme coded by a bacterial ADC gene.

In some embodiments, the ADC gene may be derived from an *S. avermitilis* panD gene encoding the amino acid sequence set forth in SEQ ID NO: 17. In some embodiments, the ADC gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 17. In certain embodiments, an *S. avermitilis*-derived ADC gene may comprise the nucleotide sequence set forth in any one of SEQ ID NOs: 130, 145, 146, or 147; or a nucleotide sequence with at least 50%, at least 60%, at least 70%, at least 80%, at least 85%, at least 90%, at least 95%, at least 97%, or at least 99% sequence identity to the nucleotide sequence set forth in any one of SEQ ID NOs: 130, 145, 146, or 147.

In other embodiments, the ADC gene may be derived from a *C. acetobutylicum* panD gene encoding the amino acid sequence set forth in SEQ ID NO: 18. In some embodiments, the ADC gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 18. In certain embodiments, a *C. acetobutylicum*-derived ADC gene may comprise the nucleotide sequence set forth in SEQ ID NO: 131, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 131.

In other embodiments, the ADC gene may be derived from a *H. pylori* ADC gene encoding the amino acid sequence set forth in SEQ ID NO: 133. In some embodiments, the ADC gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 133. In certain embodiments, a *H. pylori*-derived ADC gene may comprise the nucleotide sequence set forth in SEQ ID NO: 133, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 133.

In other embodiments, the ADC gene may be derived from a *Bacillus* sp. TS25 ADC gene encoding the amino acid sequence set forth in SEQ ID NO: 135. In some embodiments, the ADC gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 135. In certain embodiments, a *Bacillus* sp. TS25-derived ADC gene may comprise the nucleotide sequence set forth in SEQ ID NO: 134, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 134.

In other embodiments, the ADC gene may be derived from a *C. glutamicum* ADC gene encoding the amino acid sequence set forth in SEQ ID NO: 137. In some embodiments, the ADC gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 137. In certain embodiments, a *C. glutamicum*-derived ADC gene may comprise the nucleotide sequence set forth in SEQ ID NO: 136, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 136.

In other embodiments, the ADC gene may be derived from a *B. licheniformis* ADC gene encoding the amino acid sequence set forth in SEQ ID NO: 139. In some embodiments, the ADC gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 139. In certain embodiments, a *B. licheniformis*-derived ADC gene may comprise the nucleotide sequence set forth in any one of SEQ ID NOs: 138, 148, 149, 150, or 151; or a nucleotide sequence with at least 50%, at least 60%, at least 70%, at least 80%, at least 85%, at least 90%, at least 95%, at least 97%, or at least 99% sequence identity to the nucleotide sequence set forth in any one of SEQ ID NOs: 138, 148, 149, 150, or 151.

A "β-alanine aminotransferase gene" or "BAAT gene" as used herein refers to any gene that encodes a polypeptide with β-alanine aminotransferase activity, meaning the ability to catalyze the conversion of 1-alanine to malonate semialdehyde. Enzymes having β-alanine aminotransferase activity are classified as EC 2.6.1.19. In certain embodiments, a BAAT gene may be derived from a yeast source. For example, a BAAT gene may be derived from the *I. orientalis* homolog to the pyd4 gene encoding the amino acid sequence set forth in SEQ ID NO: 20. In some embodiments, the BAAT gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 20. In certain embodiments, an *I. orientalis*-derived BAAT gene may comprise the nucleotide sequence set forth in SEQ ID NO: 19 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 19. In other embodiments, the BAAT gene may be derived from the *S. kluyveri* pyd4 gene encoding the amino acid sequence set forth in SEQ ID NO: 21. In some embodiments, the BAAT gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 21. In certain embodiments, a *S. kluyveri*-derived BAAT gene may comprise the nucleotide sequence set forth in SEQ ID NO: 142 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 142. In other embodiments, the BAAT gene may be derived from a bacterial source. For example, a BAAT gene may be derived from an *S. avermitilis* BAAT gene encoding the amino acid sequence set forth in SEQ ID NO: 22. In some embodiments, the BAAT gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 22. In certain embodiments, a *S. avermitilis*-derived BAAT gene may comprise the nucleotide sequence set forth in SEQ ID NO: 140 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 140.

A BAAT gene may also be a "4-aminobutyrate aminotransferase" or "gabT gene" meaning that it has native activity on 4-aminobutyrate as well as β-alanine. Alternatively, a BAAT gene may be derived by random or directed engineering of a native gabT gene from a bacterial or yeast source to encode a polypeptide with BAAT activity. For example, a BAAT gene may be derived from the *S. avermitilis* gabT encoding the amino acid sequence set forth in SEQ ID NO: 23. In some embodiments, the *S. avermitilis*-derived BAAT gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 23. In other embodiments, a BAAT gene may be derived from the *S. cerevisiae* gabT gene UGA1 encoding the amino acid sequence set forth in SEQ ID NO: 24. In some embodiments, the *S. cerevisiae*-derived BAAT gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 24. In certain embodiments, an *S. cerevisiae*-derived BAAT gene may comprise the nucleotide sequence set forth in SEQ ID NO: 141 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 141.

A "3-HP dehydrogenase gene" or "3-HPDH gene" as used herein refers to any gene that encodes a polypeptide with 3-HP dehydrogenase activity, meaning the ability to catalyze the conversion of malonate semialdehyde to 3-HP. Enzymes having 3-HP dehydrogenase activity are classified as EC 1.1.1.59 if they utilize an NAD(H) cofactor, and as EC 1.1.1.298 if they utilize an NADP(H) cofactor. Enzymes classified as EC 1.1.1.298 are alternatively referred to as malonate semialdehyde reductases.

In certain embodiments, a 3-HPDH gene may be derived from a yeast source. For example, a 3-HPDH gene may be derived from the *I. orientalis* homolog to the YMR226C gene encoding the amino acid sequence set forth in SEQ ID NO: 26. In some embodiments, the 3-HPDH gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 26. In certain embodiments, an *I. orientalis*-derived 3-HPDH gene may comprise the nucleotide sequence set forth in SEQ ID NO: 25 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 25. In other embodiments, a 3-HPDH gene may be derived from the *S. cerevisiae* YMR226C gene encoding the amino acid sequence set forth in SEQ ID NO: 129. In some embodiments, the 3-HPDH gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 129. In certain embodiments, an *S. cerevisiae*-derived 3-HPDH gene may comprise the nucleotide sequence set forth in SEQ ID NO: 144 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 144.

In other embodiments, the 3-HPDH gene may be derived from a bacterial source. For example, a 3-HPDH gene may be derived from an *E. coli* ydfG gene encoding the amino acid sequence in SEQ ID NO: 27. In some embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO: 27. In certain embodiments, an *E. coli*-derived 3-HPDH gene may comprise the nucleotide sequence set forth in SEQ ID NO: 143 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 143. In other embodiments, a 3-HPDH gene may be derived from an *M. sedula* malonate semialdehyde reductase gene encoding the amino acid sequence set forth in SEQ ID NO: 29. In some embodiments, the 3-HPDH gene may encode an amino acid sequence with at least 50%, at least 60%, at least 70%, at least 80%, at least 85%, at least 90%, at least 95%, at least 97%, or at least 99% sequence identity to the amino acid sequence set forth in SEQ ID NO: 29. In certain embodiments, an *M. sedula*-derived 3-HPDH gene may comprise the nucleotide sequence set forth in SEQ ID NO: 343 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 343.

A "3-hydroxyisobutyrate dehydrogenase gene" or "HIBADH gene" as used herein refers to any gene that encodes a polypeptide with 3-hydroxyisobutyrate dehydrogenase activity, meaning the ability to catalyze the conversion of 3-hydroxyisobutyrate to methylmalonate semialdehyde. Enzymes having 3-hydroxyisobutyrate dehydrogenase activity are classified as EC 1.1.1.31. Some 3-hydroxyisobutyrate dehydrogenases also have 3-HPDH activity. In certain embodiments, an HIBADH gene may be derived from a bacterial source. For example, an HIBADH gene may be derived from an *A. faecalis* M3A gene encoding the amino acid sequence set forth in SEQ ID NO: 28, a *P. putida* KT2440 or E23440 mmsB gene encoding the amino acid sequence set forth in SEQ ID NO: 30 or SEQ ID NO: 31, respectively, or a *P. aeruginosa* PAO1 mmsB gene encoding the amino acid sequence set forth in SEQ ID NO: 32. In certain embodiments, an HIBADH gene may encode an amino acid sequence with at least 50%, at least 60%, at least 70%, at least 80%, at least 85%, at least 90%, at least 95%, at least 97%, or at least 99% sequence identity to the amino acid sequence set forth in SEQ ID NOs: 28, 30, 31, or 32.

A "4-hydroxybutyrate dehydrogenase gene" as used herein refers to any gene that encodes a polypeptide with 4-hydroxybutyrate dehydrogenase activity, meaning the ability to catalyze the conversion of 4-hydroxybutanoate to succinate semialdehyde. Enzymes having 4-hydroxybutyrate dehydrogenase activity are classified as EC 1.1.1.61. Some 4-hydroxybutyrate dehydrogenases also have 3-HPDH activity. In certain embodiments, a 4-hydroxybutyrate dehydrogenase gene may be derived from a bacterial source. For example, a 4-hydroxybutyrate dehydrogenase gene may be derived from a *R. eutropha* H16 4hbd gene encoding the amino acid sequence set forth in SEQ ID NO: 33 or a *C. kluyveri* DSM 555 hbd gene encoding the amino acid sequence set forth in SEQ ID NO: 34. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence set forth in SEQ ID NOs: 33 or 34.

A "PEP carboxykinase gene" or "PCK gene" as used herein refers to any gene that encodes a polypeptide with PEP carboxykinase activity, meaning the ability to catalyze the conversion of PEP, $CO_2$, and ADP or GDP to OAA and ATP or GTP, or vice versa. Enzymes having PEP carboxykinase activity are classified as EC 4.1.1.32 (GTP/GDP utilizing) and EC 4.1.1.49 (ATP/ADP utilizing). In certain embodiments, a PCK gene may be derived from a yeast source. In other embodiments, a PCK gene may be derived from a bacterial source, and in certain of these embodiments the gene may be derived from a bacteria in which the PCK reaction favors the production of OAA rather than the more common form of the reaction where decarboxylation is dominant. For example, a PCK gene may be derived from an *M. succiniciproducens* PCK gene encoding the amino acid sequence set forth in SEQ ID NO: 35, an *A. succiniciproducens* PCK gene encoding the amino acid sequence set forth in SEQ ID NO: 36, an *A. succinogenes* PCK gene encoding the amino acid sequence set forth in SEQ ID NO: 37, or an *R. eutropha* PCK gene encoding the amino acid sequence set forth in SEQ ID NO: 38. In other embodiments, a PCK gene has undergone one or more mutations versus the native gene from which it was derived, such that the resultant gene encodes a polypeptide that preferably catalyzes the conversion of PEP to OAA. For example, a PCK gene may be derived from an *E. coli* K12 strain PCK gene encoding the amino acid sequence set forth in SEQ ID NO: 39, where the gene has been mutated to preferably catalyze the conversion of PEP to OAA. In other embodiments the conversion of PEP to OAA is catalyzed by a PEP carboxytransphosphorylase such as is found in propionic acid bacteria (e.g., *P. shermanii*, *A. woodii*) which use inorganic phosphate and diphosphate rather than ATP/ADP or GTP/GDP.

A "malate dehydrogenase gene" as used herein refers to any gene that encodes a polypeptide with malate dehydrogenase activity, meaning the ability to catalyze the conversion of OAA to malate. In certain embodiments, a malate dehydrogenase gene may be derived from a bacterial or yeast source.

A "malate decarboxylase gene" as used herein refers to any gene that encodes a polypeptide with malate decarboxylase activity, meaning the ability to catalyze the conversion of malate to 3-HP. Malate decarboxylase activity is not known to occur naturally. Therefore, a malate decarboxylase gene may be derived by incorporating one or more mutations into a native source gene that encodes a polypeptide with acetolactate decarboxylase activity. Polypeptides with acetolactate decarboxylase activity catalyze the conversion of 2-hydroxy-2-methyl-3-oxobutanoate to 2-acetoin, and are classified as EC 4.1.1.5. In certain embodiments, a malate decarboxylase gene may be derived from a bacterial source. For example, a malate decarboxylase gene may be derived from an *L. lactis* aldB gene encoding the amino acid sequence set forth in SEQ ID NO: 40, an *S. thermophilus* aldB gene encoding the amino acid sequence set forth in SEQ ID NO: 41, a *B. brevis* aldB gene encoding the amino acid sequence set forth in SEQ ID NO: 42, or a *E. aerogenes* budA gene encoding the amino acid sequence set forth in SEQ ID NO: 43.

An "alpha-ketoglutarate (AKG) decarboxylase gene" or "KGD gene" as used herein refers to any gene that encodes a polypeptide with alpha-ketoglutarate decarboxylase activity, meaning the ability to catalyze the conversion of alpha-ketoglutarate (2-oxoglutarate) to succinate semialdehyde. Enzymes having AKG decarboxylase activity are classified as EC 4.1.1.71. A KGD gene may be used to derive a gene encoding a polypeptide capable of catalyzing the conversion of OAA to malonate semialdehyde. This activity may be found in a native KGD gene, or it may derived by incorporating one or more mutations into a native KGD gene. In certain embodiments, a KGD gene may be derived from a bacterial source. For example, a KGD gene may be derived from a *M. tuberculosis* KGD gene encoding the amino acid sequence set forth in SEQ ID NO: 44, a *B. japonicum* KGD gene encoding the amino acid sequence set forth in SEQ ID NO: 45, or a *M. loti* (aka *Rhizobium loti*) KGD gene encoding the amino acid sequence set forth in SEQ ID NO: 46.

A "branched-chain alpha-keto acid decarboxylase gene" or "BCKA gene" as used herein refers to any gene that encodes a polypeptide with branched-chain alpha-keto acid decarboxylase activity, which can serve to decarboxylate a range of alpha-keto acids from three to six carbons in length. Enzymes having BCKA activity are classified as EC 4.1.1.72. A BCKA gene may be used to derive a gene encoding a polypeptide capable of catalyzing the conversion of OAA to malonate semialdehyde. This activity may be found in a native BCKA gene, or it may be derived by incorporating one or more mutations into a native BCKA gene. In certain embodiments, a BCKA gene may be derived from a bacterial source. For example, a BCKA gene may be derived from a *L. lactis* kdcA gene encoding the amino acid sequence set forth in SEQ ID NO: 47.

An "indolepyruvate decarboxylase gene" or "IPDA gene" as used herein refers to any gene that encodes a polypeptide with indolepyruvate decarboxylase activity, meaning the ability to catalyze the conversion of indolepyruvate to indoleacetaldehyde. Enzymes having IPDA activity are classified as EC 4.1.1.74. An IPDA gene may be used to derive a gene encoding a polypeptide capable of catalyzing the conversion of OAA to malonate semialdehyde. This activity may be found in a native IPDA gene, or it may be derived by incorporating one or more mutations into a native IPDA gene. In certain embodiments, an indolepyruvate decarboxylase gene may be derived from a yeast, bacterial, or plant source.

A "pyruvate decarboxylase gene" or "PDC gene" as used herein refers to any gene that encodes a polypeptide with pyruvate decarboxylase activity, meaning the ability to catalyze the conversion of pyruvate to acetaldehyde. Enzymes having PDC activity are classified as EC 4.1.1.1. In preferred embodiments, a PDC gene that is incorporated into a modified yeast cell as provided herein has undergone one or more mutations versus the native gene from which it was derived such that the resultant gene encodes a polypeptide capable of catalyzing the conversion of OAA to malonate semialdehyde. In certain embodiments, a PDC gene may be derived from a yeast source. For example, a PDC gene may be derived from an *I. orientalis* PDC gene encoding the amino acid sequence set forth in SEQ ID NO: 49, an *S. cerevisiae* PDC1 gene encoding the amino acid sequence set forth in SEQ ID NO: 50, or a *K. lactis* PDC encoding the amino acid sequence set forth in SEQ ID NO: 51. In certain embodiments, a PDC gene derived from the *I. orientalis* PDC gene may comprise the nucleotide sequence set forth in SEQ ID NO: 48 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO: 48. In other embodiments, a PDC gene may be derived from a bacterial source. For example, a PDC gene may be derived from a *Z. mobilis* PDC gene encoding the amino acid sequence set forth in SEQ ID NO: 52 or an *A. pasteurianus* PDC gene encoding the amino acid sequence set forth in SEQ ID NO: 53.

A "benzoylformate decarboxylase" gene as used herein refers to any gene that encodes a polypeptide with benzoylformate decarboxylase activity, meaning the ability to catalyze the conversion of benzoylformate to benzaldehyde. Enzymes having benzoylformate decarboxylase activity are classified as EC 4.1.1.7. In preferred embodiments, a benzoylformate decarboxylase gene that is incorporated into a modified yeast cell as provided herein has undergone one or more mutations versus the native gene from which it was derived such that the resultant gene encodes a polypeptide capable of catalyzing the conversion of OAA to malonate semialdehyde. In certain embodiments, a benzoylformate decarboxylase gene may be derived from a bacterial source. For example, a benzoylformate decarboxylase gene may be derived from a *P. putida* mdlC gene encoding the amino acid sequence set forth in SEQ ID NO: 54, a *P. aeruginosa* mdlC gene encoding the amino acid sequence set forth in SEQ ID NO: 55, a *P. stutzeri* dpgB gene encoding the amino acid sequence set forth in SEQ ID NO: 56, or a *P. fluorescens* ilvB-1 gene encoding the amino acid sequence set forth in SEQ ID NO: 57.

An "OAA formatelyase gene" as used herein refers to any gene that encodes a polypeptide with OAA formatelyase activity, meaning the ability to catalyze the conversion of an acylate ketoacid to its corresponding CoA derivative. A polypeptide encoded by an OAA formatelyase gene may have activity on pyruvate or on another ketoacid. In certain embodiments, an OAA formatelyase gene encodes a polypeptide that converts OAA to malonyl-CoA.

A "malonyl-CoA reductase gene" as used herein refers to any gene that encodes a polypeptide with malonyl-CoA reductase activity, meaning the ability to catalyze the conversion of malonyl-CoA to malonate semialdehyde (also referred to as Co-A acylating malonate semialdehyde dehydrogenase activity). In certain embodiments, a malonyl-CoA reductase gene may be derived from a bifunctional malonyl-CoA reductase gene which also has the ability to catalyze the conversion of malonate semialdehyde to 3-HP. In certain of these embodiments, a malonyl-CoA reductase gene may be derived from a bacterial source. For example, a malonyl-CoA reductase gene may be derived from a *C. aurantiacus* malonyl-CoA reductase gene encoding the amino acid sequence set forth in SEQ ID NO: 58, an *R. castenholzii* malonyl-CoA reductase gene encoding the amino acid sequence set forth in SEQ ID NO: 59, or an *Erythrobacter* sp. NAP1 malonyl-CoA reductase gene encoding the amino acid sequence set forth in SEQ ID NO: 60. In other embodiments, a malonyl-CoA reductase gene may be derived from a malonyl-CoA reductase gene encoding a polypeptide that only catalyzes the conversion of malonyl-CoA to malonate semialdehyde. For example, a malonyl-CoA reductase gene may be derived from an *M. sedula* Msed_0709 gene encoding the amino acid sequence set forth in SEQ ID NO: 61 or a *S. tokodaii* malonyl-CoA reductase encoding the amino acid sequence set forth in SEQ ID NO: 62.

A "pyruvate dehydrogenase gene" or "PDH gene" as used herein refers to any gene that encodes a polypeptide with pyruvate dehydrogenase activity, meaning the ability to catalyze the conversion of pyruvate to acetyl-CoA. In certain embodiments, a PDH gene may be derived from a yeast source. For example, a PDH gene may be derived from an *S. cerevisiae* LAT1, PDA1, PDB1, or LPD gene encoding the amino acid sequence set forth in SEQ ID NOs: 63-66, respectively. In other embodiments, a PDH gene may be derived from a bacterial source. For example, a PDH gene may be derived from an *E. coli* strain K12 substr. MG1655 aceE, aceF, or lpd gene encoding the amino acid sequence set forth in SEQ ID NOs: 67-69, respectively, or a *B. subtilis* pdhA, pdhB, pdhC, or pdhD gene encoding the amino acid sequence set forth in SEQ ID NOs: 70-73, respectively.

An "acetyl-CoA carboxylase gene" or "ACC gene" as used herein refers to any gene that encodes a polypeptide with acetyl-CoA carboxylase activity, meaning the ability to catalyze the conversion of acetyl-CoA to malonyl-CoA. Enzymes having acetyl-CoA carboxylase activity are classified as EC 6.4.1.2. In certain embodiments, an acetyl-CoA carboxylase gene may be derived from a yeast source. For example, an acetyl-CoA carboxylase gene may be derived from an *S. cerevisiae* ACC1 gene encoding the amino acid sequence set forth in SEQ ID NO: 74. In other embodiments, an acetyl-CoA carboxylase gene may be derived from a bacterial source. For example, an acetyl-CoA carboxylase gene may be derived from an *E. coli* accA, accB, accC, or accD gene encoding the amino acid sequence set forth in SEQ ID NOs: 75-78, respectively, or a *C. aurantiacus* accA, accB, accC, or accD gene encoding the amino acid sequence set forth in SEQ ID NOs: 79-82, respectively.

An "alanine dehydrogenase gene" as used herein refers to any gene that encodes a polypeptide with alanine dehydrogenase activity, meaning the ability to catalyze the NAD-dependent reductive amination of pyruvate to alanine. Enzymes having alanine dehydrogenase activity are classified as EC 1.4.1.1. In certain embodiments, an alanine dehydrogenase gene may be derived from a bacterial source. For example, an alanine dehydrogenase gene may be derived from an *B. subtilis* alanine dehydrogenase gene encoding the amino acid sequence set forth in SEQ ID NO: 83.

A "pyruvate/alanine aminotransferase gene" as used herein refers to any gene that encodes a polypeptide with pyruvate/alanine aminotransferase activity, meaning the ability to catalyze the conversion of pyruvate and L-glutamate to alanine and 2-oxoglutarate. In certain embodiments, a pyruvate/alanine aminotransferase gene is derived from a yeast source. For example, a pyruvate/alanine aminotransferase gene may be derived from an *S. pombe* pyruvate/alanine aminotransferase gene encoding the amino acid sequence set forth in SEQ ID NO: 84 or an *S. cerevisiae* ALT2 gene encoding the amino acid sequence set forth in SEQ ID NO: 85.

An "alanine 2,3 aminomutase gene" or "AAM gene" as used herein refers to a gene that encodes a polypeptide with alanine 2,3 aminomutase activity, meaning the ability to catalyze the conversion of alanine to β-alanine. Alanine 2,3 aminomutase activity is not known to occur naturally. Therefore, an alanine 2,3 aminomutase gene can be derived by incorporating one or more mutations into a native source gene that encodes a polypeptide with similar activity such as lysine 2,3 aminomutase activity (see, e.g., U.S. Pat. No. 7,309,597). In certain embodiments, the native source gene may be a *B. subtilis* lysine 2,3 aminomutase gene encoding the amino acid sequence set forth in SEQ ID NO: 86, a *P. gingivalis* lysine 2,3 aminomutase gene encoding the amino acid sequence set forth in SEQ ID NO: 87, or a *F. nucleatum* (ATCC-10953) lysine 2,3 aminomutase gene encoding the amino acid sequence set forth in SEQ ID NO: 88.

A "CoA transferase gene" as used herein refers to any gene that encodes a polypeptide with CoA transferase activity, which in one example includes the ability to catalyze the conversion of β-alanine to β-alanyl-CoA and/or the conversion of lactate to lactyl-CoA. In certain embodiments, a CoA transferase gene may be derived from a yeast source. In other embodiments, a CoA transferase gene may be derived from a bacterial source. For example, a CoA transferase gene may be derived from an *M. elsdenii* CoA transferase gene encoding the amino acid sequence set forth in SEQ ID NO: 89.

A "CoA synthetase gene" as used herein refers to any gene that encodes a polypeptide with CoA synthetase activity. In one example this includes the ability to catalyze the conversion of β-alanine to β-alanyl-CoA. In another example, this includes the ability to catalyze the conversion of lactate to lactyl-CoA. In certain embodiments, a CoA synthetase gene may be derived from a yeast source. For example, a CoA synthetase gene may be derived from an *S. cerevisiae* CoA synthetase gene. In other embodiments, a CoA synthetase gene may be derived from a bacterial source. For example, a CoA synthetase gene may be derived from an *E. coli* CoA synthetase, *R. sphaeroides*, or *S. enterica* CoA synthetase gene.

A "β-alanyl-CoA ammonia lyase gene" as used herein refers to any gene that encodes a polypeptide with β-alanyl-CoA ammonia lyase activity, meaning the ability to catalyze the conversion of β-alanyl-CoA to acrylyl-CoA. In certain embodiments, a β-alanyl-CoA ammonia lyase gene may be derived from a bacterial source, such as a *C. propionicum* β-alanyl-CoA ammonia lyase gene encoding the amino acid sequence set forth in SEQ ID NO: 90.

A "3-HP-CoA dehydratase gene" or "acrylyl-CoA hydratase gene" as used herein refers to any gene that encodes a polypeptide with 3-HP-CoA dehydratase gene activity, meaning the ability to catalyze the conversion of acrylyl-CoA to 3-HP-CoA. Enzymes having 3-HP-CoA dehydratase activity are classified as EC 4.2.1.116. In certain embodiments, a 3-HP-CoA dehydratase gene may be derived from a yeast or fungal source, such as a *P. sojae* 3-HP-CoA dehydratase gene encoding the amino acid sequence set forth in SEQ ID NO: 91. In other embodiments, a 3-HP-CoA dehydratase gene may be derived from a bacterial source. For example, a 3-HP-CoA dehydratase gene may be derived from a *C. aurantiacus* 3-HP-CoA dehydratase gene encoding the amino acid sequence set forth in SEQ ID NO: 92, an *R. rubrum* 3-HP-CoA dehydratase gene encoding the amino acid sequence set forth in SEQ ID NO: 93, or an *R. capsulates* 3-HP-CoA dehydratase gene encoding the amino acid sequence set forth in SEQ ID NO: 94. In still other embodiments, a 3-HP-CoA dehydratase gene may be derived from a mammalian source. For example, a 3-HP-CoA dehydratase gene may be derived from a *H. sapiens* 3-HP-CoA dehydratase gene encoding the amino acid sequence set forth in SEQ ID NO: 95.

A "3-HP-CoA hydrolase gene" as used herein refers to any gene that encodes a polypeptide with 3-HP-CoA hydrolase activity, meaning the ability to catalyze the conversion of 3-HP-CoA to 3-HP. In certain embodiments, a 3-HP-CoA gene may be derived from a yeast or fungal source. In other embodiments, a 3-HP-CoA gene may be derived from a bacterial or mammalian source.

A "3-hydroxyisobutyryl-CoA hydrolase gene" as used herein refers to any gene that encodes a polypeptide with 3-hydroxyisobutyryl-CoA hydrolase activity, which in one example includes the ability to catalyze the conversion of 3-HP-CoA to 3-HP. In certain embodiments, a 3-hydroxyisobutyryl-CoA hydrolase gene may be derived from a bacterial source, such as a *P. fluorescens* 3-hydroxyisobutyryl-CoA hydrolase gene encoding the amino acid sequence set forth in SEQ ID NO: 96 or a *B. cereus* 3-hydroxyisobutyryl-CoA hydrolase gene encoding the amino acid sequence set forth in SEQ ID NO: 97. In other embodiments, a 3-hydroxyisobutyryl-CoA hydrolase gene may be derived from a mammalian source, such as a *H. sapiens* 3-hydroxyisobutyryl-CoA hydrolase gene encoding the amino acid sequence set forth in SEQ ID NO: 98.

A "lactate dehydrogenase gene" or "LDH gene" as used herein refers to any gene that encodes a polypeptide with lactate dehydrogenase activity, meaning the ability to catalyze the conversion of pyruvate to lactate. In certain embodiments, an LDH gene may be derived from a fungal, bacterial, or mammalian source.

A "lactyl-CoA dehydratase gene" as used herein refers to any gene that encodes a polypeptide with lactyl-CoA dehydratase activity, meaning the ability to catalyze the conversion of lactyl-CoA to acrylyl-CoA. In certain embodiments, a lactyl-CoA dehydratase gene may be derived from a bacterial source. For example, a lactyl-CoA dehydratase gene may be derived from an *M. elsdenii* lactyl-CoA dehydratase EI, EIIa, or EIIb subunit gene encoding the amino acid sequence set forth in SEQ ID NOs: 99-101.

An "aldehyde dehydrogenase gene" as used herein refers to any gene that encodes a polypeptide with aldehyde dehydrogenase activity, which in one example includes the ability to catalyze the conversion of 3-HPA to 3-HP and vice versa. In certain embodiments, an aldehyde dehydrogenase gene may be derived from a yeast source, such as an *S. cerevisiae* aldehyde dehydrogenase gene encoding the amino acid sequence set forth in SEQ ID NO: 102 or an *I. orientalis* aldehyde dehydrogenase gene encoding the amino acid sequence set forth in SEQ ID NOs: 122, 124, or 126. In other embodiments, an aldehyde dehydrogenase may be derived from a bacterial source, such as an *E. coli* aldH gene encoding the amino acid sequence set forth in SEQ ID NO: 103 or a *K. pneumoniae* aldehyde dehydrogenase gene encoding the amino acid sequence set forth in SEQ ID NO: 104.

A "glycerol dehydratase gene" as used herein refers to any gene that encodes a polypeptide with glycerol dehydratase activity, meaning the ability to catalyze the conversion of glycerol to 3-HPA. In certain embodiments, a glycerol dehydratase gene may be derived from a bacterial source, such as a *K. pneumonia* or *C. freundii* glycerol dehydratase gene.

In certain embodiments, the genetically modified yeast cells provided herein further comprise a deletion or disruption of one or more native genes. "Deletion or disruption" with regard to a native gene means that either the entire coding region of the gene is eliminated (deletion) or the coding region of the gene, its promoter, and/or its terminator region is modified (such as by deletion, insertion, or mutation) such that the gene no longer produces an active enzyme, produces a severely reduced quantity (at least 75% reduction, preferably at least 90% reduction) of an active enzyme, or produces an enzyme with severely reduced (at least 75% reduced, preferably at least 90% reduced) activity.

In certain embodiments, deletion or disruption of one or more native genes results in a deletion or disruption of one or more native metabolic pathways. "Deletion or disruption" with regard to a metabolic pathway means that the pathway is either inoperative or else exhibits activity that is reduced by at least 75%, at least 85%, or at least 95% relative to the native pathway. In certain embodiments, deletion or disruption of a native metabolic pathway is accomplished by incorporating one or more genetic modifications that result in decreased expression of one or more native genes that reduce 3-HP production.

In certain embodiments, deletion or disruption of native gene can be accomplished by forced evolution, mutagenesis, or genetic engineering methods, followed by appropriate selection or screening to identify the desired mutants. In certain embodiments, deletion or disruption of a native host cell gene may be coupled to the incorporation of one or more exogenous genes into the host cell, i.e., the exogenous genes may be incorporated using a gene expression integration construct that is also a deletion construct. In other embodiments, deletion or disruption may be accomplished using a deletion construct that does not contain an exogenous gene or by other methods known in the art.

In certain embodiments, the genetically modified yeast cells provided herein comprise a deletion or disruption of one or more native genes encoding an enzyme involved in ethanol fermentation, including for example pyruvate decarboxylase (PDC, converts pyruvate to acetaldehyde) and/or alcohol dehydrogenase (ADH, converts acetaldehyde to ethanol) genes. These modifications decrease the ability of the yeast cell to produce ethanol, thereby maximizing 3-HP production. However, in certain embodiments the genetically modified yeast cells provided herein may be engineered to co-produce 3-HP and ethanol. In those embodiments, native genes encoding an enzyme involved in ethanol fermentation are preferably not deleted or disrupted, and in certain embodiments the yeast cells may comprise one or more exogenous genes that increase ethanol production.

In certain embodiments, the genetically modified yeast cells provided herein comprise a deletion or disruption of one or more native genes encoding an enzyme involved in producing alternate fermentative products such as glycerol or other byproducts such as acetate or diols. For example, the cells provided herein may comprise a deletion or disruption of one or more of glycerol 3-phosphate dehydrogenase (GPD, catalyzes reaction of dihydroxyacetone phosphate to glycerol 3-phosphate), glycerol 3-phosphatase (GPP, catalyzes conversion of glycerol-3 phosphate to glycerol), glycerol kinase (catalyzes conversion of glycerol 3-phosphate to glycerol), dihydroxyacetone kinase (catalyzes conversion of dihydroxyacetone phosphate to dihydroxyacetone), glycerol dehydrogenase (catalyzes conversion of dihydroxyacetone to glycerol), aldehyde dehydrogenase (ALD, e.g., converts acetaldehyde to acetate or 3-HP to 3-HPA), or butanediol dehydrogenase (catalyzes conversion of butanediol to acetoin and vice versa) genes.

In certain embodiments, the genetically modified yeast cells provided herein comprise a deletion or disruption of one or more native genes encoding an enzyme that catalyzes a reverse reaction in a 3-HP fermentation pathway, including for example PEP carboxykinase (PCK), enzymes with OAA decarboxylase activity, or CYB2A or CYB2B (catalyzes the conversion of lactate to pyruvate). PCK catalyzes the conversion of PEP to OAA and vice versa, but exhibits a preference for the OAA to PEP reaction. To reduce the conversion of OAA to PEP, one or more copies of a native PCK gene may be deleted or disrupted. In certain embodiments, yeast cells in which one or more native PCK genes have been deleted or disrupted may express one or more exogenous PCK genes that have been mutated to encode a polypeptide that favors the conversion of PEP to OAA. OAA decarboxylase catalyzes the conversion of OAA to pyruvate. Enzymes with OAA decarboxylase activity have been identified, such as that coded by the eda gene in *E. coli* and malic enzyme (MAE) in yeast and fungi. To reduce OAA decarboxylase activity, one or more copies of a native gene encoding an enzyme with OAA decarboxylase activity may be deleted or disrupted. In certain embodiments, yeast cells in which one or more native OAA decarboxylation genes have been deleted or disrupted may express one or more exogenous OAA decarboxylation genes that have been mutated to encode a polypeptide that catalyzes the conversion of pyruvate to OAA.

In certain embodiments, the genetically modified yeast cells provided herein comprise a deletion or disruption of one or more native genes encoding an enzyme involved in an undesirable reaction with a 3-HP fermentation pathway product or intermediate. Examples of such genes include those encoding an enzyme that converts 3HP to an aldehyde of 3HP, which are known to be toxic to bacterial cells.

In certain embodiments, the genetically modified yeast cells provided herein comprise a deletion or disruption of one or more native genes encoding an enzyme that has a neutral effect on a 3-HP fermentation pathway, including for example GAL6 (negative regulator of the GAL system that converts galactose to glucose). Deletion or disruption of neutral genes allows for insertion of one or more exogenous genes without affecting native fermentation pathways.

In certain embodiments, the yeast cells provided herein are 3-HP resistant yeast cells. A "3-HP-resistant yeast cell" as used herein refers to a yeast cell that exhibits an average glycolytic rate of at least 2.5 g/L/hr in media containing 75 g/L or greater 3-HP at a pH of less than 4.0. Such rates and conditions represent an economic process for producing 3-HP. In certain of these embodiments, the yeast cells may exhibit 3-HP resistance in their native form. In other embodiments, the cells may have undergone mutation and/or selection (e.g., chemostat selection or repeated serial subculturing) before, during, or after introduction of genetic modifications related to an active 3-HP fermentation pathway, such that the mutated and/or selected cells possess a higher degree of resistant to 3-HP than wild-type cells of the same species. For example, in some embodiments, the cells have undergone mutation and/or selection in the presence of 3-HP or lactic acid before being genetically modified with one or more exogenous 3-HP pathway genes. In certain embodiments, mutation and/or selection may be carried out on cells that exhibit 3-HP resistance in their native form. Cells that have undergone mutation and/or selection may be tested for sugar consumption and other characteristics in the presence of varying levels of 3-HP in order to determine their potential as industrial hosts for 3-HP production. In addition to 3-HP resistance, the yeast cells provided herein may have undergone mutation and/or selection for resistance to one or more additional organic acids (e.g., lactic acid) or to other fermentation products, byproducts, or media components.

Selection, such as selection for resistance to 3-HP or to other compounds, may be accomplished using methods well known in the art. For example, as mentioned supra, selection may be chemostat selection. Chemostat selection uses a chemostat that allows for a continuous culture of microorganisms (e.g., yeast) wherein the specific growth rate and cell number can be controlled independently. A continuous culture is essentially a flow system of constant volume to which medium is added continuously and from which continuous removal of any overflow can occur. Once such a system is in equilibrium, cell number and nutrient status remain constant, and the system is in a steady state. A chemostat allows control of both the population density and the specific growth rate of a culture through dilution rate and alteration of the concentration of a limiting nutrient, such as a carbon or nitrogen source. By altering the conditions as a culture is grown (e.g., decreasing the concentration of a secondary carbon source necessary to the growth of the inoculum strain, among others), microorganisms in the population that are capable of growing faster at the altered conditions will be selected and will outgrow microorganisms that do not function as well under the new conditions. Typically such selection requires the progressive increase or decrease of at least one culture component over the course of growth of the chemostat culture. The operation of chemostats and their use in the directed evolution of microorganisms is well known in the art (see, e.g., Novick Proc Natl Acad Sci USA 36:708-719 (1950), Harder J Appl Bacteriol 43:1-24 (1977). Other methods for selection include, but are not limited to, repeated serial subculturing under the selective conditions as described in e.g., U.S. Pat. No. 7,629,162. Such methods can be used in place of, or in addition to, using the glucose limited chemostat method described above.

Yeast strains exhibiting the best combinations of growth and glucose consumption in 3-HP media as disclosed in the examples below are preferred host cells for various genetic modifications relating to 3-HP fermentation pathways. Yeast genera that possess the potential for a relatively high degree of 3-HP resistance, as indicated by growth in the presence of 75 g/L 3-HP or higher at a pH of less than 4, include for example *Candida, Kluyveromyces, Issatchenkia, Saccharomyces, Pichia, Schizosaccharomyces, Torulaspora,* and *Zygosaccharomyces*. Species exhibiting 3-HP resistance included *I. orientalis* (also known as *C. krusei*), *C. lambica* (also known as *Pichia fermentans*), and *S. bulderi* (also known as *Kazachstania bulden*). *I. orientalis* and *C. lambica* are from the *I. orientalis/P. fermentans* clade, while *S. bulderi* is from the *Saccharomyces* clade. Specific strains exhibiting 3-HP resistance included *I. orientalis* strains 24210, PTA-6658, 60585, and CD1822, *S. bulderi* strains MYA-402 and MYA-404, and *C. lambica* strain ATCC 38617.

Other wild-type yeast or fungi may be tested in a similar manner and identified to have acceptable levels of growth and glucose utilization in the presence of high levels of 3-HP as described herein. For example, Gross and Robbins (Hydrobiologia 433(103):91-109) have compiled a list of 81 fungal species identified in low pH (<4) environments that could be relevant to test as potential production hosts.

In certain embodiments, the modified yeast cells provided herein are generated by incorporating one or more genetic modifications into a Crabtree-negative host yeast cell. In certain of these embodiments the host yeast cell belongs to the genus *Issatchenkia, Candida,* or *Saccharomyces,* and in certain of these embodiments the host cell belongs to the *I. orientalis/P. fermnnentans* or *Saccharomyces* clade. In certain of embodiments, the host cell is *I. orientalis* or *C. lambica,* or *S. bulderi*.

The *I. orientalis/P. fermentans* clade is the most terminal clade that contains at least the species *I. orientalis, P. galeiformis, P.* sp. YB-4149 (NRRL designation), *C. ethanolica, P. deserticola, P. membranifaciens,* and *P. fermentans*. Members of the *I. orientalis/P. fermentans* clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences," Antonie van Leeuwenhoek 73:331-371, 1998, incorporated herein by reference (see especially p. 349). Analysis of the variable D1/D2 domain of the 26S ribosomal DNA from hundreds of ascomycetes has revealed that the *I. orientalis/P. fermentans* clade contains very closely related species. Members of the *I. orientalis/P. fermentans* clade exhibit greater similarity in the variable D1/D2 domain of the 26S ribosomal DNA to other members of the clade than to yeast species outside of the clade. Therefore, other members of the *I. orientalis/P. fermentans* clade can be identified by comparison of the D1/D2 domains of their respective ribosomal DNA and comparing to that of other members of the clade and closely related species outside of the clade, using Kurtzman and Robnett's methods.

In certain embodiments, the genetically modified yeast cells provided herein belong to the genus *Issatchenkia,* and in certain of these embodiments the yeast cells are *I. orientalis*. When first characterized, the species *I. orientalis* was assigned the name *Pichia kudriavzevii*. The anamorph (asexual form) of *I. orientalis* is known as *Candida krusei*. Numerous additional synonyms for the species *I. orientalis* have been listed elsewhere (Kurtzman and Fell, The Yeasts, a Taxonomic Study. Section 35. *Issatchenkia kudryavtsev,* pp 222-223 (1998)).

The ideal yeast cell for 3-HP production is ideally capable of growing at low pH levels. The ability to conduct fermentation at a low pH decreases downstream recovery costs, resulting in more economical production. Therefore, in certain embodiments the yeast host cell is capable of growing at low pH levels (e.g., at pH levels less than 7, 6, 5, 4, or 3).

A suitable host cell may possess one or more favorable characteristics in addition to 3-HP resistance and/or low pH growth capability. For example, potential host cells exhibiting 3-HP resistance may be further selected based on glycolytic rates, specific growth rates, thermotolerance, tolerance to biomass hydrolysate inhibitors, overall process robustness, and so on. These criteria may be evaluated prior to any genetic modification relating to a 3-HP fermentation pathway, or they may be evaluated after one or more such modifications have taken place.

Because most yeast are native producers of ethanol, elimination or severe reduction in the enzyme catalyzing the first step in ethanol production from pyruvate (PDC) is required for sufficient yield of an alternate product. In Crabtree-positive yeast such as *Saccharomyces,* a deleted or disrupted PDC gene causes the host to acquire an auxotrophy for two-carbon compounds such as ethanol or acetate, and causes a lack of growth in media containing glucose. Mutants capable of overcoming these limitations can be obtained using progressive selection for acetate independence and glucose tolerance (see, e.g., van Maris Appl Environ Microbiol 70:159 (2004)). Therefore, in certain embodiments a preferred yeast host cell is a Crabtree-negative yeast cell, in which PDC deletion strains are able to grow on glucose and retain C2 prototrophy.

The level of gene expression and/or the number of exogenous genes to be utilized in a given cell will vary depending on the yeast species selected. For fully genome-sequenced yeasts, whole-genome stoichiometric models may be used to determine which enzymes should be expressed to develop a desired pathway 3-HP fermentation pathway. Whole-genome stoichiometric models are described in, for example, Hjersted et al., "Genome-scale analysis of *Saccharomyces cerevisiae* metabolism and ethanol production in fed-batch culture," *Biotechnol. Bioeng.* 2007; and Famili et al., "*Saccharomyces cerevisiae* phenotypes can be predicted by using constraint-based analysis of a genome-scale reconstructed metabolic network," *Proc. Natl. Acad. Sci.* 2003, 100(23): 13134-9.

For yeasts without a known genome sequence, sequences for genes of interest (either as overexpression candidates or as insertion sites) can typically be obtained using techniques such as those described below in Example 2A. Routine experimental design can be employed to test expression of various genes and activity of various enzymes, including genes and enzymes that function in a 3-HP pathway. Experiments may be conducted wherein each enzyme is expressed in the yeast individually and in blocks of enzymes up to and including preferably all pathway enzymes, to establish which are needed (or desired) for improved 3-HP production. One illustrative experimental design tests expression of each individual enzyme as well as of each unique pair of enzymes, and further can test expression of all required enzymes, or each unique combination of enzymes. A number of approaches can be taken, as will be appreciated.

In certain embodiments, methods are provided for producing 3-HP from a genetically modified yeast cell as provided herein. In certain embodiments, these methods comprise culturing a genetically modified yeast cell as provided herein in the presence of at least one carbon source, allowing the cell to produce 3-HP for a period of time, and then isolating 3-HP produced by the cell from culture. The carbon source may be any carbon source that can be fermented by the provided yeast. The carbon source may be a twelve carbon sugar such as sucrose, a hexose sugar such as glucose or fructose, glycan or other polymer of glucose, glucose oligomers such as maltose, maltotriose and isomaltotriose, panose, and fructose oligomers. If the cell is modified to impart an ability to ferment pentose sugars, the fermentation medium may include a pentose sugar such as xylose, xylan or other oligomer of xylose, and/or arabinose. Such pentose sugars are suitably hydrolysates of a hemicellulose-containing biomass. In the case of oligomeric sugars, it may be necessary to add enzymes to the fermentation broth in order to digest these to the corresponding monomeric sugar for fermentation by the cell. In certain embodiments, more than one type of genetically modified yeast cell may be present in the culture. Likewise, in certain embodiments one or more native yeast cells of the same or a different species than the genetically modified yeast cell may be present in the culture.

In certain embodiments, culturing of the cells provided herein to produce 3-HP may be divided up into phases. For example, the cell culture process may be divided into a cultivation phase, a production phase, and a recovery phase. One of ordinary skill in the art will recognize that the conditions used for these phases may be varied based on factors such as the species of yeast being used, the specific 3-HP fermentation pathway utilized by the yeast, the desired yield, or other factors.

The medium will typically contain nutrients as required by the particular cell, including a source of nitrogen (such as amino acids, proteins, inorganic nitrogen sources such as ammonia or ammonium salts, and the like), and various vitamins, minerals and the like. In some embodiments, the cells of the invention can be cultured in a chemically defined medium. In one example, the medium contains around 5 g/L ammonium sulfate, around 3 g/L potassium dihydrogen phosphate, around 0.5 g/L magnesium sulfate, trace elements, vitamins and around 150 g/L glucose. The pH may be allowed to range freely during cultivation, or may be buffered if necessary to prevent the pH from falling below or rising above predetermined levels. In certain embodiments, the fermentation medium is inoculated with sufficient yeast cells that are the subject of the evaluation to produce an $OD_{600}$ of about 1.0. Unless explicitly noted otherwise, $OD_{600}$ as used herein refers to an optical density measured at a wavelength of 600 nm with a 1 cm pathlength using a model DU600 spectrophotometer (Beckman Coulter). The cultivation temperature may range from around 30-40° C., and the cultivation time may be up to around 120 hours.

In one example, the concentration of cells in the fermentation medium is typically in the range of about 0.1 to 20, preferably from 0.1 to 5, even more preferably from 1 to 3 g dry cells/liter of fermentation medium during the production phase. The fermentation may be conducted aerobically, microaerobically, or anaerobically, depending on pathway requirements. If desired, oxygen uptake rate (OUR) can be varied throughout fermentation as a process control (see, e.g., WO03/102200). In some embodiments, the modified yeast cells provided herein are cultivated under microaerobic conditions characterized by an oxygen uptake rate from 2 to 45 mmol/L/hr, e.g., 2 to 25, 2 to 20, 2 to 15, 2 to 10, 10 to 45, 15 to 40, 20 to 35, or 25 to 35 mmol/L/hr. In certain embodiments, the modified yeast cells provided herein may perform especially well when cultivated under microaerobic conditions characterized by an oxygen uptake rate of from 2 to 25 mmol/L/hr. The medium may be buffered during the production phase such that the pH is maintained in a range of about 3.0 to about 7.0, or from about 4.0 to about 6.0. Suitable buffering agents are basic materials that neutralize the acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here.

In those embodiments where a buffered fermentation is utilized, acidic fermentation products may be neutralized to the corresponding salt as they are formed. In these embodiments, recovery of the acid involves regeneration of the free acid. This may be done by removing the cells and acidulating the fermentation broth with a strong acid such as sulfuric acid. This results in the formation of a salt by-product. For example, where a calcium salt is utilized as the neutralizing agent and sulfuric acid is utilized as the acidulating agent, gypsum is produced as a salt by-product. This by-product is separated from the broth, and the acid is recovered using techniques such as liquid-liquid extraction, distillation, absorption, and others (see, e.g., T. B. Vickroy, Vol. 3, Chapter 38 of *Comprehensive Biotechnology*, (ed. M. Moo-Young), Pergamon, Oxford, 1985; R. Datta, et al., FEMS Microbiol Rev, 1995, 16:221-231; U.S. Pat. Nos. 4,275,234, 4,771,001, 5,132,456, 5,420,304, 5,510,526, 5,641,406, and 5,831,122, and WO93/00440.

In other embodiments, the pH of the fermentation medium may be permitted to drop during cultivation from a starting pH that is at or above the pKa of 3-HP, typically 4.5 or higher, to at or below the pKa of the acid fermentation product, e.g., less than 4.5 or 4.0, such as in the range of about 1.5 to about 4.5, in the range of from about 2.0 to about 4.0, or in the range from about 2.0 to about 3.5.

In still other embodiments, fermentation may be carried out to produce a product acid by adjusting the pH of the fermentation broth to at or below the pKa of the product acid prior to or at the start of the fermentation process. The pH may thereafter be maintained at or below the pKa of the product acid throughout the cultivation. In certain embodiments, the pH may be maintained at less than 4.5 or 4.0, such as in a range of about 1.5 to about 4.5, in a range of about 2.0 to about 4.0, or in a range of about 2.0 to about 3.5.

In certain embodiments of the methods provided herein, the genetically modified yeast cells produce relatively low levels of ethanol. In certain embodiments, ethanol may be produced in a yield of 10% or less, preferably in a yield of 2% or less. In certain of these embodiments, ethanol is not detectably produced. In other embodiments, however, 3-HP and ethanol may be co-produced. In these embodiments, ethanol may be produced at a yield of greater than 10%, greater than 25%, or greater than 50%.

In certain embodiments of the methods provided herein, the final yield of 3-HP on the carbon source is at least 10%, at least 20%, at least 30%, at least 40%, at least 50%, or greater than 50% of the theoretical yield. The concentration, or titer, of 3-HP will be a function of the yield as well as the starting concentration of the carbon source. In certain embodiments, the titer may reach at least 1-3, at least 5, at least 10, at least 20, at least 30, at least 40, at least 50, or greater than 50 g/L at some point during the fermentation, and preferably at the end of the fermentation. In certain embodiments, the final yield of 3-HP may be increased by altering the temperature of the fermentation medium, particularly during the production phase.

Once produced, any method known in the art can be used to isolate 3-HP from the fermentation medium. For example, common separation techniques can be used to remove the biomass from the broth, and common isolation procedures (e.g., extraction, distillation, and ion-exchange procedures) can be used to obtain the 3-HP from the microorganism-free broth. In addition, 3-HP can be isolated while it is being produced, or it can be isolated from the broth after the product production phase has been terminated.

3-HP produced using the methods disclosed herein can be chemically converted into other organic compounds. For example, 3-HP can be hydrogenated to form 1,3 propanediol, a valuable polyester monomer. Propanediol also can be created from 3-HP using polypeptides having oxidoreductase activity in vitro or in vivo. Hydrogenating an organic acid such as 3-HP can be performed using any method such as those used to hydrogenate succinic acid and/or lactic acid. For example, 3-HP can be hydrogenated using a metal catalyst. In another example, 3-HP can be dehydrated to form acrylic acid using any known method for performing dehydration reactions. For example, 3-HP can be heated in the presence of a catalyst (e.g., a metal or mineral acid catalyst) to form acrylic acid.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Media and Solutions

TE was composed of 10 mM Tris Base and 1 mM EDTA, pH 8.0.

2×YT+amp plates were composed of 16 g/L tryptone, 10 g/L yeast extract, 5 g/L NaCl, 100 mg/L ampicillin, and 15 g/L Bacto agar.

ura selection plates were composed of 6.7 g yeast nitrogen base with ammonium sulfate, 5 g casamino acids, 100 mL 0.5 M succinic acid pH 5, 20 g Noble agar, and 855 mL deionized water. Following autoclave sterilization, 40 mL sterile 50% glucose and 2 mL 10 mg/mL chloraphenicol were added and plates poured.

ura selection media was composed of 6.7 g yeast nitrogen base with ammonium sulfate, 5 g casamino acids, 100 mL 0.5 M succinic acid pH 5, and 855 mL deionized water. Following autoclave sterilization, 40 mL sterile 50% glucose and 2 mL 10 mg/mL chloraphenicol were added.

YP+10% glucose media was composed of 500 mL YP broth and 100 mL sterile 50% glucose.

YP broth was composed of 10 g/L of yeast extract, 20 g/L of peptone.

YPD plates were composed of 10 g of yeast extract, 20 g of peptone, 20 g bacto agar, and deionized water to 960 mL. Following autoclave sterilization, 40 mL sterile 50% glucose was added and plates poured.

TAE was composed of 4.84 g/L of Tris base, 1.14 ml/L of glacial acetic acid, and 2 mL/L of 0.5 M EDTA pH 8.0.

TBE was composed of 10.8 g/L of Tris base, 5.5 g/L boric acid, and 4 mL/L of 0.5 M EDTA pH 8.0.

LiOAc/TE solution was composed of 8 parts sterile water, 1 part 1 M LiOAc, and 1 part 10×TE.

10×TE (200 mL) was composed of 2.42 g Tris Base, 4 mL 0.5M EDTA, pH 8.0. 5 M HCl was used to adjust the pH to 7.5 and the solution was sterilized by autoclave.

PEG/LiOAc/TE Solution was composed of 8 parts 50% PEG3350, 1 part 1 M LiOAc, and 1 part 10×TE.

50% PEG3350 was prepared by adding 100 g PEG3350 to 150 mL water and heating and stirring until dissolved. The volume was then brought up to 200 mL with water and the sterilized by autoclave.

ScD FOA plates were composed of 275 mL 2×-ScD 2×FOA liquid media and 275 mL 2×-ScD 2×FOA plate media, melted and cooled to 65° C.

2×-ScD 2×FOA liquid media was composed of 6.66 g yeast nitrogen base without amino acids, 1.54 g ura– DO supplement (Clontech, Mountain View, Calif., USA), 20 g dextrose, 50 mg uracil, 2 mg uridine, and 2 g 5-FOA (5-fluoroorotic acid, monohydrate; Toronto Research Chemicals, North York, ON, Canada) and water to 1 L. The resulting solution was filtered to sterilize.

2×-ScD 2×FOA plate media was composed of 11 g bacto agar and 275 mL water. The resulting solution was autoclaved to sterilize.

DM2 medium was composed of ammonium sulfate (5.0 g/L), magnesium sulfate heptahydrate (0.5 g/L), potassium phosphate monobasic (3.0 g/L), trace element solution (1 mL/L) and vitamin solution (1 mL/L). After dissolving all medium components, the pH of the medium was adjusted to the desired initial pH using an appropriate base (e.g, KOH).

Trace element solution was composed of EDTA (15.0 g/L), zinc sulfate heptahydrate (4.5 g/L), manganese chloride dehydrate (1.0 g/L), Cobalt(II)chloride hexahydrate (0.3 g/L), Copper(II)sulfate pentahydrate (0.3 g/L), disodium molybdenum dehydrate (0.4 g/L), calcium chloride dehydrate (4.5 g/L), iron sulphate heptahydrate (3 g/L), boric acid (1.0 g/L), and potassium iodide (0.1 g/L).

Vitamin solution was composed of biotin (D−; 0.05 g/L), calcium pantothenate (D+; 1 g/L), nicotinic acid (5 g/L), myo-inositol (25 g/L), pyridoxine hydrochloride (1 g/L), p-aminobenzoic acid (0.2 g/L), and thiamine hydrochloride (1 g/L).

DM1 X-α-gal plates were composed of DM1 salts, 20 g/L glucose, trace element solution, vitamin solution, 2 mL/L X-α-gal (16 mg/mL), 20 g/L agar.

DM1 salt solution was composed of 2.28 g/L urea, 3 g/L potassium phosphate monobasic, and 0.5 g/L magnesium sulfate heptahydrate.

Butterfields Phosphate Buffer was composed of 1.25 mL/L of Stock Solution (26.22 g/L Potassium Dihydrogen Phosphate and 7.78 g/L Sodium Carbonate) and 5 mL/L of a Magnesium Chloride solution (81.1 g/L $MgCl_2 \cdot 6H_2O$). The resulting solution was autoclaved to sterilize, and pH adjusted to 7.2.

CNB1 shake flask media was composed of urea (2.3 g/L), magnesium sulfate heptahydrate (0.5 g/L), potassium phosphate monobasic (3.0 g/L), trace element solution (1 mL/L) and vitamin solution (1 mL/L), glucose (120.0 g/L), 2-(N-Morpholino)ethanesulfonic acid (MES) (97.6 g/L). After dissolving all medium components, the pH of the medium was adjusted to an initial pH of 5.8 using an appropriate base (e.g, KOH).

TABLE 0

Primers sequences

| Identifier | SEQ ID NO: | Sequence (5'-3') |
| --- | --- | --- |
| 0611166 | 152 | TAAAACGACGGCCAGTGAATTCCGCGGCGGCCGCGAGTCCATCGGTTCCTGTCA |
| 0611167 | 153 | CATAAGAAAATCAAAGACAGAAGGCGCGCCTTTGCTAGCATTTTTGTGTTTTGCTGTGT |
| 0611168 | 154 | ACACAGCAAAACACAAAAATGCTAGCAAAGGCGCGCCTTCTGTCTTTGATTTTCTTATG |
| 0611169 | 155 | GGGGGAAAGAACTACCAATAGGCCTCCTTTAATTCGGAGAAAATC |
| 0611170 | 156 | GATTTTCTCCGAATTAAAGGAGGCCTATTGGTAGTTCTTTCCCCC |
| 0611171 | 157 | AAAATAAACTAGTAAAATAAATTAATTAATTATCTAGAGAGGGGGTTATAT |
| 0611172 | 158 | ATATAACCCCTCTCTAGATAATTAATTAATTTATTTTACTAGTTTATTTT |
| 0611173 | 159 | GACCATGATTACGCCAAGCTCCGCGGCGGCCGCCCAGTCAAAACCTTCTTCTC |
| 0611174 | 160 | TAAAACGACGGCCAGTGAATTCCGCGGCGGCCGCCTTTGAAGGAGCTTGCCA |
| 0611175 | 161 | CTATTCCTTCCTCAAATTGCTGTTTAAACGCGTTGAAGATCTATTCTCC |
| 0611176 | 162 | GGAGAATAGATCTTCAACGCGTTTAAACAGCAATTTGAGGAAGGAATAG |
| 0611177 | 163 | AATGTTCATTTTACATTCAGATGTTAATTAAGGTCTAGATGTGTTTGTTTG TGTG |
| 0611178 | 164 | CACACAAACAAACACATCTAGACCTTAATTAACATCTGAATGTAAAATGAACATT |
| 0611179 | 165 | GACCATGATTACGCCAAGCTCCGCGGCGGCCGCAATGCCAAGAGTTATGGGGC |
| 0611184 | 166 | GGCTACCCTATATATGGTGAGCG |
| 0611185 | 167 | GGGTCCAAGTTATCCAAGCAG |
| 0611186 | 168 | CCTTAATTAACCGTAAAGTTGTCTCAATG |
| 0611189 | 169 | CAGCAAAACACAAAAATTCTAGAAAATTTAATTAACATCTGAATGTAAAATGAAC |
| 0611191 | 346 | CCTTAATTAATTATCCACGGAAGATATGATG |
| 0611195 | 170 | GTTCATTTTACATTCAGATGTTAATTAAATTTTCTAGAATTTTTGTGTTTTGCTG |
| 0611196 | 171 | GCTCTAGATAAAATGCCCTCTTATTCTGTCGC |
| 0611199 | 347 | GCTCTAGATAAAATGTCCCAAGGTAGAAAAGC |

TABLE 0-continued

Primers sequences

| Identifier | SEQ ID NO: | Sequence (5'-3') |
|---|---|---|
| 0611225 | 172 | GACTGGATCATTATGACTCC |
| 0611245 | 272 | CGAACCAATTCAAGAAAACCAAC |
| 0611250 | 173 | ACGCCTTGCCAAATGCGGCCGCGAGTCCATCGGTTCCTGTCAGA |
| 0611251 | 174 | TCAAAGACAGAATTAATTAAGCTCTAGAATTTTTGTGTTTTGCTGTGTT |
| 0611252 | 175 | AACACAAAAATTCTAGAGCTTAATTAATTCTGTCTTTGATTTTCTTATG |
| 0611253 | 176 | GTTTAAACCTTTAATTCGGAGAAAATCTGATC |
| 0611254 | 177 | GTTAACGGTACCGAGCTCTAAGTAGTGGTG |
| 0611255 | 178 | AACCGATGGACTCGCGGCCGCATTTGGCAAGGCGTATCTAT |
| 0611256 | 179 | GGCGCCAGCAATTTGAGGAAGGAATAGGAG |
| 0611257 | 180 | AAACTATTAGATTAATTAAGCTCGCGATGTGTTTGTTTGTGTGTTTTGTGTG |
| 0611258 | 181 | CAAACAAACACATCGCGAGCTTAATTAATCTAATAGTTTAATCACAGCTTAT |
| 0611259 | 182 | TACATTATGGTAGCGGCCGCGTGTGACATTTTGATCCACTCG |
| 0611260 | 183 | TGGATCAAAATGTCACACGCGGCCGCTACCATAATGTATGCGTTGAG |
| 0611261 | 184 | GGGCCCTAAAAGTGTTGGTGTATTAGA |
| 0611263 | 185 | GCTAGCTCAACAAACTCTTTATCAGATTTAGCA |
| 0611264 | 186 | GCTAGCGAGGAAAAGAAGTCTAACCTTTGT |
| 0611266 | 187 | TCGCGATAAAATGTCAACTGTGGAAGATCACTCCT |
| 0611267 | 188 | TTAATTAAGCTGCTGGCGCTTCATCTT |
| 0611268 | 189 | TCGCGATAAAATGTCCAGAGGCTTCTTTACTG |
| 0611269 | 190 | TTAATTAACTAAAGGTCTCTCACGACAGAG |
| 0611283 | 191 | GTTAACCCGGTTTAAACATAGCCTCATGAAATCAGCCATT |
| 0611284 | 192 | GGGCCCATATGGCGCCCGGGGCGTTGAAGATCTATTCTCCAGCA |
| 0611295 | 193 | GTTTAAACGATTGGTAGTTCTTTCCCCCTC |
| 0611296 | 194 | AATAAATTAAGGGCCCTTTATCGCGAGAGGGGGTTATATGTGTAAA |
| 0611297 | 195 | TATAACCCCCTCTCGCGATAAAGGGCCCTTAATTTATTTTACTAGTTTAT |
| 0611298 | 196 | GTTTAAACTTTTGTAGCACCTCCTGGT |
| 0611376 | 197 | CAGCAAAACACAAAAAGCTAGCTAAAATGTTACGTACCATGTTCAAAA |
| 0611377 | 198 | GAAAATCAAAGACAGAAGGCGCGCCTTATGCTGTAACAGCCTGCGG |
| 0611378 | 199 | CAGCAAAACACAAAAAGCTAGCTAAAATGTTAAGAACCATGTTCAAATC |
| 0611379 | 200 | GAAAATCAAAGACAGAAGGCGCGCCTTATGCAGTAACAGCTTGTGGG |
| 0611552 | 273 | TCTGTCCCTTGGCGACGC |
| 0611553 | 274 | CTTTTCAAACAGATAAGTACC |
| 0611554 | 201 | GCATGGTGGTGCAAGCGACG |
| 0611555 | 202 | GGTGCTGCATTTGCTGCTG |
| 0611622 | 275 | ATGGGCTGACCTGAAAATTC |
| 0611631 | 203 | TGTATACAGGATCGAAGAATAGAAG |

TABLE 0-continued

Primers sequences

| Identifier | SEQ ID NO: | Sequence (5'-3') |
|---|---|---|
| 0611632 | 204 | GAACGTCTACAACGAGGTGAAC |
| 0611661 | 205 | GGCGCGCCTCGCGATAAAATG |
| 0611662 | 206 | AGGGCCCTTAATTAATTATGCAGTAACAGCTT |
| 0611717 | 207 | CGCTACGATACGCTACGATA |
| 0611718 | 208 | CTCCCTTCCCTGATAGAAGG |
| 0611814 | 209 | GGGGAGCAATTTGCCACCAGG |
| 0611815 | 210 | CTCCTTCATTTAACTATACCAGACG |
| 0611816 | 211 | GACAGATGTAAGGACCAATAGTGTCC |
| 0611817 | 212 | CCATATCGAAATCTAGCCCGTCC |
| 0611828 | 213 | CATAAGAAAATCAAAGACAGAAGGCGCGCCTTTGCTAGCTTTTTGTGTTTTGCTGTGT |
| 0611954 | 348 | GCTAGCTAAAATGTTTGGTAATATTTCCCA |
| 0611957 | 349 | TTAATTAACTATTTATCTAATGATCCTC |
| 0611997 | 350 | TCTAGATAAAATGTCTATTAGTGAAAAATATTTTCCTCAAG |
| 0611998 | 351 | TTAATTAACTTTTAAATTTTGGAAAAAGCTTGATCAATAATGG |
| 0612055 | 214 | ATTGGACACAACATTATAT |
| 0612150 | 238 | ACGCGTCGACTCGACATTTGCTGCAACGGC |
| 0612151 | 239 | CTAGTCTAGATGTTGTTGTTGTTGTCGTT |
| 0612271 | 215 | GTAAAACGACGGCCAGTGAATTGTTAACATAGGCTCCAACATCTCG |
| 0612272 | 216 | GGAACCGATGGACTCGCGGCCGCGTGGGATATTGGAAG |
| 0612273 | 217 | GGAGGTGCTACAAAAGGAATTC |
| 0612274 | 218 | GACCATGATTACGCCAAGCTCCGCGGAGTCAAAACCTTCTTCTCTACC |
| 0612275 | 219 | GTAAAACGACGGCCAGTGAATTCTTTGAAGGAGCTTGCCAAGAAAC |
| 0612276 | 220 | CCTATTCCTTCCTCAAATTGCTG |
| 0612277 | 221 | ATAACTCTTGGCATTGCGGCCGCCAAGTTAGTTAGAGC |
| 0612278 | 222 | ATGACCATGATTACGCCAAGCTCCGCGGCAAAGACGGTGTATTAGTGCTTG |
| 0612356 | 223 | CACAAAACACACAAACAAACACAGCTAGCAAAGGCGCGCCATCTAATAGTTTAATCACAGCTTA |
| 0612357 | 224 | GCCGTTGCAGCAAATGTCGAGGCCTGTGTGACATTTTGATCCACTCG |
| 0612358 | 225 | CGAGTGGATCAAAATGTCACACAGGCCTCGACATTTGCTGCAACGGC |
| 0612359 | 226 | CATTTTACATTCAGATGTTAATTAATTATCTAGATGTTGTTGTTGTTGTCG |
| 0612360 | 227 | CGACAACAACAACAACATCTAGATAATTAATTAACATCTGAATGTAAAATG |
| 0612361 | 228 | GCTCTAACTAACTTGGCGGCCGCTTTTATTATAAAATTATATATTATTCTT |
| 0612366 | 276 | GCTGAAAATATCATTCAGAGCAT |
| 0612367 | 277 | ACTGTTGATGTCGATGCC |
| 0612378 | 229 | AACACACAAACAAACACAGCTAGCTAAAATGTTAAGAACTATGTTTA |
| 0612379 | 230 | GATTAAACTATTAGATGGCGCGCCTTATGCAGTAACTGCTTGTGGA |

TABLE 0-continued

Primers sequences

| Identifier | SEQ ID NO: | Sequence (5'-3') |
|---|---|---|
| 0612470 | 231 | CGACGGCCAGTGAATTCGTTAACCCGTTTCGATGGGATTCCC |
| 0612471 | 232 | CAGGAACCGATGGACTCGCGGCCGCTCCCTTCTCTAAATGGACTGC |
| 0612472 | 233 | TATATAATTTTATAATAAAAGCGGCCGCACCAGGGGTTTAGTGAAGTC |
| 0612473 | 234 | CATGATTACGCCAAGCTCCGCGGCCATAACTGACATTTATGGTAAGG |
| 0612579 | 278 | TCTGAATGCAGTACGAGTTG |
| 0612695 | 240 | CAAAACACAGCAAAACACAAAAAGCTAGCATGTATAGAACCTTGATGAG |
| 0612698 | 242 | CAAAACACACAAACAAACACAGCTAGCATGTACAGAACGTTAATGTCTGC |
| 0612724 | 241 | CAAAGACAGAAGGCGCGCCTTATAAGATGGTTCTCGCTGG |
| 0612725 | 243 | GTGATTAAACTATTAGATGGCGCGCCTTACAGGATGGTTCTGGCAGG |
| 0612794 | 279 | GAAGGGGGTCCAAGTTATCC |
| 0612795 | 235 | CCAACAATCTTAATTGGTGAC |
| 0612891 | 236 | GGCTGTTACCGCCTAATTAA |
| 0612893 | 237 | GTTCTTAACATTTTAGCTAGCTG |
| 0612908 | 280 | GATATGGGCGGTAGAGAAGA |
| 0612909 | 281 | GCTCCTTCAAAGGCAACACA |
| 0612910 | 282 | TGAACTATCACATGAACGTA |
| 0612911 | 283 | TCAAGGTAGGGTCACTTAAC |
| 0613034 | 284 | TGATTCCTTCAATCACAGGT |
| 0613035 | 285 | AACCGACCTATCGAATGCCT |
| 0613178 | 286 | ACCATGATTACGCCAAGCTTGGTACCTTGGGGTTTACGCTTACAGCGTACT |
| 0613179 | 287 | TCAACGCCCCGGGGGATCTGGATCCGCGGCCGCAAGAAATTCCTTTCTTTTCCCCTTTATA |
| 0613180 | 288 | AACCGATGGACTCCTCGAGGGATCCGCGGCCGCGCATAACAAAATTGTGCCTAACCCA |
| 0613181 | 289 | ACGACTCACTATAGGGCGAATTGGGCCCCGGGAAAAGGAGAGAGAAAGGAGA |
| 0613183 | 290 | TATGACCATGATTACGCCAAGCTTGGTACCTCCTACAGAAGTAGCACCAGCACCA |
| 0613184 | 291 | GGAACCGATGGACTCCTCGAGGGATCCGCGGCCGCAGACTACCGTGTAAATAAGAGTACC |
| 0613185 | 292 | TCTTCAACGCCCCGGGGGATCTGGATCCGCGGCCGCATTTGATATAAACGCTTCTATAATA |
| 0613186 | 293 | GTAATACGACTCACTATAGGGCGAATTGGGCCCAACATCTGCTGCTGTAATATATTCA |
| 0613241 | 294 | GCATGTCTGTTAACTCTCAAACCAT |
| 0613242 | 295 | TCCATAATCCAATAGATCATCCC |
| 0613243 | 296 | AACACAATGGAACCAACCTAGT |
| 0613416 | 297 | ATTTACACGGTAGTCTGCGGCCGCCATAGCCTCATGAAATCAGCC |
| 0613417 | 298 | CTCTAGGTTCACTGGTTGTTTCTTGGGCTGCCTCCTTCAA |
| 0613418 | 299 | TTGAAGGAGGCAGCCCAAGAAACAACCAGTGAACCTAGAG |

TABLE 0-continued

Primers sequences

| Identifier | SEQ ID NO: | Sequence (5'-3') |
|---|---|---|
| 0613419 | 300 | TATTATAGAAGCGTTTATATCAAATGCGGCCGCGGATCCAGATCCCCCGGGGCGTT |
| 0613550 | 301 | AATGATCAACTTGAGAGGTA |
| 0613551 | 302 | CAGGTCTGTTACATAAAGCA |
| 0613688 | 303 | GTTTACGCTCAAATCTCCTCC |
| 0613689 | 304 | GGTACATGAAGCAGGCTTTGAAGG |
| 0613695 | 305 | GATTGTGTCCGTCAGCCTTTGCTC |
| 0613746 | 306 | TACCATATTTTCAGAGGATCA |
| 0613747 | 307 | AGGATGTTCTTGCCTGCAAGT |
| 0614233 | 308 | GATGATATAGTTGATGCTTTCCAAAG |
| 0614626 | 344 | AGGGTACCTTAGTACGAAGG |
| 0614627 | 345 | CTATTCTTACGATGAAGGCG |
| CM647 | 262 | AATGATCCATGGTCCGAGAG |
| oACN48 | 309 | GGGCCCCTTCATTTACGAAATAAAGTGCCGCGG |
| oACN49 | 310 | GCGGCCGCAAATAAATTTAAAATAAACGATATCAAAATTC |
| oACN50 | 311 | CGACGCCAAAGAAGGGCTCAGCCGAAAAAG |
| oACN51 | 312 | CCATTTCTTTTTCGGCTGAGCCCTTCTTTGGC |
| oACN52 | 313 | GCGGCCGCAATAACCTCAGGGAGAACTTTGGC |
| oACN53 | 314 | GAGCTCCCAAACAAGGTCTCAGTAGGATCG |
| oACN54 | 315 | CGCCATAAGGAGAGGCTGTAGATTTGTC |
| oACN55 | 316 | CCAGGACATCTTGCTTGCAATGTCG |
| oANN1 | 317 | GTTCCATCGGGCCCCTAAAGGTCTCTCACGACAG |
| oANN2 | 318 | CAAACACATCGCGATAAAATGTCCAGAGGCTTC |
| oANN5 | 319 | GCAAGACCTTGGATCTGAAGGG |
| oANN6 | 320 | CGAACCAATTCAAGAAAACCAACAG |
| oANN7 | 321 | GGGCCCGTCCCTTGGCGACGCCCTGATC |
| oANN8 | 322 | GCGGCCGCTATTTTTGTGTTTTGCTGTGTTTTG |
| oANN9 | 323 | GCGGCCGCCATCTGAATGTAAAATGAACATTAAAATG |
| oANN10 | 324 | GAGCTCCCCCAGTTGTTGTTGCAATTAAC |
| oANN11 | 325 | GAAGAGACGTACAAGATCCGCC |
| oANN12 | 326 | TAGGAATGGTGCATCATCCAAC |
| oANN13 | 327 | TTCTTATCTGAAAACTCCGAGTTCGCAAAGAAGGTTGAAG |
| oANN14 | 328 | TTATTGAAATTAATCCAAGGATTCAAGTTGAACATACAATTACTG |
| oANN15 | 329 | TTTCCAAAAAAGTTCGTGAGTTCGATGGTTGTATGATTATGG |
| oANN16 | 330 | CCTCTACCACCACCACCAAATG |
| oANN20 | 331 | GGGAAGAAACTAAGAAGAAGTATG |
| oCA405 | 260 | GCAACTGATGTTCACGAATGCG |
| oCA406 | 261 | TTGCCGTTGCAGCAAATCTC |

TABLE 0-continued

Primers sequences

| Identifier | SEQ ID NO: | Sequence (5'-3') |
|---|---|---|
| oHJ1 | 332 | CAATCCTTCTAGAGAGGGGGTTATATGTGTAAATATAGAGTTTG |
| oHJ2 | 333 | TTCTACCCTCGAGATTGGTTCTTTCCCCCTCTCAAG |
| oHJJ116 | 334 | GTGGTCAATCTAGAAAATATGACTGACAAAATCTCCCTAGGTAC |
| oHJJ117 | 335 | CAATTTTGGAGCTGATTCCAAATCGTAAAC |
| oJLJ28 | 264 | GCACCAAGAGCAGTTTTCCCATCTATTG |
| oJLJ29 | 265 | CCATATAGTTCTTTTCTAACATCAACATCACACTTC |
| oJLJ30 | 266 | GGAGAATAGATCTTCAACGCTTTAATAAAGTAGTTTG |
| oJLJ31 | 267 | CGTGTTGCGCAATAAAACCAATGAC |
| oJLJ43 | 336 | CAAGAGTATCCCATCTGACAGGAACCGATGG |
| oJLJ44 | 337 | GCTGGAGAATAGATCTTCAACGCCCCG |
| oJLJ45 | 338 | CGGAGAAGGCGTATAAAAAGGACACGGAG |
| oJLJ46 | 339 | GGATAAAAGTATTACATACGTACAGGATTGTGTATTAGTGTATTTCG |
| oJLJ57 | 340 | CCTCCAGTGTTTTCTCTCTGTCTCTTTGTTTTTTTTTC |
| oJY11 | 268 | CCTCGAAGAGCTTGAATTTG |
| oJY12 | 269 | GTAGTGAATGTCCGGATAAG |
| oJY13 | 270 | GCAAGGTCATGAGGTTAAAG |
| oJY14 | 271 | AACACTTATGGCGTCTCCTC |
| oJY44 | 341 | GGTTAATTAATTTATTTGTACATAAAAACCACATAAATGTAAAAGC |
| oJY45 | 342 | GAATTCCTTTAATTCGGAGAAAATCTGATCAAGAG |
| WG26 | 263 | ACGGCAGTATACCCTATCAGG |

Miscellaneous Sequences

Promoters: The PDC, TDH3, ENO1, and PGK1 promoters described in the Examples were derived from the *I. orientalis* sequences of SEQ ID NOs: 244, 245, 246, and 247, respectively. Terminators: The TAL, TKL, RKI, and PDC terminators described in the Examples were derived from the *I. orientalis* sequences of SEQ ID NOs: 248, 249, 250, and 251, respectively. The URA3 promoter, ORF, and terminator described in the Examples were derived from the *I. orientalis* sequence of SEQ ID NO: 252.

Example 1A: Selection of Host Yeast Cells Based on 3-HP Tolerance

A set of wild-type yeast strains were tested for their ability to grow in the presence of 3-HP.

The range of 3-HP concentrations to utilize in primary screening procedures was determined by evaluating the ability of seven wild-type yeast strains (Table 1, set A) to grow on media containing varying levels of 3-HP. 3-HP used in these experiments was chemically synthesized from an aqueous acrylic acid solution (30%) and a $CO_2$ catalyst at 200 psi and 175° C. as described in WO04/076398. Residual acrylic acid was removed using a countercurrent extraction with isopropyl ether at room temperature (see WO05/021470).

Cells were streaked onto YPD plates and grown overnight. A cell slurry with an $OD_{600}$ of around 4 was made in YPD media, pH 3.0, and this slurry was used to inoculate microtiter wells containing various concentrations of 3-HP (pH 3.9) to an $OD_{600}$ of 0.05. Plates were covered with a gas permeable membrane and incubated in a 30° C./300 RPM shaker overnight. Optical densities for each well were measured at a wavelength of 600 nm in a GENios model plate reader (Tecan), and plates were observed visually for growth. The highest 3-HP concentration that one or more of the strains grew in (125 g/L) was chosen as the upper range for primary screening procedure.

Primary Screening

For the primary screening procedure, 89 wild-type yeast strains were screened for growth on microtiter plates at 0 g/L, 75 g/L, 100 g/L, or 125 g/L 3-HP (pH 3.9) using the same protocol used for range finding. A fresh YPD plate was used for each strain, and a slurry with an $OD_{600}$ of around 4 was made in YPD media, pH 3.0. The slurry was used to inoculate each well to an $OD_{600}$ of 0.05. Plates were covered with a gas permeable membrane, and incubated in a 30° C./300 RPM shaker overnight. Optical densities for each well were measured at a wavelength of 600 nm in a GENios model plate reader, and plates were observed visually for growth. A similar protocol was run to evaluate growth at lactic acid concentrations of 0 g/L, 30 g/L, 45 g/L, and 60 g/L. Table 1 summarizes the highest concentration of 3-HP or lactic acid at which growth was observed.

Fifteen strains were identified that were capable of growing at 100 g/L 3-HP or grew well at 75 g/L 3-HP (Table 1, set B). To further narrow the strains, a second microtiter plate test was conducted. This test was similar to the first, but utilized 3-HP concentrations of 100 g/L, 112.5 g/L, and 125 g/L (pH 3.9). From this test, eleven strains were identified (Table 1, set C) that grew well at 75 g/L 3-HP or showed some growth at both 75 and 112.5 g/L 3-HP. These eleven strains were advanced to the secondary screening. Four strains that had poor growth at 75 g/L 3-HP and no growth at 112.5 g/L 3-HP were not advanced to the secondary screening. It is expected that strains not advancing to the secondary screen would exhibit economically inferior performance in a commercial fermentation process. However, it is possible that one or more such strains could nonetheless meet the minimum requirements for a commercially viable fermentation process.

TABLE 1

Growth in 3-HP or lactic acid

| Yeast strain | Culture collection # | Set | Primary screen: 3-HP (g/L) | Primary screen: lactic acid (g/L) |
|---|---|---|---|---|
| *Bulleromyces albus* | ATCC 96272 | | No growth at 0 g/L (NG) | NG |
| *Candida blankii* | ATCC 18735 | | 0 | 30 |
| *Candida boidinii* | PYCC 70-104 | | 0 | 30 |
| *Candida catenulata* | ATCC 20117 | | 0 | NG |
| *Candida etchellsii* | PYCC 60-8 | | 0 | 30 |
| *Candida famata* | ATCC 20284 | | 0 | 0 |
| *Candida fluviatilis* | ATCC 38623 | | 0 | 0 |
| *Candida geochares* | Cargill 1978 | | 75 | 60 |
| *Candida guilliermondii* | ATCC 20118 | | 0 | 0 |
| *Candida intermedia* | ATCC 20178 | | 0 | 0 |
| *Candida kefyr* | ATCC 44691 | | 75 | 30 |
| *Candida lactiscondensi* | ATCC 96927 | | 0 | NG |
| *Candida lambica* | ATCC 38617 | B, C | 75 | 45 |
| *Candida methanosorbosa* | ATCC 20361 | | 0 | NG |
| *Candida milleri* | ATCC 60591 | | 0 | 30 |
| *Candida milleri* | ATCC 60592 | | 0 | 45 |
| *Candida naeodendra* | ATCC 56465 | | 0 | NG |
| *Candida parapsilosis* | ATCC 20179 | | 0 | 0 |
| *Candida pignaliae* | ATCC 36592 | | 0 | NG |
| *Candida pseudolambica* | ATCC 96309 | | 0 | 0 |
| *Candida rugosa* | ATCC 20306 | | 0 | 45 |
| *Candida shehatae* | NCYC 2389 | | 0 | 0 |
| *Candida sonorensis* | ATCC 32109 | A | 0 | 30 |
| *Candida sorbophila* | Cargill 1973 | | 75 | 45 |
| *Candida sorboxylosa* | ATCC 24120 | | 0 | 30 |
| *Candida sorosivorans* | ATCC 38619 | B | 100 | 60 |
| *Candida tenuis* | MUCL 47216 or MUCL 31253B | | 0 | NG |
| *Candida valida* | ATCC 28525 | B | 75 | 45 |
| *Candida vanderwaltii* | MUCL 300000 | | 0 | 45 |
| *Candida zemplinina* | PYCC 04-501 | A, B, C | 100 | 60 |
| *Candida zeylanoides* | ATCC 20347 | | 75 | 45 |
| *Citeromyces matritensis* | ATCC 34087 | | 0 | NG |
| *Debaryomyces castellii* | PYCC 70-1022 | | 0 | 30 |
| *Debaryomyces hansenii* | ATCC 90624 | | 0 | NG |
| *Debaryomyces polymorphus* | ATCC 20280 | | 0 | 0 |
| *Dekkera anomala* | ATCC 20277 | | 0 | 0 |
| *Dekkera lambica* | ATCC 10563 | | 0 | 0 |
| *Hyphopichia burtonii* | ATCC 20030 | | 0 | 0 |
| *Issatchenkia orientalis* | ATCC 24210 | B, C | 100 | 45 |
| *Issatchenkia orientalis* | ATCC 60585 | B, C | 100 | 45 |
| *Issatchenkia orientalis* | ATCC PTA-6658 | A, B, C | 100 | 60 |
| *Issatchenkia orientalis* | CD1822 (Cargill collection - see description below) | A, B, C | 100 | 60 |
| *Kluyveromyces lactis* | ATCC 8585 | A | 0 | 0 |
| *Kluyveromyces marxianus* | ATCC 52486 | A | 75 | 45 |
| *Kluyveromyces thermotolerans* | ATCC 52709 | | 0 | 30 |
| *Kodamaea ohmeri* | ATCC 20282 | | 0 | 45 |
| *Kluyveromyces yarrowii* | ATCC 36591 | | NG | NG |
| *Lipomyces starkeyi* | ATCC 12659 | | 0 | 0 |
| *Lipomyces tetrasporus* | ATCC 56306 | | NG | NG |
| *Metschnikowia pulcherrima* | ATCC 9889 | | 0 | 0 |
| *Myxozyma kluyveri* | ATCC 76214 | | NG | NG |
| *Nematospora coryli* | ATCC 20292 | | 0 | NG |
| *Pachysolen tannophilus* | NCYC 614 | | 0 | 30 |

TABLE 1-continued

Growth in 3-HP or lactic acid

| Yeast strain | Culture collection # | Set | Primary screen: 3-HP (g/L) | Primary screen: lactic acid (g/L) |
|---|---|---|---|---|
| Pichia anomala | ATCC 2102 | | 0 | 0 |
| Pichia fermentans | ATCC 28526 | | 0 | 30 |
| Pichia fluxuum | ATCC 28778 | | NG | NG |
| Pichia jadinii | ATCC 9950 | | 0 | 0 |
| Pichia membranifaciens | NCYC 2696 | B, C | 125 | 60 |
| Pichia nakasei | ATCC 24116 | | 0 | 0 |
| Pichia silvicola | ATCC 16768 | | 0 | 0 |
| Pichia stipitis | CBS 6054 | | 0 | 0 |
| Pichia strasburgensis | ATCC 34024 | | 0 | 0 |
| Pichia tannicola | ATCC 2261 | | 0 | 0 |
| Pichia toletana | ATCC 58362 | | NG | NG |
| Saccharomyces cerevisiae | ATCC 96784 | | 75 | 30 |
| Saccharomyces bayanus | ATCC 90739 | | 0 | 45 |
| Saccharomyces bulderi | MYA-402 | B, C | 100 | 60 |
| Saccharomyces bulderi | MYA-404 | B, C | 100 | 45 |
| Saccharomyces capsularis | ATCC 20033 | | 0 | 0 |
| Saccharomyces cerevisiae | CEN-PK 113-7D | A, B | 100 | 45 |
| Saccharomyces ludwigii | NCYC 734 | | 75 | 45 |
| Saccharomycopsis crataegensis | MUCL 44417 | | 0 | 0 |
| Saccharomycopsis javensis | MUCL 31237 | | 0 | 45 |
| Saccharomycopsis vini | NRRL Y-7290 | | 0 | 0 |
| Saccharomyces uvarum | ATCC 76514 | | 0 | 0 |
| Schizosaccharomyces japonicus | ATCC 10660 | | 0 | 0 |
| Schizosaccharomyces pombe | NCYC 535 | B, C | 100 | 60 |
| Torulaspora delbrueckii | ATCC 52714 | | 75 | 0 |
| Torulaspora pretoriensis | ATCC 42479 | B | 75 | 0 |
| Wickerhamiella occidentalis | CBS 8452 | | 0 | 30 |
| Yamadazyma guilliermondii | ATCC 90197 | | 0 | 0 |
| Yamadazyma haplophila | ATCC 20321 | | 0 | 0 |
| Yamadazyma stipitis | ATCC 201225 | | 0 | 0 |
| Yarrowia lipolytica | ATCC 46330 | | 0 | 45 |
| Zygosaccharomyces bailii | ATCC 36946 | | 75 | 45 |
| Zygosaccharomyces bisporus | NCYC 3134 | | 0 | 45 |
| Zygosaccharomyces kombuchaensis | NCYC2897 | | 0 | 60 |
| Zygosaccharomyces lentus | NCYC 2928 | B, C | 100 | 45 |
| Zygosaccharomyces rouxii | ATCC 34890 | | 75 | 30 |

*I. orientalis* strain CD1822 tested above was generated by evolving *I. orientalis* ATCC PTA-6658 for 91 days in a glucose limited chemostat. The system was fed with 15 g/L dextrose in a DM medium, and operated at a dilution rate of 0.06 h$^{-1}$ at pH=3 with added lactic acid in the feed medium. The conditions were maintained with a low oxygen transfer rate of approximately 2 mmol L$^{-1}$ h$^{-1}$, and dissolved oxygen concentration remained constant at 0% of air saturation. Single colony isolates from the final time point were characterized in two shake flask assays. In the first assay, the strains were characterized for their ability to ferment glucose to ethanol in the presence of 25 g/L total lactic acid with no pH adjustment in the DM1 defined medium. In the second assay, the growth rate of the isolates were measured in the presence of 25, 32 and 45 g/L of total lactic acid, with no pH adjustment in DM1 defined medium. Strain CD1822 was a single isolate selected based on the measured fermentation rates and growth rates. Other methods for evolving *I. orientalis* include, but are not limited to, repeated serial subculturing under the selective conditions as described in e.g., U.S. Pat. No. 7,629,162. Such methods can be used in place of, or in addition to, using the glucose limited chemostat method described above. As can be appreciated by one of skill in the art, strains could be generated using a similar evolution procedure in the presence of added 3-HP rather than lactic acid to develop improved 3-HP tolerance. Additionally, strains could be mutagenized prior to selection, as described herein (e.g., see Example 1B).

Secondary Screening

For the first part of the secondary screen, growth rates were measured at pH 3.9 in YPD media containing 0 g/L, 35 g/L, or 75 g/L 3-HP. Shake flasks were inoculated with biomass harvested from seed flasks grown overnight to an OD$_{600}$ of 6 to 10. 250 mL baffled growth rate flasks (50 mL working volume) were inoculated to an OD$_{600}$ of 0.1 and grown at 250 rpm and 30° C. Samples were taken throughout the time course of the assay and analyzed for biomass growth via $OD_{600}$. The resulting $OD_{600}$ data was plotted and growth rates were established.

TABLE 2

Growth rate (μ) in 3-HP

| Strain | 0 g/L 3-HP | 35 g/L 3-HP | 75 g/L 3-HP |
|---|---|---|---|
| Issatchenkia orientalis ATCC 60585 | 0.56 | 0.51 | 0.29 |
| Issatchenkia orientalis CD1822 | 0.62 | 0.52 | 0.28 |
| Candida lambica ATCC 38617 | 0.65 | 0.53 | 0.30 |
| Candida valida | 0.51 | 0.32 | 0.14 |
| Issatchenkia orientalis PTA-6658 | 0.61 | 0.53 | 0.32 |
| Issatchenkia orientalis 24210 | 0.58 | 0.51 | 0.26 |
| Saccharomyces bulderi MYA 402 | 0.53 | 0.45 | 0.28 |
| Pichia membranifaciens | 0.41 | 0.39 | 0.32 |
| Saccharomyces bulderi MYA 404 | 0.55 | 0.44 | 0.27 |
| Schizosaccharomyces pombe | 0.41 | 0.35 | 0.21 |
| Zygosaccharomyces lentus | 0.61 | 0.41 | 0.20 |

For the second part of the secondary screen, glucose consumption was measured for the same ten strains at pH 3.9 in YPD media containing 100 g/L glucose and 0 g/L, 35 g/L, or 75 g/L 3-HP. Shake flasks were inoculated with biomass harvested from seed flasks grown overnight to an $OD_{600}$ of 6 to 10. 250 mL baffled glycolytic assay flasks (50 mL working volume) were inoculated to an $OD_{600}$ of 0.1 and grown at 250 RPM and 30° C. Samples were taken throughout the time course of the assay and analyzed for glucose consumption using a 2700 Biochemistry Analyzer from Yellow Springs Instruments (YSI). The resulting data was plotted and glucose consumption rates were established.

TABLE 3

Glucose consumption rate (g/L/hr) in 3-HP

| Strain | 0 g/L 3-HP | 35 g/L 3-HP | 75 g/L 3-HP |
|---|---|---|---|
| Issatchenkia orientalis ATCC 60585 | 5.5 | 4.2 | 3.3 |
| Issatchenkia orientalis CD1822 | 5.5 | 4.2 | 4.2 |
| Candida lambica ATCC 38617 | 4.2 | 4.2 | 3.5 |
| Candida valida | 5.5 | 2.2 | 2.1 |
| Issatchenkia orientalis PTA-6658 | 5.5 | 4.2 | 4.1 |
| Issatchenkia orientalis 24210 | 4.2 | 4.2 | 3.8 |
| Saccharomyces bulderi MYA 402 | 4.2 | 4.2 | 4.0 |
| Pichia membranifaciens | 0.4 | 2.1 | 1.2 |
| Saccharomyces bulderi MYA 404 | 4.2 | 4.2 | 3.8 |
| Schizosaccharomyces pombe | 2.5 | 3.1 | 2.0 |
| Zygosaccharomyces lentus | 3.4 | 0.8 | 0.3 |

Four of the strains (*P. membranifaciens*, *S. pombe*, *C. valida*, and *Z. lentus*) did not achieve the 2.5 g/L/hr glucose utilization rate under the 75 g/L 3-HP (pH 3.9) conditions that would be required for an economic fermentation process.

To identify the leading strains in 3-HP, strain performance was graded in three categories. Two of these categories were based on different aspects of growth rate: 1) growth rate at highest acid concentration and 2) slope of the growth rates plotted against acid concentration. The third category was the glycolytic rate at the highest acid concentration. This grading was done on a normalized scale using the highest and lowest value for each rating as the normalized boundaries. Each strain thus received a grade between 0 and 1 for each category, with 1 being the highest possible score. The overall rating of a strain was the sum of the normalized value for the three categories. A weighted score was made in which the growth rate and glycolytic rate were equally weighted. In this case the glycolytic rate at the highest acid concentration was weighted at 50%, while the two growth rate ratings were weighted at 25% each. Normalized values per category and sum and weighted scores are summarized in Table 4.

TABLE 4

Strain grades in 3-HP

| Strain | Growth rate @ 75 g/L 3-HP | Growth rate slope | Glycolic rate | Sum Score | Weighted score |
|---|---|---|---|---|---|
| Issatchenkia orientalis ATCC PTA-6658 | 1.00 | 0.37 | 0.97 | 2.34 | 0.83 |
| Saccharomyces bulderi MYA 402 | 0.78 | 0.49 | 0.94 | 2.21 | 0.79 |
| Issatchenkia orientalis CD1822 | 0.78 | 0.21 | 1.00 | 1.99 | 0.75 |
| Saccharomyces bulderi MYA 404 | 0.72 | 0.42 | 0.90 | 2.04 | 0.74 |
| Issatchenkia orientalis ATCC 60585 | 0.83 | 0.44 | 0.77 | 2.04 | 0.70 |
| Issatchenkia orientalis 24210 | 0.67 | 0.28 | 0.90 | 1.85 | 0.69 |
| Candida lambica ATCC 38617 | 0.89 | 0.19 | 0.82 | 1.90 | 0.68 |
| Pichia membranifaciens | 1.00 | 1.00 | 0.23 | 2.23 | 0.62 |
| Schizosaccharomyces pombe | 0.39 | 0.65 | 0.47 | 1.51 | 0.50 |
| Candida valida | 0 | 0.14 | 0.40 | 0.54 | 0.24 |
| Zygosaccharomyces lentus | 0.33 | 0 | 0 | 0.33 | 0.08 |

Of the strains tested, strains from the species *I. orientalis, C. lambica*, and *S. bulderi* showed the greatest potential as production hosts for 3-HP at low pH.

The same procedures were utilized to screen, rate, and score the original 91 wild-type yeast strains from the primary screen with media containing 0, 25, and 50 g/L lactic acid at pH 2.85 (~80% free acid). Normalized values and weighted and summed scores were derived for 13 strains that were advanced to the secondary screen.

TABLE 5

Strain grades in lactic acid

| Strain | Growth rate @ 50 g/L lactic acid | Growth rate slope | Glycolic rate | Sum Score | Weighted score |
|---|---|---|---|---|---|
| *Candida lambica* ATCC 38617 | 0.92 | 1.00 | 1.00 | 2.92 | 0.98 |
| *Issatchenkia orientalis* ATCC PTA-6658 | 0.94 | 0.95 | 1.00 | 2.89 | 0.97 |
| *Issatchenkia orientalis* CD1822 | 1.00 | 0.86 | 1.00 | 2.86 | 0.97 |
| *Issatchenkia orientalis* 24210 | 0.89 | 0.73 | 1.00 | 2.62 | 0.91 |
| *Candida zemplinina* | 0.22 | 0.95 | 1.00 | 2.17 | 0.79 |
| *Saccharomyces bulderi* MYA 404 | 0.47 | 0.45 | 1.00 | 1.92 | 0.73 |
| *Saccharomyces bayanus* | 0.08 | 0.91 | 0.96 | 1.95 | 0.73 |
| *Saccharomyces bulderi* MYA 402 | 0.50 | 0.23 | 1.00 | 1.73 | 0.68 |
| *Candida milleri* | 0 | 0.64 | 0.92 | 1.56 | 0.62 |
| *Candida sorosivorans* | 0.28 | 0.95 | 0.59 | 1.82 | 0.60 |
| *Kodamaea ohmeri* | 0.42 | 0 | 0.76 | 1.18 | 0.49 |
| *Candida geochares* | 0.17 | 0.27 | 0.69 | 1.13 | 0.46 |
| *Saccharomyces javensis* | 0.11 | 0.68 | 0 | 0.79 | 0.20 |

For lactic acid only *S. javensis* did not achieve the 2.5 g/L/hr glucose utilization rate at pH 2.85 in media with 50 g/L lactic acid. While *I. orientalis, C. lambica*, and *S. bulderi* showed acid tolerance for both 3-HP and lactic acids, there were a number of strains that were tolerant for only one of the acids. This can also be seen in the results of the primary screen (Table 1). For example, *C. milleri, C. rugosa, C. vanderwaltii, K. ohmeri, S. bayanus, S. javensis, Y. lipolytica, Z. bisporus*, and *Z. kombuchaensis* all demonstrated growth at 45-60 g/L lactic acid but no growth at even the lowest concentration of 3-HP tested (35 g/L). Thus, the tolerance of a strain to one organic acid cannot definitively be used as a predictor of its tolerance for other acids. This is further highlighted by comparing the strains that showed 3-HP resistance above with the list of eight strains identified as preferred hosts for organic acid production in WO03/049525. While two of those strains (*C. diddensiae* and *C. entomophila*) could not be obtained for testing, the other six were included in the primary screen described above. Of these six, only *C. krusei* (tested as *I. orientalis*) was able to grow in the presence of 35 g/L 3-HP.

Example 1B: Mutagenesis and Selection of Mutant Strains Having Resistance to 3-HP Yeast cells selected in Example 1A are subjected to mutagenesis and exposed to selection pressure in order to identify mutants with high 3-HP tolerance.

For example, yeast cells from a fresh YP (yeast extract/peptone)+20 g/L glucose plate or liquid culture ($OD_{600}$ 1-4) are resuspended in sterile water to an $OD_{600}$ of around 10. 200 μL aliquots of this cell suspension are pipetted into individual tubes and exposed to 3 μL ethane methyl sulfonate (EMS) for approximately one hour, which kills around 65% of the cells. Higher EMS concentrations can also be used to increase the kill rate. After exposure, cells are neutralized with 5% sodium thiosulfate, washed in PBS buffer, recovered in rich media for approximately four hours, and cultured on selective media. Mock samples (no EMS) are also run to ensure that the conditions are selective. Alternatively, cells can be mutagenized using UV irradiation.

To select for 3-HP resistant mutant strains, aliquots of the EMS-treated cell suspension (approximately $2\times10^8$ of mutagenized cells) are plated onto a potato dextrose agar (PDA) or another media containing 3-HP at a level at which the parental strain does not grow or grows very slowly. These plates are incubated for several days until colonies appear. Single colonies are purified, streaked on non-selective media to eliminate any adaptive effects of the selection, and re-tested on selective media to confirm increased resistance. Resistant strains are then tested in a shake flask format with periodic sampling for HPLC analysis of products and substrates. Alternatively, selection for 3-HP tolerance may be done by chemostat or serial shake flask evolution. Additional rounds of mutagenesis and selection can be performed. Mutagenesis can be used to increase the resistance of a host that does not natively meet 3-HP production requirements so that it has the necessary attributes for commercial 3-HP production.

Example 2A: Procedure for Transformation of DNA into the Host Genome

DNA transformation into the yeast host genome to generate the modified yeast strains described in the following examples was conducted based on the specific procedure below.

Four mL of YP+10% glucose media was added to a 14 mL Falcon tube and the desired strain was inoculated into this media using a sterile loop. The culture was grown with shaking at 250 rpm overnight (~16 hr) at 37° C. 1 mL of the overnight culture was added to a 250 mL baffled flask containing 50 mL of liquid YP+10% glucose media. The flask was grown with shaking at 250 rpm at 37° C. Small aliquots of the culture were withdrawn at approximately hourly intervals and the $OD_{600}$ was measured. The culture was grown until the $OD_{600}$ was 0.6-1.0.

The cells were harvested by centrifugation at 2279×g at room temperature, the pellet was resuspended in 25 mL sterile water, then centrifuged at 2279×g at room temperature. The pellet was resuspended in 1 mL sterile water, and the resuspended cells were transferred to a 1.5 mL tube and then pelleted at 16,100×g. The cells were resuspended in 1 mL LiOAc/TE solution and then pelleted at 16,100×g. The cell pellet was then resuspended in 500 μL LiOAc/TE solution.

The following components were added to a 1.5 mL tube: 100 μL of the above cells, 10 μL freshly boiled then iced salmon sperm DNA (Agilent Technologies, Santa Clara, Calif., USA), and 10 μL of the desired, linearized transforming DNA. A control reaction with water instead of DNA was also prepared. To each transformation reaction, 600 μL of PEG/LiOAc/TE Solution was added and the reaction incubated on its side at 30° C. on a 250 rpm shaker platform for 30 minutes. 40 μL DMSO and was added to each reaction and then incubated in a 42° C. water bath for 5 minutes. Cells were pelleted at 5,400×g for 1 min. Cells were resuspended in water, split in two, and each half of the transformation reaction was plated to a ura selection media plate. Plates were placed at 37° C. Colonies were generally visible after 18 to 24 hr growth, depending on strain background.

A sterile loop was used to transfer a small amount of yeast from a petri dish to a 1.5 mL tube containing 300 μL Yeast Lysis Solution (EPICENTRE® Biotechnologies, Madison, Wis., USA) and the genomic DNA was extracted using the MasterPure™ Yeast DNA Purification Kit (EPICENTRE® Biotechnologies) according to the manufacturer's instructions.

Genomic DNA prepared using the MasterPure™ Yeast DNA Purification Kit (EPICENTRE® Biotechnologies) was used in PCR reactions to determine if the correct integration event had occurred in the isolated transformant. A PCR reaction (25 μL) contained 0.5 μL genomic DNA for the strain to be screened, 1× Crimson Taq™ Reaction Buffer (New England Biolabs, Ipswich, Mass., USA), 25 pmol each of the sense and anti-sense primers, 200 μM each of dATP, dCTP, dGTP, and dTTP, and 0.625 units of Crimson Taq™ DNA polymerase (New England Biolabs). The PCR was performed in an EPPENDORF® MASTERCYCLER® (Eppendorf Scientific, Westbury, N.Y., USA) programmed for one cycle at 95° C. for 30 seconds followed by 30 cycles each at 95° C. for 30 seconds, 50° C. for 30 seconds, and 68° C. for 1 minute per kbp of the largest expected product, with a final extension at 68° C. for 10 minutes. Following thermocycling, the PCR reaction products were separated by 1% agarose gel electrophoresis in TAE or TBE buffer and the sizes of the bands visualized and interpreted as for the specific primers sets as described.

Example 2B: Selection of Insertion Sites

Suitable insertion sites for incorporating exogenous genes into host yeast cells may be loci for genes that have beneficial or neutral effects on 3-HP production when deleted in the yeast host cell. Non-limiting examples of suitable insertion sites for selected yeast strains are described in the working examples herein. One skilled in the art can easily apply the teachings herein for use of these and other insertions sites, for example, loci for one or more PDC (e.g., *I. orientalis* PDC gene encoding the amino acid sequence set forth in SEQ ID NO: 49 and/or comprising the coding region of the nucleotide sequence set forth in SEQ ID NO: 48), ADH (e.g., *I. orientalis* ADH gene encoding the amino acid sequence set forth in SEQ ID NOs: 106, 108, or 110 and/or comprising the coding region of the nucleotide sequence set forth in SEQ ID NOs: 105, 107, or 109), GAL6 (e.g., *I. orientalis* GAL6 gene encoding the amino acid sequence set forth in SEQ ID NO: 112 and/or comprising the coding region of the nucleotide sequence set forth in SEQ ID NO: 111), CYB2A (e.g., *I. orientalis* CYB2A gene encoding the amino acid sequence set forth in SEQ ID NO: 114 and/or comprising the coding region of the nucleotide sequence set forth in SEQ ID NO: 113), CYB2B (e.g., *I. orientalis* CYB2B gene encoding the amino acid sequence set forth in SEQ ID NO: 116 and/or comprising the coding region of the nucleotide sequence set forth in SEQ ID NO: 115), GPD (e.g., *I. orientalis* GPD gene encoding the amino acid sequence set forth in SEQ ID NO: 118 and/or comprising the coding region of the nucleotide sequence set forth in SEQ ID NO: 117), ALD (e.g., *I. orientalis* ALD homolog gene 5680 encoding the amino acid sequence set forth in SEQ ID NO: 120 and/or comprising the coding region of the nucleotide sequence set forth in SEQ ID NO: 119, *I. orientalis* ALD homolog gene 42026 encoding the amino acid sequence set forth in SEQ ID NO: 122 and/or comprising the coding region of the nucleotide sequence set forth in SEQ ID NO: 121, *I. orientalis* ALD homolog gene 42426 encoding the amino acid sequence set forth in SEQ ID NO: 124 and/or comprising the coding region of the nucleotide sequence set forth in SEQ ID NO: 123, or *I. orientalis* ALD homolog gene 42727 encoding the amino acid sequence set forth in SEQ ID NO: 126 and/or comprising the coding region of the nucleotide sequence set forth in SEQ ID NO: 125), or PCK (e.g., *I. orientalis* PCK gene encoding the amino acid sequence set forth in SEQ ID NO: 128 and/or comprising the coding region of the nucleotide sequence set forth in SEQ ID NO: 127) genes or homologs thereof. Where sequences for these genes are unpublished, they can be obtained using standard procedure such as genome sequencing, probe hybridization of genomic or cDNA libraries, or amplification of gene fragments using degenerate primers based on known homolog sequence, followed by genome walking to obtain the full sequence. Other suitable locations for insertion sites include intergenic regions that do not contain open reading frames.

Example 2C: Techniques for Insertion Vectors, Selection Marker Cassettes, Gene Expression Cassettes, and Integration Constructs Insertion site vectors are generated for integrating one or more exogenous genes into host yeast cells. The host yeast cells may be cells that have undergone a selection process as described in Example 1, or they may be cells that have not undergone mutagenesis and/or selection.

To generate insertion site vectors, a region upstream (5') and a region downstream (3') of the desired insertion site are both amplified using host genomic DNA as template. The upstream region is preferably greater than 70 bp and less than 1.5 kbp. The resultant target sequences are ligated into a cloning vector either simultaneously or sequentially to obtain a vector with one copy of each fragment so that the fragments are contiguous or nearly contiguous. A unique restriction site may be incorporated between the fragments to allow for insertion of gene expression cassettes and/or selection marker cassettes. Unique restriction enzyme sites may also be incorporated at or near the 5' end of the upstream fragment and at or near the 3' end of the downstream fragment to allow for later removal of the DNA between these sites from the cloning vector.

Selection marker cassettes for incorporation into insertion site vectors are generated using standard cloning techniques. These selection marker cassettes contain a gene for a selectable marker, and may also contain an upstream promoter and/or a downstream terminator sequence. Examples of suitable selection marker genes include the URA3, TRP1, HIS, MEL5, CYB2A, LEU2, and G418 genes. Flanking sequences may be incorporated into the cassette on either side of the promoter/marker gene/terminator sequences to allow for future loss of the marker through recombination. These flanking sequences may include a direct or inverted repeated sequence (either functional or nonfunctional sequence) or one or more loxP sites.

Gene expression cassettes are generated using standard cloning techniques. These gene expression cassettes contain the gene to be over-expressed, and may also contain an upstream promoter and/or a downstream terminator sequence. In certain embodiments, two or more copies of these promoter/gene/terminator combinations may be incorporated into a single gene-expression cassette. Heterologous genes may be codon-optimized for improved expression in the host yeast strain. A selection marker cassette as described in herein can be cloned into the gene expression cassette such that it is contiguous or nearly contiguous with the gene to be over-expressed and any associated promoter and/or terminator.

Alternatively, for replacement of native promoters with an exogenous promoter, the expression cassette may have the selection cassette upstream of the promoter to be integrated, in between targeting sequences.

Gene expression cassettes can be inserted between the two target site sequences in the insertion site vectors described herein using standard cloning techniques to generate gene expression integration constructs. One or more selection marker cassettes may also be inserted between the target sequences, either as part of the gene expression cassette or separately. In certain variations, pieces of the gene expression cassette can be cloned into different insertion site vectors so that there is an over-lapping fragment in common between the integration fragments. For example, one vector might contain an upstream insertion fragment, a promoter, a gene, and a terminator and the second vector might contain the terminator, selection marker cassette, and downstream insertion fragment. In another example, to allow simultaneous insertion of two genes, one vector could contain the upstream insertion fragment, a promoter, a gene, terminator and all or part of a selection marker cassette, and the second vector might contain all or part of the selection marker cassette, a second promoter, gene, terminator, and the downstream insertion fragment.

To generate gene knockout constructs, the insertion site vectors are made using target DNA sequences derived from the upstream and downstream flanking regions of the gene to be deleted or disrupted. The selected target sequences may include upstream and downstream flanking regions of a target gene and/or all or a portion of the target gene coding sequence or its regulatory elements (e.g., promoter or terminator). One or more selection marker cassettes may be incorporated into the insertion site vector between the two target sequences. Where the knockout is to be coupled with expression of an exogenous gene, one or more gene expression cassettes are also incorporated into the insertion site vector.

DNA fragments to be integrated into a host yeast genome can be linearized by restriction enzyme digest of the fragment from a cloning vector, or of overlapping fragments from multiple vectors. Alternatively, linear integration fragments can be generated using PCR, or a combination of PCR and restriction enzyme digest. The insertion site flanking regions can be incorporated into the integration fragment either by their presence in the vector template or by incorporation into the amplification primers. In the latter case, a minimum of 70 nucleotides of a flanking region is preferably incorporated into a primer.

Non-limiting examples of suitable insertion vectors, selection marker cassettes, gene expression cassettes, and integration constructs for selected yeast strains are described in the following working examples. One skilled in the art can easily apply the teachings from these examples and the preceding specification to generate alternative modified yeast strains that produce 3-HP.

Example 2D: Construction of Insertion Vector for Expressing an Exogenous Gene at the Adh1202 Locus The plasmid pMIBa107 was created to allow integration of a single gene at the *I. orientalis* adh1202 locus under the control of the PDC promoter and terminator using URA3 as a selectable marker. The PDC promoter and terminator with the ura selectable marker were PCR amplified and cloned into pCR4™ 4BLUNT TOPO® (Invitrogen, La Jolla, Calif., USA) as described below. The PCR fragment containing the PDC promoter, terminator and URA3 selectable marker was constructed by SOE PCR. The PDC promoter was amplified with a primer that contains homology to the PDC terminator on the 3' end of the PCR product and the PDC terminator and URA3 selectable marker were amplified using a primer with homology to the PDC promoter on the 5' end of the product. These two fragments were then put together via SOE PCR.

Figure 19:
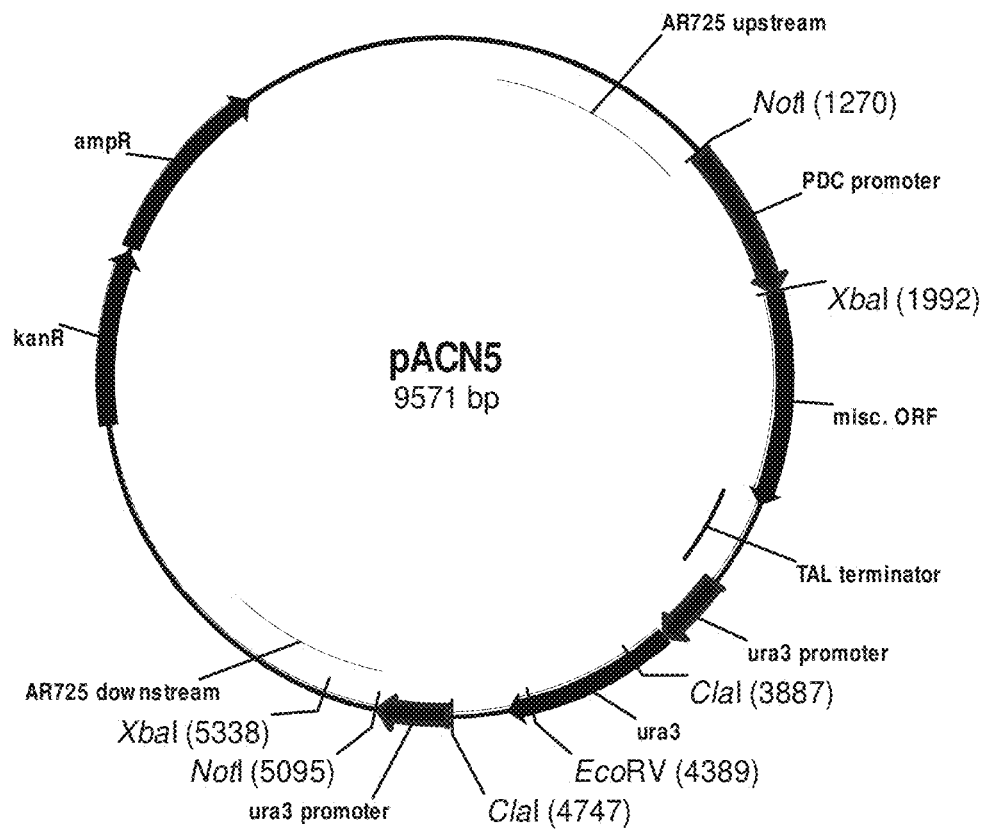
FIG. 19: Plasmid pACN5

The PDC promoter was amplified from pACN5 (FIG. 19) using primers 0611184 and 0611195. Primer 0611184 introduces a NotI restriction site to the 5' end of the PCR product. Primer 0611195 introduces an XbaI restriction site after the PDC promoter and introduces homology to the PDC terminator on the 3' end of the PCR product.

The amplification reactions were performed using Platinum® Pfx DNA polymerase (Invitrogen) according to manufacturer's instructions. Each PCR reaction contained 0.5 μL of diluted pACN5 (FIG. 19), 25 pM each of primers 0611184 and 0611195, 1× Pfx amplification buffer (Invitrogen), 2 mm MgSO$_4$, 0.2 mM dNTP mix, 1.25 Units Platinum® Pfx DNA polymerase (Invitrogen) in a final volume of 50 μL. The amplification reactions were incubated in an EPPENDORF® MASTERCYCLER® (Eppendorf Scientific) programmed for 1 cycle at 95° C. for 2 minutes; 30 cycles each at 95° C. for 30 seconds, 55° C. for 30 seconds, and 72° C. for 2 minutes; with a final extension at 72° C. for 3 minutes.

The PCR product was purified by 1% agarose gel electrophoresis using 89 mM Tris base-89 mM Boric Acid-2 mM disodium EDTA (TBE) buffer. A fragment of approximately 700 bp was excised from the gel and extracted from the agarose using a QIAQUICK® Gel Extraction Kit (Qiagen, Valencia, Calif., USA).

Figure 24:
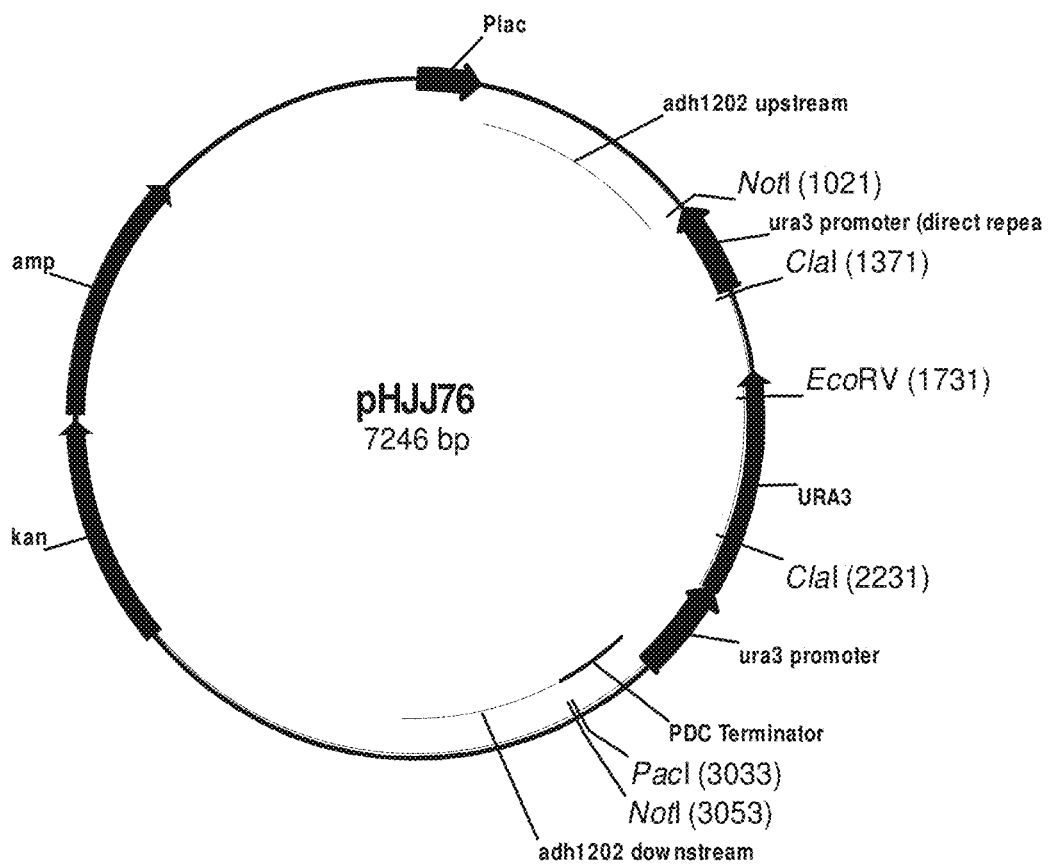
FIG. 24: Plasmid pHJJ76

The PDC terminator and URA3 selectable marker were amplified from pHJJ76 (FIG. 24) using primers 0611189 and 0611185. Primer 0611189 introduces homology to the PDC promoter on the 5' end of the PCR product and a PacI restriction site directly in front of the PDC terminator. Primer 0611185 introduces a NotI restriction site to the 3' end of the PCR product. The amplification reactions were performed using Platinum® Pfx DNA polymerase (Invitrogen) according to manufacturer's instructions. Each PCR reaction contained 0.5 µL of diluted pHJJ76, 25 pM each of primers 0611189 and 0611185, 1× Pfx amplification buffer (Invitrogen), 2 mm MgSO$_4$, 0.2 mM dNTP mix, 1.25 Units Platinum® Pfx DNA polymerase (Invitrogen) in a final volume of 50 µL. The amplification reactions were incubated in an EPPENDORF® MASTERCYCLER® (Eppendorf Scientific) programmed for 1 cycle at 95° C. for 2 minutes; 30 cycles each at 95° C. for 30 seconds, 55° C. for 30 seconds, and 72° C. for 2 minutes; with a final extension at 72° C. for 3 minutes.

The PCR product was purified by 1% agarose gel electrophoresis using 89 mM Tris base-89 mM Boric Acid-2 mM disodium EDTA (TBE) buffer. A fragment of approximately 2000 bp was excised from the gel and extracted from the agarose using a QIAQUICK® Gel Extraction Kit (Qiagen).

The 2000 bp PDC terminator and URA3 selectable marker PCR product and the 700 bp PDC promoter PCR product were fused using SOE-PCR. The amplification reactions were performed using Platinum® Pfx DNA polymerase (Invitrogen) according to manufacturer's instructions. Each PCR reaction contained 8 ng of 2000 bp PDC terminator and URA3 selectable marker PCR product, 24 ng of the 700 bp PDC promoter PCR product, 50 pM each of primers 0611184 and 0611185, 1× Pfx amplification buffer (Invitrogen), 2 mm MgSO$_4$, 0.2 mM dNTP mix, 2.5 Units Platinum® Pfx DNA polymerase (Invitrogen) in a final volume of 100 µL. The amplification reactions were incubated in an EPPENDORF® MASTERCYCLER® (Eppendorf Scientific) programmed for 1 cycle at 95° C. for 2 minutes; 30 cycles each at 95° C. for 30 seconds, 55° C. for 30 seconds, and 68° C. for 3 minutes; and 1 cycle at 68° C. for 3 minutes.

The 2700 bp PCR product was purified by 1% agarose gel electrophoresis using 89 mM Tris base-89 mM Boric Acid-2 mM disodium EDTA (TBE) buffer. A fragment of approximately 2700 bp was excised from the gel and extracted from the agarose using a QIAQUICK® Gel Extraction Kit (Qiagen).

The 2700 bp PCR product was cloned into pCRM4BLUNT TOPO® (Invitrogen) vector using the Zero Blunt® TOPO® PCR cloning kit for sequencing (Invitrogen) according to the manufacturer's instructions. In a total reaction volume of 6 µL either 1 or 4 µL of the 2700 bp PCR product, 1 µL salt solution (Invitrogen) and 1 µL pCR™ 4BLUNT TOPO® (Invitrogen) were incubated together at room temperature for 15 minutes. 2 µL of each cloning reaction was transformed into One Shot® TOP10 Chemically Competent E. coli (Invitrogen) cells according to manufacturer's instructions. Transformants were plated onto 2×YT+amp plates and incubated at 37° C. overnight. Several of the resulting transformants were screened for proper insertion of the desired PCR product by NotI digestion. A clone yielding the desired band sizes was confirmed to be correct by DNA sequencing and designated pMIBa100.

The plasmid pHJJ76 (FIG. 24) contains homology to allow gene integration at the adh1202 locus. Plasmid pHJJ76 was digested with NotI to remove the URA3 selectable marker present inside of the adh1202 homology sequences. The digested pHJJ76 was purified by 1% agarose gel electrophoresis using 89 mM Tris base-89 mM Boric Acid-2 mM disodium EDTA (TBE) buffer. A 5.2 kbp fragment was extracted from the agarose using a QIAQUICK® Gel Extraction Kit (Qiagen), and then ligated back together using T4 DNA ligase. The ligation products were transformed into One Shot® TOP10 Chemically Competent E. coli (Invitrogen) cells according to manufacturer's instructions. Transformants were plated onto 2×YT+amp plates and incubated at 37° C. overnight. Several resulting transformants were screened by ApaI and SacI digestion. A clone yielding the desired digestion products was designated pHJJ76-no ura.

Figure 2:
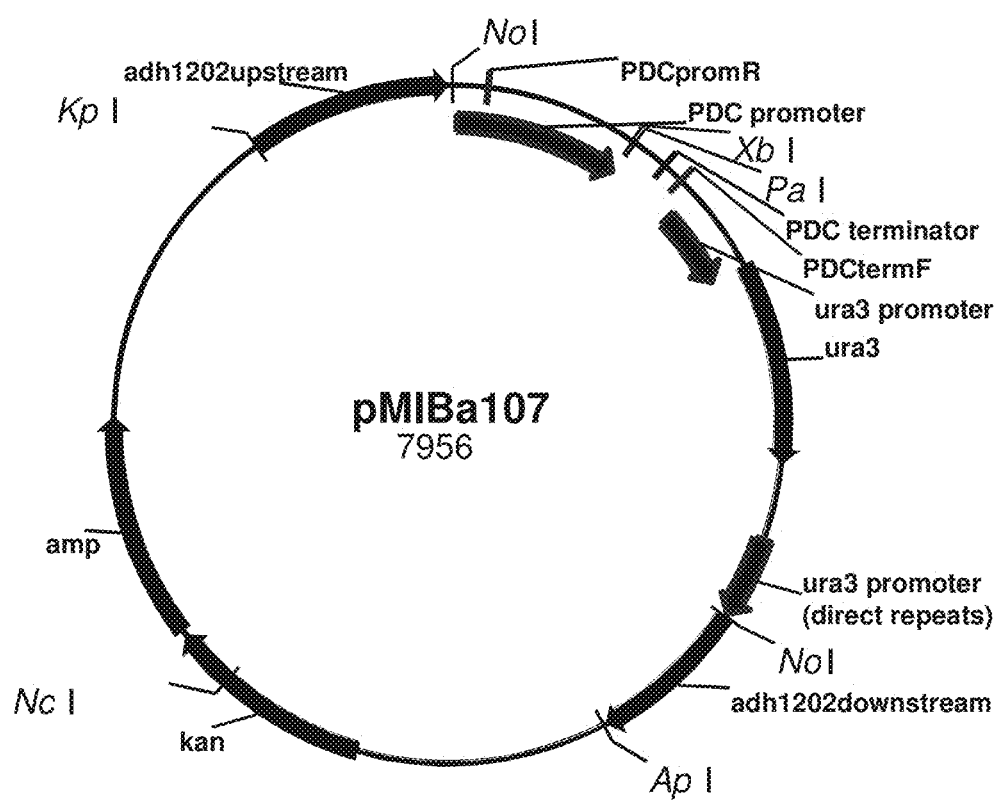
FIG. 2: Plasmid pMIBa107

The PDC promoter and terminator and URA3 selectable marker from pMIBa100 (supra) was cloned into pHJJ76-no ura to create a plasmid where a gene could be placed under the control of the PDC promoter and terminator for integration at adh1202. pHJJ76-no ura was digested with NotI followed by treatment with CIP. The linear 5.2 kbp fragment was purified using a QIAQUICK® PCR Purification Kit (Qiagen). pMIBa100 was digested with NotI and run on a 1% agarose gel using 89 mM Tris base-89 mM Boric Acid-2 mM disodium EDTA (TBE) buffer. A 2742 bp fragment was excised from the gel, extracted using a QIAQUICK® Gel Extraction Kit (Qiagen), and then ligated into the 5.2 kbp fragment of pHJJ76-no ura using T4 DNA Ligase. The ligation products were transformed into One Shot® TOP10 Chemically Competent E. coli (Invitrogen) cells according to manufacturer's instructions. Transformants were plated onto 2×YT+amp plates and incubated at 37° C. overnight. Several of the resulting transformants were screened by KpnI and XbaI digestion. A clone yielding the desired digestion products was designated pMIBa107 (FIG. 2).

Example 2E: Construction of Insertion Vector Fragments for Expressing Multiple Exogenous Genes at the PDC Locus The following insertion vector fragments can be used to generate a designed DNA construct that replaces an endogenous I. orientalis PDC gene with a cassette that expresses multiple genes, e.g., three genes described herein expressed from the PDC, ENO1, and TDH3 promoters. Homologous recombination between the left construct (pMhCt068 and derivatives) and the right construct (pMhCt069 and derivatives) results in expression of the URA3 protein, resulting in conversion of the strain from uracil auxotrophy to uracil prototrophy, allowing for selection of desired integrants. The 5' end of each left-hand construct is homologous to the DNA upstream of the PDC locus, while the 3' end of each right-hand construct is homologous to the DNA downstream of the PDC locus. These homologous regions serve to target the expression cassette to the PDC locus. This targeting approach is depicted schematically in FIG. 3, and can be modified to use any combination of multiple genes described herein to target any suitable locus, e.g., any locus described above, such as an ADH locus (see example below) or an ALD locus.

Construction of a Left-Hand Fragment

An empty vector left-hand construct, pMhCt068, was cloned in multiple steps as described below.

A PCR fragment containing the PDC promoter region and desired additional restriction sites and flanking DNA was amplified from genomic I. orientalis DNA using primers 0611166 and 0611167.

The PCR reaction (50 µL) contained 100 ng of genomic *I. orientalis* DNA (preparable, e.g., using a MasterPure™ Yeast DNA Purification Kit from EPICENTRE® Biotechnologies), 1× ThermoPol Reaction buffer (New England Biolabs), 100 pmol each of primers 0611166 and 0611167, 200 µM each of dATP, dCTP, dGTP, and dTTP, 2 µL 100 mM MgSO$_4$, and 2 units of Vent$_R$® (exo-) DNA polymerase (New England Biolabs). The PCR was performed in an EPPENDORF® MASTERCYCLER® (Eppendorf Scientific) programmed for one cycle at 94° C. for 2 minutes followed by 34 cycles each at 94° C. for 30 seconds, 54° C. for 30 seconds, and 72° C. for 1 minute, with a final extension at 72° C. for 10 minutes. Following thermocycling, the PCR reaction products were separated by 0.9% agarose gel electrophoresis in TAE buffer where an approximately 780 base pair PCR product was excised from the gel and purified using a NUCLEOSPIN® Extract II Kit (Macherey-Nagel, Bethlehem, Pa., USA) according to the manufacturer's instructions.

A PCR fragment containing the TAL terminator region and desired additional restriction sites and flanking DNA was amplified from pACN5 (FIG. 19) using primers 0611168 and 0611169. The PCR reaction (50 µL) contained 1 µL of pACN5 mini-prep plasmid DNA, 1× iProof™ HF buffer (Bio-Rad Laboratories, Hercules, Calif., USA), 100 pmol each of primers 0611168 and 0611169, 200 µM each of dATP, dCTP, dGTP, and dTTP, 1.5 µL DMSO and 1 unit of iProof™ High Fidelity DNA polymerase (Bio-Rad Laboratories). The PCR was performed in an EPPENDORF® MASTERCYCLER® (Eppendorf Scientific) programmed for one cycle at 98° C. for 30 seconds followed by 34 cycles each at 98° C. for 10 seconds, 59° C. for 20 seconds, and 72° C. for 45 seconds, with a final extension at 72° C. for 10 minutes. Following thermocycling, the PCR reaction products were separated by 0.9% agarose gel electrophoresis in TAE buffer where an approximately 460 base pair PCR product was excised from the gel and purified using a NUCLEOSPIN® Extract II Kit (Macherey-Nagel) according to the manufacturer's instructions.

PCR then was used to create a single amplification product fusing both of the products above. The PCR reaction (50 µL) contained 125 ng of the PDC promoter containing PCR product, 76 ng of the TAL terminator containing PCR product, 1× ThermoPol Reaction buffer (New England Biolabs), 100 pmol each of primers 0611166 and 0611169, 200 µM each of dATP, dCTP, dGTP, and dTTP, 2 µL 100 mM MgSO$_4$, and 2 units of Vent$_R$® (exo-) DNA polymerase (New England Biolabs). The PCR was performed in an EPPENDORF® MASTERCYCLER® (Eppendorf Scientific) programmed for one cycle at 94° C. for 2 minutes followed by 34 cycles each at 94° C. for 30 seconds, 54° C. for 30 seconds, and 72° C. for 1 minute and 30 seconds, with a final extension at 72° C. for 10 minutes. Following thermocycling, the PCR reaction products were separated by 0.9% agarose gel electrophoresis in TAE buffer where an approximately 1,250 base pair PCR product was excised from the gel and purified using a NUCLEOSPIN® Extract II Kit (Macherey-Nagel) according to the manufacturer's instructions.

Figure 22:
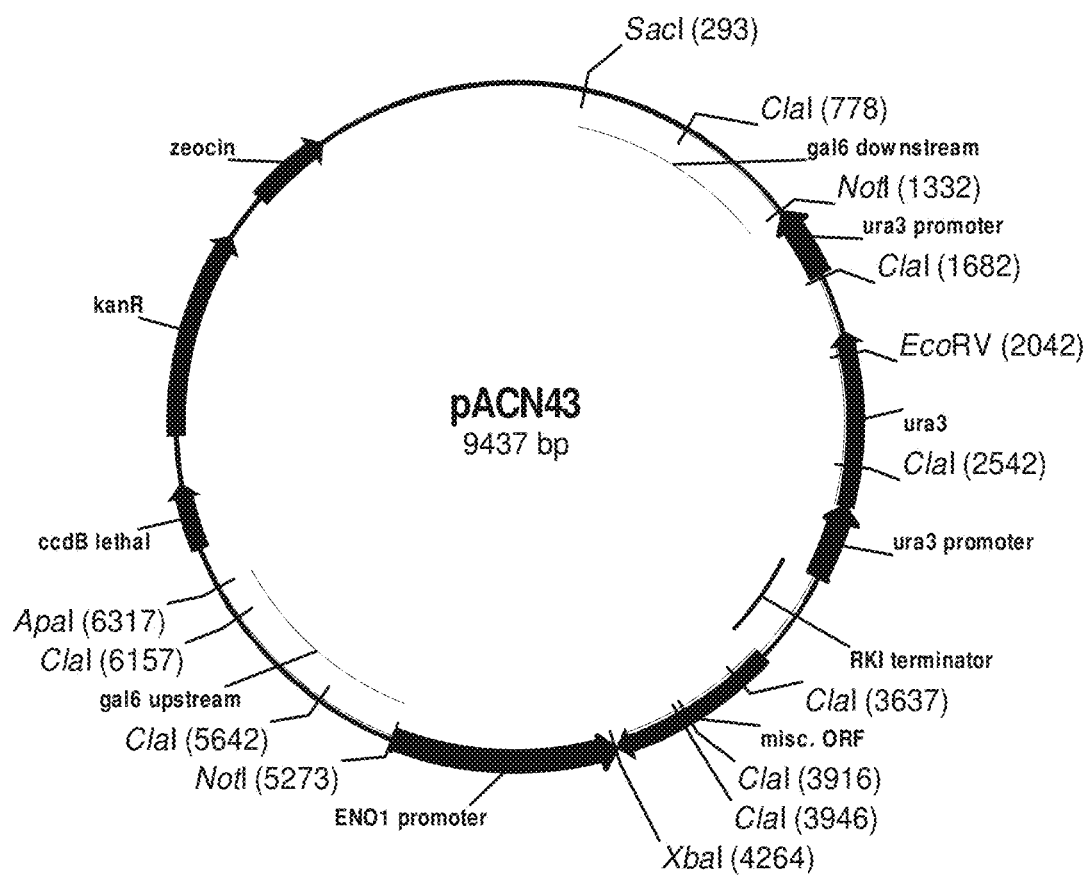
FIG. 22: Plasmid pACN43

A PCR fragment containing the ENO1 promoter region and desired additional restriction sites and flanking DNA was amplified from pACN43 (FIG. 22) using primers 0611170 and 0611171. The PCR reaction (50 µL) contained 1 µL of pACN43 mini-prep plasmid DNA, 1× Phusion HF buffer (New England Biolabs), 100 pmol each of primers 0611170 and 0611171, 200 µM each of dATP, dCTP, dGTP, and dTTP, and 1 unit of Phusion™ High-Fidelity DNA polymerase (New England Biolabs). The PCR was performed in an EPPENDORF® MASTERCYCLER® (Eppendorf Scientific) programmed for one cycle at 98° C. for 30 seconds followed by 34 cycles each at 98° C. for 10 seconds, 59° C. for 20 seconds, and 72° C. for 45 seconds, with a final extension at 72° C. for 10 minutes. Following thermocycling, the PCR reaction products were separated by 0.9% agarose gel electrophoresis in TAE buffer where an approximately 1050 base pair PCR product was excised from the gel and purified using a NUCLEOSPIN® Extract II Kit (Macherey-Nagel) according to the manufacturer's instructions.

A PCR fragment containing the RKI terminator region followed by the URA3 promoter region and the 5' end of the URA3 ORF, along with desired additional restriction sites and flanking DNA, was amplified from pACN43 (FIG. 22) using primers 0611172 and 0611173. The PCR reaction (50 µL) contained 1 µL of pACN43 mini-prep plasmid DNA, 1× iProof™ HF buffer (Bio-Rad Laboratories), 100 pmol each of primers 0611172 and 0611173, 200 µM each of dATP, dCTP, dGTP, and dTTP, 1.5 µL DMSO and 1 unit of iProof™ High Fidelity DNA polymerase (Bio-Rad Laboratories). The PCR was performed in an EPPENDORF® MASTERCYCLER® (Eppendorf Scientific) programmed for one cycle at 98° C. for 30 seconds followed by 34 cycles each at 98° C. for 10 seconds, 59° C. for 20 seconds, and 72° C. for 45 seconds, with a final extension at 72° C. for 10 minutes. Following thermocycling, the PCR reaction products were separated by 0.9% agarose gel electrophoresis in TAE buffer where an approximately 1400 base pair PCR product was excised from the gel and purified using a NUCLEOSPIN® Extract II Kit (Macherey-Nagel) according to the manufacturer's instructions.

PCR was used to create a single amplification product fusing both of the products above. The PCR reaction (50 µL) contained 93 ng of the ENO1 promoter containing PCR product (supra); 125 ng of the RKI terminator, URA3 promoter and partial ORF containing PCR product (supra); 1× Phusion HF buffer (New England Biolabs); 100 pmol each of primers 0611170 and 0611173; 200 µM each of dATP, dCTP, dGTP, and dTTP; 1.5 µL DMSO; and 1 unit of Phusion™ High-Fidelity DNA polymerase (New England Biolabs). The PCR was performed in an EPPENDORF® MASTERCYCLER® (Eppendorf Scientific) programmed for one cycle at 98° C. for 30 seconds followed by 34 cycles each at 98° C. for 10 seconds, 56° C. for 20 seconds, and 72° C. for 2 minutes and 45 seconds, with a final extension at 72° C. for 10 minutes. Following thermocycling, the PCR reaction products were separated by 0.9% agarose gel electrophoresis in TAE buffer where an approximately 2460 base pair PCR product was excised from the gel and purified using a NUCLEOSPIN® Extract II Kit (Macherey-Nagel) according to the manufacturer's instructions.

To create a recipient vector for the PCR products, the plasmid pMhCt017 (the standard cloning vector pUC19 with an irrelevant insert) was digested with Hind III and EcoRI, treated with 10 units calf intestinal phosphatase (New England Biolabs) at 37° C. for 30 minutes, and purified by 0.9% agarose gel electrophoresis in TAE buffer, and an approximately 2.6 kbp band was excised from the gel and purified using a NUCLEOSPIN® Extract II Kit (Macherey-Nagel) according to the manufacturer's instructions. The resulting Hind III to EcoRI purified fragment was identical to that found in pUC18 (Yanisch-Perron, C., Vieira, J. and Messing, J. (1985) Gene, 33, 103-119).

The purified 1250 bp and 2460 bp PCR products from above were then inserted into the digested pMhCt017 fragment using an IN-FUSION™ Advantage PCR Cloning Kit (Clontech) in a total reaction volume of 10 μL composed of 125 ng pMhCt017 Hind III to EcoRI vector fragment, 92 ng of the PDC promoter and TAL terminator PCR product, 165 ng of the ENO1 promoter and URA3 promoter and partial ORF containing PCR product, 1× In-Fusion reaction buffer (Clontech) and 1 μL of IN-FUSION™ enzyme (Clontech). The reaction was incubated at 37° C. for 15 minutes, 50° C. for 15 minutes, and then placed on ice. The reaction then was diluted with 40 μL of TE buffer and 2.5 μL was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired PCR products by Apa LI digestion. A clone yielding the desired band sizes was confirmed to be correct by DNA sequencing and designated pMhCt068.

The plasmid pMhCt068 contains the PDC promoter region followed by NheI and AscI restriction sites for addition of an ectopic gene of interest described herein, the TAL terminator, the ENO1 promoter region followed by XbaI and PacI restriction sites for cloning of a second ectopic gene of interest described herein, the RKI terminator, the *I. orientalis* URA3 promoter and the 5' end of the *I. orientalis* URA3 ORF. Plasmid pMhCt068 was found to have an A to T nucleotide change at about 200 bp into the PDC promoter, a G to T change at about ⅔ of the way into the PDC promoter, and a premature start codon (ATG) present on the 5' side of the NheI restriction site. Accordingly, a corrected version of pMhCt068 was constructed as described below.

The PDC promoter region was PCR amplified from pACN5 (FIG. 19) with primer 0611166 and 0611828, which do not introduce the undesired start codon above. The PCR reaction (50 μL) contained 1 μL of a 1 to 50 dilution of a mini-prep of pACN5, 1× ThermoPol Reaction buffer (New England Biolabs), 100 pmol each of primers 0611166 and 0611828, 200 μM each of dATP, dCTP, dGTP, and dTTP, 2 μL 100 mM $MgSO_4$, and 2 units of $Vent_R$® (exo-) DNA polymerase (New England Biolabs). The PCR was performed in an EPPENDORF® MASTERCYCLER® (Eppendorf Scientific) programmed for one cycle at 94° C. for 2 minutes followed by 34 cycles each at 94° C. for 30 seconds, 54° C. for 30 seconds, and 72° C. for 1 minute, with a final extension at 72° C. for 10 minutes. Following thermocycling, the PCR reaction products were separated by 0.9% agarose gel electrophoresis in TAE buffer where an approximately 780 base pair PCR product was excised from the gel and purified using a NUCLEOSPIN® Extract II Kit (Macherey-Nagel) according to the manufacturer's instructions.

The PDC promoter containing PCR product was then fused to the TAL terminator containing PCR product as described above. Since the TAL terminator PCR fragment was made with the 0611168 primer, the resulting PCR fusion products should be a mixture, with products that lack the premature start codon and include the undesired start codon. The resulting ~1250 bp PCR product was purified and combined via IN-FUSION™ Advantage PCR Cloning Kit (Clontech) with the RKI terminator, URA3 promoter and partial ORF containing fusion PCR product and pUC18 as described above. A clone yielding the expected ApaLI digestion pattern was shown to be correct by DNA sequencing, including the desired absence of mutations in the PDC promoter and lack of premature ATG 5' of the NheI restriction site, and designated pMhCt082.

Construction of a Right-Hand Fragment

The empty vector right-hand construct, pMhCt069, was cloned in multiple steps as described below.

A PCR fragment containing the 3' end of the *I. orientalis* URA3 ORF, the URA3 terminator (the 275 bp downstream of the URA3 stop codon), the URA3 promoter (to serve as a repeat region for looping out of the marker after integration into the yeast host) and desired additional restriction sites and flanking DNA was amplified from pACN43 (FIG. 22) using primers 0611174 and 0611175. The PCR reaction (50 μL) contained 1 μL of pACN43 mini-prep plasmid DNA, 1× Phusion HF buffer (New England Biolabs), 100 pmol each of primers 0611174 and 0611175, 200 μM each of dATP, dCTP, dGTP, and dTTP, and 1 unit of Phusion™ High-Fidelity DNA polymerase (New England Biolabs). The PCR was performed in an EPPENDORF® MASTERCYCLER® (Eppendorf Scientific) programmed for one cycle at 98° C. for 30 seconds followed by 34 cycles each at 98° C. for 10 seconds, 59° C. for 20 seconds, and 72° C. for 45 seconds, with a final extension at 72° C. for 10 minutes. Following thermocycling, the PCR reaction products were separated by 0.9% agarose gel electrophoresis in TAE buffer where an approximately 1210 bp PCR product was excised from the gel and purified using a NUCLEOSPIN® Extract II Kit (Macherey-Nagel) according to the manufacturer's instructions.

Figure 20:
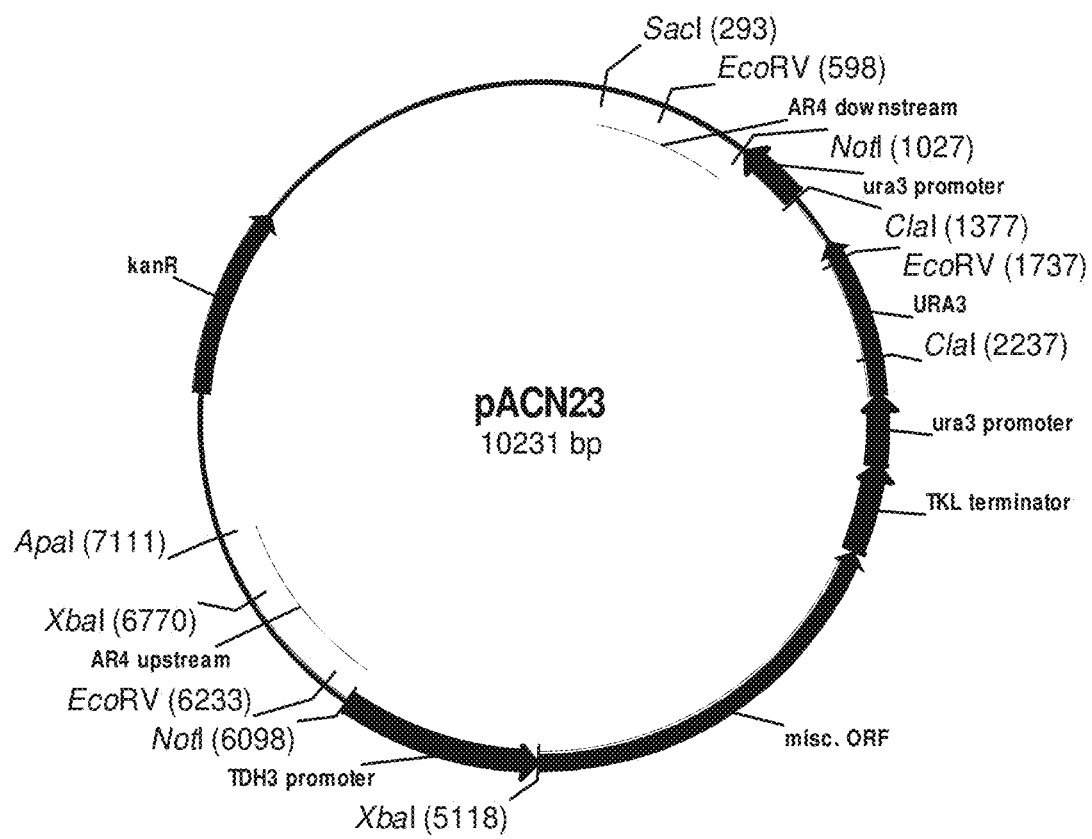
FIG. 20: Plasmid pACN23

A PCR fragment containing the TDH3 promoter region and desired additional restriction sites and flanking DNA was amplified from pACN23 (FIG. 20) using primers 0611176 and 0611177. The PCR reaction (50 μL) contained 1 μL of pACN23 mini-prep plasmid DNA, 1× Phusion HF buffer (New England Biolabs), 100 pmol each of primers 0611176 and 0611177, 200 μM each of dATP, dCTP, dGTP, and dTTP, and 1 unit of Phusion™ High-Fidelity DNA polymerase (New England Biolabs). The PCR was performed in an EPPENDORF® MASTERCYCLER® (Eppendorf Scientific) programmed for one cycle at 98° C. for 30 seconds followed by 34 cycles each at 98° C. for 10 seconds, 59° C. for 20 seconds, and 72° C. for 45 seconds, with a final extension at 72° C. for 10 minutes. Following thermocycling, the PCR reaction products were separated by 0.9% agarose gel electrophoresis in TAE buffer where an approximately 1028 bp PCR product was excised from the gel and purified using a NUCLEOSPIN® Extract II Kit (Macherey-Nagel) according to the manufacturer's instructions.

A PCR fragment containing the region 3' of the stop codon of the *I. orientalis* PDC gene region (PDC terminator region) and desired additional restriction sites and flanking DNA was amplified from *I. orientalis* genomic DNA using primers 0611178 and 0611179. The PCR reaction (50 μL) contained 100 ng of *I. orientalis* genomic DNA, 1× iProof™ HF buffer (Bio-Rad Laboratories), 100 pmol each of primers 0611178 and 0611179, 200 μM each of dATP, dCTP, dGTP, and dTTP, 1.5 μL DMSO and 1 unit of iProof™ High Fidelity DNA polymerase (Bio-Rad Laboratories). The PCR was performed in an EPPENDORF® MASTERCYCLER® (Eppendorf Scientific) programmed for one cycle at 98° C. for 30 seconds followed by 34 cycles each at 98° C. for 10 seconds, 59° C. for 20 seconds, and 72° C. for 45 seconds, with a final extension at 72° C. for 10 minutes. Following thermocycling, the PCR reaction products were separated by 0.9% agarose gel electrophoresis in TAE buffer where an approximately 938 base pair PCR product was excised from the gel and purified using a NUCLEOSPIN® Extract II Kit (Macherey-Nagel) according to the manufacturer's instructions.

PCR was used to create a single amplification product fusing both of the last two PCR products described above. The PCR reaction (50 μL) contained 125 ng of the TDH3 promoter containing PCR product, 114 ng of the PDC terminator region containing PCR product, 1× Phusion HF buffer (New England Biolabs), 100 pmol each of primers 0611176 and 0611179, 200 μM each of dATP, dCTP, dGTP, and dTTP, and 1 unit of Phusion™ High-Fidelity DNA polymerase (New England Biolabs). The PCR was performed in an EPPENDORF® MASTERCYCLER® (Eppendorf Scientific) programmed for one cycle at 98° C. for 30 seconds followed by 34 cycles each at 98° C. for 10 seconds, 56° C. for 20 seconds, and 72° C. for 2 minutes and 30 seconds, with a final extension at 72° C. for 10 minutes. Following thermocycling, the PCR reaction products were separated by 0.9% agarose gel electrophoresis in TAE buffer where an approximately 1966 base pair PCR product was excised from the gel and purified using a NUCLEOSPIN® Extract II Kit (Macherey-Nagel) according to the manufacturer's instructions.

The purified 1210 bp PCR product and the 1966 bp PCR fusion product from above were then inserted into the Hind III and EcoRI digested pMhCt017 fragment as described above using an IN-FUSION™ Advantage PCR Cloning Kit (Clontech) in a total reaction volume of 10 μL composed of 125 ng pMhCt017 Hind III to EcoRI vector fragment, 54 ng of PCR product containing the 3' end of the URA3 ORF followed by the URA3 terminator, 200 ng of the TDH3 promoter and PDC terminator fusion PCR product, 1× In-Fusion reaction buffer (Clontech) and 1 μL of IN-FUSION™ enzyme (Clontech). The reaction was incubated at 37° C. for 15 minutes, 50° C. for 15 minutes, and then placed on ice. The reaction was diluted with 40 μL of TE buffer and 2.5 μL was used to transform SoloPack Gold SuperCompetent Cells (Agilent Technologies) according to the manufacturer's instructions. Transformants were plated onto 2×YT+ amp plates and incubated at 37° C. overnight. Several of the resulting transformants were screened for proper insertion of the desired PCR products by Apa LI digestion. A clone yielding the desired band sizes was confirmed to be correct by DNA sequencing and designated pMhCt069.

Plasmid pMhCt069 contains the 3' end of the *I. orientalis* URA3 marker, the corresponding URA3 terminator, the URA3 promoter (for later looping out of the URA3 marker), the TDH3 promoter, XbaI and PacI restriction sites for subcloning of desired genes for ectopic expression, and the 3' flanking region of the PDC locus.

Example 2F: Construction of Insertion Vector Fragments for Expressing Multiple Exogenous Genes at the Adh9091 Locus The following insertion vector fragments were designed using a similar approach to that described in Example 2E in order to replace an endogenous *I. orientalis* adh9091 gene with a cassette that expresses multiple genes of interest described herein.
Construction of a Left-Hand Fragment
An empty vector left-hand construct, pGREr125, was cloned in multiple steps as described below.

A construct comprising the 5' flank needed for homologous recombination at the *I. orientalis* adh9091 locus and the empty expression cassette PDC promoter/TAL terminator was PCR cloned into vector plasmid pCR2.1-TOPO (Invitrogen). The PDC promoter fragment was PCR amplified from plasmid pACN5 (FIG. 19) using primers 0611250 and 0611251. The PCR reaction (50 μL) contained 15 ng of plasmid pACN5 DNA, 1× Phusion HF buffer (New England Biolabs), 50 pmol each of primers 0611250 and 0611251, 200 μM each of dATP, dCTP, dGTP, and dTTP, 1.5 μL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute and 30 seconds, with a final extension at 72° C. for 7 minutes. Following thermocycling, the PCR reaction products were separated by 0.8% agarose gel electrophoresis in TBE buffer where an approximately 900 bp PCR product was excised from the gel and purified using a QIAQUICK® Gel Extraction Kit (Qiagen) according to the manufacturer's instructions. The total length of the resulting PCR fragment was approximately 753 bp with a NotI restriction site at the 5' end of the fragment and a PacI and an XbaI restriction site at the 3' end of the fragment.

A second PCR fragment containing 5' homology to the PCR product above including the XbaI and PacI restriction sites was generated to amplify the TAL terminator region from plasmid pACN5 (FIG. 19) using primers 0611252 and 0611253. The PCR reaction (50 μL) contained 15 ng of plasmid pACN5 DNA (supra), 1× Phusion HF buffer (New England Biolabs), 50 pmol each of primers 0611252 and 0611253, 200 μM each of dATP, dCTP, dGTP, and dTTP, 1.5 μL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute and 30 seconds, with a final extension at 72° C. for 7 minutes. Following thermocycling, the PCR reaction products were separated by 0.8% agarose gel electrophoresis in TBE buffer where an approximately 900 bp PCR product was excised from the gel and purified using a QIAQUICK® Gel Extraction Kit (Qiagen) according to the manufacturer's instructions. The total length of the resulting PCR fragment was about 435 bp with XbaI and PacI restriction sites at the 5' end of the fragment and a PmeI restriction site at the 3' end.

The 753 bp fragment and the 435 bp fragment were fused together by PCR using the primers 0611250 and 0611253, leading to a resulting 1149 bp fragment in which the PDC promoter is upstream of the TAL terminator. The PCR reaction (50 μL) contained 125 ng of the 753 bp fragment, 75 ng of the 435 bp fragment, 1× Phusion HF buffer (New England Biolabs), 50 pmol each of primers 0611250 and 0611253, 200 μM each of dATP, dCTP, dGTP, and dTTP, 1.5 μL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute, with a final extension at 72° C. for 7 minutes. Following thermocycling, the PCR reaction product was separated by 0.8% agarose gel electrophoresis in TBE buffer where an approximately 1149 bp PCR product was excised from the gel and purified using a QIAQUICK® Gel Extraction Kit (Qiagen) according to the manufacturer's instructions.

Figure 21:
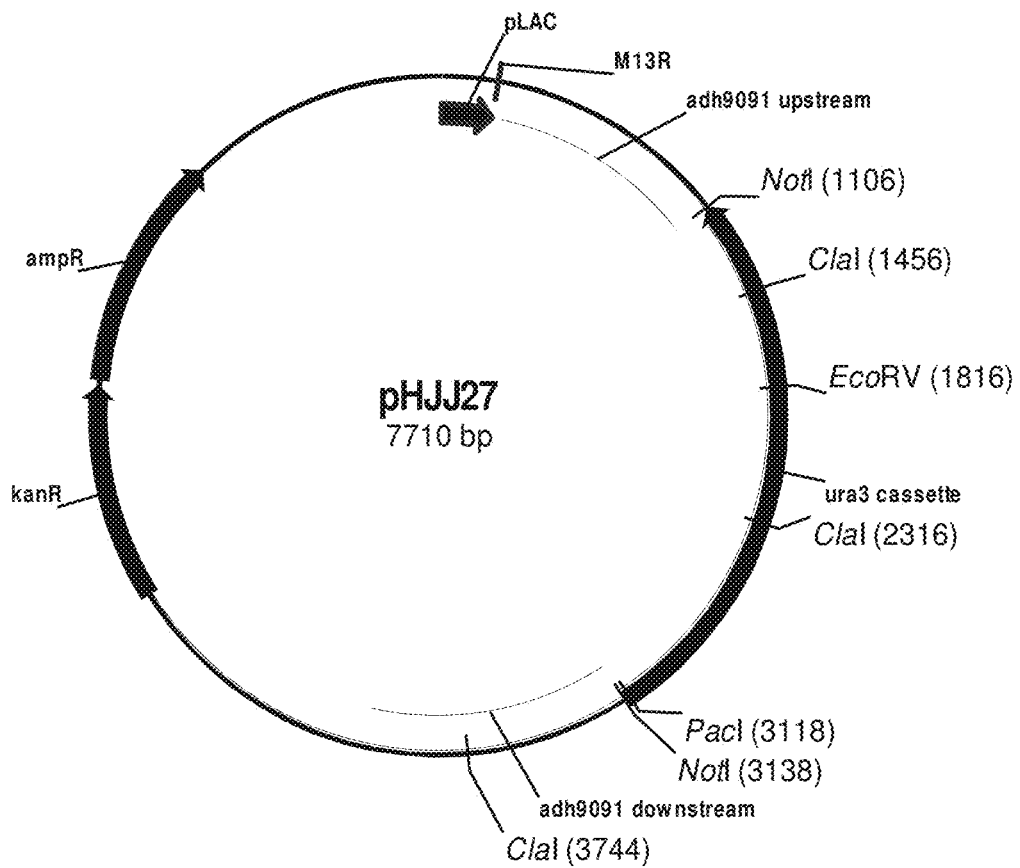
FIG. 21: Plasmid pHJJ27

A PCR fragment containing 3' homology to the 1149 bp PCR product above including the NotI restriction site, was generated to amplify the 5' flank for the *I. orientalis* adh9091 locus using primers 0611254 and 0611255. The PCR reaction (50 µL) contained 15 ng of plasmid pHJJ27 (FIG. 21) as template DNA, 1× Phusion HF buffer (New England Biolabs), 50 pmol each of primers 0611254 and 0611255, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute and 30 seconds, with a final extension at 72° C. for 7 minutes. Following thermocycling, the PCR reaction products were separated by 0.8% agarose gel electrophoresis in TBE buffer where an approximately 900 bp PCR product was excised from the gel and purified using a QIAQUICK® Gel Extraction Kit (Qiagen) according to the manufacturer's instructions. The total length of the resulting PCR fragment is approximately 891 bp with an HpaI restriction site at the 5' end of the fragment and a NotI restriction site at the 3' end.

The 891 bp fragment then was fused upstream of the 1149 bp PDC promoter/TAL terminator fragment by PCR using the primers 0611254 and 0611253 generating an approximately 2005 bp fragment. The PCR reaction (50 µL) contained 125 ng of the 1149 bp fragment, 95 ng of the 891 bp fragment, 1× Phusion HF buffer (New England Biolabs), 50 pmol each of primers 0611254 and 0611253, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 2 minutes, with a final extension at 72° C. for 7 minutes. Following thermocycling, the PCR reaction products were separated by 0.8% agarose gel electrophoresis in TBE buffer where an approximately 2005 bp PCR product was excised from the gel and purified using a QIAQUICK® Gel Extraction Kit (Qiagen) according to the manufacturer's instructions.

The resulting 2005 bp fragment, comprising the 5' flank for integration at the adh9091 locus, the PDC promoter and the TAL terminator, was cloned into pCR2.1-TOPO vector and transformed into One-Shot TOP10 *E. coli* cells using a TOPO TA Cloning kit (Invitrogen) according to the manufacturer's instructions. Transformants were plated onto 2×YT+amp plates and incubated at 37° C. overnight. Several of the resulting transformants were screened for proper insertion of the desired fragment by AvaI digestion. A done yielding the desired band sizes was confirmed and designated pGMEr112. Plasmid pGMEr112 comprises the 5' flank for homologous recombination at the adh9091 locus followed the empty expression cassette PDC promoter/TAL terminator.

The truncated 5' URA3 marker gene driven by the URA3 promoter fragment was PCR amplified from plasmid pHJJ27 (FIG. 21) using primers 0611283 and 0611263. The PCR reaction (50 µL) contained 15 ng of plasmid pHJJ27, 1× Phusion HF buffer (New England Biolabs), 50 pmol each of primers 0611263 and 0611283, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute and 30 seconds, with a final extension at 72° C. for 7 minutes. Following thermocycling, the PCR reaction products were separated by 0.8% agarose gel electrophoresis in TBE buffer where an approximately 900 bp PCR product was excised from the gel and purified using a QIAQUICK® Gel Extraction Kit (Qiagen) according to the manufacturer's instructions. The total length of the resulting PCR fragment was approximately 885 bp with HpaI and PmeI restriction sites at the 5' end of the fragment and a NheI restriction site at its 3' end.

The resulting 885 bp fragment was cloned into pCR2.1-TOPO vector and transformed into One-Shot TOP10 *E. coli* cells using a TOPO TA Cloning kit (Invitrogen) according to the manufacturer's instructions. Transformants were plated onto 2×YT+amp plates and incubated at 37° C. overnight. Several of the resulting transformants were screened for proper insertion of the desired insert by BglI digestion. A clone yielding the desired band sizes was confirmed and designated pGMEr108. Plasmid pGMEr108 comprises the URA3 promoter followed by the truncated 5' segment of the URA3 gene, such fragment is flanked by HpaI and PmeI restriction sites at the 5' end and by the NotI restriction site at the 3' end.

A 1998 bp HpaI and PmeI restriction fragment from plasmid pGMEr112 (supra), comprising the 5' adh9091 flank followed by the construct PDC promoter/TAL terminator, was ligated to the 4806 bp vector from pGMEr108 (supra) linearized by HpaI and PmeI. The double restriction reaction products were separated by 0.8% agarose gel electrophoresis in TBE buffer where the 1998 bp insert fragment and the 4806 bp vector fragment were excised from the gel and purified using a QIAQUICK® Gel Extraction Kit (Qiagen) according to the manufacturer's instructions. The ligation reaction was performed using a 1:3 vector insert ratio; in particular the reaction was set up with 2 µL of the 4806 bp linearized vector, 6 µL of the 1998 bp insert fragment, 9 µL of 2× Quick Ligation reaction Buffer and 1 µL Quick T4 DNA Ligase (New England Biolabs), and performed according to the manufacturer's instructions.

Five µL of the ligation product was transformed into *E. coli* XL10-Gold Ultracompetent Cells (Agilent Technologies) according to the manufacturer's instructions. Transformants were plated onto 2×YT+amp plates and incubated at 37° C. overnight. Several of the resulting transformants were screened for proper insertion of the desired insert by Hind III digestion. A clone yielding the desired band sizes was confirmed and designated pGMEr117.

Plasmid pGMEr117 comprises the 5' adh9091 flank, followed by the empty expression cassette PDC promoter/TAL terminator and by the truncated 5' URA3 gene driven by the URA3 promoter. Additionally, plasmid pGMEr117 bears two different XbaI restriction sites: a first restriction site between the PDC promoter and the TAL terminator (and adjacent to restriction site Pac I) which can be used to insert the gene of interest, and a second XbaI restriction site that was inherited from the original pCR2.1-TOPO back bone. In order to eliminate this second XbaI restriction site, plasmid pGMEr117 was digested with restriction enzyme ApaI, and the linearized plasmid was then treated with the enzyme DNA polymerase I, large (Klenow) fragment (New England Biolabs) according to the manufacturer's instructions. The resulting linear vector (containing blunt ends) was digested with restriction enzyme Eco RV, which cut a 43 bp fragment from the vector comprising the XbaI restriction site. The restriction reaction products were separated by 0.8% agarose gel electrophoresis in TBE buffer and the 6761 bp vector fragment was excised from the gel and purified using a QIAQUICK® Gel Extraction Kit (Qiagen) according to the manufacturer's instructions. The self ligation reaction was set up with 3 µL of the linearized vector, 6 µL of sterile double-distilled water, 10 µL of 2× Quick Ligation reaction Buffer and 1 µL Quick T4 DNA Ligase (New England Biolabs) and performed according to the manufacturer's instructions.

Five µL of the ligation product was transformed into E. coli XL10-Gold Ultracompetent Cells (Agilent Technologies) according to the manufacturer's instructions. Transformants were plated onto 2×YT+amp plates and incubated at 37° C. overnight. Several of the resulting transformants were screened for proper insertion of the desired insert by XbaI digestion. A clone yielding the desired band sizes was confirmed and designated pGMEr122.

The ENO1 promoter fragment was PCR amplified from plasmid pACN43 (FIG. 22) using the primers 0611295 and 0611296. The PCR reaction (50 µL) contained 15 ng of plasmid pACN43, 1× Phusion HF buffer (New England Biolabs), 50 pmol each of primers 0611295 and 0611296, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute, with a final extension at 72° C. for 7 minutes. Following thermocycling, the PCR reaction products were separated by 0.8% agarose gel electrophoresis in TBE buffer where an approximately 1009 bp PCR product was excised from the gel and purified using a QIAQUICK® Gel Extraction Kit (Qiagen) according to the manufacturer's instructions. The total length of the resulting PCR fragment was approximately 1009 bp with a PmeI restriction site at the 5' end of the fragment and ApaI and NruI restriction sites at the 3' end.

A second PCR fragment containing 5' homology to the PCR product above, including the NruI and the ApaI restriction sites, was generated to amplify the RKI terminator region from plasmid pACN43 (FIG. 22) using the primers 0611297 and 0611298. The PCR reaction (50 µL) contained 15 ng of plasmid pACN43 DNA, 1× Phusion HF buffer (New England Biolabs), 50 pmol each of primers 0611297 and 0611298, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute, with a final extension at 72° C. for 7 minutes. Following thermocycling, the PCR reaction products were separated by 0.8% agarose gel electrophoresis in TBE buffer where an approximately 438 bp PCR product was excised from the gel and purified using a QIAQUICK® Gel Extraction Kit (Qiagen) according to the manufacturer's instructions. The total length of the resulting PCR fragment was about 438 bp with NruI and ApaI restriction sites at the 5' end of the fragment and a PmeI restriction site at the 3' end of the fragment.

The 1009 bp promoter fragment and the 438 bp terminator fragment were fused together by PCR using primers 0611295 and 0611298, leading to an approximately 1447 bp fragment in which the ENO1 promoter is upstream of the RKI terminator. The PCR reaction (50 µL) contained 125 ng of the 1009 bp fragment, 65 ng of the 438 bp fragment, 1× Phusion HF buffer (New England Biolabs), 50 pmol each of primers 0611295 and 0611298, 200 µM each of dATP, dCTP, dGTP, and dTTP, 1.5 µL DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 2 minute, with a final extension at 72° C. for 7 minutes. Following thermocycling, the PCR reaction product was separated by 0.8% agarose gel electrophoresis in TBE buffer where an approximately 1447 bp PCR product was excised from the gel and purified using a QIAQUICK® Gel Extraction Kit (Qiagen) according to the manufacturer's instructions.

The resulting 1447 bp fragment, comprising the ENO1 promoter/RKI terminator construct, was cloned into pCR2.1-TOPO vector and transformed into One-Shot TOP10 E. coli cells using a TOPO TA Cloning kit (Invitrogen) according to the manufacturer's instructions. Transformants were plated onto 2×YT+amp plates and incubated at 37° C. overnight. Several of the resulting transformants were screened for proper insertion of the desired fragment by Bam HI digestion. A clone yielding the desired band sizes was confirmed and designated pGMEr114, comprising the empty expression cassette ENO1 promoter/RKI terminator.

Plasmids pGMEr122 and pGMEr114 were digested with restriction enzyme PmeI at 37° C. for 3 hours. Approximately one hour before stopping each digestion reaction, 1 µL of Calf Intestinal Alkaline Phosphatase (New England Biolabs) was added to each digestion tube in order to de-phosphorylate the ends and prevent self-ligation. The resulting 6761 bp vector fragment from plasmid pGMEr122, and the resulting insert fragment comprising the construct ENO1 promoter/TAL terminator (1439 bp) from plasmid pGMEr114, were separated by 0.8% agarose gel electrophoresis in 1×TBE buffer, excised from the gel, and purified using the QIAQUICK® Gel Extraction Kit (Qiagen) according to the manufacturer's instructions.

Figure 4:
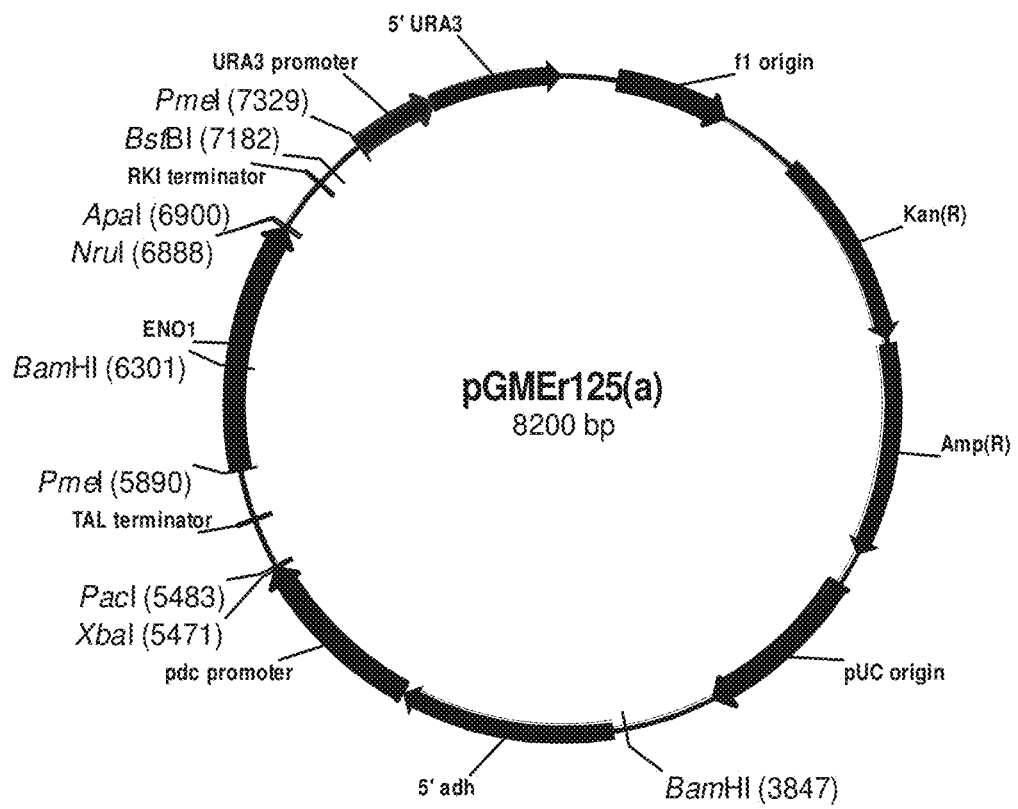
FIG. 4: Plasmid pGMEr125(a)
Figure 5:
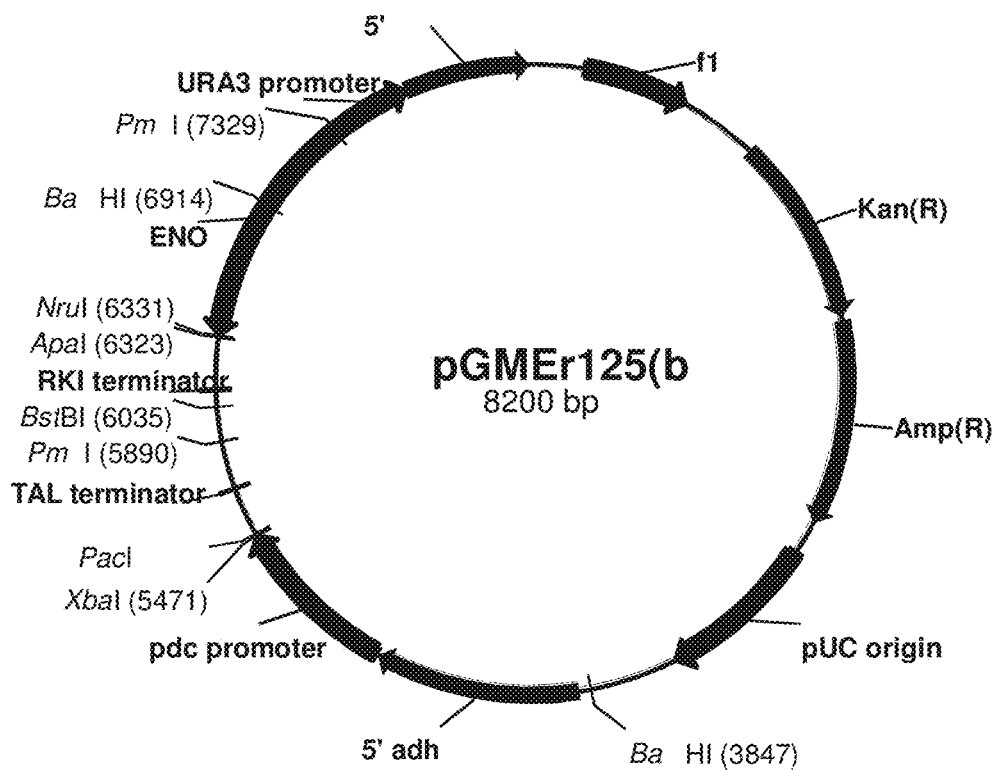
FIG. 5: Plasmid pGMRr125(b)

A subsequent ligation reaction was then prepared comprising 3 µL of the vector fragment from plasmid pGMEr122, 4 µL of the insert fragment from plasmid pGMEr114, 2 µL of sterile dd water, 10 µL of 2× Quick Ligase Buffer and 1 µL of Quick T4 Ligase (New England Biolabs) and performed according to the manufacturer's instructions. A 5 µL aliquot of the ligation reaction above was transformed into XL10-Gold® Ultracompetent E. coli cells (Agilent Technologies) according to the manufacturer's instructions. Transformants were plated onto 2×YT+amp plates and incubated at 37° C. overnight. Several of the resulting transformants were screened for proper insertion of the desired insert by digestion using XbaI and Bst BI. A clone yielding the desired band sizes was confirmed by sequencing and designated pGMEr125. The ENO1 promoter/RKI terminator construct was inserted in opposite orientations, resulting in two versions of plasmid pGMEr125 designated (a) and (b) (FIGS. 4 and 5).

The plasmids pGMEr125a and pGMEr125b contain the PDC promoter region, the TAL terminator, the ENO1 promoter region, the RKI terminator, the I. orientalis URA3 promoter, the 5' end of the corresponding URA3 marker and the 5' flanking region of the I. orientalis adh9091 locus.

Construction of a Right-Hand Fragment

An empty vector right-hand construct, pGREr121, was cloned in multiple steps as described below.

The TDH3 promoter fragment was PCR amplified from plasmid pACN23 (FIG. 20) using primers 0611256 and 0611257. The PCR reaction (50 µL) contained 15 ng of plasmid pACN23 DNA, 1× Phusion HF buffer (New England Biolabs), 50 pmol each of primers 0611256 and 0611257, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute and 30 seconds, with a final extension at 72° C. for 7 minutes. Following thermocycling, the PCR reaction products were separated by 0.8% agarose gel electrophoresis in TBE buffer where an approximately 994 bp PCR product was excised from the gel and purified using a QIAQUICK® Gel Extraction Kit (Qiagen) according to the manufacturer's instructions. The total length of the resulting PCR fragment was approximately 994 bp with a SfoI restriction site at the 5' end of the fragment and PacI and NruI restriction sites at the 3' end.

A second PCR fragment containing 5' homology to the PCR product above, including the NruI and PacI restriction sites, was generated to amplify the TKL terminator region from plasmid pACN23 (FIG. 20) using primers 0611258 and 0611259. The PCR reaction (50 µL) contained 15 ng of plasmid pACN23 DNA, 1× Phusion HF buffer (New England Biolabs), 50 pmol each of primers 0611258 and 0611259, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute and 30 seconds, with a final extension at 72° C. for 7 minutes. Following thermocycling, the PCR reaction products were separated by 0.8% agarose gel electrophoresis in TBE buffer where an approximately 469 bp PCR product was excised from the gel and purified using a QIAQUICK® Gel Extraction Kit (Qiagen) according to the manufacturer's instructions. The total length of the resulting PCR fragment was about 469 bp with NruI and PacI restriction sites at the 5' end of the fragment and a NotI restriction site at the 3' end.

The 994 bp and 469 bp fragments above were fused together by PCR using primers 0611256 and 0611259, leading to an approximately 1433 bp fragment in which the TDH3 promoter is upstream of the TKL terminator. The PCR reaction (50 µL) contained 125 ng of the 994 bp fragment, 60 ng of the 469 bp fragment, 1× Phusion HF buffer (New England Biolabs), 50 pmol each of primers 061159 and 0611256, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute, with a final extension at 72° C. for 7 minutes. Following thermocycling, the PCR reaction product was separated by 0.8% agarose gel electrophoresis in TBE buffer where an approximately 1433 bp PCR product was excised from the gel and purified using a QIAQUICK® Gel Extraction Kit (Qiagen) according to the manufacturer's instructions.

A PCR fragment containing 5' homology to the 3' end of the 1433 bp PCR product above which includes the NotI restriction site was generated to amplify the 3' flank for the adh9091 locus using primers 0611260 and 0611261. The PCR reaction (50 µL) contained 15 ng of plasmid pHJJ27 DNA (FIG. 21) as template DNA, 1× Phusion HF buffer (New England Biolabs), 50 pmol each of primers 0611260 and 0611261, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute and 30 seconds, with a final extension at 72° C. for 7 minutes. Following thermocycling, the PCR reaction products were separated by 0.8% agarose gel electrophoresis in TBE buffer where an approximately 1019 bp PCR product was excised from the gel and purified using a QIAQUICK® Gel Extraction Kit (Qiagen) according to the manufacturer's instructions. The total length of the resulting PCR fragment is approximately 1019 bp with a NotI restriction site at the 5' end of the fragment and an ApaI restriction site at the 3' end.

The 1019 bp fragment was then fused downstream of the 1433 bp TDH3 promoter/TKL terminator fragment by PCR using primers 0611256 and 0611261 generating an approximately 2405 bp fragment. The PCR reaction (50 µL) contained 125 ng of the 1433 bp fragment, 90 ng of the 1019 bp fragment, 1× Phusion HF buffer (New England Biolabs), 50 pmol each of primers 0611256 and 0611261, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 2 minutes, with a final extension at 72° C. for 7 minutes. Following thermocycling, the PCR reaction products were separated by 0.8% agarose gel electrophoresis in TBE buffer where an approximately 2405 bp PCR product was excised from the gel and purified using a QIAQUICK® Gel Extraction Kit (Qiagen) according to the manufacturer's instructions.

The resulting 2405 bp fragment comprising the 3' flank for integration at the adh9091 locus downstream of the TDH3 promoter/TAL terminator construct was cloned into pCR2.1-TOPO vector and transformed into One-Shot TOP10 E. coli cells using a TOPO TA Cloning kit, (Invitrogen) according to the manufacturer's instructions. Transformants were plated onto 2×YT+amp plates and incubated at 37° C. overnight. Several of the resulting transformants were screened for proper insertion of the desired fragment by AvaI digestion. A clone yielding the desired band sizes was confirmed and designated pGMEr113. Plasmid pGMEr113 comprises the 3' flank for homologous recombination at the I. orientalis adh9091 locus preceded by the empty expression cassette TDH3 promoter/TKL terminator.

PCR was used to amplify the truncated 3' fragment of the URA3 ORF, the URA3 terminator, and the URA3 promoter (to serve as a repeat region for looping out of the marker after integration into the yeast host as described above) from plasmid pHJJ27 (FIG. 21) using primers 0611264 and 0611284. The PCR reaction (50 µL) contained 15 ng of plasmid pHJJ27 DNA, 1× Phusion HF buffer (New England Biolabs), 50 pmol each of primers 0611264 and 0611284, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCY- CLER® (Eppendorf Scientific) programmed for one cycle at 98° C. for 2 minutes followed by 35 cycles each at 98° C. for 30 seconds, 55° C. for 30 seconds, and 72° C. for 1 minute and 30 seconds, with a final extension at 72° C. for 7 minutes. Following thermocycling, the PCR reaction products were separated by 0.8% agarose gel electrophoresis in TBE buffer where an approximately 1324 bp PCR product was excised from the gel and purified using a QIAQUICK® Gel Extraction Kit (Qiagen) according to the manufacturer's instructions. The total length of the resulting PCR fragment was approximately 1324 bp with a NheI restriction site at the 5' end of the fragment and ApaI and SfoI restriction sites at the 3' end.

The gel-purified 1324 bp fragment above was cloned into the pCR2.1-TOPO vector and transformed into One-Shot TOP10 E. coli cells using a TOPO TA Cloning kit (Invitrogen) according to the manufacturer's instructions. Transformants were plated onto 2×YT+amp plates and incubated at 37° C. overnight. Several of the resulting transformants were screened for proper insertion of the desired insert by Hind III digestion. A clone yielding the desired band sizes was confirmed and designated pGMEr109. Plasmid pGMEr109 comprises the 3' fragment of the URA3 ORF and the URA3 terminator, followed by the URA3 promoter. The upstream portion of the 3' fragment of the URA3 gene in plasmid pGMEr109 bears a 460 bp homology with the extremity of the truncated 5' URA3 fragment cloned into plasmid pGMEr108. The region of homology allows recombination between the two portions of the gene creating a functional selection marker upon co-transformation of the host organism with the construct containing both segments.

Plasmid pGMEr109 was digested with KpnI, and treated with DNA polymerase I, large (Klenow) fragment (New England Biolabs) according to the manufacturer's instructions. The linearized pGMEr109 plasmid (containing blunt ends) was digested with Bam HI. The products were separated by 0.8% agarose gel electrophoresis in TBE buffer and the 5247 bp vector fragment was excised from the gel and purified using a QIAQUICK® Gel Extraction Kit (Qiagen) according to the manufacturer's instructions.

Plasmid pGMEr113 was digested with Bam HI and Eco RV resulting in a 2466 bp fragment bearing the construct TDH3 promoter/TKL terminator followed by the truncated 3' fragment of the URA3 ORF with the URA3 terminator, followed by the URA3 promoter. The double restriction reaction products were separated by 0.8% agarose gel electrophoresis in TBE buffer and the approximately 2466 bp vector fragment was excised from the gel and purified using a QIAQUICK® Gel Extraction Kit (Qiagen) according to the manufacturer's instructions. The 2466 bp Bam HI/Eco RV digested fragment then was ligated to the 5247 bp vector fragment from plasmid pGMEr109. The ligation reaction was set up with 3 µL of the 5247 bp linearized vector, 3 µL of the 2466 bp insert fragment, 3 µL of sterile dd water, 10 µL of 2× Quick Ligation reaction Buffer and 1 µL Quick T4 DNA Ligase (New England Biolabs), and performed according to the manufacturer's instructions.

Figure 6:
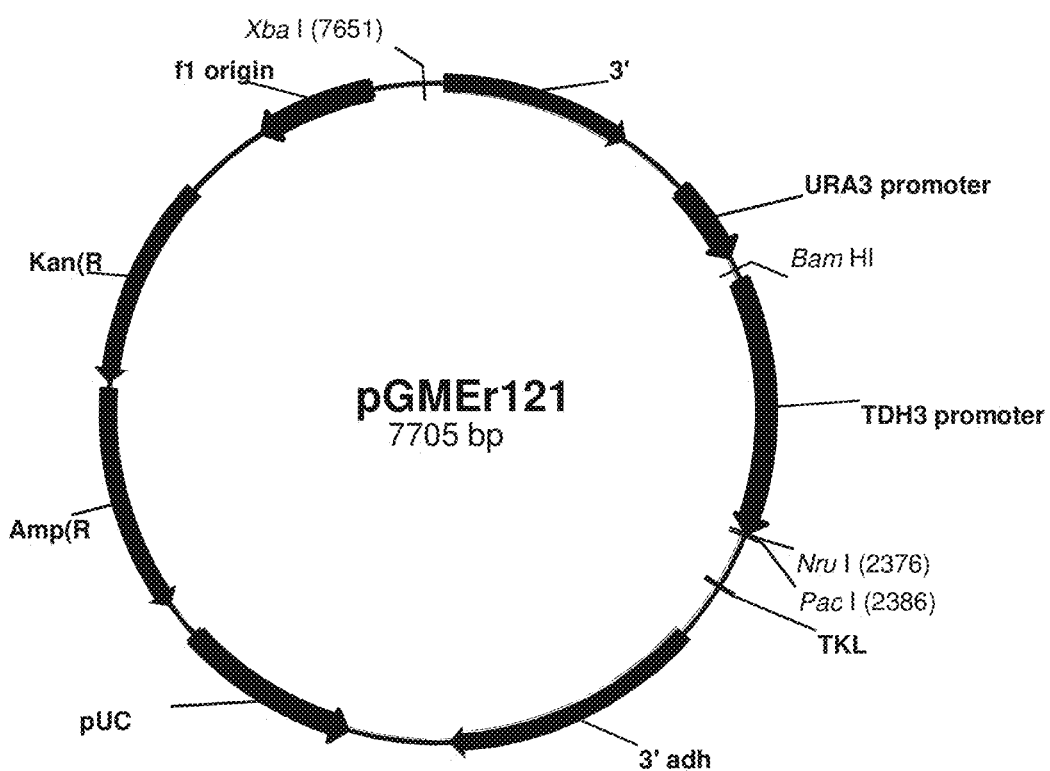
FIG. 6: Plasmid pGMEr121

Five µL of the ligation product was transformed into E. coli XL10-Gold Ultracompetent Cells (Agilent Technologies) according to the manufacturer's instructions. Transformants were plated onto 2×YT+amp plates and incubated at 37° C. overnight. Several of the resulting transformants were screened for proper insertion of the desired insert by digestion with XbaI and Pac I. A clone yielding the desired band sizes was confirmed and designated pGMEr121 (FIG. 6).

Plasmid pGMEr121 contains the 3' end of the I. orientalis URA3 marker followed by the corresponding URA3 promoter, the TDH3 promoter, the TKL terminator and the 3' flanking region of the adh9091 locus.

Example 2G: Construction of I. orientalis CNB1

I. orientalis CNB1 was constructed from I. orientalis CD1822 as described below (see Example 1A for generation of I. orientalis CD1822 from I. orientalis ATCC PTA-6658). Both copies of the URA3 gene contained in strain CD1822 were deleted to allow use of this gene as a selection marker for genetic engineering. URA3 is a versatile marker for yeast genetics due to the selection available for both the presence (by growth in uracil deficient media) and absence (by growth in the presence of 5-fluoorotic acid) of the gene. Disruption of one of the URA3 genes was done by replacement with a selection cassette containing the MEL5 selection marker flanked by repeated DNA sequences. Strains testing positive for the MEL5 selection cassette were then screened for the loss of MEL5 marker gene. Loss of the second URA3 gene was then selected for by growth in the presence of 5-fluoorotic acid.

Figure 27:
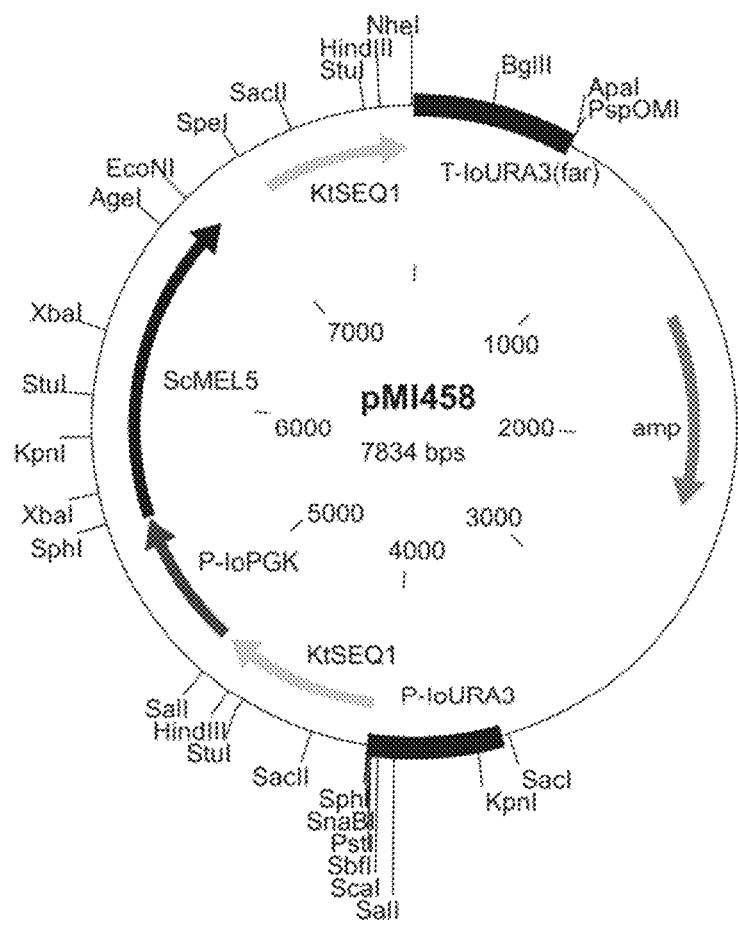
FIG. 27: Plasmid pM1458

CD1822 was transformed with 2.8 µg of Sac I/PspOMI digested DNA of vector pMI458 (FIG. 27). Plasmid pMI458 contains the S. cerevisiae MEL5 gene (SEQ ID NO: 255) under control of the I. orientalis PGK promoter (P-IoPGK, SEQ ID NO: 247), flanked by DNA fragments homologous to sequence upstream (P-IoURA3, SEQ ID NO: 253) and downstream (T-IoURA3, SEQ ID NO: 254) of the I. orientalis URA3 gene. The P-IoURA3 and T-IoURA3 fragments are in the same relative orientation as in the I. orientalis genome. Roughly 500 Mel+ colonies were obtained after five days at 30° C. Ten colonies were single colony isolated by inoculating a 10 mL BFP (Butterfields Phosphate buffer) tube and plating 25 µL onto DM1 X-α-gal plates. A single blue colony from each of the initial isolates was then picked onto YPD for further analysis.

PCR was used to screen transformants for the desired genetic events. To obtain genomic DNA for use as template in PCR screenings, cells from 1.5 mL overnight cultures were spun down in a screw-cap microcentrifuge tube and resuspended in 0.2 ml of 2% Triton X-100, 1% SDS, 100 mM NaCl, 10 mM Tris-HCl pH 8.0, 1 mM $Na_2EDTA$ pH 8.0 solution. 0.2 mL of a phenol:chloroform:isoamyl alcohol (25:24:1) mixture equilibrated with 10 mM Tris pH 8.0/1 mM EDTA (Sigma) and 0.3 g of glass beads were added. The tube was shaken for 2 minutes at full speed with a Mini-BeadBeater-8 (BioSpec). 0.2 mL of TE was added and the tube was vortexed briefly. The aqueous phase was separated by centrifugation at 16,100×g for 5 minutes. The supernatant was removed to a new tube and 1 mL of 100% ethanol added. The tube was placed at 20° C. for 30 minutes, centrifuged at 16,100×g for 5 minutes, and the liquid decanted off. The DNA was air dried and resuspended in 500 µL TE.

The PCR screen for the desired 5' cross-over was done using primers oCA405 and oCA406, which produce a 1.5 kbp product. The screen for the desired 3' cross-over was done using primers WG26 and CM647, which produce a 1.6 kbp product. Primers outside (farther upstream or downstream) the URA3 regions used to create pMI458 are oCA405 and CM647, which produce a 3.2 kbp product for the wild type, 5.0 kbp product for a pMI458 disrupted allele, and 2.2 kbp product when the selection marker has been looped out. These PCR reactions were done using a 55° C. annealing temperature. PCR was also used to screen for the loss of URA3 open reading frame using a four-primer approach. Primers pJLJ28 and pJLJ29 amplify an 800 bp fragment of the actin gene and primers pJLJ30 and pJLJ31 amplify a 600 bp fragment of the URA3 gene. Use of all the primers in one reaction provides a positive internal control (the actin fragment). Taq DNA polymerase from Roche was used as per manufacturer's protocol, with an annealing temperature of 61° C. Strains 1822ura het MEL-1 and 1822ura het MEL-2 were confirmed as having integrated the MEL5 selection cassette in the URA3 locus.

The MEL5 marker was then removed from the genomes of 1822ura het MEL-1 and 1822ura het MEL-2 by allowing recombination between the KtSEQ1a (SEQ ID NO: 256) and KtSEQ1b (SEQ ID NO: 257) sequences. The MEL+ strains were grown overnight in YPD media to an $OD_{600}$ of roughly 0.5 to 2.0. The cultures were then diluted back to an $OD_{600}$ of approximately 0.00001 in YPD medium. 200 µL of culture dilution was transferred into each well of a 96 well microtiter plate. The plates were covered with an adhesive cover and incubated in a 30° C. incubator, with maximum agitation for 6-7 hours (roughly 6 cell divisions, depending on growth rate of the strain). 100 µL from each well (approximately ~1000 cfu per plate) was plated onto DM1+ X-α-gal medium. Plates were incubated at 30° C. overnight or at room temperature for 2 days to observe color differentiation. White colonies (putative mel-) were streaked onto similar media, and screened by PCR as described above. Two independent loop-outs were found, one from 1822ura het MEL-1, saved as 1822ura het mel-1 and the other from 1822ura het MEL-2, saved as 1822ura het mel-2. Oddly, the vast majority of white colonies obtained did not give the expected band of 2.2 kbp.

To obtain ura– derivatives, 1822ura het mel-1 and 1822ura het mel-2 were grown overnight in YP5D media (YP+100 g/L Dextrose) and aliquots (0.5, 5 and 50 µL) of the overnight culture were plated on ScD-2×FOA plates. FOA-resistant colonies were streaked for single colonies and verified for the ura– phenotype by plating on ScD-ura plates. Two colonies from 1822ura het mel-2 and six colonies from 1822ura het mel-1 were picked for further analysis. These colonies were grown overnight in YPD and genomic DNA was extracted using the above phenol/chloroform method.

Figure 28:
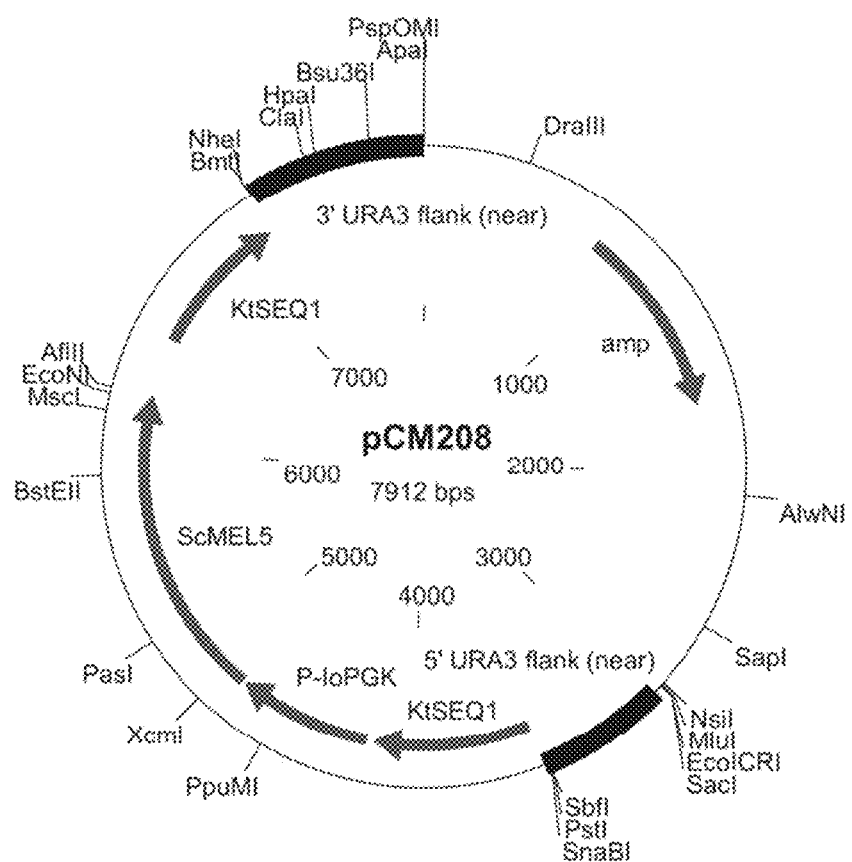
FIG. 28: Plasmid pCM208

The presence of the URA3 open reading frame was screened with PCR; none of the eight strains contained the URA3 gene. Two ura– descendents of 1822ura het mel-1 were named yJLJ3 (CNB1) and yJLJ4. Based genomic sequencing, yJLJ3 (CNB1) and yJLJ4 were determined to contain a deletion of both the URA3 gene and a nearby permease gene; preferably only the URA3 gene would be deleted. To create a ura3 auxotroph of CD1822 without disruption of this permease gene, CD1822 was transformed with 1 µg of Sac I/ApaI digested pCM208 (FIG. 28). Plasmid pCM208 contains DNA sequence homologous to the upstream (5' URA flank (near), SEQ ID NO: 258) and downstream (3' URA3 flank (near), SEQ ID NO: 259) flanking regions of the *I. orientalis* URA3 gene. Roughly 200 MeI+ colonies were obtained after five days at 30° C. Eight blue colonies were isolated by streaking on ScD X-α-gal plates. PCR was used to screen transformants for the desired genetic events. The 5' cross-over screen was done using primers oJY11 and oJY12, which produce a 0.9 kbp product in desired transformants. The 3' cross-over screen was done using primers oJY13 and oJY14, which produce a 1.0 kbp product in desired transformants. Three of eight colonies showed the desired PCR products. The MEL markers for these colonies can be looped out and the second URA3 gene deleted as described above. Alternatively, the URA3 and permease gene deletions in strains derived from yJLJ3 or yJLJ4 can be fixed in a one-step transformation, as described in Example 2H.

Figure 26:
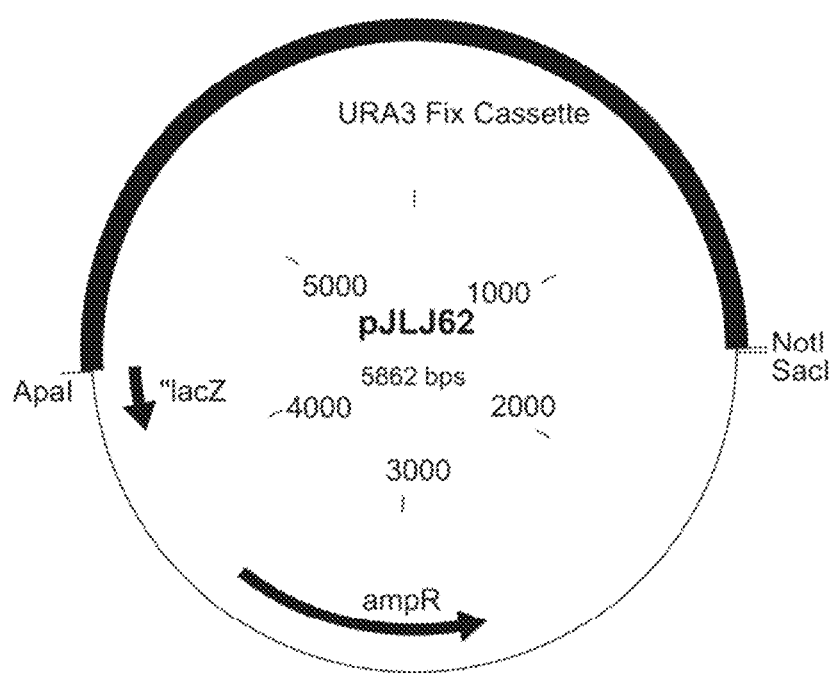
FIG. 26: Plasmid pJLJ62

Example 2H: Construction of MBin500 Control Strain Containing the URA3 Selection Marker As described supra, the *I. orientalis* strain designated CNB1 used herein was a uridine auxotroph due to the homozygous deletion of the URA3 gene. A heterozygous repair of the URA3 locus was made using the ura fix vector, pJLJ62 (FIG. 26) which contains a ura fix cassette comprised of the URA3 gene with 691 bp of 5' flanking DNA, and 1500 bp of 3' flanking DNA. The ura fix cassette is flanked by a 5' NotI restriction site and a 3' ApaI restriction site. A restriction digest using NotI and ApaI was performed to remove the 2796 bp ura fix cassette from the vector backbone. The digest was purified using a QIAquick PCR Purification kit (Qiagen) as specified by the manufacturer. The DNA was eluted in glass distilled water and 1 µg was used to transform *I. orientalis* CNB1. Transformants were selected on ura selection plates, and a single colony that does not require uridine supplementation was designated MBin500.

Example 2I: Removal of the URA3 Selection Marker

In order to isolate strains in which the URA3 selection marker gene was removed via recombination of the two URA3 promoter regions present in the integration cassettes, the ura+ strain of interest was inoculated into in 3 mL of YP+10% glucose media and grown with shaking at 250 rpm at 37° C. for at least four hours and up to overnight. 50-100 µL of the culture was plated onto ScD FOA plates and grown at 37° C. for 48-60 hours until colonies appeared. Growth on FOA selected for the removal of the URA3 marker since FOA is converted to a toxic compound by the URA3 protein, resulting in the death of ura+ cells. Several FOA-resistant colonies were purified twice by growing on YPD plates 37° C. These purified isolates were then screened for appropriate URA3 loop-out via PCR as described herein.

Example 2J: Procedure for Shake Flask Growth of Modified Yeast Strains for Sodium Dodecyl Sulfate Polyacrylamide Gel Electrophoresis (SDS-PAGE) Analysis and Enzyme Assays Four mL of ura selection media was added to a 14 mL Falcon tube and the desired strain was inoculated into this media using a sterile loop. The culture was grown with shaking at 250 rpm overnight (~16 hrs) at 37° C. For strains that have at least one wild-type copy of the *I. orientalis* locus, 500 µL of the overnight culture was added to a 125 mL baffled flask containing 25 mL of YP+10% glucose media. For pdcA/pdcA strains, 1 mL of the overnight culture was added to a 125 mL baffled flask containing 25 mL of liquid YP+100 g/L dextrose media. The flask was grown with shaking at 250 rpm at 37° C. Small aliquots of the culture were withdrawn at approximately hourly intervals and the $OD_{600}$ was measured. The culture was grown until the $OD_{600}$ was between 4 and 6.

In order to prepare a small sample of cells for SDS-PAGE analysis, a volume of culture corresponding to 2.5 OD units was taken for the culture and placed in a 1.5 mL tube. The cells were pelleted at 16,100×g, the supernatant removed, and the cell pellet stored at −20° C. until use.

The remaining cells in the growth flask were harvested by centrifugation at 2279×g at room temperature, the pellet was resuspended in 12.5 mL 0.85 M NaCl, then centrifuged at 2279×g at room temperature. The pellet was resuspended in 1 mL 0.85 M NaCl, and the resuspended cells were transferred to a 2.0 mL tube and then pelleted at 16,100×g. The supernatant was then removed and the pellet stored at −20° C. if they would be used for enzymatic assays within one week, or at −80° C. for longer term storage.

For SDS-PAGE analysis of the cell pellet corresponding to 2.5 OD units, the cells were resuspended in 100 dH$_2$O, then 100 μL 0.2 M NaOH was added. The sample was incubated at room temperature for 5 minutes, then the cells were pelleted by centrifugation at 16,100×g and resuspended in 100 μL SDS sample buffer (Bio-Rad Laboratories). The sample was heated at 95° C. for 5 minutes and cells were pelleted by brief centrifugation. 1 to 5 μL of the supernatant was analyzed on a Criterion 8-16% Pre-Cast gel (Bio-Rad Laboratories) according to the manufacturer's instructions. Bands were visualized using InstantBlue™ Coomassie-Based Staining Solution (Expedeon Protein Solutions, San Diego, Calif., USA).

Example 2K: Procedure for Shake Flask Growth of Modified Yeast Strains for Product Analysis Strains were streaked out for single colonies on Ura Selection Plates and incubated at 30° C. for 1-2 days. Seed cultures were prepared in 250 ml baffled flasks containing 50 mL CNB1 shake flask media inoculated with 1-2 colonies from the Ura Selection Plate. Seed cultures were grown for approximately 18 hours at 30° C. with shaking at 200 rpm. Small aliquots of the culture were then withdrawn to measure the OD$_{600}$ until reaching an OD$_{600}$ of 4-6. The residual glucose present was measured using an Uristix® Reagent Strip (Bayer, Elkhart, Ind., USA). The seed flask cultivation was used to inoculate 125 ml baffled flasks containing 50 mL CNB1 shake flask media to an OD$_{600}$=0.2. Cultures were incubated at 30° C. with shaking at 140 rpm for 20 hr. Samples of the broth were removed for analysis as described below. An aliquot of the sample was used to measure the optical density (OD) of the culture and residual glucose present was measured using a Uristix® Reagent Strip. The rest of the sample was then centrifuged and the supernatant used for product analysis.

Example 2L: Procedure for Fermentation of Modified Yeast Strains for Product Analysis Strains described herein are cultivated using a seed propagation stage and followed by a single stage fermentation in a 2 L bioreactor (Applikon, Foster City, Calif., USA).

For seed stage preparation 25 mL of 1×DM2 medium (adjusted to the desired pH with KOH) was added to a 125 mL baffled flask, followed by inoculation with the strain of interest using a sterile loop. The culture was grown with shaking at 250 rpm at the desired temperature overnight for approximately 16 hr. Small aliquots of the culture were then withdrawn at approximately hourly intervals to measure the OD$_{600}$ until reaching an OD$_{600}$ of 4-6.

The residual glucose present was measured using a Uristix® Reagent Strip (Bayer, Elkhart, Ind., USA). 12 mL of the culture was then added to 4 mL of sterile chilled 75% glycerol, mix thoroughly, and incubated on ice for ten minutes. The culture and glycerol mixture was then remixed and 1.0 mL was aliquoted to each of 10 sterile 1.8 mL cryovials (Thermo Scientific, Rochester, N.Y., USA) and stored at −80° C.

25 mL of the seed flasks cultivation was used to inoculate the 2 L bioreactor containing 1.5 L of DM2 medium. The fermentation in the bioreactor was performed at a temperature of about 30° C.-40° C., with the pH controlled in the range of about 2.0-7.0 and under agitation and aeration conditions that lead to an oxygen uptake rate (OUR) in the range of 2-45 mmol/L/hr. In the examples presented herein, the temperature, pH and OUR for the culture in the bioreactor were 30° C., 4.0 and 25-30, respectively.

Samples of the fermentation broth were removed periodically for analysis. Briefly, an aliquot of the sample was used to measure the optical density (OD) of the culture, the glucose concentration and pH. The rest of the sample was then centrifuged. The pellet was stored at −80° C. for enzyme assays, and the supernatant was used for analysis of 3-HP and other extracellular compounds All 3-HP production values reported herein are for the 48-hour time point in the fermentation unless specified otherwise. Carbon dioxide production and oxygen consumption during the fermentation process were measured by determining the carbon dioxide content and oxygen content of the gasses vented from the bioreactor.

Example 2M: Procedure for Analysis of 3-HP and β-Alanine Produced by Modified Yeast Strains Culture samples were acidified by 10× dilution into 1% formic acid and filtered through a 0.46 μm 96-well filter plate. Further dilution was made in water depending on analyte concentration in the sample. A further 10× dilution was made in a sample buffer of 1 mM NH$_4$Ac, 0.1% NH$_3$ and 5 mg/L of $^{13}$C uniformly labeled 3-HP (as internal standard for 3-HP), or 1% formic acid and 3 mg/L of $^{13}$C uniformly labeled β-alanine (as internal standard for β-alanine). The total dilution factor was approximately 100 to 1000 was used depending on the concentrations of β-alanine or 3-HP.

A 2 μL sample was injected into an Agilent 1200 HPLC (Agilent) controlled by MassHunter program with an Agilent 6410 Triple Quad MS/MS detector using the instrument settings and columns listed in Table 6. The ratio of the quantifying ion fragment peak area to its stable isotope counterpart (from internal standard) was used for quantification to eliminate ion suppression effect and instrument drifting. Standard deviation was below 5% from day to day assays.

TABLE 6

| LC/MS/MS Settings for β-Alanine and 3-HP analysis | | |
|---|---|---|
| | 3-HP ($^{13}$C 3-HP) | β-Alanine ($^{13}$C β-Alanine) |
| Column | Xbridge HILIC Silica 3.5 μm, 2.1 × 150 mm | Atlantis HILIC Silica 3 μm 2.1 × 150 mm |
| Elution buffer | 62% acetonitrile, 0.35 mM NH$_4$Ac | 38% acetonitrile, 0.6% formic acid |
| Flow rate (mL/min) | 0.30 | 0.30 |
| Column temperature | 50° C. | 45° C. |
| Retention time (mm) | 1.07 | 1.64 |
| Run time (min) | 3 | 3 |
| Pre-cursor ion | 89 (92) | 90 (93) |
| Product ion as quantifier | 59 (61) | 72 (75) |

TABLE 6-continued

LC/MS/MS Settings for β-Alanine and 3-HP analysis

|  | 3-HP ($^{13}$C 3-HP) | β-Alanine ($^{13}$C β-Alanine) |
|---|---|---|
| Product ion as qualifier | 41 (43) | 30 (31) |
| Fragmentor Voltage | 50 | 70 |
| Collision energy | 5 for quantifier; 21 for qualifier | 3 for quantifier; 7 for qualifier |
| Polarity | Negative | Positive |
| Nebulizer N$_2$ pressure(psi) | 10 | 11 |
| N$_2$ flow (L/min) | 32 | 35 |
| N$_2$ temperature | 300° C. | 340° C. |
| Capillary (V) | 4000 | 4000 |
| Delta EMV | 450 | 400 |

Example 3: Modified Yeast Strains Expressing 3-HP Fermentation Pathway Genes One or more genes encoding enzymes involved in various 3-HP fermentation pathways can be expressed, either alone or in combination, in yeast host cells. The 3-HP pathway enzymes may be expressed from exogenous genes, endogenous genes, or some combination thereof. Exogenous genes to be expressed may be introduced into the yeast cell using gene expression constructs, e.g., expression constructs described in Example 2. Exogenous genes may be integrated into the host yeast genome at a single site or at multiple locations, and integration of the exogenous gene may be coupled with deletion or disruption of a target gene at the insertion site as described below.

Example 3A: Modified Yeast Strains Expressing Aspartate/Malonate Semialdehyde Pathway Genes Yeast cells that produce 3-HP via a pathway that utilizes PEP and/or pyruvate, OAA, aspartate, β-alanine, and malonate semialdehyde intermediates can be engineered by expressing one or more enzymes involved in the pathway. The expressed genes may include one or more of a PPC, PYC, AAT, ADC, BAAT, gabT, 3-HPDH (including malonate semialdehyde reductase), HIBADH, or 4-hydroxybutyrate dehydrogenase gene.

The expressed genes may be derived from a gene that is native to the host cell. For example, where the yeast host cell is *I. orientalis*, expressed genes may be derived from an *I. orientalis* PYC (e.g., *I. orientalis* PYC gene encoding the amino acid sequence set forth in SEQ ID NO: 2 and/or comprising the coding region of the nucleotide sequence set forth in SEQ ID NO: 1), AAT (e.g., *I. orientalis* AAT gene encoding the amino acid sequence set forth in SEQ ID NO: 14 and/or comprising the coding region of the nucleotide sequence set forth in SEQ ID NO: 13), BAAT (e.g., *I. orientalis* pyd4 homolog gene encoding the amino acid sequence set forth in SEQ ID NO: 20 and/or comprising the coding region of the nucleotide sequence set forth in SEQ ID NO: 19), or 3-HPDH (e.g., *I. orientalis* homolog to the YMR226C gene encoding the amino acid sequence set forth in SEQ ID NO: 26 and/or comprising the coding region of the nucleotide sequence set forth in SEQ ID NO: 25) gene. Where the yeast host cell is another 3-HP tolerant yeast strain, gene sequences can be obtained using techniques known in the art and the native homologs for pathways genes can be expressed exogenously or in conjunction with exogenous regulatory elements. Native pathway genes may include one or more PPC, PYC, AAT, BAAT, and/or 3-HPDH genes.

Alternatively, one or more of the expressed 3-HP genes may be derived from a source gene that is non-native to the host cell. For example, where the yeast host cell is *I. orientalis*, the cell may be engineered to express one or more non-native PYC genes such as an *R. sphaeroides* PYC gene encoding the amino acid sequence of SEQ ID NO: 3, an *R. etli* PYC gene encoding the amino acid sequence of SEQ ID NO: 4, a *P. fluorescens* PYC gene encoding the amino acid sequence of SEQ ID NOs: 5 or 6, a *C. glutamicum* PYC gene encoding the amino acid sequence of SEQ ID NO: 7, or an *S. meliloti* PYC gene encoding the amino acid sequence of SEQ ID NO: 8; one or more non-native PPC genes such as an *E. coli* PPC gene encoding the amino acid sequence of SEQ ID NO: 10, an *M. thermoautotrophicum* PPC gene encoding the amino acid sequence of SEQ ID NO: 11, or a *C. perfringens* PPC gene encoding the amino acid sequence of SEQ ID NO: 12; one or more non-native AAT genes such as an *E. coli* aspC gene encoding the amino acid sequence of SEQ ID NO: 16 or an *S. cerevisiae* AAT2 gene encoding the amino acid sequence of SEQ ID NO: 15; one or more non-native ADC genes such as an *S. avermitilis* panD gene encoding the amino acid sequence of SEQ ID NO: 17 (and/or comprising the coding region of the nucleotide sequence set forth in any one of SEQ ID NOs: 130, 145, 146, or 147), a *C. acetobutylicum* panD gene encoding the amino acid sequence of SEQ ID NO: 18 (and/or comprising the coding region of the nucleotide sequence set forth in SEQ ID NO: 131), an *H. pylori* ADC gene encoding the amino acid sequence of SEQ ID NO: 133 (and/or comprising the coding region of the nucleotide sequence set forth in SEQ ID NO: 132), a *Bacillus* sp. TS25 ADC gene encoding the amino acid sequence of SEQ ID NO: 135 (and/or comprising the coding region of the nucleotide sequence set forth in SEQ ID NO: 134), a *C. glutamicum* ADC gene encoding the amino acid sequence of SEQ ID NO: 137 (and/or comprising the coding region of the nucleotide sequence set forth in SEQ ID NO: 136), or a *B. licheniformis* ADC gene encoding the amino acid sequence of SEQ ID NO: 139 (and/or comprising the coding region of the nucleotide sequence set forth in any one of SEQ ID NOs: 138, 148, 149, 150, or 151); one or more non-native BAAT or gabT genes such as an *S. kluyveri* pyd4 gene encoding the amino acid sequence of SEQ ID NO: 21 (and/or comprising the coding region of the nucleotide sequence set forth in SEQ ID NO: 142), an *S. avermitilis* BAAT gene encoding the amino acid sequence of SEQ ID NO: 22 (and/or comprising the coding region of the nucleotide sequence set forth in SEQ ID NO: 140), an *S. avermitilis* gabT gene encoding the amino acid sequence set forth in SEQ ID NO: 23, or an *S. cerevisiae* UGA1 gene encoding the amino acid sequence set forth in SEQ ID NO: 24 (and/or comprising the coding region of the nucleotide sequence set forth in SEQ ID NO: 141); one or more non-native 3-HPDH genes such as an *E. coli* ydfG gene encoding the amino acid sequence of SEQ ID NO: 27 (and/or comprising the coding region of the nucleotide sequence set forth in SEQ ID NO: 143) or an *S. cerevisiae* YMR226C gene encoding the amino acid sequence of SEQ ID NO: 129 (and/or comprising the coding region of the nucleotide sequence set forth in SEQ ID NO: 144); one or more non-native malonate semialdehyde reductase genes such as an *M. sedula* malonate semialdehyde reductase gene encoding the amino acid sequence set forth in SEQ ID NO: 29 (and/or comprising the coding region of the nucleotide sequence set forth in SEQ ID NO: 343); one or more non-native HIBADH genes such as an *A. faecalis* M3A gene encoding the amino acid sequence set forth in SEQ ID NO: 28, a *P. putida* KT2440 or E23440 mmsB gene encoding the amino acid sequence set forth in SEQ ID NO: 30 or SEQ ID NO: 31, respectively, or a *P. aeruginosa* PAO1 mmsB gene encoding the amino acid sequence set forth in SEQ ID NO: 32; and/or one or more non-native 4-hydroxybutyrate dehydrogenase genes such as an *R. eutropha* H16 4hbd gene encoding the amino acid sequence set forth in SEQ ID NO: 33 or a *C. kluyveri* DSM 555 hbd gene encoding the amino acid sequence set forth in SEQ ID NO: 34.

Example 3A-0: Enzymatic Activity Assays for Modified Yeast Strains Expressing Aspartate/Malonate Semialdehyde Pathway Genes Preparation of Crude Cell-Free Extracts (CFE) for Enzyme Assays:

The indicated cells herein from shake flask or bioreactor cultures were collected by centrifugation, the supernatant discarded, and the cell pellet stored at −80° C. as described above. For preparation of CFE, the cells pellets were thawed, washed with phosphate-buffered saline (PBS) and again collected by centrifugation. The supernatant was discarded and the cell pellet was resuspended in an approximately equal volume of lysis buffer containing 1% Protease Inhibitor Cocktail, P8215 from Sigma) in 2.0 mL microcentrifuge tubes. Approximately 300 μL of 0.5 mm zirconia beads (BioSpec) were added, and cell lysis was performed on FastPrep)-24 disruptor (MP Biomedicals) for 3 rounds at setting $^6/_{20}$ seconds. Sample tubes were cooled on ice for 5 minutes between each round. After lysis, the samples were centrifuged at maximum speed in a microcentrifuge for 15 minutes at 4° C. The supernatants were transferred to fresh 1.5 mL tubes and kept on ice. Total protein concentrations in the lysates were determined using the Bio-Rad protein assay reagent (Bradford assay) and bovine serum albumin as the standard, according to the instructions provided by the manufacturer.

Pyruvate Carboxylase (PYC) Activity:

Pyruvate carboxylase activity in CFE of the indicated cells herein was determined as follows. A stock reaction mix solution was prepared that, when combined with CFE in the assay reaction mixture, provides the following final concentration of components: Tris (pH 8.0), 100 mM; NaHCO$_3$, 10 mM; MgCl$_2$, 5 mM; NADH, 0.2 mM; ATP, 1 mM; acetyl CoA, 1 mM; pyruvate, 1 mM; biotin (if required by the PYC enzyme being assayed), 5 μM; bovine heart malate dehydrogenase, 0.02 units/mL. 270 μL of this mixture was added to the wells of a 96-well microtiter plate and 30 μL of an appropriately diluted CFE was added to start the reaction. Consumption of NADH was monitored at 340 nm using a SpectraMax 340 PC plate reader. Pyruvate carboxylase activity is expressed as nmoles NADH consumed/sec/mg protein.

Phosphoenolpyruvate Carboxylase (PPC) Activity:

Phosphoenolpyruvate Carboxylase (PPC) activity in CFE may be determined as follows. A stock reaction mix solution is prepared that, when combined with CFE in the assay reaction mixture, provides the following final concentration of components: Tris (pH 8.0), 100 mM; NaHCO$_3$, 10 mM; MgCl$_2$, 5 mM; NADH, 0.1 mM; acetyl CoA, 0.5 mM; phosphoenolpyruvate, 3.3 mM; bovine heart (or porcine heart) malate dehydrogenase, 0.02 units/mL. 270 μL of this mixture is added to the wells of a 96-well microtiter plate and 30 μL of an appropriately diluted CFE is added to start the reaction. Consumption of NADH is monitored at 340 nm using a SpectraMax 340 PC plate reader.

Aspartate Aminotransferase (AAT) Activity:

Aspartate aminotransferase activity in CFE of the indicated cells herein was determined as follows. A stock reaction mix solution was prepared that, when combined with CFE in the assay reaction mixture, provides the following final concentration of components: 100 mM Tris (pH 8.0), 100 mM; NaHCO$_3$, 10 mM; MgCl$_2$, 5 mM; NADH, 0.1 mM; aspartate, 1 mM; α-ketoglutarate, 1 mM; and malate dehydrogenase, 0.02 units/mL. In some assays, the stock reaction mixture also contained pyridoxal 5'-phosphate (0.1 mM). 270 μL of this mixture was added to the wells of a 96-well microtiter plate and 30 μL of an appropriately diluted CFE was added to start the reaction. Consumption of NADH was monitored at 340 nm using a SpectraMax 340 PC plate reader. Aspartate aminotransferase activity is expressed as nmoles NADH consumed/sec/mg protein.

Aspartate Decarboxylase (ADC) Activity:

Aspartate Decarboxylase activity in CFE of the indicated cells herein was determined as follows. 165 μL of 100 mM NH$_4$Ac buffer (pH 6.8), and 25 μL of 80 mM aspartate were added to each well of a 96-well mictotiter plate thermostatted at 37° C. The reaction was initiated by adding 10 μL of CFE. At different time intervals (5, 10, 15, 20, 25, 30, 40, 60 minutes), 20 μL of sample was withdrawn from the reaction mixture and added to 180 μL of quenching buffer (2% formic acid plus 2 mg/L of $^{13}$C labeled β-Alanine as internal standard). After filtration, β-Alanine in the sample was analyzed by LC/MS/MS. Slopes were obtained from β-Alanine vs time plots. Activity was calculated by dividing the slope by total cellular protein concentration in the reaction. ADC activity is expressed as pmoles β-alanine formed/sec/g protein.

A modified ADC assay was used in some experiments. In these cases, ADC activity in CFE of the indicated cells herein was determined as follows. 110 μL of 100 mM NH$_4$Ac buffer (pH 7.6), and 80 μL of 25 mM aspartate (after neutralizing with NaOH) were added to each well of a 96-well mictotiter plate thermostatted at 40° C. The reaction was initiated by adding 10 μL of CFE. At different time intervals (2, 4, 6, 8, 10 minutes), 20 μL of sample was withdrawn from the reaction mixture and added to 180 μL of quenching buffer (2% formic acid with 2 mg/L of $^{13}$C labeled β-Alanine as internal standard or quenched in 2% formic acid and then transferred 1:10 into 20% methanol/ 80% water with 2 mg/L of $^{13}$C labeled β-Alanine as internal standard). After filtration, β-Alanine in the sample was analyzed by LC/MS/MS. Slopes were obtained from β-Alanine vs time plots. Activity was calculated by dividing the slope by total cellular protein concentration in the reaction. ADC activity is expressed as pmoles β-alanine formed/sec/g protein.

β-Alanine Aminotransferase (BAAT) Activity:

β-Alanine aminotransferase (BAAT) activity in CFE was determined as follows. 190 μL of a reaction mixture containing 100 mM of NH$_4$HCO$_3$ (pH 7.6), 8 mM α-ketoglutarate, 0.5 mM acetyl-CoA, 0.1 mM pyridoxal-5'-phosphate, and 200 mM β-alanine was added to a 96 well microtiter plate at room temperature. The reaction was initiated by adding 10 μL of CFE. Samples of 20 μL each were taken at 2, 4, 6, 8, 10, 12, 15, and 20 minutes and added to 75 μL of quenching buffer (2.5% formic acid). Samples were neutralized and pH controlled by adding 5 μl 10 M NaOH and 50 μl 100 mM NaCO$_3$ (pH 10). Filtered samples were derivatized by mixing, at injection, with OPA (o-phthaldialdehyde) reagent, 10 mg/mL (Agilent Technologies 5061-3335). Glutamate derivatized with OPA was quantified after HPLC separation by fluorescence detection (excitation at 340 nm; emission at 460 nm). Samples of 15 μL were injected onto an analytical reverse phase Gemini C18 column with 5 μm packing (Phenomonex 150×4.6 mm). The column was equilibrated in 62.5% 20 mM phosphate buffer (pH 7.8) (A) and 37.5% methanol (B). Linear gradients were as follows: ramp to 40% B, 0-0.3 min; 40% B, 0.3-1 min; ramp to 85% B, 1-1.75 min; 85% B, 1.75-2.25 min; ramp to 37.5%, 2.25-3 min; 37.5% B, 3-4 min. The flow rate was 2 mL/min. Standard curves of glutamate in reaction buffer were used to determine the concentration of the samples. Slopes were obtained from [glutamate] vs time plots. Activity was calculated by dividing the slope with total cellular protein concentration in the reaction.

3-HP Dehydrogenase (3-HPDH) Activity:

3-HP dehydrogenase activity in CFE of the indicated cells herein was determined as follows. 190 μL of diluted (typically a 100× dilution) CFE in 100 mM of $NH_4HCO_3$ (pH 7.6) and NADPH were added to each well of a 96-well mictotiter plate thermostatted at 37° C. The reaction was initiated by adding 10 μL of 60 mM malonate semialdehyde (MSA, freshly prepared in 10 mM $H_2SO_4$ from 200 mM MSA stock solution in 10 mM $H_2SO_4$). Samples of 20 μL each were taken at 1, 2, 4, 6, 8, 10, and 12 minutes, and quenched in 80 μL of boiling water. After cooling, mix 75 μL of quenched mixture with 75 μL of buffer containing 2 mM $NH_4Ac$ (pH 6.8) and 3 mg/L of $^{13}C$ labeled 3-HP. After filtration, 3-HP in the sample was quantified by LC/MS/MS. Slopes were obtained from 3-HP vs time plots. Activity was calculated by dividing the slope by total cellular protein concentration in the reaction. 3-HP dehydrogenase activity is expressed as nmoles NADPH formed/sec/mg protein.

A modified 3-HPDH assay was used in some experiments. In these cases, 3-HPDH activity in CFE of the indicated cells herein was determined as follows. Malonate semi-aldehyde reduction was measured by following the disappearance of the NADPH over time at 340 nm. Malonate semi-aldehyde was synthesized in-house according to the protocol developed by Yamada and Jacoby (Yamada, E. W., Jacoby, W. B., 1960, Direct conversion of malonic semialdehyde to acetyl-coenzyme A, Journal of Biological Chemistry, Volume 235, Number 3, pp. 589-594). The assay was conducted in a 96 well micro-plate, and the final volume was 200 μL. The reaction was started by adding 30 μL of CCE into 170 μL of assay buffer (2 mM malonate semi-aldehyde, 100 mM Tris pH 8.0 and 0.5 mM NADPH). Absorbance at 340 nm was followed on a micro-plate reader (Spectra Max 340PC, Molecular Devices LLC, Sunnyvale, Calif.) for 10 minutes at room temperature (~25° C.). One unit of 3-HPDH activity is defined as the amount of enzyme necessary to oxidize 1 pmol of NADPH in one minute in the presence of malonate semi-aldehyde.

Example 3A-1: Insertion Vectors for Expressing Aspartate Decarboxylase (ADC) at the Adh1202 Locus Several aspartate decarboxylase genes were codon-optimized for expression in *I. orientalis* and synthesized by GeneArt® (Burlingame, Calif., USA) resulting in the plasmids listed in the Table 7. The synthetic genes arrived in the vector pMA-T and can be elicited from the vector via XbaI and PacI restriction digest. The restriction fragment can then be cloned into the same sites in pMIBa107 placing the gene under the control of the PDC proMt pr terminator, and allowing integration to occur at the *I. orientalis* adh1202 locus.

TABLE 7

Transformant constructs

| Construction Plasmid | Gene Source | Gene Number | Gene SEQ ID NO | Integration construct | Transformant |
|---|---|---|---|---|---|
| 1051387 | *Helicobacter pylori* | P56065 | 132 | pWTY10-0033-1 | yWTY1-1 yWTY1-2 |
| 1051391 | *Bacillus* sp. TS25 | ZY440006.gene3 | 134 | pWTY10-0033-2 | yWTY1-5 yWTY1-6 |
| 1051389 | *Corynebacterium glutamicum* | Q9X4N0 | 136 | pWTY10-0033-3 | yWTY1-9 yWTY1-10 |
| 1051388 | *Clostridium acetobutylicum* | P58285 | 131 | pWTY10-0033-4 | yWTY1-13 yWTY1-14 |
| 1051390 | *Bacillus licheniformis* | Q65I58 | 138 | pWTY10-0033-5 | yWTY1-17 yWTY1-18 |
| 1045172 | *Streptomyces avermitilis* | | 130 | pWTY10-0033-7 | yWTY1-25 yWTY1-26 |

Plasmids 1045172, 105387, 105388, 105389, 105390, and 105391 were digested with XbaI and PacI and run on a 1.3% agarose gel using TBE buffer. Fragments of 400-500 bp from each digest corresponding to the ADC (panD) gene were excised from the gel and extracted from the agarose using a QIAQUICK® Gel Extraction Kit (Qiagen).

Plasmid pMIBa107 was digested with XbaI and PacI, treated with calf intestinal phosphatase (New England Biolabs) and the vector band purified after agarose gel electrophoresis in TBE buffer. The XbaI and PacI digested panD fragments were ligated into this purified pMIBa107 vector using T4 DNA ligase and a Quick ligation kit (New England Biolabs) according to the manufacturer's instructions. The ligation products were transformed into XL10-GOLD ULTRA cells (Agilent Technologies) according to manufacturer's instructions. Transformants were plated onto 2×YT+amp plates and incubated at 37° C. overnight. Twenty-four transformants from each reaction were picked to 2×YT+amp plates. Mini-prep DNA from four each of the resulting transformants was screened by ApaI, NcoI and SacI digestion. Clones yielding the desired band sizes were confirmed to be correct by DNA sequencing and were designated as shown in Table 7. The resulting plasmids allow integration of each ADC gene at the adh1202 locus with the expression cassette oriented in the forward direction.

Approximately 10 μg each of each integration construct was digested with ApaI and KpnI and run on a 1% agarose gel using 89 mM Tris base-89 mM Boric Acid-2 mM disodium EDTA (TBE) buffer. Fragments of approximately 4450 bp for each plasmid were excised from the gel and extracted using the QIAquick gel extraction kit (Qiagen) according to the manufacturer's instructions. The concentration of the purified products was found to be between 39-138 ng/ul. 0.39-1.4 µg of the fragments from the integration constructs (digested with ApaI and Kpn I) were transformed into *I. orientalis* CNB1 as described above. Transformants were plated onto ura selection media and incubated at 37° C., re-streaked onto ura selection media, and incubated at 37° C. overnight. Genomic DNA was prepared from the URA3+ colonies and checked by PCR to confirm integration. Primers 0611718 and 0611632 were used to amplify a 2.5 kbp fragment to confirm integration. Each PCR reaction contained 2.5 µL of genomic DNA, 12.5 pM each of primers 0611718 and 0611632, 1× Crimson Taq™ Reaction Buffer (New England Biolabs), 0.2 mM dNTP mix, 0.625 Units Crimson TaqgT DNA polymerase (New England Biolabs) in a final volume of 25 µL. The amplification reactions were incubated in an EPPENDORF® MASTERCYCLER® (Eppendorf Scientific) programmed for 1 cycle at 95° C. for 30 seconds; 30 cycles each at 95° C. for 30 seconds, 50° C. for 30 seconds, and 68° C. for 3 minutes; and 1 cycle at 68° C. for 10 minutes.

Two URA3+ confirmed transformants for each construct were designated as shown in Table 7. These strains are heterozygous at the adh1202 for the indicated ADC gene with expression driven by the PDC promoter and terminator from *I. orientalis*.

PanD expression and enzyme activity from strains listed in Table 7 (and strain MBin500, supra, as negative control) was tested. Overnight cultures of each strain were grown overnight in YPD ON at 37° C., diluted 1:50 into 25 mL of fresh YPD in 125 mL baffled flask at 37° C., and grown to an $OD_{600}$ ~2-8. The cell pellets were then used to prepare CFE, which was then assayed for ADC activity as described supra. Representative results are shown in Table 8.

25 that yielded a PCR fragment of 1100 bp with primers 0611718 and 0611632 were designated MIBa331 and MIBa332, respectively.

10 µg each of pWTY10-0033-5 and pWTY10-0033-7 were digested with ApaI, KpnI, and NcoI and run on a 1% agarose gel using 89 mM Tris base-89 mM Boric Acid-2 mM disodium EDTA (TBE) buffer. Fragments of approximately 4450 bp for each plasmid were excised from the gel and extracted using a QIAQUICK® Gel Extraction Kit (Qiagen). The purified fragments from pWTY10-0033-5 and pWTY10-0033-7 were transformed into MIBa331 and MIBa332, respectively as described above. Transformants were plated onto ura selection media and incubated overnight at 37° C., and then re-streaked onto ura selection media and incubated at 37° C. overnight. Genomic DNA was prepared and Crimson Taq™ PCRs were run to confirm integration as described above. Primers 0611718 and 0611632 amplify a 2.4 kbp fragment for integration with the ura marker present, and amplify a 1100 bp fragment in the absence of the ura marker. Transformants of MIBa331 and MIBa332 that yielded PCR fragments of 1100 bp and 2.4 kbp with primers 0611718 and 0611632 were saved and designated MIBa338 and MIBa337, respectively. MIBa337 is homozygous for ADC gene from *S. avermitilis* at the adh1202 loci and MIBa338 is homozygous for the ADC gene from *B. licheniformis* at the adh1202 loci. Both strains have the control of the respective ADC gene under the PDC promoter and terminator from *I. orientalis*.

ADC expression and enzyme activity from the panD homozygous strains MIBa337 and MIBa338 were compared to the heterozygous panD strains yWTY5-17 and yWTY7-25. Cultures were grown in YPD overnight at 37° C., and then diluted 1:50 into 25 mL of fresh YPD in 125 mL baffled flasks at 37° C. and grown to an $OD_{600}$ ~2-8. The cell pellets were used to prepare CFE, which was then assayed for ADC activity as described above. Representative results for two independent experiments are shown in Table 9A.

TABLE 8

Transformant enzyme activity data

| Strain | Source of ADC Gene | Gene SEQ ID NO | ADC activity |
|---|---|---|---|
| MBin500 (control) | N/A | N/A | 0 |
| yWTY1-1 | *Helicobacter pylori* | 132 | 0 |
| yWTY1-2 | | | |
| yWTY2-5 | *Bacillus* sp. TS25 | 134 | 0.31 |
| yWTY2-6 | | | 0.15 |
| yWTY3-9 | *Corynebacterium glutamicum* | 136 | 0.31 |
| yWTY3-10 | | | 0.19 |
| yWTY4-13 | *Clostridium acetobutylicum* | 131 | 0.37 |
| yWTY4-14 | | | 0.23 |
| yWTY5-17 | *Bacillus licheniformis* | 138 | 0.56 |
| yWTY5-18 | | | 0.61 |
| yWTY7-25 | *Streptomyces avermitilis* | 130 | 0.23 |
| yWTY7-26 | | | 0.30 |

Next, homozygous versions of yWTY5-17 and yWTY7-25 were created. First, ura− derivatives yWTY5-17 and yWTY7-25 were isolated as described above. Genomic DNA was prepared from the FOA-resistant colonies and checked by PCR as describe above to confirm loss of the URA3 selectable marker. Primers 0611718 and 0611632 were used to amplify a 2.4 kbp fragment for integration with the ura marker present and 1100 bp fragment in the absence of the ura marker. Ura− strains of yWTY5-17 and yWTY7-

TABLE 9A

Transformant enzyme activity data

| Strain | Source of panD Gene | Allele Type | Gene SEQ ID NO | ADC activity (Exp. 1, Exp. 2) |
|---|---|---|---|---|
| MBin500 (control) | N/A | N/A | N/A | 0, 0 |
| yWTY5-17 | *Bacillus licheniformis* | heterozygous | 138 | 0.6, 0.29 |
| MIBa338 | *Bacillus licheniformis* | homozygous | 138 | 0, 0.22 |
| yWTY7-25 | *Streptomyces avermitilis* | heterozygous | 130 | 0.19, 0.13 |
| MIBa337 | *Streptomyces avermitilis* | homozygous | 130 | 0.28, 0.19 |

The results of a third independent experiment to compare ADC activity in CFE prepared from strains MIBa337 and MIBa338 are shown in Table 9B.

TABLE 9B

Transformant enzyme activity data

| Strain | Source of panD gene | Allele type | Gene SEQ ID NO | ADC activity |
|---|---|---|---|---|
| MBin500 (control) | N/A | N/A | N/A | 0 |

TABLE 9B-continued

Transformant enzyme activity data

| Strain | Source of panD gene | Allele type | Gene SEQ ID NO | ADC activity |
|---|---|---|---|---|
| yWTY5-17 | Bacillus licheniformis | heterozygous | 138 | 0.218 |
| MIBa338 | Bacillus licheniformis | homozygous | 138 | 0.453 |
| yWTY7-25 | Streptomyces avermitilis | heterozygous | 130 | 0.087 |
| MIBa337 | Streptomyces avermitilis | homozygous | 130 | 0.188 |

SDS-PAGE analysis of the samples above indicated that panD expression from MIBa338 was the highest among these strains.

Strains MBin500, MIBa337 and MIBa338 were evaluated in bioreactors for 3-HP production, using the method described herein. Control strain MBin500 produced no detectable 3-HP (average of two independent fermentations). Strain MIBa337 produced 1.33 g/L 3-HP (one fermentation performed) and strain MIBa338 produced 3.15 g/L 3-HP (average of three independent fermentations). Individual fermentations of strains MIBa337 and MIBa338 were further compared with respect to their 3-HP production performance and ADC activity (Table 10). In order to account for differences in cell mass in these fermentations, the 3-HP production performance is reported in Table 10 as 3-HP concentration per unit of cell mass (expressed as [g/L 3-HP]/[g/L dry cell weight]). The results show the improved ADC activity and 3-HP production performance when using the Bacillus licheniformis panD gene (strain MIBa338) vs. the Streptomyces avermitilis panD gene (strain MIBa337).

TABLE 10

3-HP production performance and ADC activity in strains MIBa337 and MIBa338

| | MIBa337 | | MIBa338 | |
|---|---|---|---|---|
| Fermentation time (hr) | ADC Activity (mmol/min/ g prot) | 3HP/DCW | Activity (mmol/min/ g prot) | 3HP/DCW |
| 11 | 0.005 | 0.00 | 0.021 | 0.024 |
| 22 | 0.011 | 0.05 | 0.055 | 0.131 |
| 31 | 0.003 | 0.04 | 0.029 | 0.159 |
| 48 | 0.001 | 0.05 | 0.018 | 0.142 |

Example 3A-2: Insertion Vectors for Expressing β-Alanine Aminotransferase (BAAT) or 3-Hydroxypropionic Acid Dehydrogenase (3-HPDH) at the Adh1202 Locus I. orientalis codon-optimized versions of BAAT from S. avermitilis, UGA1 from S. cerevisiae, PYD4 from S. kluyveri, YMR226c from S. cerevisiae, and ydfG from E. coli were synthesized by GeneArt® resulting in the plasmids listed below. The synthetic genes arrived in the vector pMA-T and can be elicited from the vector via digest using XbaI and Pac I. The digested fragment can then be cloned into the same sites in pMIBa107, placing the gene under the control of the PDC promoter and terminator and allowing integration to occur at the adh1202 locus.

TABLE 11

Transformant constructs

| Construction Plasmid | Gene | Gene Source | SEQ ID NO | Integration construct | Transformant |
|---|---|---|---|---|---|
| 1045169 | gabT (UGA1) | S. cerevisiae | 141 | pMIBa122 | MIBa310 |
| 1045170 | BAAT | S. avermitilis | 140 | pMIBa121 | MIBa309 |
| 1045171 | BAAT (PYD4) | S. kluyveri | 142 | pMIBa124 | MIBa312 |
| 1045173 | 3-HPDH (YMR226C) | S. cerevisiae | 144 | pMIBa123 | MIBa311 |
| 1045168 | 3-HPDH (ydfG) | E. coli | 143 | pMIBa120 | MIBa308 |

Plasmids 1054168, 1054169, 1054170, 1054171, 1054172, and 1054173 were digested with XbaI and PacI and run on a 1% agarose gel using 89 mM Tris base-89 mM Boric Acid-2 mM disodium EDTA (TBE) buffer. Fragments of 761 (ydfG) bp from 1045168, 1430 (UGA1) bp from 1045169, 1370 (BAAT) bp from 1045170, 1442 (PYD4) bp from 1045171, or 814 (YMR226c) bp from 1045173 were excised from the gel and extracted from the agarose using a QIAQUICK® Gel Extraction Kit (Qiagen). Plasmid pMIBa107 was digested with XbaI and PacI followed by treatment with CIP resulting in a 7.9 kbp linear fragment. The digest was purified using a QIAQUICK® PCR Purification Kit (Qiagen). The digested fragments of ydfG, UGA1, BAAT, PYD4, or YMR226c were then ligated into pMIBa107 (digested with XbaI and PacI and treated with CIP) using T4 DNA ligase as described herein. The ligation products were transformed into One Shot® TOP10 Chemically Competent E. coli cells (Invitrogen) according to manufacturer's instructions. Transformants were plated onto 2×YT+amp plates and incubated at 37° C. overnight. Several of the resulting transformants were screened by digestion with XbaI and Pac I. Clones yielding the desired band sizes were confirmed to be correct by DNA sequencing and designated pMIBa120, pMIBa121, pMIBa122, pMIBa123, and pMIBa124 for ydfG, BAAT, UGA1, YMR226c, or PYD4, respectively. The resulting plasmids allow integration of the desired gene at the adh1202 locus with the expression cassette oriented in the forward direction.

The integration constructs in Table 11 were used to integrate the genes of interest codon-optimized for expression in I. orientalis into the adh1202 locus under the control of the PDC promoter and terminator. The expression cassette also contains a URA3 selectable marker to allow selection of transformants within a ura− host as described herein. The expression cassettes and adh1202 homology regions are flanked by ApaI and KpnI restriction sites to allow release of the fragment from the plasmid.

15 μg each of integration constructs in Table 11 were digested with ApaI, KpnI, and NcoI and run on a 1% agarose gel using 89 mM Tris base-89 mM Boric Acid-2 mM disodium EDTA (TBE) buffer. Digestion with NcoI breaks up the vector backbone and makes it easier to extract the fragment of interest from the agarose gel. Fragments of 4884 bp, 5493 bp, 5553 bp, 4937 bp, and 5565 bp from pMIBa120, pMIBa121, pMIBa122, pMIBa123, and pMIBa124, respectively, were excised from the gel and extracted from the agarose using a QIAQUICK® Gel Extraction Kit (Qiagen). The concentration of the purified products was found to be between 80-120 ng/μL. 0.8-1.2 μg of the restriction fragments from pMIBa120-4 were transformed into I. orientalis CNB1 (ura−) as described herein.

The transformants then were plated onto ura selection media and grown at room temperature for 60 hours. Transformants were re-streaked onto ura selection media and incubated at 37° C. overnight.

Several transformants of each were checked by colony PCR to confirm integration. Correct integration was confirmed by using primer pairs that check the 5' and 3' ends of the integrations and are listed below. The primer 0611717 anneals in the PDC promoter in the reverse direction, while primer 0611225 anneals in the URA3 selectable marker in the forward direction. Primers 0611631 and 0611632 anneal outside of the site of integration going in the forward and reverse directions, respectively; primers 0611717 and 0611631 amplify a 976 bp fragment in correct integrants; primers 0611225 and 0611632 amplify a 1.4 kbp fragment in correct integrants; and primers 0611631 and 0611632 amplify a 2.7 kbp fragment indicating a wildtype chromosome and will amplify fragments ~5 kbp for integrations. To create genomic DNA, one colony of each transformant was incubated in 50 µL of 0.05 U/µL lyticase (Sigma, St. Louis, Mo., USA) in TE at 37° C. for 30 minutes followed incubation at 95° C. for 10 minutes. PCRs were run as described herein to confirm integration. One transformant of each heterozygous integrant that yielded PCR fragments of 976 bp with 0611717 and 0611631, 1.4 kbp with 0611225 and 0611632, and 2.7 kbp with 0611631 and 0611632 was saved and designated MIBa308, MIBa309, MIBa310, MIBa311, and MIBa312 as shown in Table 11.

Cultures of the transformants MIBa308, MIBa309, MIBa310, MIBa311, and MIBa312 were grown overnight in YPD at 37° C. Cultures were then diluted 1:50 into 25 mL of fresh YPD in 125 mL baffled flask at 37° C. and grown to an $OD_{600}$ ~4-10. Samples of the cells were analyzed for protein expression by SDS-PAGE using the methods described herein. CFE were also prepared from cell pellets from the cultures, and 3HP dehydrogenase activity was measured in the CFE using the method described herein. Expression of UGA1 and PYD4 from strains MIBa310 and MIBa312, respectively, was detected by SDS-PAGE by the appearance of a ~53 KDa band that was absent in strains not integrated for either gene. Expression of BAAT in MIBa309 was not detected by SDS-PAGE under these conditions. Table 12A shows the 3-HP dehydrogenase (3-HPDH) activity in the CFE of the strains.

TABLE 12A

Transformant enzyme activity data

| Strain | Gene Overexpressed | Gene Source | Gene SEQ ID NO | 3-HPDH activity |
|---|---|---|---|---|
| MBin500 | N/A | N/A | N/A | 0.28, 0.24 |
| MIBa310 | gabT (UGA1) | S. cerevisiae | 141 | 0.39 |
| MIBa309 | BAAT | S. avermitilis | 140 | 0.39 |
| MIBa312 | BAAT (PYD4) | S. kluyveri | 142 | 0.45 |
| MIBa311 | 3-HPDH (YMR226C) | S. cerevisiae | 144 | 1.1 |
| MIBa308 | 3-HPDH (ydfG) | E. coli | 143 | 0.67 |

In an independent experiment using improved assay conditions, the BAAT activity in CFE prepared from strains MBin500 (control), MIBa310, MIBa309 and MIBa312 was compared. The results of this experiment are shown in Table 12B.

TABLE 12B

Transformant enzyme activity data.

| Strain | Gene Overexpressed | Gene Source | Gene SEQ ID NO | BAAT activity |
|---|---|---|---|---|
| MBin500 | N/A | N/A | N/A | 0.67 |
| MIBa310 | gabT (UGA1) | S. cerevisiae | 141 | 9.05 |
| MIBa309 | BAAT | S. avermitilis | 140 | 0.42 |
| MIBa312 | BAAT (PYD4) | S. kluyveri | 142 | 105.85 |

The plasmids pMIBa120-4 (supra) contain NotI restriction sites that flank the expression cassette as follows: PDC promoter, gene of interest (BAAT or 3-HPDH), PDC terminator, and the URA3 selection marker. The homology for integration at the adh1202 locus is outside of the NotI restriction sites. These plasmids all have the expression cassette in forward orientation.

New plasmids were constructed with the expression cassette oriented in the reverse direction to allow ease of screening homozygous integration strains. Plasmids pMIBa120-4 were digested with NotI and run on a 1% agarose gel using 89 mM Tris base-89 mM Boric Acid-2 mM disodium EDTA (TBE) buffer. Fragments of 3.5 kbp (pMIBA120), 4.2 kbp (pMIBa121), 4.2 kbp (pMIBa122), 3.5 kbp (pMIBa123), and 4.2 kbp (pMIBa124) were excised from the gel and extracted from the agarose using a QIAQUICK® Gel Extraction Kit (Qiagen). Each of these fragments was ligated into the 5.2 kbp linear NotI/CIP treated pHJJ76-no ura using T4 DNA ligase as described herein. The ligation products were transformed into One Shot® TOP10 Chemically Competent E. coli cells (Invitrogen) according to manufacturer's instructions. Transformants were plated onto 2×YT+amp plates and incubated at 37° C. overnight. Several of the resulting transformants were screened by XbaI and KpnI digestion. Clones yielding the desired band sizes were designated pMIBa131, pMIBa132, pMIBa133, pMIBa134, and pMIBa135 for UGA1, YMR226c, PYD4, ydfG, and BAAT, respectively. The resulting plasmids allow integration of the desired gene at the adh1202 locus with the expression cassette oriented in the reverse direction.

Ura– derivatives of MIBa308-12 were isolated as described herein. Several FOA-resistant colonies for MIBA308-12 were colony purified twice by growing on YPD plates 37° C. Genomic DNA was prepared from the FOA-resistant colonies and checked by PCR to confirm loss of URA3 selectable marker as described herein. Primers 0611631 and 0611632 anneal outside of the site of integration going in the forward and reverse directions, respectively. Primer 0611718 anneals in the PDC terminator upstream of the ura selectable marker; primers 0611632 and 0611631 amplify a 2.7 kbp fragment for a wildtype chromosome; and primers 0611718 and 0611632 amplify a 2.4 kbp fragment for an integration with the ura marker present and 1100 bp fragment in the absence of the ura marker. One ura– strain of MIBa308-12 that yielded the PCR fragments of 1100 bp with 0611718 and 0611632, and 2.7 kbp with 0611631 and 0611632 was saved and designated MIBa314 (ura– strain of MIBa310), MIBa315 (ura– strain of MIBa312), MIBa316 (ura– strain of MIBa311), MIBa326 (ura– strain of MIBa308), and MIBA328 (ura– strain of MIBa309).

10-15 µg each of pMIBa131, pMIBa132, pMIBa133, and pMIBa135 were digested with ApaI, KpnI, and NcoI and run on a 1% agarose gel using 89 mM Tris base-89 mM Boric Acid-2 mM disodium EDTA (TBE) buffer. Digestion with NcoI facilitates extraction of the fragment of interest from the agarose gel. Fragments of 5553 bp, 4937 bp, 5565 bp, 5493 bp from pMIBa131-3, pMIBa135, respectively, were excised from the gel and extracted from the agarose using a QIAQUICK® Gel Extraction Kit (Qiagen). The concentration of the purified products was found to be between 67-80 ng/μL. 0.67-0.8 μg of the restricted fragments from pMIBa131-3, and pMIBa135 were transformed into MIBa314, MIBa316, MIBa315, or MIBa328 as described herein. Transformants were plated onto ura selection media and incubated overnight at 37° C., and then re-streaked onto ura selection media and incubated overnight at 37° C. overnight. Genomic DNA was prepared from the URA3+ colonies and checked by PCR as described herein to confirm integration of the second expression cassette, making the strain homozygous for the gene of interest Primers 0611718 and 0611632 amplify a 1100 bp fragment for the first integration as described above, and primers 0611632 and 0611717 amplify a 814 bp fragment for the second integration in the reverse orientation. URA3+ transformants of each lineage that amplified a 1100 bp fragment with 0611718 and 0611632 and a 814 bp fragment with 0611717 and 0611632 were designated MIBA317, MIBA318, MIBA319, and MIBa329 (see Table 13).

TABLE 13

Transformant genotypes

| Strain | Genotype |
|---|---|
| MIBa317 | adh1202Δ:: (PDC$_{promo}$-Opt.ScYMR226c, URA3-Scar)/ adh1202Δ::(PDC$_{promo}$-Opt.ScYMR226c, URA3) ura3–/ura3– |
| MIBa318 | adh1202Δ::(PDC$_{promo}$-Opt.ScUGA1, URA3-Scar)/ adh1202Δ::(PDC$_{promo}$-Opt.ScUGA1, URA3) ura3–/ura3– |
| MIBa319 | adh1202Δ::(PDC$_{promo}$-Opt.SkPYD4, URA3-Scar)/ adh1202Δ::(PDC$_{promo}$-Opt.SkPYD4, URA3) ura3–/ura3– |
| MIBa329 | adh1202Δ:: (PDC$_{promo}$-Opt.SaBAAT, URA3-Scar/ adh1202Δ:: (PDC$_{promo}$-Opt.SaBAAT, URA3) ura3–/ura3– |

The expression and enzyme activities from strains homozygous or heterozygous for YMR226c, UGA1, PYD4, and BAAT were determined. Overnight cultures of MIBA309-12, MIBa317-9 and MIBa329 were grown in YPD ON at 37° C., and then diluted 1:50 into 25 mL of fresh YPD in 125 mL baffled flask at 37° C. and grown to an OD$_{600}$ ~4-10. Samples of the cells were analyzed for protein expression by SDS-PAGE using the method described herein. CFE were also prepared from cell pellets from the cultures, and 3HP dehydrogenase activity was measured in the CFE using the method described herein. Based on SDS-PAGE results, strains MIBa310, MIBa318, MIBa312 and MIBa319 contained a protein with a mass of ~53 KDa (the expected size of the proteins encoded by UGA1 or PYD4 genes). The band corresponding to this protein was not observed in the SDS-PAGE analysis of strain MBin500. In addition, expression of UGA1 and PYD4 from homozygous strains MIBa318 and MIBa319, respectively, was greater than the corresponding heterozygous strains MIBa310 or MIBa312 (as judged by the SDS-PAGE analysis). BAAT expression was not detected (by SDS-PAGE) in strains MIBa309 or MIBa329 under these conditions. Table 14A shows the 3-HP dehydrogenase ("3-HPDH") activity in CFE of strains MBin500, MIBa311 and MIBa317.

TABLE 14A

Transformant enzyme activity data

| Strain | Gene Over-expressed | Gene SEQ ID NO | Source | Allele Type | 3-HPDH activity |
|---|---|---|---|---|---|
| MBin500 (control) | N/A | N/A | N/A | N/A | 0.13 |
| MIBa311 | 3-HPDH (YMR226c) | 144 | S. cerevisiae | heterozygous | 1.49 |
| MIBa317 | 3-HPDH (YMR226c) | 144 | S. cerevisiae | homozygous | 2.85 |

In an independent experiment using improved assay conditions, the BAAT activity in CFE prepared from strains MBin500 (control), MIBa319 and MIBa329 was compared. The results of this experiment are shown in Table 14B.

TABLE 14B

Transformant enzyme activity data

| Strain | Gene Over-expressed | Gene SEQ ID NO | Source | BAAT activity |
|---|---|---|---|---|
| MBin500 (control) | N/A | N/A | N/A | 0.67 |
| MIBa319 | BAAT (PYD4) | 142 | S. kluyveri | 228.01 |
| MIBa329 | BAAT | 140 | S. avermitilis | 0.38 |

Ura– derivatives of strains MIBa317, MIBa318, and MIBa319 were isolated as described herein. Several FOA-resistant colonies for MIBa317, MIBa18, and MIBa19 were colony purified by growing on YPD plates at 37° C. Genomic DNA was prepared from the FOA-resistant colonies and checked by PCR as described herein to confirm loss of URA3 selectable marker. Primers 0611718 and 0611632 amplify a 1100 bp fragment indicating the first integration as described above, and primers 0611632 and 0611717 amplify a 814 bp fragment indicating the presence of the second integration in the reverse orientation. Primers 0611718 and 0611631 amplify a 2.6 kbp fragment indicating the second integration with the ura marker and a 1200 bp fragment without the ura marker. Ura– strains of MIBa317 and MIBa318 that yielded PCR fragments of 1100 bp with 0611718 and 0611632, 814 bp with 0611632 and 0611717, or 1200 bp with 0611718 and 0611631 were saved and designated MIBa320 and MIBa321, respectively. When the ura marker was removed from MIBa319 a possible gene conversion event occurred resulting in MIBa322 as indicated by PCR (no 2.7 kbp fragment with 0611632 and 0611631 primers or 814 bp fragment with 0611632 and 0611717, but amplified 1100 bp fragment with 0611718 and 0611632) so that both expression cassettes were oriented in the forward direction.

Example 3A-3: Construction of Left-Hand Fragments of Insertion Vectors for Expressing Aspartate 1-Decarboxylase (ADC), β-Alanine Aminotransferase (BAAT), and 3-Hydroxypropionic Acid Dehydrogenase (3-HPDH) at the pdc Locus Left-Hand Fragment Containing S. avermitilis ADC (SEQ ID NO: 130) and S. avermitilis BAAT (SEQ ID NO: 140)

To allow insertion of a gene for expression between the ENO1 promoter and PDC terminator regions, the pMhCt068 vector was digested with XbaI and PacI, treated with 10 units calf intestinal phosphatase (New England Biolabs) at 37° C. for 30 minutes, and purified by 0.9% agarose gel electrophoresis in TAE buffer, and an approximately 6.1 kbp band was excised from the gel and purified using a NUCLEOSPIN® Extract II Kit (Macherey-Nagel) according to the manufacturer's instructions.

The *Saccharomyces kluvyeri* BAAT (pyd4) gene (SEQ ID NO: 142) was then amplified with primers 0611196 and 0611186 which contain restriction sites for subsequent subcloning. The PCR reaction (50 µL) contained 1 µL of a 1 to 50 dilution of a mini-prep of plasmid containing the *S. kluvyeri* pyd4 gene, 1× Pfx Amplification Buffer (Invitrogen), 100 pmol each of primers 0611196 and 0611186, 200 µM each of dATP, dCTP, dGTP, and dTTP, 1.5 µL DMSO and 2.5 units of PlatinumR Pfx DNA Polymerase (Invitrogen). The PCR was performed in an EPPENDORF® MASTERCYCLER® (Eppendorf Scientific) programmed for one cycle at 95° C. for 2 minutes followed by 34 cycles each at 95° C. for 30 seconds, 40.8° C. for 30 seconds, and 72° C. for 1 minute 30 seconds, with a final extension at 72° C. for 5 minutes. Following thermocycling, the PCR reaction products were separated by 0.9% agarose gel electrophoresis in TAE buffer where an approximately 1428 bp PCR product was excised from the gel and purified using a NUCLEOSPIN® Extract II Kit (Macherey-Nagel) according to the manufacturer's instructions.

The pyd4 PCR product generated above was digested with XbaI and PacI and purified by 0.9% agarose gel electrophoresis in TAE buffer, and an approximately 1.4 kbp band was excised from the gel and purified using a NUCLEOSPIN® Extract II Kit (Macherey-Nagel) according to the manufacturer's instructions. This purified DNA was cloned into the XbaI and PacI restricted pMhCt068 vector described above in a ligation reaction (20 µL) containing 1× Quick ligation buffer (New England Biolabs), 100 ng XbaI/PacI pMhCt068 vector, 70.5 ng Xba I/PacI pyd4 insert, and 1 µL Quick T4 DNA ligase (New England Biolabs). The ligation reaction was incubated for 5 min at room temperature, and then cooled on ice. 5 µL of this reaction was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired PCR products by digestion with XbaI and PacI as described herein, with one verified isolate designated "left+pyd4#1".

A polynucleotide encoding the *S. avermitilis* ADC of SEQ ID NO: 17 and codon-optimized for expression in *E. coli* was amplified with the primers 0611376 and 0611377 (note that primer 0611376 results in the removal of the "T" base on the 5' end of the NheI restriction site following insertion via In-Fusion into pMhCt068, which removes an unwanted ATG start codon present in the initial pMhCt068 clone). The PCR reaction (50 µL) contained 1 µL of a 1 to 50 dilution of a mini-prep of plasmid containing the *S. avermitilis* ADC gene optimized for *E. coli*, 1× ThermoPol Reaction buffer (New England Biolabs), 100 pmol each of primers 0611376 and 0611377, 200 µM each of dATP, dCTP, dGTP, and dTTP, 2 µL 100 mM MgSO$_4$, and 2 units of Vent$_R$® (exo-) DNA polymerase (New England Biolabs). The PCR was performed in an EPPENDORF® MASTERCYCLER® (Eppendorf Scientific) programmed for one cycle at 94° C. for 2 minutes followed by 34 cycles each at 94° C. for 30 seconds, 54° C. for 30 seconds, and 72° C. for 1 minute, with a final extension at 72° C. for 10 minutes. Following thermocycling, the PCR reaction products were separated by 0.9% agarose gel electrophoresis in TAE buffer where an approximately 420 bp PCR product was excised from the gel and purified using a NUCLEOSPIN® Extract II Kit (Macherey-Nagel) according to the manufacturer's instructions.

The "left+pyd4#1" plasmid then was digested with NheI and AscI, treated with 10 units calf intestinal phosphatase (New England Biolabs) at 37° C. for 30 minutes, and purified by 0.9% agarose gel electrophoresis in TAE buffer, and an approximately 7.5 kbp band was excised from the gel and purified using a NUCLEOSPIN® Extract II Kit (Macherey-Nagel) according to the manufacturer's instructions. The purified PCR fragment above containing the *S. avermitilis* ADC gene optimized for *E. coli* was digested with NheI and AscI and purified by 0.9% agarose gel electrophoresis in TAE buffer, and an approximately 420 bp band was excised from the gel and purified using a NUCLEOSPIN® Extract II Kit (Macherey-Nagel) according to the manufacturer's instructions. The resulting fragment then was ligated into the linearized "left+pyd4#1" vector in a ligation reaction (20 µL) containing 1× Quick ligation buffer (New England Biolabs), 100 ng NheI/AscI "left+pyd4#1" vector, 31 ng of the NheI and AscI digested panD insert, and 1 µL Quick T4 DNA ligase (New England Biolabs). The ligation reaction was incubated for 5 min at room temperature and then placed on ice. 5 µL of this reaction was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the *S. avermitilis* ADC gene optimized for *E. coli* by digestion with AscI and Pvu II as described herein. A clone yielding the desired band sizes was confirmed to be correct by DNA sequencing and designated pMhCt070.

The plasmid pMhCt070 served as the base vector for the addition of ADC and BAAT homologs that had been codon-optimized for expression in the yeast host. pMhCt070 was digested with XbaI and PacI, treated with 10 units calf intestinal phosphatase (New England Biolabs) at 37° C. for 30 minutes, and purified by 0.9% agarose gel electrophoresis in TAE buffer, and an approximately 6.5 kbp band was excised from the gel and purified using a NUCLEOSPIN® Extract II Kit (Macherey-Nagel) according to the manufacturer's instructions. An XbaI and PacI digested fragment described above containing a polynucleotide that encodes the *S. avermitilis* BAAT (SEQ ID NO: 140) and codon-optimized for expression in *I. orientalis* was ligated into the pMhCt070 cut vector as follows: A ligation reaction (20 µL) containing 1× Quick ligation buffer (New England Biolabs), 42 ng of the XbaI and PacI digested pMhCt070 vector, 4 µL of the codon-optimized *S. avermitilis* BAAT XbaI and PacI digested insert, and 1 µL Quick T4 DNA ligase (New England Biolabs). The ligation reaction was incubated for 5 min at room temperature, and then placed on ice. 5 µL of this reaction was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired BAAT ORF by XbaI, PacI, and Eco RV digestion as described herein. A clone yielding the desired band sizes was confirmed to be correct by DNA sequencing and designated pMhCt072.

The *S. avermitilis* ADC gene codon-optimized for expression in *E. coli* in pMhCt072 then was replaced with a version codon-optimized for expression in *I. orientalis* (SEQ ID NO: 130). The *I. orientalis* codon-optimized ADC gene (SEQ ID NO: 130) and desired additional restriction sites and flanking DNA were amplified with primers 0611378 and 0611379. The PCR reaction (50 µL) contained 1 µL of a 1 to 50 dilution of mini-prep of the plasmid containing the codon-optimized S. avermitilis panD (GeneArt®), 1× ThermoPol Reaction buffer (New England Biolabs), 100 pmol each of primers 0611378 and 0611379, 200 µM each of dATP, dCTP, dGTP, and dTTP, 2 µL 100 mM MgSO$_4$, and 2 units of Vent$_R$® (exo-) DNA polymerase (New England Biolabs). The PCR was performed in an EPPENDORF® MASTERCYCLER® (Eppendorf Scientific) programmed for one cycle at 94° C. for 2 minutes followed by 34 cycles each at 94° C. for 30 seconds, 54° C. for 30 seconds, and 72° C. for 45 seconds, with a final extension at 72° C. for 10 minutes. Following thermocycling, the PCR reaction products were separated by 1% agarose gel electrophoresis in TAE buffer where an approximately 420 base pair PCR product was excised from the gel and purified using a NUCLEOSPIN® Extract II Kit (Macherey-Nagel) according to the manufacturer's instructions.

Figure 7:
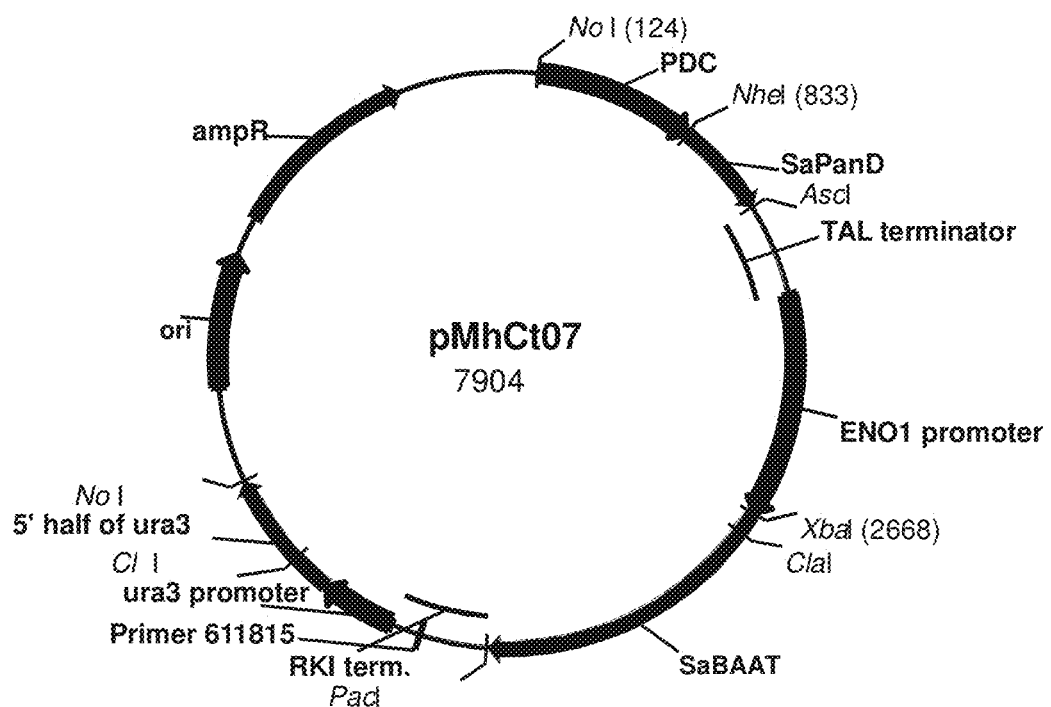
FIG. 7: Plasmid pMhCt074

5 µL of a mini-prep of pMhCt072 was digested with XbaI and PacI, treated with 10 units calf intestinal phosphatase (New England Biolabs) at 37° C. for 30 minutes, and purified by 1% agarose gel electrophoresis in TAE buffer, and an approximately 7.5 kbp band was excised from the gel and purified using a NUCLEOSPIN® Extract II Kit (Macherey-Nagel) according to the manufacturer's instructions. The isolated PCR product containing the codon-optimized S. avermitilis ADC gene from above was added to the vector in the following IN-FUSION™ Advantage PCR Cloning Kit (Clontech) reaction: the 10 µL reaction volume was composed of 6 µL of the pMhCt072 digested and purified vector, 1 µL of the purified codon-optimized panD PCR product, 1× In-Fusion reaction buffer (Clontech) and 1 µL of IN-FUSION™ enzyme (Clontech). The reaction was incubated at 37° C. for 15 minutes, 50° C. for 15 minutes, and then placed on ice. The reaction was diluted with 40 µL of TE buffer and 2.5 µL was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired PCR products by NheI, AscI, and ClaI digestion. A clone yielding the desired band sizes was confirmed to be correct by DNA sequencing and designated pMhCt074 (FIG. 7).

pMhCt074 is a left-hand PDC targeting construct containing the PDC promoter driving expression of the codon-optimized S. avermitilis ADC (panD, SEQ ID NO: 130), the TAL terminator, the ENO1 promoter driving expression of the codon-optimized S. avermitilis BAAT (SEQ ID NO: 140), the RKI terminator, the I. orientalis URA3 promoter and the 5' fragment of the I. orientalis URA3 ORF.
Left-Hand Fragment Containing S. avermitilis ADC (SEQ ID NO: 130) and S. kluyveri BAAT (SEQ ID NO: 142)

To create a left-hand DNA construct that expresses the S. kluyveri BAAT (pyd4), a fragment from XbaI and PacI digestion containing the S. kluyveri BAAT sequence codon-optimized for expression in I. orientalis (SEQ ID NO: 142, supra) was ligated into the pMhCt070 digested vector above as follows: A ligation reaction (20 µL) containing 1× Quick ligation buffer (New England Biolabs), 42 ng of the XbaI and PacI digested pMhCt070 vector, 4 µL of the codon-optimized S. kluyveri pyd4 insert digested with XbaI and PacI, and 1 µL Quick T4 DNA ligase (New England Biolabs). The ligation reaction was incubated for 5 minutes at room temperature, and then placed on ice. 5 µL of this reaction was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired pyd4 ORF by XbaI, PacI, and Eco RV digestion. A clone yielding the desired band sizes was confirmed to be correct by DNA sequencing and designated pMhCt073.

The plasmid pMhCt073 contains the desired S. kluyveri BAAT (pyd4) sequence codon-optimized for expression in I. orientalis but does not contain the desired S. avermitilis ADC (panD) sequence codon-optimized for expression in I. orientalis. To move in this ORF, 5 µL of a mini-prep of pMhCt073 was digested with XbaI and PacI, treated with 10 units calf intestinal phosphatase (New England Biolabs) at 37° C. for 30 minutes, and purified by 1% agarose gel electrophoresis in TAE buffer. An approximately 7.5 kbp band was excised from the gel and purified using a NUCLEOSPIN® Extract II Kit (Macherey-Nagel) according to the manufacturer's instructions. The isolated PCR product containing the codon-optimized S. avermitilis panD (supra) was added to the vector in the following IN-FUSION™ Advantage PCR Cloning Kit (Clontech) reaction: the 10 µL reaction volume was composed of 6 µL of the pMhCt073 digested and purified vector, 1 µL of the purified codon-optimized panD PCR product, 1× In-Fusion reaction buffer (Clontech) and 1 µL of IN-FUSION™ enzyme (Clontech). The reaction was incubated at 37° C. for 15 minutes, 50° C. for 15 minutes, and then placed on ice. The reaction was diluted with 40 µL of TE buffer and 2.5 µL was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired PCR products by NheI, AscI, and ClaI digestion. A clone yielding the desired band sizes was confirmed to be correct by DNA sequencing and designated pMhCt076.

Plasmid pMhCt076 is a left-hand PDC targeting construct containing the PDC promoter driving expression of the S. avermitilis ADC codon-optimized for expression in I. orientalis (panD, SEQ ID NO: 130), the TAL terminator, the ENO1 promoter driving expression of the S. kluyveri BAAT codon-optimized for expression in I. orientalis (pyd4, SEQ ID NO: 142), the RKI terminator, the I. orientalis URA3 promoter and the 5' fragment of the I. orientalis URA3 ORF.

Sequencing determined that plasmid pMhCt076 contains an A to T nucleotide change at about 200 bp into the PDC promoter, and a G to T nucleotide change ~⅔ of the way thru the PDC promoter that are present in the pMhCt068 parent vector (supra). To address any concern about potential alteration in gene expression, a construct similar to pMhCt076 but containing the corrected PDC promoter was cloned as described below.

Figure 8:
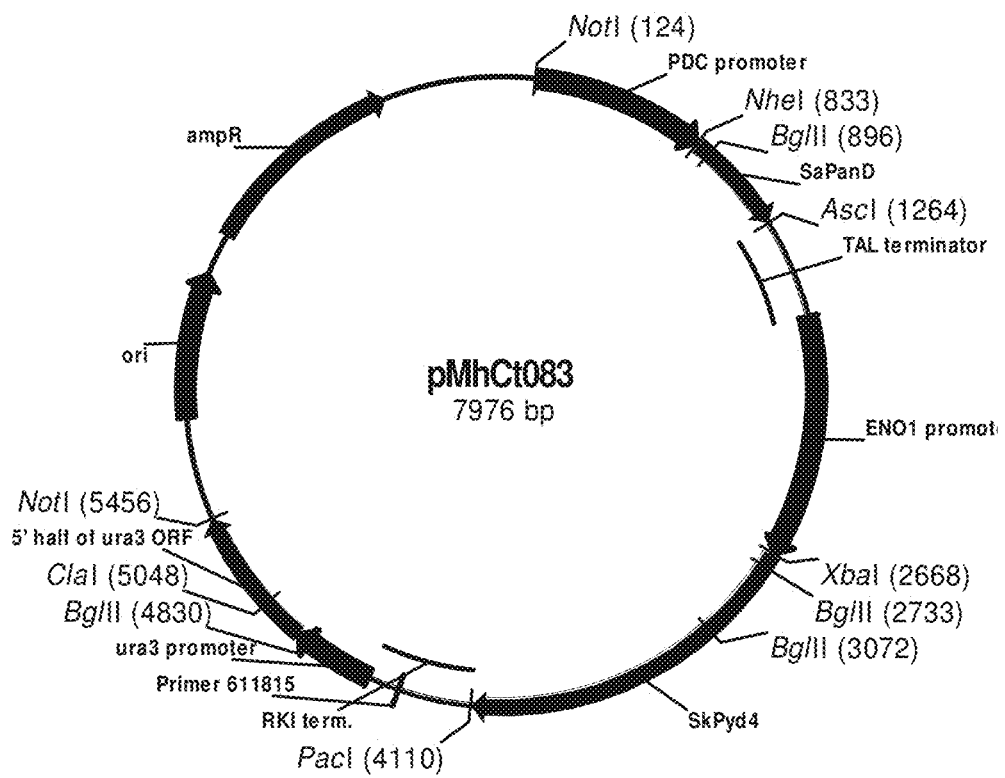
FIG. 8: Plasmid pMhCt083

5 µL of a mini-prep of pMhCt082 was digested with Nhe and PacI, treated with 10 units calf intestinal phosphatase (New England Biolabs) at 37° C. for 30 minutes, and purified by 0.9% agarose gel electrophoresis in TAE buffer, and an approximately 4.7 kbp band was excised from the gel and purified using a NUCLEOSPIN® Extract II Kit (Macherey-Nagel) according to the manufacturer's instructions. 4 µL of a mini-prep of pMhCt076 was digested with NheI and PacI and purified by 0.9% agarose gel electrophoresis in TAE buffer, and an approximately 3.3 kbp band was excised from the gel and purified using a NUCLEOSPIN® Extract II Kit (Macherey-Nagel) according to the manufacturer's instructions. The purified 4.7 kbp vector and 3.3 kbp insert were then ligated together in a ligation reaction (20 μL) containing 1× Quick ligation buffer (New England Biolabs), 3 μL pMhCt082 vector, 6 μL pMhCt076 insert, and 1 μL Quick T4 DNA ligase (New England Biolabs). The ligation reaction was incubated for 5 min at room temperature, and then placed on ice. 5 μL of this reaction was used to transform ONE SHOT® TOP10 chemically competent E. coli cells (Invitrogen) according to the manufacturer's instructions. Transformants were plated onto 2×YT+amp plates and incubated at room temperature for three days. Several of the resulting transformants were screened for proper insertion of the desired PCR products by digestion with StuI and Not I. A clone yielding the desired band sizes was confirmed to be correct by DNA sequencing and designated pMhCt083 (FIG. 8).

Plasmid pMhCt083 is identical to pMhCt076 except at the former contains the correct PDC promoter sequence, while the latter has one A to T nucleotide change and one G to T nucleotide change described above. Testing showed no difference in panD enzymatic activity from strains expressing S. avermitilis panD from integration of pMhCt076 and pMhCt077 as compared to pMhCt083 and pMhCt077.

Left-Hand Fragment Containing S. avermitilis ADC (SEQ ID NO: 130) and Saccharomyces cerevisiae gabT (SEQ ID NO: 141)

Figure 9:
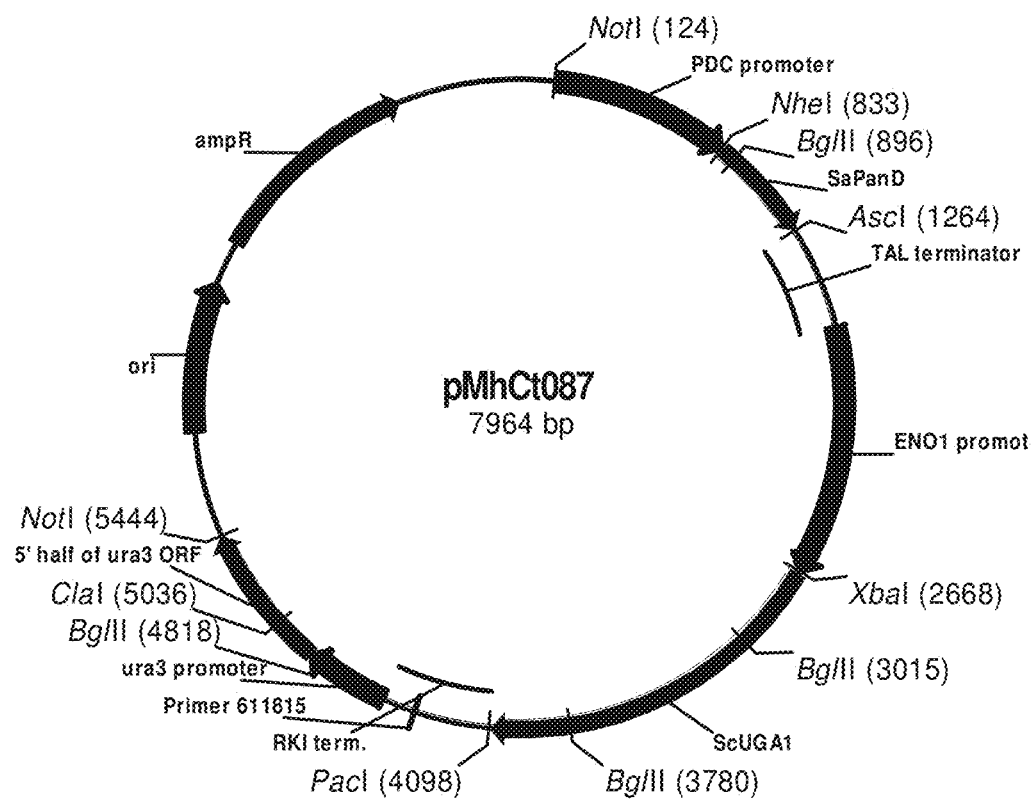
FIG. 9: Plasmid pMhCt087

4 μL of a mini-prep of pMhCt083 was digested with XbaI and PacI, treated with 10 units calf intestinal phosphatase (New England Biolabs) at 37° C. for 30 minutes, and purified by 0.9% agarose gel electrophoresis in TAE buffer, and an approximately 6.5 kbp band was excised from the gel and purified using a NUCLEOSPIN® Extract II Kit (Macherey-Nagel) according to the manufacturer's instructions. A fragment digested with XbaI and PacI containing the Saccharomyces cerevisiae gabT codon-optimized for expression in I. orientalis (UGA1, SEQ ID NO: 141) was ligated into the pMhCt083 cut vector as follows: A ligation reaction (20 μL) containing 1× Quick ligation buffer (New England Biolabs), 1 μL of the purified pMhCt083 vector digested with XbaI and PacI, 3 μL codon-optimized S. cerevisiae UGA1 XbaI and PacI digested insert, and 1 μL Quick T4 DNA ligase (New England Biolabs). The ligation reaction was incubated for 5 min at room temperature and then the tube was placed on ice. 5 μL of this reaction was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired BAAT ORF by XbaI and BglI digestion. A clone yielding the desired band sizes was designated pMhCt087 (FIG. 9).

Plasmid pMhCt087 is a left-hand PDC targeting construct containing the PDC promoter driving expression of the S. avermitilis ADC codon-optimized for expression in I. orientalis (panD, SEQ ID NO: 130), the TAL terminator, the ENO1 promoter driving expression of the S. cerevisiae gabT codon-optimized for expression in I. orientalis (UGA1, SEQ ID NO: 141), the RKI terminator, the I. orientalis URA3 promoter and the 5' fragment of the I. orientalis URA3 ORF.

Example 3A-4: Construction of Right-Hand Fragments of Insertion Vectors for Expressing Aspartate 1-Decarboxylase (ADC), β-Alanine Aminotransferase (BAAT), and 3-Hydroxypropionic Acid Dehydrogenase (3-HPDH) at the pdc Locus Right-Hand Fragment Containing E. coli 3-HPDH (SEQ ID NO: 143)

Figure 10:
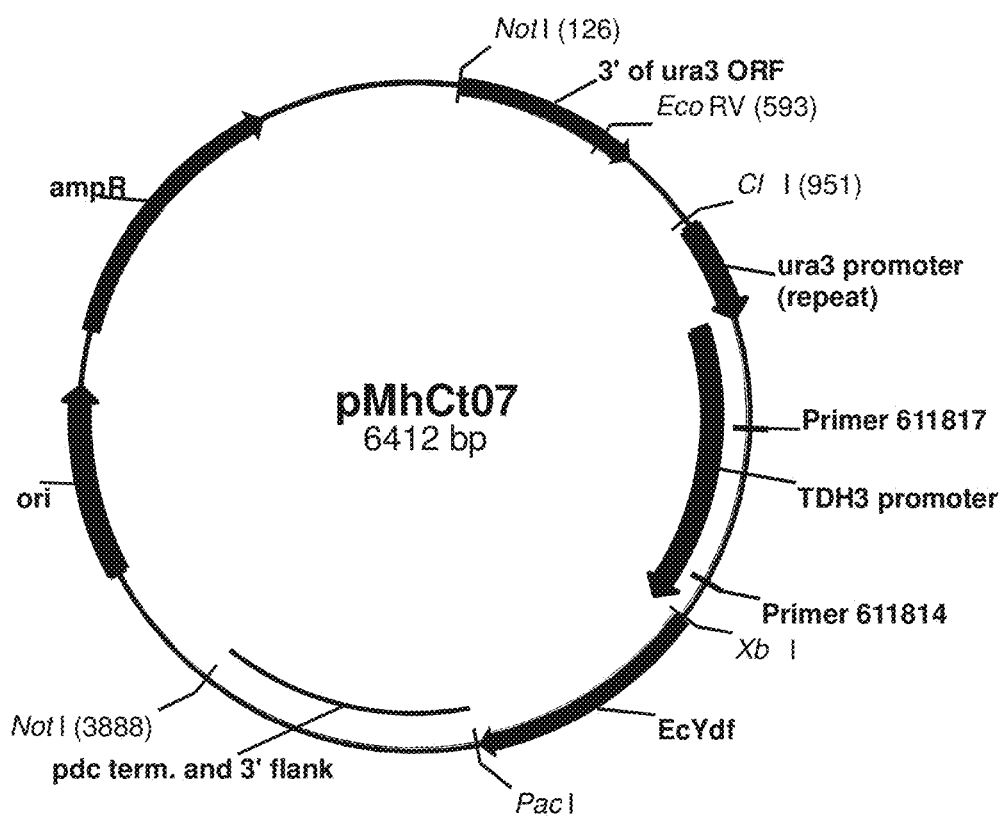
FIG. 10: Plasmid pMhCt075

2 μg of a mini-prep of pMhCt069 (supra) was digested with XbaI and PacI, treated with 10 units calf intestinal phosphatase (New England Biolabs) at 37° C. for 30 minutes, and purified by 0.9% agarose gel electrophoresis in TAE buffer, and an approximately 2.2 kbp band was excised from the gel and purified using a NUCLEOSPIN® Extract II Kit (Macherey-Nagel) according to the manufacturer's instructions. A fragment digested with XbaI and PacI containing E. coli 3-HPDH gene codon-optimized for expression in I. orientalis (ydfG, SEQ ID NO: 143) was ligated into the pMhCt069 cut vector as follows: A ligation reaction (20 μL) containing 1× Quick ligation buffer (New England Biolabs), 2 μL of the purified pMhCt069 vector digested with XbaI and PacI, 4 μL of the codon-optimized E. coli ydfG insert digested with XbaI and PacI, and 1 μL Quick T4 DNA ligase (New England Biolabs). The ligation reaction was incubated for 5 min at room temperature, and then placed on ice. 5 μL of this reaction was used to transform SoloPack Gold SuperCompetent Cells (Agilent Technologies) according to the manufacturer's instructions. Transformants were plated onto 2×YT+amp plates and incubated at room temperature for three days. Several of the resulting transformants were screened for proper insertion of the desired ydfG ORF by XbaI, PacI, and Eco RV digestion. A clone yielding the desired band sizes was confirmed to be correct by DNA sequencing as described herein and designated pMhCt075 (FIG. 10).

Plasmid pMhCt075 contains the 3' fragment of the I. orientalis URA3 ORF, the URA3 terminator from I. orientalis followed by the URA3 promoter (for later looping out of the URA3 marker), E. coli 3-HPDH gene codon-optimized for expression in I. orientalis (ydfG, SEQ ID NO: 143) driven by the I. orientalis TDH3 promoter, and the I. orientalis PDC terminator regions.

Right-Hand Fragment Containing Saccharomyces cerevisiae 3-HPDH (SEQ ID NO: 144)

Figure 11:
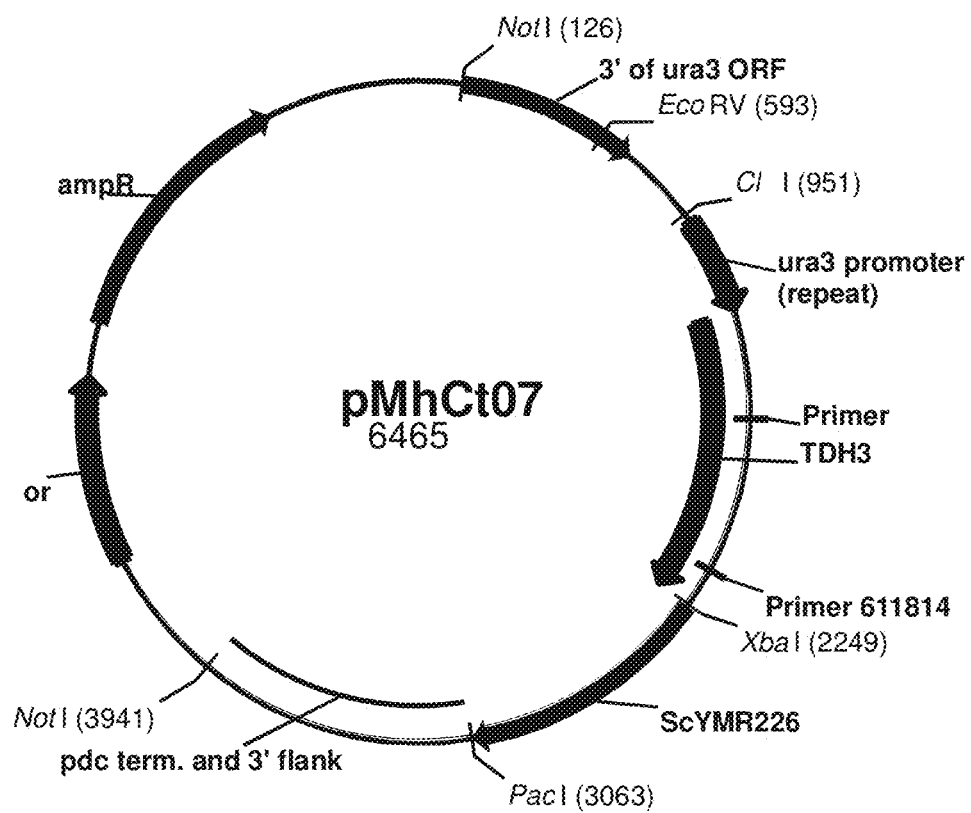
FIG. 11: Plasmid pMhCt077

A fragment digested with XbaI and PacI containing the S. cerevisiae YMR226C gene codon-optimized for expression in I. orientalis (supra) was ligated into the pMhCt069 cut vector as follows: A ligation reaction (20 μL) containing 1× Quick ligation buffer (New England Biolabs), 2 μL of the purified pMhCt069 vector digested with XbaI and PacI, 4 μL of the codon-optimized S. cerevisiae 3-HPDH (YMR226C, SEQ ID NO: 144) insert digested with XbaI and PacI, and 1 μL Quick T4 DNA ligase (New England Biolabs). The ligation reaction was incubated for 5 min at room temperature, and then placed on ice. 5 μL of this reaction was used to transform SoloPack Gold SuperCompetent Cells (Agilent Technologies) according to the manufacturer's instructions. Transformants were plated onto 2×YT+amp plates and incubated at room temperature for three days. Several of the resulting transformants were screened for proper insertion of the desired YMR226C ORF by XbaI, PacI, and Eco RV digestion. A clone yielding the desired band sizes was confirmed to be correct by DNA sequencing and was designated pMhCt077 (FIG. 11).

Plasmid pMhCt077 contains the 3' fragment of the I. orientalis URA3 ORF, the URA3 terminator from I. orientalis followed by the URA3 promoter (for later looping out of the URA3 marker), the S. cerevisiae 3-HPDH gene codon-optimized for expression in I. orientalis (YMR226C, SEQ ID NO: 144) driven by the I. orientalis TDH3 promoter, and the I. orientalis PDC terminator regions.

Example 3A-5: Heterozygous and Homozygous Yeast Strains Expressing Aspartate 1-Decarboxylase (ADC), β-Alanine Aminotransferase (BAAT), and 3-Hydroxypropionic Acid Dehydrogenase (3-HPDH) at the PDC Locus Examples 3A-3 and 3A-4 above describe the construction of various left-hand or right-hand constructs for targeting expression of three ectopic genes simultaneously to the *I. orientalis* PDC locus. Prior to transformation, approximately 10 μg of each construct (one desired left-hand construct and one desired right-hand construct) was digested with NotI to release the desired transforming DNA from the pUC18 backbone vector; for most digestions, the restriction enzyme PvuI was also included with the NotI digestion. Restriction enzyme PvuI digests the pUC18 vector fragment approximately in half, making separation of the larger, desired DNA fragment more facile by gel electrophoresis. The larger, expression cassette containing band was separated from the pUC18 backbone DNA by gel electrophoresis, excised from the gel, and purified using a NUCLEO-SPIN® Extract II Kit (Macherey-Nagel) according to the manufacturer's instructions. 30 μL elution buffer was used for the elution step. An equimolar ratio of one left-hand and one right-hand construct totaling 10 μL were used to transform the *I. orientalis* strain CNB1 or appropriate derivative. Transformants were selected on ura selection plates and placed at 37° C. for growth. The next day, approximately twelve transformants were picked and restreaked for single colonies to ura selection plates and grown at 37° C. The following day, a single colony was picked from each of the streaks generated by each initial transformant and restreaked to ura selection plates for single colonies. After another night of growth at 37° C., a final single colony was picked from each streak and restreaked to a ura selection plate and grown overnight at 37° C. After this second round of single colony purification and outgrowth, genomic DNA was prepared for use in PCR to verify the desired targeted integration occurred as described above. For targeting to PDC using the left- and right-hand constructs, verification of the desired integration event was determined using primers 0611814, 0611554, and 0611555. Primer 0611554 binds in the *I. orientalis* genomic DNA just 3' of the PDC terminator region present in the right-hand PDC targeting constructs; primer 0611555 binds in PDC ORF and amplifies toward stop; and primer 0611814 binds near the 3' end of the TDH3 promoter region present in the right-hand constructs and amplifies in the 3' direction. Generation of an approximately 1.9 kbp band from PCRs that contained primers 0611814 and 0611554 indicated the occurrence of the desired integration event at the PDC locus. Generation of an approximately 1.4 kbp band from PCRs that contained primers 0611555 and 0611554 indicated the presence of a wild-type PDC locus. Since this integration event is the first targeting event in the diploid *I. orientalis* CNB1, the desired integrants will show both a 1.9 kbp band for primers 0611814 and 0611554 and a 1.4 kbp band from primers 0611555 and 0611554. Two independent transformants giving the desired band pattern for each plasmid were designated as shown in Table 15.

TABLE 15

Transformant genotypes

| Strain | Plasmid w/left-hand fragment | Plasmid w/right-hand fragment | Genotype |
|---|---|---|---|
| yMhCt002 74/75 #1 | pMhCt074 | pMhCt075 | pdcΔ::(PDC$_{promo}$-Opt.SaPanD, ENO1$_{promo}$-Opt.SaBAAT, URA3, TDH3$_{promo}$-Opt.EcYdfG)/PDC ura3–/ura3– |
| yMhCt004 83/77 #2 | pMhCt083 | pMhCt077 | pdcΔ::(PDC$_{promo}$-Opt.SaPanD, ENO1$_{promo}$-Opt.SkPyd4, URA3, TDH3$_{promo}$-Opt.ScYMR226C)/PDC ura3–/ura3– |
| yMhCt005 87/77 #2 | pMhCt087 | pMhCt077 | pdcΔ::(PDC$_{promo}$-Opt.SaPanD, ENO1$_{promo}$-Opt.ScUGA1, URA3, TDH3$_{promo}$-Opt.ScYMR226C)/PDC ura3–/ura3– |

Next, a ura– derivative of yMhCt004 or yMhCt005 was isolated as described above. Genomic DNAs from several FOA resistant colonies of each parent strain were screened by PCR for the desired loop-out event with primers 0611815 and 0611817. Primer 0611815 anneals in the RKI terminator of the left-hand construct and amplifies toward the URA3 promoter. Primer 0611817 anneals in TDH3 promoter and amplifies back toward the URA3 cassette. The presence of an 828 bp band indicates the presence of only the ura3 scar site (a single URA3 promoter left behind after homologous recombination between the two URA3 promoters in the parent strain) as desired, while a band of approximately 2.2 kbp indicates the presence of the intact URA3 promoter-URA3 ORF-URA3 terminator-URA3 promoter cassette, indicating the desired recombination event did not occur. PCR reactions with Crimson Taq™ DNA polymerase (New England Biolabs) were carried out as described above. One FOA resistant colony from parent strain yMhCt004, designated yMhCt012, and one FOA resistant colony from parent strain yMhCt005, designated yMhCt007, gave the desired 828 bp band.

Strains yMhCt012 and yMhCt007 were next transformed to create homozygous strains with the PDC gene deleted and replaced with expression cassettes for panD, pyd4, and YMR226C or panD, UGA1, and YMR226C, respectively. Strain yMhCt012 was transformed with linear DNA from pMhCt083 and pMhCt077, while yMhCt007 was transformed with linear DNA from pMhCt087 and pMhCt077. After two rounds of single colony purification, genomic DNAs from several transformants from each parent strain were screened by PCR with primers 0611815 and 0611817 as described above. Two independently isolated integrants from each parent strain that had both the 828 bp band (from amplification of the ura3 scar region from the originally targeted PDC locus) and the 2.2 kbp band (from integration of the URA3 promoter-URA3 ORF-URA3 terminator-URA3 promoter cassette from the second integration event on the other chromosome) were designated as shown in Table 16.

TABLE 16

Transformant geneotypes

| Strain designation | Parent strain | Genotype |
|---|---|---|
| yMhCt013 yMhCt014 | yMhCt012 | pdcΔ::(PDC$_{promo}$-Opt.SaPanD, ENO1$_{promo}$-Opt.SkPyd4, URA3-Scar, TDH3$_{promo}$-Opt.ScYMR226C)/ pdcΔ::(PDC$_{promo}$-Opt.SaPanD, ENO1$_{promo}$Opt.SkPyd4-URA3, TDH3$_{promo}$-Opt.ScYMR226C) ura3–/ura3– |
| yMhCt008 yMhCt009 | yMhCt007 | pdcΔ::(PDC$_{promo}$-Opt.SaPanD, ENO1$_{promo}$-Opt.ScUGA1, URA3-Scar, TDH3$_{promo}$-Opt.ScYMR226C)/ pdcΔ::(PDC$_{promo}$-Opt.SaPanD, ENO1$_{promo}$-Opt.ScUGA1, URA3, TDH3$_{promo}$-Opt.ScYMR226C) ura3–/ura3– |

A ura– derivative of yMhCt008 was isolated as described above. Genomic DNAs from several FOA resistant colonies from the yMHCt008 parent strain were screened by PCR for the desired loop-out event with the primers 0611815 and 0611817 as described herein. The presence of an 828 bp band indicated the presence of only the ura3 scar site (a single URA3 promoter left behind after homologous recombination between the two URA3 promoters in the parent strain) as desired. Isolates that showed only the 828 bp band were further screened using primers 0611555 and 0611554 as described herein. Generation of an approximately 1.4 kbp band from PCRs that contained primers 0611555 and 0611554 indicated the presence of a wild-type PDC locus. An isolate lacking this band, indicating that the PDC locus on both chromosomes had been lost, was designated yMhCt010.

Strains were grown in shake flasks and CFE were prepared and assayed for aspartate decarboxylase (ADC) activity and 3-HP dehydrogenase (3-HPDH) activity as described in herein. The experimental results for several assay sets (denoted as Trials 1-4) are shown in Table 17. The strains from Trial 1 of Table 17 were also analyzed by SDS-PAGE as described herein. Strain 74/75 #1 and strain yMhCt002 of Trial 1 gave a band in SDS-PAGE analysis at 27 kD that was not present in the control strain of Trial 1 (MBin500). The size of this protein band is consistent with its identity as the protein encoded by the ydfG gene.

TABLE 17

Transformant enzyme activity data

| Trial | Strain | Gene Overexpressed | Allele Type | ADC activity | 3-HPDH activity |
|---|---|---|---|---|---|
| 1 | MBin500 (control) | N/A | N/A | Not tested | 0.25 |
| 2 | | | | 0.00 | 0.12 |
| 3 | | | | 0.00 | 0.23 |
| 4 | | | | 0.00 | 0.45 |
| 4 | | | | 0.00 | 0.54 |
| 1 | 74/75 #1 | ADC (SEQ ID NO: 130) 3-HPDH (SEQ ID NO: 143) BAAT (SEQ ID NO: 140) | heterozygous | Not tested | 0.68 |
| 1 | yMhCt002 | ADC (SEQ ID NO: 130) 3-HPDH (SEQ ID NO: 143) BAAT (SEQ ID NO: 140) | heterozygous | Not tested | 0.93 |
| 2 | yMhCt004 | ADC (SEQ ID NO: 130) 3-HPDH (SEQ ID NO: 144) BAAT (SEQ ID NO: 142) | heterozygous | 0.26 | 1.81 |
| 4 | | | | 0.30 | 2.20 |
| 4 | | | | 0.24 | 1.81 |
| 2 | 83/77 #2 | ADC (SEQ ID NO: 130) 3-HPDH (SEQ ID NO: 144) BAAT (SEQ ID NO: 142) | heterozygous | 0.25 | 1.80 |
| 2 | yMhCt005 | ADC (SEQ ID NO: 130) 3-HPDH (SEQ ID NO: 144) gabT (SEQ ID NO: 141) | heterozygous | 0.17 | 1.51 |
| 4 | | | | 0.17 | 1.26 |
| 4 | | | | 0.14 | 1.24 |
| 2 | 87/77 #2 | ADC (SEQ ID NO: 130) 3-HPDH (SEQ ID NO: 144) gabT (SEQ ID NO: 141) | heterozygous | 0.20 | 1.68 |
| 3 | yMhCt005 | ADC (SEQ ID NO: 130) 3-HPDH (SEQ ID NO: 144) gabT (SEQ ID NO: 141) | heterozygous | 0.16 | 1.27 |
| 3 | yMhCt008 | ADC (SEQ ID NO: 130) 3-HPDH (SEQ ID NO: 144) gabT (SEQ ID NO: 141) | homozygous | 0.80 | 2.29 |
| 4 | | | | 0.25 | 0.85 |
| 4 | | | | 0.42 | 1.37 |

TABLE 17-continued

Transformant enzyme activity data

| Trial | Strain | Gene Overexpressed | Allele Type | ADC activity | 3-HPDH activity |
|---|---|---|---|---|---|
| 3 | yMhCt009 | ADC (SEQ ID NO: 130) | homozygous | .045 | 1.33 |
| 4 | | 3-HPDH (SEQ ID NO: 144) | | 0.22 | 0.55 |
| 4 | | gabT (SEQ ID NO: 141) | | 0.43 | 1.15 |
| 4 | yMhCt013 | ADC (SEQ ID NO: 130) | homozygous | 0.47 | 0.65 |
| 4 | | 3-HPDH (SEQ ID NO: 144) BAAT (SEQ ID NO: 142) | | 0.50 | 0.82 |
| 4 | yMhCt014 | ADC (SEQ ID NO: 130) | homozygous | 0.34 | 0.51 |
| 4 | | 3-HPDH (SEQ ID NO: 144) BAAT (SEQ ID NO: 142) | | 0.54 | 1.06 |

The experimental results for another assay set are shown in Table 17 (Trial 2). The strains from Trial 2 of Table 17 were also analyzed by SDS-PAGE as described herein. All strains of Trial 2 except MBin500 gave a band at 29 kD in the SDS-PAGE analysis. The size of this protein band is consistent with its identity as the protein encoded by the YMR226c gene. Strains yMhCt005 and 87/77 #2 for Trial 2 gave a band at 53 kD that was not present in the three other samples for this trial. The size of this protein band is consistent with its identity as the protein encoded by the UGA1 gene.

The experimental results for another assay set are shown in Table 17 (Trial 3). The strains from Trial 3 of Table 17 were also analyzed by SDS-PAGE as described herein. All strains of Trial 3 except MBin500 gave a band at 53 kD and a band at 29 kD in the SDS-PAGE analysis. The sizes of these protein bands are consistent with the proteins encoded by the UGA1 and YMR226c genes, respectively. Strains MBin500 and yMhCt005 of Trial 3 showed a band at 64 kD in the SDS-PAGE analysis that was absent in yMhCt008 and yMhCt009 for this trial. The size of this protein band is consistent with its identity as the protein encoded by the native pyruvate decarboxylase (PDC) gene in $I.$ $orientalis$ CNB1.

The experimental results for another assay set are shown in Table 17 (Trial 4). The strains from Trial 4 of Table 17 were also analyzed by SDS-PAGE as described herein. All strains of Trial 4 except MBin500 gave a band at 29 kD The size of this protein band is consistent with its identity as the protein encoded by the YMR226c gene. Strains yMhCt005, yMhCt008, and yMhCt009 of Trial 4 showed a band at 53 kD. The size of this band is consistent with the protein encoded by the UGA1 gene. Strains yMhCt013, and yMhCt014 of Trial 4 showed a faint band at 53 kD The size of this band is consistent with the protein encoded by the PYD4 gene. Strains MBin500, yMhCt004, and yMhCt005 of Trial 4 showed a band at 64 kD that was absent in strains yMhCt008, yMhCt009, yMhCt013, and yMhCt014. The size of this protein band is consistent with its identity as the protein encoded by the native pyruvate decarboxylase (PDC) gene in $I.$ $orientalis$ CNB1.

Strains MBin500 and yMhCt008 were tested evaluated in bioreactors for 3-HP production, using the method described herein. Control strain MBin500 produced no detectable 3-HP (average of two independent fermentations). Strain yMhCt008 produced 2.45 g/L 3-HP (average of twelve independent fermentations).

Example 3A-6: Yeast Strains Expressing β-Alanine Aminotransferase (BAAT) or 3-Hydroxypropionic Acid Dehydrogenase (3-HPDH) at the Adh1202 Locus, and Expressing Aspartate 1-Decarboxylase (ADC), β-Alanine Aminotransferase (BAAT), and 3-Hydroxypropionic Acid Dehydrogenase (3-HPDH) at the pdc Locus 20 μg of pMhCt077, pMhCt083, and pMhCt087 (supra) were digested with NotI and PvuI and then run on a 1% agarose gel using 89 mM Tris base-89 mM Boric Acid-2 mM disodium EDTA (TBE) buffer. NotI digested fragments of 3815 bp, 5332 bp, or 5320 bp from pMhCt077, pMhCt083, and pMhCt087, respectively, were excised from the gel and extracted from the agarose using a QIAQUICK® Gel Extraction Kit (Qiagen). 560 ng of NotI digested pMhCt077 and 560 ng of NotI digested pMhCt083 or pMhCt087 were transformed into strains MIBa320, MIBa321, and MIBa322. MIBa320 was transformed with pMhCt077/83 and pMhCt077/87 combinations. MIBa321 was transformed with pMhCt077/87 and MIBa322 was transformed with pMhCt077/83 as described herein. Transformants were plated onto ura selection media and incubated for approximately 60 hours at room temperature. Transformants were re-streaked onto ura selection media and incubated at 37° C. overnight. Genomic DNA was prepared from the URA3+ colonies and checked by PCR as described herein to confirm integration of the expression cassette. The primer pair 611814 and 611554 amplify a 1.9 kbp fragment indicating integration. The primer pair 611555 and 611554 amplify a 1.4 kbp fragment indicating a wildtype locus. One URA3+ transformant of each lineage that amplified PCR fragments of 1.9 kbp with 611554 and 611814 and 1.4 kbp with 611555 and 611554 was saved; these were designated MIBa323, MIBa324, MIBa325, and MIBa327 (see Table 18 for genotypes). Promoters and terminators were derived from $I.$ $orientalis$ genes.

TABLE 18

Transformant genotypes

| Strain designation | Genotype |
|---|---|
| MIBa323 | adh1202Δ::(PDC$_{promo}$-Opt.ScYMR226c, URA3-Scar)/ adh1202Δ::(PDC$_{promo}$-Opt.ScYMR226c, URA3-Scar) pdcΔ::(PDC$_{promo}$-Opt.SaPanD, ENO1$_{promo}$-Opt.ScUGA1, URA3, TDH3$_{promo}$-Opt.ScYMR226c)/PDC ura3–/ura3– |

TABLE 18-continued

Transformant genotypes

| Strain designation | Genotype |
|---|---|
| MIBa324 | adh1202Δ::(PDC$_{promo}$-Opt.ScYMR226c, URA3-Scar)/ adh1202Δ::(PDC$_{promo}$-Opt.ScYMR226c, URA3-Scar) pdcΔ::(PDC$_{promo}$-Opt.SaPanD, ENO1$_{promo}$-Opt.SkPyd4, URA3, TDH3$_{promo}$-Opt.ScYMR226c)/PDC ura3–/ura3– |
| MIBa325 | adh1202Δ::(PDC$_{promo}$-Opt.ScUGA1, URA3-Scar)/ adh1202Δ::(PDC$_{promo}$-Opt.ScUGA1, URA3-Scar) pdcΔ::(PDC$_{promo}$-Opt.SaPanD, ENO1$_{promo}$-Opt.ScUGA1, URA3, TDH3$_{promo}$-Opt.ScYMR226c)/PDC ura3–/ura3– |
| MIBa327 | adh1202Δ::(PDC$_{promo}$-Opt.SkPyd4, URA3-Scar)/ adh1202Δ::(PDC$_{promo}$-Opt.SkPyd4, URA3-Scar) pdcΔ::(PDC$_{promo}$-Opt.SaPanD, ENO1$_{promo}$-Opt.SkPyd4, URA3, TDH3$_{promo}$-Opt.ScYMR226c)/PDC ura3–/ura3– |

Strains were grown in shake flasks and CFE were prepared and assayed for 3-HP dehydrogenase (3-HPDH) activity as described herein. The results are shown in Table 19.

TABLE 19

Transformant enzyme activity data

| Strain | Gene Overexpressed | 3-HPDH activity |
|---|---|---|
| MBin500 (control) | N/A | 0.14 |
| MIBa314 | gabT (SEQ ID NO: 141) | 0.09 |
| MIBa318 | gabT (SEQ ID NO: 141) | 0.41 |
| MIBa321 | gabT (SEQ ID NO: 141) | 0.08 |
| MIBa325 | gabT (SEQ ID NO: 141) ADC (SEQ ID NO: 130) 3-HPDH (SEQ ID NO: 144) | 1.15 |
| MIBa315 | BAAT (SEQ ID NO: 142) | 0.12 |
| MIBa319 | BAAT (SEQ ID NO: 142) | 0.17 |
| MIBa322 | BAAT (SEQ ID NO: 142) | 0.09 |
| MIBa327 | BAAT (SEQ ID NO: 142) ADC (SEQ ID NO: 130) 3-HPDH (SEQ ID NO: 144) | 0.98 |
| MIBa316 | 3-HPDH (SEQ ID NO: 144) | 0.48 |
| MIBa317 | 3-HPDH (SEQ ID NO: 144) | 2.15 |
| MIBa320 | 3-HPDH (SEQ ID NO: 144) | 1.07 |
| MIBa323 | 3-HPDH (SEQ ID NO: 144) ADC (SEQ ID NO: 130) gabT (SEQ ID NO: 141) | 2.66 |
| MIBa324 | 3-HPDH (SEQ ID NO: 144) ADC (SEQ ID NO: 130) BAAT (SEQ ID NO: 142) | 2.12 |

Ura– derivatives of MIBa323, MIBa324, MIBa325 and MIBa327 were isolated as described herein. Genomic DNA was prepared from the FOA-resistant colonies and checked by PCR as described herein to confirm loss of URA3 selectable marker. Primer 0611815 anneals in the RKI terminator of the left-hand construct and amplifies toward the URA3 promoter, and primer 0611817 anneals in TDH3 promoter and amplifies back toward the URA3 cassette. The presence of an 828 bp band indicates the presence of only the URA3 scar site (a single URA3 promoter left behind after homologous recombination between the two URA3 promoters in the parent strain) as desired, while a band of approximately 2.2 kbp indicates the presence of the intact URA3 promoter-URA3 ORF-URA3 terminator-URA3 promoter cassette, indicating the desired recombination event did not occur. Ura– strains of MIBa323, MIBa324, MIBa325, and MIBa327, that yielded PCR fragments of 828 bp with primers 0611815 and 0611817 were saved and designated MIBa335, MIBa333, MIBa334, and MIBa336, respectively.

Strains MIBa333 and MIBa334 were transformed with the fragments from pMhCt077 and pMhCt087, and strains MIBa335 and MIBa336 were transformed with the fragments from pMhCt077 and pMhCt083 as described above in the section on MIBa320-2 transformations. Transformants were selected for by growth on ura selection media as described herein. Genomic DNA was prepared from the URA3+ colonies and checked by PCR as described herein to confirm integration of the expression cassette. Primer 0611815 anneals in the RKI terminator of the left-hand construct and amplifies toward the URA3 promoter. Primer 0611817 anneals in TDH3 promoter and amplifies back toward the URA3 cassette. The presence of an 828 bp band indicates the presence of only the URA3 scar site (a single URA3 promoter left behind after homologous recombination between the two URA3 promoters in the parent strain) as desired for the first integration, and a band of approximately 2.2 kbp indicates the presence of the intact URA3 promoter-URA3 ORF-URA3 terminator-URA3 promoter cassette for the second integration. Primer pair 0611815 and 0611816 amplifies a 625 bp fragment when the ura marker is present. Primers 0611555 and 0611554 amplify a 1.4 kbp fragment when the PDC locus is present. Homozygous integrants should not amplify a fragment with these primers. One URA3+ transformant of each lineage that amplified PCR fragments of 828 bp and 2.2 kbp with primers 0611815 and 0611817, 625 bp with primers 0611815 and 0611816 and no fragment with primers 0611555 and 0611554 was saved; these were designated MIBa340, MIBa341, MIBa345, and MIBa348 (see Table 20A). Promoters and terminators were derived from *I. orientalis* genes.

TABLE 20A

Transformant genotypes

| Strain Designation | Genotype |
|---|---|
| MIBa345 | adh1202Δ::(PDC$_{promo}$-Opt.ScYMR226c URA3-Scar)/<br>adh1202Δ::(PDC$_{promo}$-Opt.ScYMR226c URA3-Scar)<br>pdcΔ::(PDC$_{promo}$-Opt.SaPanD ENO1$_{promo}$-Opt.ScUGA1,<br>URA3-Scar, TDH3$_{promo}$-Opt.ScYMR226c)/pdcΔ::(PDC$_{promo}$-Opt.SaPanD,<br>ENO1$_{promo}$-Opt.ScUGA1, URA3, TDH3$_{promo}$-Opt.ScYMR226c) ura3−/ura3− |
| MIBa348 | adh1202Δ::(PDC$_{promo}$-Opt.ScYMR226c URA3-Scar)/<br>adh1202Δ::(PDC$_{promo}$-Opt.ScYMR226c URA3-Scar)<br>pdcΔ::(PDC$_{promo}$-Opt.SaPanD, ENO1$_{promo}$-Opt.SkPyd4, URA3-Scar,<br>TDH3$_{promo}$-Opt.ScYMR226c)/pdcΔ::(PDC$_{promo}$-Opt.SaPanD,<br>ENO1$_{promo}$-Opt.SkPyd4, URA3, TDH3$_{promo}$-Opt.ScYMR226c) ura3−/ura3− |
| MIBa340 | adh1202Δ::(PDC$_{promo}$-Opt.ScUGA1 URA3-Scar)/<br>adh1202Δ::(PDC$_{promo}$Opt.ScUGA1 URA3-Scar)<br>pdcΔ::(PDC$_{promo}$-Opt.SaPanD, ENO1$_{promo}$-Opt.ScUGA1,<br>URA3-Scar, TDH3$_{promo}$-Opt.ScYMR226c)/pdcΔ::(PDC$_{promo}$-Opt.SaPanD,<br>ENO1$_{promo}$-Opt.ScUGA1, URA3, TDH3$_{promo}$-Opt.ScYMR226c) ura3−/ura3− |
| MIBa341 | adh1202Δ::(PDC$_{promo}$-Opt.SkPyd4 URA3-Scar)/<br>adh1202Δ::(PDC$_{promo}$Opt.SkPyd4 URA3-Scar)<br>pdcΔ::(PDC$_{promo}$-Opt.SaPanD, ENO1$_{promo}$-Opt.SkPyd4, URA3-Scar,<br>TDH3$_{promo}$-Opt.ScYMR226c)/pdcΔ::(PDC$_{promo}$-Opt.SaPanD,<br>ENO1$_{promo}$-Opt.SkPyd4, URA3, TDH3$_{promo}$-Opt.ScYMR226c) ura3−/ura3− |

The aspartate 1-decarboxylase (ADC), beta-alanine aminotransferase (BAAT) and 3-HP dehydrogenase (3-HPDH) activities in CFE prepared from strains MBin500 (control), MIBa345, MIBa348, MIBa340 and MIBa341 were compared. The results of this experiment are shown in Table 20B.

To prevent recombination from occurring between the multiple copies of the nucleotide sequences encoding the same ADC sequence, four distinct nucleotide sequences codon-optimized for expression in *I. orientalis* (SEQ ID NOs: 130, 145, 146, and 147) were designed to encode the same ADC sequence of SEQ ID NO: 17. Additionally, since

TABLE 20B

Transformant enzyme activity data

| Strain | Genes Overexpressed | Gene Sources | ADC Activity | BAAT Activity | 3-HPDH Activity |
|---|---|---|---|---|---|
| MBin500 (control) | N/A | N/A | 0.002 | 0.61 | 0.4 |
| MIBa345 | YMR226c (SEQ ID NO: 144)<br>ADC (SEQ ID NO: 130)<br>UGA1 (SEQ ID NO: 141) | S. cerevisiae<br>S. avermitilis<br>S. cerevisiae | 0.194 | 14.37 | 79.5 |
| MIBa348 | YMR226c (SEQ ID NO: 144)<br>ADC (SEQ ID NO: 130)<br>PYD4 (SEQ ID NO: 142) | S. cerevisiae<br>S. avermitilis<br>S. kluyveri | 0.169 | 173.67 | 76.7 |
| MIBa340 | YMR226c (SEQ ID NO: 144)<br>ADC (SEQ ID NO: 130)<br>UGA1 (SEQ ID NO: 141) | S. cerevisiae<br>S. avermitilis<br>S. cerevisiae | 0.239 | 19.51 | 64.8 |
| MIBa341 | YMR226c (SEQ ID NO 144)<br>ADC (SEQ ID NO: 130)<br>PYD4 (SEQ ID NO: 142) | S. cerevisiae<br>S. avermitilis<br>S. kluyveri | 0.22 | 386.92 | 65.5 |

Figure 3:
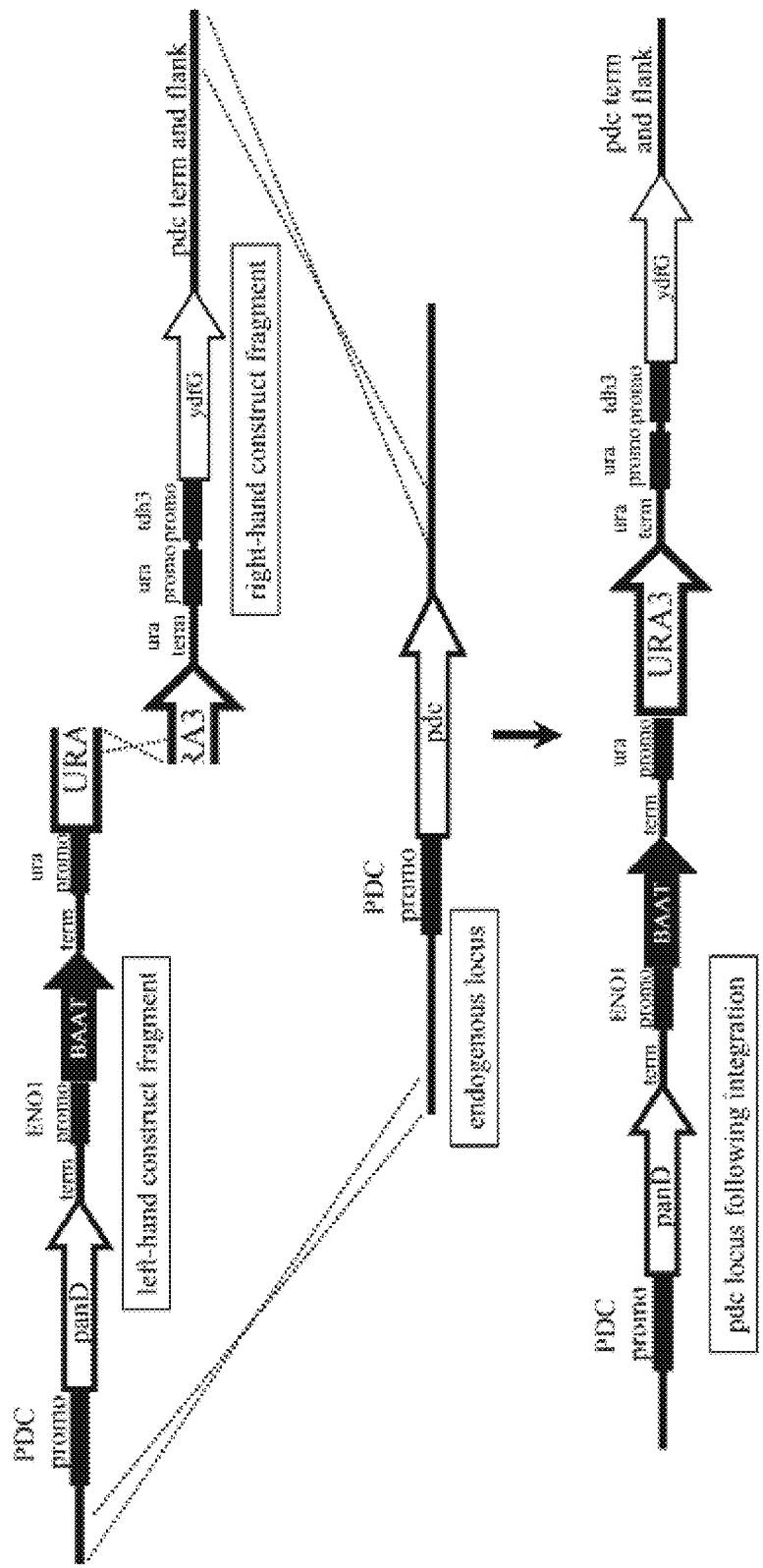
FIG. 3: Schematic representation of a targeted integration technique

Example 3A-7: Left-Hand Fragments of Insertion Vectors with Multiple Nucleotide Sequences for Expressing Aspartate 1-Decarboxylase (ADC) at the Adh1202 Locus Constructs were designed to incorporate four copies of nucleotides encoding an ADC (SEQ ID NO: 17) at the *I. orientalis* adh1202 locus. In a similar approach to that described herein for the PDC locus, a left-hand and a right-hand construct were designed to allow homologous recombination. The general design of the integration vectors and desired recombination event is shown in FIG. 3. This approach was also used for expression of an alternative ADC (SEQ ID NO: 139) as described in the examples below.

the initial set of constructs was designed to target the ald5680 locus of *I. orientalis*, the adh1202 targeting sequences were incorporated into these vectors at a late step in the cloning. The ald5680 constructs can be used to target a second locus in an *I. orientalis* CNB1 strain already homozygous for ectopic four copies of panD at adh1202 with four additional copies of panD at ald5680.

Figure 23:
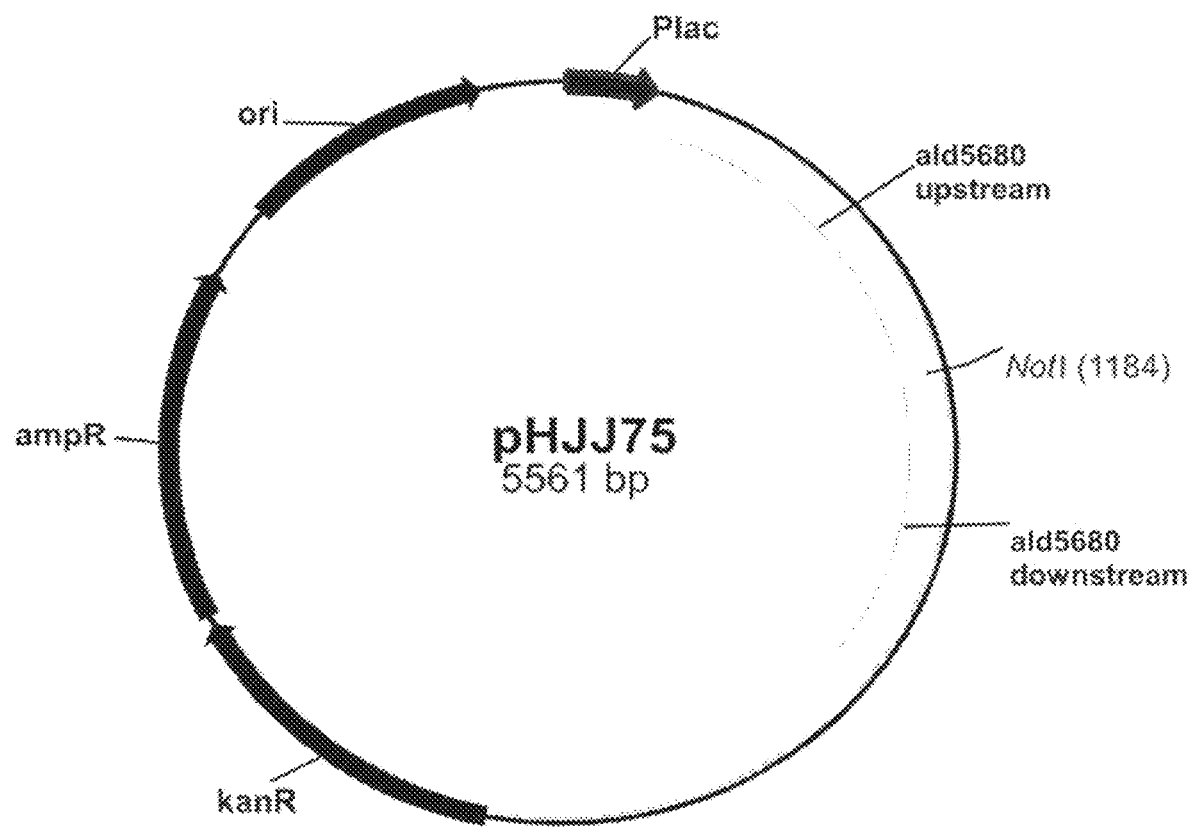
FIG. 23: Plasmid pHJJ75

The left-hand ald5680 targeting vector was constructed as follows. A PCR product containing the sequence just 5' of the ald5680 ORF, along with the desired additional restriction sites and flanking DNA for cloning was amplified with primers 0612271 and 0612272. The PCR reaction (50 µL) contained 1 µL of a 1 to 50 dilution of pHJJ75 mini-prep plasmid DNA (FIG. 23), 1× iProof™ HF buffer (Bio-Rad Laboratories), 100 pmol each of primers 0612271 and 0612272, 200 µM each of dATP, dCTP, dGTP, and dTTP, and 1 unit of iProof™ High Fidelity DNA polymerase (Bio-Rad Laboratories). The PCR was performed in an EPPENDORF® MASTERCYCLER® (Eppendorf Scientific) programmed for one cycle at 98° C. for 30 seconds followed by 32 cycles each at 98° C. for 10 seconds, 59° C. for 20 seconds, and 72° C. for 45 seconds, with a final extension at 72° C. for 10 minutes. Following thermocycling, the PCR reaction products were separated by 1% agarose gel electrophoresis in TAE buffer where an approximately 930 base pair PCR product was excised from the gel and purified using a NUCLEOSPIN® Extract II Kit (Macherey-Nagel) according to the manufacturer's instructions.

In order to allow purification of a greater quantity of DNA, the PCR reaction described above was repeated using the purified 930 bp PCR product as the template DNA. Five 50 µL reactions were set up and amplified with the conditions described above except that 1 µL of the purified 930 bp PCR product replaced the pHJJ75 plasmid (supra) as template DNA. Following thermocycling, the amplified 930 bp product was purified as above.

A fragment containing PDC promo-optPanD-ENO1-UGA1 (which contains the *I. orientalis* codon-optimized *S. avermitilis* ADC encoding sequence of SEQ ID NO: 130) was excised from pMhCt087 (supra) via NotI and EcoRI digestion. 10 µg of a midi-prep of pMhCt087 was digested with NotI and EcoRI and then purified by 0.9% agarose gel electrophoresis in TAE buffer. An approximately 4.4 kbp band was excised from the gel and purified using a NUCLEOSPIN® Extract II Kit (Macherey-Nagel) according to the manufacturer's instructions.

A PCR product containing the 5' half of the URA3 split marker with the desired additional restriction sites and flanking DNA for cloning was amplified using the primers 0612273 and 0612274. The PCR reaction (50 µL) contained 1 µL of a 1 to 50 dilution of pMhCt082 mini-prep plasmid DNA (supra), 1× iProof™ HF buffer (Bio-Rad Laboratories), 100 pmol each of primers 0612273 and 0612274, 200 µM each of dATP, dCTP, dGTP, and dTTP, and 1 unit of iProof™ High Fidelity DNA polymerase (Bio-Rad Laboratories). The PCR was performed in an EPPENDORF® MASTERCYCLER® (Eppendorf Scientific) programmed for one cycle at 98° C. for 30 seconds followed by 32 cycles each at 98° C. for 10 seconds, 59° C. for 20 seconds, and 72° C. for 45 seconds, with a final extension at 72° C. for 10 minutes. Following thermocycling, the PCR reaction products were separated by 1% agarose gel electrophoresis in TAE buffer where an approximately 960 base pair PCR product was excised from the gel and purified using a NUCLEOSPIN® Extract II Kit (Macherey-Nagel) according to the manufacturer's instructions.

To create a recipient vector for the above DNA fragments, the plasmid pUC19 (Yanisch-Perron, C., Vieira, J. and Messing, J. (1985) Gene, 33, 103-119) was digested with Hind III and EcoRI, treated with 10 units calf intestinal phosphatase (New England Biolabs) at 37° C. for 30 minutes, and purified by 0.9% agarose gel electrophoresis in TAE buffer, and an approximately 2.6 kbp band was excised from the gel and purified using a NUCLEOSPIN® Extract II Kit (Macherey-Nagel) according to the manufacturer's instructions.

The purified 930 bp, 4.4 kbp, and 960 bp DNA fragments from above were then inserted into the digested pUC19 fragment using an IN-FUSION™ Advantage PCR Cloning Kit (Clontech) in a total reaction volume of 10 µL composed of 150 ng of the pUC19 vector digested with Hind III and EcoRI, 56 ng of the 930 bp DNA containing the ald5680 flanking DNA, 250 ng of the PDC promo-optPanD-ENO1-UGA1 fragment from pMhCt087 digested with NotI and EcoRI, 55 ng of the 960 bp PCR product 5' containing the 5' half of the URA3 split marker, 1× In-Fusion reaction buffer (Clontech) and 1 µL of IN-FUSION™ enzyme (Clontech). The reaction was incubated at 37° C. for 15 minutes, 50° C. for 15 minutes, and then placed on ice. The reaction then was diluted with 40 µL of TE buffer and 2.5 µL was used to transform SoloPack Gold SuperCompetent Cells (Agilent Technologies) according to the manufacturer's instructions. Transformants were plated onto 2×YT+amp plates and incubated at room temperature for three days. Several of the resulting transformants were screened for proper insertion of the desired PCR products by SalI and HpaI digestion. A done yielding the desired band sizes was confirmed to be correct by DNA sequencing and designated pMhCt089.

Next, the UGA1 ORF in pMhCt089 was replaced with the *S. avermitilis* panD gene codon-optimized for expression in *I. orientalis* which encodes the ADC of SEQ ID NO: 17. *S. avermitilis* panD version r1 (SEQ ID NO: 145) was synthesized by GeneArt® in the vector pMA-T. The plasmid pMA-T was digested with XbaI and PacI and the resulting fragments were separated by 0.9% agarose gel electrophoresis in TAE buffer, and an approximately 434 bp band was excised from the gel and purified using a NUCLEOSPIN® Extract II Kit (Macherey-Nagel) according to the manufacturer's instructions. Plasmid pMhCt089 was digested with XbaI and PacI, treated with 10 units calf intestinal phosphatase (New England Biolabs) at 37° C. for 30 minutes, and the resulting fragments were separated by 0.9% agarose gel electrophoresis in TAE buffer, and an approximately 4.5 kbp band was excised from the gel and purified using a NUCLEOSPIN® Extract II Kit (Macherey-Nagel) according to the manufacturer's instructions. The pMhCt089 vector and *S. avermitilis* panD version r1 were joined in a ligation reaction (20 µL) containing 1× Quick ligation buffer (New England Biolabs), 2 µL XbaI/PacI pMhCt089 vector, 2 µL XbaI/PacI *S. avermitilis* panD version r1 insert, and 1 µL Quick T4 DNA ligase (New England Biolabs). The ligation reaction was incubated for 5 min at room temperature, and then placed on ice. 5 µL of this reaction was used to transform ONE SHOT® TOP10 chemically competent *E. coli* cells (Invitrogen) according to the manufacturer's instructions. Transformants were plated onto 2×YT+amp plates and incubated at room temperature for three days. Several of the resulting transformants were screened for proper insertion of the desired PCR products by XbaI and PacI digestion. A clone yielding the desired band sizes was confirmed to be correct by DNA sequencing and designated pMhCt092.

The final cloning step for the left-hand construct was to replace the ald5680 5' homology region present in pMhCt092 with the adh1202 5' homology region. A PCR product containing the sequence 5' of the adh1202 ORF, along with the desired additional restriction sites and flanking DNA for cloning was amplified with the primers 0612470 and 0612471. The PCR reaction (50 µL) contained 1 µL of a 1 to 50 dilution of pGMEr140 mini-prep plasmid DNA (a derivative of pMIBa107 described herein wherein the PCR amplified region is identical), 1× iProof™ HF buffer (Bio-Rad Laboratories), 100 pmol each of primers 0612470 and 0612471, 200 µM each of dATP, dCTP, dGTP, and dTTP, and 1 unit of iProof™ High Fidelity DNA polymerase (Bio-Rad Laboratories). The PCR was performed in an EPPENDORF® MASTERCYCLER® (Eppendorf Scientific) programmed for one cycle at 98° C. for 30 seconds followed by 34 cycles each at 98° C. for 10 seconds, 59° C. for 20 seconds, and 72° C. for 30 seconds, with a final extension at 72° C. for 10 minutes. Following thermocycling, the PCR reaction products were separated by 1% agarose gel electrophoresis in TAE buffer where an approximately 790 bp PCR product was excised from the gel and purified using a NUCLEOSPIN® Extract II Kit (Macherey-Nagel) according to the manufacturer's instructions.

Figure 12:
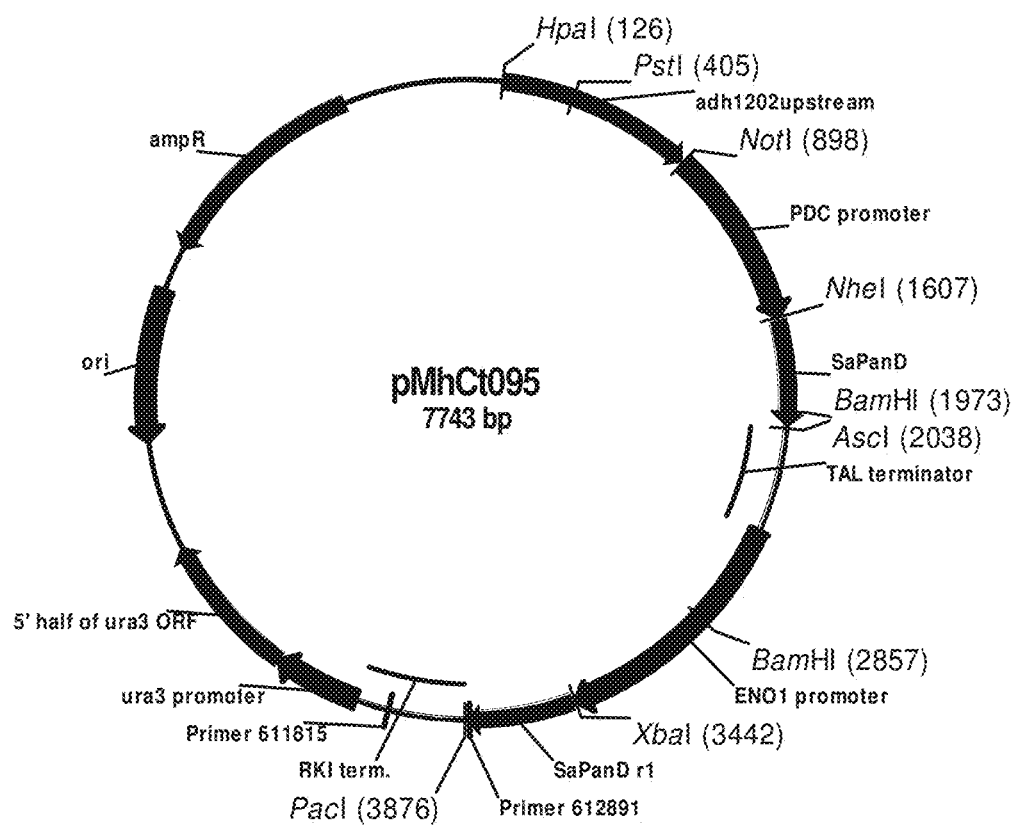
FIG. 12: Plasmid pMhCt095

To create a recipient vector for the above PCR product, the plasmid pMhCt092 was digested with HpaI and NotI, treated with 10 units calf intestinal phosphatase (New England Biolabs) at 37° C. for 30 minutes, and purified by 0.9% agarose gel electrophoresis in TAE buffer, and an approximately 7.0 kbp band was excised from the gel and purified using a NUCLEOSPIN® Extract II Kit (Macherey-Nagel) according to the manufacturer's instructions. The PCR product and linear vector were joined using an IN-FUSION™ Advantage PCR Cloning Kit (Clontech) in a total reaction volume of 10 µL composed of 120 ng pMhCt092 vector digested with HpaI and NotI, 30 ng of the adh1202 5' homology containing PCR product, 1× In-Fusion reaction buffer (Clontech) and 1 µL of IN-FUSION™ enzyme (Clontech). The reaction was incubated at 37° C. for 15 minutes, 50° C. for 15 minutes, and then placed on ice. The reaction was diluted with 40 µL of TE buffer and 2.5 µL was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired PCR products by digestion with BamHI and PstI. A clone yielding the desired band sizes was confirmed to be correct by DNA sequencing and designated pMhCt095 (FIG. 12).

Plasmid pMhCt095 is a left-hand *I. orientalis* adh1202 targeting construct containing the PDC promoter driving expression of a *S. avermitilis* ADC gene codon-optimized for expression in *I. orientalis* (SEQ ID NO: 130), the TAL terminator, the ENO1 promoter driving expression of a second *S. avermitilis* ADC gene codon-optimized for expression in *I. orientalis* (SEQ ID NO: 145), the *I. orientalis* RKI terminator, the *I. orientalis* URA3 promoter and the 5' fragment of the *I. orientalis* URA3 ORF.

Example 3A-8: Right-Hand Fragments of Insertion Vectors with Multiple Nucleotide Sequences for Expressing Aspartate 1-Decarboxylase (ADC) at the Adh1202 Locus A PCR product containing the 3' fragment of the *I. orientalis* URA3 ORF, along with the desired additional restriction sites and flanking DNA for cloning was amplified with primers 0612275 and 0612276. The PCR reaction (50 µL) contained 1 µL of a 1 to 50 dilution of pMhCt069 mini-prep plasmid DNA (supra), 1× iProof™ HF buffer (Bio-Rad Laboratories), 100 pmol each of primers 0612275 and 0612276, 200 µM each of dATP, dCTP, dGTP, and dTTP, and 1 unit of iProof™ High Fidelity DNA polymerase (Bio-Rad Laboratories). The PCR was performed in an EPPENDORF® MASTERCYCLER® (Eppendorf Scientific) programmed for one cycle at 98° C. for 30 seconds followed by 32 cycles each at 98° C. for 10 seconds, 59° C. for 20 seconds, and 72° C. for 45 seconds, with a final extension at 72° C. for 10 minutes. Following thermocycling, the PCR reaction products were separated by 1% agarose gel electrophoresis in TAE buffer where an approximately 1155 bp PCR product was excised from the gel and purified using a NUCLEOSPIN® Extract II Kit (Macherey-Nagel) according to the manufacturers instructions.

A fragment containing the TDH3 promoter, XbaI and PacI restriction sites for insertion of an ectopic gene, and the PDC terminator was excised from pMhCt069 via digestion with NotI and PmeI. 10 µg of a midi-prep of pMhCt069 was digested with NotI and PmeI and then purified by 0.9% agarose gel electrophoresis in TAE buffer, and an approximately 1.85 kbp band was excised from the gel and purified using a NUCLEOSPIN® Extract II Kit (Macherey-Nagel) according to the manufacturer's instructions.

A PCR product containing the sequence 3' of the ald5680 ORF, along with the desired additional restriction sites and flanking DNA for cloning was amplified with the primers 0612277 and 0612278. The PCR reaction (50 µL) contained 1 µL of a 1 to 50 dilution of pHJJ75 mini-prep plasmid DNA (FIG. 23), 1× iProof™ HF buffer (Bio-Rad Laboratories), 100 pmol each of primers 0612277 and 0612278, 200 µM each of dATP, dCTP, dGTP, and dTTP, and 1 unit of iProof™ High Fidelity DNA polymerase (Bio-Rad Laboratories). The PCR was performed in an EPPENDORF® MASTERCYCLER® (Eppendorf Scientific) programmed for one cycle at 98° C. for 30 seconds followed by 32 cycles each at 98° C. for 10 seconds, 59° C. for 20 seconds, and 72° C. for 45 seconds, with a final extension at 72° C. for 10 minutes. Following thermocycling, the PCR reaction products were separated by 1% agarose gel electrophoresis in TAE buffer where an approximately 844 bp PCR product was excised from the gel and purified using a NUCLEOSPIN® Extract II Kit (Macherey-Nagel) according to the manufacturer's instructions.

The purified 1155 bp, 1.85 kbp, and 844 bp DNA fragments from above were then inserted into pUC19 digested with EcoRI and HindIII using an IN-FUSION™ Advantage PCR Cloning Kit (Clontech) in a total reaction volume of 10 µL composed of 150 ng of the fragment from the pUC19 vector digested with HindIII and EcoRI; 66 ng of the 1155 bp DNA containing the 3' portion of the URA3 split marker; 106 ng of the 1.85 kbp fragment digested with PmeI and NotI and containing the TDH3 promoter, XbaI and PacI restriction sites for insertion of an ectopic gene, and PDC terminator from pMhCt069; 48 ng of the 844 bp PCR product containing the 3' ald5680 flanking DNA; 1× In-Fusion reaction buffer (Clontech) and 1 µL of IN-FUSION™ enzyme (Clontech). The reaction was incubated at 37° C. for 15 minutes, 50° C. for 15 minutes, and then placed on ice. The reaction was diluted with 40 µL of TE buffer and 2.5 µL was used to transform SoloPack Gold SuperCompetent Cells (Agilent Technologies) according to the manufacturer's instructions. Transformants were plated onto 2×YT+amp plates and incubated at room temperature for three days. Several of the resulting transformants were screened for proper insertion of the desired PCR products by SalI and HpaI digestion. A clone yielding the desired band sizes was confirmed to be correct by DNA sequencing and designated ald5680 right #20.

The TKL terminator, the PGK1 promoter, XbaI and PacI restriction sites, and a shorter version of the PDC terminator region was added between the TDH3 promoter and 3' ald5680 flanking DNA of ald5680 right #20 as follows. The TKL terminator along with the desired additional restriction sites and flanking DNA for cloning was amplified with the primers 0612356 and 0612357. The desired PCR product was amplified using a temperature gradient for the annealing temperature and DMSO in some reactions. Four identical PCR reactions were prepared, with each PCR reaction (50 µL) containing 1 µL of a 1 to 50 dilution of pACN23 mini-prep plasmid DNA (FIG. 20), 1× iProof™ HF buffer (Bio-Rad Laboratories), 100 pmol each of primers 0612356 and 0612357, 200 µM each of dATP, dCTP, dGTP, and dTTP, and 1 unit of iProof™ High Fidelity DNA polymerase (Bio-Rad Laboratories). A second set of four tubes was set up as above except that the reactions each included the addition of 1.5 µL of DMSO. The PCRs were performed in an EPPENDORF® MASTERCYCLER® (Eppendorf Scientific) programmed for one cycle at 98° C. for 30 seconds followed by 32 cycles each at 98° C. for 10 seconds, X° C. for 20 seconds, where X=47.6° C., 51.8° C., 57.1° C., or 62.1° C., and 72° C. for 45 seconds, with a final extension at 72° C. for 10 minutes. A PCR with and without DMSO was run for each annealing temperature shown. Following thermocycling, 10 µL of each PCR reaction was separated by 1% agarose gel electrophoresis in TAE buffer. Visualization of this gel revealed that PCR reactions performed with DMSO at the two highest annealing temperatures and without DMSO at the two lowest annealing temperature gave the highest yield of the desired 844 bp product. These four PCRs were combined, separated by 1% agarose gel electrophoresis in TAE buffer, where the approximately 844 base pair PCR product was excised from the gel and purified using a NUCLEOSPIN® Extract II Kit (Macherey-Nagel) according to the manufacturer's instructions.

Figure 25:
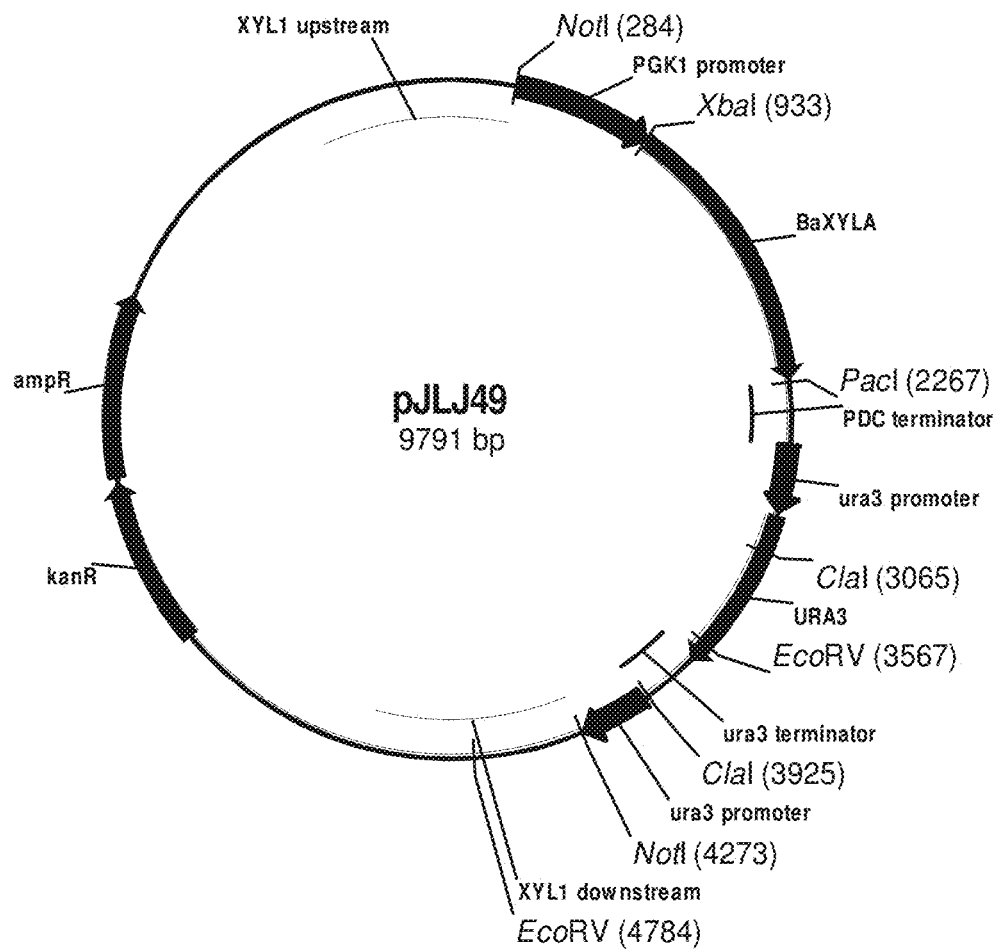
FIG. 25: Plasmid pJLJ49

PCR amplification of the desired PGK1 promoter region was done as a two step process. First, a PCR product containing the PGK1 promoter DNA was cloned following amplification with the following primers 0612150 and 0612151. The PCR reaction (50 µL) contained 3 µL of pJLJ49 mini-prep DNA (FIG. 25), 1× Pfx amplification buffer (Invitrogen), 2 mm MgSO$_4$, 100 pmol each of primers 0612150 and 0612151, 200 µM each of dATP, dCTP, dGTP, and dTTP, and 1.25 Units Platinum® Pfx DNA polymerase (Invitrogen). The PCR was performed in an EPPENDORF® MASTERCYCLER® (Eppendorf Scientific) programmed for one cycle at 95° C. for 2 minutes followed by 25 cycles each at 95° C. for 1 minute, 55° C. for 1 minute, and 72° C. for 3 minutes, with a final extension at 72° C. for 10 minutes. Following thermocycling, the PCR reaction products were separated by 1% agarose gel electrophoresis in TAE buffer where an approximately 630 bp PCR product was excised from the gel and purified using a NUCLEOSPIN® Extract II Kit (Macherey-Nagel) according to the manufacturer's instructions.

The approximately 630 bp PCR product was cloned into pCR4™ BLUNT TOPO® (Invitrogen) vector using the Zero Blunt® TOPO® PCR cloning kit for sequencing (Invitrogen) according to the manufacturer's instructions. In a total reaction volume of 6 µL either 0.5 or 4 µL of the 630 bp PCR product, 1 µL salt solution (Invitrogen) and 1 µL pCR4™ BLUNT TOPO® (Invitrogen) were incubated together at room temperature for 15 minutes. 2 µL of each cloning reaction was transformed into One Shot® TOP10 Chemically Competent *E. coli* (Invitrogen) cells according to manufacturer's instructions. Transformants were plated onto LB+kan plates and incubated at 37° C. overnight. Several of the resulting transformants were screened for proper insertion of the desired PCR product by EcoRI digestion. A clone yielding the desired band sizes was confirmed to be correct by DNA sequencing and designated PGK1_in_TOPO.

The PGK1 promoter from PGK1_in_TOPO was isolated and purified prior to use as a PCR template as follows. 25 µL of a midi-prep of PGK1_in_TOPO was digested with XbaI and PacI and purified by 0.9% agarose gel electrophoresis in TAE buffer, and an approximately 640 bp band was excised from the gel and purified using a NUCLEOSPIN® Extract II Kit (Macherey-Nagel) according to the manufacturer's instructions.

The PGK1 promoter along with the desired additional restriction sites and flanking DNA for cloning was amplified with the primers 0612358 and 0612359 using a temperature gradient. Eight identical PCR reactions were set up, each PCR reaction (50 µL) contained 20 ng of purified PGK1 promoter DNA via XbaI and PacI digestion of PGK1_in_TOPO, 1× Herculase reaction buffer (Agilent Technologies), 100 pmol each of primers 0612358 and 0612359, 200 µM each of dATP, dCTP, dGTP, and dTTP, and 2.5 units of Herculase HotStart DNA Polymerase (Agilent Technologies). The PCRs were performed in an EPPENDORF® MASTERCYCLER® (Eppendorf Scientific) programmed for one cycle at 98° C. for 30 seconds followed by 32 cycles each at 98° C. for 10 seconds, X° C. for 20 seconds, where X=53.7° C., 55.4° C., 57.6° C., 60.0° C., 62.4° C., 64.8° C., 66.9° C., 68.6° C., and 72° C. for 45 seconds, with a final extension at 72° C. for 10 minutes. Following thermocycling, 10 µL of each PCR reaction was separated by 1% agarose gel electrophoresis in TAE buffer. Visualization of this gel revealed that four PCR reactions performed with the highest annealing temperature gave the highest yield of the desired approximately 700 bp product. These four PCRs were combined, separated by 1% agarose gel electrophoresis in TAE buffer, where the approximately 700 base pair PCR product was excised from the gel and purified using a NUCLEOSPIN® Extract II Kit (Macherey-Nagel) according to the manufacturer's instructions.

Plasmid ald5680_right #20 contains approximately 870 bp of the region downstream from the *I. orientalis* PDC ORF as the PDC terminator region. However, this region is likely larger than necessary for proper function as a terminator and if maintained in its current size might serve as a catalyst for unwanted homologous recombination to the PDC locus. Therefore, a PCR product to replace the PDC terminator in ald5680_right #20 with a smaller version was amplified with the primers 0612360 and 0612361. The desired PCR product was amplified using a temperature gradient for the annealing temperature and DMSO in some reactions. Four identical PCR reactions were set up, each PCR reaction (50 µL) contained 1 µL of a 1 to 50 dilution of pJLJ49 mini-prep plasmid DNA (FIG. 25), 1× iProof™ HF buffer (Bio-Rad Laboratories), 100 pmol each of primers 0612360 and 0612361, 200 µM each of dATP, dCTP, dGTP, and dTTP, and 1 unit of iProof™ High Fidelity DNA polymerase (Bio-Rad Laboratories). A second set of four tubes was set up as above except that the reactions each included the addition of 1.5 µL of DMSO. The PCRs were performed in an EPPENDORF® MASTERCYCLER® (Eppendorf Scientific) programmed for one cycle at 98° C. for 30 seconds followed by 32 cycles each at 98° C. for 10 seconds, X° C. for 20 seconds, where X=47.6° C., 51.8° C., 57.1° C., or 62.1° C., and 72° C. for 45 seconds, with a final extension at 72° C. for 10 minutes. A PCR with and without DMSO was run for each annealing temperature shown. Following thermocycling, 10 µL of each PCR reaction was separated by 1% agarose gel electrophoresis in TAE buffer. Visualization of this gel revealed that the four PCR reactions performed with DMSO, regardless of annealing temperature, gave the highest yield of the desired 338 bp product. These four PCRs were combined, separated by 1% agarose gel electrophoresis in TAE buffer, where the approximately 338 base pair PCR product was excised from the gel and purified using a NUCLEOSPIN® Extract II Kit (Macherey-Nagel) according to the manufacturer's instructions.

PCR was used to create a single amplification product fusing approximately 700 bp PGK1 containing PCR product to the 338 bp PDC terminator product. The PCR reaction (50 µL) contained 107 ng of the PGK1 containing PCR product, 56 ng of the PDC terminator containing PCR product, 1× Phusion HF buffer (New England Biolabs), 100 pmol each of primers 0612358 and 0612361, 200 µM each of dATP, dCTP, dGTP, and dTTP, and 1 unit of Phusion™ High-Fidelity DNA polymerase (New England Biolabs). The PCR was performed in an EPPENDORF® MASTERCYCLER® (Eppendorf Scientific) programmed for one cycle at 98° C. for 30 seconds followed by 34 cycles each at 98° C. for 10 seconds, 56° C. for 20 seconds, and 72° C. for 2 minutes and 45 seconds, with a final extension at 72° C. for 10 minutes. Following thermocycling, the PCR reaction products were separated by 0.9% agarose gel electrophoresis in TAE buffer where an approximately 1020 base pair PCR product was excised from the gel and purified using a NUCLEOSPIN® Extract II Kit (Macherey-Nagel) according to the manufacturer's instructions.

The plasmid ald5680_right #20 was digested with XbaI and NotI, treated with 10 units calf intestinal phosphatase (New England Biolabs) at 37° C. for 30 minutes, and purified by 0.9% agarose gel electrophoresis in TAE buffer. A band of approximately 5.6 kbp was excised from the gel and purified using a NUCLEOSPIN® Extract II Kit (Macherey-Nagel) according to the manufacturer's instructions.

The purified 487 bp and 1020 bp PCR products from above were then inserted into the digested ald5680_right#20 fragment using an IN-FUSION™ Advantage PCR Cloning Kit (Clontech) in a total reaction volume of 10 µL composed of 150 ng of the ald5680_right #20 vector digested with XbaI and NotI, 13 ng of the TKL terminator PCR product, 28 ng of the PGK1 promoter-PDC terminator PCR product, 1× In-Fusion reaction buffer (Clontech) and 1 µL of IN-FUSION™ enzyme (Clontech). The reaction was incubated at 37° C. for 15 minutes, 50° C. for 15 minutes, and then placed on ice. The reaction was diluted with 40 µL of TE buffer and 2.5 µL was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired PCR products by AccI digestion. A clone yielding the desired band sizes was confirmed to be correct by DNA sequencing and designated pMhCt091.

Plasmid pMhCt091 is an empty right-hand I. orientalis ald5680 targeting construct containing the 3' fragment of the I. orientalis URA3 ORF, the I. orientalis TDH3 promoter followed by NheI and AscI restriction sites for addition of a gene of interest, the I. orientalis TKL terminator, the I. orientalis PGK1 promoter followed by XbaI and PacI restriction sites for addition of a second gene of interest, the I. orientalis PDC terminator, and flanking DNA to target homologous recombination to the 3' ald5680 locus.

S. avermitilis panD version r5 (SEQ ID NO: 146) was synthesized in the vector 1075328_SaPanD_r5 by GeneArt. The XbaI and PacI restriction sites were changed to the desired NheI and AscI sites for cloning into the 5' cloning site of pMhCt091 by PCR. The PCR reaction (50 µL) contained 1 µL of a 1 to 50 dilution of 1075328_SaPanD_r5 mini-prep plasmid DNA (GeneArt®), 1× iProof™ HF buffer (Bio-Rad Laboratories), 100 pmol each of primers 0612378 and 0612379, 200 µM each of dATP, dCTP, dGTP, and dTTP, 1.5 µL DMSO and 1 unit of iProof™ High Fidelity DNA polymerase (Bio-Rad Laboratories). The PCR was performed in an EPPENDORF® MASTERCYCLER® (Eppendorf Scientific) programmed for one cycle at 98° C. for 30 seconds followed by 34 cycles each at 98° C. for 10 seconds, 59° C. for 20 seconds, and 72° C. for 30 seconds, with a final extension at 72° C. for 10 minutes. Following thermocycling, the PCR reaction products were separated by 0.9% agarose gel electrophoresis in TAE buffer where an approximately 471 base pair PCR product was excised from the gel and purified using a NUCLEOSPIN® Extract II Kit (Macherey-Nagel) according to the manufacturer's instructions.

The plasmid pMhCt091 (supra) was digested with NheI and AscI, treated with 10 units calf intestinal phosphatase (New England Biolabs) at 37° C. for 30 minutes, and purified by 0.9% agarose gel electrophoresis in TAE buffer. A band of approximately 6.9 kbp was excised from the gel and purified using a NUCLEOSPIN® Extract II Kit (Macherey-Nagel) according to the manufacturer's instructions. The purified panD r5 containing PCR product from above was then inserted into the digested pMhCt091 fragment using an IN-FUSION™ Advantage PCR Cloning Kit (Clontech) in a total reaction volume of 10 µL composed of 150 ng of the pMhCt091 vector digested from NheI and AscI, 19 ng of the panD r5 PCR product, 1× In-Fusion reaction buffer (Clontech) and 1 µL of IN-FUSION™ enzyme (Clontech). The reaction was incubated at 37° C. for 15 minutes, 50° C. for 15 minutes, and then placed on ice. The reaction was diluted with 40 µL of TE buffer and 2.5 µL was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired PCR products by SmaI digestion. A clone yielding the desired band sizes was confirmed to be correct by DNA sequencing and designated pMhCt093.

The plasmid pMhCt093 was digested with XbaI and PacI, treated with 10 units calf intestinal phosphatase (New England Biolabs) at 37° C. for 30 minutes, and purified by 0.9% agarose gel electrophoresis in TAE buffer, and an approximately 7.4 kbp band was excised from the gel and purified using a NUCLEOSPIN® Extract II Kit (Macherey-Nagel) according to the manufacturer's instructions. S. avermitilis panD version r2 (SEQ ID NO: 147) was codon-optimized for expression in I. orientalis and synthesized in the vector pMA-T by GeneArt®. The plasmid was digested with XbaI and PacI and the resulting fragments were separated by 0.9% agarose gel electrophoresis in TAE buffer. A band of approximately 434 bp was excised from the gel and purified using a NUCLEOSPIN® Extract II Kit (Macherey-Nagel) according to the manufacturer's instructions.

The purified ~434 bp fragment above was cloned into the pMhCt093 vector digested with XbaI and PacI in a ligation reaction (20 µL) containing 1× Quick ligation buffer (New England Biolabs), 2 µL of the pMhCt093 vector digested with XbaI and PacI, 2 µL of the ~434 bp fragment above, and 1 µL Quick T4 DNA ligase (New England Biolabs). The ligation reaction was incubated for 5 min at room temperature, and then the tube placed on ice. 5 µL of this reaction was used to transform SoloPack Gold SuperCompetent Cells (Agilent Technologies) according to the manufacturer's instructions. Transformants were plated onto 2×YT+amp plates and incubated at room temperature for three days. Several of the resulting transformants were screened for proper insertion of the desired PCR products by digestion with XbaI and PacI. Isolate pMhCt094 was chosen for future work.

The final cloning step for the right-hand construct was to replace the ald5680 3' homology region present in pMhCt094 with the adh1202 3' homology region. A PCR product containing the sequence just 3' of the adh1202 ORF, along with the desired additional restriction sites and flanking DNA for cloning was amplified with the primers 612472 and 612473. The PCR reaction (50 µL) contained 1 µL of a 1 to 50 dilution of pGMEr140 (supra) mini-prep plasmid DNA, 1× iProof™ HF buffer (Bio-Rad Laboratories), 100 pmol each of primers 0612472 and 0612473, 200 µM each of dATP, dCTP, dGTP, and dTTP, and 1 unit of iProof™ High Fidelity DNA polymerase (Bio-Rad Laboratories). The PCR was performed in an EPPENDORF® MASTERCYCLER® (Eppendorf Scientific) programmed for one cycle at 98° C. for 30 seconds followed by 34 cycles each at 98° C. for 10 seconds, 59° C. for 20 seconds, and 72° C. for 30 seconds, with a final extension at 72° C. for 10 minutes. Following thermocycling, the PCR reaction products were separated by 1% agarose gel electrophoresis in TAE buffer where an approximately 620 base pair PCR product was excised from the gel and purified using a NUCLEOSPIN® Extract II Kit (Macherey-Nagel) according to the manufacturer's instructions.

Figure 13:
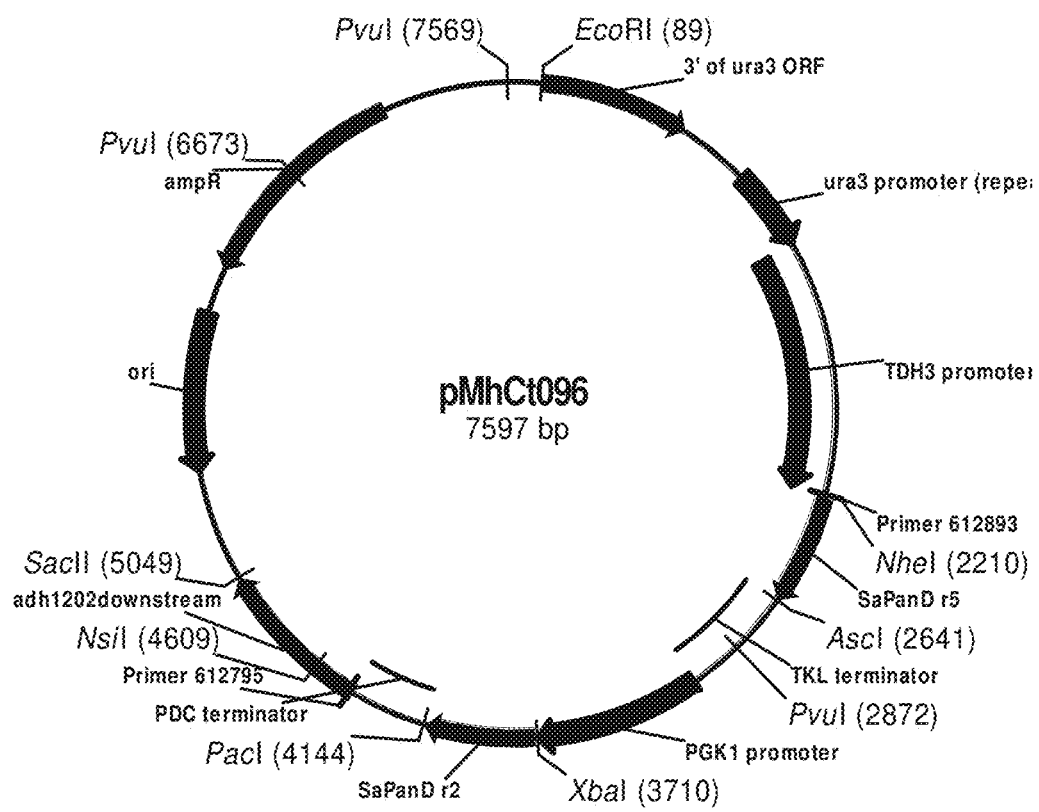
FIG. 13: Plasmid pMhCt096

To create a recipient vector for the above PCR product, the plasmid pMhCt094 was digested with SacII and NotI, treated with 10 units calf intestinal phosphatase (New England Biolabs) at 37° C. for 30 minutes, and purified by 0.9% agarose gel electrophoresis in TAE buffer, and an approximately 7.0 kbp band was excised from the gel and purified using a NUCLEOSPIN® Extract II Kit (Macherey-Nagel) according to the manufacturer's instructions. The PCR product and linear vector were joined using an IN-FUSION™ Advantage PCR Cloning Kit (Clontech) in a total reaction volume of 10 µL composed of 191 ng of the pMhCt094 vector digested with SacII and NotI, 36 ng of the adh1202 3' homology containing PCR product, 1× In-Fusion reaction buffer (Clontech) and 1 µL of IN-FUSION™ enzyme (Clontech). The reaction was incubated at 37° C. for 15 minutes, 50° C. for 15 minutes, and then placed on ice. The reaction was diluted with 40 µL of TE buffer and 2.5 µL was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper insertion of the desired PCR products by digestion with NsiI and PvuI. A clone yielding the desired band sizes was confirmed to be correct by DNA sequencing and designated pMhCt096 (FIG. 13).

Plasmid pMhCt096 is a right-hand *I. orientalis* adh1202 targeting construct containing the 3' fragment of the *I. orientalis* URA3 ORF, the *I. orientalis* TDH3 promoter driving expression of a third *S. avermitilis* ADC gene codon-optimized for expression in *I. orientalis* (SEQ ID NO: 146), the *I. orientalis* TKL terminator, the *I. orientalis* PGK1 promoter driving expression of a forth *S. avermitilis* ADC gene codon-optimized for expression in *I. orientalis* (SEQ ID NO: 147), the *I. orientalis* PDC terminator, and flanking DNA to target homologous recombination to the 3' adh1202 locus.

Example 3A-9: Yeast Strains Expressing Aspartate 1-Decarboxylase (ADC), β-Alanine Aminotransferase (BAAT), and 3-Hydroxypropionic Acid Dehydrogenase (3-HPDH) at the pdc Locus; and Aspartate 1-Decarboxylase (ADC) from Four Nucleotide Sequences at the Adh1202 Locus Examples 3A-7 and 3A-8 above describe creation of left-hand and right-hand constructs for targeting expression of four nucleotide variants of the *S. avermitilis* ADC gene codon-optimized for expression in *I. orientalis* at the adh1202 locus. Prior to transformation into *I. orientalis* CNB1, 10 µg of pMhCt095 was digested with HpaI and SacII to release the desired transforming DNA from the pUC19 backbone vector. Likewise, 10 µg of pMhCt096 was digested with EcoRI and SacII to release the desired transforming DNA from the pUC19 backbone vector. The ~5 kbp expression cassette containing band was separated from the pUC19 backbone DNA by gel electrophoresis, excised from the gel, and purified using a NUCLEOSPIN® Extract II Kit (Macherey-Nagel) according to the manufacturer's instructions. 30 µL elution buffer was used for the elution step. An equimolar ratio of pMhCt095 and pMhCt096 linear transformation DNA totaling 10 µL were used to transform strain yMhCt010 (supra). Transformants were selected on ura selection plates and placed at 37° C. for growth. Approximately twelve transformants were picked the following day and restreaked for single colonies to ura selection plates and grown at 37° C. overnight, and then a single colony was picked from each of the streaks generated by each initial transformant and restreaked to ura selection plates. After another night of growth at 37° C., a final single colony was picked from each streak and restreaked to a ura selection plate and grown overnight at 37° C. After this second round of single colony purification and outgrowth, genomic DNA was prepared for use in PCR to verify the desired targeted integration occurred as described herein. Correct targeting of the pMhCt095 and pMhCt096 fragments to the adh1202 locus was verified using primers 0611718 and 0611632 (supra). Primer 0611718 binds in the PDC terminator region present in pMhCt096, while primer 0611632 binds in adh1202 locus DNA 3' of the region targeted and amplifies in the anti-sense direction. Generation of an approximately 727 bp band from PCRs with these primers indicated the occurrence of the desired integration event at the adh1202 locus.

A PCR reaction (25 µL) contained 0.5 µL genomic DNA for the strain to be screened, 1× Crimson Taq™ Reaction Buffer (New England Biolabs), 25 pmol of the sense primer, 25 pmol of the anti-sense primer, 200 µM each of dATP, dCTP, dGTP, and dTTP, and 0.625 units of Crimson Taq™ DNA polymerase (New England Biolabs). The PCR was performed in an EPPENDORF® MASTERCYCLER® (Eppendorf Scientific) programmed for one cycle at 95° C. for 30 seconds followed by 30 cycles each at 95° C. for 30 seconds, 50° C. for 30 seconds, and 68° C. for 2.5 minutes, with a final extension at 68° C. for 10 minutes. Following thermocycling, the PCR reaction products were separated by 1% agarose gel electrophoresis in TAE buffer and the sizes of the bands visualized and interpreted as described above. Two independently isolated transformants giving the desired 727 bp band were designated yMhCt019 or 95/96 2 (see genotype in Table 21).

TABLE 21

Transformant genotype

| Strain | Parent strain | Genotype |
|---|---|---|
| yMhCt019 95/96 2 | yMhCt010 | adh1202Δ::(PDC$_{promo}$-Opt.SaPanD r10, ENO1$_{promo}$-Opt.SaPanD r1, URA3, TDH3$_{promo}$-Opt.SaPanD r5, PGK1$_{promo}$-Opt.SaPanD r2)/ADH1202 pdcΔ::(PDC$_{promo}$-Opt.SaPanD ENO1$_{promo}$-Opt.ScUGA1, URA3-Scar, TDH3$_{promo}$-Opt.ScYMR226C)/pdcΔ::(PDC$_{promo}$-Opt.SaPanD, ENO1$_{promo}$-Opt.ScUGA1, URA3-Scar, TDH3$_{promo}$-Opt.ScYMR226C) ura3−/ura3− |

A ura− derivative of yMhCt019 then was isolated as described herein. Genomic DNAs from several FOA resistant colonies of yMhCt019 were screened by PCR for the desired loop-out event with the primers 0611815 and 0612795. Primer 0611815 anneals in the RKI terminator of the left-hand construct and amplifies toward the URA3 promoter, while primer 0612795 anneals within 3' adh1202 homology (of pMhCt096 or endogenous adh1202 locus) back toward 5' region. PCR reactions were carried out as described for the isolation of yMhCt019 above except that the length of the extension phase was changed to 3.5 minutes. Generation of a 3.7 kbp band with these primers indicates that the desired loop-out event has occurred and only the URA3 promoter scar remains at the modified adh1202 locus, while an approximately 5.1 kbp band would indicate the presence of the intact URA3 promoter-URA3 ORF-URA3 terminator-URA3 promoter cassette, indicating the desired recombination event did not occur. A strain that gave the desired 3.7 kbp band was kept and designated yMhCt021.

In order to isolate a derivative of yMhCt021 homozygous for the multiple panD expression cassette at adh1202, yMhCt021 was transformed with linearized pMhCt095 and pMhCt096 as described above. After two rounds of single colony purification and outgrowth, genomic DNA was prepared for use in PCR to verify the desired targeted integration occurred. Correct targeting of the pMhCt095 and pMhCt096 fragments to the remaining wild-type adh1202 locus of yMhCt021 was verified with the primers 0612891 and 0612893. Primer 0612891 anneals in the 3' region of SaPanD r1 plus half of the PacI site after r1 stop of pMhCt095. Primer 0612893 anneals in the extreme 5' region of SaPanD r5, includes the NheI site and leader of pMhCt096, and amplifies in reverse complementary direction.

Generation of a 3.2 kbp band with these primers indicates the presence of an intact URA3 promoter-URA3 ORF-URA3 terminator-URA3 promoter cassette as expected from the second integration event via pMhCt095 and pMhCt096 on the remaining adh1202 wild-type locus of yMhCt021, while an approximately 1.7 kbp band would indicate the presence of the URA3 scar site at the other adh1202 locus (from the initial integration event and subsequent URA3 marker loop-out). PCR reactions were carried out as described for the isolation of yMhCt019 above except that the length of the extension phase was changed to 3.5 minutes. A strain that gave both of these band sizes was designated yMhCt022 (see genotype in Table 22).

TABLE 22

Transformant genotype

| Strain | Parent strain | Genotype |
|---|---|---|
| yMhCt022 | yMhCt021 | adh1202Δ::(PDC$_{promo}$-Opt.SaPanD r10, ENO1$_{promo}$-Opt.SaPanD r1, URA3, TDH3$_{promo}$-Opt.SaPanD r5, PGK1$_{promo}$-Opt.SaPanD r2)/adh1202Δ::(PDC$_{promo}$-Opt.SaPanD r10, ENO1$_{promo}$-Opt.SaPanD r1, URA3-Scar, TDH3$_{promo}$-Opt.SaPanD r5, PGK1$_{promo}$-Opt.SaPanD r2) pdcΔ::(PDC$_{promo}$-Opt.SaPanD, ENO1$_{promo}$-Opt.ScUGA1, URA3-Scar, TDH3$_{promo}$-Opt.ScYMR226C)/pdcΔ::(PDC$_{promo}$-Opt.SaPanD, ENO1$_{promo}$-Opt.ScUGA1, URA3-Scar, TDH3$_{promo}$-Opt.ScYMR226C) ura3−/ura3− |

Strains were grown in shake flasks and CFE were prepared and assayed for aspartate decarboxylase (ADC) activity as herein. The experimental results are shown in Table 23A.

TABLE 23A

Transformant enzyme activity data

| Strain | Gene Overexpressed | ADC activity |
|---|---|---|
| MBin500 (control) | N/A | 0.00 |
| yMhCt019 | ADC (SEQ ID NOs: 130, 145, 146, and 147) | 2.18 |

TABLE 23A-continued

Transformant enzyme activity data

| Strain | Gene Overexpressed | ADC activity |
|---|---|---|
| 95/96 2 | gabT (SEQ ID NO: 14) 3-HPDH (SEQ ID NO: 144) | 2.52 |

The aspartate 1-decarboxylase (ADC), beta-alanine aminotransferase (BAAT) and 3HP dehydrogenase (3-HPDH) activities in CFE prepared from strains MBin500 (control), yMhCt019, 95/96-2, yMhCt008 and yMhCt022 were compared. The results of this experiment are shown in Table 23B.

TABLE 23B

Transformant enzyme activity data

| Strain | Genes Overexpressed | Gene Sources | ADC Activity | BAAT Activity | 3HP DH Activity |
|---|---|---|---|---|---|
| MBin500 (control) | N/A | N/A | 0.002 | 0.61 | 0.4 |
| yMhCt019 | YMR226c (SEQ ID NO: 44) ADC (SEQ ID NOs: 130, 145, 146 and 147) UGA1 (SEQ ID NO: 141) | S. cerevisiae S. avermitilis S. cerevisiae | 0.789 | 14.53 | 72.0 |
| 95/96-2 | YMR226c (SEQ ID NO: 144) ADC (SEQ ID NOs: 130, 145, 146 and 147) UGA1 (SEQ ID NO: 141) | S. cerevisiae S. avermitilis S. cerevisiae | 0.891 | 20.42 | 73.2 |
| yMhCt008 | YMR226c (SEQ ID NO: 144) ADC (SEQ ID NO: 130) UGA1 (SEQ ID NO: 141) | S. cerevisiae S. avermitilis S. cerevisiae | 0.272 | 13.14 | 61.1 |
| yMhCt022 | YMR226c (SEQ ID NO: 144) ADC (SEQ ID NOs: 130, 145, 146 and 147) UGA1 (SEQ ID NO: 141) | S. cerevisiae S. avermitilis S. cerevisiae | 1.233 | 15.44 | 66.7 |

Strains yMhCt019 and 95/96 2 were also analyzed by SDS-PAGE as described herein. Both strains showed a protein band at 53 kD, 29 kD, ~14 kD, and at ~3 kD. The sizes of the 53 kD and 29 kD protein bands are consistent with the sizes of the proteins encoded by the UGA1 and YMR226c genes, respectively. The combined sizes of the 14 and 3 kD protein bands are consistent with the post-translationally cleaved protein encoded by the panD gene. The 53 kD, 29 kD, 14 kD and 3 kD proteins were not observed in the SDS-PAGE analysis of the control strain MBin500.

Strains MBin500 and yMhCt019 were evaluated in bioreactors for 3-HP production, using the method described herein. Control strain MBin500 produced no detectable 3-HP (average of two independent fermentations). Strain yMhCt019 produced 5.23 g/L 3-HP (average of three independent fermentations).

Example 3A-10: Yeast Strains Expressing Aspartate 1-Decarboxylase (ADC) from Four Nucleotide Sequences at the Adh1202 Locus Additional constructs were designed to incorporate four copies of nucleotides encoding an alternate ADC from B. licheniformis (SEQ ID NO: 139) at the adh1202 locus. In a similar approach to that described above, a left-hand and a right-hand construct were designed to allow homologous recombination at the I. orientalis adh1202 locus.

Construction of a Left-Hand Fragment

The plasmid pMhCt095 (supra) was digested with XbaI and PacI and purified by 1% agarose gel electrophoresis in TBE buffer as described herein. A band at approximately 7.3 kbp was excised from the gel and purified using a NUCLEOSPIN® Extract II Kit (Macherey-Nagel) according to the manufacturer's instructions.

A Bacillus licheniformis aspartate decarboxylase (ADC) panD gene was codon-optimized for expression in I. orientalis (version 1; SEQ ID NO: 149) and synthetically constructed into plasmid 1110206 (GeneArt®). Plasmid 1110206 was digested with XbaI and PacI and purified by 1% agarose gel electrophoresis in TBE buffer as described herein. A band at approximately 380 bp was excised from the gel and purified using a NUCLEOSPIN® Extract II Kit (Macherey-Nagel) according to the manufacturer's instructions.

The ~380 bp purified fragment was ligated into the 7.3 kbp pMhCt095 linearized vector using T4 ligase (New England Biolabs) in a total reaction volume of 10 μL composed of 60.5 ng of the digested pMhCt095, 6.3 ng of the 380 bp fragment from 1110206, 1 μL 10× ligation buffer with 10 mM ATP (New England Biolabs), and 1 μL T4 ligase (New England Biolabs). The reaction was incubated for 1.5 hr at room temperature and a 3 μL aliquot of the reaction was transformed into ONE SHOT® TOP10 chemically competent E. coli cells (Invitrogen) according to manufacturer's instructions. Transformants were plated on 2×YT+amp plates and incubated at 37° C. overnight. Several of the resulting transformants were screened for proper insertion by restriction digest using XbaI and PacI. A clone yielding the correct digested band size was designated pMeJi309.

The plasmid pMeJi309 was digested with NheI and AscI and purified by 1% agarose gel electrophoresis in TBE buffer. A band of approximately 7.3 kbp was excised from the gel and purified using a NUCLEOSPIN® Extract II Kit (Macherey-Nagel) according to the manufacturer's instructions.

The *Bacillus licheniformis* aspartate decarboxylase panD gene was again codon-optimized for expression in *I. orientalis* (version 2; SEQ ID NO: 148) and synthetically constructed into plasmid 1110205 (GeneArt®). A PCR was performed on a mixture containing 3 μL 1110205, 25 pM each of primers 0612695 and 0612724, 1× pfx amplification buffer (Invitrogen), 2 mm $MgSO_4$, 1.25 Units Platinum® pfx DNA polymerase (Invitrogen) in a final volume of 50 μL. The amplification reactions were incubated in an EPPENDORF® MASTERCYCLER® (Eppendorf Scientific) programmed for 1 cycle at 95° C. for 2 minutes; 25 cycles each at 95° C. for 1 minute, 55° C. for 1 minute, and 72° C. for 1 minute; and 1 cycle at 72° C. for 3 minutes.

Figure 14:
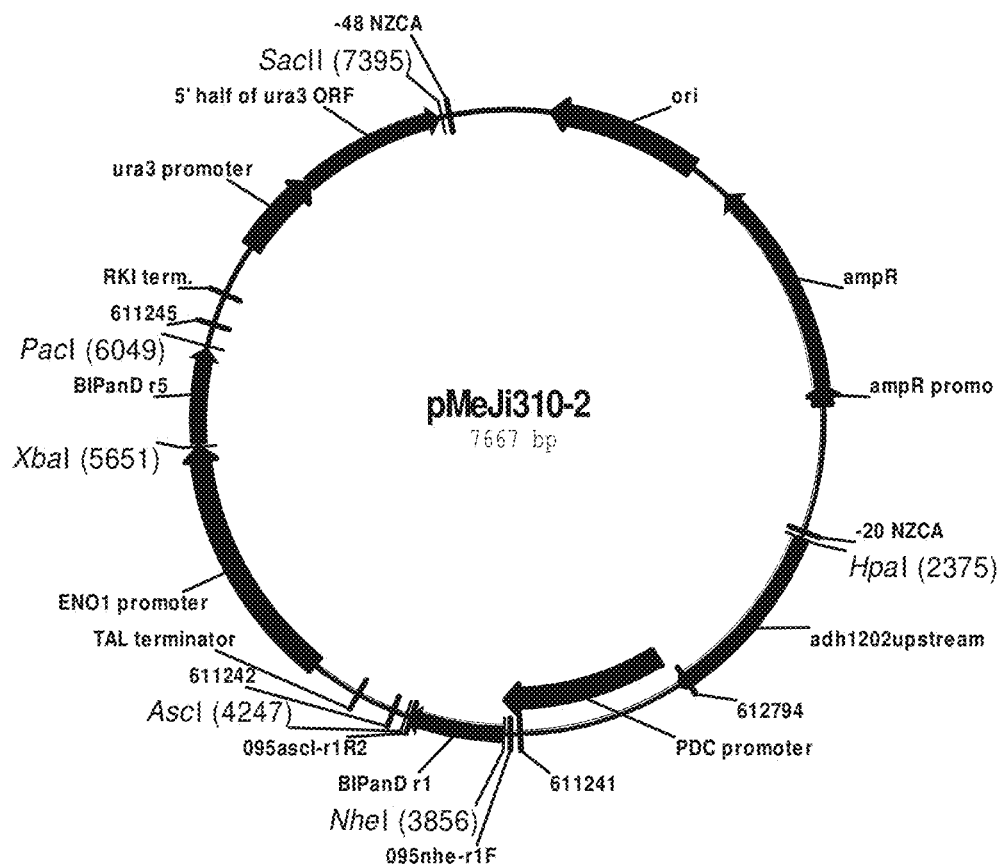
FIG. 14: Plasmid pMeJi310-2

The PCR product from the amplification reactions was purified by 1% agarose gel electrophoresis in TBE buffer. The approximately 400 bp band was excised from the gel and purified using a NUCLEOSPIN® Extract II Kit (Macherey-Nagel) according to manufacturer's instructions. The purified PCR product was inserted into the digested pMeJi309 vector above using an IN-FUSION™ Advantage PCR Cloning Kit (Clontech) in a reaction containing 93 ng pMeJi309 vector fragment, 52 ng PCR product above, 2 μL 1× IN-FUSION™ reaction buffer (Clontech), and 1 μL of IN-FUSION™ enzyme (Clontech). The reaction was incubated at 37° C. for 15 minutes, 50° C. for 15 minutes, and then placed on ice. A 2.5 μL sample of the reaction was transformed into ONE SHOT® TOP10 chemically competent *E. coli* cells (Invitrogen) according to manufacturer's instructions. Transformants were plated on 2×YT+amp plates and incubated at 37° C. overnight. Several of the resulting transformants were screened for proper insertion by restriction digest using XbaI and PacI. A clone yielding the correct digested band size was confirmed to be correct by DNA sequencing and designated pMeJi310-2 (FIG. 14).

Construction of a Right-Hand Fragment

The plasmid pMhCt096 (supra) was digested with XbaI and PacI and purified by 1% agarose gel electrophoresis in TBE buffer. A band at approximately 4.8 kbp was excised from the gel and purified using a NUCLEOSPIN® Extract II Kit (Macherey-Nagel) according to the manufacturer's instructions.

The *Bacillus licheniformis* aspartate decarboxylase panD gene was again codon-optimized for expression in *I. orientalis* (version 3; SEQ ID NO: 151) and synthetically constructed into plasmid 1110208 (GeneArt®). Plasmid 1110208 was digested with XbaI and PacI and purified by 1% agarose gel electrophoresis in TBE buffer, and an approximately 380 bp band was excised from the gel and purified using a NUCLEOSPIN® Extract II Kit (Macherey-Nagel) according to the manufacturer's instructions.

The 380 bp fragment above was ligated into the 7.3 kbp pMhCt096 linearized vector using T4 ligase (New England Biolabs) in a total reaction volume of 10 μL composed of 72.2 ng digested pMhCt096, 6.9 ng 380 bp fragment from 1110208, 1 μL 10× ligation buffer with 10 mM ATP, and 1 μL T4 ligase. The reaction was incubated for 1 and a half hours at room temperature and a 3 μL aliquot of the reaction was transformed into ONE SHOT® TOP10 chemically competent *E. coli* cells (Invitrogen) according to manufacturer's instructions. Transformants were plated on 2×YT+amp plates and incubated at 37° C. overnight. Several of the resulting transformants were screened for proper insertion by restriction digest using nheI and ascI. A done yielding correct digested band size was designated pMeJi311.

The plasmid pMeJi311 was digested with enzymes NheI and AscI and purified by 1% agarose gel electrophoresis in TBE buffer, and an approximately 7.3 kbp band was excised from the gel and purified using a NUCLEOSPIN® Extract II Kit (Macherey-Nagel) according to the manufacturer's instructions.

The *Bacillus licheniformis* aspartate decarboxylase panD gene was again codon-optimized for expression in *I. orientalis* (version 4; SEQ ID NO: 150) and synthetically constructed into plasmid 1110207 (GeneArt®). A PCR was performed on a mixture containing 3 μL 1110207, 25 pM each of 0612698 and 0612725, 1× pfx amplification buffer (Invitrogen), 2 mM $MgSO_4$, 1.25 units Platinum® pfx DNA polymerase (Invitrogen) in a final volume of 50 μL. The amplification reaction was incubated in an EPPENDORF® MASTERCYCLER® (Eppendorf Scientific) programmed for 1 cycle at 95° C. for 2 minutes; 25 cycles each at 95° C. for 1 minute, 55° C. for 1 minute, and 72° C. for 1 minute; and 1 cycle at 72° C. for 3 minutes.

Figure 15:
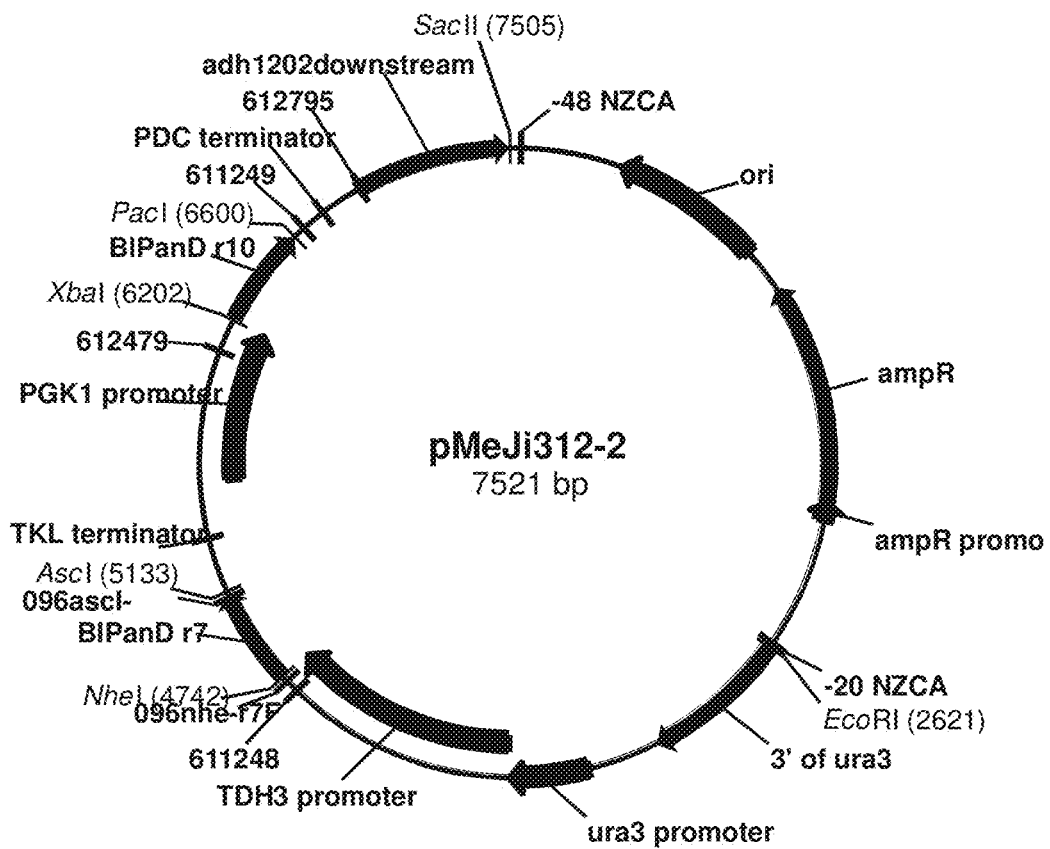
FIG. 15: Plasmid pMeJi312-2

The PCR product from the amplification reaction was purified by 1% agarose gel electrophoresis in TBE buffer. A band at approximately 400 bp was excised from the gel and purified using a NUCLEOSPIN® Extract II Kit (Macherey-Nagel) according to manufacturer's instructions. The purified PCR product was inserted into the digested pMeJi311 vector above using an IN-FUSION™ Advantage PCR Cloning Kit (Clontech) in a reaction containing 65.1 ng of the pMeJi311 NheI to AscI digested vector fragment, 85 ng of the PCR product above, 2 μL 1× IN-FUSION™ reaction buffer (Clontech), and 1 μL of IN-FUSION™ enzyme (Clontech). The reaction was incubated at 37° C. for 15 minutes, 50° C. for 15 minutes, and then placed on ice. A 2.5 μL sample of the reaction was transformed into ONE SHOT® TOP10 chemically competent *E. coli* cells (Invitrogen) according to manufacturer's instructions. Transformants were plated on 2×YT+amp plates and incubated for two days at room temperature. Several of the resulting transformants were screened for proper insertion by restriction digest using NheI and AscI. A clone yielding the correct digested band size was confirmed to be correct by DNA sequencing and designated pMeJi312-2 (FIG. 15).

Integration of Left-Hand and Right-Hand Fragments

Plasmid pMeJi310-2 was digested with HpaI and Sac II and plasmid pMeJi312-2 was digested with EcoRI and SacII as described herein. These were purified by 1% agarose gel electrophoresis in TBE buffer, and the two approximately 5 kbp bands were excised from the gel and purified using a NUCLEOSPIN® Extract II Kit (Macherey-Nagel) according to the manufacturer's instructions.

*I. orientalis* CNB1 was transformed with the digested pMeJi310-2 and pMeJi312-2 DNA and correct locus targeting and transformation was verified by Crimson Taq (New England Biolabs) PCR as described in herein. Primers 0612794 and 0611245 yielded an approximately 3.17 kbp band; primers 612479 and 0611632 yielded an approximately 1.48 kbp band; and primers 611248 and 612795 yielded an approximately 2.3 kbp band. A strain which gave the expected bands for proper integration of the expression cassette was designated MeJi409-2. A ura− derivative of strain MeJi409-2 was then obtained as described above.

Strains MBin500 and MeJi409-2 were evaluated in fermentation bioreactors for 3-HP production, using the method described herein. Control strain MBin500 produced no detectable 3-HP (average of two independent fermentations). Strain MeJi409-2 (one fermentation) produced 4.62 g/L. In order to account for differences in the amount of cell mass in these fermentations compared to other (e.g., future) fermentations, the 3-HP concentration per unit of cell mass (expressed as [g/L 3-HP]/[g/L dry cell weight]) was calculated to be 0.20 for MeJi409-2.

Example 3A-11: Yeast Strains Expressing Aspartate 1-Decarboxylase (ADC) and Aspartate Aminotransferase (AAT) at the Adh9091 Locus The nucleotide sequence (SEQ ID NO: 13) that encodes the *I. orientalis* aspartate aminotransferase (AAT) of SEQ ID NO: 14 was PCR amplified from *I. orientalis* genomic DNA using the primers 0611268 and 0611269. The PCR reaction (50 μL) contained 50 ng of strain *I. orientalis* genomic DNA, 1× Phusion HF buffer (New England Biolabs), 50 pmol each of primers 0611268 and 0611269, 200 μM each of dATP, dCTP, dGTP, and dTTP, 1.5 μL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute and 30 seconds, with a final extension at 72° C. for 7 minutes. Following thermocycling, the PCR reaction products were separated by 0.8% agarose gel electrophoresis in TBE buffer where an approximately 1278 bp PCR product was excised from the gel and purified using a QIAQUICK® Gel Extraction Kit (Qiagen) according to the manufacturer's instructions. The total length of the resulting PCR fragment was approximately 1278 bp, with an NruI restriction site at the 5' end of the fragment and a PacI restriction site at its 3' end.

The resulting 1278 bp fragment above comprising the AAT gene CDS (SEQ ID NO: 13) was then cloned into pCR2.1-TOPO vector and transformed into One-Shot TOP10 *E. coli* cells (Invitrogen) according to the manufacturer's instructions. Transformants were plated onto 2×YT+amp plates and incubated at 37° C. overnight. Several of the resulting transformants were screened for proper insertion of the desired fragment by Bam HI digestion. A clone yielding the desired band sizes was confirmed by sequencing and designated pGMEr11.

Plasmids pGMEr121 and pGMEr111 were double-digested with restriction enzymes PacI and NruI. The resulting 7695 bp vector fragment, from plasmid pGMEr121, and the resulting 1272 bp insert fragment comprising the AAT coding sequence, from plasmid pGMEr111, were separated by 0.8% agarose gel electrophoresis in 1×TBE buffer, excised from the gel, and purified using the QIAQUICK® Gel Extraction Kit (Qiagen) according to the manufacturer's instructions.

Figure 16:
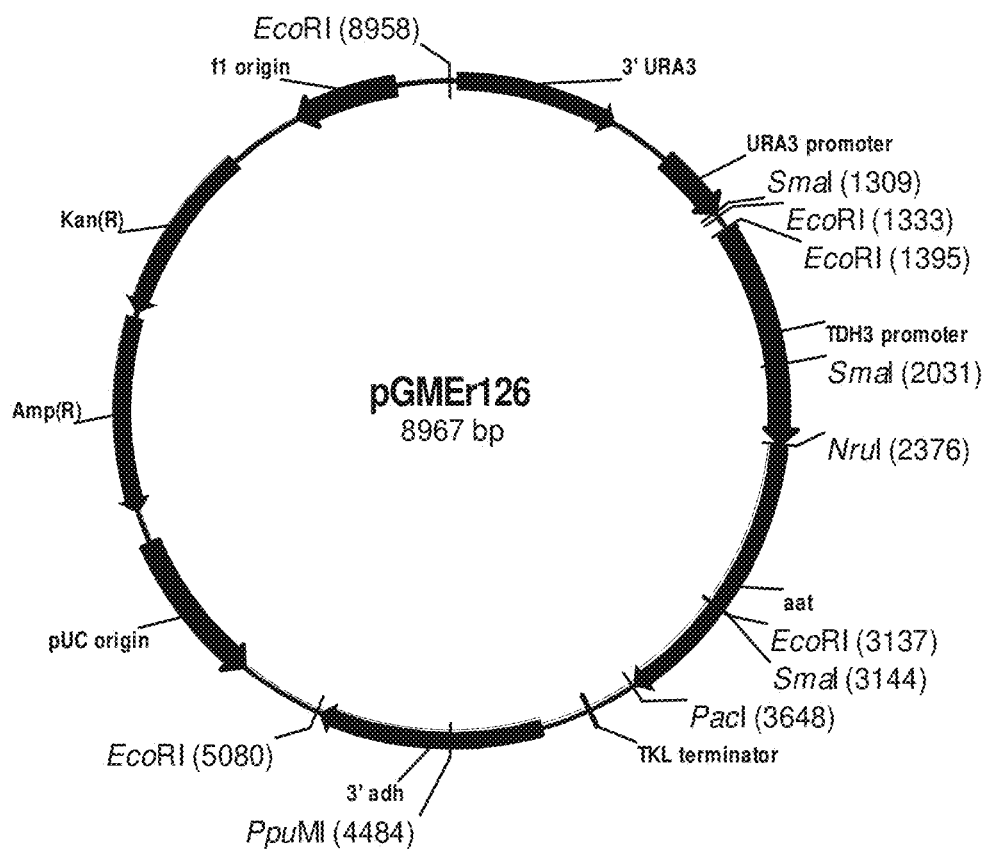
FIG. 16: Plasmid pGMEr126

A ligation reaction was then set up with 3 μL of vector fragment, 4 μL of insert fragment, 2 μL of sterile dd water, 10 μL of 2× Quick Ligase Buffer and 1 μL of Quick T4 Ligase (Quick Ligation Kit, New England Biolabs) and performed according to the manufacturer's instructions. A 5 μL aliquot of the ligation reaction above was transformed into XL10-Gold® Ultracompetent *E. coli* cells (Agilent Technologies) according to the manufacturer's instructions. Transformants were plated onto 2×YT+amp plates and incubated at 37° C. overnight. Several of the resulting transformants were screened for proper insertion of the desired insert by SmaI/PpuMI double digestion. A clone yielding the desired band sizes was confirmed by sequencing and designated pGMEr126 (FIG. 16).

Plasmids pGMEr126 comprises the *I. orientalis* AAT expression cassette, in which the gene transcription is controlled by the *I. orientalis* TDH3 promoter and the TKL terminator, flanked by the truncated 3' region of the URA3 coding sequence and the URA3 promoter, upstream; and by the 3' homology region with the *I. orientalis* adh9091 locus, downstream.

The *S. avermitilis* panD gene codon-optimized for expression in *I. orientalis* (SEQ ID NO: 130) was PCR amplified from the pMA-T vector received from GeneArt® using the primers 061166 and 0611662. The PCR reaction (50 μL) contained 50 ng of strain plasmid DNA, 1× Phusion HF buffer (New England Biolabs), 50 pmol each of primers 0611661 and 0611662, 200 μM each of dATP, dCTP, dGTP, and dTTP, 1.5 μL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 30 seconds, with a final extension at 72° C. for 7 minutes. Following thermocycling, the PCR reaction products were separated by 0.8% agarose gel electrophoresis in TBE buffer where an approximately 453 bp PCR product was excised from the gel and purified using a QIAQUICK® Gel Extraction Kit (Qiagen) according to the manufacturer's instructions. The total length of the resulting PCR fragment was approximately 453 bp with an NruI restriction site at the 5' end of the fragment and an ApaI restriction site at the 3' end.

The resulting 453 bp fragment, comprising the codon-optimized version of *S. avermitilis* panD gene, was cloned into pCR2.1-TOPO vector and transformed into One-Shot TOP10 *E. coli* cells (Invitrogen) according to the manufacturer's instructions. Transformants were plated onto 2×YT+amp plates and incubated at 37° C. overnight. Several of the resulting transformants were screened for proper insertion of the desired fragment by EcoRI digestion. A plasmid yielding the desired band sizes was confirmed by sequencing and designated pGMEr127.

Plasmids pGMEr127 and pGMEr125(a) were digested with restriction enzymes NruI and Apa I. Before stopping the digestion reactions 1 μL of Calf Intestinal Alkaline Phosphatase (New England Biolabs) was added to the pGMEr125(a) digestion in order to de-phosphorylate the ends and prevent self-ligation. The resulting 8188 bp vector fragment, from plasmid pGMEr125(a) (supra), and the 440 bp insert fragment, comprising the codon-optimized version of the *S. avermitilis* panD gene (SEQ ID NO: 130) from plasmid pGMEr127 (supra), were separated by 0.8% agarose gel electrophoresis in 1×TBE buffer, excised from the gel and purified using a QIAQUICK® Gel Extraction Kit (Qiagen) according to the manufacturer's instructions.

Figure 17:
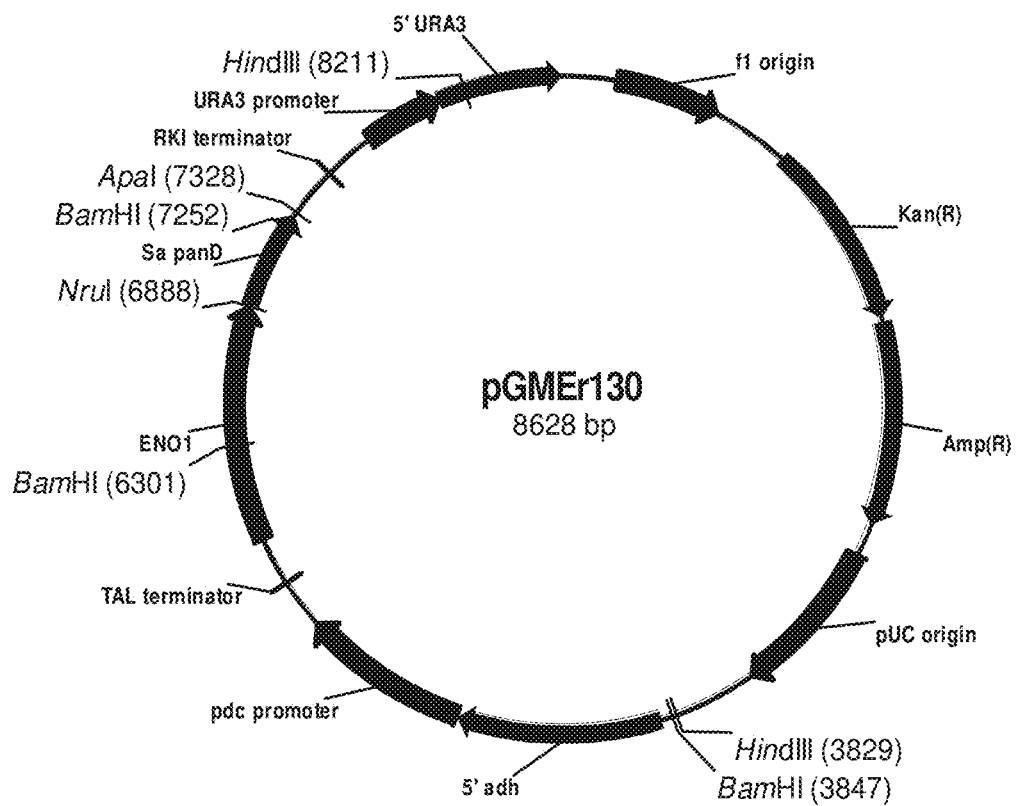
FIG. 17: Plasmid pGMEr130

A ligation reaction was then set up with 4 μL of vector fragment, 4 μL of insert fragment, 9 μL of 2× Quick Ligase Buffer and 1 μL of Quick T4 Ligase (New England Biolabs) and performed according to the manufacturer's instructions. A 5 μL aliquot of the ligation reaction above was transformed into XL10-Gold® Ultracompetent *E. coli* cells (Stratagene) according to the manufacturer's instructions. Transformants were plated onto 2×YT+amp plates and incubated at 37° C. overnight. Several of the resulting transformants were screened for proper insertion of the desired insert by BamHI digestion. A clone yielding the desired band sizes was confirmed and designated pGMEr130 (FIG. 17).

Plasmid pGMEri30 comprises a construct made of the following fragments: the 5' flank of the *I. orientalis* adh9091 locus, an empty expression cassette with the *I. orientalis* PDC promoter/TAL terminator, the panD expression cassette (containing SEQ ID NO: 130) under control of the *I. orientalis* ENO1 promoter and the RKI terminator, and the truncated 5' fragment of the URA3 marker gene under control of the *I. orientalis* URA3 promoter.

To determine whether yeast strain *I. orientalis* CNB1 was able to express the *I. orientalis* codon-optimized version of *S. avermitilis* panD gene (SEQ ID NO: 130) and the *I. orientalis* AAT gene (SEQ ID NO: 13), the expression plasmids pGMEr130 and pGMEr126 were constructed. Plasmid pGMEr130 comprises (from 5'-3') the 5' flanking region for genomic integration of the construct at the *I. orientalis* adh9091 locus, the panD expression cassette under control by the ENO1 promoter and the RKI terminator, and the truncated 5' portion of the URA3 selection marker driven by the URA3 promoter. Plasmid pGMEr126 comprises (from 5'-3') the 3' portion of the URA3 selection marker, the AAT gene expression cassette under control by the TDH3 promoter and the TKL terminator, and the 3' flank for genomic integration of the construct at the *I. orientalis* adh9091 locus. All promoters and terminators were derived from *I. orientalis*.

Plasmid pGMEr126 was digested with restriction enzyme EcoRI, which excised a 4758 bp fragment of interest, while plasmid pGMEr130 was digested with restriction enzyme Hind III creating a 5034 bp fragment needed for transformation. The 4758 bp and the 5034 bp fragments were separated by 0.8% agarose gel electrophoresis in 1×TBE buffer, excised from the gel, and purified using the QIAQUICK® Gel Extraction Kit (Qiagen) according to the manufacturer's instructions.

*I. orientalis* CNB1 was cultured and co-transformed as described herein with approximately 500 ng of both the 4758 bp and 5034 bp linear fragments. Eight transformant strains were obtained and then cultured in shake flasks. The resulting broths were used to run an SDS-PAGE, Tris-HCl (Bio-Rad Laboratories) gel to detect the expression of the *S. avermitilis* panD gene codon-optimized for expression in *I. orientalis* (SEQ ID NO: 130) and of the *I. orientalis* AAT gene (SEQ ID NO: 13). A positive strain was designated yGMEr008 and its broth was also used to determine the ADC and the AAT activity levels as described above.

Example 3A-12: Yeast Strains Expressing Pyruvate Carboxylase (PYC), Aspartate 1-Decarboxylase (ADC) and Aspartate Aminotransferase (AAT) at the Adh9091 Locus The nucleotide sequence that encodes the *I. orientalis* pyruvate carboxylase (PYC) of SEQ ID NO: 2 was PCR amplified from *I. orientalis* genomic DNA using the primers 0611266 and 0611267. The PCR reaction (50 µL) contained 50 ng of *I. orientalis* genomic DNA, 1× Phusion HF buffer (New England Biolabs), 50 pmol each of primers 0611266 and 0611267, 200 µM each of dATP, dCTP, dGTP, and dTTP, 1.5 µL of 100% DMSO (New England Biolabs) and 1 unit of Phusion High Fidelity DNA polymerase (New England Biolabs). The PCR was performed in an EPPENDORF® MASTERCYCLER® (Eppendorf Scientific) programmed for one cycle at 98° C. for 2 minutes followed by 35 cycles each at 98° C. for 30 seconds, 55° C. for 30 seconds, and 72° C. for 1 minute and 30 seconds, with a final extension at 72° C. for 7 minutes. Following thermocycling, the PCR reaction products were separated by 0.8% agarose gel electrophoresis in TBE buffer where an approximately 3557 bp PCR product was excised from the gel and purified using a QIAQUICK® Gel Extraction Kit (Qiagen) according to the manufacturer's instructions. The resulting PCR fragment had an XbaI restriction site at the 5' end of the fragment and a PacI restriction site at its 3' end.

The resulting 3557 bp fragment, comprising the *I. orientalis* PYC gene CDS (SEQ ID NO: 1), was cloned into pCR2.1-TOPO vector and transformed into One-Shot TOP10 *E. coli* cells (Invitrogen) according to the manufacturer's instructions. Transformants were plated onto 2×YT+amp plates and incubated at 37° C. overnight. Several of the resulting transformants were screened for proper insertion of the desired fragment by EcoRI digestion. Six clones yielding the desired band sizes were confirmed and designated pGMEr132.7, pGMEr132.14, pGMEr132.16, pGMEr132.25, pGMEr132.27 and pGMEr132.30. Sequencing analysis revealed that plasmid pGMER132.14 has the proper PYC CDS but was missing the XbaI restriction site at the CDS 5' end. Since this restriction site is needed to insert the PYC CDS in expression plasmid pGMEr125, the 315 bp HindIII fragment of plasmid pGMEr132.14 (comprising the 5' end on the PYC CDS with the altered XbaI site) was replaced with the 315 bp HindIII fragment from plasmid pGMEr132.7, which has a unaltered 5' end of the PYC CDS including the correct XbaI site. The resulting 7173 bp HindIII vector fragment, from plasmid pGMEr132.14, and the 315 bp HindIII insert fragment, from plasmid pGMEr132.7, were separated by 0.8% agarose gel electrophoresis in 1×TBE buffer, excised from the gel, and purified using a QIAQUICK® Gel Extraction Kit (Qiagen) according to the manufacturer's instructions.

A ligation reaction was then set up with 4 µL of vector fragment, 5 µL of insert fragment, 10 µL of 2× Quick Ligase Buffer and 1 µL of Quick T4 Ligase (New England Biolabs) and performed according to the manufacturer's instructions. A 5 µL aliquot of the ligation reaction above was transformed into One-Shot TOP10 *E. coli* cells (Invitrogen) according to the manufacturer's instructions. Transformants were plated onto 2×YT+amp plates and incubated at 37° C. overnight. Several of the resulting transformants were screened for proper insertion and orientation of the desired insert by BamHI and XbaI double digestion. A clone yielding the desired band sizes was confirmed and designated pGMEr133.

In order to insert the *I. orientalis* PYC CDS downstream of the PDC promoter in plasmid pGMEr125(b), plasmids pGMEr125(b) and pGMEr133 (supra) were digested with PacI and XbaI. The resulting 8188 bp vector fragment, from plasmid pGMEr125(b), and the 3553 bp insert fragment, comprising the *I. orientalis* PYC CDS (SEQ ID NO: 1) from plasmid pGMEr133, were separated by 0.8% agarose gel electrophoresis in 1×TBE buffer, excised from the gel, and purified using the QIAQUICK® Gel Extraction Kit (Qiagen) according to the manufacturer's instructions.

A ligation reaction was then set up with 3 µL of vector fragment, 6 µL of insert fragment, 10 µL of 2× Quick Ligase Buffer and 1 µL of Quick T4 Ligase (New England Biolabs) and performed according to the manufacturer's instructions. A 5 µL aliquot of the ligation reaction above was transformed into One-Shot TOP10 *E. coli* cells (Invitrogen) according to the manufacturer's instructions. Transformants were plated onto 2×YT+amp plates and incubated at 37° C. overnight Several of the resulting transformants were screened for proper insertion of the desired fragment by BamHI digestion. A clone yielding the desired band sizes was confirmed and designated pGMEr136.

Plasmid pGMEr136 comprises the 5' flank of the *I. orientalis* adh9091 locus, the *I. orientalis* PYC gene expression cassette (SEQ ID NO: 1) under control of the *I. orientalis* PDC promoter and TAL terminator, an empty expression cassette with an *I. orientalis* ENO1 promoter/RKI terminator, and the truncated 5' fragment of the *I. orientalis* URA3 marker gene under control of the URA3 promoter.

About 5 µg of plasmid pGMEr136 (supra) and 4 µg of plasmid pGMEr127 were digested with restriction enzymes ApaI and Nru I. The resulting 11729 bp vector fragment, from plasmid pGMEr136, and the resulting insert fragment comprising the *S. avermitilis* panD gene codon-optimized for expression in *I. orientalis* (SEQ ID NO: 130) (436 bp) from plasmid pGMEr127, were purified by 0.8% agarose gel electrophoresis in 1×TBE buffer using a NucleoSpin™ Extract II (Macherey-Nagel) according to the manufacturer's instructions.

Figure 18:
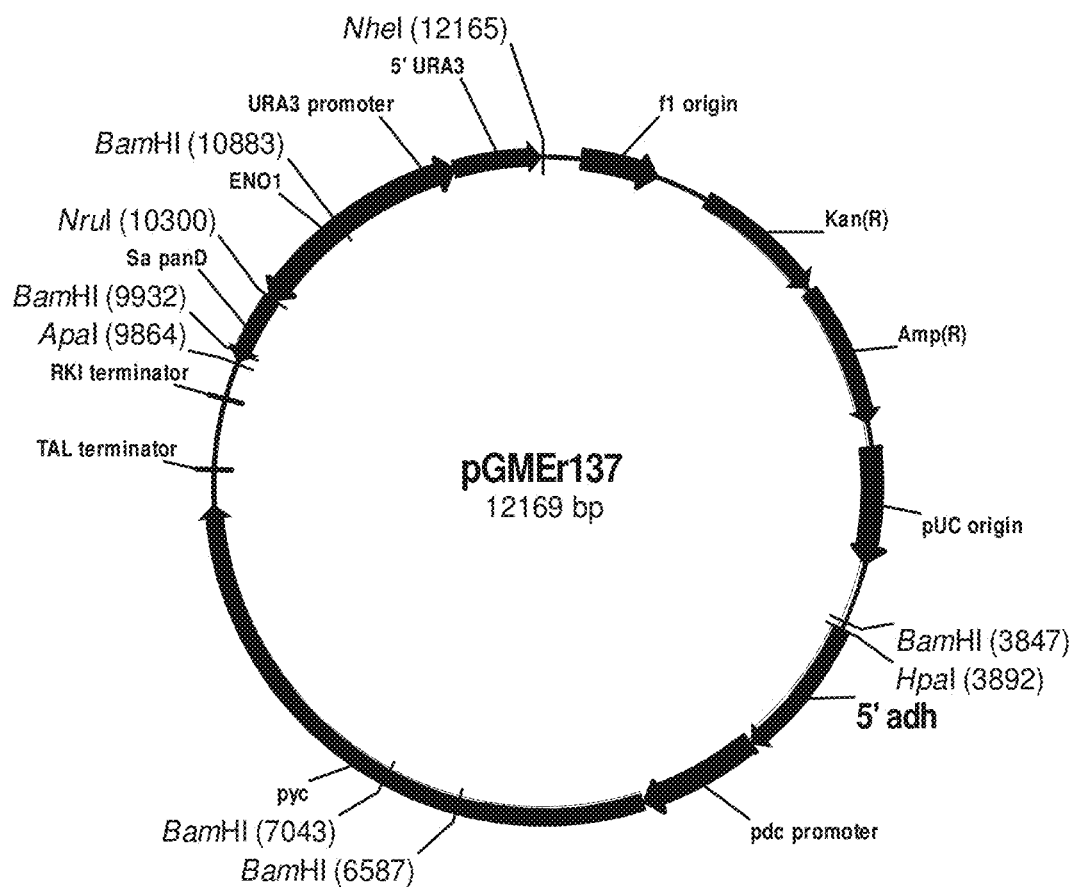
FIG. 18: Plasmid pGMEr137

A ligation reaction was then set up comprising 5 µL of vector fragment, 4 µL of insert fragment, 9 µL of 2× Quick Ligase Buffer and 1 µL of Quick T4 Ligase (New England Biolabs). The reaction was incubated at room temperature for 1 hour. A 5 µL aliquot of the ligation reaction above was transformed into ONE SHOT® TOP10 chemically competent *E. coli* cells (Invitrogen) according to the manufacturer's instructions. Transformants were plated onto 2×YT+ amp plates and incubated at 37° C. overnight. Several of the resulting transformants were screened for the desired insert by BamHI digestion. A clone yielding the desired band sizes was chosen and designated pGMEr137 (FIG. 18).

Plasmid pGMEr137 comprises the *I. orientalis* PYC gene (SEQ ID NO: 1) under transcriptional control of the *I. orientalis* PDC promoter and TAL terminator, the *S. avermitilis* panD gene codon-optimized for expression in *I. orientalis* (SEQ ID NO: 130) under transcriptional control of the *I. orientalis* ENO1 promoter and RKI terminator, the URA3 promoter followed by the 5' end of the URA3 marker and the 5' flanking region of the *I. orientalis* adh9091 locus.

Plasmid pGMEr126 (supra) was digested with restriction enzyme EcoRI, which excised a 4758 bp fragment of interest; while plasmid pGMEr137 (supra) was digested with restriction enzymes HpaI and NheI creating a 8400 bp fragment. Both the 4758 bp and the 8400 bp fragments were separated by 0.8% agarose gel electrophoresis in 1×TBE buffer; the bands were excised from the gel and purified using the NucleoSpin® Extract II (Macherey-Nagel) according to the manufacturer's instructions. *I. orientalis* CNB1 was cultured and co-transformed with approximately 500 ng of both the 4758 bp and 8400 bp linear fragments as described herein, resulting in transformant yGMEr009.

Example 3A-13: Yeast Strains Expressing Aspartate 1-Decarboxylase (ADC), β-Alanine Aminotransferase (BAAT), and 3-Hydroxypropionic Acid Dehydrogenase (3-HPDH) at the pdc Locus; and Expressing Pyruvate Carboxylase (PYC), Aspartate 1-Decarboxylase (ADC), and Aspartate Aminotransferase (AAT) at the Adh9091 Locus To increase pyruvate carboxylase (PYC) and aspartate aminotransferase (AAT) activity in a strain already over-expressing an aspartate aminotransferase (AAT), a β-alanine aminotransferase (BAAT), and a 3-HP dehydrogenase (3-HPDH), strain yMhCt010 (supra) was transformed with linear fragments of pGMEr137 (supra) and pGMEr126 (supra) as described above. After two rounds of single colony purification and outgrowth, genomic DNA was prepared for use in PCR to verify the desired targeted integration occurred as described above. Correct targeting of pGMEr137 and pGMEr126 fragments to the adh9091 locus was confirmed using the primers 0611814 and 0612055. Primer 0611814 anneals in the 3' end of the TDH3 promoter of pGMEr126 and amplifies in the 3' direction. Primer 0612055 anneals 3' of the adh9091 3' flanking homology present in pGMEr126, so amplification of a PCR product with this primer pair will only occur if the integration DNA targeted to the correct locus via homologous recombination. The presence of an approximately 3066 bp band from a PCR containing primers 0611814 and 0612055 indicates the desired integration of pGMEr126 and pGMEr137 fragments occurred at the adh9091 locus.

After two rounds of single colony purification and outgrowth of several independent transformants of yMhCt010 with linear fragments of pGMEr137 and pGMEr126, genomic DNA was prepared for use in PCR to verify the desired targeted integration occurred as described above. Three independently isolated strains that gave an approximately 3066 bp band from a PCR containing primers 0611814 and 0612055 were designated yMhCt020, GMErin010#2, and GMErin010#3. These strains contain a polynucleotide (SEQ ID NO: 130) encoding the corresponding ADC (SEQ ID NO: 17) at both of the pdc loci and one of the adh9091 loci; a polynucleotide (SEQ ID NO: 141) encoding the corresponding gabT (SEQ ID NO: 24) at both of the pdc loci; a polynucleotide (SEQ ID NO: 144) encoding the corresponding 3-HPDH (SEQ ID NO: 129) at both of the pdc loci; a polynucleotide (SEQ ID NO: 1) encoding the corresponding PYC (SEQ ID NO: 2) at one of the adh9091 loci; and a polynucleotide (SEQ ID NO: 13) encoding the corresponding AAT (SEQ ID NO: 14) at one of the adh9091 loci (see Table 24).

TABLE 24

Transformant genotypes

| Strain | Parent strain | Genotype |
| --- | --- | --- |
| yMhCt020<br>GMErin010 #2<br>GMErin010 #3 | yMhCt010 | adh9091Δ::(PDC$_{promo}$-pycCNB1, ENO1$_{promo}$-SaPanD(reverse), URA3, TDH3$_{promo}$-aat)/ADH9091 pdcΔ::(PDC$_{promo}$-Opt.SaPanD, ENO1$_{promo}$-Opt.ScUGA1, URA3-Scar, TDH3$_{promo}$-Opt.ScYMR226C)/pdcΔ::(PDC$_{promo}$-Opt.SaPanD, ENO1$_{promo}$-Opt.ScUGA1, URA3-Scar, TDH3$_{promo}$-Opt.ScYMR226C) ura3−/ura3− |

Strains yMhCt020, GMErin010#2, and GMErin010#3 were grown in shake flasks and CFEs were prepared and assayed for PYC, AAT and 3-HPDH activities as described in herein. The experimental results shown in Table 25.

TABLE 25

Transformant enzyme activity data

| Strain | Gene Overexpressed | PYC activity | AAT activity | ADC activity | 3-HPDH activity |
|---|---|---|---|---|---|
| MBin500 (control) | N/A | 0.14 | 0.03 | 0.00 | 0.14 |
| yMhCt008 | ADC (SEQ ID NO: 130), gabT (SEQ ID NO: 141), 3-HPDH (SEQ ID NO: 144) | 0.22 | 2.05 | 0.64 | 2.95 |
| GMEr009-2 | ADC (SEQ ID NO: 130), PYC (SEQ ID NO: 1), AAT (SEQ ID NO: 13) | 1.15 | 24.62 | 0.05 | 0.07 |
| yMhCt020 | ADC (SEQ ID NO: 130), gabT (SEQ ID NO: 141), HPDH (SEQ ID NO: 144), | 2.74 | 35.02 | 0.50 | 1.68 |
| GMErin010 #2 | | 1.97 | 40.32 | 0.59 | 1.87 |
| GMErin010 #3 | PYC (SEQ ID NO: 1), AAT (SEQ ID NO: 13), | 1.50 | 23.79 | 0.42 | 3.30 |

The strains in Table 25 were also analyzed by SDS-PAGE as described herein. MBin500 and GMEr009-2 showed a protein band a ~64 kD that was absent in the four other samples. The mass of these proteins is consistent with their identity as the native pyruvate decarboxylase in *I. orientalis* CNB1. Strains yMhCt008, yMhCt020, GMErin010 #2, and GMErin010 #3 showed bands at 53 kD and 29 kD. The mass of these proteins is consistent with mass of the proteins encoded by the UGA1 and YMR226c genes, respectively. Strains GMEr009-2, yMhCt020, GMErin010 #2, and GMErin010 #3 all showed bands at 46.3 kD. The mass of these proteins is consistent with mass of the protein encoded by the AAT gene.

Example 3A-14: Yeast Strains Expressing Aspartate 1-Decarboxylase (ADC) from Four Nucleotide Sequences at Both Adh1202 Loci A ura3− derivative of MeJi409-2 containing four copies of nucleotides encoding the *B. licheniformis* ADC of SEQ ID NO: 139 (supra) was isolated using the FOA counter-selection loop-out protocol described above. Genomic DNA of several FOA resistant colonies of parent strain MeJi409-2 was screened by PCR for the desired loop-out event with primers 0611815 and 0611817. Primer 0611815 anneals in the RKI terminator of the left-hand construct and amplifies toward the ura3 promoter. Primer 0611817 anneals in TDH3 promoter and amplifies back toward the ura3 cassette. The presence of an 828 bp band indicates the presence of only the ura3 scar site (a single URA3 promoter left behind after homologous recombination between the two URA3 promoters in the parent strain) as desired, while a band of approximately 2.2 kbp indicates the presence of the intact URA3 promoter-URA3 ORF-URA3 terminator-URA3 promoter cassette, indicating the desired recombination event did not occur. PCR reactions with Crimson Taq™ DNA polymerase (New England Biolabs) were carried out as described above. One FOA resistant colony from parent strain MeJi409-2, designated MeJi411, gave the desired 828 bp band. Integration of the Left-Hand and Right-Hand Fragments Plasmid pMeJi310-2 was digested with HpaI and SacII and plasmid pMeJi312-2 was digested with EcoRI and SacII as described herein. These were purified by 1% agarose gel electrophoresis in TBE buffer, and the two approximately 5 kbp bands were excised from the gel and purified using a NUCLEOSPIN® Extract II Kit (Macherey-Nagel) according to the manufacturer's instructions.

MeJi411 was transformed with the digested pMeJi310-2 and pMeJi312-2 DNA and correct loci targeting and transformation was verified by Crimson Taq (New England Biolabs) PCR as described herein. Primers 0611225 and 0611632 yielded an approximately 5 kbp band; primers 0611815 and 0611632 yielded an approximately 6 kbp band with the ura marker, and a 4.5 kbp band without. Primers 0611631 and 0612579 yield an approximately 936 bp band when the wildtype adh1202 locus is still intact (strains that did not show this band were selected). A strain which gave the expected bands for proper integrating of the expression cassette was designated MeJi412.

Example 3A-15: Yeast Strains Expressing Four Copies of Nucleotides Encoding an Aspartate 1-Decarboxylase (ADC) at the Adh1202 Locus, with Two Copies of the Nucleotides Encoding the Aspartate 1-Decarboxylase (ADC) Under the Control of the a PDC Promoter and Two Copies Under the Control of a TDH3 Promoter This example describes constructs designed to incorporate four copies of nucleotides encoding the *B. licheniformis* ADC of SEQ ID NO: 139 at the adh1202 locus with two copies of under control of the *I. orientali* PDC promoter and two copies under the control of the *I. orientali* TDH3 promoter. In a similar approach to that described above, a left-hand and a right-hand constructs were designed to allow homologous recombination at the *I. orientalis* CNB1 adh1202 locus.

Construction of a Left-Hand Fragment

The plasmid pMeJi310-2 (supra; see FIG. 14) was digested with XbaI and StuI followed by treatment with CIP and purified by 1% agarose gel electrophoresis in TBE buffer as described herein. A band at approximately 6.7 kbp was excised from the gel and purified using QIAQUICK® Gel Extraction Kit (Qiagen) according to the manufacturer's instructions.

The PDC promoter was excised from pMeJi310-2 by digestion with NotI followed by a fill-in reaction with Klenow and subsequent digestion with NheI. A band at approximately 708 bp was excised from the gel and purified using QIAQUICK® Gel Extraction Kit (Qiagen) according to the manufacturer's instructions.

The 708 bp of purified fragment was ligated into the 6.7 kbp pMeJi310-2 linearized vector using T4 ligase (New England Biolabs) in a total reaction volume of 10 μL composed of 1 μL of the 6.7 kbp fragment from pMeJi310-2, 1 or 5 μL of the 708 bp fragment from pMeJi310-2, 1 μL 10× ligation buffer with 10 mM ATP (New England Biolabs), and 1 μL T4 ligase (New England Biolabs). The reaction was incubated overnight at 16° C. and a 4 μL aliquot of the reaction was transformed into ONE SHOT® TOP10 chemically competent E. coli cells (Invitrogen) according to manufacturer's instructions. Transformants were plated on 2×YT+amp plates and incubated at 37° C. overnight. Several of the resulting transformants were screened for proper insertion by restriction digest using ApaLI. A clone yielding correct digested band size was designated pMIBa137.

Construction of a Right-Hand Fragment

The plasmid pMeJi312-2 (supra) was digested with XbaI and StuI followed by treatment with CIP and purified by 1% agarose gel electrophoresis in TBE buffer as described herein. A band at approximately 6.8 kbp was excised from the gel and purified using QIAQUICK® Gel Extraction Kit (Qiagen) according to the manufacturer's instructions.

The TDH3 promoter was excised from pMeJi312-2 by digestion with PmeI and NheI. A band at approximately 966 bp was excised from the gel and purified using QIAQUICK® Gel Extraction Kit (Qiagen) according to the manufacturer's instructions.

The 966 bp of purified fragment was ligated into the 6.8 kbp pMeJi312-2 linearized vector using T4 ligase (New England Biolabs) in a total reaction volume of 10 μL composed of 1 μL of the 6.8 kbp fragment from pMeJi312-2, 1 or 5 μL of the 966 bp fragment from pMeJi312-2, 1 μL 10× ligation buffer with 10 mM ATP (New England Biolabs), and 1 μL T4 ligase (New England Biolabs). The reaction was incubated for approximately 6 hours at 16° C. and a 4 μL aliquot of the reaction was transformed into ONE SHOT® TOP10 chemically competent E. coli cells (Invitrogen) according to manufacturer's instructions. Transformants were plated on 2×YT+amp plates and incubated at 37° C. overnight. Several of the resulting transformants were screened for proper insertion by restriction digest using SalI. A clone yielding correct digested band size was designated pMIBa136.

Integration of the Left-Hand and Right-Hand Fragments

Plasmid pMIBa137 was digested with HpaI and SacII and plasmid pMIBa136 was digested with EcoRI and SacII as described herein. These were purified by 1% agarose gel electrophoresis in TBE buffer, and the two approximately 5 kbp bands were excised from the gel and purified using QIAQUICK® Gel Extraction Kit (Qiagen) according to the manufacturer's instructions.

I. orientalis CNB1 was transformed with the digested pMIBa137 and pMIBa136 DNA and correct loci targeting and transformation was verified by Crimson Taq (New England Biolabs) PCR as described in herein. Primers 0611717 and 0611631 yielded bands of approximately 2.5 kbp and 955 bp; primers 0611718 and 0611632 yielded an approximately 733 bp band; primers 0612794 and 0611245 yielded an approximately 2.7 kbp band; primers 0611225 and 0612795 yielded an approximately 4.2 kbp band. A strain which gave the expected bands for proper integration of the expression cassette was designated MIBa351.

Removal of the Ura Marker from MIBa351

A ura– derivative of MIBa351 was isolated as described above. Genomic DNAs from several FOA resistant colonies of MIBa351 were screened by PCR for the desired loop-out event with primers 0611815 and 0611817. Primer 0611815 anneals in the RKI terminator of the left-hand construct and amplifies toward the ura3 promoter. Primer 0611817 anneals in TDH3 promoter and amplifies back toward the ura3 cassette. The presence of an 828 bp band indicates the presence of only the ura3 scar site (a single URA3 promoter left behind after homologous recombination between the two URA3 promoters in the parent strain) as desired, while a band of approximately 2.2 kbp indicates the presence of the intact URA3 promoter-URA3 ORF-URA3 terminator-URA3 promoter cassette, indicating the desired recombination event did not occur. PCR reactions with Crimson Taq™ DNA polymerase (New England Biolabs) were carried out as described above. FOA resistant colonies that yielded the 828 bp fragment with the above primers were further tested with primers 0612794 and 0611245, which yield a 2.7 kbp product, and primers 0611815 and 0612795, which yield a 4 kbp product, to confirm that the four copies of the nucleotide sequence SEQ ID NO: 138 encoding the B. licheniformis ADC of SEQ ID NO: 139 remained intact. One FOA resistant colony from parent strain MIBa351, designated MIBa353, gave the desired PCR products with all 3 primer sets.

Construction of a Reverse Expression Cassette Right-Hand Fragment

Plasmid pMIBa136 contains two expression cassettes going in the forward orientation. To ease screening of homozygous strains, a new plasmid was constructed where the panDbI expression cassettes of pMIBa136 were placed in the reverse orientation. The plasmid pMIBa136 (supra) was digested with NotI and PmeI followed by a fill-in reaction with Klenow and purified by 1% agarose gel electrophoresis in TBE buffer as described herein. Bands at approximately 3.4 and 4.4 kbp were excised from the gel and purified using QIAQUICK® Gel Extraction Kit (Qiagen) according to the manufacturer's instructions. The 4.4 kbp fragment from pMIBa136 was treated with CIP and purified using the QIAQUICK® PCR Purification Kit (Qiagen) according to the manufacturer's instructions.

The 3.4 kbp purified fragment from pMIBa136 was ligated into the 4.4 kbp pMIBa136 vector using T4 ligase (New England Biolabs) in a total reaction volume of 10 μL composed of 1 μL of the 4.4 kbp fragment from pMIBa136, 1 or 5 μL of the 3.4 kbp fragment from pMIBa136, 1 μL 10× ligation buffer with 10 mM ATP (New England Biolabs), and 1 μL T4 ligase (New England Biolabs). The reaction was incubated overnight at 16° C. and a 4 μL aliquot of the reaction was transformed into ONE SHOT® TOP10 chemically competent E. coli cells (Invitrogen) according to manufacturer's instructions. Transformants were plated on 2×YT+amp plates and incubated at 37° C. overnight. Several of the resulting transformants were screened for proper insertion by restriction digest using PacII and EcoRI. A clone yielding correct digested band size was designated pMIBa138.

Integration of Left-Hand and Right-Hand Fragments

Plasmid pMIBa137 was digested with HpaI and SacII and plasmid pMIBa138 was digested with EcoRI and SacII as described herein. These were purified by 1% agarose gel electrophoresis in TBE buffer, and the two approximately 5 kbp bands were excised from the gel and purified using QIAQUICK® Gel Extraction Kit (Qiagen) according to the manufacturer's instructions.

MIBa353 was transformed with the digested pMIBa137 and pMIBa138 DNA and correct loci targeting and transformation was verified by PCR using the Phire® Plant Direct PCR kit (Finnzymes) according to the manufacturer's instructions. Primers 0611718 and 0611632 yielded an approximately 733 bp band (to confirm the first integration is still present); primers 0612367 and 0611632 yielded an approximately 960 bp band (to confirm that the second copy integrated); primers 0611631 and 0612579 yielded an approximately 936 bp band if the wildtype adh1202 locus is still present (lack of this band confirms loss of wt adh1202 locus). Two strains which gave the expected bands for proper integrating of the expression cassette were saved and designated MIBa355 and MIBa356.

Aspartate 1-Decarboxylase Activity in MeJi409-2, MeJi412, MIBa351 and MIBa355

Strains MeJi409-2, MeJi412, MIBa351 and MIBa355 were grown in shake flasks and CFE were prepared and assayed for aspartate 1-decarboxylase (ADC) activity as described herein. The results are shown in Table 26. The activity for each strain is an average of two independent shake flask cultures. Strains MeJi409-2, MeJi412, MIBa351 and MIBa355 were also tested in bioreactors for 3-HP production, using the methods described herein. The results from these bioreactor experiments are also shown in Table 26. In order to account for differences in cell mass in these fermentations, the 3-HP production performance shown in Table 26 is expressed as 3-HP concentration per unit of cell mass (expressed as g/L 3-HP/g/L dry cell weight). The results show that as the level of ADC activity in the cells increased, the 3-HP production performance increased.

TABLE 26

Transformant ADC activity and 3-HP production data

| Strain | Gene overexpressed | ADC activity | 3-HP/DCW |
| --- | --- | --- | --- |
| MBin500 | NA | 0 | 0 |
| MeJi409-2 | ADC (SED ID NO: 138) | 0.629 | 0.19 |
| MeJi412 | | 1.151 | 0.43 |
| MIBa351 | | 0.659 | 0.32 |
| MIBa355 | | 1.173 | 0.52 |

Example 3A-16: Plasmid Construction for Expressing Pyruvate Carboxylase (PYC) at the PDC Locus Plasmid pANN28 contining the nucleotide sequence of SEQ ID NO: 1 (encoding the *I. orientalis* PYC of SEQ ID NO: 2) for integration at the PDC locus was constructed as described below.

The upstream and downstream flanking regions of *I. orientalis* PDC were amplified by PCR using genomic DNA as a template (Pfu polymerase, Stratagene) according to the manufacturer's instructions. The primers oANN7 and oANN8 allowed the incorporation of unique restriction sites flanking the upstream region and the primers oANN9 and oANN10 allowed the incorporation of unique restriction sites flanking the downstream region. The PCR products were purified by 1% agarose gel electrophoresis in TBE buffer as described herein. A band of approximately 800 bp for each PCR product was excised from the gel and purified using a gel extraction kit (Qiagen) according to the manufacturer's instructions. The purified PCR products were cloned into TOPO vectors (Invitrogen) and transformed into electro-competent *E. coli* DH10B cells (Invitrogen) according to manufacturer's instructions. Several of the resulting transformants were screened for proper insertion by colony PCR with the same primers used to create the PCR products. Positive clones were further confirmed by sequencing. A clone yielding the correct PDC downstream flank was designated pANN04. A clone yielding the correct PDC upstream flank was designated pANN07.

Plasmid pANN04 was digested with ApaI and SacI (for use as vector/backbone); plasmid pANN04 was digested with NotI and SacI; plasmid pANN07 was digested with NotI and ApaI. Each fragment was purified by 1% agarose gel electrophoresis in TBE buffer as described herein. A band of approximately 3.5 kbp for the vector, and approximately 1 kbp for each insert were excised from the gel and purified using a gel extraction kit (Qiagen) according to the manufacturer's instructions. The purified products were ligated using T4 ligase (New England Biolabs) in a total reaction volume of 10 µL composed of 49 ng of the vector, 120 ng of the downstream insert, 41 ng of the upstream insert, 1 µL 10× ligation buffer with 10 mM ATP (New England Biolabs), and 1 µL T4 ligase (New England Biolabs). The reaction was incubated for 30 minutes at room temperature and a 2 µL aliquot of the reaction was transformed into electro-competent *E. coli* OneShot TOP10 cells (Invitrogen) according to manufacturer's instructions. Transformants were plated on LB+Kanamycin plates and incubated at 37° C. overnight. Several of the resulting transformants were screened for proper insertion by colony PCR with primers oANN7 and oANN10 (yielding a band of approximately 1.7 kbp). A clone yielding the correct insertion was designated pANN12.

The *I. orientalis* PYC coding sequence (SEQ ID NO: 1) from pGMEr137 (supra) was modified by site directed mutagenesis to eliminate three EcoRI restriction sites which do not alter the amino acid sequence of the encoded enzyme. Plasmid pGMEr137 was used as a template with primers oANN13, oANN14 and oANN15 used to elimination of the above mentioned restriction sites using a Multi change kit (Stratagene) according to the manufacturer's instructions. Several of the resulting transformants were screened by restriction digest using EcoRI. Positive clones were further confirmed by sequencing. A clone yielding the correct pyc coding sequence was designated pANN14.

Figure 29:
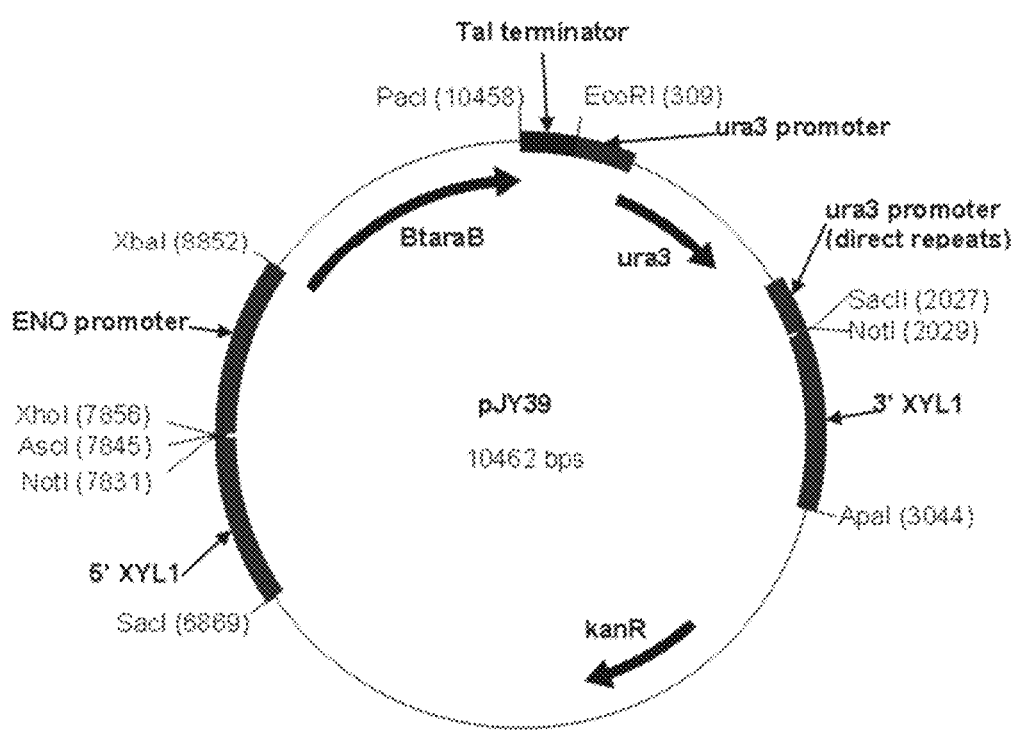
FIG. 29: Plasmid pJY39

Plasmid pJY39 (FIG. 29) was digested with XhoI and PacI; plasmid pACN5 (supra; see FIG. 19) was digested with XhoI and XbaI; plasmid pANN14 was digested with XbaI and PacI. Each fragment was purified by 1% agarose gel electrophoresis in TBE buffer as described herein. A band of approximately 8 kbp for the vector, approximately 700 bp for the first insert, and approximately 3.6 kbp for the second insert encoding the PYC were excised from the gel and purified using a gel extraction kit (Qiagen) according to the manufacturer's instructions. The purified products were ligated using T4 ligase (New England Biolabs) in a total reaction volume of 10 µL composed of 51 ng of the vector, 49 ng of the first insert, 210 ng of the second insert, 1 µL 10× ligation buffer with 10 mM ATP (New England Biolabs), and 1 µL T4 ligase (New England Biolabs). The reaction was incubated for 30 minutes at room temperature and a 2 µL aliquot of the reaction was transformed into electro-competent *E. coli* OneShot TOP10 cells (Invitrogen) according to manufacturer's instructions. Transformants were plated on LB+Kanamycin plates and incubated at 37° C. overnight.

Several of the resulting transformants were screened for proper insertion by colony PCR with primers oJLJ57 and oJLJ43 (yielding a band of approximately 1 kbp), primers oJLJ45 and oANN16 (yielding a band of approximately 730 bp), and primers oANN20 and oJY45 (yielding a band of approximately 1.2 kbp). A clone yielding the correct insertion was designated pANN15.

Plasmids pANN12 and pANN15 were digested with NotI. Plasmid pANN15 was additionally digested with NcoI for further fractionation of the backbone and improved separation of desired fragment. The digested pANN12 was purified using a Qiagen kit according to the manufacturer's instructions. The NotI fragments were purified by agarose gel electrophoresis in TBE buffer as described herein. The bands of approximately 5 kbp (from pANN12) and approximately 6.3 kbp (from pANN15) were gel purified using a gel extraction kit (Qiagen) according to the manufacturer's instructions.

The purified product from pANN15 was ligated into the pANN12 linearized vector using T4 ligase (New England Biolabs) in a total reaction volume of 10 µL composed of 50 ng of the vector, 115 ng of the insert, 1 µL 10× ligation buffer with 10 mM ATP (New England Biolabs), and 1 µL T4 ligase (New England Biolabs). The reaction was incubated for 1.5 hr at room temperature and a 2 µL aliquot of the reaction was transformed into electro-competent E. coli OneShot TOP10 cells (Invitrogen) according to manufacturer's instructions. Transformants were plated on LB+Kanamycin plates and incubated at 37° C. overnight. Several of the resulting transformants were screened for proper insertion by colony PCR with primers oANN20 and oJY45 (yielding a band of approximately 1.2 kbp). Clones yielding correct insertion were further screened by restriction enzyme digestion with SacI/EcoRI and with SacI/EcoRV in order to differentiate the insert orientation. A clone yielding the ura3 marker near the upstream PDC flank was designated pANN27. A clone yielding the ura3 marker near the downstream PDC flank was designated pANN28.

Example 3A-17: Yeast Strains Expressing Aspartate 1-Decarboxylase (ADC) from Four Nucleotide Sequences at the Adh1202 Locus and Pyruvate Carboxylase (PYC) at the pdc Locus This example describes the construction of yeast strains expressing four copies of nucleotides encoding the B. licheniformis ADC of SEQ ID NO: 139 at the adh1202 locus and a nucleotide encoding the I. orientalis PYC of SEQ ID NO: 2 at the pdc locus.

Removal of the Ura Marker from MeJi412

A ura– derivative of MeJi412 was isolated as described above. Several FOA resistant colonies of MeJi412 were screened by colony PCR for the desired loop-out event with primers 0611815 and 0611817. Primer 0611815 anneals in the RKI terminator of the left-hand construct and amplifies toward the ura3 promoter. Primer 0611817 anneals in TDH3 promoter and amplifies back toward the ura3 cassette. The presence of an 869 bp band indicates the presence of only the ura3 scar site (a single URA3 promoter left behind after homologous recombination between the two URA3 promoters in the parent strain) as desired, while a band of approximately 2.6 kbp indicates the presence of the intact URA3 promoter-URA3 ORF-URA3 terminator-URA3 promoter cassette, indicating the desired recombination event did not occur. PCR reactions with Phire® Plant Direct PCR Kit (Finnzymes) were carried out as described above. FOA resistant colonies that yielded the 869 bp fragment with the above primers were further tested with primers 0612794 and 0611817, which yield a 3.8 kbp product, and primers 611815 and 612795, which yield a 3.7 kbp product, to confirm that the four copies of the nucleotide sequence SEQ ID NO: 138 encoding the B. licheniformis ADC of SEQ ID NO: 139 remained intact. One FOA resistant colony from parent strain MeJi412, designated MeJi413, gave the desired PCR products with all 3 primer sets.

Integration of Fragment

Plasmid pANN28 (supra) was digested with AscI and SacI and purified by agarose gel electrophoresis in TBE buffer. The band at approximately 7.1 kbp was excised from the gel and purified using a gel purification kit (Qiagen) according to the manufacturer's instructions.

Strain MeJi413 was transformed with the digested and purified fragment from pANN28 and correct loci targeting and transformation was verified by colony PCR (Failsafe, mix E, Epicenter) according to the manufacturer's instructions. Primers oANN12 and oJLJ44 yielded an approximately 1 kbp band; primers oANN11 and oANN16 yielded an approximately 1.3 kbp band. A strain which gave the expected bands for proper integration of the expression cassette was designated yANN35.

A ura– derivative of yANN35 then was isolated as described above. Several FOA resistant colonies were screened by colony PCR for the desired loop-out event with primers oANN12 and oJY44. Primer oANN12 anneals outside of the downstream flanking region. Primer oJY44 anneals to the TAL terminator. The presence of a 1.5 kbp band indicates the presence of only the ura3 scar site (a single URA3 promoter left behind after homologous recombination between the two URA3 promoters in the parent strain) as desired, while a band of approximately 2.8 kbp indicates the presence of the intact URA3 promoter-URA3 ORF-URA3 terminator-URA3 promoter cassette, indicating the desired recombination event did not occur. PCR reactions with Failsafe DNA polymerase (Epicenter) were carried out as described above. Isolates positive for this event were further confirmed by colony PCR with primers oANN16 and oANN11. One FOA resistant colony was designated yANN37.

Strain yANN37 was transformed with the digested and purified fragments from pANN28 and correct loci targeting and transformation was verified by colony PCR (Failsafe, mix E, Epicenter) according to the manufacturer's instructions. The preliminary screen was done with primers oHJJ116 and oHJJ117 which are specific for the PDC gene. A band of approximately 500 bp indicates the presence of the gene and thus a negative result for the desired integration. Isolates that were positive for deletion of PDC were further confirmed with additional PCR reactions. Primers oANN11 and oANN16 yielded an approximately 1.3 kbp band. Primers oANN12 and oJLJ44 yielded an approximately 1 kbp band; primers oANN12 and oJY44 yielded an approximately 1.5 kbp band and an approximately 2.9 kbp band (corresponding to the first and second integration events respectively).

Additionally, the previous integration events at the adh1202 locus were confirmed by colony PCR as described above. Primers 0611631 and 0611245 yielded an approximately 3.8 kbp band. Primers 0611245 and oNovo3 yielded an approximately 3 kbp band. Primers 0611815 and 0612795 yielded an approximately 3.6 kbp band. A strain which gave the expected bands for proper integration of the expression cassette was designated yANN41.

Example 3A-18: Yeast Strains Expressing Aspartate 1-Decarboxylase (ADC) from Four Nucleotide Sequences at the Adh1202 Locus and Pyruvate Carboxylase (PYC) at the pdc Locus This example describes the construction of yeast strains expressing four copies of nucleotides encoding the *B. licheniformis* ADC of SEQ ID NO: 139 at the adh1202 locus (with two copies under the control of the a PDC promoter and two copies under the control of a TDH3 promoter) and a nucleotide encoding the *I. orientalis* PYC of SEQ ID NO: 2 at the pdc locus.

Removal of Ura Marker from MIBa355

A ura− derivative of MIBa355 was isolated as described above. Genomic DNA from several FOA resistant colonies of MIBa355 were screened by PCR for the desired loop-out event with primers 0611815 and 0611718. The presence of an approximately 500 bp band indicates the presence of only the ura3 scar site (a single URA3 promoter left behind after homologous recombination between the two URA3 promoters in the parent strain) as desired, while a band of approximately 1.9 kbp indicated the presence of the intact URA3 promoter-URA3 ORF-URA3 terminator-URA3 promoter cassette, indicating the desired recombination event did not occur. PCR was performed using the Phire® Plant Direct PCR kit (Finnzymes) according to the manufacturer's instructions. FOA resistant colonies that yielded the approximately 500 bp fragment with the above primers were further tested with primers 0611631 and 0611245, which yield a 3.5 kbp product, and primers 0611815 and 0611632, which yield a 4.5 kbp product, to confirm that the four copies of the nucleotide sequence SEQ ID NO: 138 encoding the *B. licheniformis* ADC of SEQ ID NO: 139 remained intact. They were also tested with PCR using primers 0611815 and 0611817 to confirm that the first modification at adh1202 was present. These PCR primers yielded a 828 bp fragment. One FOA resistant colony from parent strain MIBa355, designated MIBa357, gave the desired PCR products with all four primer sets.

The plasmid pANN28 (supra) was digested with AscI and SacI and purified by 1% agarose gel electrophoresis in TBE buffer. Approximately 7.1 kbp band was excised from the gel and purified using a NUCLEOSPIN® Extract II Kit (Macherey-Nagel) according to the manufacturer's instructions.

MIBa357 was transformed with the digested pANN28 DNA and correct loci targeting and transformation was verified by PCR using Phire Plant Direct PCR Kit (Finnzymes). Primers 0611622 and 0611552 yielded an approximately 850 bp band; primers 0611245 and 0612794 yielded an approximately 2.8 kbp band; primers 0611815 and 0612795 yielded an approximately 3.9 kbp band. A strain which gave the expected bands for proper integrating of the expression cassette was designated McTs241.

A ura− derivative of McTs241 then was isolated as described previously. Several FOA resistant colonies of McTs241 were screened by PCR for the desired loop-out event with primers 0614233 and 0611554 and lack of growth on ura minus selection plates. The presence of an 4.6 kbp band indicated the presence of only the ura3 scar site (a single URA3 promoter left behind after homologous recombination between the two URA3 promoters in the parent strain) as desired, while a band of approximately 5.9 kbp indicated the presence of the intact URA3 promoter-URA3 ORF-URA3 terminator-URA3 promoter cassette, indicating the desired recombination event did not occur. PCR reactions using Phire Plant Direct PCR Kit (Finnzymes) were carried out as described above. One FOA resistant colony from parent strain McTs241 that had the desired loop-out event was designated McTs247.

To create the homozygous integration McTs247 was transformed with the digested pANN28 DNA and correct loci targeting and transformation was verified by PCR using Phire Plant Direct PCR Kit (Finnzymes). As a first screen transformants were screen by PCR with primers 0611552 and 0611553 which should yield an approximately 850 bp band only if the pdc locus is intact and thus the homozygous integration of PYC at the PDC locus did not occur. Of those that were negative for a band from this PCR were then screened by additional PCR with primers 0611555 and 0611554. With these primers a product should only amplify 1.4 kbp band if PDC is intact and thus not a homozygous integration of PYC at PDC locus. Further screening of transformants was done by PCR using primers 0611622 and 0611552 yielding an approximately 850 bp band; primers 0611245 and 0612794 yielded an approximately 2.8 kbp band; primers 0611815 and 0612795 yielded an approximately 3.9 kbp band. A strain which gave the expected bands for proper integrating of the expression cassette was designated McTs253.

Example 3A-19: PYC Activity, ADC Activity and 3-HP Production Performance of Strains MeJi412, yANN35, yANN41, MIBa355, McTs241 and McTs253

Strains MeJi412, yANN35, yANN41, MIBa355, McTs241 and McTs253 were grown in shake flasks and CFE were prepared and assayed for pyruvate carboxylase (PYC) activity and aspartate 1-decarboxylase (ADC) activity as described herein. The results are shown in Table 27. Strains MeJi412, yANN35, yANN41, MIBa355, McTs241 and McTs253 were also tested in bioreactors for 3-HP production, using the methods described herein. The results from these bioreactor experiments are also shown in Table 27. In order to account for differences in cell mass in these fermentations, the 3-HP production performance shown is expressed as 3-HP concentration per unit of cell mass (expressed as g/L 3-HP/g/L dry cell weight). The results show that as the level of PYC activity in the cells increased, the 3-HP production performance increased.

TABLE 27

Transformant PYC and ADC activity and 3-HP production performance

| Strain | Gene Overexpressed | PYC activity | ADC activity | 3-HP/DCW |
|---|---|---|---|---|
| MeJi412 | ADC (SED ID NO: 138) | 6.8 | 1.151 | 0.43 |
| yANN35 | ADC (SED ID NO: 138) PYC (SEQ ID NO: 1) | 47.2 | 1.090 | 0.64 |

TABLE 27-continued

Transformant PYC and ADC activity and 3-HP production performance

| Strain | Gene Overexpressed | PYC activity | ADC activity | 3-HP/DCW |
|---|---|---|---|---|
| yANN41 | ADC (SED ID NO: 138)<br>PYC (SEQ ID NO: 1) | 49.0 | 1.263 | 1.30 |
| MiBa355 | ADC (SED ID NO: 138) | 6.9 | 1.173 | 0.52 |
| McTs241 | ADC (SED ID NO: 138)<br>PYC (SEQ ID NO: 1) | 24.8 | 1.119 | 0.76 |
| McTs253 | ADC (SED ID NO: 138)<br>PYC (SEQ ID NO: 1) | 55.5 | 1.347 | 1.30 |

Example 3A-20: Yeast Strains Expressing Aspartate 1-Decarboxylase (ADC) from Four Nucleotide Sequences at the Adh1202 Locus and Deletion of Beta-Alanine Aminotransferase (BAAT)

This example describes the construction and performance of yeast strains expressing four copies of nucleotides encoding the B. licheniformis ADC of SEQ ID NO: 139 at the adh1202 locus and deletion of the native I. orientalis gene encoding the BAAT (PYD4) of SEQ ID NO: 20.

Construction of I. orientalis BAAT (PYD4) Deletion Plasmid

The plasmid pMIBa123 (supra) was digested with NotI, KpnI, ApaI and the purified by 1% agarose gel electrophoresis in TBE buffer as described herein. Two bands at approximately 3.6 kbp and 3.8 kbp were excised from the gel and purified using a NUCLEOSPIN® Extract II Kit (Macherey-Nagel) according to the manufacturer's instructions. These two pieces comprised the plasmid backbone and the ura selection cassette with S. cerevisiae 3-HPDH gene (YMR226c) of SEQ ID NO: 144.

A PCR product for the upstream I. orientalis PYD4 homology was generated by PCR amplification using I. orientalis MBin500 genomic DNA prepared as described previously using primers 0613178 and 0613180. The downstream I. orientalis PYD4 homology piece was prepared by PCR amplification from MBin500 genomic DNA using primers 0613179 and 0613181. Fifty pmoles of each primer was used in a PCR reaction containing 0.5 µL of MBin500 genomic DNA as template, 0.2 mM each dATP, dGTP, dCTP, dTTP, 1× Expand High Fidelity Buffer (Roche), 3.5 U Expand High Fidelity Enzyme Mix (Roche) in a final volume of 50 µL. The amplification reaction was performed in an EPPENDORF® MASTERCYCLER® 5333 (Eppendorf) programmed for one cycle at 95° C. for 3 minutes; and 30 cycles each at 95° C. for 30 seconds, 55° C. for 30 seconds, and 72° C. for 1 minute. After the cycles, the reaction was incubated at 72° C. for 5 minutes and then cooled at 10° C. until further processed. The approximately 800 bp band from PCR using primers 0613178 and 0613180 and the approximately 900 bp band from PCR using primers 0613179 and 0613181 were purified by 1% agarose gel electrophoresis in TBE buffer. The bands were excised from the gel and purified using a NUCLEOSPIN® Extract II Kit (Macherey-Nagel) according to the manufacturer's instructions.

The PYD4 upstream PCR product, PYD4 downstream PCR product, and pMIBa123 NotI/KpnI/ApaI digested plasmid were assembled in a reaction with IN-FUSION HD™ (Clontech Laboratories, Inc.) according to manufacturer's instructions. From the In-FUSION reaction 2 µL was transformed into ONE SHOT® TOP10 chemically competent E. coli cells (Invitrogen) according to manufacturer's instructions. After a recovery period, two 100 µL aliquots from the transformation reaction were plated onto 150 mm 2×YT plates supplemented with 100 µg of ampicillin per mL. The plates were incubated overnight at 37° C. Putative recombinant clones were selected from the selection plates and plasmid DNA was prepared from each one using a BIOROBOT® 9600 (Qiagen). Clones were analyzed by restriction digest and sequencing. A plasmid with the correct sequence were verified by sequencing and named pMcTs61.

Figure 30:
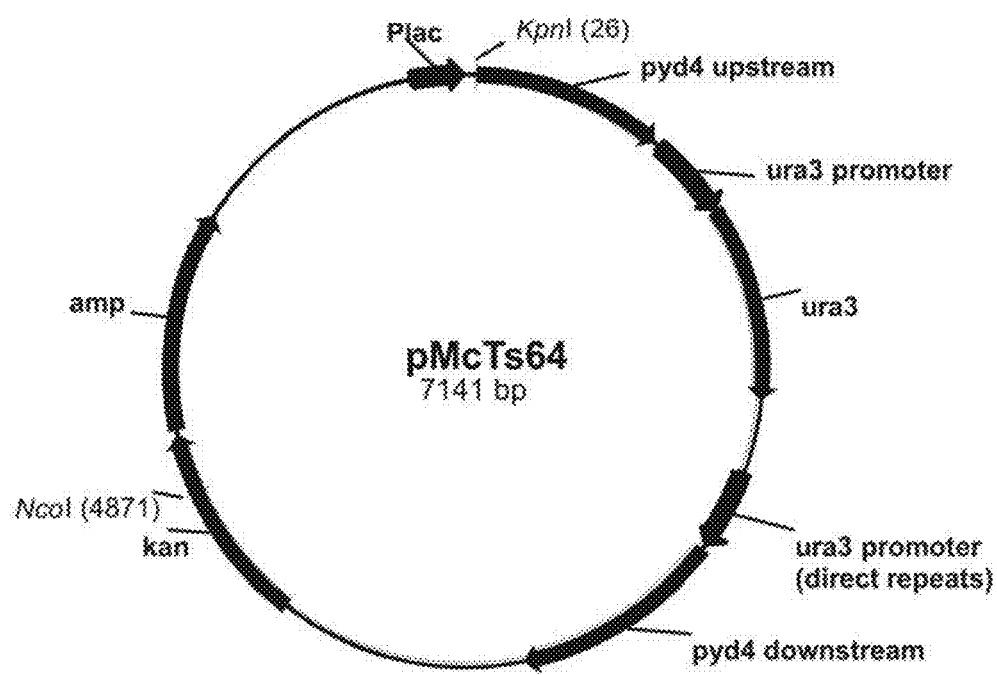
FIG. 30: Plasmid pMcTs64

The plasmid pMcTs61 still contains the PDC promoter, YMR226c gene from S. cerevisiae, and the PDC terminator. To remove these undesired segments, pMcTs61 was digested with EcoRI and XhoI followed by addition of Klenow fragment to create blunt ends. The 7.1 kbp fragment was purified by 1% agarose gel electrophoresis in TBE buffer. The band was excised from the gel and purified using a NUCLEOSPIN® Extract II Kit (Macherey-Nagel) according to the manufacturer's instructions. The digested blunt plasmid was ligated together using T4 DNA ligase (New England Biolabs, Ipswich, Mass., USA). The reaction mixture contained 1× T4 DNA ligase buffer, 1 µL T4 DNA ligase, 5 µL pMcTs61 digested and blunted purified DNA in total volume of 20 µL. The reaction was incubated at room temperature for 2 hours. A 10 µL sample of the ligation reaction was used to transform ONE SHOT® TOP10 chemically competent E. coli cells (Invitrogen) according to according to the manufacturer's instructions. After a recovery period, two 100 µL aliquots from the transformation reaction were plated onto 150 mm 2×YT plates supplemented with 100 µg of ampicillin per mL. The plates were incubated overnight at 37° C. Putative recombinant clones were selected from the selection plates. Clones were analyzed by colony PCR. Template DNA from each colony was prepared by dissolving 1 colony in 50 µL sterile water, heated at 95° C. for 10 minutes, then cooled on ice until use. Primers 0612911 and 0612909 were used to screen the transformants. The PCR reaction with these primers would amplify a 1 kbp band if the plasmid was correct. Ten pmoles of each primer was used in a PCR reaction containing 2 µL colony DNA template, 0.1 mM each dATP, dGTP, dCTP, dTTP, 1× Crimson Taq Reaction Buffer (New England Biolabs), 1 U Crimson Taq DNA Polymerase (New England Biolabs) in a final volume of 20 µL. The amplification reaction was performed in an EPPENDORF® MASTERCYCLER® 5333 (Eppendorf) programmed for one cycle at 95° C. for 3 minutes; and 30 cycles each at 95° C. for 30 seconds, 55° C. for 30 seconds, and 72° C. for 3 minutes. After the cydes, the reaction was incubated at 72° C. for 5 minutes and then cooled at 10° C. until further processed. From 5 µL of the PCR reaction a 1 kbp PCR fragment was visualized on a 1% TAE-agarose gel with ethidium bromide in TAE buffer. One transformant with the correct size PCR product was selected and named pMcTs64 (FIG. 30). Plasmid DNA of pMcTs64 was prepared using a BIOROBOT® 9600 (Qiagen).

Deletion of Native *I. orientalis* BAAT (PYD4) from MeJi413 Using pMcTs64 Construct Plasmid pMcTs64 (supra; see FIG. 30) was digested with ApaI, NcoI, KpnI and purified by 1% agarose gel electrophoresis in TBE buffer. Approximately 3.3 kbp band was excised from the gel and purified using a NUCLEOSPIN® Extract II Kit (Macherey-Nagel) according to the manufacturer's instructions.

Strain MeJi413 (supra) was transformed with the digested pMcTs64 DNA and correct loci targeting and transformation was verified by PCR using Phire Plant Direct PCR Kit (Finnzymes). Primers 0612908 and 0613242 yield an approximately 1.7 kbp band; primers 0613241 and 0612909 yield an approximately 1.5 kbp band to confirm the integration of the deletion cassette. Primers 0611815 and 0611632 yield an approximately 4.2 kbp band; primers 0611817 and 0611631 yield an approximately 4.8 kbp band to confirm the ADC cassette at the ADH1202 locus was still intact. A strain which gave the expected bands for proper integrating of the deletion cassette and ADC cassette was designated McTs225.

A ura– derivative of McTs225 then was isolated as described previously. Several FOA resistant colonies of McTs225 were screened by PCR for the desired loop-out event with primers 0612911 and 0612910. The presence of an 1.1 kbp band indicates the presence of only the ura3 scar site (a single URA3 promoter left behind after homologous recombination between the two URA3 promoters in the parent strain) as desired, while a band of approximately 2.5 kbp indicates the presence of the intact URA3 promoter-URA3 ORF-URA3 terminator-URA3 promoter cassette, indicating the desired recombination event did not occur. Primers 0611815 and 0611632 yield an approximately 4.2 kbp band; primers 0611817 and 0611631 yield an approximately 4.8 kbp band to confirm the ADC cassette at the adh1202 locus was still intact. PCR reactions using Phire Plant Direct PCR Kit (Finnzymes) were carried out as described above. One FOA resistant colony from parent strain McTs225 that had the desired loop-out event was designated McTs228.

To create a homozygous deletion of the native gene encoding the *I. orientalis* BAAT (PYD4) of SEQ ID NO: 20, McTs228 was transformed with digested pMcTs64 and correct loci targeting and transformation was verified by PCR using Phire Plant Direct PCR Kit (Finnzymes). Two primer sets were used to screen by PCR for PYD4 locus deletion. Primers 0613550 and 0612910 yield an approximately 700 bp band only if the PYD4 locus is intact which would indicate that homozygous deletion of PYD4 did not occur. Additionally transformants were screen with primers 0612911 and 0613551 which yield an approximately 600 bp band if PYD4 was not deleted. Transformants that were negative for the *I. orientalis* PYD4 locus were further screened with primers 0613242 and 0613243 yielding an approximately 3.5 kbp and 2.1 kbp band; primers 0612908 and 0613243 yielded an approximately 1.7 kbp band; primers 0612909 and 0612911 yielded an approximately 950 bp band. The ADC cassette at adh1202 locus was confirmed to still be intact with primers 0611817 and 0611631 yielding an approximate 4.8 kbp band and primers 611815 and 612712 yielding an approximate 4.2 kbp band. A strain which gave the expected bands for proper integrating of the expression cassette was designated McTs236.

A ura– derivative of McTs236 then was isolated as described previously. Several FOA resistant colonies of McTs236 were screened by PCR for the desired loop-out event with primers 0613242 and 0613243 yielding an approximately 2.1 kbp band. The ADC cassette at ADH1202 locus was confirmed to still be intact with primers 0611245 and 0612794 yielding an approximate 3 kbp and primers 0611815 and 0612795 yielding an approximate 3.6 kbp band. A strain which gave the expected bands for proper integrating of the expression cassette was designated McTs245.

Strains MIBa372 and McTs245 were tested in bioreactors for 3-HP production, using the methods described herein. In order to account for differences in cell mass in these fermentations, the 3-HP production performance is expressed as 3-HP concentration per unit of cell mass (expressed as g/L 3-HP/g/L dry cell weight). The g/L 3-HP/g/L dry cell weight for strains MIBa372 and McTs245 were 1.66 and 0.16, respectively. These results suggest that the native PYD4 gene in *I. orientalis* is responsible for the conversion of beta-alanine to malonate semialdehyde, since deletion of this gene led to a 10-fold decrease in 3-HP production performance.

Example 3A-21: Yeast Strains Expressing Aspartate 1-Decarboxylase (ADC) from Four Nucleotide Sequences at the Adh1202 Locus and Deletion of 3-HP Dehydrogenase (3-HPDH)

This example describes the construction and performance of yeast strains expressing four copies of nucleotides encoding the *B. licheniformis* ADC of SEQ ID NO: 139 at the adh1202 locus and deletion of the native *I. orientalis* gene encoding the 3-HPDH of SEQ ID NO: 26.

Construction of *I. orientalis* 3-HPDH Deletion Plasmid

The plasmid pMIBa123 (supra) was digested with NotI, KpnI, ApaI and the purified by 1% agarose gel electrophoresis in TBE buffer as described herein. Two bands at approximately 3.6 kbp and 3.8 kbp were excised from the gel and purified using a NUCLEOSPIN® Extract II Kit (Macherey-Nagel) according to the manufacturer's instructions. These two pieces comprised the plasmid backbone and the ura selection cassette with *S. cerevisiae* 3-HPDH gene of SEQ ID NO: 144.

A PCR product for the upstream *I. orientalis* 3-HPDH homology was amplified from *I. orientalis* MBin500 genomic DNA prepared as described previously using primers 0613183 and 0613184. A downstream *I. orientalis* 3-HPDH homology piece was amplified from *I. orientalis* MBin500 genomic DNA using primers 0613185 and 0613186. Fifty pmol of each primer was used in a PCR reaction containing 0.5 µl of MBin500 genomic DNA as template, 0.2 mM each dATP, dGTP, dCTP, dTTP, 2% DMSO, 1× Phusion HF Buffer (FinnzymeS), 2U Phusion® Hot Start High-Fidelity DNA Polymerase (Finnzymes) in a final volume of 50 µl. The amplification reaction was performed in an EPPENDORF® MASTERCYCLER® 5333 (Eppendorf Scientific, Inc., Westbury, N.Y., USA) programmed for one cycle at 95° C. for 3 minutes; and 30 cycles each at 95° C. for 30 seconds, 55° C. for 30 seconds, and 72° C. for 1 minute. After the cycles, the reaction was incubated at 72° C. for 5 minutes and then cooled at 4° C. until further processed. The approximately 640 bp band from PCR of primers 0613183 and 0613184 and the approximately 670 bp band of the PCR from primers 0613185 and 0613186 was purified by 1% agarose gel electrophoresis in TBE buffer. The bands were excised from the gel and purified using a NUCLEOSPIN® Extract II Kit (Macherey-Nagel) according to the manufacturer's instructions.

The *I. orientalis* 3-HPDH upstream PCR product, *I. orientalis* 3-HPDH downstream PCR product, and pMIBa123 NotI/KpnI/ApaI digested plasmid were assembled in a reaction with IN-FUSION HD™ (Clontech Laboratories, Inc.) according to manufacturer's instructions. From the In-FUSION reaction 2 µL was transformed into ONE SHOT® TOP10 chemically competent *E. coli* cells (Invitrogen) according to manufacturer's instructions. After a recovery period, two 100 µl aliquots from the transformation reaction were plated onto 150 mm 2×YT plates supplemented with 100 µg of ampicillin per mL. The plates were incubated overnight at 37° C. Putative recombinant clones were selected from the selection plates and plasmid DNA was prepared from each one using a BIOROBOT® 9600 (Qiagen). Clones were analyzed by restriction digest and sequencing. A plasmid with the correct sequence was verified by sequencing and named pMcTs60.

Figure 31:
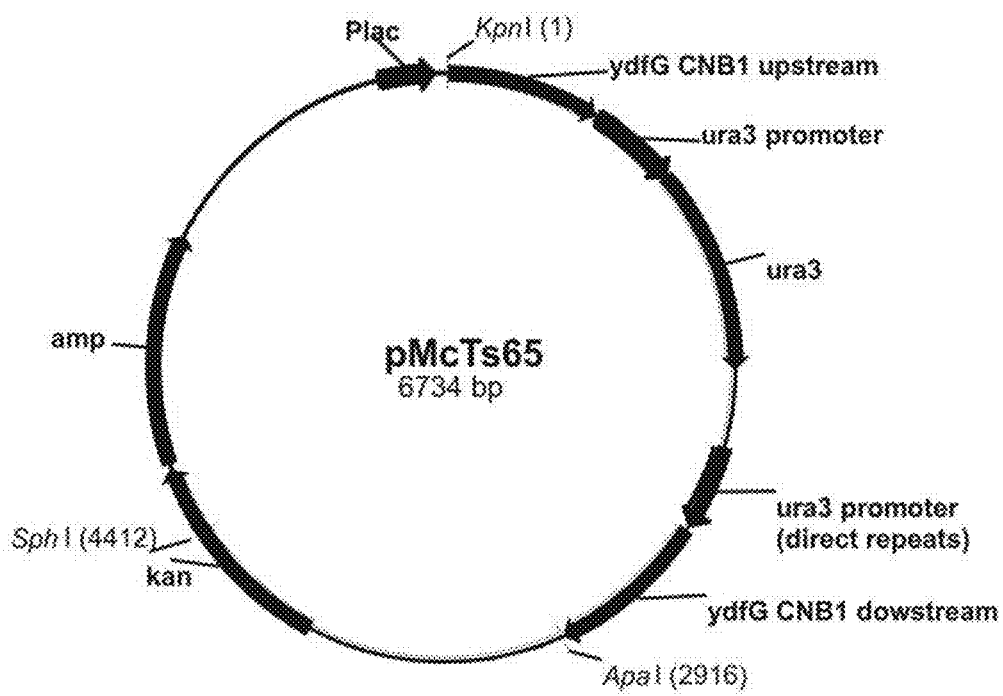
FIG. 31: Plasmid pMcTs65

The plasmid pMcTs60 still contains the PDC promoter, YMR226c gene from *S. cerevisiae*, and the PDC terminator. To remove these undesired segments, pMcTs60 was digested with NotI and XbaI and the approximately 5 kbp band containing the 3-HPDH homology regions and the plasmid backbone were purified by 1% agarose gel electrophoresis in TBE buffer. The bands were excised from the gel and purified using a NUCLEOSPIN® Extract II Kit (Macherey-Nagel) according to the manufacturer's instructions. The ura3 selection cassette was amplified with 2 PCR reactions one with primers 0613416 and 0613417 and the other with primers 0613418 and 0613419. Fifty pmol of each primer was used in a PCR reaction containing 0.5 µL of pMcTs60 plasmid DNA as template, 0.2 mM each dATP, dGTP, dCTP, dTTP, 1× Expand High Fidelity Buffer (Roche), 3.5 U Expand High Fidelity Enzyme Mix (Roche) in a final volume of 50 µL. The amplification reaction was performed in an EPPENDORF® MASTERCYCLER® 5333 (Eppendorf Scientific, Inc.) programmed for one cycle at 95° C. for 3 minutes; and 30 cycles each at 95° C. for 30 seconds, 55° C. for 30 seconds, and 72° C. for 1 minute. After the cycles, the reaction was incubated at 72° C. for 5 minutes and then cooled at 4° C. until further processed. The approximately 700 bp band from PCR of primers 0613416 and 0613417 and the approximately 1 kbp band of the PCR from primers 0613418 and 0613419 was purified by 1% agarose gel electrophoresis in TBE buffer. The bands were excised from the gel and purified using a NUCLEOSPIN® Extract II Kit (Macherey-Nagel) according to the manufacturer's instructions. The plasmid backbone containing the *I. orientalis* 3-HPDH homology regions and the ura3 cassette PCR products were assembled in a reaction with IN-FUSION HD™ (Clontech Laboratories, Inc.) according to manufacturer's instructions. From the In-FUSION reaction 2 µL was transformed into Solo Pack Gold Super Competent Cells (Stratagene) according to manufacturer's instructions. After a recovery period, two 100 µL aliquots from the transformation reaction were plated onto 150 mm 2×YT plates supplemented with 100 µg of ampicillin per mL. The plates were incubated overnight at 37° C. Putative recombinant clones were selected from the selection plates and plasmid DNA was prepared from each one using a BIOROBOT® 9600 (Qiagen). Clones were analyzed by restriction digest and a plasmid with the correct restriction digest pattern was named pMcTs65 (FIG. 31).

Deletion of Native *I. orientalis* 3-HPDH from MeJi413 Using pMcTs65 Construct

Plasmid pMcTs65 (supra; see FIG. 31) was digested with ApaI, Sph, KpnI and purified by 1% agarose gel electrophoresis in TBE buffer. Approximately 2.9 kbp band was excised from the gel and purified using a NUCLEOSPIN® Extract II Kit (Macherey-Nagel) according to the manufacturer's instructions.

Strain MeJi413 (supra) was transformed with the digested pMcTs65 DNA and correct loci targeting and transformation was verified by PCR using Phire Plant Direct PCR Kit (Finnzymes). Primers 0613034 and 0613035 yielded an approximately 2.7 kbp band to confirm the integration of the deletion cassette. Primers 0611815 and 0611632 yielded an approximately 4.2 kbp band; primers 0611817 and 0611631 yielded an approximately 4.8 kbp band to confirm the ADC cassette at the adh1202 locus was still intact. A strain which gave the expected bands for proper integrating of the deletion cassette and ADC cassette was designated McTs229.

A ura− derivative of McTs229 then was isolated as described previously. Several FOA resistant colonies of McTs229 were screened by PCR for the desired loop-out event with primers 0613034 and 0613241. The presence of an 1.4 kbp band indicates the presence of only the ura3 scar site (a single URA3 promoter left behind after homologous recombination between the two URA3 promoters in the parent strain) as desired, while a band of approximately 2.8 kbp indicates the presence of the intact URA3 promoter-URA3 ORF-URA3 terminator-URA3 promoter cassette, indicating the desired recombination event did not occur. The presence of a 1.9 kbp band indicates the wild-type locus which is present in these transformants since these are heterozygous for the deletion. Primers 0611815 and 0611632 yielded an approximately 4.2 kbp band; primers 0611631 and 0612366 yielded an approximately 4.5 kbp band to confirm the ADC cassette at the ADH1202 locus was still intact. PCR reactions using Phire Plant Direct PCR Kit (Finnzymes) were carried out as described above. One FOA resistant colony from parent strain McTs225 that had the desired loop-out event was designated McTs238.

To create a homozygous deletion of the native gene encoding the *I. orientalis* 3-HPDH of SEQ ID NO: 26, McTs238 was transformed with digested pMcTs65 and correct loci targeting and transformation was verified by PCR using Phire Plant Direct PCR Kit (Finnzymes). Two primer sets were used to screen by PCR for YMR226c locus deletion. Primers 0613034 and 0613747 would yield an approximately 500 bp band if the 3-HPDH locus is intact to indicate that homozygous deletion of 3-HPDH did not occur. Additionally transformants were screened with primers 0613746 and 0613241 which would yield an approximately 660 bp band if 3-HPDH was not deleted. Transformants that were wild-type negative for the *I. orientalis* 3-HPDH locus were further screened with primers 0613034 and 0613241 yielding an approximately 2.8 kbp and 1.4 kbp band; primers 0612908 and 0613241 yielded an approximately 1.5 kbp band; primers 0613034 and 0612909 yielded an approximately 1 kbp band. The ADC cassette at ADH1202 locus was confirmed to still be intact with primers 0611245 and 0612794 yielding an approximate 3 kbp and primers 0611815 and 0612795 yielding an approximate 3.6 kbp band. A strain which had the expected bands for proper integrating of the expression cassette was designated McTs244.

A ura− derivative of McTs244 wthen as isolated as described previously. Several FOA resistant colonies of McTs244 were screened by PCR for the desired loop-out event with primers 0613034 and 0613241 yielding an approximately 1.4 kbp band. The ADC cassette at ADH1202 locus was confirmed to still be intact with primers 0611245 and 0612794 yielding an approximately 3 kbp band and primers 0611815 and 0612795 yielding an approximately 3.6 kbp band. One FOA resistant colony from parent strain McTs244 that had the desired loop-out event was designated McTs259.

Strains MIBa372 and McTs244 were tested in bioreactors for 3-HP production, using the methods described herein. In order to account for differences in cell mass in these fermentations, the 3-HP production performance is expressed as 3-HP concentration per unit of cell mass (expressed as g/L 3-HP/g/L dry cell weight). The g/L 3-HP/g/L dry cell weight for strains MIBa372 and McTs259 were 1.66 and <0.1, respectively. These results indicate that the native 3-HPDH gene in *I. orientalis* is responsible for the conversion of malonate semialdehyde to 3-HP, since deletion of this gene abolished 3-HP production.

Example 3A-22: Yeast Strains Expressing Pyruvate Carboxylase (PYC), Aspartate Aminotransferase (AAT), β-Alanine Aminotransferase (BAAT), and 3-Hydroxypropionic Acid Dehydrogenase (3-HPDH) at the pdc Locus; and Aspartate 1-Decarboxylase (ADC) from Four Nucleotide Sequences at the Adh1202 Locus Additional constructs were designed to incorporate the nucleotide sequence SEQ ID NO: 1 encoding the *I. orientalis* PYC of SEQ ID NO: 2, the nucleotide sequence SEQ ID NO: 13 encoding the *I. orientalis* AAT of SEQ ID NO: 14, the nucleotide sequence SEQ ID NO: 142 encoding the *S. kluyveri* BAAT of SEQ ID NO: 21, and the nucleotide sequence SEQ ID NO: 144 encoding the *S. cerevisiae* 3-HPDH of SEQ ID NO: 129 at the *I. orientalis* pdc locus in stains that also contain four copies of nucleotides encoding the *B. licheniformis* ADC of SEQ ID NO: 139 at the adh1202 locus. In a similar approach to that described above, a left-hand and a right-hand construct were designed to allow homologous recombination at the *I. orientalis* CNB1 pdc locus. These constructs were prepared and transformed into MIBa357 as described below.

Construction of a Left-Hand Fragment

The nucleotide sequence SEQ ID NO: 13 encoding the *I. orientalis* AAT of SEQ ID NO: 14 was amplified by PCR using plasmid pGMEr126 (FIG. 16) as a template according to the manufacturer's instructions (Pfu polymerase, Stratagene). The primers oANN1 and oANN2 allowed the incorporation of unique restriction sites flanking the gene coding sequence. The PCR product was purified by 1% agarose gel electrophoresis in TBE buffer as described herein. A band of approximately 1.3 kbp was excised from the gel and purified using a gel extraction kit (Qiagen) according to the manufacturer's instructions. The purified PCR product was digested with ApaI and NruI and gel purified as described herein.

The plasmid pGMEr135 (identical to pGMEr136 above, except that the ENO1 promoter/RKI terminator insert is in opposite orientation) was digested with ApaI and NruI and purified by agarose gel electrophoresis in TBE buffer as described herein. A band of approximately 11.7 kbp was excised from the gel and purified using a gel extraction kit (Qiagen) according to the manufacturer's instructions.

The purified 1.3 kbp PCR product was ligated into the 11.7 kbp pGMEr135 linearized vector using T4 ligase (New England Biolabs) in a total reaction volume of 10 µL composed of 49.8 ng of the vector, 354 ng of the 1.3 kbp insert, 1 µL 10× ligation buffer with 10 mM ATP (New England Biolabs), and 1 µL T4 ligase (New England Biolabs). The reaction was incubated for 30 minutes at room temperature and a 2 µL aliquot of the reaction was transformed into electro-competent *E. coli* DH10B cells (Invitrogen) according to manufacturer's instructions. Transformants were plated on LB+Kanamycin plates and incubated at 37° C. overnight. Several of the resulting transformants were screened for proper insertion by colony PCR with primers oHJ2 and oANN1 (yielding a band of approximately 2.3 kbp) and primers oANN5 and oANN6 (yielding a band of approximately 877 bp). The sequence of the aat fragment amplified by PCR was also confirmed. A clone yielding correct insertion and sequence was digested with ApaI and NruI and gel purified as described herein. A band of approximately 1.3 kbp was excised from the gel and purified using a gel extraction kit (Qiagen) according to the manufacturer's instructions.

The plasmid pGMEr137 (supra; see FIG. 18), containing the desired nucleotide sequence SEQ ID NO: 1 encoding the *I. orientalis* PYC of SEQ ID NO: 2, was digested with ApaI and NruI and purified by agarose gel electrophoresis in TBE buffer as described herein. A band of approximately 11.7 kbp was excised from the gel and purified using a gel extraction kit (Qiagen) according to the manufacturer's instructions.

The purified 1.3 kbp PCR product was ligated into the 11.7 kbp pGMEr137 linearized vector using T4 ligase (New England Biolabs) in a total reaction volume of 10 µL composed of 49.4 ng of the vector, 54 ng of the 1.3 kbp insert, 1 µL 10× ligation buffer with 10 mM ATP (New England Biolabs), and 1 µL T4 ligase (New England Biolabs). The reaction was incubated for 30 minutes at room temperature and a 2 µL aliquot of the reaction was transformed into electro-competent *E. coli* DH10B cells (Invitrogen) according to manufacturer's instructions. Transformants were plated on LB+Kanamycin plates and incubated at 37° C. overnight. Several of the resulting transformants were screened for proper insertion by colony PCR with primers oHJ2 and oANN1 (yielding a band of approximately 2.3 kbp) and primers oANN5 and oANN6 (yielding a band of approximately 877 bp). A clone yielding correct insertion and sequence was designated pANN02.

Construction of a Left-Hand Fragment with the AAT Encoding Sequence in the Opposite Orientation The plasmid pANN02 was digested with PmeI and purified by agarose gel electrophoresis in TBE buffer as described herein. A band of approximately 10.3 kbp and a band of approximately 2.7 kbp were excised from the gel and purified using a gel extraction kit (Qiagen) according to the manufacturer's instructions. The 10.3 kbp vector fragment from pANN2 was dephosphorylated with CIP (New England Biolabs) and purified with a purification kit (Qiagen) according to the manufacturer's instructions. The 2.7 kbp fragment from pANN02 was ligated into the dephosphorylated 10.3 kbp linearized vector from pANN02 using T4 ligase (New England Biolabs) in a total reaction volume of 10 µL composed of 36 ng of the vector, 28 ng of the insert, 1 µL 10× ligation buffer with 10 mM ATP (New England Biolabs), and 1 µL T4 ligase (New England Biolabs). The reaction was incubated for 30 minutes at room temperature and a 2 µL aliquot of the reaction was transformed into electro-competent *E. coli* TOP10 cells (Invitrogen) according to manufacturer's instructions. Transformants were plated on LB+Kanamycin plates and incubated at 37° C. overnight. Several of the resulting transformants were screened for proper insertion by colony PCR with primers oJY44 and oHJ1 (yielding a band of approximately 1.3 kbp). A clone yielding correct insertion was designated pANN5.

Construction of a Right-Hand Fragment

A right-hand construct containing two *B. licheniformis* ADC coding regions and the *I. orientalis* PDC locus 3' targeting flanking DNA was constructed as follows. The pMhCt071 plasmid (a plasmid identical to pMhCt077 above except that the *S. cerevisiae* 3-HPDH ORF is not codon optimized for *I. orientalis*) was digested with PmeI and PacI, treated with 10 units calf intestinal phosphatase (New England Biolabs), and purified by 0.9% agarose gel electrophoresis in TAE buffer, and an approximately 4.7 kbp band was excised from the gel and purified using a NUCLEOSPIN® Extract II Kit according to the manufacturer's instructions.

The plasmid pMeJi312-2 (supra; see FIG. 15) was digested with PmeI and PacI to extract two *B. licheniformis* ADC expression cassettes and purified by 0.9% agarose gel electrophoresis in TAE buffer. An approximately 2.8 kbp band was excised from the gel and purified using a NUCLEOSPIN® Extract II Kit according to the manufacturer's instructions.

The fragment containing dual *B. licheniformis* ADC coding regions from pMeJi312-2 was then ligated into the linearized pMhCt071 vector fragment in a ligation reaction (20 µL) containing 1× Quick ligation buffer (New England Biolabs), 1 µl 4.7 kbp fragment of pMhCt071 vector, 3 µL 2.8 kbp insert from pMeJi312-2, and 1 µl Quick T4 DNA ligase (New England Biolabs). The ligation reaction was incubated for 5 min at room temperature, and then the tube was placed on ice. 5 uL of this reaction was used to transform SoloPack Gold SuperCompetent Cells (Agilent Technologies) according to the manufacturer's instructions. Transformants were plated onto 2×YT+amp plates and incubated at 37° C. overnight. Several of the resulting transformants were screened for proper ligation of the desired fragments by ApaLI digestion. A clone yielding the desired band sizes was kept and designated pMhCt110.

The plasmid pMhCt110 was digested with XbaI and PacI followed by treatment with CIP and purified by 1% agarose gel electrophoresis in TBE buffer as described herein. A band at approximately 7.1 kbp was excised from the gel and purified using QIAQUICK® Gel Extraction Kit (Qiagen) according to the manufacturer's instructions.

The codon-optimized *S. cerevisiae* 3-HPDH coding sequence of SEQ ID NO: 144 was excised from pMIBa123 (supra) by digestion with XbaI and PacI and purified by 1% agarose gel electrophoresis in TBE buffer as described herein. A band at approximately 814 bp was excised from the gel and purified using QIAQUICK® Gel Extraction Kit (Qiagen) according to the manufacturer's instructions. The 814 bp purified fragment was ligated into the 7.1 kbp fragment from pMhCt110 using T4 ligase (New England Biolabs) in a total reaction volume of 10 µL composed of 1 µL of the digested pMhCt110, 1 or 7 µL of the 814 bp fragment from pMIBa123, 1 µL 10× ligation buffer with 10 mM ATP (New England Biolabs), and 1 µL T4 ligase (New England Biolabs). The reaction was incubated for 30 minutes at room temperature and a 4 µL aliquot of the reaction was transformed into ONE SHOT® TOP10 chemically competent *E. coli* cells (Invitrogen) according to manufacturer's instructions. Transformants were plated on 2×YT+amp plates and incubated over the weekend at room temperature. Several of the resulting transformants were screened for proper insertion by restriction digest using 2 combinations of enzymes XbaI and PacI and AscI and PacI. A clone yielding correct digested band sizes from each digest was designated pMIBa142.

Plasmid pMIBa142 was digested with AscI followed by a fill-in reaction with Klenow and subsequent digestion with NheI and CIP treatment. The digestion was purified by 1% agarose gel electrophoresis in TBE buffer as described herein. A band at approximately 7.5 kbp was excised from the gel and purified using QIAQUICK® Gel Extraction Kit (Qiagen) according to the manufacturer's instructions.

The nucleotide sequence SEQ ID NO: 142 encoding the *S. kluyveri* BAAT of SEQ ID NO: 21, was excised from pMIBa124 (supra) by digestion with PacI followed by a fill-in reaction with Klenow and subsequent digestion with XbaI. The digestion was purified by 1% agarose gel electrophoresis in TBE buffer as described herein. A band at approximately 1.4 kbp was excised from the gel and purified using QIAQUICK® Gel Extraction Kit (Qiagen) according to the manufacturer's instructions.

The 1.4 kbp purified fragment from pMIBa124 was ligated into the 7.5 kbp fragment from pMIBa142 using T4 ligase (New England Biolabs) in a total reaction volume of 10 µL composed of 1 µL of the digested pMIBa142, 7 µL of the 1.4 fragment from pMIBa124, 1 µL 10× ligation buffer with 10 mM ATP (New England Biolabs), and 1 µL T4 ligase (New England Biolabs). The reaction was incubated for 2.5 hours at 16° C. and the entire ligation was transformed into Sure cells (Agilent) according to manufacturer's instructions. Transformants were plated on 2×YT+amp plates and incubated overnight at 37° C. Several of the resulting transformants were screened for proper insertion by restriction digest with StuI and PmeI. A clone yielding correct digested band size was designated pMIBa144.

Integration of a Left-Hand and Tight-Hand Fragments into MIBa357

Plasmid pANN5 was digested with NotI and NheI and plasmid pMIBa144 was digested with NotI as described herein. These were purified by 1% agarose gel electrophoresis in TBE buffer, and the 8.2 kbp fragment from pANN5 and the 6 kbp fragment from pMIBa144 were excised from the gel and purified using a NUCLEOSPIN® Extract II Kit (Macherey-Nagel) according to manufacturer's instructions.

MIBa357 was transformed with the digested pANN5 and pMIBa144 DNA and correct loci targeting and transformation was verified by PCR using the Phire® Plant Direct PCR kit (Finnzymes) according to the manufacturer's instructions. Primers 0611552 and 0613695 yielded an approximately 4.1 kbp band (to confirm the left half integration at the pdc locus); primers 0612358 and 0611554 yielded an approximately 2.5 kbp band (to confirm the right half integration at the pdc locus); 0611245 and 0611631 yielded an approximately 3.5 kbp band (to confirm the left half 4×ADC integration remained at the adh1202 locus); and primers 0611815 and 0611632 yielded an approximately 4.6 kbp band (to confirm the right half 4×ADC integration remained at the adh1202 locus). One isolate which gave the expected bands for proper integrating of the expression cassette at the pdc locus and retained the expression cassette at the adh1202 locus was saved and designated MIBa360.

Removal of Ura Marker from MIBa360

A ura– derivative of MIBa360 was isolated as described above. Genomic DNAs from several FOA resistant colonies of MIBa360 were screened by PCR for the desired loop-out event with primers 0611815 and 0613689. The presence of an approximately 1.9 kbp band indicates the removal of the ura marker with the ura3 scar site (a single URA3 promoter left behind after homologous recombination between the two URA3 promoters in the parent strain) as desired, while a band of approximately 3.3 kbp indicates the presence of the intact URA3 promoter-URA3 ORF-URA3 terminator-URA3 promoter cassette, indicating the desired recombination event did not occur. PCR was performed using the Phire® Plant Direct PCR kit (Finnzymes) according to the manufacturer's instructions. Two FOA resistant colonies that yielded the approximately 1.9 kbp fragment with the above primers were saved and designated MIBa363 and MIBa364.

Construction of a Reverse Expression Cassette Right-Hand Fragment

Plasmid pMIBa144 contains the desired ADC and 3-HPDH expression cassettes going in the forward orientation. To ease screening of homozygous strains, a new plasmid was constructed where the ADC expression cassette of pMIBa144 was placed in the reverse orientation. The plasmid pMIBa144 (supra) was digested with StuI and PmeI purified by 1% agarose gel electrophoresis in TBE buffer as described herein. Bands at approximately 6.1 kbp and 2.8 kbp were excised from the gel and purified using QIAQUICK® Gel Extraction Kit (Qiagen) according to the manufacturer's instructions. The 6.1 kbp fragment from pMIBa144 was treated with CIP and purified using the QIAQUICK® PCR Purification Kit (Qiagen) according to the manufacturer's instructions.

The 2.8 kbp purified fragment from pMIBa144 was ligated into the 6.1 kbp pMIBa144 linearized vector using T4 ligase (New England Biolabs) in a total reaction volume of 10 µL composed of 1 µL of the 6.1 kbp fragment from pMIBa144, 7 µL of the 2.8 kbp fragment from pMIBa144, 1 µL 10× ligation buffer with 10 mM ATP (New England Biolabs), and 1 µL T4 ligase (New England Biolabs). The reaction was incubated for 4 hours at 16° C. and a 4 µL aliquot of the reaction was transformed into ONE SHOT® TOP10 chemically competent *E. coli* cells (Invitrogen) according to manufacturer's instructions. Transformants were plated on 2×YT+amp plates and incubated at 37° C. overnight. Several of the resulting transformants were screened for proper insertion by restriction digest using SphI and XbaI. A clone yielding correct digested band size was designated pMIBa146.

Integration of a Left-Hand and Right-Hand Fragments into MIBa363

Plasmid pANN5 was digested with NotI and NheI and plasmid pMIBa146 was digested with NotI as described herein. These were purified by 1% agarose gel electrophoresis in TBE buffer, and the 8.2 kbp fragment from pANN5 and the 6.2 kbp fragment from pMIBa146 were excised from the gel and purified the QIAQUICK® PCR Purification Kit (Qiagen) according to the manufacturer's instructions.

MIBa363 was transformed with the digested pANN5 and pMIBa144 DNA and correct loci targeting and transformation was verified by PCR using the Phire® Plant Direct PCR kit (Finnzymes) or Kapa Robust DNA polymerase according to the manufacturer's instructions. To confirm integrations at pdc locus, the following primer pairs were used. Primers 0613689 and 0611815 yielded an approximately 1.9 kbp band; primers 0612366 and 0611554 yielded an approximately 2.5 kbp band; 0613688 and 0611815 yielded an approximately 3.2 kbp band; 0611622 and 0611552 yielded an approximately 945 bp band. To check the integrations at adh1202 the following primer pairs were used. Primers 0611245 and 0612794 yielded an approximately 2.8 kbp band and primers 0611815 and 0612795 yielded an approximately 3.9 kbp band. Two isolates which gave the expected bands for proper integrating of the expression cassette at the pdc locus and retained the expression cassette at the adh1202 locus were saved and designated MIBa372 and MIBa373.

Removal of Ura Marker from MIBa372

A ura- derivative of MIBa372 was isolated as described above. Genomic DNAs from several FOA resistant colonies of MIBa372 were screened by PCR for the desired loop-out event with primers 0611815 and 0613688. The presence of an approximately 2.1 kbp band indicates the removal of the ura marker with the ura3 scar site (a single URA3 promoter left behind after homologous recombination between the two URA3 promoters in the parent strain) as desired, while a band of approximately 3.3 kbp indicates the presence of the intact URA3 promoter-URA3 ORF-URA3 terminator-URA3 promoter cassette, indicating the desired recombination event did not occur. FOA resistant colonies of MIBA372 were also screened by PCR with primers 0611815 and 0613689 (amplifies 1.9 kbp fragment) to confirm modification of the first chromosome and 0611552 and 0611553 (amplifies 850 bp fragment if the pdc locus is present) to confirm loss of the pdc locus. PCR was performed using the Phire® Plant Direct PCR kit (Finnzymes) according to the manufacturer's instructions. An FOA resistant colony that yielded the approximately 1.9 kbp fragment with 0611815 and 0613689, but did not amplify fragments with 0613688 and 0611815, or with 0611552 and 0611553 was saved and designated MIBa375. The genotype of MIBa375 is shown in Table 28.

TABLE 28

Transformant genotype

| Strain | Genotype |
|---|---|
| MIBa375 | adh1202Δ::(PDC$_{promo}$-Opt.BlpanD PDC$_{promo}$-Opt.BlpanD Ura3-Scar TDH3$_{promo}$ Opt.BlpanD TDH3$_{promo}$ Opt.BlpanD)/adh1202Δ::(PDC$_{promo}$-Opt.BlpanD PDC$_{promo}$-Opt.BlpanD Ura3-Scar [TDH3$_{promo}$ Opt.BlpanD TDH3$_{promo}$ Opt.BlpanD]reverse) pdcΔ::(PDC$_{promo}$-CNB1pyc ENO1$_{promo}$-CNB1aat Ura3-Scar TDH3$_{promo}$-OptSkPYD4 PGK1$_{promo}$-OptScYMR226c/pdcΔ::(PDC$_{promo}$-CNB1pyc ENO1$_{promo}$-CNB1aat Ura3-Scar TDH3$_{promo}$-OptSkPYD4 PGK1$_{promo}$-OptScYMR226c ura3-/ura3- |

Example 3A-23: Yeast Strains Deleted for the Glycerol 3-Phosphate Dehydrogenase (GPD) Gene Deletion of the GPD Gene in Strain MIBa375

Additional constructs were designed to delete both copies of glycerol 3-phosphate dehydrogenase gene (SEQ ID NO: 117, which encodes GPD of SEQ ID NO: 118) from the host *I. orientalis* genome. These constructs contained approximately 1003 bp of nucleotide sequence homologous to the sequence upstream of the GPD gene and approximately 852 bp of sequence homologous to the sequence downstream of the GPD gene, with a T$_{PDC}$-URA3 marker cassette (PDC terminator-URA3 promoter-URA3 gene-URA3 terminator-URA3 promoter) cloned in between.

The regions upstream and downstream of GPD were amplified from *I. orientalis* CNB1 genomic DNA using Pfu DNA polymerase as per manufacturer's specifications. The upstream region contained an ApaI site; this was eliminated by PCR using overlapping primers designed with a mismatch to one of the nucleotides in the ApaI recognition sequence. Primer pairs oACN48/oACN51 and oACN49/oACN50 were used to amplify these two overlapping fragments for the upstream region. These PCR products were separated on and excised from a 1% agarose gel and purified using a Qiaquick Gel Extraction Kit (Qiagen) according to the manufacturer's instructions, and were used as template for a second round of PCR with primers oACN48/oACN49 (having forward ApaI/reverse NotI sites). The downstream region was amplified with primers oACN52/oACN53 (having forward NotI/reverse SacI sites) from *I. orientalis* genomic DNA using Pfu DNA polymerase as per manufacturer's specifications. Both PCR products were gel purified and cloned separately into the vector pCRO-BluntII-TOPO® (Invitrogen). Isolates were confirmed to have the desired insert by restriction digest of plasmid DNA, and were verified by sequencing. Vector pACN58 contained the cloned upstream fragment and pACN59 contained the downstream fragment. Plasmid pACN58 was digested with ApaI/NotI to release the upstream flank, plasmid pACN59 was digested with SacI/NotI to release the downstream flank, and pACN59 was digested with ApaI/Sac/to provide the vector backbone. The three desired fragments were separated on a 1% agarose gel, excised and purified, and ligated in a 3-piece ligation reaction using T4 ligase (New England Biolabs). The ligation reaction was transformed into *E. coli* TOP10 electrocompetent cells and transformants were confirmed by restriction digest of plasmid DNA. During this procedure, an additional SacI site in the downstream region was detected, which resulted in a downstream region of 853 bp (as opposed to 1 kbp). Two isolates with the desired inserts were named pACN62 and pACN63.

Figure 32:
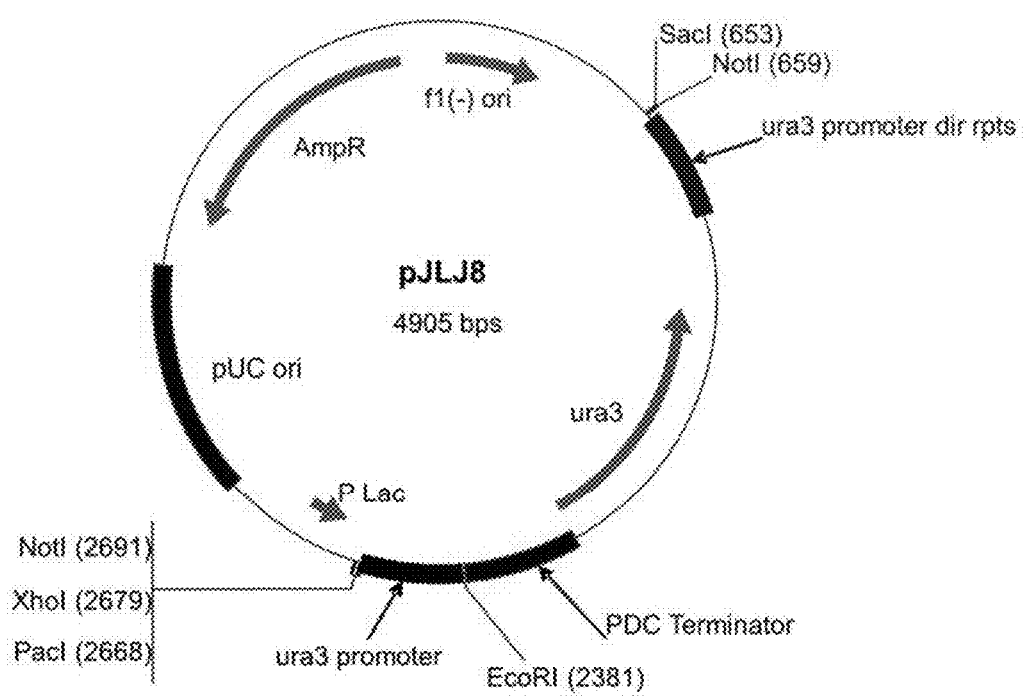
FIG. 32: Plasmid pJLJ8.

The $T_{PDC_1}$-URA3 cassette was isolated from vector pJLJ8 (FIG. 32) using a NotI digest and gel purification. This fragment was then ligated into pACN62 (supra) that had been digested with NotI and dephosphorylated, and the ligation was transformed into *E. coli* DH10B electrocompetent cells (Invitrogen). Colonies with the URA3 insert were confirmed by PCR using primers oACN48/oJLJ44 and oACN48/oJLJ46. Primer oJLJ44 anneals at the end of the downstream URA3 promoter and amplifies outward from the $T_{PDC_1}$-URA3 cassette. Primer oJLJ46 anneals at the 5' end of the PDC terminator and amplifies outward from the $T_{PDC_1}$-URA3 cassette. Vector pHJJ56 contains the URA3 facing the downstream GPD region and pHJJ57 contains the URA3 facing the upstream GPD region.

Plasmids pHJJ56 and pHJJ57 were linearized by digestion with KpnI and ApaI and the fragments containing the deletion cassette were purified by gel extraction. Linearized pHJJ56 was transformed into the ura– strain MIBa375. Single colonies were restreaked for purification and tested by PCR for the desired GPD deletion using primers oJLJ44, oJLJ46, oACN54 and oACN55. Cells were lysed in 40 uL Y-Lysis buffer and 2 uL Zymolyase (ZymoResearch) at 37° C. for 30 minutes and 1 uL of the lysis reaction used in a 25 uL PCR reaction. PCR reactions used Failsafe DNA polymerase and Buffer E according to manufacturer's specifications, with an annealing temperature of 55° C. and the following cycling profile: 1 cycle at 94° C. for 2 minutes; 29 cycles each at 94° C. for 30 seconds, 55° C. for 30 seconds, and 72° C. for 1.5 minutes; and 1 cycle at 72° C. for 3 minutes. Strains with one copy of the GPD knockout produced bands of approximately 0.9 and 1.2 kbp and were named yHJN1 and yHJN2.

Strains yHJN1 and yHJN2 were grown overnight in YPD media and plated onto ScD-2×FOA media to select to loss of the URA3 marker. Single colonies were purified on YPD and patched to ScD-ura and YPD media to confirm the ura– phenotype. Ura– colonies were confirmed to have retained the knockout using the same PCR reaction used to confirm the first integration. A ura– derivative of yHJN1 was named yHJN3 and a ura– derivative of yHJN2 was named yHJN4.

Linearized pHJJ57 was transformed into yHJN3 and yHJN4 and single colonies were purified on ScD-ura media. The presence of two copies of the GPD knockout was confirmed by PCR using primers oJLJ44, oACN54, and oACN55 in one reaction, and primers oJLJ46, oACN54, and oACN55 in a second reaction. Primer oACN54 anneals to a region approximately 37 bp upstream of the upstream flanking sequence for GPD, while oACN55 anneals to a region approximately 24 bp downstream of the downstream flank. The former reaction produces bands of approximately 900 and 1050 bp if both copies of the GPD are deleted, and the latter reaction produces bands of approximately 1025 and 1200 bp. Colonies with two copies of the GPD knockout grew more slowly on ScD-ura plates than those with a single copy of the deletion. Strains having both copies of the GPD gene deleted were named yHJN7 (derived from yHJN3) and yHJN8 (derived from yHJN4).

Strains MIBa372, yHJN7 and yHJN8 were tested in bioreactors for glycerol production, using the methods described herein. Strain MIBa372 produced 29.5 g/L glycerol in 48 hours. No detectable glycerol was produced by strains yHJN7 or yHJN8 during the fermentation. The absence of glycerol in the final fermentation broth may provide advantages in the recovery and purification of 3-HP from the fermentation broth.

3A-24: Yeast Strains Expressing Aspartate 1-Decarboxylase (ADC) from Four Nucleotide Sequences at the Adh1202 Locus, 3-HP Dehydrogenase (3-HPDH) at the Adh9091 Locus and Deletion of Native 3-HP Dehydrogenase (3-HPDH)

Plasmid Construction for Integration of *I. orientalis* 3-HPDH at the Adh9091 Locus The nucleotide sequences of SEQ ID NO: 25 encoding the *I. orientalis* 3-HPDH of SEQ ID NO: 26 and SEQ ID NO: 19 encoding the *I. orientalis* BAAT (PYD4) of SEQ ID NO: 20 were amplified from MBin500 *I. orientalis* genomic DNA prepared as described previously using primers 0611954 and 0611957 (for 3-HPDH) or 0611997 and 0611998 (PYD4). Primer 0611954 adds a kozak sequence (TAAA) and NheI site to the 5' end, and primer 0611957 adds a PacI site to the 3' end of 3-HPDH during amplification. Primer 0611997 adds a kozak sequence (TAAA) and PacI site to the 5' end, and primer 0611998 adds a PacI site to the 3' end of PYD4 during amplification. Fifty pmoles of each primer was used in a PCR reaction containing 50 ng of MBin500 genomic DNA as template, 0.2 mM each dATP, dGTP, dCTP, dTTP, 1× Expand High Fidelity Buffer (Roche), and 2.6 units of Expand High Fidelity DNA Polymerase (Roche) in a final volume of 50 μL. The PCR was performed in an EPPENDORF® MASTERCYCLER® (Eppendorf Scientific) programmed for one cycle at 95° C. for 3 minutes followed by 30 cycles each at 95° C. for 1 minute, 55° C. for 1 minute, and 72° C. for 1 minute (3-HPDH PCR) or 2 minutes (PYD4 PCR), with a final extension at 72° C. for 5 minutes. Following thermocycling, the PCR reaction products were separated by 1.0% agarose gel electrophoresis in TAE buffer where an approximately 831 bp 3-HPDH or 1.4 kbp PYD4 PCR product was excised from the gel and purified using a using a QIAQUICK® Gel Extraction Kit (Qiagen) according to the manufacturer's instructions. Five µl of the purified 3-HPDH or PYD4 was cloned into pCR2.1 (Invitrogen) using a TOPO-TA Cloning Kit (Invitrogen) according to the manufacturer's instructions. The transformations were plated onto 2×YT+amp plates and incubated at 37° C. overnight. Several of the resulting transformants were screened by digestion with EcoRI. Clones yielding the desired insert size were confirmed to be correct by DNA sequencing. One clone containing 3-HPDH was designated pMBin190, and another containing PYD4 was designated pMBin193.

Plasmid pMBin193 was digested with XbaI and PacI and run on a 1.0% agarose gel in TAE buffer where the 1.4 kbp PYD4 band was excised from the gel and purified using a QIAQUICK® Gel Extraction Kit (Qiagen) according to the manufacturer's instructions. The digested PYD4 fragment was ligated into the XbaI and PacI restricted linear pMIBa107 plasmid (supra) using T4 DNA ligase. The ligation product was transformed into One Shot® TOP10 Chemically Competent E. coli cells (Invitrogen) according to manufacturer's instructions. Transformants were plated onto 2×YT+amp plates and incubated at 37° C. overnight. Several of the resulting transformants were screened by digestion with SnaBI or EcoRI. One clone yielding the desired band sizes was designated pMBin203. Plasmid pMBin203 contains NotI sites that flank the following expression cassette: PDC promoter and terminator up and downstream of the PYD4 CDS, the URA3 promoter, the URA3 ORF, and the URA3 terminator followed by the URA3 promoter.

Plasmid pMBin203 was digested with NotI and separated on a 1.0% agarose gel in TAE buffer where the approximately 4.1 kbp fragment (containing the PDC promoter, PYD4 CDS, the PDC terminator, and the URA3 selection marker) was excised from the gel and purified using a QIAQUICK® Gel Extraction Kit (Qiagen) according to the manufacturer's instructions. Plasmid pHJJ27 (containing 5' and 3' homology regions to the adh9091 locus; see FIG. 21) was digested with NotI, treated with CIP and separated on a 1.0% agarose gel in TAE buffer where the approximately 5.7 kbp linear plasmid was purified as described above. The fragment from pMBin203 was then ligated into the NotI restricted pHJJ27 using T4 DNA ligase as described above. The ligation product was transformed into One Shot® TOP10 Chemically Competent E. coli cells (Invitrogen) according to manufacturer's instructions. Transformants were plated onto 2×YT+amp plates and incubated at 37° C. overnight. Several of the resulting transformants were screened by digestion with PstI. One done yielding the desired band sizes was designated pMBin204. Plasmid pMBin204 allows targeting of PYD4 to the adh9091 locus.

The nucleotide sequence of SEQ ID NO: 25 encoding the I. orientalis 3-HPDH of SEQ ID NO: 26 was removed from plasmid pMBin190 (supra) by digestion with NheI and PacI and purified by agarose gel electrophoresis in TBE buffer as described herein. A band of approximately 827 bp was excised from the gel and purified using a NUCLEOSPIN® Extract II Kit (Macherey-Nagel) according to the manufacturer's instructions. The plasmid pMBin204 (supra) was digested with XbaI and PacI and purified by agarose gel electrophoresis in TBE buffer as described herein. A band of approximately 8.4 kbp was excised from the gel and purified using a NUCLEOSPIN® Extract II Kit (Macherey-Nagel) according to the manufacturer's instructions.

The purified approximately 827 bp I. orientalis 3-HPDH gene product above was ligated into the 8.4 kbp pMBin204 linearized vector using T4 ligase (New England Biolabs) in a total reaction volume of 20 µL composed of 1 µL of the 8.4 kbp vector, 10 µL of the 827 bp insert, 2 µL 10× ligation buffer with 10 mM ATP (New England Biolabs), and 1 µL T4 ligase (New England Biolabs). The reaction was incubated for 18 hours at 16° C. and a 10 µL aliquot of the reaction was transformed into One Shot TOP10 cells (Invitrogen) according to manufacturer's instructions. After a recovery period, two 100 µL aliquots from the transformation reaction were plated onto 150 mm 2×YT plates supplemented with 100 µg of ampicillin per ml. The plates were incubated overnight at 37° C. Putative recombinant clones were selected from the selection plates and plasmid DNA was prepared from each one using a BIOROBOT® 9600 (Qiagen). Clones were analyzed by restriction digest and a plasmid with the correct restriction digest pattern was designated pMcTs90.

Plasmid Construction for Integration of S. cerevisiae 3-HPDH at the Adh9091 Locus The 826 bp wild-type nucleotide sequence encoding the S. cerevisiae 3-HPDH of SEQ ID NO: 129 was PCR amplified from JG169 genomic DNA and amended with an XbaI site on the 5' end of the gene and a PacI site on the 3' end of the gene. The amplification reaction was performed using Platinum® Pfx DNA polymerase (InVitrogen) according to manufacturer's instructions. A Master PCR reaction containing 1.125 µl of S. cerevisiae genomic DNA, 112.5 pM each of primers 611191 and 611199, 1× Pfx amplification buffer (InVitrogen), 2 mm MgSO$_4$, 0.2 mM dNTP mix, 5 Units Platinum® Pfx DNA polymerase (InVitrogen) in a final volume of 200 µL. The mix was aliquoted into eight tubes and gradient PCR performed. The amplification reactions were incubated in an EPPENDORF® MASTERCYCLER® (Eppendorf Scientific Inc.) programmed for 1 cycle at 95° C. for 2 minutes; 30 cycles each at 95° C. for 30 seconds, Gradient 40-55° C. for 30 seconds, and 72° C. for 2 minutes; and 1 cycle at 72° C. for 3 minutes.

The 826 bp wild-type YMR226c PCR gene product was purified by 1% agarose gel electrophoresis in TBE buffer as described herein. A fragment of approximately 826 bp was excised from the gel and extracted from the agarose using a QIAQUICK® Gel Extraction Kit (Qiagen). The PCR product was digested overnight at 37° C. with XbaI and PacI then purified using the QIAQUICK® PCR purification Kit (Qiagen).

The plasmid pMIBa100 (supra) was digested with XbaI and PacI followed by treatment with CIP resulting in an approximately 6.8 kbp linear fragment. The digestion was purified using the QIAQUICK® PCR purification Kit (Qiagen) according to the manufacturer's instructions.

The 826 bp YMR226c purified and digested PCR fragment was ligated into the 6.8 kbp pMIBa100 linearized vector using T4 ligase (New England Biolabs) in a total reaction volume of 10 µL composed of 1 µL of the 6.7 kbp fragment from pMIBa100, 1 µL or 7 µL of the 826 bp YMR226c PCR product, 1 µL 10× ligation buffer with 10 mM ATP (New England Biolabs), and 1 µL T4 ligase (New England Biolabs). The reaction was incubated for approximately 4 hours at 16° C. and the entire reaction was transformed into Sure chemically competent cells (Aglient) according to manufacturer's instructions. Transformants were plated on 2×YT+amp plates and incubated at 37° C. overnight. Several of the resulting transformants were screened for proper insertion by restriction digest using XbaI and PacI. Correct clones by digest were confirmed by DNA sequencing. A clone yielding correct digested band size and DNA sequence was designated pMIBa101.

Plasmid pHJJ76-no ura (supra) was digested with NotI followed by treatment with CIP. The linear 5.2 kbp fragment was purified using a QIAQUICK® PCR Purification Kit (Qiagen).

The YMR226c expression cassette was excised from pMIBa101 by digestion with NotI. A band at approximately 3546 bp was excised from the gel and purified using QIAQUICK® Gel Extraction Kit (Qiagen) according to the manufacturer's instructions.

The 3546 bp purified fragment from pMIBa101 was ligated into the 5.2 kbp pHJJ76-no ura linearized vector using T4 ligase (New England Biolabs) in a total reaction volume of 10 µL composed of 1 µL of the 5.2 kbp fragment from pHJJ76-no ura, 1 µL or 5 µL of the 3546 bp fragment from pMIBa101, 1 µL 10× ligation buffer with 10 mM ATP (New England Biolabs), and 1 µL T4 ligase (New England Biolabs). The reaction was incubated overnight at 16° C. and a 4 µL aliquot of the reaction was transformed into ONE SHOT® TOP10 chemically competent E. coli cells (Invitrogen) according to manufacturer's instructions. Transformants were plated on 2×YT+amp plates and incubated at 37° C. overnight. Several of the resulting transformants were screened for proper insertion by restriction digest using XbaI and KpnI. A clone yielding correct digested band size was designated pMIBa109.

The wild-type nucleotide sequence encoding the S. cerevisiae 3-HPDH of SEQ ID NO: 129 was removed from plasmid pMIBa109 by digestion with XbaI and PacI and purified by agarose gel electrophoresis in TBE buffer as described herein. A band of approximately 818 bp was excised from the gel and purified using a NUCLEOSPIN® Extract II Kit (Macherey-Nagel) according to the manufacturer's instructions.

The purified approximately 818 bp S. cerevisiae 3-HPDH gene product was ligated into the 8.4 kbp pMBin204 linearized vector above using T4 ligase (New England Biolabs) in a total reaction volume of 20 µL composed of 1 µL of the 8.4 kbp vector, 10 µL of the 818 bp insert, 2 µL 10× ligation buffer with 10 mM ATP (New England Biolabs), and 1 µL T4 ligase (New England Biolabs). The reaction was incubated for 18 hours at 16° C. and a 10 µL aliquot of the reaction was transformed into One Shot TOP10 cells (Invitrogen) according to manufacturer's instructions. After a recovery period, two 100 µL aliquots from the transformation reaction were plated onto 150 mm 2×YT plates supplemented with 100 µg of ampicillin per mL. The plates were incubated overnight at 37° C. Putative recombinant clones were selected from the selection plates and plasmid DNA was prepared from each one using a BIOROBOT® 9600 (Qiagen). Clones were analyzed by restriction digest and a plasmid with the correct restriction digest pattern was designated pMcTs91.

Plasmid Construction for Integration of M. sedula 3-HPDH at the Adh9091 Locus

An I. orientalis codon-optimized nucleotide sequence of SEQ ID NO: 343 encoding the M. sedula 3-HPDH of SEQ ID NO: 29 was synthesized by GeneArt® resulting in the plasmid 11AAE2AP. The synthetic gene was digested from the plasmid with XbaI and PacI and purified by agarose gel electrophoresis in TBE buffer as described herein. A band of approximately 959 bp was excised from the gel and purified using a NUCLEOSPIN® Extract II Kit (Macherey-Nagel) according to the manufacturer's instructions.

The purified approximately 959 bp M. sedula 3-HPDH gene product was ligated into the 8.4 kbp pMBin204 linearized vector above using T4 ligase (New England Biolabs) in a total reaction volume of 20 µL composed of 1 µl of the 8.4 kbp vector, 16 µl of the 959 bp insert, 2 µL 10× ligation buffer with 10 mM ATP (New England Biolabs), and 1 µL T4 ligase (New England Biolabs). The reaction was incubated for 1 hour at room temperature and a 10 µL aliquot of the reaction was transformed into Solo Pack Gold Super Competent cells (Agilent) according to manufacturer's instructions. After a recovery period, two 100 µl aliquots from the transformation reaction were plated onto 150 mm 2×YT plates supplemented with 100 µg of ampicillin per ml. The plates were incubated overnight at 37° C. Putative recombinant clones were selected from the selection plates and plasmid DNA was prepared from each one using a BIOROBOT® 9600 (Qiagen). Clones were analyzed by restriction digest and a plasmid with the correct restriction digest pattern was designated pMcTs76.

Plasmid Construction for Integration of E. coli 3-HPDH at Adh9091 Locus

An I. orientalis codon-optimized nucleotide sequence of SEQ ID NO: 143 encoding the E. coli 3-HPDH of SEQ ID NO: 27 was synthesized by GeneArt® resulting in the plasmid 1045168. The synthetic gene was digested from the plasmid with XbaI and PacI and purified by agarose gel electrophoresis in TBE buffer as described herein. A band of approximately 761 bp was excised from the gel and purified using a NUCLEOSPIN® Extract II Kit (Macherey-Nagel) according to the manufacturer's instructions.

The purified approximately 761 bp E. coli 3-HPDH gene product was ligated into the 8.4 kbp pMBin204 linearized vector above using T4 ligase (New England Biolabs) in a total reaction volume of 20 µL composed of 1 µL of the 8.4 kbp vector, 16 µL of the 761 bp insert, 2 µL 10× ligation buffer with 10 mM ATP (New England Biolabs), and 1 µL T4 ligase (New England Biolabs). The reaction was incubated for 1 hr at room temperature and a 10 µL aliquot of the reaction was transformed into Solo Pack Gold Super Competent cells (Agilent) according to manufacturer's instructions. After a recovery period, two 100 µL aliquots from the transformation reaction were plated onto 150 mm 2×YT plates supplemented with 100 µg of ampicillin per ml. The plates were incubated overnight at 37° C. Putative recombinant clones were selected from the selection plates and plasmid DNA was prepared from each one using a BIOROBOT® 9600 (Qiagen). Clones were analyzed by restriction digest and a plasmid with the correct restriction digest pattern was designated pMcTs77.

Integration of 3-HPDH Fragments at Adh9091 in McTs259

Plasmids pMcTs76, pMcTs77, pMcTs91 were digested with KpnI and ApaI, and plasmid pMcTs90 was digested with SacI and ApaI as described herein. The resulting digestion products were purified by 1% agarose gel electrophoresis in TBE buffer, and the 5.5 kbp fragment from pMcTs76, the 5.3 kbp fragment from pMcTs77, the 5.4 kbp fragment from pMcTs90, and 5.4 kbp fragment from pMcTs91 were excised from the gel and purified using a NUCLEOSPIN® Extract II Kit (Macherey-Nagel) the according to the manufacturer's instructions.

Strain McTs259 which expressing four copies of nucleotides encoding the B. licheniformis ADC of SEQ ID NO: 139 at the adh1202 locus and deletion of the native I. orientalis gene encoding the 3-HPDH of SEQ ID NO: 26 (supra), was transformed with the digested pMcTs76, pMcTs77, pMcTs90, or pMcTs91 DNA. The correct loci targeting and transformation was verified by PCR using the Phire® Plant Direct PCR kit (Finnzymes) according to the manufacturer's instructions. To confirm integrations at adh9091 locus, the following primer pairs were used. Primers 0614627 and 0612909 yielded an approximately 3.47 kbp band for fragment from pMcTs76 integrated, approximately 3.27 kbp band for fragment from pMcTs77 integrated, approximately 3.34 kbp band for fragment from pMcTs90 integrated, approximately 3.33 kbp band for fragment from pMcTs91 integrated; primers 0612908 and 0614626 yielded an approximately 1.97 kbp band. To check the integrations at adh1202 the following primer pairs were used. Primers 0611245 and 0612794 yielded an approximately 3.0 kbp band and primers 0611815 and 0612795 yielded an approximately 3.6 kbp band. To check the deletion of the native *I. orientalis* 3-HPDH gene the following primers were used. Primers 0613034 and 0613241 yielded an approximately 1.4 kbp band. Isolates which gave the expected bands for proper integrating of the expression cassette at the adh9091 locus, retained the expression cassette at the adh1202 and retained the deletion *I. orientalis* 3-HPDH locus were saved and designated McTs261 (pMcTs76 fragment), McTs263 (pMcTs77 fragment), McTs267 (pMcTs90 fragment), and McTs269 (pMcTs91 fragment) as shown in Table 29.

TABLE 29

Transformant constructs

| Construction Plasmid | Gene | Gene Source | Gene Product SEQ ID NO | Integration construct | Transformant |
|---|---|---|---|---|---|
| pMBin190 | 3-HPDH (YMR226C) | *I. orientalis* | 26 | pMcTs90 | McTs267 |
| 11AAE2AP | 3-HPDH (Msed_1993) | *M. sedula* | 29 | pMcTs76 | McTs261 |
| pMIBa109 | 3-HPDH (YMR226C) | *S. cerevisiae* | 129 | pMcTs91 | McTs269 |
| 1045168 | 3-HPDH (ydfG) | *E. coli* | 27 | pMcTs77 | McTs263 |

The transformant strains were tested for 3-HP production using the shake flask method described above. The heterozygous transformants McTs267, McTs269, and McTs263 produced 0.149 (+/−0.024), 0.168 (+/−0.052), and 0.162 (+/−0.018) g/L 3-HP per g/L dry cell weight, respectively. Native strain MeJi412 produced 0.263 (+/−0.026) g/L 3-HP per g/L dry cell weight, and the 3-HPDH deletion strain produced no detectable 3-HP. The heterozygous transformant McTs261 did not produce detectable 3-HP with this experiment. These results suggest that even heterozygous 3-HPDH transformants can restore some 3-HPDH activity of 3-HPDH deletion strain using either exogenous or endogenous 3-HPDH gene sequences.

Example 3B: Modified Yeast Strains Expressing Malate Pathway Genes

Yeast cells that produce 3-HP via a pathway that utilizes PEP, OAA, and malate intermediates can be engineered by expressing one or more enzymes involved in the pathway. The expressed genes may include one or more of a PPC, malate dehydrogenase, and malate decarboxylase gene. The expressed genes may be derived from a gene that is native to the host cell, or they may be derived from a source gene that is non-native to the host cell.

Example 3C: Modified Yeast Strains Expressing Malonate Semialdehyde Pathway Genes Yeast cells that produce 3-HP via a pathway that utilizes PEP, OAA and malonate semialdehyde intermediates can be engineered by expressing one or more enzymes involved in the pathway. The expressed genes may include one or more of a PPC, 2-keto acid decarboxylase, KGD, BCKA, indolepyruvate decarboxylase, 3-HPDH (including malonate semialdehyde reductase), HIBADH, and 4-hydroxybutyrate dehydrogenase gene. The expressed genes may be derived from a gene that is native to the host cell, or they may be derived from a source gene that is non-native to the host cell.

Example 3D: Modified Yeast Strains Expressing Malonyl-CoA Pathway Genes

Yeast cells that produce 3-HP via a pathway that utilizes PEP, OAA, malonyl-CoA, and, optionally, malonate semialdehyde intermediates can be engineered by expressing one or more enzymes involved in the pathway. The expressed genes may include one or more of a PPC, OAA formate-lyase, malonyl-CoA reductase, CoA acylating malonate semialdehyde dehydrogenase, 3-HPDH (including malonate semialdehyde reductase), HIBADH, and 4-hydroxybutyrate dehydrogenase gene. The expressed genes may be derived from a gene that is native to the host cell, or they may be derived from a source gene that is non-native to the host cell.

Example 3E: Modified Yeast Strains Expressing Malonyl-CoA Pathway Genes

Yeast cells that produce 3-HP via a pathway that utilizes pyruvate, acetyl-CoA, malonyl-CoA, and, optionally, malonate semialdehyde intermediates can be engineered by expressing one or more enzymes involved in the pathway. The expressed genes may include one or more of a PDH, acetyl-CoA carboxylase, malonyl-CoA reductase, CoA acylating malonate semialdehyde dehydrogenase, 3-HPDH (including malonate semialdehyde reductase), HIBADH, and 4-hydroxybutyrate dehydrogenase gene. The expressed genes may be derived from a gene that is native to the host cell, or they may be derived from a source gene that is non-native to the host cell.

Example 3F: Modified Yeast Strains Expressing Alanine Pathway Genes

Yeast cells that produce 3-HP via a pathway that utilizes pyruvate, alanine, β-alanine, and, optionally, malonate semialdehyde, β-alanyl-CoA, acrylyl-CoA, and 3-HP-CoA intermediates can be engineered by expressing one or more enzymes involved in the pathway. The expressed genes may include one or more of an alanine dehydrogenase, pyruvate/alanine aminotransferase, alanine 2,3 aminomutase, CoA transferase, CoA synthetase, β-alanyl-CoA ammonia lyase, 3-HP-CoA dehydratase, 3-HP-CoA hydrolase, 3-hydroxy-isobutyryl-CoA hydrolase, BAAT, 3-HPDH (including malonate semialdehyde reductase), HIBADH, and 4-hydroxybutyrate dehydrogenase gene. The expressed genes may be derived from a gene that is native to the host cell, or they may be derived from a source gene that is non-native to the host cell.

Example 3G: Modified Yeast Strains Expressing Lactate Pathway Genes

Yeast cells that produce 3-HP via a pathway that utilizes pyruvate, lactate, lactyl-CoA, acrylyl-CoA, and 3-HP-CoA intermediates can be engineered by expressing one or more enzymes involved in this pathway. The expressed genes may include one or more of an LDH, CoA transferase, CoA synthetase, lactyl-CoA dehydratase, 3-HP-CoA dehydratase, 3-HP-CoA hydrolase, and 3-hydroxyisobutyryl-CoA hydrolase gene. The expressed genes may be derived from a gene that is native to the host cell, or they may be derived from a source gene that is non-native to the host cell.

Example 3H: Modified Yeast Strains Expressing Glycerol Pathway Genes

Yeast cells that produce 3-HP via a pathway that utilizes glycerol and 3-HPA intermediates can be engineered by expressing one or more enzymes involved in this pathway. The expressed genes may include one or more of a glycerol dehydratase and aldehyde dehydrogenase gene. The expressed genes may be derived from a gene that is native to the host cell, or they may be derived from a source gene that is non-native to the host cell.

Example 3I: Modified Yeast Strains Expressing β-Alanyl CoA Pathway Genes

Yeast cells that produce 3-HP via a pathway that utilizes PEP or pyruvate, β-alanine, β-alanyl-CoA, acrylyl-CoA, 3-HP-CoA, and, optionally OAA, aspartate, and alanine intermediates can be engineered by expressing one or more enzymes involved in this pathway. The expressed genes may include one or more of a PPC, PYC, AAT, ADC, CoA transferase, CoA synthetase, β-alanyl-CoA ammonia lyase, 3-HP-CoA dehydratase, 3-HP-CoA hydrolase, 3-hydroxy-isobutyrl-CoA hydrolase, alanine dehydrogenase, pyruvate/alanine aminotransferase, and AAM gene. The expressed genes may be derived from a gene that is native to the host cell, or they may be derived from a source gene that is non-native to the host cell.

In some aspects, the yeast cells or methods of use thereof may be described by the following numbered paragraphs:

[B1] A genetically modified yeast cell comprising an active 3-HP fermentation pathway, wherein the cell comprises one or more exogenous 3-HP pathway genes selected from:
an exogenous PPC gene;
an exogenous PYC gene;
an exogenous AAT gene;
an exogenous ADC gene;
an exogenous BAAT or gabT gene; and
an exogenous 3-HPDH gene.

[B2] The genetically modified yeast cell of paragraph B1, comprising an exogenous AAT gene.
[B3] The genetically modified yeast cell of paragraph B1 or B2, comprising an exogenous PYC gene.
[B4] The genetically modified yeast cell of any of paragraphs B1-B3, comprising an exogenous ADC gene.
[B5] The genetically modified yeast cell of any of paragraphs B1-B4, comprising an exogenous BAAT or gabT gene.
[B6] The genetically modified yeast cell of any of paragraphs B1-B5, comprising an exogenous 3-HPDH gene.
[B7] The genetically modified yeast cell of paragraph B1, comprising:
an exogenous PYC gene;
an exogenous AAT gene;
an exogenous ADC gene;
an exogenous BAAT or gabT gene; and
an exogenous 3-HPDH gene.
[B8] The genetically modified yeast cell of any of paragraphs B1-B7, comprising an exogenous PPC gene.
[B9] The genetically modified yeast cell of any of paragraphs B1-B7, wherein the exogenous PYC gene encodes a polypeptide with at least 60%, e.g., at least 65%, 70%, 75%, 80%, 85%, 90%, 95%, 97%, 98%, 99%, or 100% sequence identity to an amino acid sequence selected from SEQ ID NOs: 2, 3, 4, 5, 6, 7, and 8.
[B10] The genetically modified yeast cell of paragraph B9, wherein the exogenous PYC gene encodes a polypeptide with at least 60%, e.g., at least 65%, 70%, 75%, 80%, 85%, 90%, 95%, 97%, 98%, 99%, or 100% sequence identity to an amino acid sequence selected from SEQ ID NOs: 2.
[B11] The genetically modified yeast cell of paragraph B9, wherein the exogenous PYC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 3.
[B12] The genetically modified yeast cell of paragraph B9, wherein the exogenous PYC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 4.
[B13] The genetically modified yeast cell of paragraph B9, wherein the exogenous PYC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 5.
[B14] The genetically modified yeast cell of paragraph B9, wherein the exogenous PYC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 6.
[B15] The genetically modified yeast cell of paragraph B9, wherein the exogenous PYC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 7.
[B16] The genetically modified yeast cell of paragraph B9, wherein the exogenous PYC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 8.
[B17] The genetically modified yeast cell of any of paragraphs B1-B16, wherein the exogenous PYC gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 1.

[B18] The genetically modified yeast cell of any of paragraphs B1-B17, wherein the AAT gene encodes a polypeptide with at least 60%, e.g., at least 65%, 70%, 75%, 80%, 85%, 90%, 95%, 97%, 98%, 99%, or 100% sequence identity to an amino acid sequence selected from SEQ ID NOs: 14, 15, and 16.

[B19] The genetically modified yeast cell of paragraph B18, wherein the AAT gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 14.

[B20] The genetically modified yeast cell of paragraph B18, wherein the AAT gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 15.

[B21] The genetically modified yeast cell of paragraph B18, wherein the AAT gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 16.

[B22] The genetically modified yeast cell of any of paragraphs B1-B21, wherein the AAT gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 13.

[B23] The genetically modified yeast cell of any of paragraphs B1-B22, wherein the ADC gene encodes a polypeptide with at least 60%, e.g., at least 65%, 70%, 75%, 80%, 85%, 90%, 95%, 97%, 98%, 99%, or 100% sequence identity to an amino acid sequence selected from SEQ ID NOs: 17, 18, 133, 135, 137, and 139.

[B24] The genetically modified yeast cell of paragraph B23, wherein the ADC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 17.

[B25] The genetically modified yeast cell of paragraph B23, wherein the ADC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 18.

[B26] The genetically modified yeast cell of paragraph B23, wherein the ADC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 133.

[B27] The genetically modified yeast cell of paragraph B23, wherein the ADC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 135.

[B28] The genetically modified yeast cell of paragraph B23, wherein the ADC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 137.

[B29] The genetically modified yeast cell of paragraph B23, wherein the ADC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 139.

[B30] The genetically modified yeast cell of any of paragraphs B1-B29, wherein the ADC gene comprises a nucleotide sequence with at least 60%, e.g., at least 65%, 70%, 75%, 80%, 85%, 90%, 95%, 97%, 98%, 99%, or 100% sequence identity to a nucleotide sequence selected from SEQ ID NOs: 130, 131, 132, 134, 136, and 138.

[B31] The genetically modified yeast cell of paragraph B30, wherein the ADC gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 130.

[B32] The genetically modified yeast cell of paragraph B30, wherein the ADC gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 131.

[B33] The genetically modified yeast cell of paragraph B30, wherein the ADC gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 132.

[B34] The genetically modified yeast cell of paragraph B30, wherein the ADC gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 134.

[B35] The genetically modified yeast cell of paragraph B30, wherein the ADC gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 136.

[B36] The genetically modified yeast cell of paragraph B30, wherein the ADC gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 138.

[B37] The genetically modified yeast cell of any of paragraphs B1-B36, wherein the exogenous BAAT or gabT gene encodes a polypeptide with at least 60%, e.g., at least 65%, 70%, 75%, 80%, 85%, 90%, 95%, 97%, 98%, 99%, or 100% sequence identity to an amino acid sequence selected from SEQ ID NOs: 20, 21, 22, 23, and 24.

[B38] The genetically modified yeast cell of paragraph B37, wherein the exogenous BAAT or gabT gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 20.

[B39] The genetically modified yeast cell of paragraph B37, wherein the exogenous BAAT or gabT gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 21.

[B40] The genetically modified yeast cell of paragraph B37, wherein the exogenous BAAT or gabT gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 22.

[B41] The genetically modified yeast cell of paragraph B37, wherein the exogenous BAAT or gabT gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 23.

[B42] The genetically modified yeast cell of paragraph B37, wherein the exogenous BAAT or gabT gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 24.

[B43] The genetically modified yeast cell any of paragraphs B1-B42, wherein the BAAT gene or gabT gene comprises a nucleotide sequence with at least 60%, e.g., at least 65%, 70%, 75%, 80%, 85%, 90%, 95%, 97%, 98%, 99%, or 100% sequence identity to a nucleotide sequence selected from SEQ ID NOs: 19, 140, 141, and 142.

[B44] The genetically modified yeast cell any of paragraph B43, wherein the BAAT gene or gabT gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 19.

[B45] The genetically modified yeast cell any of paragraph B43, wherein the BAAT gene or gabT gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 140.

[B46] The genetically modified yeast cell any of paragraph B43, wherein the BAAT gene or gabT gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 141.

[B47] The genetically modified yeast cell any of paragraph B43, wherein the BAAT gene or gabT gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 142.

[B48] The genetically modified yeast cell of any of paragraphs B1-B47, wherein said exogenous BAAT gene or exogenous gabT is a BAAT gene that is also a gabT gene.

[B49] The genetically modified yeast cell of any of paragraphs B1-B48, wherein the 3-HPDH gene encodes a polypeptide with at least 60%, e.g., at least 65%, 70%, 75%, 80%, 85%, 90%, 95%, 97%, 98%, 99%, or 100% sequence identity to an amino acid sequence selected from the group consisting of SEQ ID NOs: 26, 27, 28, 29, 30, 31, 32, 33, 34, and 129.

[B50] The genetically modified yeast cell of paragraph B49, wherein the 3-HPDH gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 26.

[B51] The genetically modified yeast cell of paragraph B49, wherein the 3-HPDH gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 27.

[B52] The genetically modified yeast cell of paragraph B49, wherein the 3-HPDH gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 28.

[B53] The genetically modified yeast cell of paragraph B49, wherein the 3-HPDH gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 29.

[B54] The genetically modified yeast cell of paragraph B49, wherein the 3-HPDH gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 30.

[B55] The genetically modified yeast cell of paragraph B49, wherein the 3-HPDH gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 31.

[B56] The genetically modified yeast cell of paragraph B49, wherein the 3-HPDH gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 32.

[B57] The genetically modified yeast cell of paragraph B49, wherein the 3-HPDH gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 33.

[B58] The genetically modified yeast cell of paragraph B49, wherein the 3-HPDH gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 34.

[B59] The genetically modified yeast cell of paragraph B49, wherein the 3-HPDH gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 129.

[B60] The genetically modified yeast cell of any of paragraphs B1-B59, wherein the 3-HPDH gene comprises a nucleotide sequence with at least 60%, e.g., at least 65%, 70%, 75%, 80%, 85%, 90%, 95%, 97%, 98%, 99%, or 100% sequence identity to a nucleotide sequence selected from SEQ ID NOs: 25, 143, 144, and 343.

[B61] The genetically modified yeast cell of paragraph B60, wherein the 3-HPDH gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 25.

[B62] The genetically modified yeast cell of paragraph B60, wherein the 3-HPDH gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 143.

[B63] The genetically modified yeast cell of paragraph B60, wherein the 3-HPDH gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 144.

[B64] The genetically modified yeast cell of paragraph B60, wherein the 3-HPDH gene comprises a nucleotide sequence with at least 60%, e.g., at least 65%, 70%, 75%, 80%, 85%, 90%, 95%, 97%, 98%, 99%, or 100% sequence identity to the nucleotide sequence of SEQ ID NO: 343.

[B65] The genetically modified yeast cell of any of paragraphs B1-B64, wherein the 3-HPDH gene is also a HIBADH gene.

[B66] The genetically modified yeast cell of any of paragraphs B1-B65, wherein the 3-HPDH gene is also a 4-hydroxybutyrate dehydrogenase gene.

[B67] The genetically modified yeast cell of any of paragraphs B1-B66, wherein the PPC gene encodes a polypeptide with at least 60%, e.g., at least 65%, 70%, 75%, 80%, 85%, 90%, 95%, 97%, 98%, 99%, or 100% sequence identity to an amino acid sequence selected from SEQ ID NOs: 10, 11, and 12.

[B68] The genetically modified yeast cell of paragraph 867, wherein the PPC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 10.

[B69] The genetically modified yeast cell of paragraph B67, wherein the PPC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 11.

[B70] The genetically modified yeast cell of paragraph B67, wherein the PPC gene encodes a polypeptide with at least 60%, e.g., at least 65%, 70%, 75%, 80%, 85%, 90%, 95%, 97%, 98%, 99%, or 100% sequence identity to the amino acid sequence of SEQ ID NO: 12.

[B71] The genetically modified yeast cell of any of paragraphs B1-870, wherein the PPC gene comprises a nucleotide sequence with at least 60%, e.g., at least 65%, 70%, 75%, 80%, 85%, 90%, 95%, 97%, 98%, 99%, or 100% sequence identity to a nucleotide sequence of SEQ ID NO: 9.

[B72] The genetically modified yeast cell of any of paragraphs B1-B71, wherein said yeast cell is Crabtree-negative.

[B73] The genetically modified yeast cell of any of paragraphs B1-B72, wherein the yeast cell belongs to a genus selected from *Issatchenkia, Candida, Kluyveromyces, Pichia, Schizosaccharomyces, Torulaspora, Zygosaccharomyces*, and *Saccharomyces*.

[B74] The genetically modified yeast cell of paragraph B73, wherein the yeast cell belongs to a clade selected from the *I. orientalis/P. fermentans* clade and the *Saccharomyces* clade.

[B75] The genetically modified yeast cell of paragraph B73, wherein the yeast cell is selected from *I. orientalis, C. lambica*, and *S. bulderi*.

[B76] The genetically modified yeast cell of any of paragraphs B1-B75, wherein said cell further comprises one or more deletions or disruptions of a native gene selected from PDC, ADH, GAL6, CYB2A, CYB2B, GPD, GPP, ALD, and PCK genes.

[B77] The genetically modified yeast cell of paragraph B76, wherein one or more of the deletions or disruptions results from insertion of one or more of the exogenous 3-HP pathway genes.

[B78] The genetically modified yeast cell of any of paragraphs B1-B77, wherein one or more of the exogenous 3-HP pathway genes are operatively linked to one or more exogenous regulatory elements.

[B79] The genetically modified yeast cell of paragraph B78, wherein the one or more regulatory elements are foreign to the one or more 3-HP pathway genes.

[B80] The genetically modified yeast cell of any of paragraphs B1-B79, wherein the exogenous PYC gene is operatively linked to an exogenous promoter that is foreign to the PYC gene.

[B81] The genetically modified yeast cell of any of paragraphs B1-B80, wherein the exogenous AAT gene is operatively linked to an exogenous promoter that is foreign to the AAT gene.

[B82] The genetically modified yeast cell of any of paragraphs B1-B81, wherein the exogenous ADC gene is operatively linked to an exogenous promoter that is foreign to the ADC gene.

[B83] The genetically modified yeast cell of any of paragraphs B1-B82, wherein the exogenous BAAT or gabT gene is operatively linked to an exogenous promoter that is foreign to the BAAT or gabT gene.

[B84] The genetically modified yeast cell of any of paragraphs B1-B83, wherein the exogenous 3-HPDH gene is operatively linked to an exogenous promoter that is foreign to the 3-HPDH gene.

[B85] The genetically modified yeast cell of any of paragraphs B1-B84, wherein the exogenous PPC gene is operatively linked to an exogenous promoter that is foreign to the PPC gene.

[B86] The genetically modified yeast cell of any of paragraphs B1-B85, wherein the cell is capable of growing at a pH of less than 4 in media containing 75 g/L or greater 3-HP.

[B87] The genetically modified yeast cell of any of paragraphs B1-B86, wherein the cell is a 3-HP-resistant yeast cell.

[B88] The genetically modified yeast cell of any of paragraphs B1-B87, wherein the cell has undergone mutation and/or selection, such that the mutated and/or selected cell possess a higher degree of resistance to 3-HP than a wild-type cell of the same species.

[B89] The genetically modified yeast cell of paragraph B88, wherein the cell has undergone mutation and/or selection before being genetically modified with the one or more exogenous 3-HP pathway genes.

[B90] The genetically modified yeast cell of paragraph B88 or B89, wherein the cell has undergone selection in the presence of lactic acid or 3-HP.

[B91] The genetically modified yeast cell of paragraph B91, wherein the selection is chemostat selection.

[B92] A method of producing 3-HP comprising:
 (i) culturing the genetically modified yeast cell of any of paragraphs B1-B91 in the presence of medium comprising at least one carbon source; and
 (ii) isolating 3-HP from the culture.

[B93] The method of paragraph B92, wherein said carbon source is selected from glucose, xylose, arabinose, sucrose, fructose, cellulose, glucose oligomers, and glycerol.

[B94] The method of paragraph B92 or B93, wherein the medium is at a pH of less than 5, e.g., in the range of about 1.5 to about 4.5, about 2.0 to about 4.0, or about 2.0 to about 3.5.

What is claimed is:

1. A genetically modified yeast cell selected from the group consisting of *I. orientalis*, *C. lambica*, and *S. bulderi*, the genetically modified yeast cell comprising an exogenous BAAT or gabT gene encoding an enzymatically active polypeptide with at least 85% sequence identity to an amino acid sequence selected from SEQ ID NOs: 20, 21, and 24.

2. The genetically modified yeast cell of claim 1, wherein the BAAT or gabT gene encodes a polypeptide having at least 90% sequence identity to the amino acid sequence selected from SEQ ID Nos: 20, 21, and 24.

3. The genetically modified yeast cell of claim 1, wherein the BAAT or gabT gene encodes a polypeptide having at least 95% sequence identity to the amino acid sequence selected from SEQ ID Nos: 20, 21 and 24.

4. The genetically modified yeast cell of claim 1, wherein the BAAT or gabT gene encodes a polypeptide having at least 97% sequence identity to the amino acid sequence selected from SEQ ID Nos: 20, 21, and 24.

5. The genetically modified yeast cell of claim 1, wherein the BAAT or gabT gene encodes a polypeptide having at least 98% sequence identity to the amino acid sequence selected from SEQ ID Nos: 20, 21, and 24.

* * * * *